United States Patent
Mainolfi

(10) Patent No.: US 10,954,220 B2
(45) Date of Patent: Mar. 23, 2021

(54) 3-PHOSPHOGLYCERATE DEHYDROGENASE INHIBITORS AND USES THEREOF

(71) Applicant: Raze Therapeutics, Inc., Cambridge, MA (US)

(72) Inventor: Nello Mainolfi, Belmont, MA (US)

(73) Assignee: RAZE THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 16/082,659

(22) PCT Filed: Mar. 8, 2017

(86) PCT No.: PCT/US2017/021420
§ 371 (c)(1),
(2) Date: Sep. 6, 2018

(87) PCT Pub. No.: WO2017/156165
PCT Pub. Date: Sep. 14, 2017

(65) Prior Publication Data
US 2019/0071431 A1     Mar. 7, 2019

Related U.S. Application Data

(60) Provisional application No. 62/305,930, filed on Mar. 9, 2016.

(51) Int. Cl.
| | |
|---|---|
| *C07D 405/12* | (2006.01) |
| *C07D 403/12* | (2006.01) |
| *C07D 401/12* | (2006.01) |
| *C07D 401/14* | (2006.01) |
| *C07D 405/14* | (2006.01) |
| *C07D 413/12* | (2006.01) |
| *C07D 491/056* | (2006.01) |
| *A61P 35/00* | (2006.01) |

(52) U.S. Cl.
CPC ............ *C07D 405/12* (2013.01); *A61P 35/00* (2018.01); *C07D 401/12* (2013.01); *C07D 401/14* (2013.01); *C07D 403/12* (2013.01); *C07D 405/14* (2013.01); *C07D 413/12* (2013.01); *C07D 491/056* (2013.01)

(58) Field of Classification Search
CPC ... C07D 405/12; C07D 401/12; C07D 403/12
See application file for complete search history.

(56) References Cited

U.S. PATENT DOCUMENTS

| | | | |
|---|---|---|---|
| 5,639,600 | A | 6/1997 | McGrath et al. |
| 6,552,065 | B2 | 4/2003 | Remiszewski et al. |
| 7,071,189 | B2 | 7/2006 | Kawashima et al. |
| 7,087,648 | B1 | 8/2006 | McGrath et al. |
| 7,390,799 | B2 | 6/2008 | Bruncko et al. |
| 8,138,347 | B2 | 3/2012 | Adams et al. |
| 2008/0293737 | A1 | 11/2008 | Martinborough et al. |
| 2011/0207767 | A1 | 8/2011 | Beusker et al. |
| 2013/0281430 | A1 | 10/2013 | Dahmann et al. |
| 2019/0071400 | A1 | 3/2019 | Mainolfi |

FOREIGN PATENT DOCUMENTS

| | | |
|---|---|---|
| WO | WO2000042213 | 7/2000 |
| WO | WO2001042246 | 6/2001 |
| WO | WO2003013484 | 2/2003 |
| WO | WO2003035621 | 5/2003 |
| WO | WO2003063794 | 8/2003 |
| WO | WO2004019973 | 3/2004 |
| WO | WO2004089925 | 10/2004 |
| WO | WO2004106328 | 12/2004 |
| WO | WO2005007623 | 1/2005 |
| WO | WO2005113554 | 12/2005 |
| WO | WO2006067445 | 6/2006 |
| WO | WO2006067446 | 6/2006 |
| WO | WO2006078846 | 7/2006 |
| WO | WO2006122806 | 11/2006 |
| WO | WO2007016176 | 2/2007 |
| WO | WO2007019344 | 2/2007 |
| WO | WO2007044729 | 4/2007 |
| WO | WO2007053452 | 5/2007 |
| WO | WO2007070514 | 6/2007 |
| WO | WO2007084786 | 7/2007 |
| WO | WO2007129161 | 11/2007 |
| WO | WO2008039218 | 4/2008 |
| WO | WO2008058037 | 5/2008 |
| WO | WO2008109943 | 9/2008 |
| WO | WO2008118802 | 10/2008 |
| WO | WO2009114512 | 9/2009 |
| WO | WO2011090760 | 7/2011 |
| WO | WO 2015/150097 A1 * | 10/2015 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
No new references cited by the Examiner.*
Berge, S. M. et al. Pharmaceutical Salts. J. Pharmaceutical Sciences, vol. 66, No. 1, Jan. 1977, pp. 1-19.
Caubre et al., Document No. 122:81117, entered in STN on Jan. 12, 1995; retrieved from STN.
Daniell et al., "Design, synthesis, and biological evaluation of achiral analogs of duocarmycin SA," Bioorganic & Medicinal Chemistry Letters, 2005, 15(1):177-180.
Hangauer et al., Document No. 153:643306, retrieved from CAPLUS; Nov. 23, 2010.
Jun et al., "Requirement of the expression of 3-phosphoglycerate dehydrogenase for traversing S phase in murine T lymphocytes following polyclonal activation," Cell Immunology, vol. 287, No. 2, Feb. 2014 (pp. 78-85).
Mullarky et al., "Identification of a small molecule inhibitor of 3-phosphoglycerate dehydrogenase to target serine biosynthesis in cancers," Proceedings of the National Academy of Sciences of the United States of America, 2016, 113(7):1778-1783.

(Continued)

*Primary Examiner* — Shawquia Jackson
(74) *Attorney, Agent, or Firm* — Dechert LLP; Andrea L. C. Reid; Todd K. Macklin

(57) ABSTRACT

The present invention provides compounds, compositions thereof, and methods of using the same.

16 Claims, No Drawings

(56) References Cited

OTHER PUBLICATIONS

PCT International Preliminary Report on Patentability from PCT/US2017/021420 dated Sep. 11, 2018.
PCT International Search Report and Written Opinion from PCT/2017/021420 dated Jul. 3, 2017.
PCT International Preliminary Report on Patentability from PCT/US2017/021436 dated Sep. 11, 2018.
PCT International Search Report and Written Opinion from PCT/2017/021436 dated Jul. 3, 2017.
Sechi et al., Document No. 157:372334, retrieved from CAPLUS; 2012.
Supplementary European Search Report issued by the European Patent Office for European Patent App. 17764026.5, dated Jun. 5, 2019.
Supplementary European Search Report issued by the European Patent Office for European Patent App. 17764038.0, dated Oct. 10, 2019.
Zogg C., "Phosphoglycerate Dehydrogenase: Potential Therapeutic Target and Putative Metabolic Oncogene," Journal of Oncology, 2014, 4(12): 2502-2513.

* cited by examiner

3-PHOSPHOGLYCERATE DEHYDROGENASE INHIBITORS AND USES THEREOF

TECHNICAL FIELD OF THE INVENTION

The present invention relates to compounds and methods useful for inhibiting 3-phosphoglycerate dehydrogenase. The invention also provides pharmaceutically acceptable compositions comprising compounds of the present invention and methods of using said compositions in the treatment of various disorders.

BACKGROUND OF THE INVENTION

Phosphoglycerate dehydrogenase (PHGDH) catalyzes the first step in the biosynthesis of L-serine, which is the conversion of 3-phosphoglycerate into 3-phosphohydroxypyruvate with a reduction of nicotinamide adenine dinucleotide ($NAD^+$) to NADH.

Certain cancers, including human melanomas and breast cancers, can have high levels of PHGDH. These cancer cells are dependent on PHGDH for their growth and survival as PHGDH catalyzes serine production and may also be a significant source of NADPH in cancer cells. Targeting PHGDH by small molecule inhibitors could be a therapeutic strategy to reduce cancer cell growth and survival. Accordingly, there remains a need to find PHGDH inhibitors useful as therapeutic agents.

SUMMARY OF THE INVENTION

It has now been found that compounds of this invention, and pharmaceutically acceptable compositions thereof, are effective as PHGDH inhibitors. Such compounds have the general formula I:

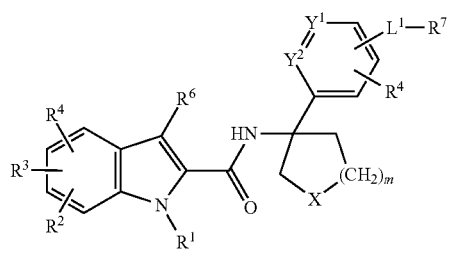

or a pharmaceutically acceptable salt thereof, wherein each of $R^1$, $R^2$, $R^3$, $R^4$, $R^5$, $R^6$, $R^7$, X, $L^1$, $Y^1$ and $Y^2$ is as defined and described herein.

Compounds of the present invention, and pharmaceutically acceptable compositions thereof, are useful for treating a variety of diseases, disorders or conditions, associated with PHGDH. Such diseases, disorders, or conditions include cellular proliferative disorders (e.g., cancer) such as those described herein.

DETAILED DESCRIPTION OF THE INVENTION

1. General Description of Certain Aspects of the Invention

Compounds of the present invention, and compositions thereof, are useful as inhibitors of PHGDH. Without wishing to be bound by any particular theory, it is believed that compounds of the present invention, and compositions thereof, may inhibit the activity of PHGDH and/or inhibit the production of NADPH, and thus reduce the growth of cells in proliferative disorders such as cancer.

In certain embodiments, the present invention provides a compound of formula I:

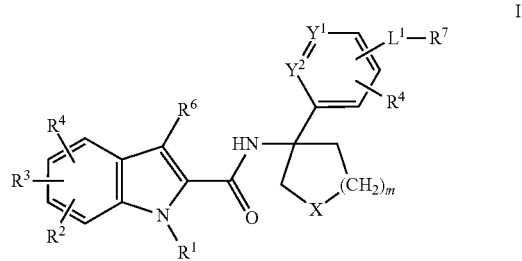

or a pharmaceutically acceptable salt thereof, wherein:
$R^1$ is hydrogen or $C_{1-4}$ alkyl;
each of $R^2$ and $R^3$ is independently halogen, —OR, —CN, $C_{1-6}$ aliphatic optionally substituted with 1, 2, or 3 halogens, or -L-R'; or $R^2$ and $R^3$ are optionally taken together with the carbon atoms to which they are attached and any intervening atoms to form a 5-8 membered partially unsaturated ring having 0-2 heteroatoms independently selected from nitrogen, oxygen, or sulfur;
$R^4$ is hydrogen, halogen, —$OR^5$, —CN, $C_{1-6}$ aliphatic optionally substituted with 1, 2, or 3 halogens, or -L-R';
each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
$R^5$ is hydrogen, —$(CH_2)_n$— phenyl, —$(CH_2)_n$— Cy', or $C_{1-6}$ alkyl optionally substituted with 1, 2, or 3 halogens;
each L is independently a $C_{1-6}$ bivalent straight or branched hydrocarbon chain wherein 1-4 methylene units of the chain are independently and optionally replaced with —O—, —C(O)—, —C(O)O—, —OC(O)—, —OC(O)N(R)—, —(R)NC(O)O—, —C(O)N(R)—, —(R)NC(O)—, —N(R)—, —N(R)C(O)N(R)—, —S—, —SO—, or —$SO_2$—;
each R' is independently hydrogen, $C_{1-6}$ aliphatic, or an optionally substituted 4-8 membered saturated or partially unsaturated monocyclic heterocyclic ring having 1-3 heteroatoms independently selected from nitrogen, oxygen, or sulfur;
$R^6$ is hydrogen or $C_{1-4}$ alkyl;
$R^7$ is hydrogen, —$CO_2R$, optionally substituted $C_{1-6}$ aliphatic, -Cy-, or a bivalent 3-7 membered ring;
$L^1$ is a covalent bond or a $C_{1-10}$ bivalent straight or branched hydrocarbon chain wherein 1-5 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, —(R)NC(S)N(R)—, or -Cy-;

each -Cy- is independently a bivalent 6-membered arylene ring containing 0-2 nitrogen atoms, or a bivalent 5-membered heteroarylene ring with 1-4 heteroatoms independently selected from nitrogen, oxygen, or sulfur, or a bivalent partially unsaturated 8-10 membered bicyclic heterocyclene ring with 1-4 heteroatoms independently selected from nitrogen, oxygen, or sulfur, wherein -Cy- is optionally substituted with 1 or 2 substituents independently selected from C$_{1-4}$ alkyl or —OR;

-Cy' is a 4-8 membered saturated or partially unsaturated monocyclic heterocyclic ring having 1-2 heteroatoms independently selected from nitrogen, oxygen, or sulfur;

R$^8$ is hydrogen, —CO$_2$R, or C$_{1-6}$ optionally substituted aliphatic;

R$^9$ is hydrogen, halogen, C$_{1-4}$ alkyl, —CN, —OR, —(CH$_2$)$_n$— (optionally substituted phenyl), or L$^2$-R$^8$;

each L$^2$ is independently C$_{1-8}$ bivalent straight or branched hydrocarbon chain wherein 1-4 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—;

R$^{10}$ is C$_{1-6}$ aliphatic optionally substituted with 1, 2, or 3 halogens, —C(O)CH$_3$, or —SO$_2$—N(R$^1$)(R$^{11}$);

R$^{11}$ is —C(O)CH$_3$, —C(O)NHR$^1$, or pyrazinyl;

n is independently 0, 1, 2, 3, 4, or 5;

m is independently 0, 1, or 2;

X is O, S, or —N(R$^{10}$)—; and each of Y$^1$ and Y$^2$ is independently =N— or =C(R$^4$)—.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C$_3$-C$_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

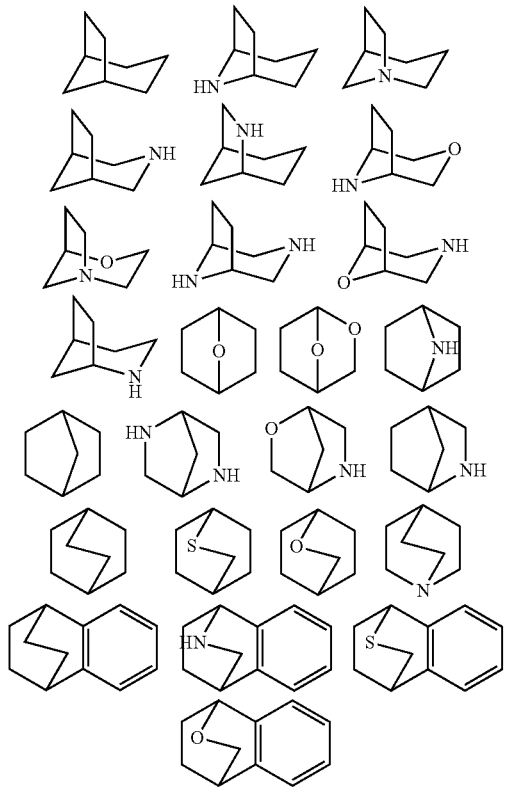

The term "lower alkyl" refers to a C$_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

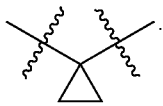

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 nt electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-4}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR')$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR°, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

As used herein, the term "inhibitor" is defined as a compound that binds to and/or inhibits PHGDH with measurable affinity. In certain embodiments, an inhibitor has an $IC_{50}$ and/or binding constant of less than about 100 µM, less than about 50 µM, less than about 1 µM, less than about 500 nM, less than about 100 nM, less than about 10 nM, or less than about 1 nM.

The terms "measurable affinity" and "measurably inhibit," as used herein, means a measurable change in PHGDH activity between a sample comprising a compound of the present invention, or composition thereof, and PHGDH, and an equivalent sample comprising PHGDH, in the absence of said compound, or composition thereof.

3. Description of Exemplary Embodiments

In certain embodiments, the present invention provides a compound of formula I:

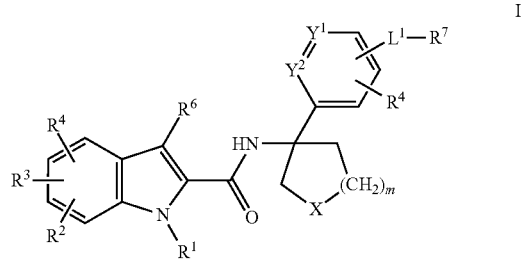

or a pharmaceutically acceptable salt thereof, wherein:
$R^1$ is hydrogen or $C_{1-4}$ alkyl;
each of $R^2$ and $R^3$ is independently halogen, —OR, —CN, $C_{1-6}$ aliphatic optionally substituted with 1, 2, or 3 halogens, or -L-R'; or $R^2$ and $R^3$ are optionally taken together with the carbon atoms to which they are attached and any intervening atoms to form a 5-8 membered partially unsaturated ring having 0-2 heteroatoms independently selected from nitrogen, oxygen, or sulfur;
$R^4$ is hydrogen, halogen, —$OR^5$, —CN, $C_{1-6}$ aliphatic optionally substituted with 1, 2, or 3 halogens, or -L-R';
each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
$R^5$ is hydrogen, —$(CH_2)_n$— phenyl, —$(CH_2)_n$— Cy', or $C_{1-6}$ alkyl optionally substituted with 1, 2, or 3 halogens;
each L is independently a $C_{1-6}$ bivalent straight or branched hydrocarbon chain wherein 1-4 methylene units of the chain are independently and optionally replaced with —O—, —C(O)—, —C(O)O—, —OC(O)—, —OC(O)N(R)—, —(R)NC(O)O—, —C(O)N(R)—, —(R)NC(O)—, —N(R)—, —N(R)C(O)N(R)—, —S—, —SO—, or —$SO_2$—;
each R' is independently hydrogen, $C_{1-6}$ aliphatic, or an optionally substituted 4-8 membered saturated or partially unsaturated monocyclic heterocyclic ring having 1-3 heteroatoms independently selected from nitrogen, oxygen, or sulfur;
$R^6$ is hydrogen or $C_{1-4}$ alkyl;
$R^7$ is hydrogen, —$CO_2R$, optionally substituted $C_{1-6}$ aliphatic, -Cy-, or a bivalent 3-7 membered ring;
$L^1$ is a covalent bond or a $C_{1-8}$ bivalent straight or branched hydrocarbon chain wherein 1-5 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2$—, —$SO_2N(R)$—, —$(R)NSO_2$—, —C(S)—, —C(S)O—, —OC(S)—, —C(S)N(R)—, —(R)NC(S)—, —(R)NC(S)N(R)—, or -Cy-;

each -Cy- is independently a bivalent 6-membered arylene ring containing 0-2 nitrogen atoms, or a bivalent 5-membered heteroarylene ring with 1-4 heteroatoms independently selected from nitrogen, oxygen, or sulfur, or a bivalent partially unsaturated 8-10 membered bicyclic heterocyclene ring with 1-4 heteroatoms independently selected from nitrogen, oxygen, or sulfur, wherein -Cy- is optionally substituted with 1 or 2 substituents independently selected from $C_{1-4}$ alkyl or —OR;

-Cy' is a 4-8 membered saturated or partially unsaturated monocyclic heterocyclic ring having 1-2 heteroatoms independently selected from nitrogen, oxygen, or sulfur, $R^8$ is hydrogen, —$CO_2R$, or $C_{1-6}$ optionally substituted aliphatic;

$R^9$ is hydrogen, halogen, $C_{1-4}$ alkyl, —CN, —OR, —$(CH_2)_n$— (optionally substituted phenyl), or $L^2$-$R^8$;

each $L^2$ is independently $C_{1-8}$ bivalent straight or branched hydrocarbon chain wherein 1-4 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2$—, —$SO_2N(R)$—, —$(R)NSO_2$—, —C(S)—, —C(S)O—, —OC(S)—, —C(S)N(R)—, —(R)NC(S)—, or —(R)NC(S)N(R)—;

$R^{10}$ is $C_{1-6}$ aliphatic optionally substituted with 1, 2, or 3 halogens, —$C(O)CH_3$, or —$SO_2$—$N(R^1)(R^{11})$;

$R^1$ is —$C(O)CH_3$, —$C(O)NHR^1$, or pyrazinyl;

n is independently 0, 1, 2, 3, 4, or 5;

m is independently 0, 1, or 2;

X is O, S, or —$N(R^{10})$—; and each of $Y^1$ and $Y^2$ is independently =N— or =$C(R^4)$—.

As defined above and described herein, $R^1$ is hydrogen or $C_{1-4}$ alkyl. In some embodiments, $R^1$ is hydrogen. In some embodiments, $R^1$ is $C_{1-4}$ alkyl. In some embodiments, $R^1$ is methyl. In some embodiments, $R^1$ is ethyl.

In some embodiments, $R^1$ is selected from those depicted in Table 1, below.

As defined above and described herein, $R^2$ is independently halogen, —OR, —CN, $C_{1-6}$ aliphatic optionally substituted with 1, 2, or 3 halogens, or -L-R'; or $R^2$ and $R^3$ are optionally taken together with the carbon atoms to which they are attached and any intervening atoms to form a 5-8 membered partially unsaturated ring having 0-2 heteroatoms independently selected from nitrogen, oxygen, or sulfur.

In some embodiments, $R^2$ is halogen. In some embodiments, $R^2$ is —OR. In some embodiments, $R^2$ is —CN. In some embodiments, $R^2$ is $C_{1-6}$ aliphatic optionally substituted with 1, 2, or 3, halogens. In some embodiments, $R^2$ is -L-R'. In some embodiments, $R^2$ and $R^3$ are taken together with the carbon atoms to which they are attached and any intervening atoms to form a 5-8 membered partially unsaturated ring having 0-2 heteroatoms independently selected from nitrogen, oxygen, or sulfur.

In some embodiments, $R^2$ is F, Cl, —$CF_3$, —$OCF_3$, —$OCHF_2$, —$OCH_2Ph$, —$OCH_3$, —CN, —$CH_3$,

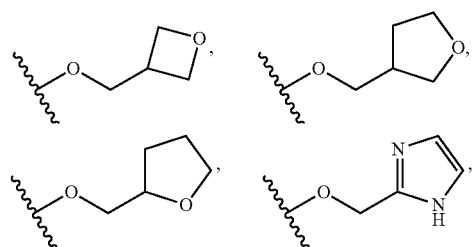

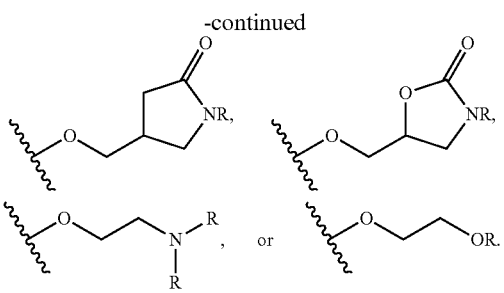

In some embodiments, $R^2$ is F or Cl. In some embodiments, $R^2$ is —$OCH_3$. In some embodiments, $R^2$ is —$CH_3$.

In some embodiments, $R^2$ is selected from those depicted in Table 1, below.

As defined above and described herein, $R^3$ is independently halogen, —OR, —CN, $C_{1-6}$ aliphatic optionally substituted with 1, 2, or 3 halogens, or -L-R'; or $R^2$ and $R^3$ are optionally taken together with the carbon atoms to which they are attached and any intervening atoms to form a 5-8 membered partially unsaturated ring having 0-2 heteroatoms independently selected from nitrogen, oxygen, or sulfur.

In some embodiments, $R^3$ is halogen. In some embodiments, $R^3$ is —OR. In some embodiments, $R^3$ is —CN. In some embodiments, $R^3$ is $C_{1-6}$ aliphatic optionally substituted with 1, 2, or 3, halogens. In some embodiments, $R^3$ is -L-R'. In some embodiments, $R^2$ and $R^3$ are taken together with the carbon atoms to which they are attached and any intervening atoms to form a 5-8 membered partially unsaturated ring having 0-2 heteroatoms independently selected from nitrogen, oxygen, or sulfur.

In some embodiments, $R^3$ is F, Cl, —$CF_3$, —$OCF_3$, —$OCHF_2$, —$OCH_2Ph$, —$OCH_3$, —CN, —$CH_3$,

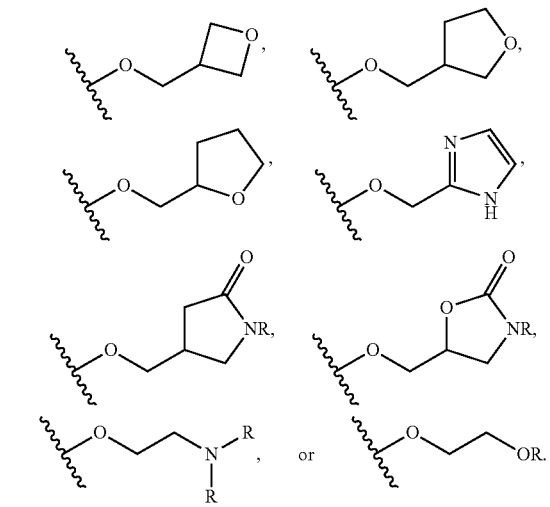

In some embodiments, $R^3$ is F or Cl. In some embodiments, $R^3$ is —$OCH_3$. In some embodiments, $R^3$ is —$CH_3$.

In some embodiments, $R^3$ is selected from those depicted in Table 1, below.

As defined above and described herein, $R^4$ is hydrogen, halogen, —$OR^5$, —CN, $C_{1-6}$ aliphatic optionally substituted with 1, 2, or 3 halogens, or -L-R'.

In some embodiments, $R^4$ is hydrogen. In some embodiments, $R^4$ is halogen. In some embodiments, $R^4$ is —$OR^5$. In some embodiments, $R^4$ is $C_{1-6}$ aliphatic optionally substituted with 1, 2, or 3 halogens. In some embodiments, $R^4$ is -L-R'.

In some embodiments, $R^4$ is F, Cl, —$CF_3$, —$OCF_3$, —$OCHF_2$, —$OCH_2Ph$, —$OCH_3$, —CN, —$CH_3$,

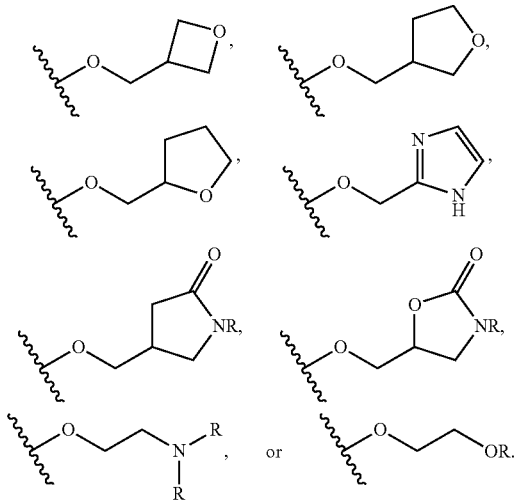

In some embodiments, $R^4$ is F or Cl. In some embodiments, $R^4$ is —$OCH_3$. In some embodiments, $R^4$ is —$CH_3$.

In some embodiments, $R^4$ is selected from those depicted in Table 1, below.

As defined above and described herein, each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, R is hydrogen. In some embodiments, R is an optionally substituted $C_{1-6}$ aliphatic group. In some embodiments, R is an optionally substituted 3-8 membered saturated or partially unsaturated monocyclic carbocyclic ring. In some embodiments, R is an optionally substituted phenyl. In some embodiments, R is an optionally substituted 8-10 membered bicyclic aromatic carbocyclic ring. In some embodiments, R is an optionally substituted 4-8 membered saturated or partially unsaturated monocyclic heterocyclic ring having 1-2 heteroatoms independently selected from nitrogen, oxygen, or sulfur. In some embodiments, R is a 5-6 membered monocyclic heteroaromatic ring having 1-4 heteroatoms independently selected from nitrogen, oxygen, or sulfur. In some embodiments, R is an optionally substituted 8-10 membered bicyclic heteroaromatic ring having 1-5 heteroatoms independently selected from nitrogen, oxygen, or sulfur.

In some embodiments, R is selected from those depicted in Table 1, below.

As defined above and described herein, each L is independently a $C_{1-6}$ bivalent straight or branched hydrocarbon chain wherein 1-4 methylene units of the chain are independently and optionally replaced with —O—, —C(O)—, —C(O)O—, —OC(O)—, —OC(O)N(R)—, —(R)NC(O)O—, —C(O)N(R)—, —(R)NC(O)—, —N(R)—, —N(R)C(O)N(R)—, —S—, —SO—, or —$SO_2$—.

In some embodiments, L is a $C_{1-6}$ bivalent straight or branched hydrocarbon chain wherein 1-4 methylene units of the chain are independently replaced with —O—, —C(O)—, —C(O)O—, —OC(O)—, —OC(O)N(R)—, —(R)NC(O)O—, —C(O)N(R)—, —(R)NC(O)—, —N(R)—, —N(R)C(O)N(R)—, —S—, —SO—, or —$SO_2$—. In some embodiments, 1 or 2 methylene units of the chain are replaced with —O—. In some embodiments, 1 or 2 methylene units of the chain are replaced with —C(O)—. In some embodiments, 1 or 2 methylene units of the chain are replaced with —C(O)O—. In some embodiments, 1 or 2 methylene units of the chain are replaced with —OC(O)—. In some embodiments, 1 or 2 methylene units of the chain are replaced with —OC(O)N(R)—. In some embodiments, 1 or 2 methylene units of the chain are replaced with —(R)NC(O)O—. In some embodiments, 1 or 2 methylene units are replaced with —C(O)N(R)—. In some embodiments, 1 or 2 methylene units of the chain are replaced with —(R)NC(O)—. In some embodiments, 1 or 2 methylene units of the chain are replaced with —N(R)—. In some embodiments, 1 or 2 methylene units of the chain are replaced with —N(R)C(O)N(R)—. In some embodiments, 1 or 2 methylene units of the chain are replaced with —S—. In some embodiments, 1 or 2 methylene units of the chain are replaced with —SO—. In some embodiments, 1 or 2 methylene units are replaced with —$SO_2$—. In some embodiments, 1 or 2 methylene units of the chain are independently replaced with —O—, —C(O)—, —C(O)O—, —OC(O)—, —OC(O)N(R)—, —(R)NC(O)O—, —C(O)N(R)—, —(R)NC(O)—, —N(R)—, —N(R)C(O)N(R)—, —S—, —SO—, or —$SO_2$—, wherein each R is independently hydrogen or methyl.

In some embodiments, L is a $C_{1-6}$ bivalent straight or branched hydrocarbon chain wherein 1, 2, or 3 methylene units of the chain are independently replaced with —O—, —C(O)—, —C(O)O—, —OC(O)—, —OC(O)N(R)—, —(R)NC(O)O—, —C(O)N(R)—, —(R)NC(O)—, —N(R)—, or —N(R)C(O)N(R)—, wherein R is hydrogen or methyl. In some embodiments, L is a $C_{1-6}$ bivalent straight or branched hydrocarbon chain wherein 1 or 2 methylene units of the chain are independently replaced with —O—, —C(O)—, —C(O)N(R)—, —(R)NC(O)—, or —N(R)—, wherein each R is independently hydrogen or methyl.

In some embodiments, L is —O—. In some embodiments, L is —O—$CH_2$—. In some embodiments, L is —O—$CH_2$—$CH_2$—. In some embodiments, L is —O—$CH_2$—$CH_2$—O—.

In some embodiments, L is selected from those depicted in Table 1, below.

As defined above and described herein, each R' is independently hydrogen, $C_{1-6}$ aliphatic, or an optionally substituted 4-8 membered saturated or partially unsaturated monocyclic heterocyclic ring having 1-3 heteroatoms independently selected from nitrogen, oxygen, or sulfur.

In some embodiments, R' is hydrogen. In some embodiments, R' is $C_{1-6}$ aliphatic. In some embodiments, R' is an optionally substituted 4-8 membered saturated or partially saturated monocyclic heterocyclic ring having 1-3 heteroatoms independently selected from nitrogen, oxygen or sulfur.

In some embodiments, R' is

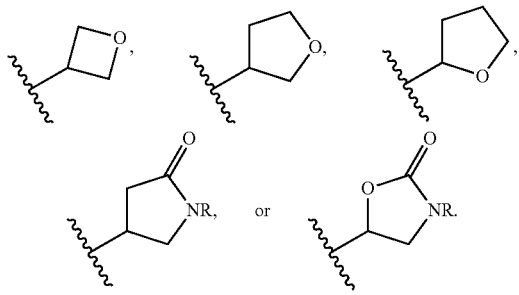

In some embodiments, R' is

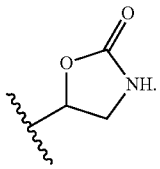 [SMILES: *C1CNC(=O)O1]

In some embodiments, R' is

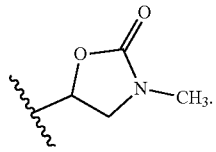 [SMILES: *C1CN(C)C(=O)O1]

In some embodiments, R' is

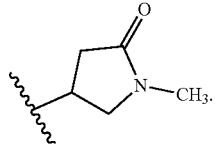 [SMILES: *C1CC(=O)N(C)C1]

In some embodiments, R' is selected from those depicted in Table 1, below.

As defined above and described herein, $R^5$ is hydrogen, —(CH$_2$)$_n$— phenyl, —(CH$_2$)$_n$— Cy', or C$_{1-6}$ alkyl optionally substituted with 1, 2, or 3 halogens;

In some embodiments, $R^5$ is hydrogen. In some embodiments, $R^5$ is —(CH$_2$)$_n$-phenyl. In some embodiments, $R^5$ is C$_{1-6}$ alkyl optionally substituted with 1, 2, or 3 halogens.

In some embodiments, $R^5$ is hydrogen, —CH$_3$, —CH$_2$CH$_3$, —CH$_2$F, —CHF$_2$, —CF$_3$, —CH$_2$CHF$_2$, —CH$_2$CF$_3$, or

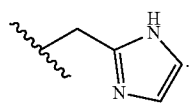 [SMILES: *Cc1ncc[nH]1]

In some embodiments, $R^5$ is selected from those depicted in Table 1, below.

As defined above, and described herein, $R^6$ is hydrogen or C$_{1-4}$ alkyl. In some embodiments, $R^6$ is hydrogen. In some embodiments, $R^6$ is C$_{1-4}$ alkyl.

In some embodiments, $R^6$ is methyl.

In some embodiments, $R^6$ is selected from those depicted in Table 1, below.

As defined above, and described herein, $R^7$ is hydrogen, —CO$_2$R, optionally substituted C$_{1-6}$ aliphatic, -Cy-, or a bivalent 3-7 membered ring.

In some embodiments, $R^7$ is hydrogen. In some embodiments, $R^7$ is —CO$_2$R. In some embodiments, $R^7$ is C$_{1-6}$ aliphatic. In some embodiments, $R^7$ is -Cy. In some embodiments, $R^7$ is a bivalent 3-7 membered ring.

In some embodiments, $R^7$ is hydrogen, methyl, ethyl, cyclopropyl, cyclobutyl, tetrazolyl, or —CO$_2$H.

In some embodiments $R^7$ is selected from those depicted in Table 1, below.

As defined above, and described herein, $L^1$ is a covalent bond or a C$_{1-8}$ bivalent straight or branched hydrocarbon chain wherein 1-5 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, —(R)NC(S)N(R)—, or -Cy-.

In some embodiments, $L^1$ is a covalent bond. In some embodiments, $L^1$ is a C$_{1-8}$ bivalent straight or branched hydrocarbon chain. In some embodiments, $L^1$ is a C$_{1-8}$ bivalent straight or branched hydrocarbon chain wherein 1-5 methylene units of the chain are independently replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, —(R)NC(S)N(R)—, or -Cy-. In some embodiments, 1, 2, or 3 methylene units of the chain are replaced with —O—. In some embodiments, 1, 2, or 3 methylene units of the chain are replaced with —C(O)—. In some embodiments, 1, 2, or 3 methylene units of the chain are replaced with —C(O)O— or —OC(O)—. In some embodiments, 1, 2, or 3 methylene units of the chain are replaced with —N(R)—. In some embodiments, 1, 2, or 3 methylene units of the chain are replaced with —C(O)N(R)— or —(R)NC(O)—. In some embodiments, 1, 2, or 3 methylene units of the chain are replaced with —OC(O)N(R)— or —(R)NC(O)O—. In some embodiments, 1, 2, or 3 methylene units of the chain are replaced with —N(R)C(O)N(R)—. In some embodiments, 1, 2, or 3 methylene units of the chain are replaced with —S—. In some embodiments, 1, 2, or 3 methylene units of the chain are replaced with —SO—. In some embodiments, 1, 2, or 3 methylene units of the chain are replaced with —SO$_2$—. In some embodiments, 1, 2, or 3 methylene units of the chain are replaced with —SO$_2$N(R)— or —(R)NSO$_2$—. In some embodiments, 1, 2, or 3 methylene units of the chain are replaced with —C(S)—. In some embodiments, 1, 2, or 3 methylene units of the chain are replaced with —C(S)O— or —OC(S)—. In some embodiments, 1, 2, or 3 methylene units of the chain are replaced with —C(S)N(R)— or —(R)NC(S)—. In some embodiments, 1, 2, or 3 methylene units of the chain are replaced with —(R)NC(S)N(R)—. In some embodiments, 1, 2, or 3 methylene units of the chain are replaced with -Cy-.

In some embodiments, $L^1$ is a C$_{1-6}$ bivalent straight or branched hydrocarbon chain wherein 1, 2, or 3 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, —(R)NC(S)N(R)—, or -Cy-, wherein each R is independently hydrogen, —CH$_2$-phenyl, phenyl, —CH$_3$, —CH$_2$CH$_3$, cyclopentyl, cyclohexyl, —CH$_2$F, —CHF$_2$, —CF$_3$, —CH$_2$CHF$_2$, or —CH$_2$CF$_3$; or each R is independently hydrogen or methyl; or R is hydrogen.

In some embodiments, $L^1$ is a $C_{1-6}$ bivalent straight or branched hydrocarbon chain wherein 1, 2, 3, or 4 methylene units of the chain are independently and optionally replaced with —O—, —C(O)—, —C(O)O—, —OC(O)—, —NH—, —C(O)NH—, —NHC(O)—, —NHC(O)NH—, —SO$_2$—, or -Cy-.

In some embodiments, $L^1$ is a $C_1$-6 bivalent straight or branched hydrocarbon chain wherein 1, 2, or 3 methylene units of the chain are independently replaced with —O—, —C(O)—, —C(O)O—, —OC(O)—, —NH—, —C(O)NH—, —NHC(O)—, —NHC(O)NH—, —SO$_2$—, or -Cy-.

In some embodiments, $L^1$ is a $C_{1-6}$ bivalent straight or branched hydrocarbon chain wherein 1, 2, or 3 methylene units of the chain are independently replaced with —C(O)—, —NH—, —C(O)NH—, —NHC(O)—, —NHC(O)NH—, —SO$_2$—, or -Cy-.

In some embodiments, $L^1$ is a $C_{3-6}$ bivalent straight or branched hydrocarbon chain wherein 2 or 3 methylene units of the chain are independently replaced with —SO$_2$—, —SO$_2$NH—, —C(O)O—, —C(O)NH—, or —NHC(O)NH—. In some embodiments, $L^1$ is a $C_{3-6}$ bivalent branched hydrocarbon chain wherein 2 or 3 methylene units of the chain are independently replaced with —SO$_2$—, —SO$_2$NH—, —C(O)O—, —C(O)NH—, or —NHC(O)NH—.

In some embodiments, the methylene unit of L is replaced with —SO$_2$—. In some embodiments, the methylene unit of $L^1$ is replaced with —SO$_2$NH—. In some embodiments, the methylene unit of $L^1$ is substituted with two methyl groups. In some embodiments, the methylene unit of $L^1$ is replaced with —C(O)NH—. In some embodiments, the methylene unit of $L^1$ is replaced with —SO$_2$— and the adjacent methylene unit is replaced with —NHC(O)NH—. In some embodiments, the methylene unit of $L^1$ is substituted with two methyl groups and the adjacent methylene unit is replaced with —NHC(O)NH—.

In some embodiments, $L^1$ is a covalent bond.

In some embodiments, $L^1$ is —SO$_2$NH—. In some embodiments, $L^1$ is

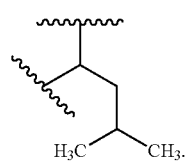

In some embodiments, $L^1$ is

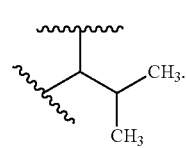 [SMILES: *C(*)C(C)C]

In some embodiments, $L^1$ is

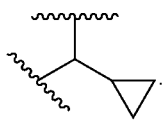 [SMILES: *C(*)C1CC1]

In some embodiments, $L^1$ is

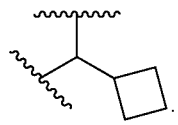

In some embodiments, $L^1$ is

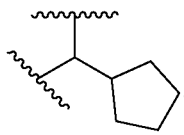

In some embodiments, $L^1$ is

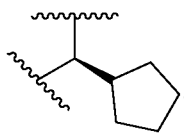

In some embodiments, $L^1$ is

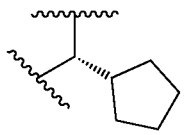

In some embodiments, $L^1$ is

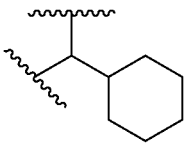

In some embodiments, $L^1$ is

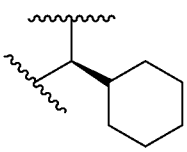

In some embodiments, $L^1$ is

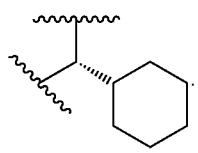

In some embodiments, $L^1$ is

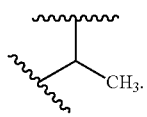

In some embodiments, $L^1$ is

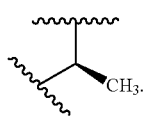

In some embodiments, L is

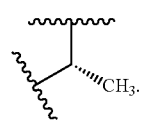

In some embodiments, $L^1$ is

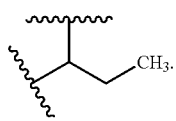

In some embodiments, $L^1$ is

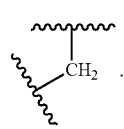

In some embodiments, $L^1$ is

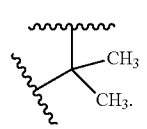

In some embodiments, $L^1$ is selected from those depicted in Table 1, below.

As defined above and described herein, each -Cy- is independently a bivalent 6-membered arylene ring containing 0-2 nitrogen atoms wherein the ring is optionally substituted with 1 or 2 substituents independently selected from $C_{1-4}$ alkyl or —OR, or a bivalent 5-membered heteroarylene ring with 1-4 heteroatoms independently selected from nitrogen, oxygen, or sulfur, or a bivalent partially unsaturated 8-10 membered bicyclic heterocyclene ring with 1-4 heteroatoms independently selected from nitrogen, oxygen, or sulfur.

In some embodiments, -Cy- is a bivalent 6-membered arylene ring containing 0-2 nitrogen atoms. In some embodiments, -Cy- is a bivalent 6-membered arylene ring containing 0-2 nitrogen atoms wherein the ring is substituted with 1 or 2 substituents independently selected from $C_{1-4}$ alkyl or —OR, wherein R is hydrogen or $C_{1-4}$ alkyl. In some embodiments, -Cy- is a bivalent 5-membered heteroarylene ring with 1-4 heteroatoms independently selected from nitrogen, oxygen, or sulfur. In some embodiments, -Cy- is a bivalent partially unsaturated 8-10 membered bicyclic heterocyclene ring with 1-4 heteroatoms independently selected from nitrogen, oxygen, or sulfur.

In some embodiments, -Cy- is

In some embodiments, -Cy- is selected from those depicted in Table 1, below.

As defined above and described herein, $R^{10}$ is $C_{1-6}$ aliphatic optionally substituted with 1, 2, or 3 halogens, —C(O)CH$_3$, or —SO$_2$—N(R$^1$)(R$^{11}$). In some embodiments, $R^{10}$ is $C_{1-6}$ aliphatic optionally substituted with 1, 2, or 3 halogens. In some embodiments, $R^{10}$ is methyl. In some embodiments, $R^{10}$ is ethyl. In some embodiments, $R^{10}$ is —CH$_2$CF$_3$. In some embodiments, $R^{10}$ is —C(O)CH$_3$. In some embodiments, $R^{10}$ is —SO$_2$—N(R$^1$)(R$^{11}$).

In some embodiments, $R^{10}$ is selected from those depicted in Table 1, below.

As defined above and described herein, $R^{11}$ is —C(O)CH$_3$, —C(O)NHR$^1$, or pyrazinyl;

In some embodiments, $R^{11}$ is —C(O)CH$_3$. In some embodiments, $R^{11}$ is —C(O)NHR$^1$. In some embodiments $R^{11}$ is pyrazinyl.

In some embodiments, $R^{11}$ is selected from those depicted in Table 1, below.

As defined above and described herein, X is O, S, or —N(R$^{10}$)—.

In some embodiments, X is O. Is some embodiments, X is S. In some embodiments X is —N(R$^{10}$)—.

In some embodiments, X is selected from those depicted in Table 1, below.

As defined above and described herein, each of $Y^1$ and $Y^2$ is independently =N— or =C(R$^4$)—. In some embodiments, $Y^1$ is N and $Y^2$ is =(CH)—. In some embodiments $Y^1$ is =(CH)— and $Y^2$ is N.

In some embodiments, the present invention provides a compound of Formulae II-a, II-b, II-c, II-d, or II-e:

In some embodiments, the present invention provides a compound of Formulae III-a, III-b, III-c, III-d, III-e, III-f, III-g, III-h, or III-i:

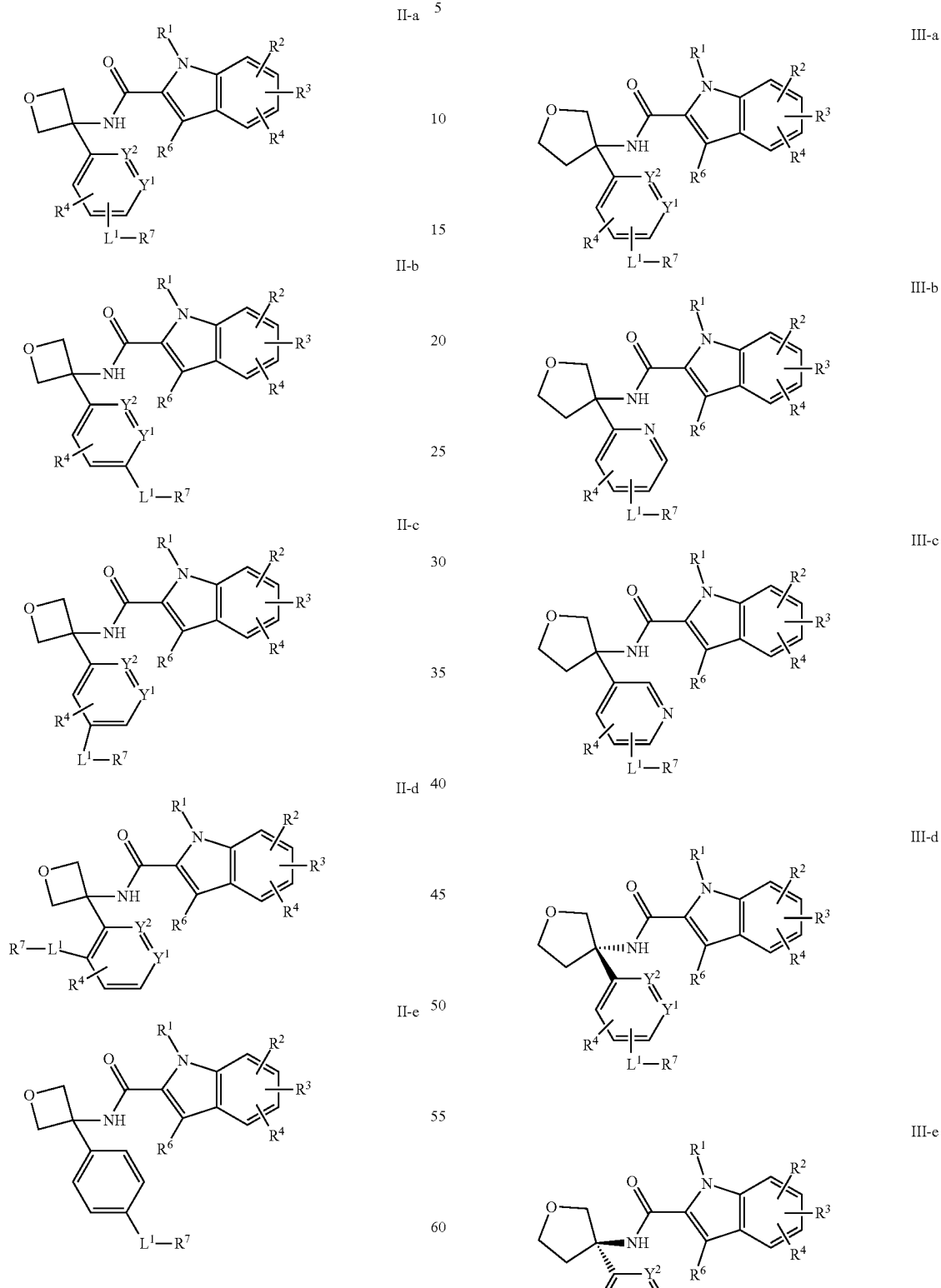

or a pharmaceutically acceptable salt thereof, wherein each of $R^1$, $R^2$, $R^3$, $R^4$, $R^5$, $R^6$, $R^7$, $R'$, $R^9$, $R^{10}$, $R^{11}$, R, R', L, -Cy-, $Y^1$, $Y^2$, and n is defined above and described in embodiments herein.

III-f
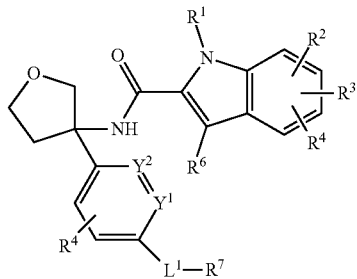
III-g
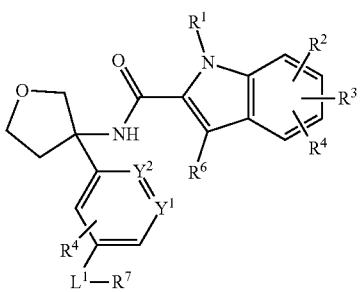
III-h
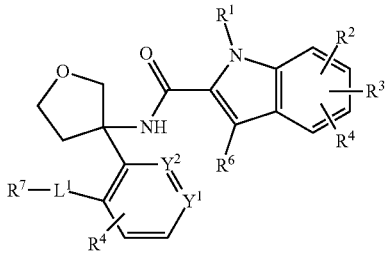
III-i
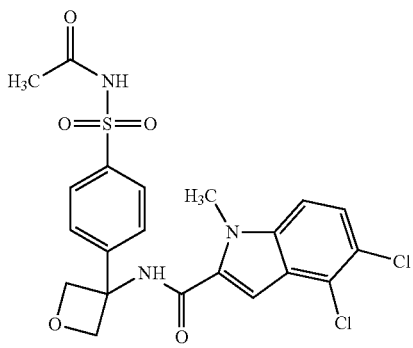 [SMILES: CC(=O)NS(=O)(=O)c1ccc(C2(NC(=O)c3cc4c(Cl)c(Cl)ccc4n3C)COC2)cc1]
or a pharmaceutically acceptable salt thereof, wherein each of $R^1$, $R^2$, $R^3$, $R^4$, $R^5$, $R^6$, $R^7$, $R^8$, $R^9$, $R^{10}$, $R^{11}$, R, R', $L^1$, -Cy-, $Y^1$, $Y^2$, and n is defined above and described in embodiments herein.
Exemplary compounds of the invention are set forth in Table 1, below.
TABLE 1
Exemplary Compounds
I-1
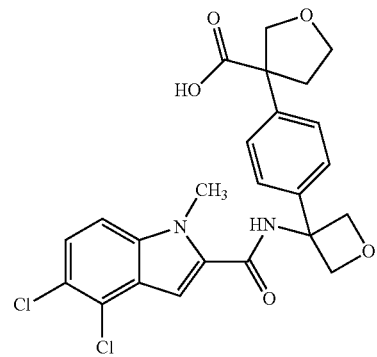 [SMILES: Cn1c(C(=O)NC2(c3ccc(C4(C(=O)O)CCOC4)cc3)COC2)cc2c(Cl)c(Cl)ccc21]
I-2

TABLE 1-continued
Exemplary Compounds
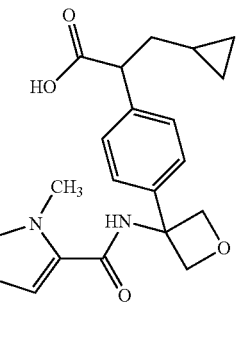
I-3
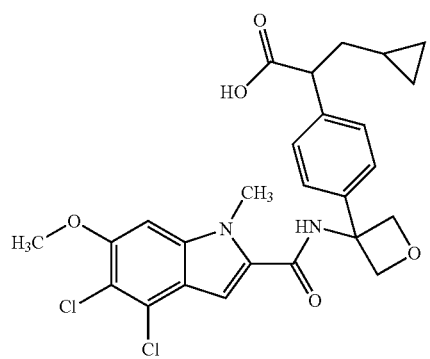 [SMILES: COc1cc2c(cc(C(=O)NC3(c4ccc(C(CC5CC5)C(=O)O)cc4)COC3)n2C)c(Cl)c1Cl]
I-4
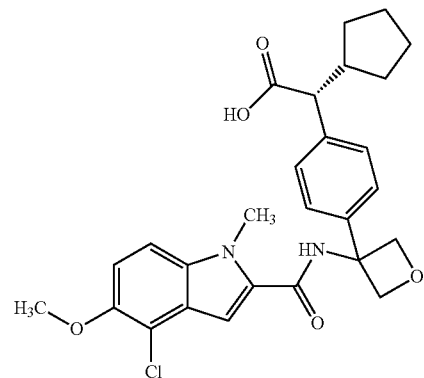 [SMILES: COc1ccc2c(cc(C(=O)NC3(c4ccc([C@H](C(=O)O)C5CCCC5)cc4)COC3)n2C)c1Cl]
I-5
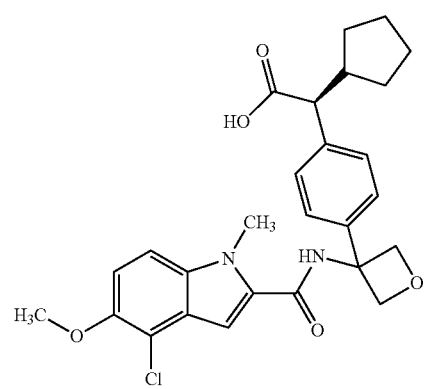 [SMILES: COc1ccc2c(cc(C(=O)NC3(c4ccc([C@@H](C(=O)O)C5CCCC5)cc4)COC3)n2C)c1Cl]
I-6

TABLE 1-continued
Exemplary Compounds
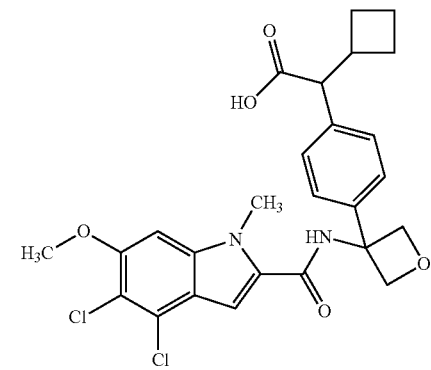 [SMILES: COc1cc2c(cc(C(=O)NC3(c4ccc(C(C(=O)O)C5CCC5)cc4)COC3)n2C)c(Cl)c1Cl]
I-7
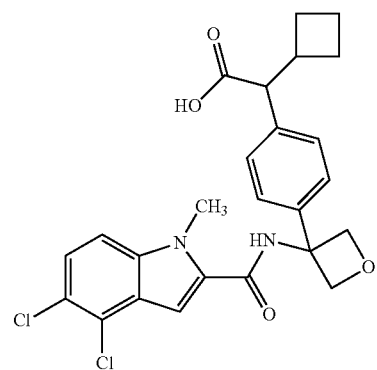 [SMILES: Cn1c(C(=O)NC2(c3ccc(C(C(=O)O)C4CCC4)cc3)COC2)cc2c(Cl)c(Cl)ccc21]
I-8
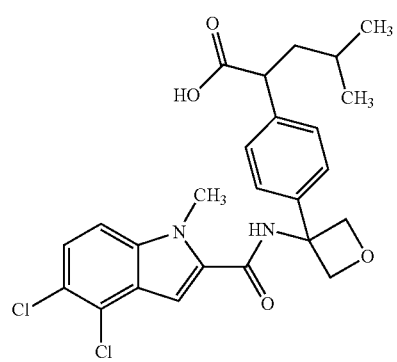 [SMILES: CC(C)CC(C(=O)O)c1ccc(C2(NC(=O)c3cc4c(Cl)c(Cl)ccc4n3C)COC2)cc1]
I-9
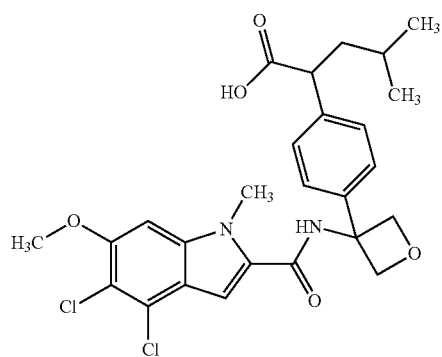 [SMILES: COc1cc2c(cc(C(=O)NC3(c4ccc(C(CC(C)C)C(=O)O)cc4)COC3)n2C)c(Cl)c1Cl]
I-10

TABLE 1-continued
Exemplary Compounds
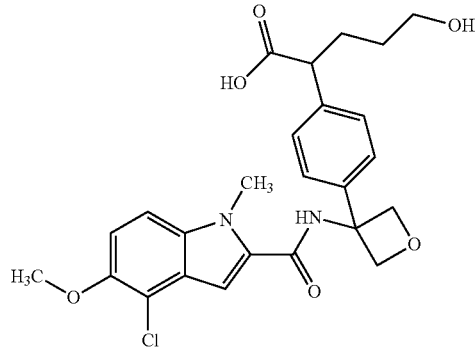 [SMILES: COc1ccc2c(cc(C(=O)NC3(c4ccc(C(CCCO)C(=O)O)cc4)COC3)n2C)c1Cl]
I-11
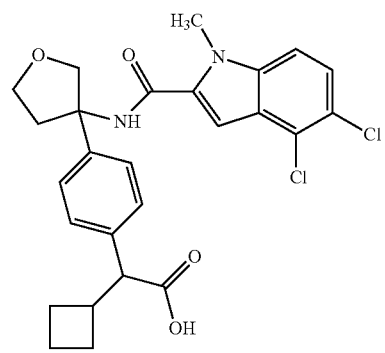 [SMILES: Cn1c(C(=O)NC2(c3ccc(C(C(=O)O)C4CCC4)cc3)CCOC2)cc2c(Cl)c(Cl)ccc21]
I-12
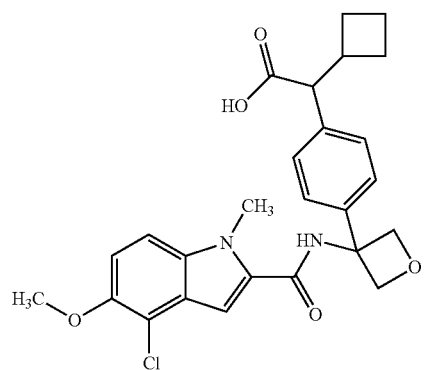 [SMILES: COc1ccc2c(cc(C(=O)NC3(c4ccc(C(C(=O)O)C5CCC5)cc4)COC3)n2C)c1Cl]
I-13
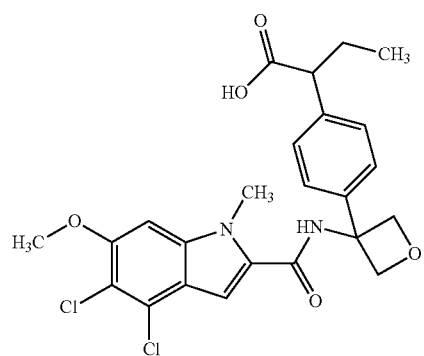 [SMILES: CCC(C(=O)O)c1ccc(C2(NC(=O)c3cc4c(Cl)c(Cl)c(OC)cc4n3C)COC2)cc1]
I-14

TABLE 1-continued
Exemplary Compounds
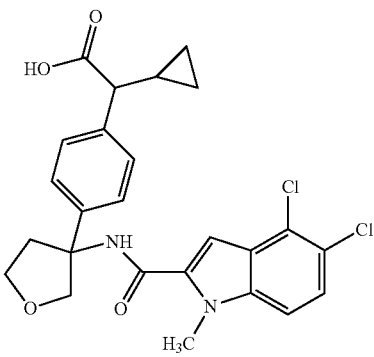 [SMILES: Cn1c(C(=O)NC2(c3ccc(C(C(=O)O)C4CC4)cc3)CCOC2)cc2c(Cl)c(Cl)ccc21]
I-15
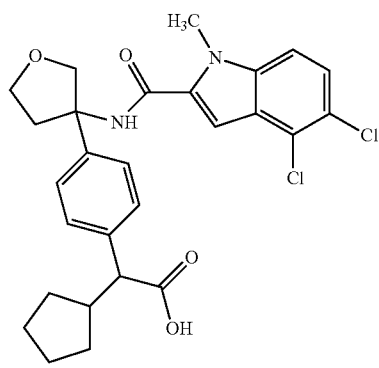 [SMILES: Cn1c(C(=O)NC2(c3ccc(C(C(=O)O)C4CCCC4)cc3)CCOC2)cc2c(Cl)c(Cl)ccc21]
I-16
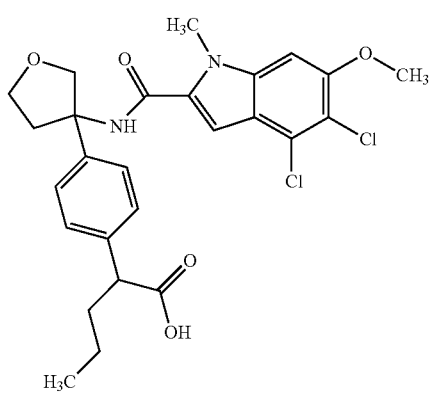 [SMILES: CCCC(C(=O)O)c1ccc(C2(NC(=O)c3cc4c(Cl)c(Cl)c(OC)cc4n3C)CCOC2)cc1]
I-17
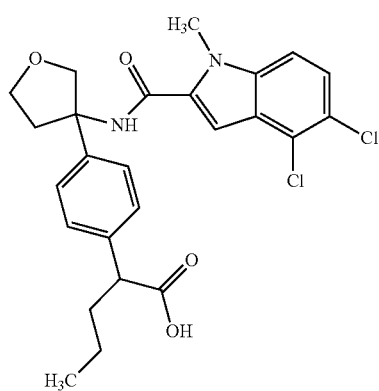 [SMILES: CCCC(C(=O)O)c1ccc(C2(NC(=O)c3cc4c(Cl)c(Cl)ccc4n3C)CCOC2)cc1]
I-18

TABLE 1-continued
Exemplary Compounds
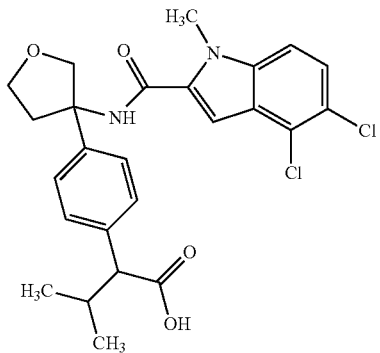 [SMILES: CC(C)C(C(=O)O)c1ccc(C2(NC(=O)c3cc4c(Cl)c(Cl)ccc4n3C)CCOC2)cc1]
I-19
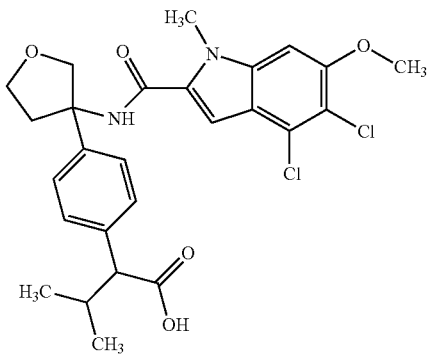 [SMILES: COc1cc2c(cc(C(=O)NC3(c4ccc(C(C(=O)O)C(C)C)cc4)CCOC3)n2C)c(Cl)c1Cl]
I-20
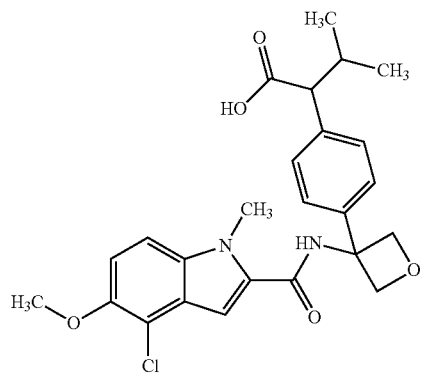 [SMILES: COc1ccc2c(cc(C(=O)NC3(c4ccc(C(C(=O)O)C(C)C)cc4)COC3)n2C)c1Cl]
I-21
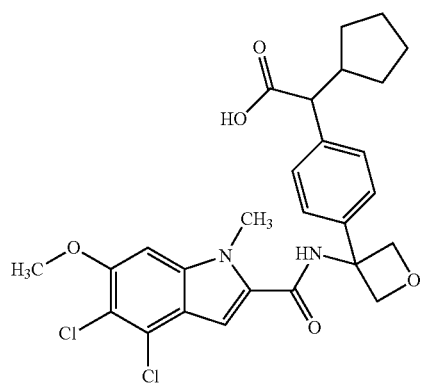 [SMILES: COc1cc2c(cc(C(=O)NC3(c4ccc(C(C(=O)O)C5CCCC5)cc4)COC3)n2C)c(Cl)c1Cl]
I-22

TABLE 1-continued
Exemplary Compounds
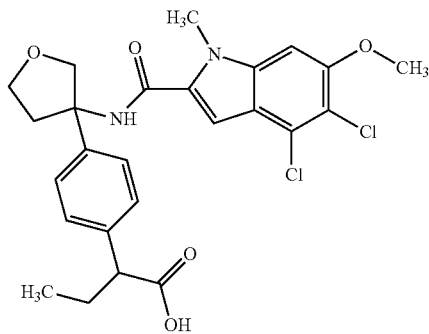 [SMILES: CCC(C(=O)O)c1ccc(C2(NC(=O)c3cc4c(Cl)c(Cl)c(OC)cc4n3C)CCOC2)cc1]
I-23
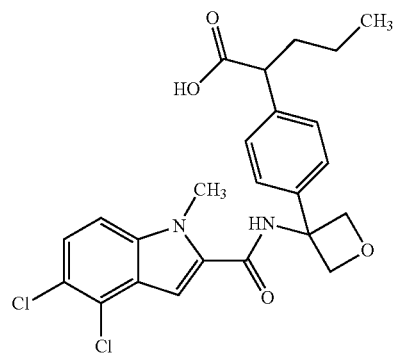 [SMILES: CCCC(C(=O)O)c1ccc(C2(NC(=O)c3cc4c(Cl)c(Cl)ccc4n3C)COC2)cc1]
I-24
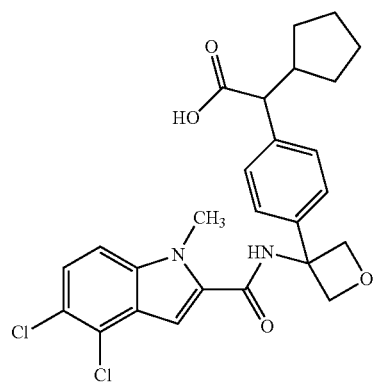 [SMILES: Cn1c(C(=O)NC2(c3ccc(C(C(=O)O)C4CCCC4)cc3)COC2)cc2c(Cl)c(Cl)ccc21]
I-25
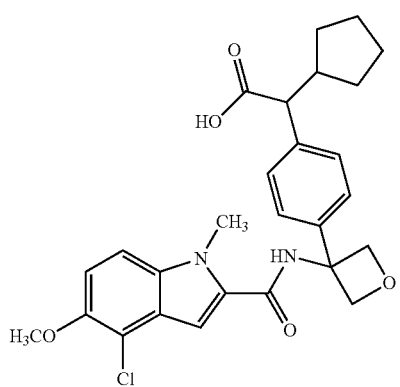 [SMILES: COc1ccc2c(cc(C(=O)NC3(c4ccc(C(C(=O)O)C5CCCC5)cc4)COC3)n2C)c1Cl]
I-26

TABLE 1-continued
Exemplary Compounds
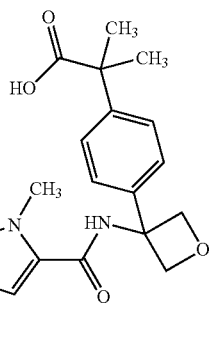
I-27
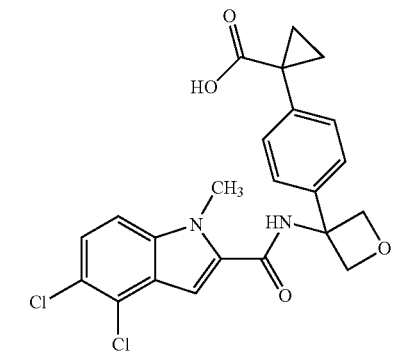 [SMILES: Cn1c(C(=O)NC2(c3ccc(C4(C(=O)O)CC4)cc3)COC2)cc2c(Cl)c(Cl)ccc21]
I-28
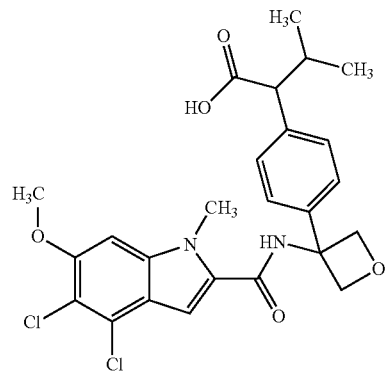 [SMILES: COc1cc2c(cc(C(=O)NC3(c4ccc(C(C(=O)O)C(C)C)cc4)COC3)n2C)c(Cl)c1Cl]
I-29
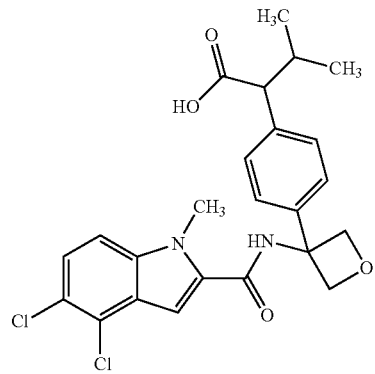 [SMILES: CC(C)C(C(=O)O)c1ccc(C2(NC(=O)c3cc4c(Cl)c(Cl)ccc4n3C)COC2)cc1]
I-30

TABLE 1-continued
Exemplary Compounds
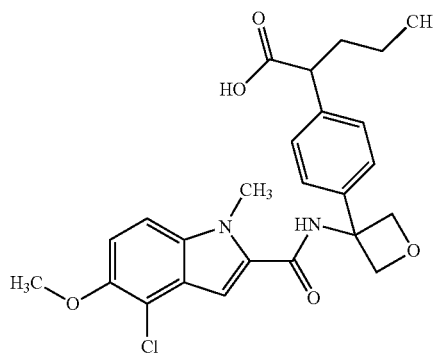
I-31
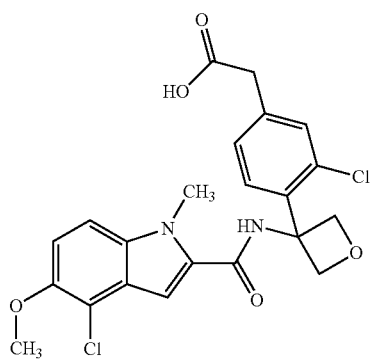 [SMILES: COc1ccc2c(cc(C(=O)NC3(c4ccc(CC(=O)O)cc4Cl)COC3)n2C)c1Cl]
I-32
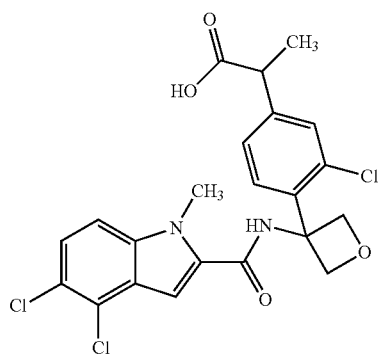 [SMILES: CC(C(=O)O)c1ccc(C2(NC(=O)c3cc4c(Cl)c(Cl)ccc4n3C)COC2)c(Cl)c1]
I-33
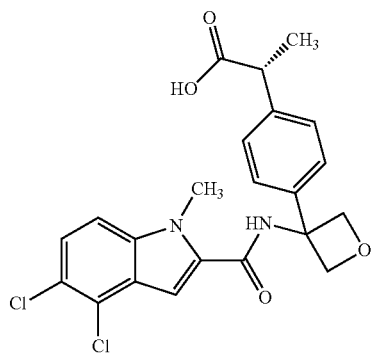 [SMILES: C[C@@H](C(=O)O)c1ccc(C2(NC(=O)c3cc4c(Cl)c(Cl)ccc4n3C)COC2)cc1]
I-34

TABLE 1-continued
Exemplary Compounds
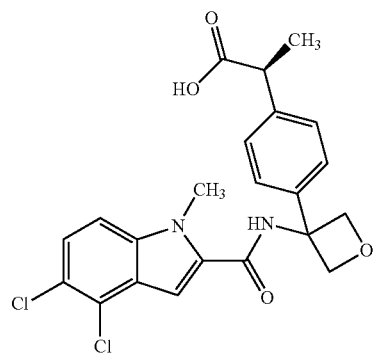 [SMILES: C[C@H](C(=O)O)c1ccc(C2(NC(=O)c3cc4c(Cl)c(Cl)ccc4n3C)COC2)cc1]
I-35
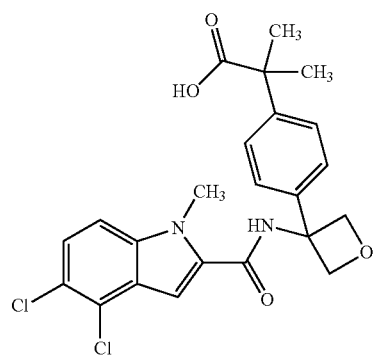 [SMILES: Cn1c(C(=O)NC2(c3ccc(C(C)(C)C(=O)O)cc3)COC2)cc2c(Cl)c(Cl)ccc21]
I-36
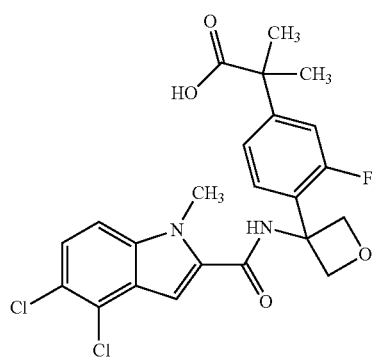 [SMILES: Cn1c(C(=O)NC2(c3ccc(C(C)(C)C(=O)O)cc3F)COC2)cc2c(Cl)c(Cl)ccc21]
I-37
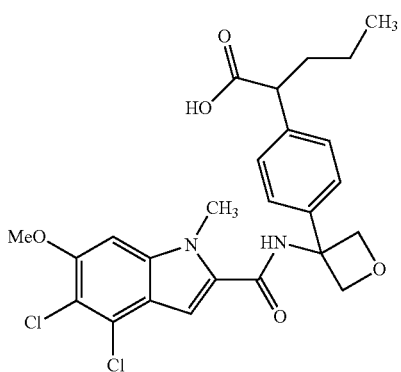 [SMILES: CCCC(C(=O)O)c1ccc(C2(NC(=O)c3cc4c(Cl)c(Cl)c(OC)cc4n3C)COC2)cc1]
I-38

TABLE 1-continued

Exemplary Compounds

I-39, I-40, I-41, I-42

TABLE 1-continued
Exemplary Compounds
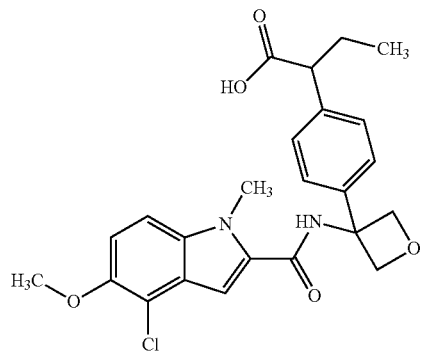 [SMILES: CCC(C(=O)O)c1ccc(C2(NC(=O)c3cc4c(Cl)c(OC)ccc4n3C)COC2)cc1]
I-43
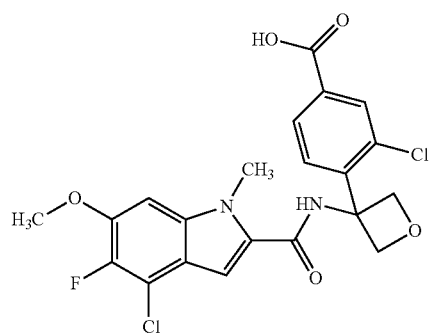 [SMILES: COc1cc2c(cc(C(=O)NC3(c4ccc(C(=O)O)cc4Cl)COC3)n2C)c(Cl)c1F]
I-44
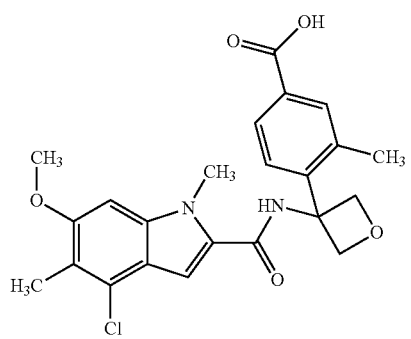
I-45
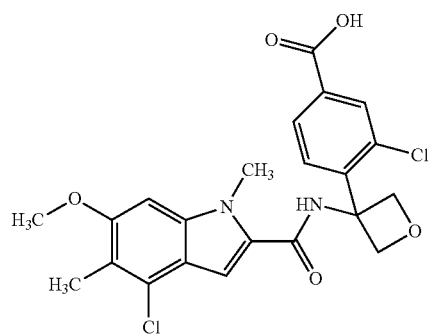 [SMILES: COc1cc2c(cc(C(=O)NC3(c4ccc(C(=O)O)cc4Cl)COC3)n2C)c(Cl)c1C]
I-46

TABLE 1-continued
Exemplary Compounds
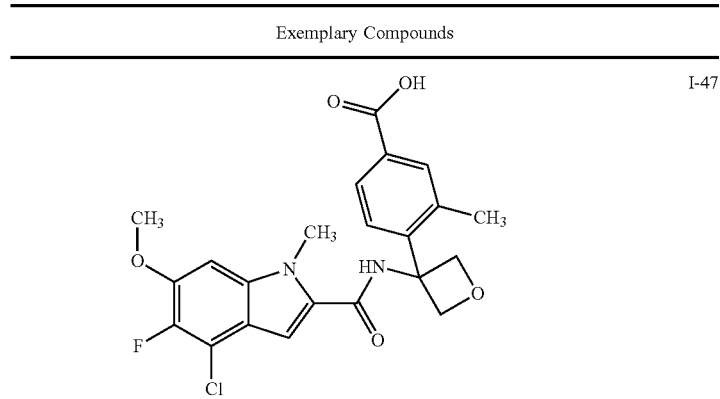
I-47
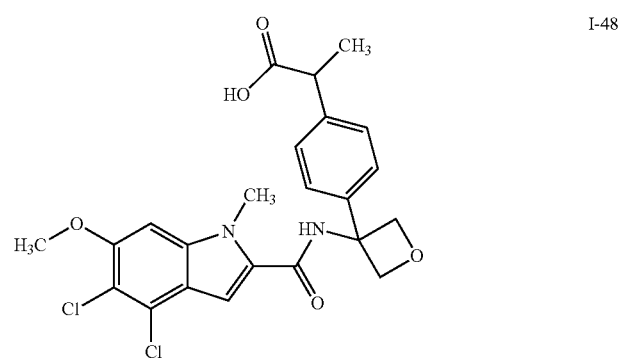
I-48
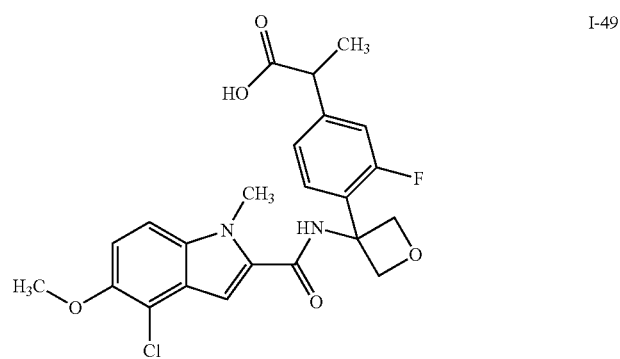
I-49
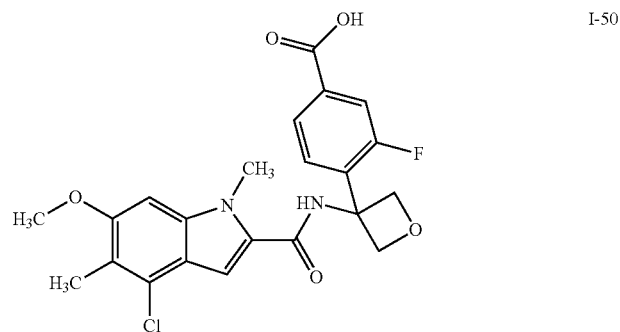
I-50

TABLE 1-continued
Exemplary Compounds
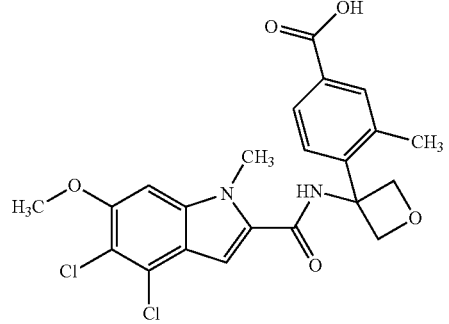
I-51
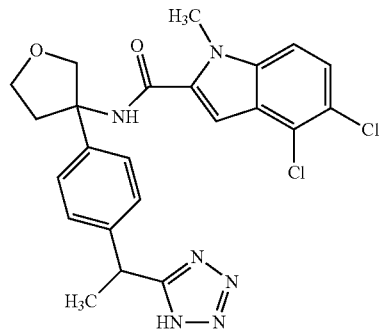 [SMILES: CC(c1ccc(C2(NC(=O)c3cc4c(Cl)c(Cl)ccc4n3C)CCOC2)cc1)c1nnn[nH]1]
I-52
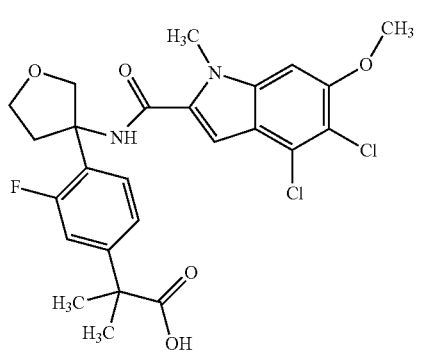 [SMILES: COc1cc2c(cc(C(=O)NC3(c4ccc(C(C)(C)C(=O)O)cc4F)CCOC3)n2C)c(Cl)c1Cl]
I-53
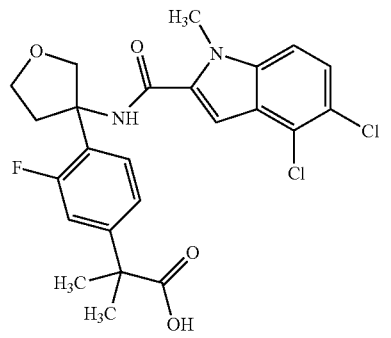 [SMILES: Cn1c(C(=O)NC2(c3ccc(C(C)(C)C(=O)O)cc3F)CCOC2)cc2c(Cl)c(Cl)ccc21]
I-54

TABLE 1-continued
Exemplary Compounds
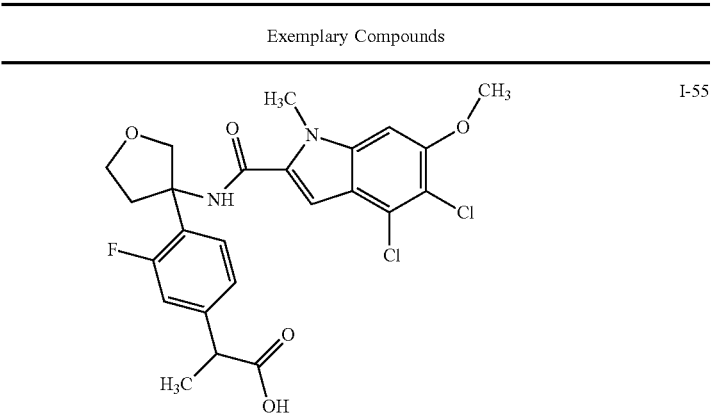
I-55
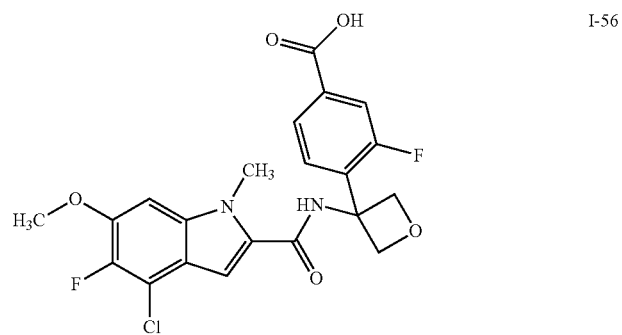
I-56
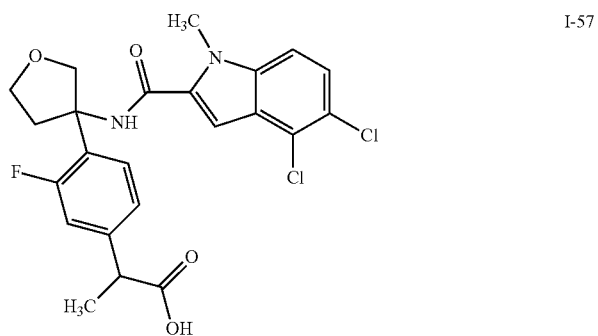
I-57
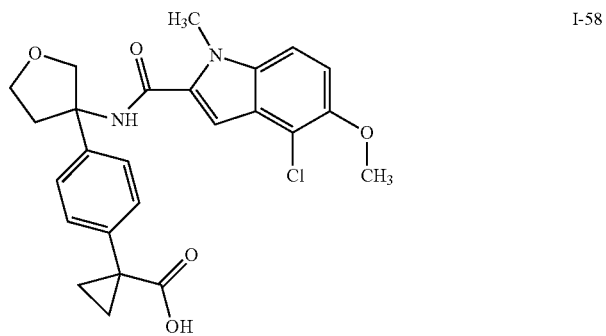
I-58

TABLE 1-continued
Exemplary Compounds
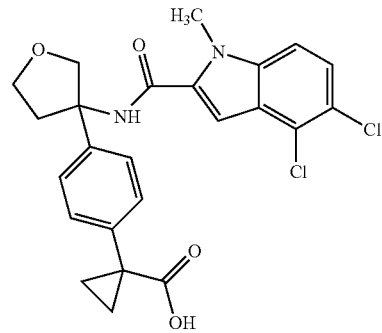 [SMILES: Cn1c(C(=O)NC2(c3ccc(C4(C(=O)O)CC4)cc3)CCOC2)cc2c(Cl)c(Cl)ccc21]
I-59
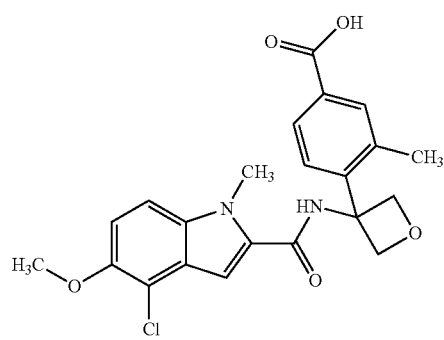
I-60
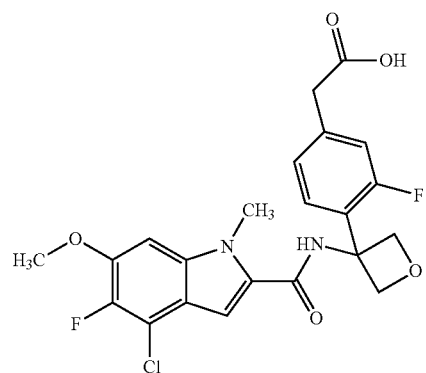 [SMILES: COc1cc2c(cc(C(=O)NC3(c4ccc(CC(=O)O)cc4F)COC3)n2C)c(Cl)c1F]
I-61
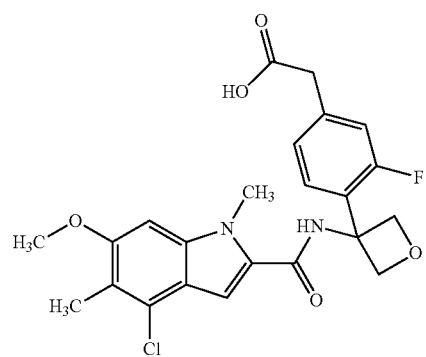 [SMILES: COc1cc2c(cc(C(=O)NC3(c4ccc(CC(=O)O)cc4F)COC3)n2C)c(Cl)c1C]
I-62

TABLE 1-continued
Exemplary Compounds
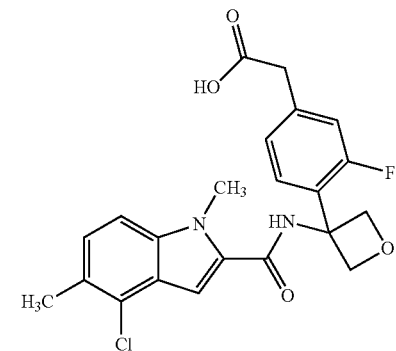 [SMILES: Cc1ccc2c(cc(C(=O)NC3(c4ccc(CC(=O)O)cc4F)COC3)n2C)c1Cl]
I-63
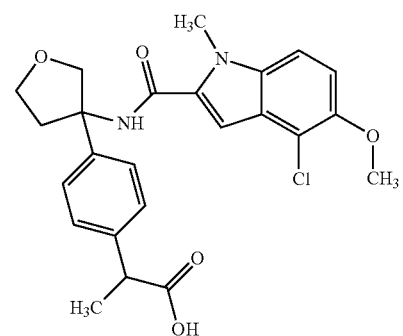 [SMILES: COc1ccc2c(cc(C(=O)NC3(c4ccc(C(C)C(=O)O)cc4)CCOC3)n2C)c1Cl]
I-64
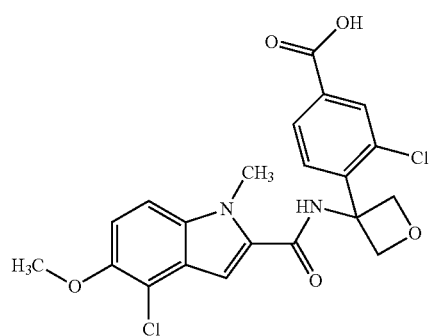 [SMILES: COc1ccc2c(cc(C(=O)NC3(c4ccc(C(=O)O)cc4Cl)COC3)n2C)c1Cl]
I-65
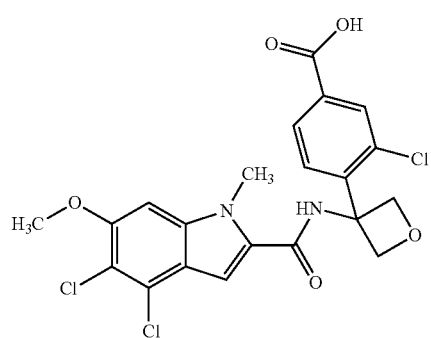 [SMILES: COc1cc2c(cc(C(=O)NC3(c4ccc(C(=O)O)cc4Cl)COC3)n2C)c(Cl)c1Cl]
I-66

TABLE 1-continued
Exemplary Compounds
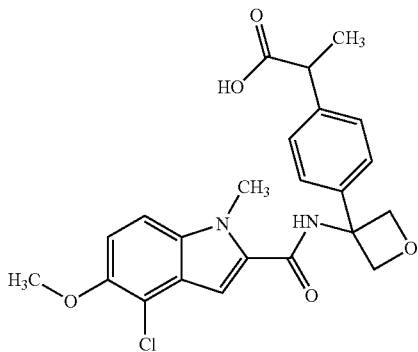 [SMILES: COc1ccc2c(cc(C(=O)NC3(c4ccc(C(C)C(=O)O)cc4)COC3)n2C)c1Cl]
I-67
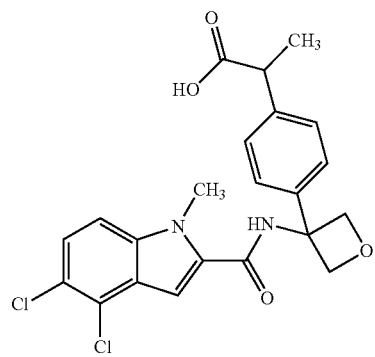 [SMILES: CC(C(=O)O)c1ccc(C2(NC(=O)c3cc4c(Cl)c(Cl)ccc4n3C)COC2)cc1]
I-68
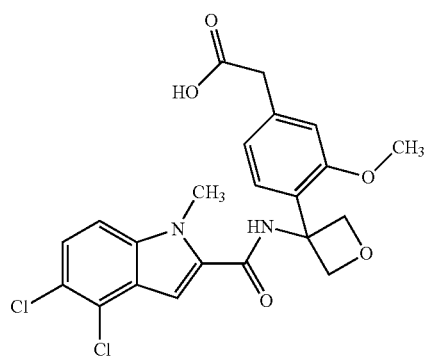 [SMILES: COc1cc(CC(=O)O)ccc1C1(NC(=O)c2cc3c(Cl)c(Cl)ccc3n2C)COC1]
I-69
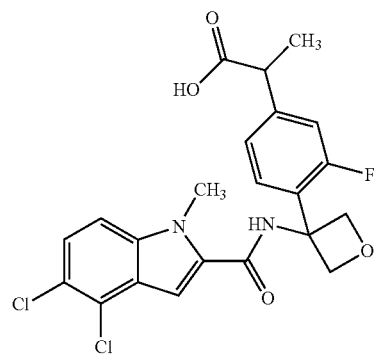 [SMILES: CC(C(=O)O)c1ccc(C2(NC(=O)c3cc4c(Cl)c(Cl)ccc4n3C)COC2)c(F)c1]
I-70

TABLE 1-continued
Exemplary Compounds
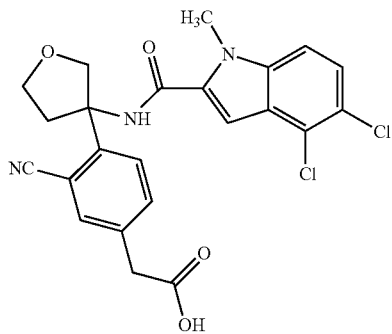 [SMILES: Cn1c(C(=O)NC2(c3ccc(CC(=O)O)cc3C#N)CCOC2)cc2c(Cl)c(Cl)ccc21]
I-71
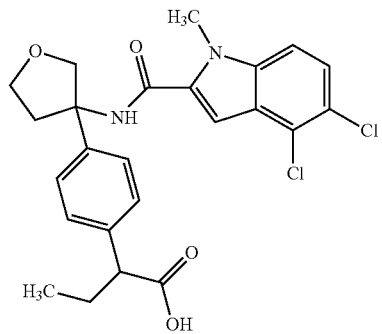 [SMILES: CCC(C(=O)O)c1ccc(C2(NC(=O)c3cc4c(Cl)c(Cl)ccc4n3C)CCOC2)cc1]
I-72
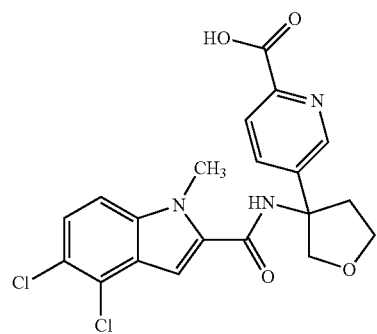 [SMILES: Cn1c(C(=O)NC2(c3ccc(C(=O)O)nc3)CCOC2)cc2c(Cl)c(Cl)ccc21]
I-73
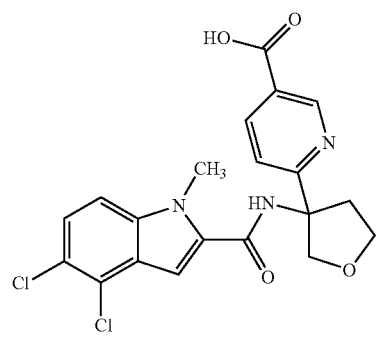 [SMILES: Cn1c(C(=O)NC2(c3ccc(C(=O)O)cn3)CCOC2)cc2c(Cl)c(Cl)ccc21]
I-74

TABLE 1-continued
Exemplary Compounds
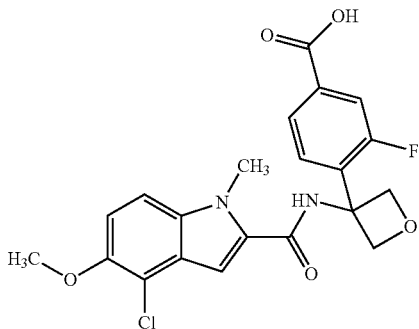 [SMILES: COc1ccc2c(cc(C(=O)NC3(c4ccc(C(=O)O)cc4F)COC3)n2C)c1Cl]
I-75
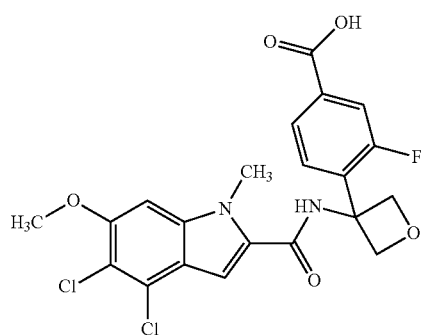 [SMILES: COc1cc2c(cc(C(=O)NC3(c4ccc(C(=O)O)cc4F)COC3)n2C)c(Cl)c1Cl]
I-76
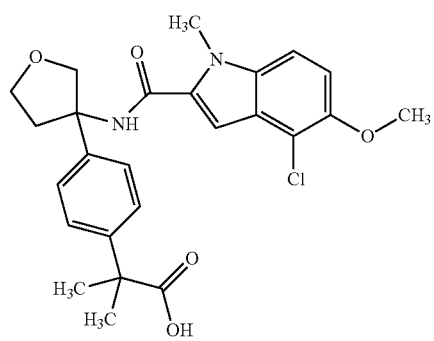 [SMILES: COc1ccc2c(cc(C(=O)NC3(c4ccc(C(C)(C)C(=O)O)cc4)CCOC3)n2C)c1Cl]
I-77
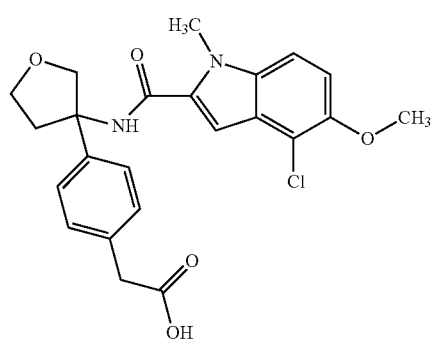 [SMILES: COc1ccc2c(cc(C(=O)NC3(c4ccc(CC(=O)O)cc4)CCOC3)n2C)c1Cl]
I-78

TABLE 1-continued
Exemplary Compounds
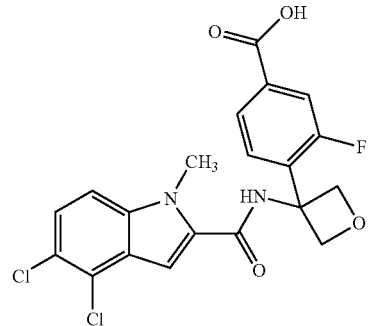 [SMILES: Cn1c(C(=O)NC2(c3ccc(C(=O)O)cc3F)COC2)cc2c(Cl)c(Cl)ccc21]
I-79
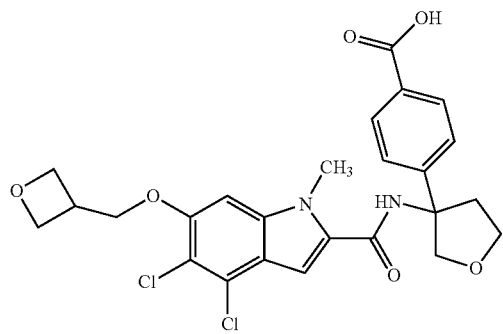 [SMILES: Cn1c(C(=O)NC2(c3ccc(C(=O)O)cc3)CCOC2)cc2c(Cl)c(Cl)c(OCC3COC3)cc21]
I-80
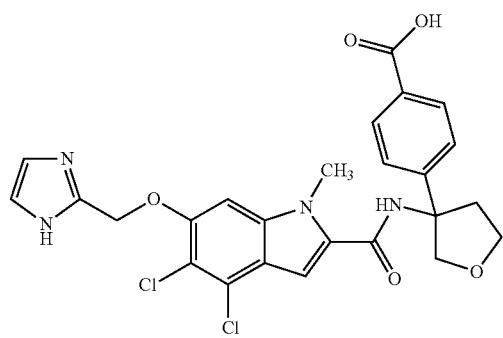 [SMILES: Cn1c(C(=O)NC2(c3ccc(C(=O)O)cc3)CCOC2)cc2c(Cl)c(Cl)c(OCc3ncc[nH]3)cc21]
I-81
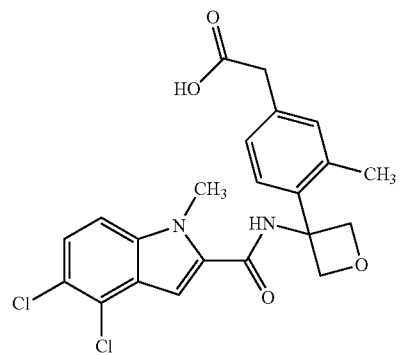 [SMILES: Cc1cc(CC(=O)O)ccc1C1(NC(=O)c2cc3c(Cl)c(Cl)ccc3n2C)COC1]
I-82

TABLE 1-continued
Exemplary Compounds
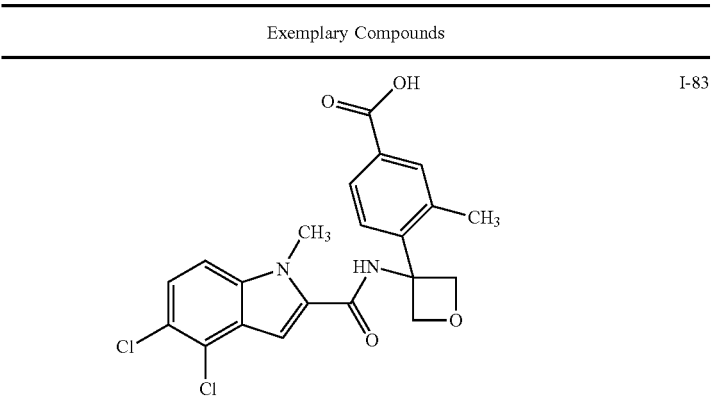
I-83
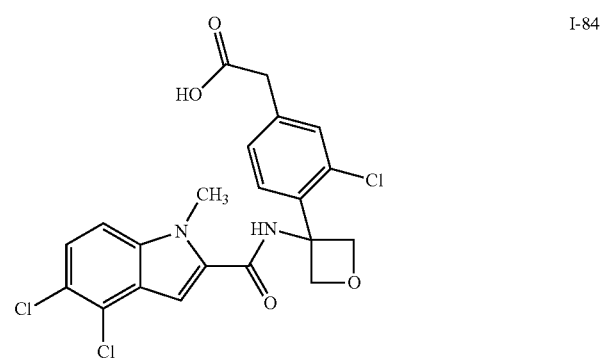
I-84
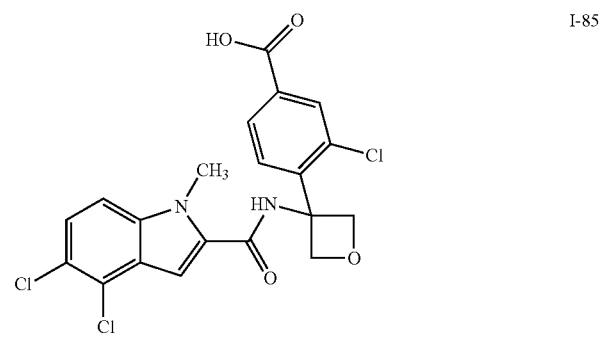
I-85
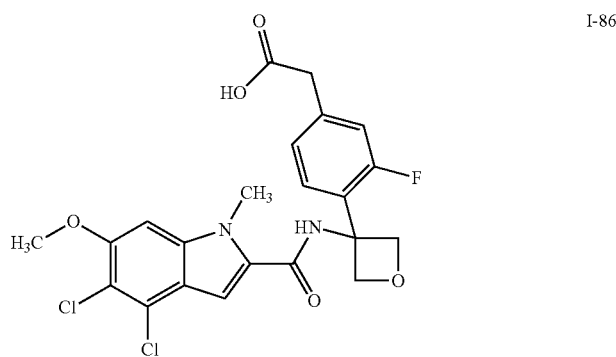
I-86

TABLE 1-continued
Exemplary Compounds
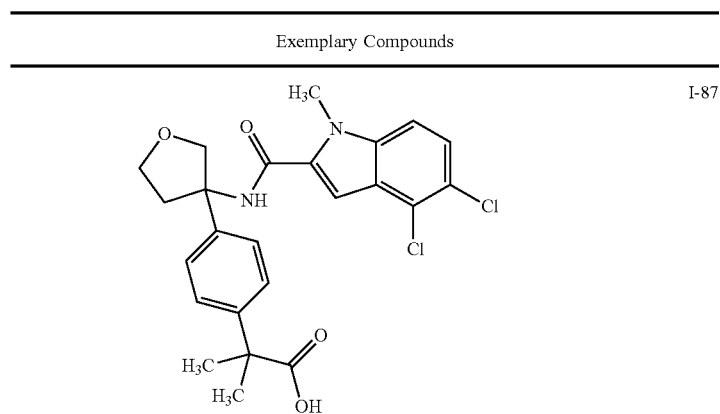
I-87
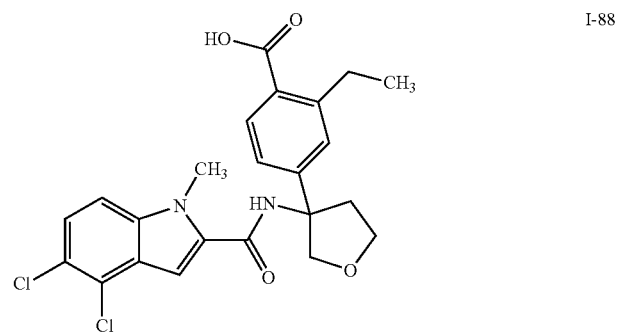
I-88
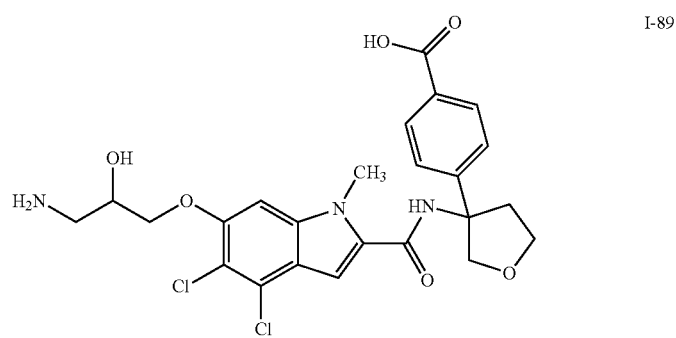
I-89
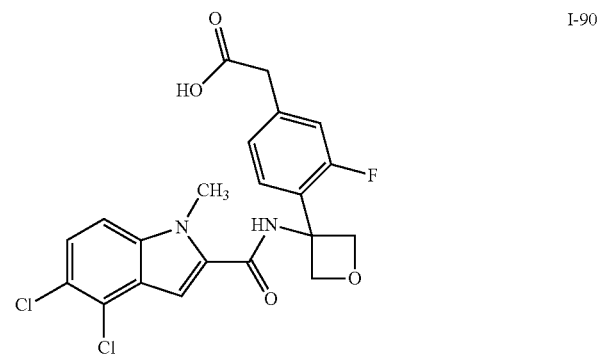
I-90

TABLE 1-continued
Exemplary Compounds
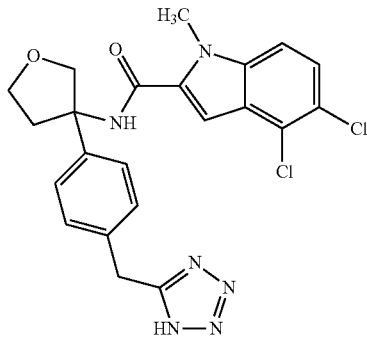 [SMILES: Cn1c(C(=O)NC2(c3ccc(Cc4nnn[nH]4)cc3)CCOC2)cc2c(Cl)c(Cl)ccc21]
I-91
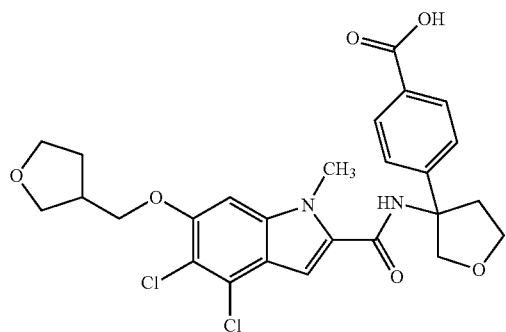 [SMILES: Cn1c(C(=O)NC2(c3ccc(C(=O)O)cc3)CCOC2)cc2c(Cl)c(Cl)c(OCC3CCOC3)cc21]
I-92
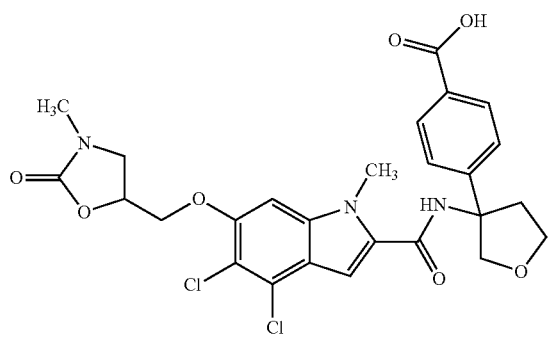 [SMILES: CN1CC(COc2cc3c(cc(C(=O)NC4(c5ccc(C(=O)O)cc5)CCOC4)n3C)c(Cl)c2Cl)OC1=O]
I-93
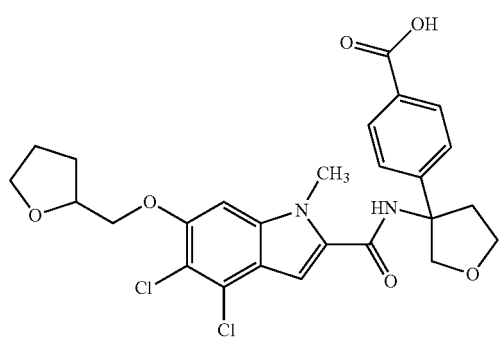 [SMILES: Cn1c(C(=O)NC2(c3ccc(C(=O)O)cc3)CCOC2)cc2c(Cl)c(Cl)c(OCC3CCCO3)cc21]
I-94

TABLE 1-continued
Exemplary Compounds
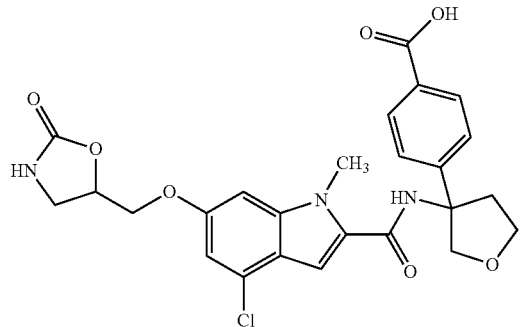 [SMILES: Cn1c(C(=O)NC2(c3ccc(C(=O)O)cc3)CCOC2)cc2c(Cl)cc(OCC3CNC(=O)O3)cc21]
I-95
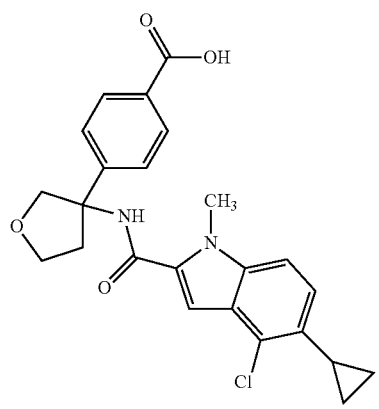 [SMILES: Cn1c(C(=O)NC2(c3ccc(C(=O)O)cc3)CCOC2)cc2c(Cl)c(C3CC3)ccc21]
I-96
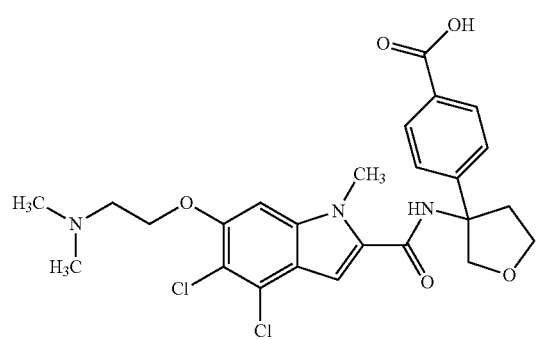 [SMILES: CN(C)CCOc1cc2c(cc(C(=O)NC3(c4ccc(C(=O)O)cc4)CCOC3)n2C)c(Cl)c1Cl]
I-97
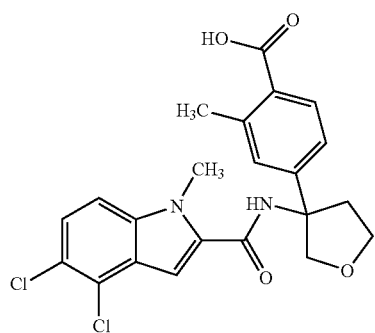 [SMILES: Cc1cc(C2(NC(=O)c3cc4c(Cl)c(Cl)ccc4n3C)CCOC2)ccc1C(=O)O]
I-98

TABLE 1-continued
Exemplary Compounds
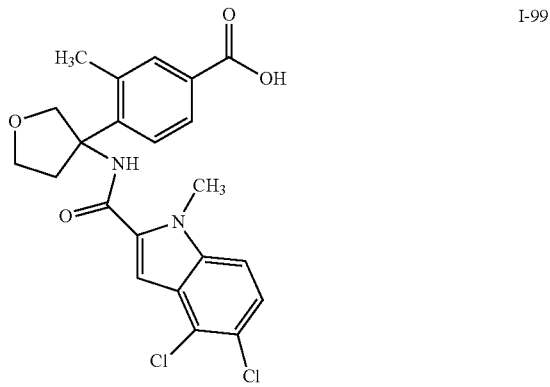
I-99
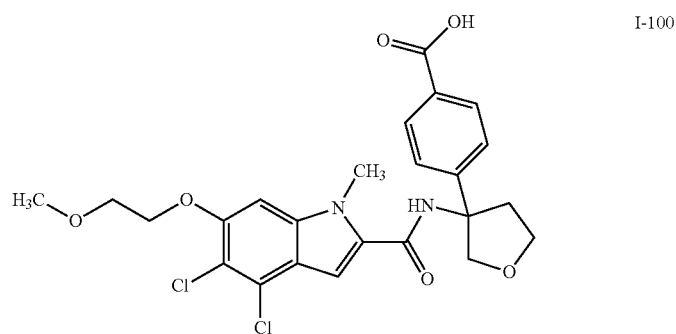
I-100
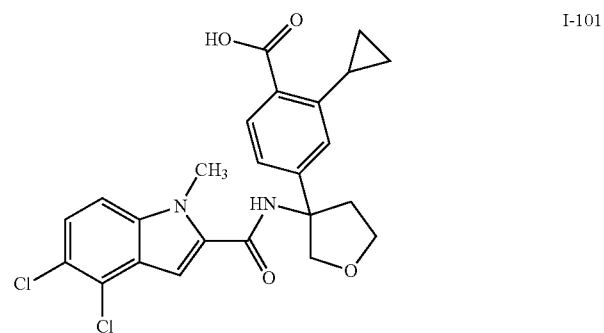
I-101
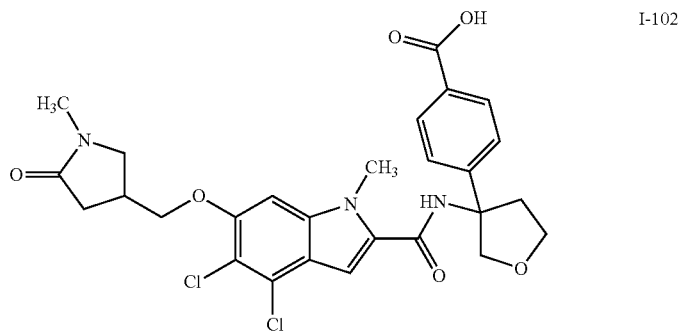
I-102

TABLE 1-continued
Exemplary Compounds
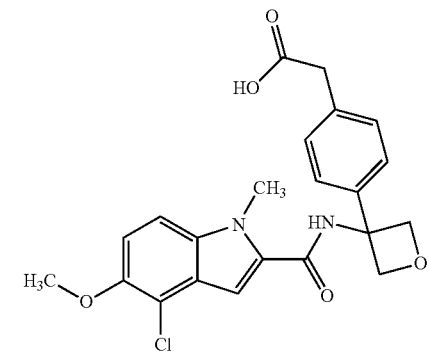 [SMILES: COc1ccc2c(cc(C(=O)NC3(c4ccc(CC(=O)O)cc4)COC3)n2C)c1Cl]
I-103
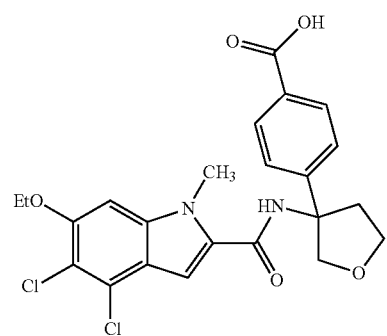 [SMILES: CCOc1cc2c(cc(C(=O)NC3(c4ccc(C(=O)O)cc4)CCOC3)n2C)c(Cl)c1Cl]
I-104
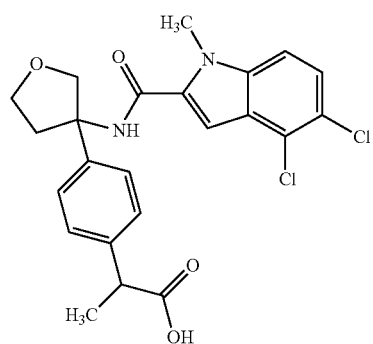 [SMILES: CC(C(=O)O)c1ccc(C2(NC(=O)c3cc4c(Cl)c(Cl)ccc4n3C)CCOC2)cc1]
I-105
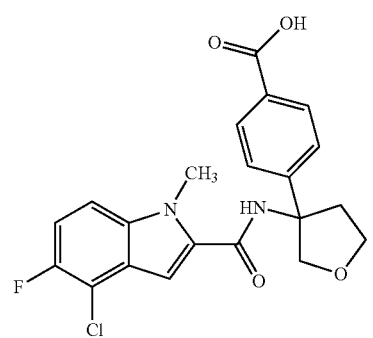 [SMILES: Cn1c(C(=O)NC2(c3ccc(C(=O)O)cc3)CCOC2)cc2c(Cl)c(F)ccc21]
I-106

TABLE 1-continued
Exemplary Compounds
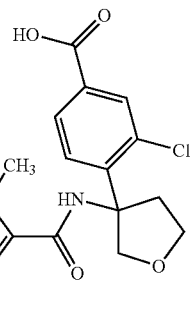
I-107
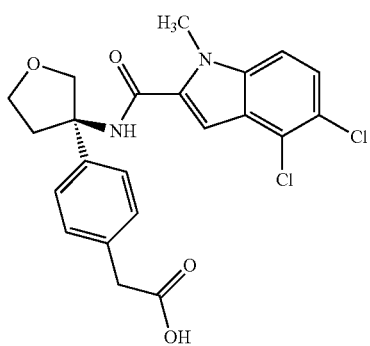 [SMILES: Cn1c(C(=O)N[C@@]2(c3ccc(CC(=O)O)cc3)CCOC2)cc2c(Cl)c(Cl)ccc21]
I-108
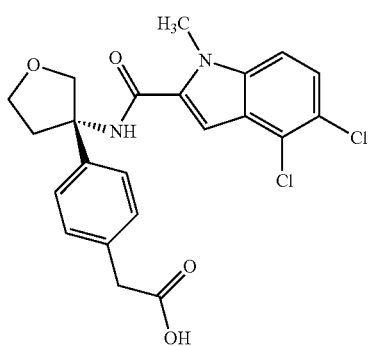 [SMILES: Cn1c(C(=O)N[C@]2(c3ccc(CC(=O)O)cc3)CCOC2)cc2c(Cl)c(Cl)ccc21]
I-109
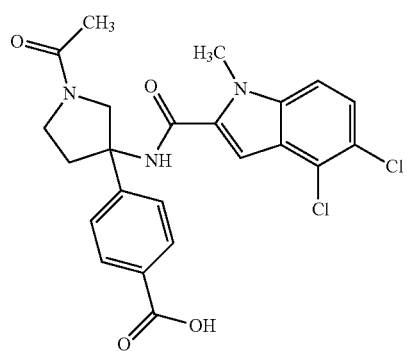 [SMILES: CC(=O)N1CCC(NC(=O)c2cc3c(Cl)c(Cl)ccc3n2C)(c2ccc(C(=O)O)cc2)C1]
I-110

TABLE 1-continued
Exemplary Compounds
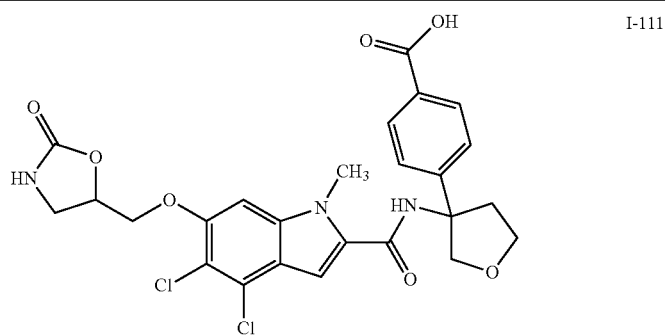
I-111
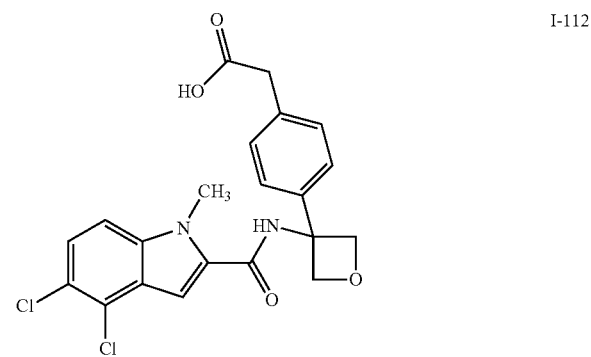
I-112
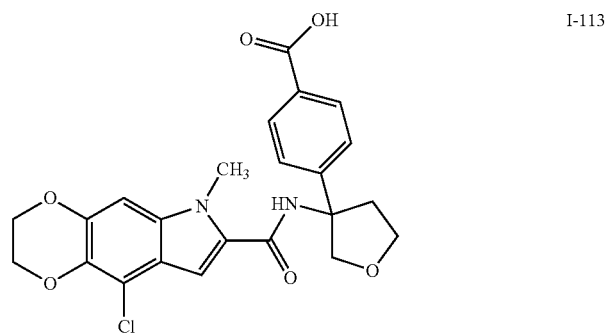
I-113
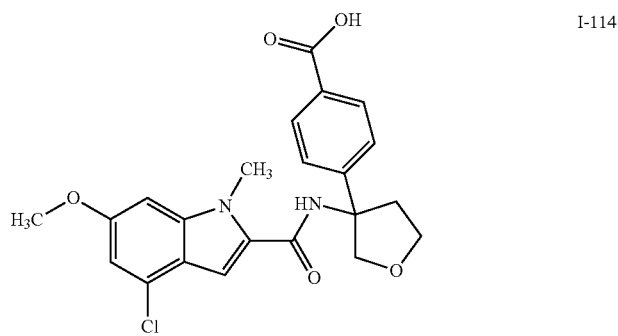
I-114

TABLE 1-continued
Exemplary Compounds
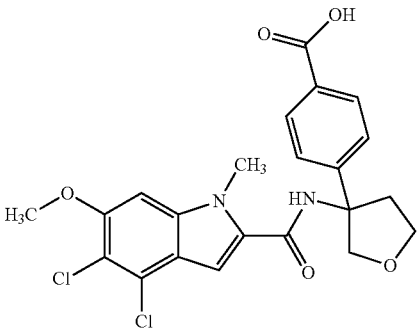 [SMILES: COc1cc2c(cc(C(=O)NC3(c4ccc(C(=O)O)cc4)CCOC3)n2C)c(Cl)c1Cl]
I-115
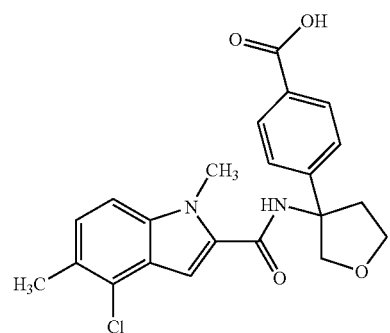 [SMILES: Cc1ccc2c(cc(C(=O)NC3(c4ccc(C(=O)O)cc4)CCOC3)n2C)c1Cl]
I-116
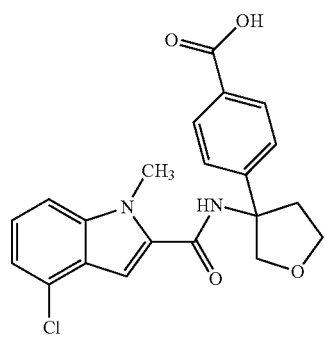 [SMILES: Cn1c(C(=O)NC2(c3ccc(C(=O)O)cc3)CCOC2)cc2c(Cl)cccc21]
I-117
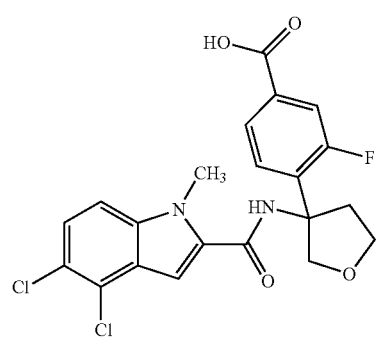 [SMILES: Cn1c(C(=O)NC2(c3ccc(C(=O)O)cc3F)CCOC2)cc2c(Cl)c(Cl)ccc21]
I-118

TABLE 1-continued
Exemplary Compounds
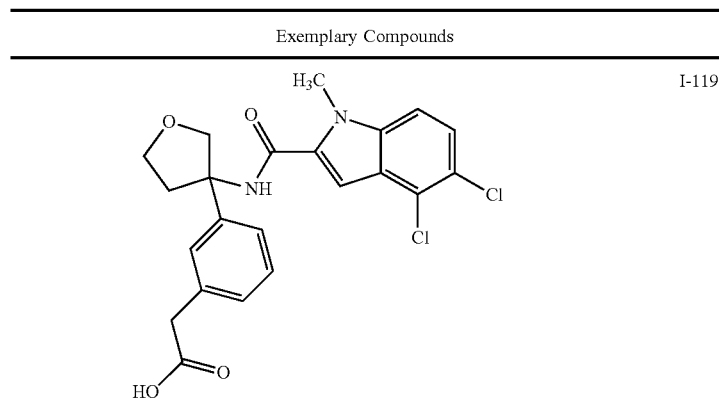
I-119
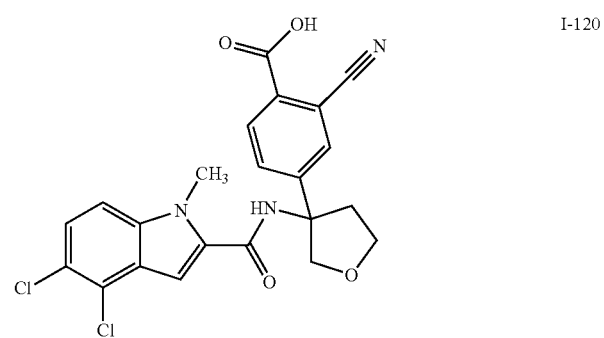
I-120
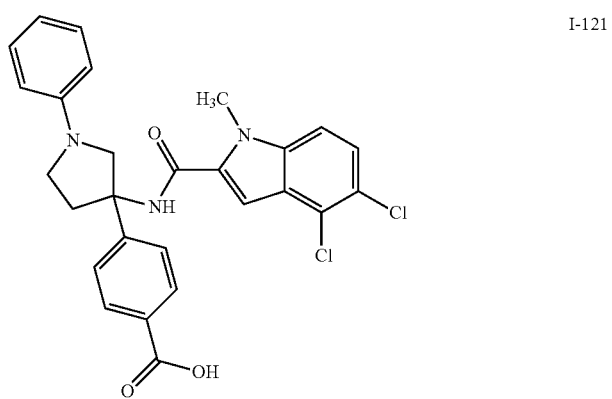
I-121
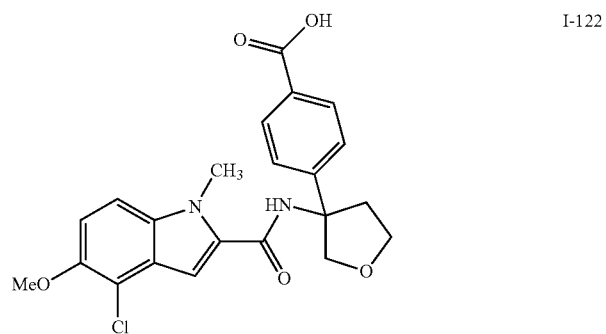
I-122

TABLE 1-continued
Exemplary Compounds
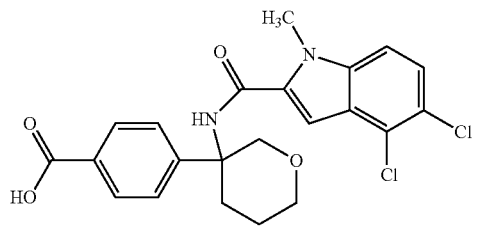 [SMILES: Cn1c(C(=O)NC2(c3ccc(C(=O)O)cc3)CCCOC2)cc2c(Cl)c(Cl)ccc21]
I-123
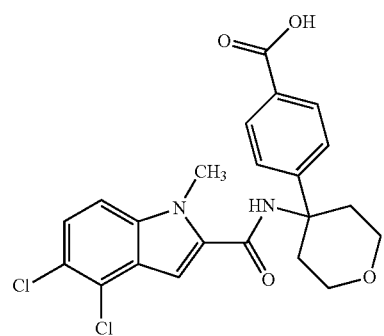 [SMILES: Cn1c(C(=O)NC2(c3ccc(C(=O)O)cc3)CCOCC2)cc2c(Cl)c(Cl)ccc21]
I-124
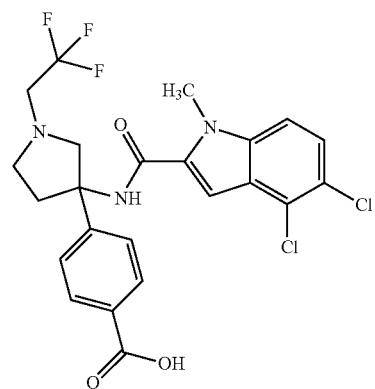 [SMILES: Cn1c(C(=O)NC2(c3ccc(C(=O)O)cc3)CCN(CC(F)(F)F)C2)cc2c(Cl)c(Cl)ccc21]
I-125
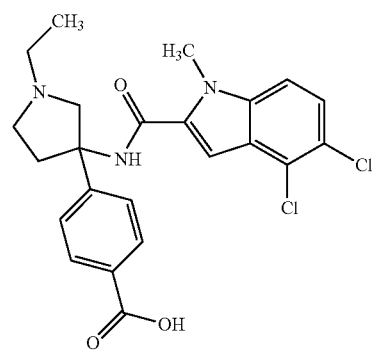 [SMILES: CCN1CCC(NC(=O)c2cc3c(Cl)c(Cl)ccc3n2C)(c2ccc(C(=O)O)cc2)C1]
I-126

TABLE 1-continued
Exemplary Compounds
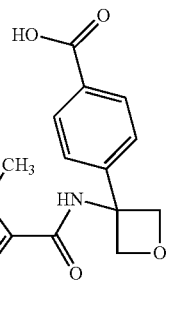
I-127
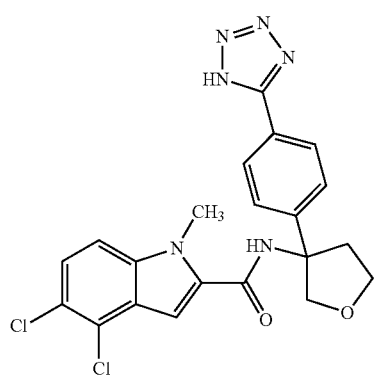 [SMILES: Cn1c(C(=O)NC2(c3ccc(-c4nnn[nH]4)cc3)CCOC2)cc2c(Cl)c(Cl)ccc21]
I-128
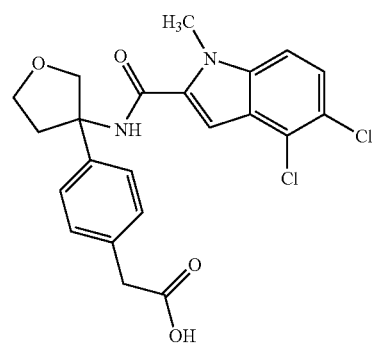 [SMILES: Cn1c(C(=O)NC2(c3ccc(CC(=O)O)cc3)CCOC2)cc2c(Cl)c(Cl)ccc21]
I-129
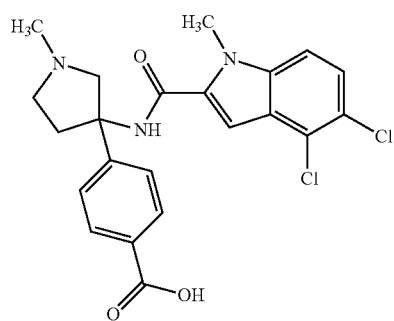 [SMILES: CN1CCC(NC(=O)c2cc3c(Cl)c(Cl)ccc3n2C)(c2ccc(C(=O)O)cc2)C1]
I-130

TABLE 1-continued

Exemplary Compounds

I-131

I-132

I-133

I-134

I-135

TABLE 1-continued
Exemplary Compounds
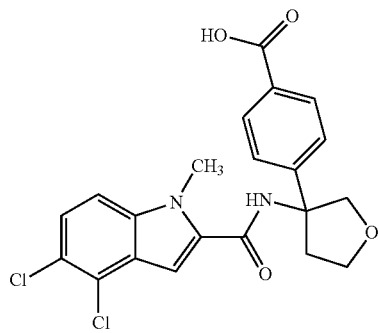 [SMILES: Cn1c(C(=O)NC2(c3ccc(C(=O)O)cc3)CCOC2)cc2c(Cl)c(Cl)ccc21]
I-136
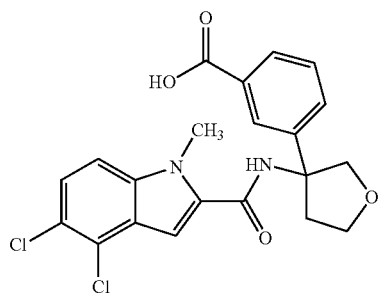 [SMILES: Cn1c(C(=O)NC2(c3cccc(C(=O)O)c3)CCOC2)cc2c(Cl)c(Cl)ccc21]
I-137
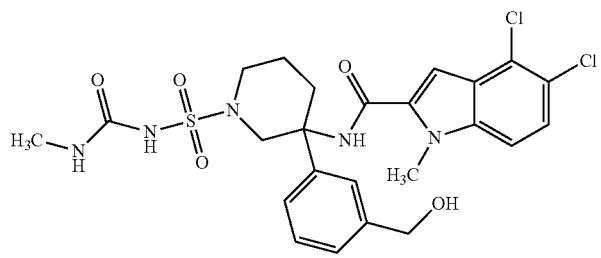 [SMILES: CNC(=O)NS(=O)(=O)N1CCCC(NC(=O)c2cc3c(Cl)c(Cl)ccc3n2C)(c2cccc(CO)c2)C1]
I-138
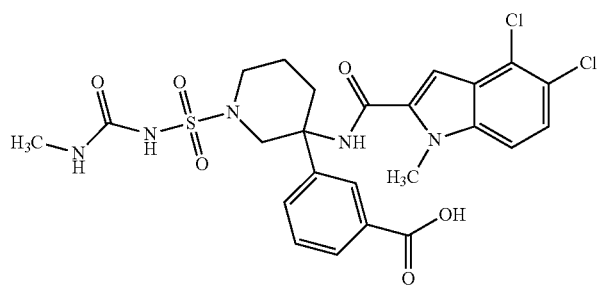 [SMILES: CNC(=O)NS(=O)(=O)N1CCCC(NC(=O)c2cc3c(Cl)c(Cl)ccc3n2C)(c2cccc(C(=O)O)c2)C1]
I-139

TABLE 1-continued
Exemplary Compounds
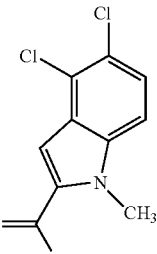
I-140
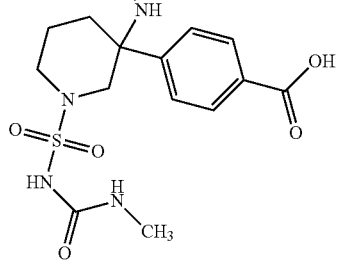
I-141
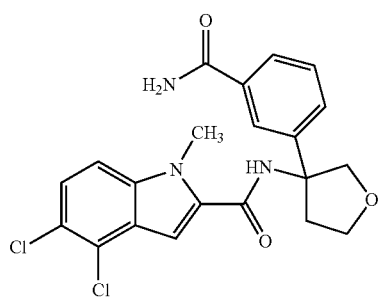 [SMILES: Cn1c(C(=O)NC2(c3cccc(C(N)=O)c3)CCOC2)cc2c(Cl)c(Cl)ccc21]
I-142
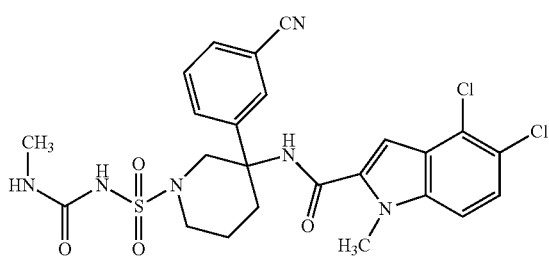 [SMILES: CNC(=O)NS(=O)(=O)N1CCCC(NC(=O)c2cc3c(Cl)c(Cl)ccc3n2C)(c2cccc(C#N)c2)C1]
I-143
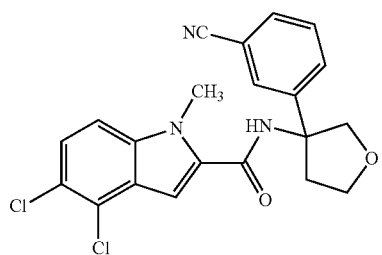 [SMILES: Cn1c(C(=O)NC2(c3cccc(C#N)c3)CCOC2)cc2c(Cl)c(Cl)ccc21]

TABLE 1-continued
Exemplary Compounds
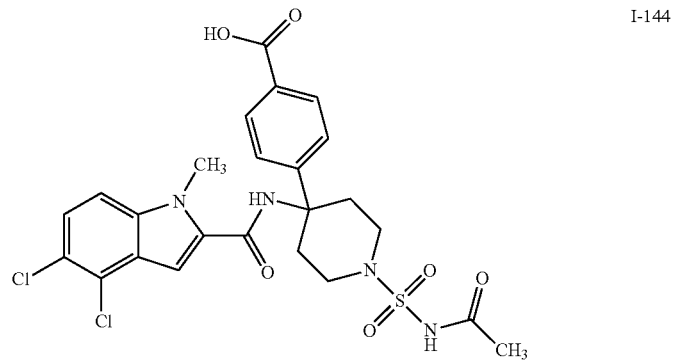
I-144
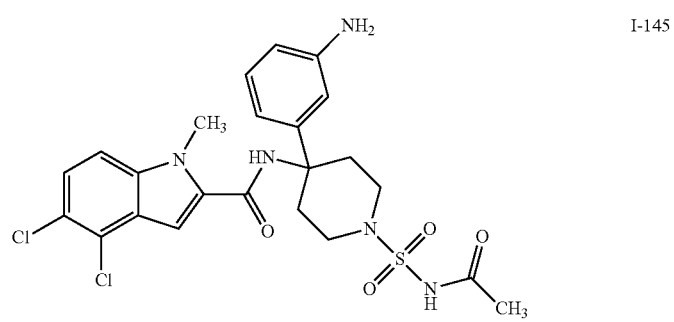
I-145
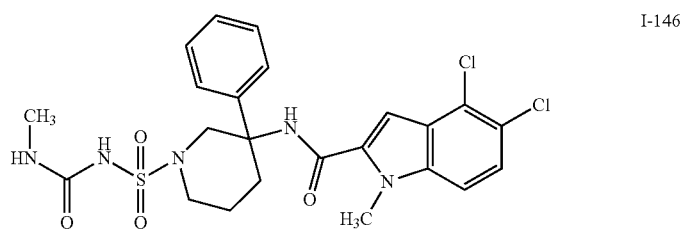
I-146
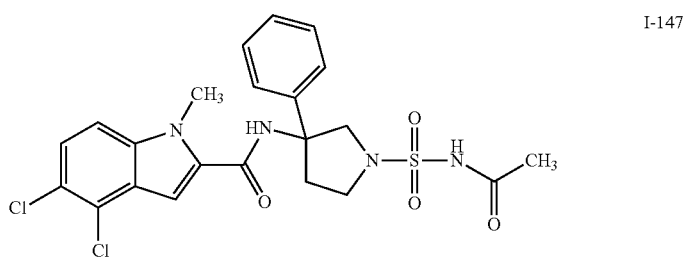
I-147
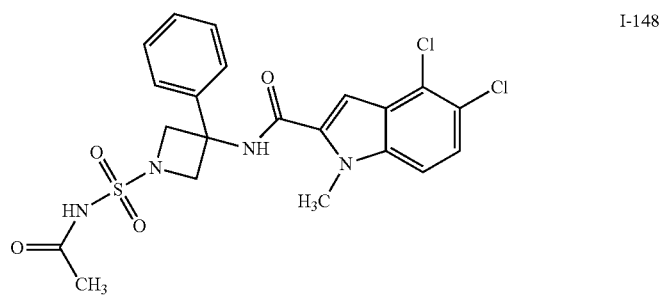
I-148

TABLE 1-continued
Exemplary Compounds
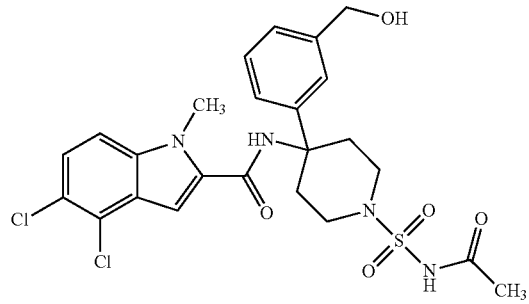 [SMILES: CC(=O)NS(=O)(=O)N1CCC(NC(=O)c2cc3c(Cl)c(Cl)ccc3n2C)(c2cccc(CO)c2)CC1]
I-149
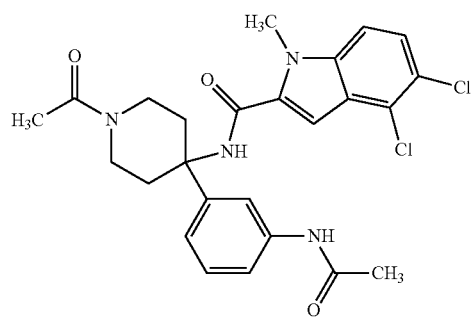 [SMILES: CC(=O)Nc1cccc(C2(NC(=O)c3cc4c(Cl)c(Cl)ccc4n3C)CCN(C(C)=O)CC2)c1]
I-150
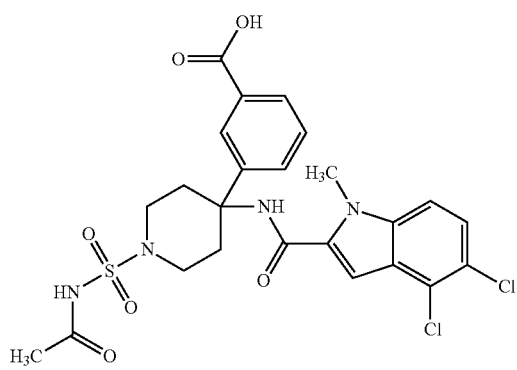 [SMILES: CC(=O)NS(=O)(=O)N1CCC(NC(=O)c2cc3c(Cl)c(Cl)ccc3n2C)(c2cccc(C(=O)O)c2)CC1]
I-151
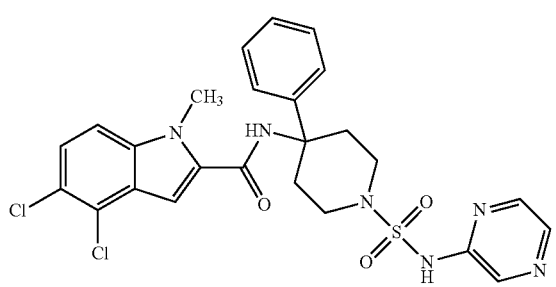 [SMILES: Cn1c(C(=O)NC2(c3ccccc3)CCN(S(=O)(=O)Nc3cnccn3)CC2)cc2c(Cl)c(Cl)ccc21]
I-152

TABLE 1-continued
Exemplary Compounds
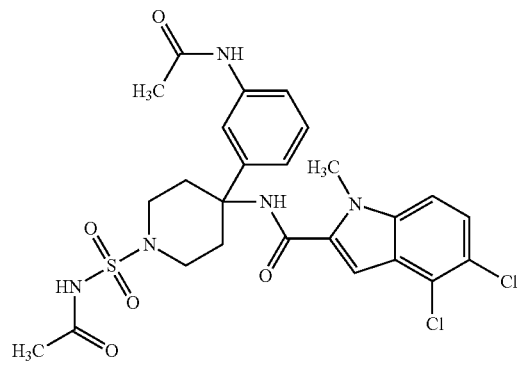 [SMILES: CC(=O)Nc1cccc(C2(NC(=O)c3cc4c(Cl)c(Cl)ccc4n3C)CCN(S(=O)(=O)NC(C)=O)CC2)c1]
I-153
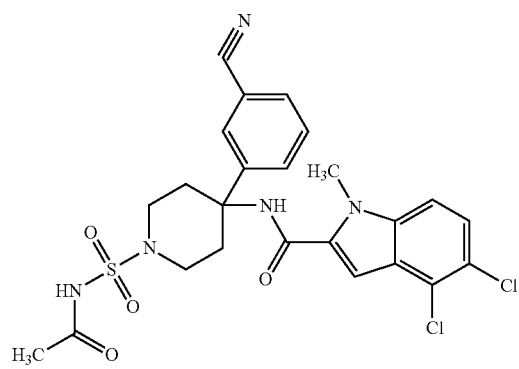 [SMILES: CC(=O)NS(=O)(=O)N1CCC(NC(=O)c2cc3c(Cl)c(Cl)ccc3n2C)(c2cccc(C#N)c2)CC1]
I-154
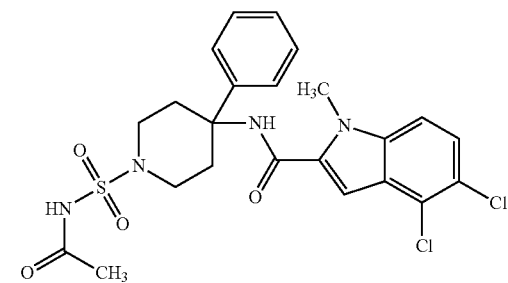 [SMILES: CC(=O)NS(=O)(=O)N1CCC(NC(=O)c2cc3c(Cl)c(Cl)ccc3n2C)(c2ccccc2)CC1]
I-155
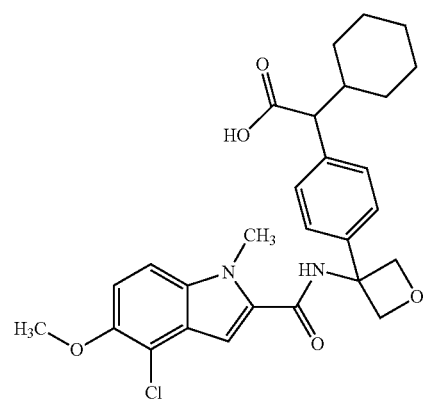 [SMILES: COc1ccc2c(cc(C(=O)NC3(c4ccc(C(C(=O)O)C5CCCCC5)cc4)COC3)n2C)c1Cl]
I-156

TABLE 1-continued
Exemplary Compounds
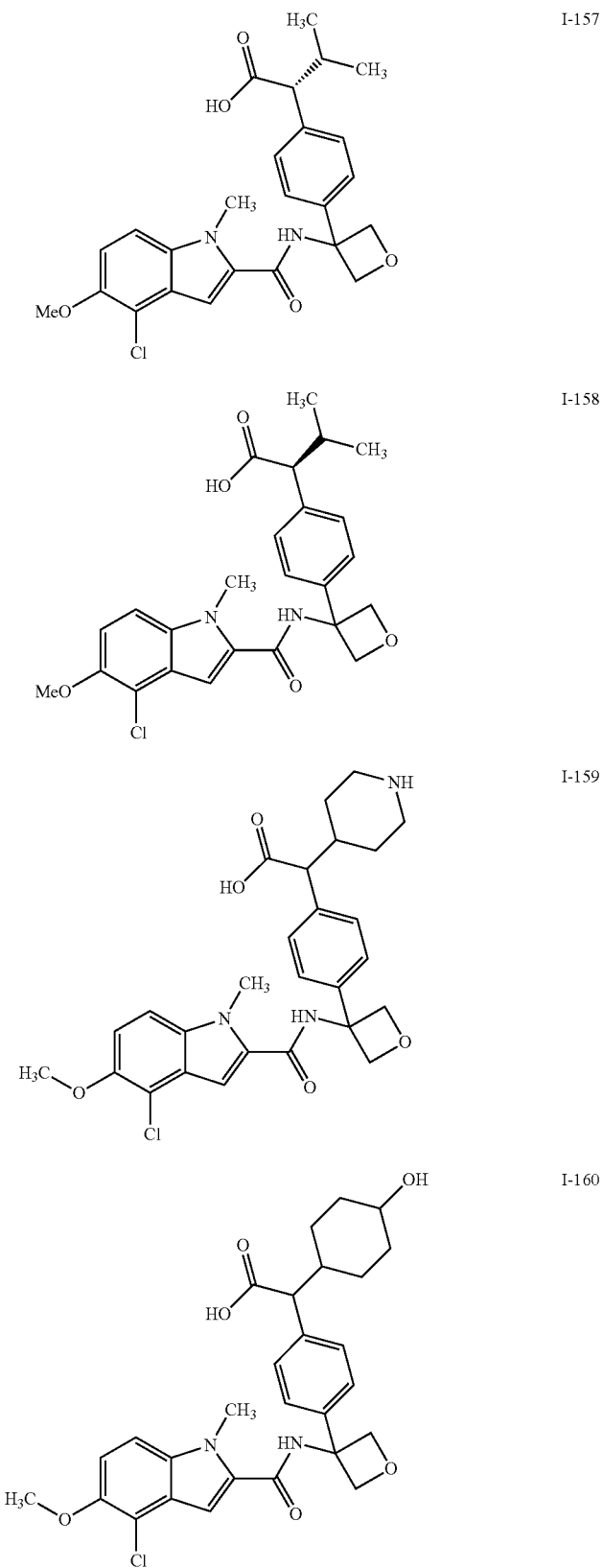

TABLE 1-continued
Exemplary Compounds
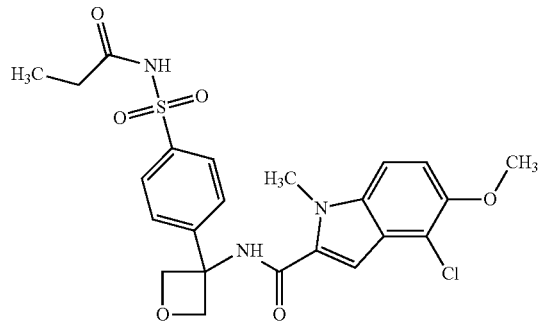 [SMILES: CCC(=O)NS(=O)(=O)c1ccc(C2(NC(=O)c3cc4c(Cl)c(OC)ccc4n3C)COC2)cc1]
I-161
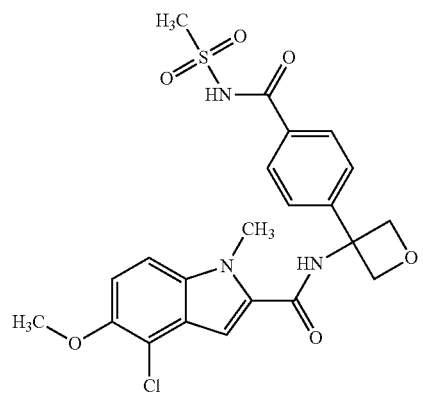 [SMILES: COc1ccc2c(cc(C(=O)NC3(c4ccc(C(=O)NS(C)(=O)=O)cc4)COC3)n2C)c1Cl]
I-162
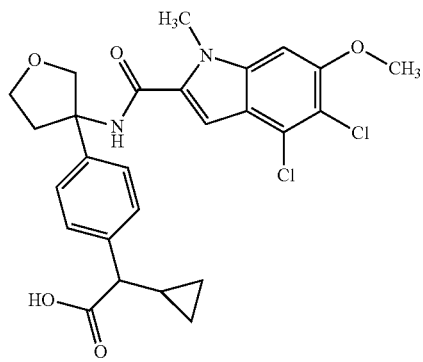 [SMILES: COc1cc2c(cc(C(=O)NC3(c4ccc(C(C(=O)O)C5CC5)cc4)CCOC3)n2C)c(Cl)c1Cl]
I-163
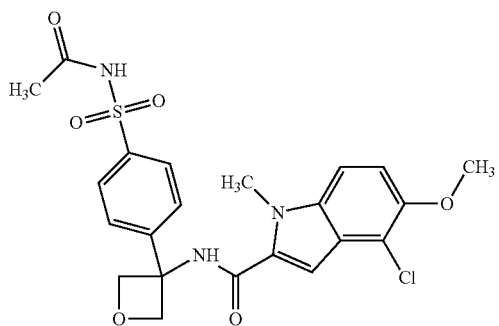 [SMILES: COc1ccc2c(cc(C(=O)NC3(c4ccc(S(=O)(=O)NC(C)=O)cc4)COC3)n2C)c1Cl]
I-164

TABLE 1-continued

Exemplary Compounds

I-165

[Chemical structure of compound I-165]

In certain embodiments, the present invention provides any compound depicted in Table 1, above, or a pharmaceutically acceptable salt thereof.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit PHGDH, or a mutant thereof, in a biological sample or in a patient. In certain embodiments, the amount of compound in compositions of this invention is such that is effective to measurably inhibit PHGDH, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of PHGDH, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of PHGDH or a mutant thereof.

The activity of a compound utilized in this invention as an inhibitor of PHGDH, or a mutant thereof, may be assayed in vitro, in vivo or in a cell line. In vitro assays include assays that determine inhibition of PHGDH, or a mutant thereof. Alternate in vitro assays quantitate the ability of the inhibitor to bind to PHGDH. Detailed conditions for assaying a compound utilized in this invention as an inhibitor of PHGDH, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of PHGDH and are therefore useful for treating one or more disorders associated with activity of PHGDH. Thus, in certain embodiments, the present invention provides a method for treating a PHGDH-mediated disorder comprising the step of administering to a patient in need thereof a compound of the present invention, or pharmaceutically acceptable composition thereof.

As used herein, the terms "PHGDH-mediated" disorders, diseases, and/or conditions as used herein means any disease or other deleterious condition in which PHGDH, or a mutant thereof, is known to play a role. Accordingly, another embodiment of the present invention relates to treating or lessening the severity of one or more diseases in which PHGDH, or a mutant thereof, are known to play a role.

In some embodiments, the present invention provides a method for treating one or more disorders, diseases, and/or conditions wherein the disorder, disease, or condition includes, but is not limited to, a cellular proliferative disorder.

Cellular Proliferative Disorders

The present invention features methods and compositions for the diagnosis and prognosis of cellular proliferative disorders (e.g., cancer) and the treatment of these disorders by targeting PHGDH of the serine biosynthetic pathway.

Cellular proliferative disorders described herein include, e.g., cancer, obesity, and proliferation-dependent diseases. Such disorders may be diagnosed using methods known in the art.

Cancer

Cancer includes, in one embodiment, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In some embodiments, the cancer is melanoma or breast cancer.

Cancers includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the present invention provides a method for treating a tumor in a patient in need thereof, comprising administering to the patient any of the compounds, salts or pharmaceutical compositions described herein. In some embodiments, the tumor comprises any of the cancers described herein. In some embodiments, the tumor comprises melanoma cancer. In some embodiments, the tumor comprises breast cancer. In some embodiments, the tumor comprises lung cancer. In some embodiments the tumor comprises small cell lung cancer (SCLC). In some embodiments the tumor comprises non-small cell lung cancer (NSCLC).

In some embodiments, the tumor is treated by arresting further growth of the tumor. In some embodiments, the tumor is treated by reducing the size (e.g., volume or mass) of the tumor by at least 5%, 10%, 25%, 50%, 75%, 90% or 99% relative to the size of the tumor prior to treatment. In some embodiments, tumors are treated by reducing the quantity of the tumors in the patient by at least 5%, 10%, 25%, 50%, 75%, 90% or 99% relative to the quantity of tumors prior to treatment.

Other Proliferative Diseases

Other proliferative diseases include, e.g., obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases that are hereby incorporated by reference include those described in U.S. Pat. Nos. 5,639,600 and 7,087,648.

Inflammatory Disorders and Diseases

It has recently been reported that PHGDH gene expression, dictated by IL-2R signaling, is a crucial event for DNA synthesis during S phase of activated T cells. Jun do Y et al., *Cell Immunol.* 2014 February; 287(2):78-85. Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterized by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitits, atompic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Metabolic Disease

In some embodiments the invention provides a method of treating a metabolic disease. In some embodiments the metabolic disease is selected from Type 1 diabetes, Type 2 diabetes, metabolic syndrome or obesity.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting PHGDH activity in a biological sample comprising the step of contacting said biological sample with a compound of this invention, or a composition comprising said compound.

According to another embodiment, the invention relates to a method of inhibiting PHGDH, or a mutant thereof, activity in a biological sample comprising the step of contacting said biological sample with a compound of this invention, or a composition comprising said compound. In certain embodiments, the invention relates to a method of irreversibly inhibiting PHGDH, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Another embodiment of the present invention relates to a method of inhibiting PHGDH in a patient comprising the step of administering to said patient a compound of the present invention, or a composition comprising said compound.

According to another embodiment, the invention relates to a method of inhibiting PHGDH, or a mutant thereof, activity in a patient comprising the step of administering to said patient a compound of the present invention, or a composition comprising said compound. According to certain embodiments, the invention relates to a method of irreversibly inhibiting PHGDH, or a mutant thereof, activity in a patient comprising the step of administering to said patient a compound of the present invention, or a composition comprising said compound. In other embodiments, the present invention provides a method for treating a disorder mediated by PHGDH, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™ Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed under the trade name Zavedos™. Mitoxantrone is marketed under the trade name Novantron.

The term "microtubule active agent" relates to microtubule stabilizing, microtubule destabilizing compounds and microtubulin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; colchicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j)

compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; ilmofosine; RO 318220 and RO 320432; GO 6976; Isis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (±) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MV1MI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in March's Advanced Organic Chemistry: Reactions, Mechanisms, and Structure, M. B. Smith and J. March, 5$^{th}$ Edition, John Wiley & Sons, 2001, Comprehensive Organic Transformations, R. C. Larock, 2$^{nd}$ Edition, John Wiley & Sons, 1999, and Protecting Groups in Organic Synthesis, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in Protecting Groups in Organic Synthesis, T. W. Greene and P. G. M. Wuts, 3$^{rd}$ edition, John Wiley & Sons, 1999, the entirety of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenyl-methyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in Protecting Groups in Organic Synthesis, T. W. Greene and P. G. M. Wuts, 3$^{rd}$ edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In certain embodiments, compounds of the present invention of formula I, or subformulae thereof, are generally prepared according to Scheme I set forth below:

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry", 5$^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below.

In one aspect, certain compounds of the present invention of formula I, or subformulae thereof, are generally prepared according to Scheme 1 set forth below:

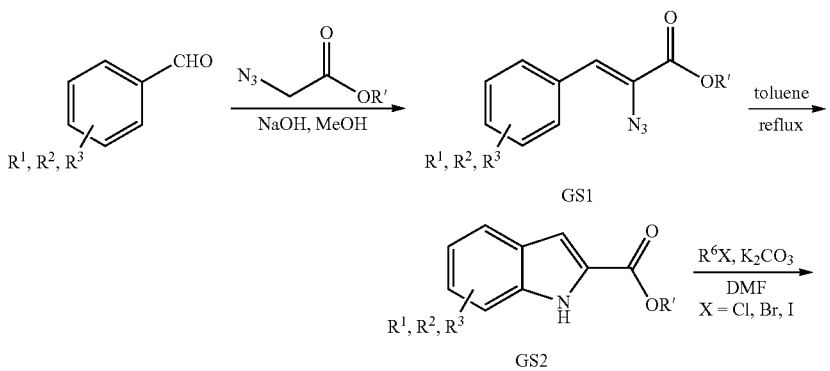

Scheme 1

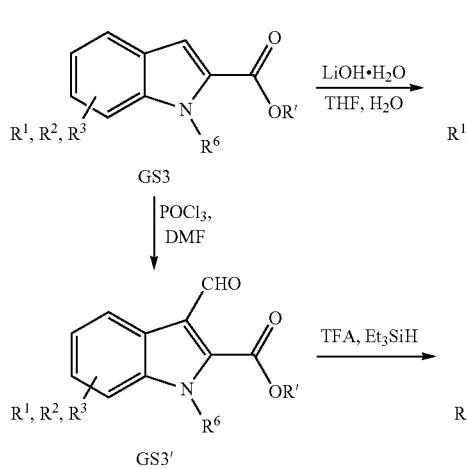

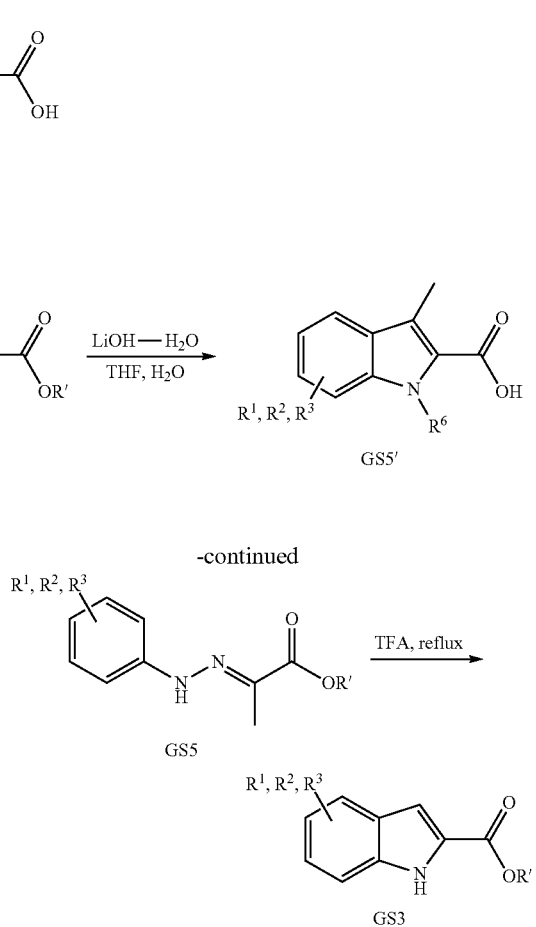

In Scheme 1 above, R' is a group such as $C_{1-6}$ aliphatic, 5- to 8-membered aromatic ring, or other functionality compatible with an ester; and $R^1$, $R^2$, $R^3$, and $R^6$ are selected consistent with formula I above and below and in classes and subclasses as described herein.

In one aspect, the present invention provides methods for preparing compounds of formula GS4 as described in Scheme 1. An optionally substituted benzaldehyde may be condensed with an azidoacetate in the presence of base such as sodium hydroxide or sodium methoxide to give intermediate GS1. Heating GS1 in a solvent such as toluene (e.g., at reflux) provides the indole-2-carboxylate ester. In some embodiments, the indole nitrogen is alkylated using an appropriate alkyl halide such as methyl or ethyl iodide and a suitable base such as, but not limited, to sodium hydride, potassium tert-butoxide, or potassium carbonate in a suitable solvent to provide GS3. In some embodiments, the ester of GS3 is hydrolyzed using a base such as LiOH, KOH, or NaOH in a solvent such as a mixture of water and THF to provide an intermediate used in the synthesis of compounds of the invention of general structure GS4.

Alternatively, in some embodiments GS3 may be treated with appropriate reagents such as $POCl_3$ and DMF to give GS3'. In some embodiments, the aldehyde in GS3' is then reduced to a methyl group with appropriate reagents such as $Et_3SiH$ and TFA to give GS4'. Finally, in some embodiments, hydrolysis of the ester in GS4' provides an intermediate used in the synthesis of compounds of the invention of general structure GS5'.

In another aspect, compounds of the present invention of formula I, or subformulae thereof, are generally prepared according to Scheme 2 set forth below:

Scheme 2

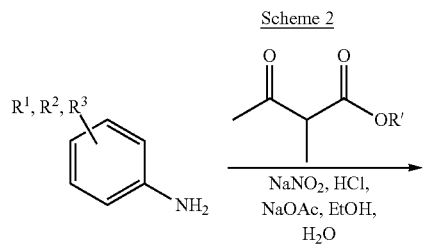

Scheme 2 describes an alternate route to prepare compounds of formula GS3. In some embodiments, treatment of an aniline with a nitrite compound and a ketoacetate of choice in a suitable solvent (for example, a mixture of ethanol/water) produces an aryl hydrazine intermediate that reacts with the ketoacetate (such as ethyl 2-methyl-3-oxobutanoate) to provide GS5. Treatment of GS5 with TFA with heat, e.g., reflux, provides general intermediate GS3 that can be elaborated to GS4 and GS7 as described above.

In another aspect, compounds of the present invention of formula I, or subformulae thereof, are generally prepared according to Scheme 3 set forth below:

Scheme 3

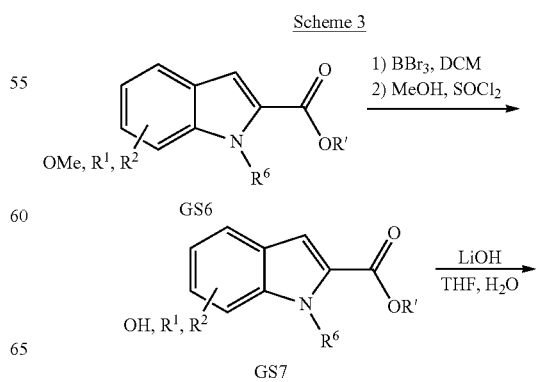

-continued

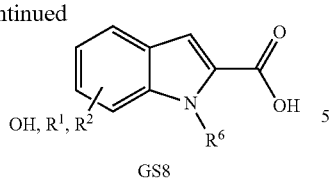
GS8

Intermediate GS6 in Scheme 3 can be accessed as described for GS3, where R³ is an methoxy group. Hydrolysis of the methoxy group and ester with boron tribromide in dichloromethane followed by treatment with thionyl chloride in methanol provides intermediate ester GS7. GS7 can be hydrolyzed to the acid as described above for GS4 to yield GS8.

In another aspect, compounds of the present invention of formula I, or subformulae thereof, are generally prepared according to Scheme 4 set forth below:

Scheme 4

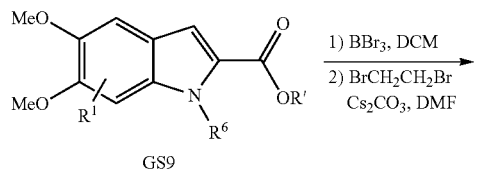
GS9

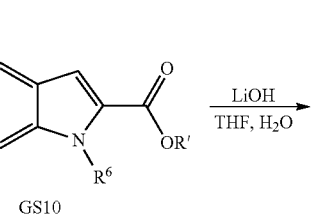
GS10

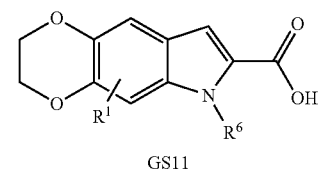
GS11

Intermediate GS9 in Scheme 4 can be accessed as described for GS3, where R² and R³ are methoxy groups. Hydrolysis of the methoxy groups and ester with boron tribromide in dichloromethane followed by treatment with 1,2-dibromoethane and a base such as cesium carbonate in as suitable solvent such as DMF provides intermediate ester GS10. GS10 can be hydrolyzed to the acid as described above for GS4 to yield GS11.

In another aspect, compounds of the present invention of formula I, or subformulae thereof, are generally prepared according to Scheme 5 set forth below:

Scheme 5

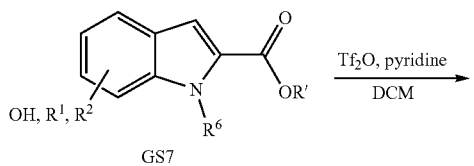
GS7

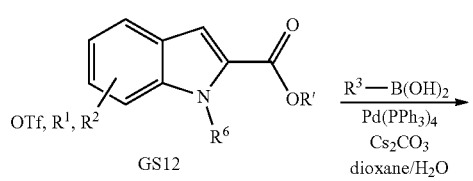
GS12

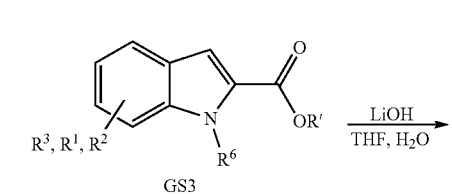
GS3

GS4

Intermediates such as GS12, Scheme 5 can be accessed by exposing alcohol intermediate GS7 to triflic anhydride and pyridine in dichloromethane. Cross coupling with the corresponding boronic acid under standard Suzuki coupling conditions with a catalyst such as Pd(PPh₃)₄ and a base such as cesium carbonate in an appropriate solvent such as dioxane/water can give rise to GS3 that can be elaborated to GS4 as described previously.

In another aspect, compounds of the present invention of formula I, or subformulae thereof, are generally prepared according to Scheme 6 set forth below:

Scheme 6

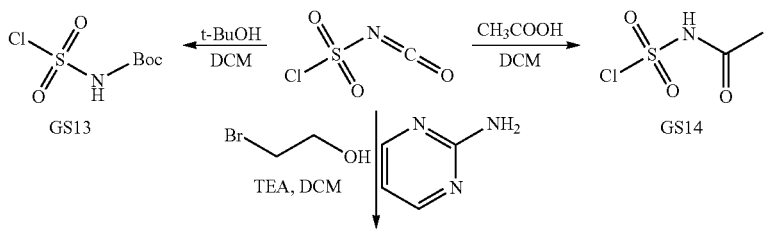

N-(oxomethylene)sulfamoyl chloride when treated with reagents such as tert-butanol in dichloromethane can provide compounds such as GS13 in Scheme 6. N-(oxomethylene) sulfamoyl chloride can be alternatively converted to GS14 with acetic acid in dichloromethane. N-(oxomethylene)sulfamoyl chloride can further be derivatized to GS28 by reaction under conditions such as 2-bromoethanol, pyrimidin-2-amine, and triethylamine in dichloromethane.

In another aspect, compounds of the present invention of formula I, or subformulae thereof, are generally prepared according to Scheme 7 set forth below:

A bromophenyl acetonitrile compound can be reacted with tert-butyl N,N-bis(2-chloroethyl)carbamate and sodium hydride in N,N-dimethylformamide to form compounds such as GS15, Scheme 7. Hydrolysis of the nitrile to the amide GS16 can be achieved via exposure to hydrogen peroxide and potassium carbonate in dimethyl sulfoxide or equivalent conditions. Formation of amine GS17 can be accomplished by reacting the amide with PhI(CF$_3$CO$_2$)$_2$ in acetonitrile/water. The bromide can be removed under hydrogenation conditions using palladium on carbon in methanol to form GS18. Alternatively, amide GS19 can be installed under coupling conditions with acetamide, Pd$_2$(dba)$_3$, Xantphos, and cesium carbonate in N,N-dimethylformamide with heating. The bromide can also be converted to ester GS20 with Pd(dppf)Cl$_2$·CH$_2$Cl$_2$ and triethylamine in ethanol in the presence of carbon monoxide (50 psi).

In another aspect, compounds of the present invention of formula I, or subformulae thereof, are generally prepared according to Scheme 8 set forth below:

-continued

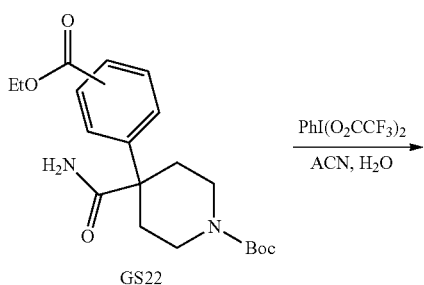

GS22

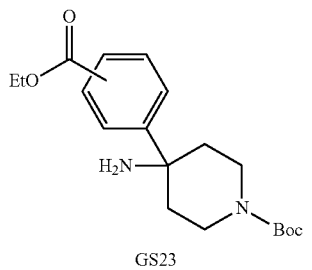

GS23

Bromide GS15 in Scheme 8 can be converted to ester GS21 with an appropriate catalyst such as Pd(dppf)Cl$_2$·CH$_2$Cl$_2$ and triethylamine in ethanol under carbon monoxide (50 psi). GS21 and GS22 can be formed as described above for GS16 and GS17.

In another aspect, compounds of the present invention of formula I, or subformulae thereof, are generally prepared according to Scheme 9 set forth below:

Scheme 9

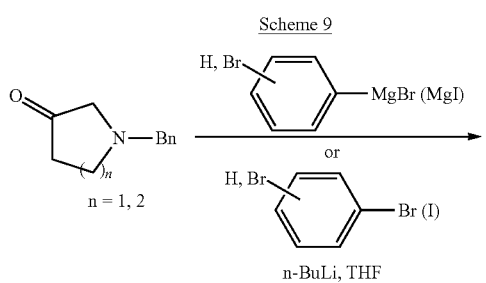

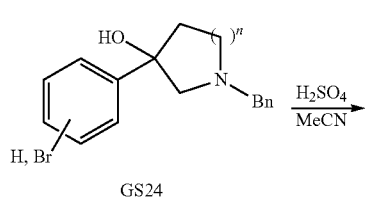

GS25

-continued

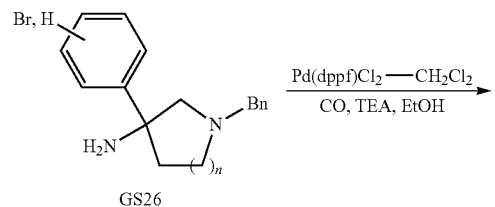

GS26

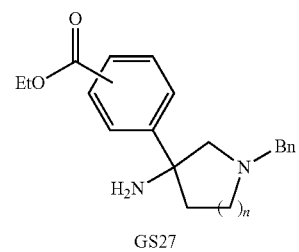

GS27

A benzylpiperidinone or benzylpyrrolidinone can be treated with an optionally substituted aryl bromide or iodide with n-butyllithium in THF to form an alcohol such as GS24 (Scheme 9). Alternatively, benzylpiperidinone or benzylpyrrolidinone can react with an unsubstituted or bromo-substituted aryl Grignard reagent in THF to also form compounds such as GS24. Amide GS25 can be formed by treatment with sulfuric acid in acetonitrile. The amide can then be hydrolyzed to the amine GS26 with hydrochloric acid. The bromide derivatives of GS26 can be converted to the ester GS27 with reagents such as Pd(dppf)Cl$_2$·CH$_2$Cl$_2$ and triethylamine in ethanol under carbon monoxide (50 psi).

In another aspect, compounds of the present invention of formula I, or subformulae thereof, are generally prepared according to Scheme 10 set forth below:

Scheme 10

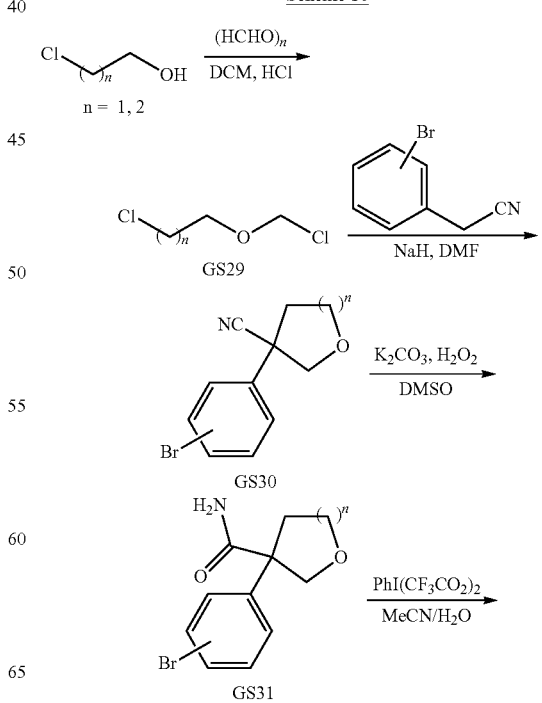

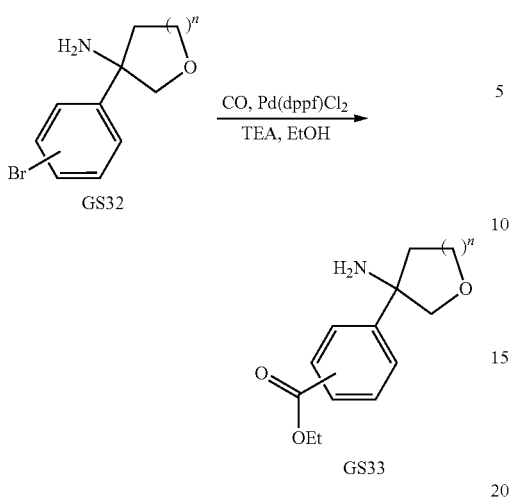

To prepare compounds such as GS33, a solution of paraformaldehyde in dichloromethane is bubbled with HCl (gas). Then, the corresponding chloro alcohol is added to form compounds such as GS29 (Scheme 10). This intermediate can then be treated with bromophenyl acetonitrile and sodium hydride in N,N-dimethylformamide to yield compounds like GS30. Exposure of GS30 to potassium carbonate and hydrogen peroxide in dimethyl sulfoxide can give amide compounds like GS31. Reduction of the amide is achieved with PhI(CF$_3$CO$_2$)$_2$, or a similar reagent like PhI(OAc)$_2$, in acetonitrile and water to form GS32. The bromide can be converted to ester GS33 by coupling with Pd(dppf)Cl$_2$·CH$_2$Cl$_2$ and triethylamine in ethanol in the presence of carbon monoxide (50 psi) with heating.

In another aspect, compounds of the present invention of formula I, or subformulae thereof, are generally prepared according to Scheme 11 set forth below:

A bromo- and methyl-disubstituted pyridine or pyridazine in an appropriate solvent such as acetonitrile or carbon tetrachloride can be treated with a radical initiator such as 2,2-azobisisobutyronitrile (AIBN) and N-bromosuccinimide (NBS) and heated to form compounds such as GS34 (Scheme 11). This can then be added to a solution of trimethylsilyl cyanide (TMSCN) and tetrabutylammonium fluoride (TBAF) in acetonitrile to yield compound like GS35. GS35 can be converted to GS36 as described above for GS30. GS37 can be formed as described above for GS33. GS38 and GS39 can be formed as described above for GS31 and GS32, respectively.

In another aspect, compounds of the present invention of formula I, or subformulae thereof, are generally prepared according to Scheme 12 set forth below:

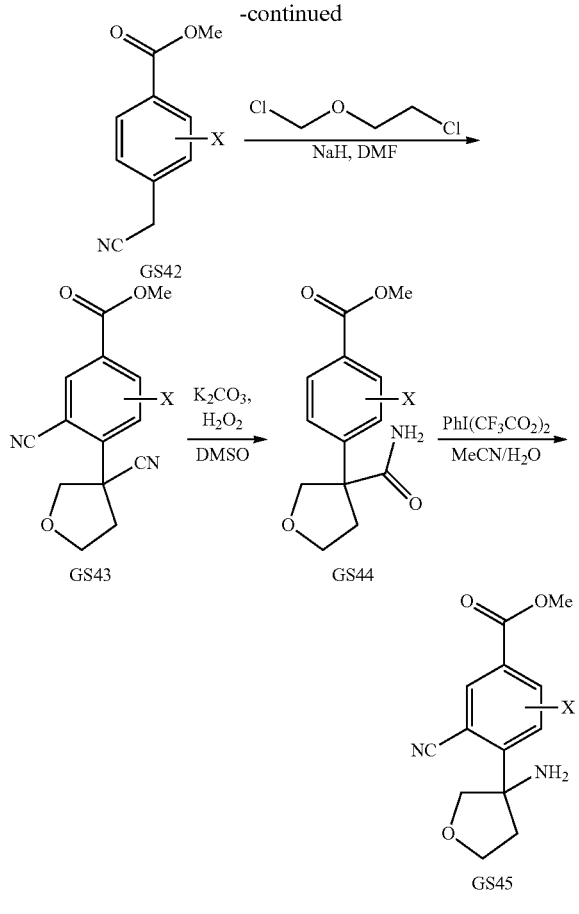

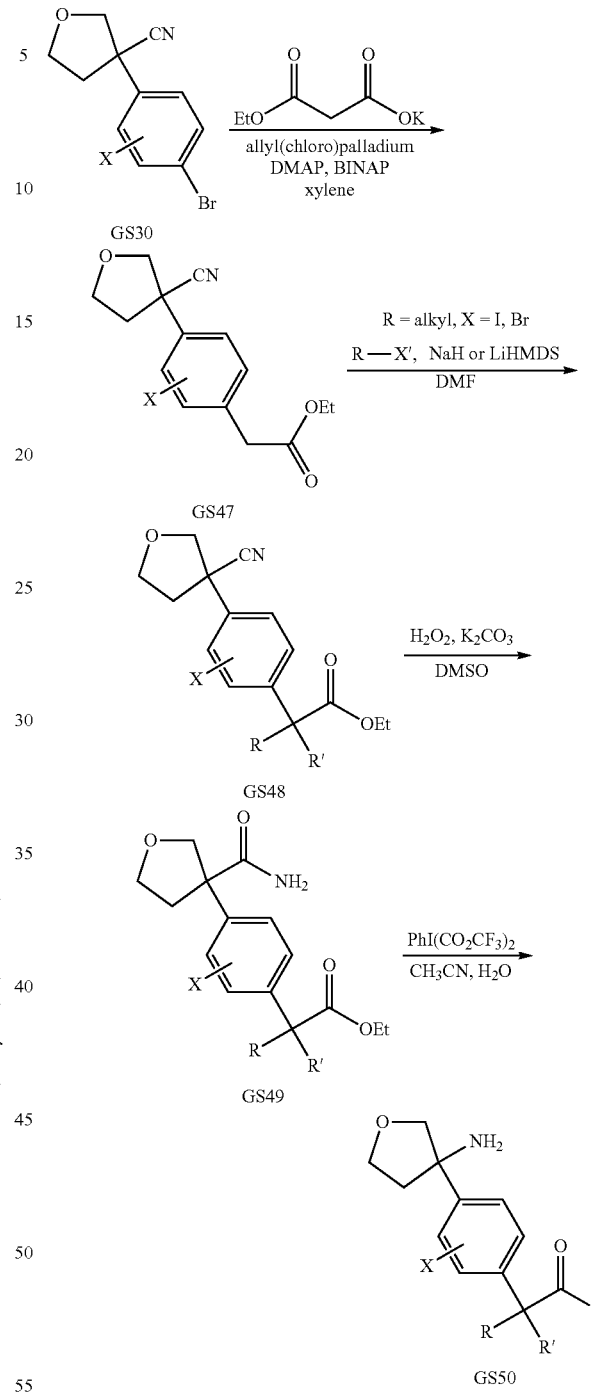

An optionally substituted benzoic acid can be treated with thionyl chloride in methanol and heated to form GS40 (Scheme 12). GS41 and GS42 can be synthesized as described above for GS34 and GS35, respectively. GS42 can be further elaborated to GS43, GS44 and GS45 as described above for GS30, GS31, and GS32.

In another aspect, compounds of the present invention of formula I, or subformulae thereof, are generally prepared according to Scheme 13 set forth below:

Scheme 13

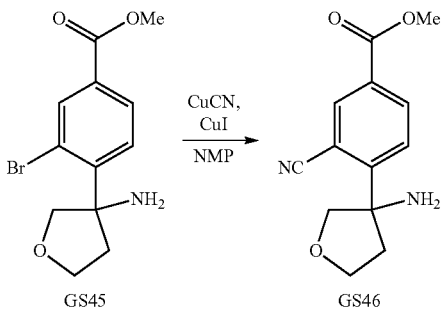

X = H, F
R = alkyl
R' = H, alkyl

When X=Br for GS45 the intermediate can be converted to the nitrile GS46 by coupling with copper cyanide and copper iodide in 1-methyl-2-pyrrolidinone with heating.

In another aspect, compounds of the present invention of formula I, or subformulae thereof, are generally prepared according to Scheme 14 set forth below:

Intermediate GS30 can be coupled with (3-ethoxy-3-oxo-propanoyl)oxypotassium with allyl(chloro)palladium, dimethylaminopyridine, and 2,2'-bis(diphenylphosphino)-1,1'-binaphthyl (BINAP) in xylene with heat to form allyl ester GS47 (Scheme 14). This ester portion can be further alkylated with the corresponding alkyl halide under basic conditions, using either LiHMIDS or sodium hydride, in a solvent such as N,N-dimethylformamide or tetrahydrofuran, to give GS48 as a mono or bis-alkylated product. GS48 can be further elaborated to GS49 and GS50 as described above for GS31 and GS32, respectively.

In another aspect, compounds of the present invention of formula I, or subformulae thereof, are generally prepared according to Scheme 15 set forth below:

sulfoxide under carbon monoxide (50 psi) with heating. Deprotection of the amine can be accomplished by treating GS53 with iodine in a mixture of tetrahydrofuran and water or with a solution of hydrochloric acid in dioxane with ethanol as the solvent to give GS54.

In another aspect, compounds of the present invention of formula I, or subformulae thereof, are generally prepared according to Scheme 16 set forth below:

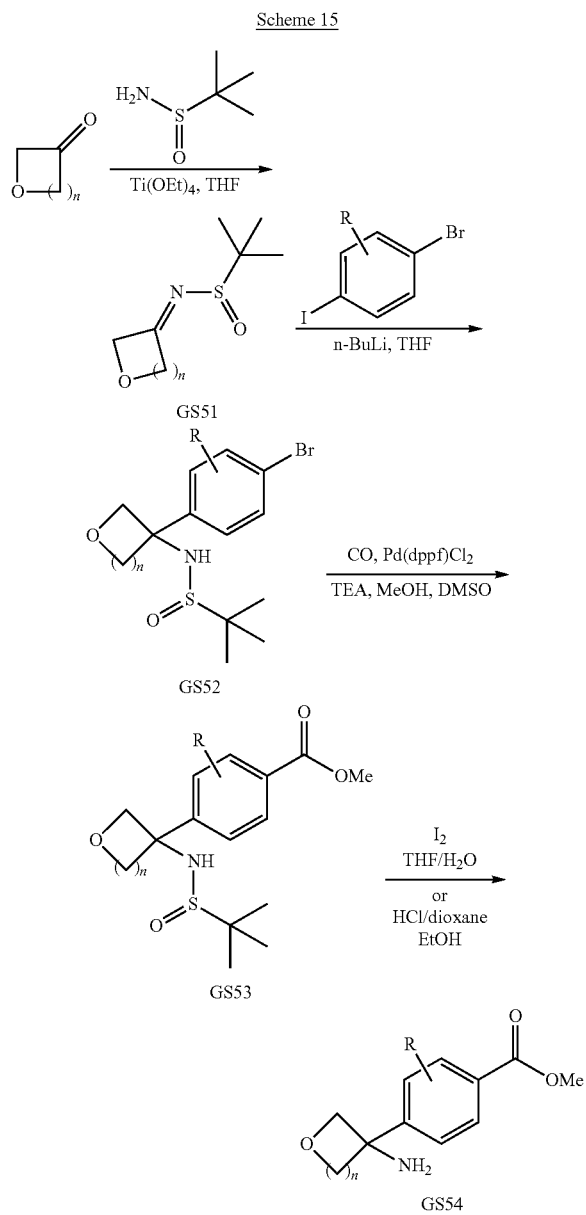

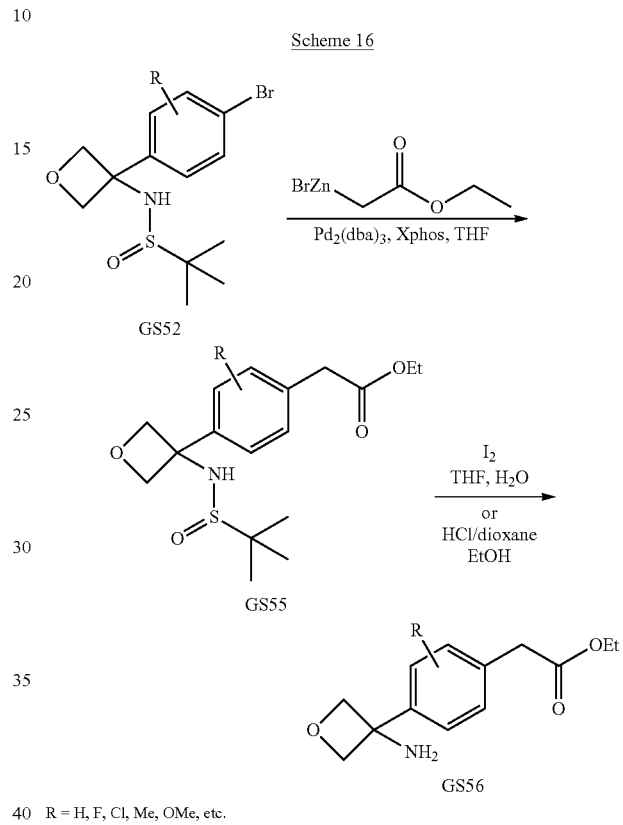

R = H, F, Cl, Me, OMe, etc.

Intermediates such as GS52 (Scheme 16) can be coupled with an organometallic reagent such as bromo-(2-ethoxy-2-oxo-ethyl)zinc, a catalyst such as $Pd_2(dba)$, and a ligand such as XPhos in an appropriate solvent such as tetrahydrofuran, usually with heating, to form GS55. GS55 can be deprotected to form amine GS56 as previously described for GS54.

In another aspect, compounds of the present invention of formula I, or subformulae thereof, are generally prepared according to Scheme 17 set forth below:

n = 1, 2, 3
R = H, F, Cl, Me, OMe

A 4-6 membered ring oxo-ketone can be reacted with (±)-2-methylpropane-2-sulfinamide and $Ti(OEt)_4$ in tetrahydrofuran to form intermediates such as GS51 (Scheme 15). The corresponding of 1-bromo-4-iodo-benzene (optionally substituted with various R such as H, F, Cl, Me, OMe) in tetrahydrofuran can be treated with n-butyllithium with cooling. Then a solution of GS51 in tetrahydrofuran can be added to the solution to give GS52. The bromide can be converted to ester GS53 via coupling with $Pd(dppf)Cl_2 \cdot CH_2Cl_2$ and TEA in a mixture of methanol and dimethyl

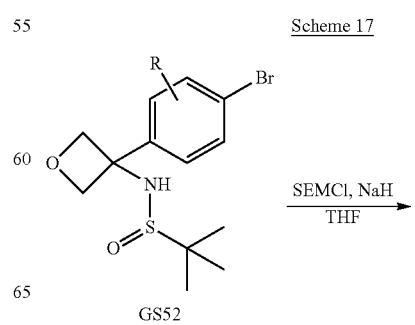

-continued

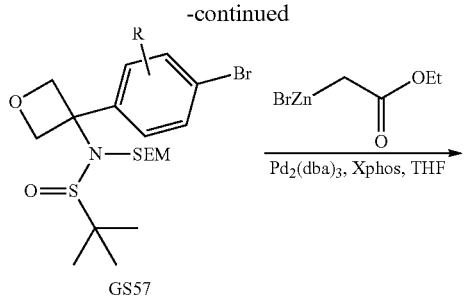

GS57

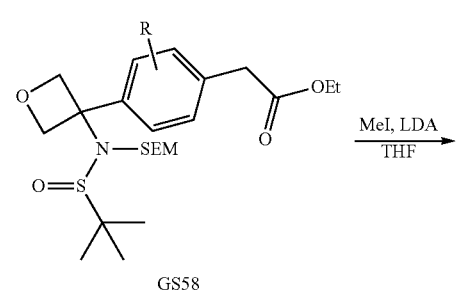

GS58

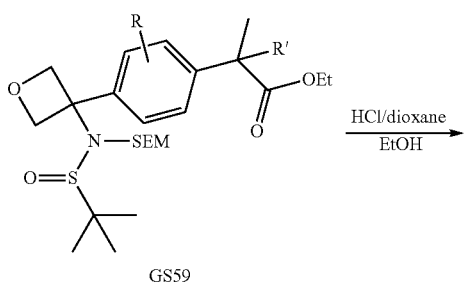

GS59

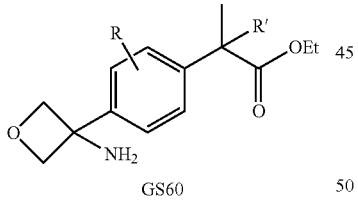

GS60

R = H, F, Cl
R' = H, Me

Compounds such as GS52 (Scheme 17) can be protected by reacting with SEMCl in tetrahydrofuran with a base such as sodium hydride. The protected GS57 can then be coupled as described for GS55 above. GS58 can then be alkylated with methyl iodide using LDA, NaH or LiHMDS as the base in tetrahydrofuran to form either the mono or bis-alkylated products if excess reagents are used. GS59 is deprotected to form amine GS60 using the method previously described for GS56.

In another aspect, compounds of the present invention of formula I, or subformulae thereof, are generally prepared according to Scheme 18 set forth below:

Scheme 18

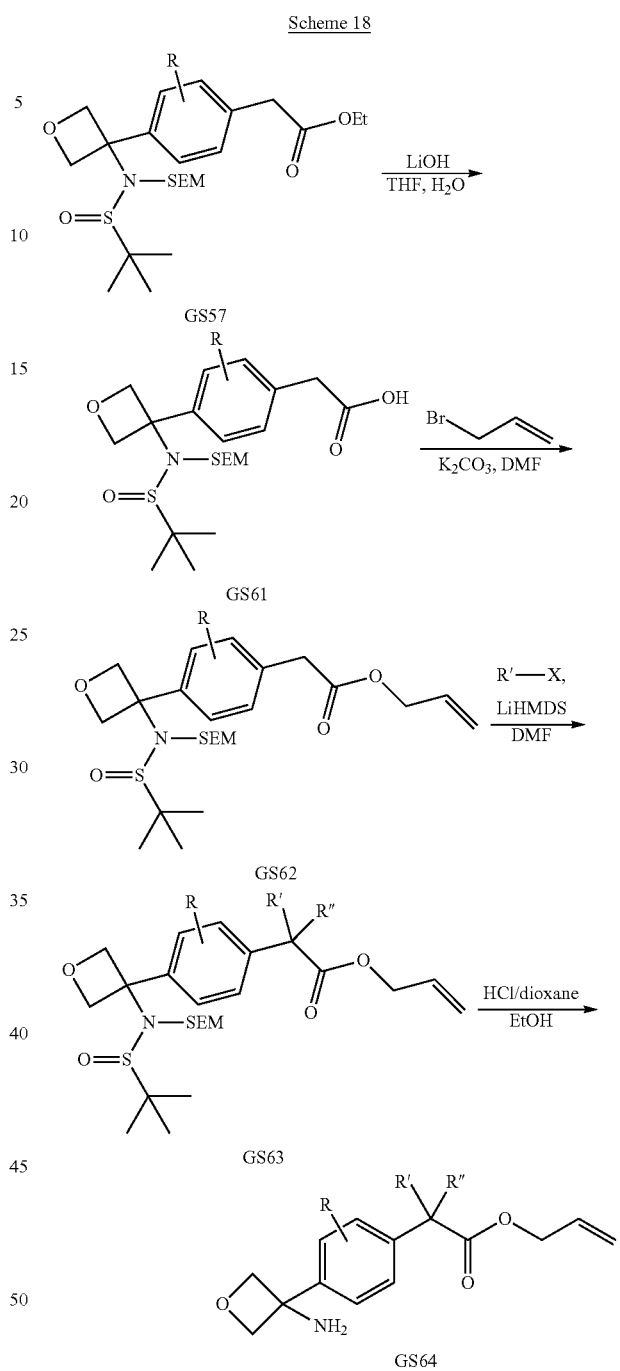

R = H, F, Cl, etc.
R' = alkyl, etc.
X = Br, I
R″ = H, alkyl, etc.

The ester of compounds such as GS57 (Scheme 18) can be saponified to acid GS61 by exposure to a base such as lithium hydroxide in a solvent such as a mixture of water and tetrahydrofuran. Acid GS61 can then be alkylated with 3-bromoprop-1-ene by addition of potassium carbonate in DMF to form GS62. GS62 can be further alkylated with a variety of groups using either the alkyl bromide or alkyl iodide with LiHMDS, LDA, or NaH as the base in an appropriate solvent such as DMF or tetrahydrofuran to form the mono or bis-alkylated product GS63. The amine GS64 is obtained by deprotection with hydrochloric acid/dioxane in ethanol.

In another aspect, compounds of the present invention of formula I, or subformulae thereof, are generally prepared according to Scheme 19 set forth below:

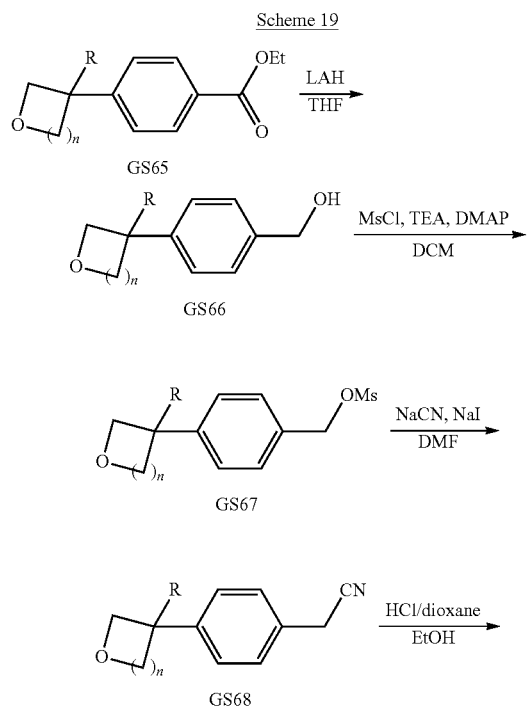

The amine of intermediate GS33 can be protected with a variety of protecting groups including Boc and SEM groups. This protected intermediate GS65 ester (Scheme 19) can then be reduced to the alcohol using lithium aluminum hydride or lithium borohydride in a solvent such as THF to yield GS66. The alcohol can then be transformed to the mesylate using methanesulfonyl chloride (MsCl), a base such as TEA, and DMAP in an appropriate solvent such as DCM. The mesylate GS67 can be converted to the nitrile GS68 by reacting it with sodium cyanide and sodium iodide in DMF. Finally, deprotection of the groups on the amine can be achieved with HCl/dioxane in ethanol or trifluoroacetic acid in dichloromethane to yield amine GS69.

In another aspect, compounds of the present invention of formula I, or subformulae thereof, are generally prepared according to Scheme 20 set forth below:

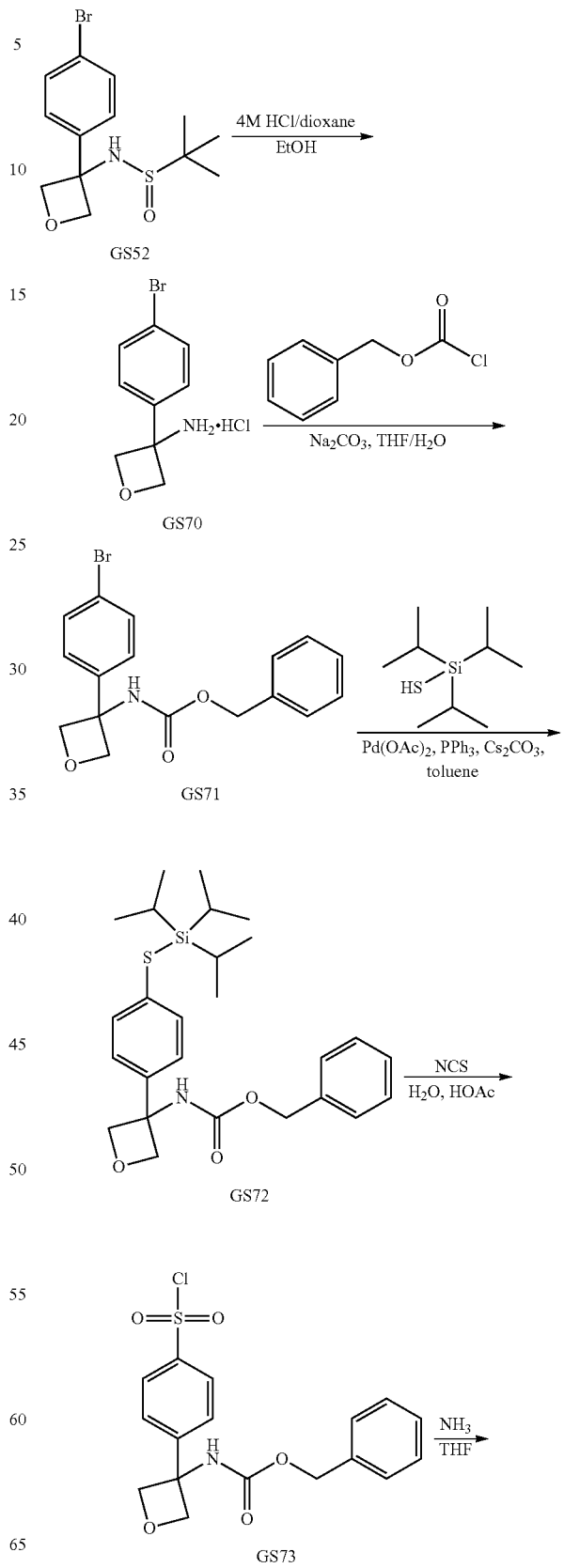

145
-continued

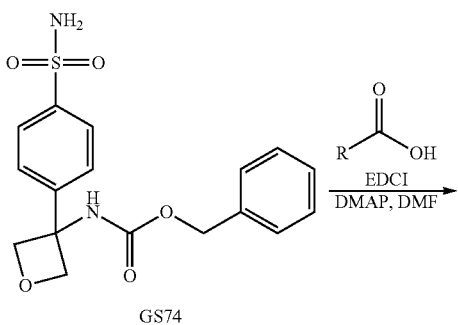
GS74

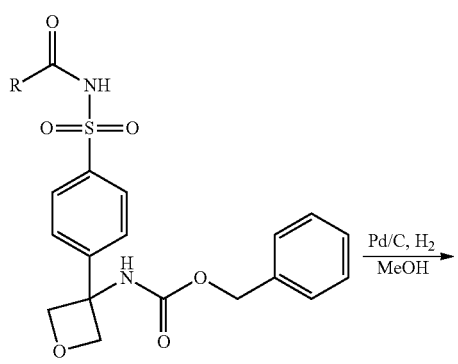
GS75

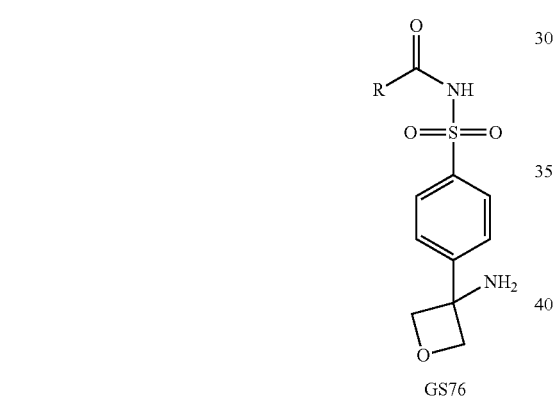
GS76

R = Me, Et, etc.

Intermediates such as GS52 in Scheme 20 can be deprotected with hydrochloride/dioxane in ethanol to form GS70. A Cbz protecting group can be then installed by treated GS70 with benzyl carbonochloridate and a base such as sodium carbonate in a solvent such as a mixture of THF/water. Coupling of GS71 and triisopropyl(sulfanyl)silane with a catalyst such as palladium acetate, ligand such as triphenylphosphine, and base such as cesium carbonate in an appropriate solvent such as toluene can give rise to intermediates such as GS72. Treatment of GS72 with N-chlorosuccinimide (NCS) in acetic acid and water can form the sulfonyl chloride GS73 which can be converted to the sulfonyl amine GS74 when exposed to ammonia in tetrahydrofuran. Coupling of the amine with an acid can be achieved with conditions such as EDCI, DMAP and acetic acid in DMF to form amide GS75. Finally, the Cbz protecting group can be removed under hydrogenation conditions with Pd/C in methanol or ethanol under hydrogen gas (50 psi).

146

In another aspect, compounds of the present invention of formula I, or subformulae thereof, are generally prepared according to Scheme 21 set forth below:

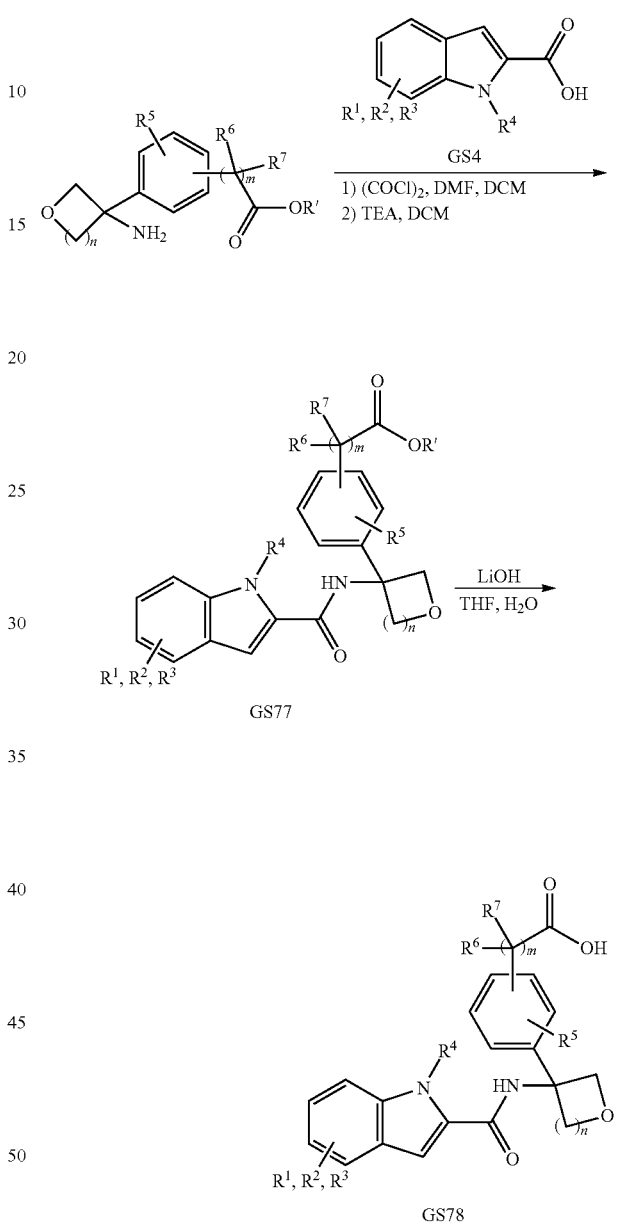

m = 0, 1
n = 1, 2, 3
R' = methyl, ethyl, etc.

In Scheme 21 above, variables $R^1$, $R^2$, $R^3$, $R^4$, $R^5$, $R^6$, and $R^7$ are selected consistent with formula I, and subformulae thereof, described above and below. Conversion of the acid group in GS4 (Scheme 21) to the acid chloride can be achieved using procedures well known to one of skills in the art. For example, the acid GS4 can be treated with oxalyl chloride or thionyl chloride with a catalytic amount of DMF in a solvent such as DCM. Reaction of acyl chloride intermediate with an amine of choice with a base such as TEA or DIPEA can afford compounds such as GS77. Hydrolysis of the ester can be achieved with lithium hydroxide in tetrahydrofuran and water to form the final acid product GS78.

In another aspect, compounds of the present invention of formula I, or subformulae thereof, are generally prepared according to Scheme 22 set forth below:

Scheme 22

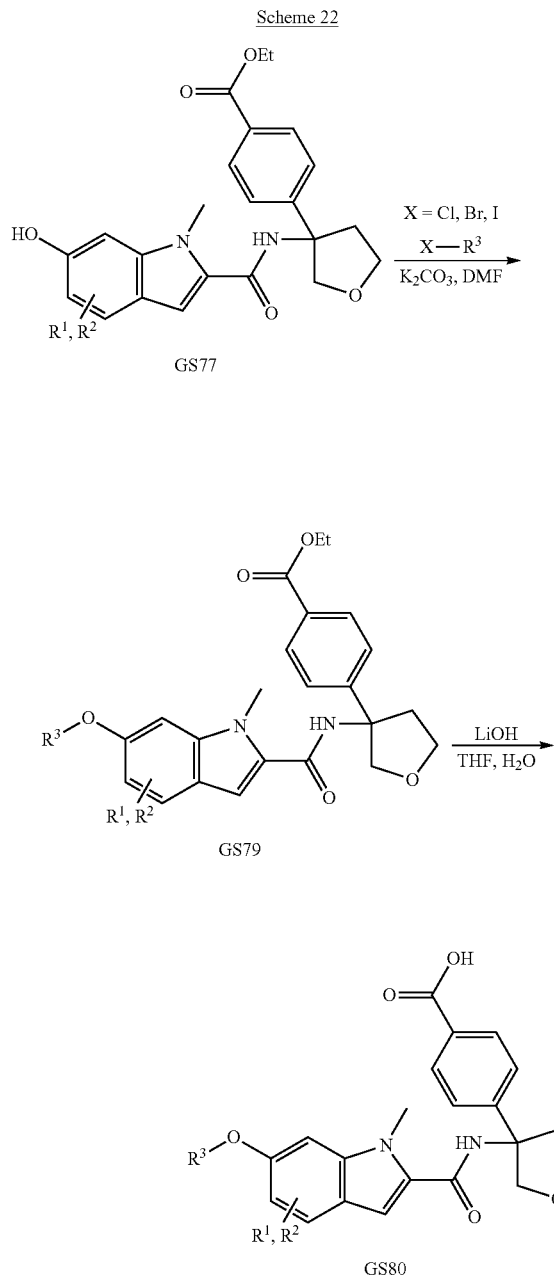

In another aspect, compounds of the present invention of formula I, or subformulae thereof, are generally prepared according to Scheme 23 set forth below:

Scheme 23

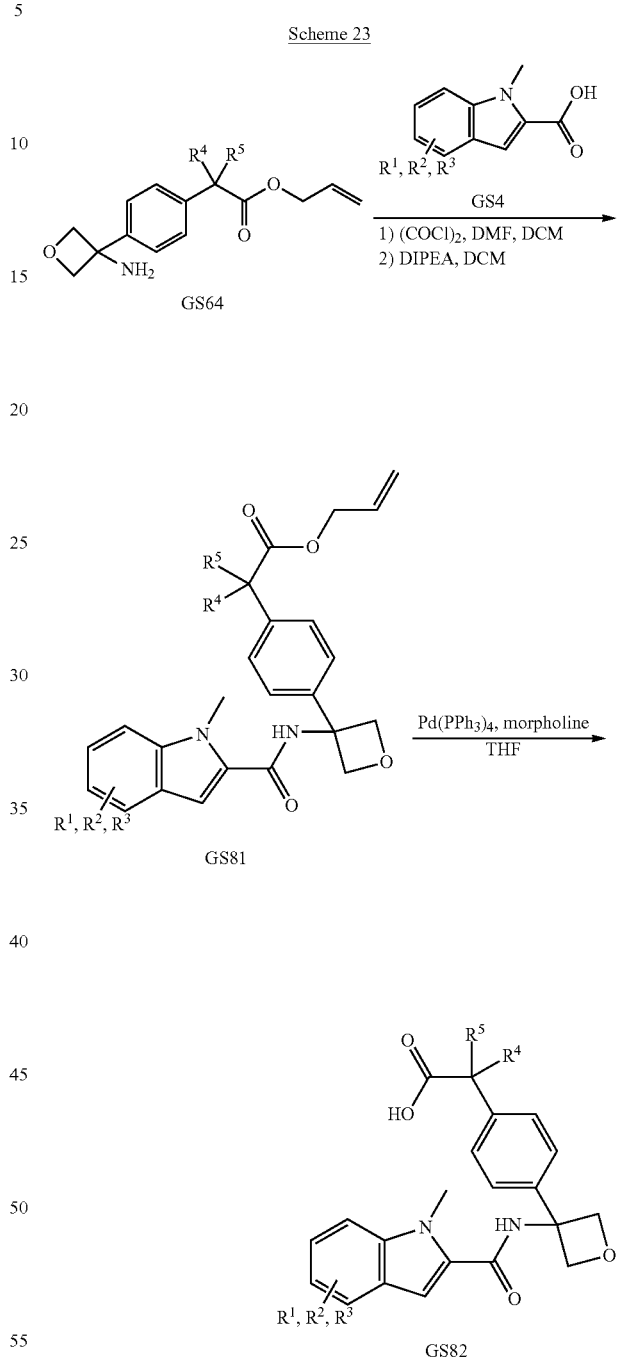

In Scheme 22 above, variables $R^1$, $R^2$, and $R^3$ are selected consistent with formula I, and subformulae thereof, described above and below. When intermediate GS77 (Scheme 22) is an hydroxyindole, it can be further alkylated using the corresponding alkyl-chloride, bromide or iodide under basic condition using conditions such as potassium carbonate in DMF to give GS79. The ester can then be hydrolyzed in similar fashion as described for GS78 to give final product GS80.

In Scheme 23 above, variables $R^1$, $R^2$, $R^3$, $R^4$, and $R^5$ are selected consistent with formula I, and subformulae thereof, described above and below. Coupling of amine compounds such as GS64 (Scheme 23) with acid GS4 is accomplished as described for GS77. Deprotection of the allyl group with Pd(PPh$_3$)$_4$ and morpholine in tetrahydrofuran provides the acid product GS82.

In another aspect, compounds of the present invention of formula I, or subformulae thereof, are generally prepared according to Scheme 24 set forth below:

Scheme 24

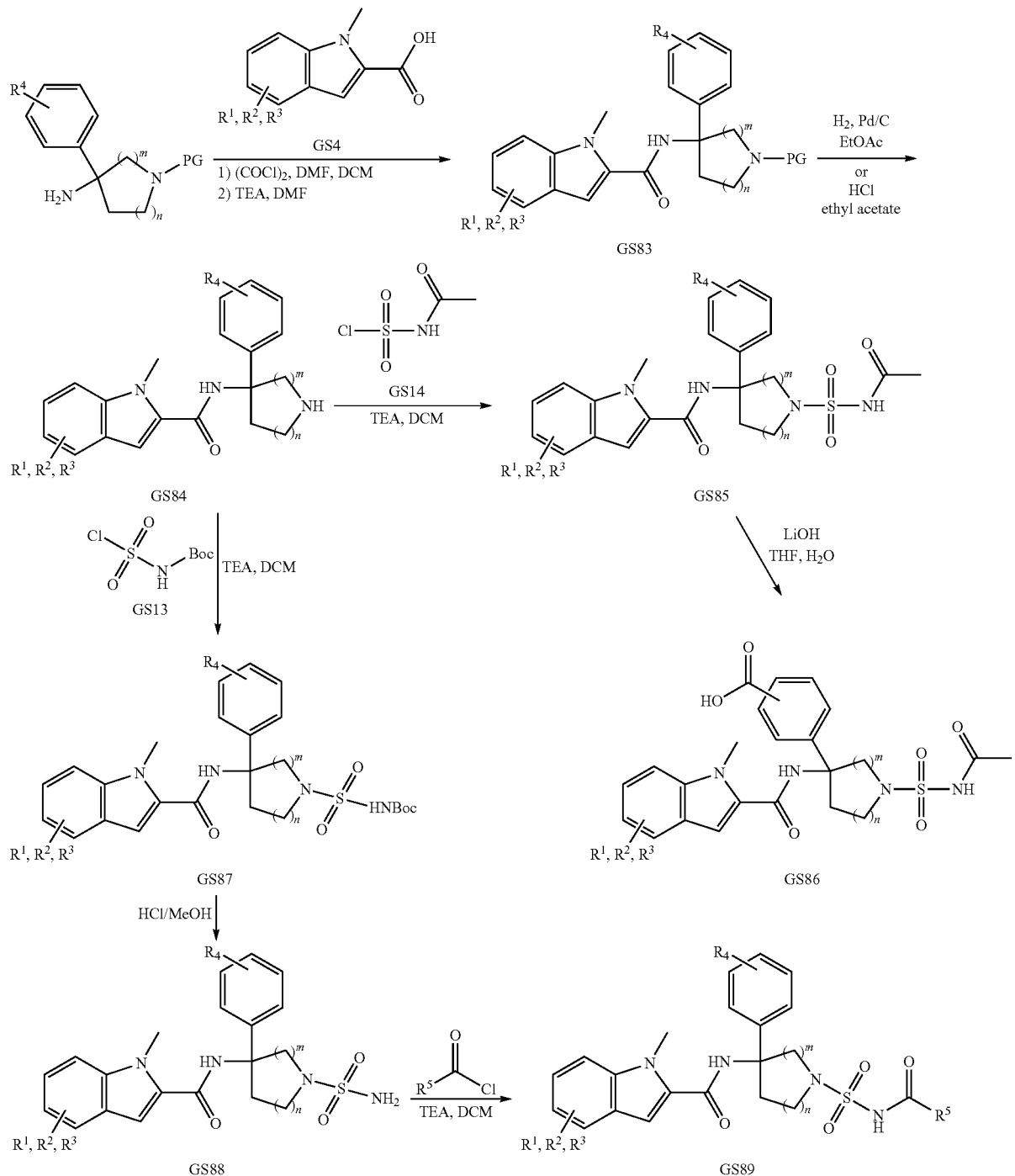

m = 1, 2
n = 0, 1, 2
PG = protecting group

In Scheme 24 above, variables $R^1$, $R^2$, $R^3$, $R^4$, and $R^5$ are selected consistent with formula I, and subformulae thereof, described above and below. A variety of tertiary amines (Scheme 24), where the 4-6 membered cyclic amine protected (with Bn, Boc, etc.), can be coupled with acid GS4 to form GS83 in a similar fashion as described for GS77. The cyclic amine can then be deprotected under standard conditions, such as hydrogenation with Pd/C for benzyl protection or hydrochloric acid in ethyl acetate or methanol for Boc deprotection to give GS84. Coupling of this cyclic amine N-acetylsulfamoyl chloride and triethylamine in dichloromethane provides final product GS85. If $R^4$ is an ester, it can further be reduced to the acid under standard conditions as described for GS78 to give final product GS86.

Alternatively, cyclic amine GS84 can be coupled with tert-butyl N-chlorosulfonylcarbamate with triethylamine in dichloromethane to form GS87. The Boc group can be removed under standard deprotection conditions such as hydrochloric acid in methanol to give GS88. The sulfamoyl group can then be coupled with various acyl or amide chlorides with triethylamine in dichloromethane to form the final product GS89.

Abbreviations
Ac: acetyl
AcOH: acetic acid
ACN: acetonitrile
Ad: adamantly
AIBN: 2,2'-azo bisisobutyronitrile
Anhyd: anhydrous
Aq: aqueous
BINAP: 2,2'-bis(diphenylphosphino)-1,1'-binaphthyl
$BH_3$: Borane
Bn: benzyl
Boc: tert-butoxycarbonyl
$Boc_2O$: di-tert-butyl dicarbonate
BPO: benzoyl peroxide
"BuOH: n-butanol
cSFC: chiral supercritical fluid chromatography
COD: cyclooctadiene
d: days
DAST: diethylaminosulfur trifluoride
dba: dibenzylideneacetone
DBU: 1,8-diazobicyclo[5.4.0]undec-7-ene
DCE: 1,2-dichloroethane
DCM: dichloromethane
DEA: diethylamine
DIBAL-H: diisobutylaluminum hydride
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide
DMSO-dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate
EtOH: ethanol
FA: formic acid
h: hours
HATU: N,N,N',N'-tetramethyl-O-(7-azabenzotriazol-1-yl)uronium hexafluorophosphate
HCl: hydrochloric acid
HPLC: high performance liquid chromatography
HOAc: acetic acid
IPA: isopropyl alcohol
KHMDS: potassium hexamethyldisilazide
$K_2CO_3$: potassium carbonate
LAH: lithium aluminum hydride
LDA: lithium diisopropylamide
m-CPBA: meta-chloroperbenzoic acid
M: molar
MeCN: acetonitrile
MeOH: methanol
$Me_2S$: dimethyl sulfide
MeONa: sodium methylate
MeI: iodomethane
min: minutes
mL: milliliters
mM: millimolar
mmol: millimoles
MOMCl: methyl chloromethyl ether
MsCl: methanesulfonyl chloride
MTBE: methyl tert-butyl ether
$NaNO_2$: sodium nitrite
$Na_2SO_4$: sodium sulfate
NBS: N-bromosuccinimide
NCS: N-chlorosuccinimide
NaOH: sodium hydroxide
NMP: N-methylpyrrolidine
NMR: Nuclear Magnetic Resonance
° C.: degrees Celsius
Pd/C: Palladium on Carbon
$Pd(OAc)_2$: Palladium Acetate
PBS: phosphate buffered saline
PE: petroleum ether
$POCl_3$: phosphorus oxychloride
$PPh_3$: triphenylphosphine
Rel: relative
R.T. or rt: room temperature
sat: saturated
SEMCl: chloromethyl-2-trimethylsilylethyl ether
SFC: supercritical fluid chromatography
$SOCl_2$: sulfur dichloride
tBuOK: potassium tert-butoxide
TBAB: tetrabutylammonium bromide
TEA: triethylamine
Tf: trifluoromethanesulfonate
TfAA: trifluoromethanesulfonic anhydride
TFA: trifluoracetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
Xantphos: 4,5-bis(diphenylphosphino)-9,9-dimethylxanthene General Synthetic Methods The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated. Optical rotations were measured in MeOH.

Proton NMR ($^1$H NMR) is conducted in deuterated solvent. In certain compounds disclosed herein, one or more 1H shifts overlap with residual protio solvent signals; these signals have not been reported in the experimental provided hereinafter

| Analytical instruments Table: | |
|---|---|
| LCMS | Shimadzu UFLC MS: LCMS-2020 |
| | Agilent Technologies 1200 series MS: Agilent Technologies 6110 |
| | Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For Acidic LCMS Data:
LCMS was recorded on an Agilent 1200 Series LC/MSD or Shimadzu LCMS2020 equipped with electro-spray ionization and quadruple MS detector [ES+ve to give MH$^+$] and equipped with Chromolith Flash RP-18e 25*2.0 mm, eluting with 0.0375 vol % TFA in water (solvent A) and 0.01875 vol % TFA in acetonitrile (solvent B).

For Basic LCMS Data:
LCMS was recorded on an Agilent 1200 Series LC/MSD or Shimadzu LCMS 2020 equipped with electro-spray ionization and quadruple MS detector [ES+ve to give MH$^+$] and equipped with Xbridge C18, 2.1×50 mm columns packed with 5 mm C18-coated silica or Kinetex EVO C18 2.1×30 mm columns packed with 5 mm C18-coated silica, eluting with 0.05 vol % NH$_3$—H$_2$O in water (solvent A) and acetonitrile (solvent B).

INTERMEDIATES 4,5-Dichloro-1-methyl-indole-2-carboxylic acid (Intermediate A)

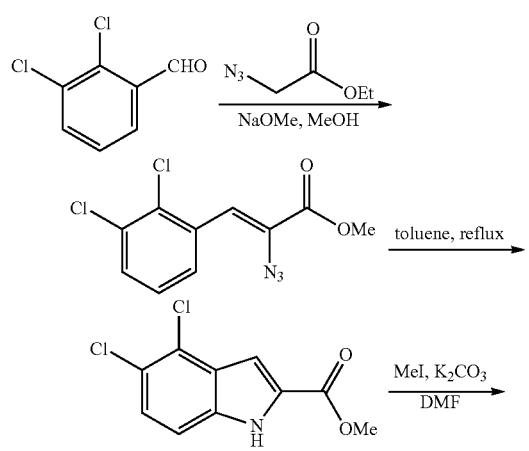

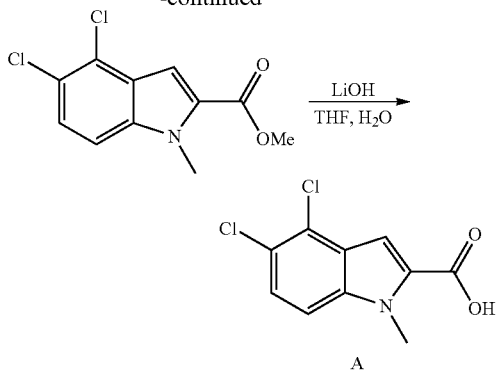

Step 1—Methyl (Z)-2-azido-3-(2,3-dichlorophenyl) prop-2-enoate

To a solution of sodium methoxide (11.1 g, 205 mmol) in anhydrous methanol (80 mL) was added a mixed solution of 2,3-dichlorobenzaldehyde (12.0 g, 68.5 mmol) and ethyl 2-azidoacetate (26.5 g, 205 mmol) in anhydrous methanol (80 mL) at −50° C. After stirring at −50° C. for 2 hrs, the mixture was warmed to rt, and stirred for 14 hrs. On completion, the suspension was poured onto ice and the azido derivative was collected by filtration, washed with cold water. The filter cake was dried in vacuo and purified by column chromatography (petroleum ether/ethyl acetate=10/1) to give the title compound as a white solid. $^1$H NMR (400 MHz, CDCl3) δ=8.06 (dd, J=1.3, 8.0 Hz, 1H), 7.45 (dd, J=1.4, 8.0 Hz, 1H), 7.30-7.24 (m, 2H), 3.97 (s, 3H).

Step 2—Methyl 4,5-dichloro-1H-indole-2-carboxylate

A solution of methyl (Z)-2-azido-3-(2,3-dichlorophenyl) prop-2-enoate (7.80 g, 28.6) in toluene (150 mL) was stirred at 120° C. for 16 hrs. On completion, the toluene was removed in vacuo to give a residue. The residue was purified by column chromatography (petroleum ether/ethyl acetate=12/1 to 5/1) to give the title compound as a white solid. $^1$H NMR (400 MHz, DMSO-d$_6$) δ=12.52 (br. s., 1H), 7.47-7.41 (m, 2H), 7.12 (d, J=2.1 Hz, 1H), 3.90 (s, 3H).

Step 3—Methyl 4,5-dichloro-1-methyl-indole-2-carboxylate

To a solution of methyl 4,5-dichloro-1H-indole-2-carboxylate (4.50 g, 18.4 mmol) in N,N-dimethylformamide (40 mL) was added potassium carbonate (6.37 g, 46.1 mmol) and iodomethane (10.4 g, 73.7 mmol). The mixture was stirred at 60° C. for 16 hrs. On completion, the reaction mixture was concentrated in vacuo to remove solvent. The residue was diluted with water 30 mL and extracted with dichloromethane (3×15 mL). The combined organic layer was dried over sodium sulfate, filtered and concentrated in vacuo to give a residue. The residue was purified by column chromatography (petroleum ether/ethyl acetate=8/1 to 3/1) to give the title compound as a white solid. $^1$H NMR (400 MHz, DMSO-d$_6$) δ=7.69 (d, J=8.8 Hz, 1H), 7.53 (d, J=8.8 Hz, 1H), 7.22 (s, 1H), 4.05 (s, 3H), 3.89 (s, 3H).

Step 4-4,5-Dichloro-1-methyl-indole-2-carboxylic acid

To a solution of methyl 4,5-dichloro-1-methyl-indole-2-carboxylate (4.10 g, 15.8 mmol) in a mixture solvent of tetrahydrofuran (40 mL) and water (10 mL) was added lithium hydroxide (1.14 g, 47.6 mmol). The mixture was stirred at rt for 16 hrs. On completion, the reaction mixture was concentrated in vacuo. The residue was acidified with 1M hydrochloric acid until pH=3. During which, a fine precipitate was formed and it was filtered and the filter cake was washed with water, dried under vacuum to give the title compound. $^1$H NMR (400 MHz, DMSO-$d_6$) δ=13.35 (br. s., 1H), 7.61 (d, J=8.9 Hz, 1H), 7.46 (d, J=8.9 Hz, 1H), 7.14 (s, 1H), 4.03 (s, 3H).

4-Chloro-5-methoxy-1-methyl-indole-2-carboxylic acid (Intermediate B)

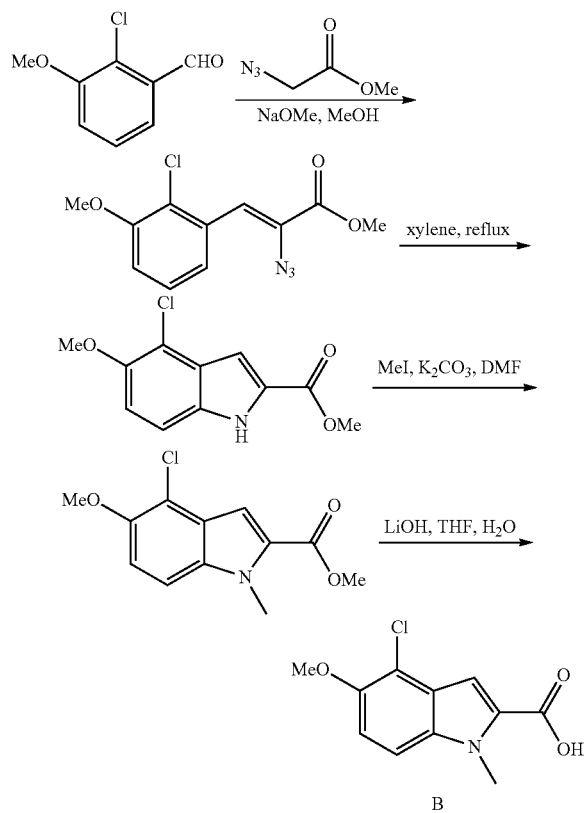

Step 1—Methyl-2-azido-3-(2-chloro-3-methoxy-phenyl)prop-2-enoate

To a solution of sodium methoxide (2.38 g, 43.9 mmol) in methanol (40 mL) was added 2-chloro-3-methoxy-benzaldehyde (2.50 g, 14.6 mmol) and ethyl 2-azidoacetate (4.73 g, 36.7 mmol) at −50° C. under nitrogen atmosphere. The mixture was stirred at the same temperature for 2 hrs, then warmed to rt and stirred for 14 hrs. On completion, the suspension was poured into ice and the azido derivative was collected by filtration and washed with cold water. The filter cake was dried over in vacuo to give the crude product. The crude product was purified by silica gel chromatography (petroleum ether:ethyl acetate=6:1) to give the title compound. $^1$H NMR (400 MHz, CDCl3) δ=7.77 (dd, J=1.0, 8.0 Hz, 1H), 7.35 (s, 1H), 7.31-7.26 (m, 1H), 6.95 (dd, J 1.3, 8.0 Hz, 1H), 3.96 (s, 3H), 3.94 (s, 3H).

Step 2—Methyl-4-chloro-5-methoxy-1H-indole-2-carboxylate

Methyl-2-azido-3-(2-chloro-3-methoxy-phenyl)prop-2-enoate (2.00 g, 7.47 mmol) was dissolved in xylol (200 mL) and the mixture was stirred at 180° C. for 30 min. On completion, the reaction mixture was concentrated in vacuo to afford a residue. The residue was triturated with (petroleum ether:ethyl acetate=10:1) to give the title compound. $^1$H NMR (400 MHz, DMSO-$d_6$) δ=12.16 (br. s., 1H), 7.40 (d, J=9.0 Hz, 1H), 7.24 (d, J=9.0 Hz, 1H), 7.04 (d, J=1.5 Hz, 1H), 3.89 (s, 3H), 3.86 (s, 3H).

Step 3—methyl 4-chloro-5-methoxy-1-methyl-indole-2-carboxylate

To a solution of methyl 4-chloro-5-methoxy-1H-indole-2-carboxylate (920 mg, 3.84 mmol) in N,N-dimethylformamide (15 mL) was added potassium carbonate (1.33 g, 9.60 mmol) and iodomethane (2.18 g, 15.4 mmol). The resulting mixture was warmed to 60° C. and stirred for 3 hrs. On completion, the reaction mixture was concentrated in vacuo to afford a residue. The residue was diluted with water (30 mL) and extracted with dichloromethane (3×25 mL). The combined organic layer was dried over anhydrous sodium sulfate, filtered and concentrated in vacuo to give the title compound. $^1$H NMR (400 MHz, DMSO-$d_6$) δ=7.57 (d, J=9.0 Hz, 1H), 7.30 (d, J=9.0 Hz, 1H), 7.10 (s, 1H), 4.00 (s, 3H), 3.88 (s, 3H), 3.86 (s, 3H).

Step 4—4-Chloro-5-methoxy-1-methyl-indole-2-carboxylic acid

To a solution of methyl 4-chloro-5-methoxy-1-methyl-indole-2-carboxylate (950 mg, 3.74 mmol) in tetrahydrofuran (16 mL) and water (4 mL) was added lithium hydroxide (268 mg, 11.2 mmol). The resulting mixture was stirred at rt for 3 hrs. On completion, the reaction mixture was concentrated in vacuo and the residue was acidified with 2N hydrochloric acid until pH=3. During which, a fine precipitate was formed. The precipitate was filtered and the filter cake was washed with water, dried in vacuo to give the title compound. $^1$H NMR (400 MHz, DMSO-$d_6$) δ=13.19 (br. s., 1H), 7.56 (d, J=9.0 Hz, 1H), 7.29 (d, J=9.0 Hz, 1H), 7.08 (s, 1H), 4.02 (s, 3H), 3.88 (s, 3H).

4-Chloro-1-methyl-indole-2-carboxylic acid (Intermediate C)

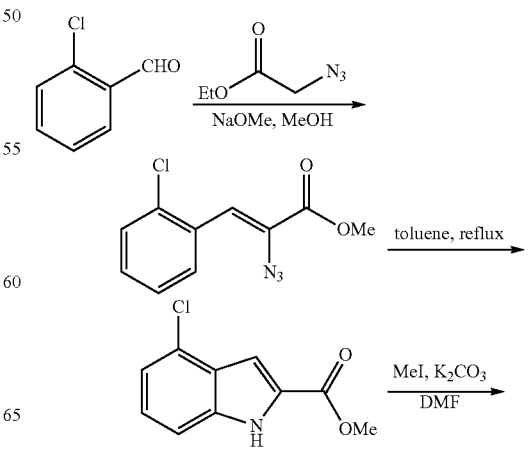

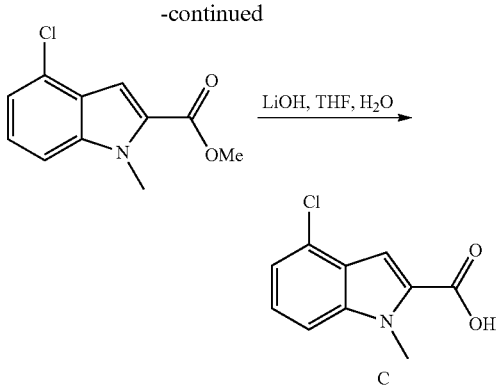

Step 1—Methyl (Z)-2-azido-3-(2-chlorophenyl)prop-2-enoate

To a solution of sodium methoxide (11.5 g, 213 mmol) in methanol (100 mL) was added a solution of 2-chlorobenzaldehyde (10.0 g, 71.1 mmol) and ethyl azidoacetate (27.5 g, 213 mmol) in methanol (50.0 mL) dropwise at −40° C. under nitrogen. After the reaction mixture was stirred at −40° C. for 1 hr, the reaction mixture was stirred at rt for 16 hrs. On completion, the resulting suspension was poured onto ice, filtrated and the filter cake was washed with cold water. The yellow solid was dried in vacuo and purified by silica gel chromatography (petroleum ether:ethyl acetate=20:1) to give the title compound. $^1$H NMR (400 MHz, CDCl3) δ=8.20 (dd, J=1.8, 7.7 Hz, 1H), 7.44 (dd, J=1.6, 7.8 Hz, 1H), 7.37-7.23 (m, 3H), 3.96 (s, 3H).

Step 2—Methyl 4-chloro-1H-indole-2-carboxylate

A solution of methyl (Z)-2-azido-3-(2-chlorophenyl)prop-2-enoate (12.9 g, 54.2 mmol) in toluene (400 mL) was stirred at 120° C. for 20 hrs under nitrogen. On completion, the reaction mixture was concentrated in vacuo to give a crude product, which was purified by silica gel chromatography (petroleum ether:ethyl acetate=5:1) to give the title compound. $^1$H NMR (400 MHz, CDCl3) δ=9.08 (br. s., 1H), 7.38-7.33 (m, 2H), 7.25 (t, J=12 Hz, 1H), 7.19 (d, J=8 Hz, 1H), 3.99 (s, 3H).

Step 3—Methyl 4-chloro-1-methyl-1H-indole-2-carboxylate

To a solution of methyl 4-chloro-1H-indole-2-carboxylate (5.30 g, 25.2 mmol) and potassium carbonate (10.4 g, 75.8 mmol) in N,N-dimethylformamide (70.0 mL) was added methyl iodide (10.7 g, 75.8 mmol) and the reaction mixture was stirred at 60° C. for 4 hrs. On completion, the reaction mixture was concentrated in vacuo to give a crude product, which was purified by silica gel chromatography (petroleum ether:ethyl acetate=5:1) to give the title compound. $^1$H NMR (400 MHz, DMSO-$d_6$) δ=7.63 (d, J=8.4 Hz, 1H), 7.36 (t, J=8.0 Hz, 1H), 7.28-7.17 (m, 2H), 4.06 (s, 3H), 3.88 (s, 3H).

Step 4—4-Chloro-1-methyl-indole-2-carboxylic acid

To a solution of methyl 4-chloro-1-methyl-indole-2-carboxylate (5.60 g, 25.0 mmol) in a mixture of tetrahydrofuran (40.0 mL) and water (40.0 mL) was added lithium hydrate (2.40 g, 100 mmol) and the reaction mixture was stirred at rt for 16 hrs. On completion, the reaction mixture was concentrated in vacuo and the aqueous phase was acidified with aqueous hydrochloric acid (4 M) until pH=3. Then the aqueous phase was extracted with ethyl acetate (3×200 mL). The combined layer was dried over anhydrous sodium sulfate, filtrated and concentrated in vacuo to give the title compound. $^1$H NMR (400 MHz, DMSO-$d_6$) δ=13.21 (br. s., 1H), 7.60 (d, J=8.4 Hz, 1H), 7.33 (t, J=7.6 Hz, 1H), 7.22 (d, J=7.2 Hz, 1H), 7.18 (s, 1H), 4.01 (s, 3H).

4-Chloro-5-fluoro-1-methyl-indole-2-carboxylic acid (Intermediate D)

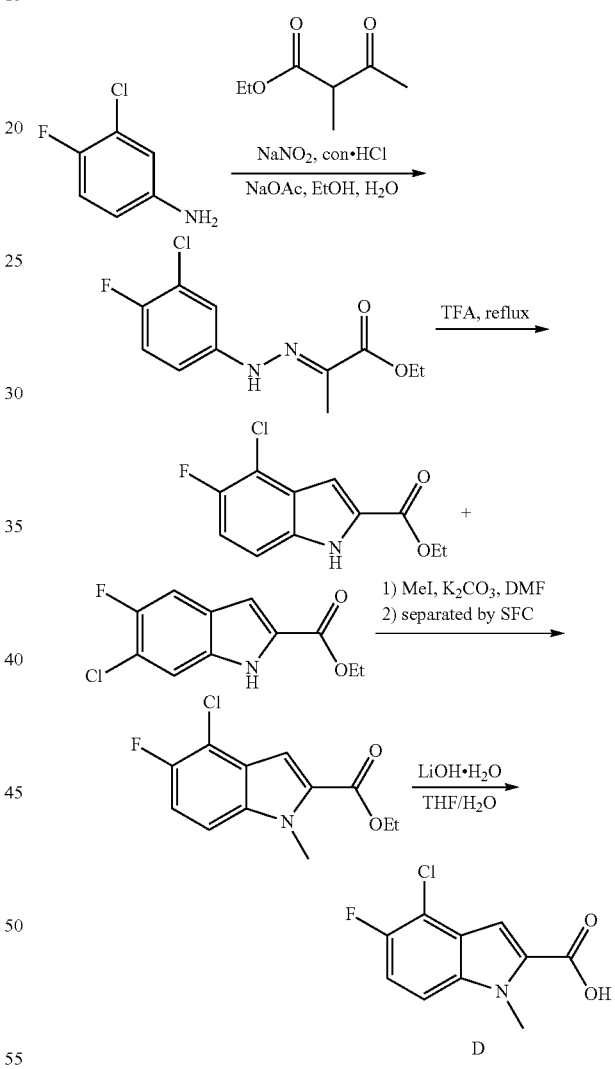

Step 1—Ethyl (2E)-2-[(3-chloro-4-fluoro-phenyl)hydrazono]propanoate

To a solution of 3-chloro-4-fluoro-aniline (15.0 g, 103 mmol) in ethanol (15 mL) and water (15 mL) was added hydrochloric acid (37%, 30 mL). The mixture was cooled to −5° C., and then a solution of NaNO$_2$ (8.00 g, 116 mmol) in water (40 mL) was added dropwise while the temperature was maintained below 5° C. A cold solution of ethyl 2-methyl-3-oxo-butanoate (15.0 g, 104 mmol) and sodium acetate (30.0 g, 366 mmol) in a mixture solvent of ethanol (75 mL) and water (30 mL) was added to the reaction mixture, and the reaction mixture was stirred at −5° C. for 4 hours. On completion, the reaction mixture was extracted with dichloromethane and concentrated in vacuo. The residue was purified by column chromatography (petroleum ether/ethyl acetate=30:1 to 10:1) to give the title compound. $^1$H NMR (400 MHz, CDCl$_3$) δ=7.33-7.25 (m, 1H), 7.05 (t, J=8.8 Hz, 1H), 6.98-6.90 (m, 1H), 4.29 (q, J=7.2 Hz, 2H), 2.17 (s, 3H), 1.38 (t, J=7.2 Hz, 3H).

Step 2—Ethyl 4-chloro-5-fluoro-1H-indole-2-carboxylate and Ethyl 6-chloro-5-fluoro-1H-indole-2-carboxylate A solution of ethyl (2E)-2-[(3-chloro-4-fluoro-phenyl)hydrazono] propanoate (6.70 g, 25.9 mmol) in trifluoroacetic acid (30 mL) was refluxed at 80° C. for 12 hours. On completion, the solvent was evaporated in vacuo, and the residue was diluted in ethyl acetate and was washed with a saturated aqueous sodium hydrogen carbonate solution and brine, then dried over sodium sulfate and concentrated. The residue was purified by silica gel column chromatography (petroleum ether/ethyl acetate=30:1 to 20:1) to give ethyl 4-chloro-5-fluoro-1H-indole-2-carboxylate (150 mg, 3% yield), ethyl 6-chloro-5-fluoro-1H-indole-2-carboxylate (700 mg, 11% yield) and a mixture of ethyl 4-chloro-5-fluoro-1H-indole-2-carboxylate and ethyl 6-chloro-5-fluoro-1H-indole-2-carboxylate (3.0 g) as yellowish solid. Ethyl 4-chloro-5-fluoro-1H-indole-2-carboxylate $^1$H NMR (300 MHz, DMSO-d6) δ=12.11 (br. s., 1H), 7.67 (d, J=10.0 Hz, 1H), 7.57 (d, J=6.4 Hz, 1H), 7.15 (d, J=1.1 Hz, 1H), 4.35 (q, J=9.2 Hz, 2H), 1.33 (t, J=9.2 Hz, 3H). Mixture ethyl 6-chloro-5-fluoro-1H-indole-2-carboxylate & ethyl 6-chloro-5-fluoro-1H-indole-2-carboxylate $^1$H NMR (300 MHz, DMSO-d6) δ=12.38 (br. s., 0.5H), 12.11 (br. s., 0.5H), 7.66 (d, J=10.0 Hz, 0.5H), 7.57 (d, J=6.4 Hz, 0.5H), 7.45 (dd, J=4.0, 8.9 Hz, 0.5H), 7.37-7.26 (m, 0.5H), 7.14 (dd, J=1.5, 5.8 Hz, 0.5H), 4.56-4.06 (m, 2H), 1.61-1.04 (m, 3H).

Step 3—Ethyl 4-chloro-5-fluoro-1-methyl-indole-2-carboxylate and ethyl 6-chloro-5-fluoro-1-methyl-indole-2-carboxylate To a solution of a mixture of ethyl 4-chloro-5-fluoro-1H-indole-2-carboxylate and ethyl 6-chloro-5-fluoro-1H-indole-2-carboxylate (5.00 g, 20.7 mmol) in N,N-dimethylformamide (20 mL) was added potassium carbonate (11.4 g, 82.7 mmol) and iodomethane (14.7 g, 103 mmol). Then the mixture was stirred at 60° C. for 12 hrs. On completion, the residue was diluted with water (100 mL), extracted with ethyl acetate (3×80 mL). The organic layers were dried over anhydrous sodium sulfate, filtrated and concentrated. The residue was purified by prep-SFC (Condition: Base-MeOH; Column: AD (250 mm*30 mm, 10 um) to give ethyl 4-chloro-5-fluoro-1-methyl-indole-2-carboxylate (2.6 g, 49% yield) and ethyl 6-chloro-5-fluoro-1-methyl-indole-2-carboxylate (2.4 g, 45% yield) as yellow solids. Ethyl 4-chloro-5-fluoro-1-methyl-indole-2-carboxylate $^1$H NMR (400 MHz, CDCl3) δ=7.38 (s, 1H), 7.31-7.22 (m, 1H), 7.22-7.15 (m, 1H), 4.42 (q, J=7.3 Hz, 2H), 4.09 (s, 3H), 1.45 (t, J=7.2 Hz, 3H). Ethyl 6-chloro-5-fluoro-1-methyl-indole-2-carboxylate $^1$H NMR (400 MHz, CDCl3) δ=7.49-7.37 (m, 2H), 7.24 (s, 1H), 4.40 (q, J=7.3 Hz, 2H), 4.09 (s, 3H), 1.45 (d, J=7.2 Hz, 3H).

Step 4—4-Chloro-5-fluoro-1-methyl-indole-2-carboxylic acid

To a mixture of ethyl 4-chloro-5-fluoro-1-methyl-indole-2-carboxylate (2.60 g, 10.2 mmol) in tetrahydrofuran (20 mL) and water (20 mL) was added lithium hydroxide (1.71 g, 40.7 mmol). Then the mixture was stirred at rt for 12 hrs. On completion, the mixture was concentrated in vacuum. The residue was diluted water (50 mL). The mixture was acidified with 2N hydrochloric acid until pH=3 and extracted with ethyl acetate (3×50 mL). The organic layers were dried over anhydrous sodium sulfate, filtrated and concentrated to give the title compound. $^1$H NMR (400 MHz, DMSO-d6) δ=7.75-7.57 (m, 1H), 7.39 (t, J=9.4 Hz, 1H), 7.19 (s, 1H), 4.05 (s, 3H).

Step 4—6-Chloro-5-fluoro-1-methyl-indole-2-carboxylic acid

To a solution of ethyl 6-chloro-5-fluoro-1-methyl-indole-2-carboxylate (2.40 g, 9.39 mmol) in a mixture solvent of tetrahydrofuran (20 mL) and water (20 mL) was added lithium hydroxide (1.58 g, 37.6 mmol). The mixture was stirred at rt for 12 hrs. On completion, the mixture was concentrated in vacuo. The residue was diluted water (50 mL), acidified with 2N hydrochloric acid until pH=3 and extracted with ethyl acetate (3×50 mL). The organic layer was dried over anhydrous sodium sulfate, filtrated and concentrated to give the title compound (2.10 g, 98% yield) as yellowish solid. $^1$HNMR (400 MHz, DMSO-d6) δ=13.18 (br. s., 1H), 8.07-7.85 (m, 1H), 7.68 (d, J=9.8 Hz, 1H), 7.21 (s, 1H), 4.09 (s, 3H).

4-Chloro-1,5-dimethyl-1H-indole-2-carboxylic acid (Intermediate E)

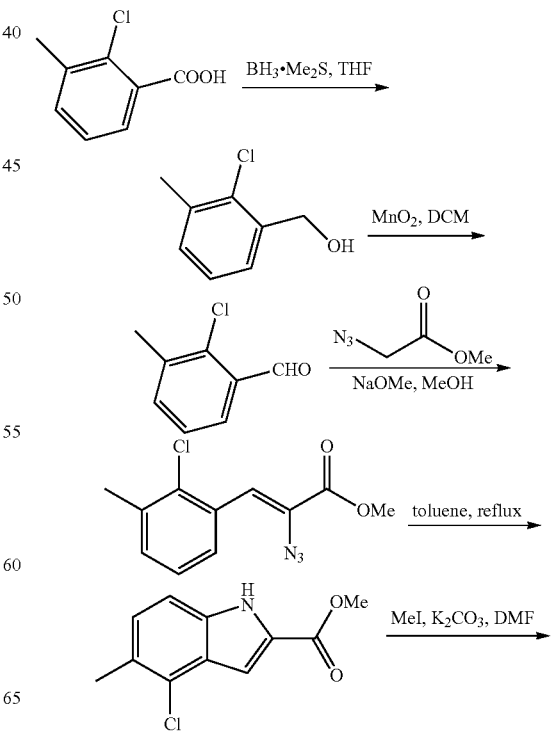

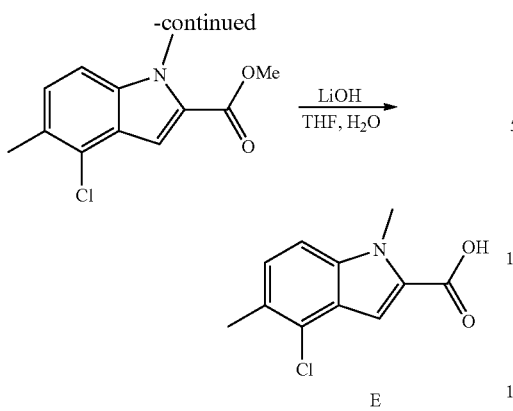

Step 1—(2-Chloro-3-methylphenyl)methanol

To a solution of 2-chloro-3-methyl-benzoic acid (30 g, 175 mmol) in anhydrous tetrahydrofuran (240 mL) was added dropwise $BH_3.Me_2S$ (10 M, 21 mL) under nitrogen. The reaction mixture was stirred at reflux at 70° C. for 12 hrs. On completion, the reaction mixture was quenched with methanol (50 mL), diluted with water (230 mL) and extracted with ethyl acetate (2×300 mL). The combined organic layers were dried over anhydrous sodium sulfate, filtered and concentrated under reduced pressure to give the crude product. The crude product was purified by silica gel chromatography (petroleum ether:ethyl acetate=5:1) to give the title compound. $^1$H NMR (400 MHz, DMSO-$d_6$) δ=7.42-7.34 (m, 1H), 7.24 (d, J=4.8 Hz, 2H), 5.36 (t, J=5.6 Hz, 1H), 4.55 (d, J=5.5 Hz, 2H), 2.32 (s, 3H).

Step 2—2-Chloro-3-methylbenzaldehyde

To a solution of (2-chloro-3-methyl-phenyl)methanol (26.2 g, 167 mmol) in dichloromethane (350 mL) was added manganese dioxide (116 g, 1.34 mol) under nitrogen. After, the reaction mixture was stirred at rt for 12 hrs. The solid was filtered, and the filtrate was concentrated under vacuum. The residue was purified by column chromatography (eluted with petroleum ether:ethyl acetate=20:1) to give the title compound. $^1$H NMR (400 MHz, DMSO-$d_6$) δ=10.42-10.34 (m, 1H), 7.68 (t, J=8.2 Hz, 2H), 7.42 (t, J=7.5 Hz, 1H), 2.39 (s, 3H).

Step 3—(Z)-Methyl 2-azido-3-(2-chloro-3-methylphenyl)acrylate

To a solution of MeONa (17.2 g, 319 mmol) in methanol (150 mL) was added a solution of ethyl 2-azidoacetate (41.2 g, 319 mmol) and 2-chloro-3-methyl-benzaldehyde (16.4 g, 106 mmol) in methanol (150 mL) dropwise at −20° C. After the mixture was stirred at −20° C. for 2 hrs, it was warmed up to rt for 12 hrs. During this time a fine precipitate was formed. The suspension was poured onto ice water and the azido derivative was collected by filtration, washed with cold water. The solid was dissolved in dichloromethane (200 mL), dried over anhydrous sodium sulfate and concentrated under reduced pressure to give the crude product. The crude product was purified by silica gel chromatography (petroleum ether:ethyl acetate=10:1) to give the title compound. $^1$H NMR (400 MHz, CDCl3) δ=8.04-7.95 (m, 1H), 7.37 (s, 1H), 7.26-7.20 (m, 2H), 3.96 (s, 3H), 2.48-2.37 (m, 3H).

Step 4—Methyl 4-chloro-5-methyl-1H-indole-2-carboxylate

A solution of methyl (Z)-2-azido-3-(2-chloro-3-methylphenyl)prop-2-enoate (20.9 g, 83.2 mmol) in toluene (250 mL) was heated to 120° C. under a nitrogen for 16 hrs. On completion, the reaction mixture was concentrated to afford the crude product as a yellow solid. The crude product was purified by silica gel chromatography (petroleum ether:ethyl acetate=20:1) to give the title compound. $^1$H NMR (400 MHz, DMSO-$d_6$) δ=12.21 (br. s., 1H), 7.34 (d, J=8.3 Hz, 1H), 7.23 (d, J=8.5 Hz, 1H), 7.07 (d, J=1.3 Hz, 1H), 3.89 (s, 3H), 2.40 (s, 3H).

Step 5—Methyl 4-chloro-1,5-dimethyl-1H-indole-2-carboxylate

To a solution of methyl 4-chloro-5-methyl-1H-indole-2-carboxylate (16.0 g, 71.8 mmol) in DMF (300 mL) was added $K_2CO_3$ (9.93 g, 71.8 mmol) and MeI (30.4 g, 215 mmol) at rt. The reaction was stirred at 60° C. under nitrogen for 16 hrs. On completion, the reaction mixture was filtered and the filter cake was washed with dichloromethane (30 mL), the filtrate was concentrated to afford the crude product. The crude product was purified by silica gel chromatography (petroleum ether:ethyl acetate=10:1) to give the title compound. $^1$H NMR (400 MHz, CDCl3) δ=7.36 (s, 1H), 7.28-7.19 (m, 2H), 4.07 (s, 3H), 3.94 (s, 3H), 2.49 (s, 3H).

Step 6—4-Chloro-1,5-dimethyl-1H-indole-2-carboxylic acid

To a solution of methyl 4-chloro-1,5-dimethyl-indole-2-carboxylate (11.0 g, 46.4 mmol) in a mixture solvent of tetrahydrofuran (90 mL) and $H_2O$ (30 ml) was added $LiOH.H_2O$ (7.80 g, 186 mmol) at rt under nitrogen. The reaction mixture was stirred at rt for 16 hrs. On completion, the reaction mixture was concentrated in vacuo, and the residue was acidified with 2 N HCl (20 mL) to pH=3, and then was filtered. The filter cake was wash with water (20 mL), dried in vacuo to give the title compound. $^1$H NMR (400 MHz, DMSO-$d_6$) δ=13.14 (br. s., 1H), 7.49 (d, J=8.5 Hz, 1H), 7.29 (d, J=8.5 Hz, 1H), 7.11 (s, 1H), 4.01 (s, 3H), 2.41 (s, 3H).

4,5-Dichloro-6-methoxy-1-methyl-indole-2-carboxylic acid (Intermediate F)

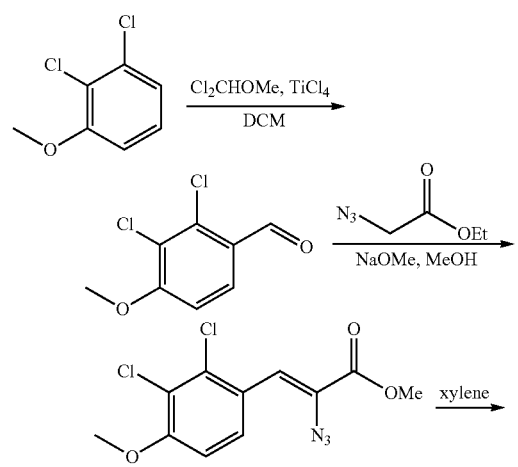

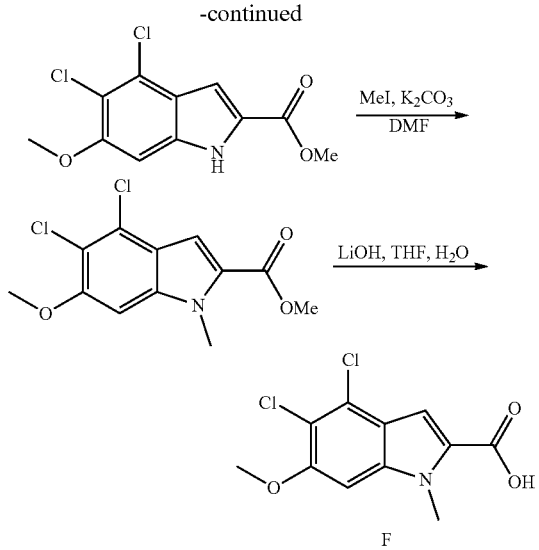

Step 1—2,3-Dichloro-4-methoxy-benzaldehyde

To a solution of 1,2-dichloro-3-methoxy-benzene (5.00 g, 28.2 mmol) in dichloromethane (30 mL) was added TiCl$_4$ (9.11 g, 48.0 mmol) dropwise at 0° C. under nitrogen. Then dichloro(methoxy)methane (3.25 g, 28.2 mmol) was added to the solution dropwise at 0° C. under nitrogen, and the solution was stirred at rt for 5 hrs. The residue was poured into water (200 mL). The aqueous phase was extracted with ethyl acetate (3×300 mL). The combined organic phase was washed with brine (3×200 mL), dried over anhydrous sodium sulfate, filtered and concentrated in vacuo. The residue was purified by silica gel chromatography (petroleum ether:ethyl acetate=100:1 to 10:1) to give the title compound. $^1$H-NMR (CD$_3$Cl$_3$, 400 MHz): δ=10.36 (s, 1H), 7.89 (d, J=8.8 Hz, 1H), 7.97 (d, J=8.8 Hz, 1H), 4.01 (s, 3H)

Step 2—Methyl(Z)-2-azido-3-(2,3-dichloro-4-methoxy-phenyl)prop-2-enoate

To a solution of sodium methoxide (7.90 g, 146 mmol) in methanol (300 mL) was added 2,3-dichloro-4-methoxy-benzaldehyde (10.0 g, 48.8 mmol) several portions at −20° C. under nitrogen, then ethyl 2-azidoacetate (18.9 g, 146.3 mmol) was added to the solution dropwise at −20° C. under nitrogen. The mixture was stirred at rt for 12 hrs. The mixture was poured into water (500 mL) and extracted with ethyl acetate (3×500 mL). The combined organic phase was washed with saturated brine (3×500 mL), dried over anhydrous sodium methoxide, filtered and concentrated in vacuo. The residue was purified by column chromatography (petroleum ether:ethyl acetate=100:1 to 1:1) to give the title compound. $^1$H NMR (400 MHz, CDCl3) δ=8.19 (d, J=8.8 Hz, 1H), 7.29 (d, J=3.5 Hz, 1H), 6.93 (d, J=9.0 Hz, 1H), 3.98 (s, 3H), 3.96 (s, 3H).

Step 3—Methyl4,5-dichloro-6-methoxy-1H-indole-2-carboxylate

Methyl (Z)-2-azido-3-(2,3-dichloro-4-methoxy-phenyl)prop-2-enoate (500 mg, 1.66 mmol) was added to xylene (100 mL) in one portion at rt, the solution was stirred at 120° C. for 12 hrs. The mixture was concentrated in vacuo. The residue was washed with (petroleum ether:ethyl acetate=10:1, 50 mL) to give the title compound. $^1$H NMR (400 MHz, DMSO-d$_6$) δ=12.31 (br. s., 1H), 7.07 (d, J=1.3 Hz, 1H), 7.01 (s, 1H), 3.91 (s, 3H), 3.88 (s, 3H).

Step 4—4,5-Dichloro-6-methoxy-1-methyl-indole-2-carboxylate

To a solution of methyl 4,5-dichloro-6-methoxy-1H-indole-2-carboxylate (220 mg, 803 umol) in N,N-dimethylformamide (5 mL) was added potassium carbonate (333 mg, 2.41 mmol) and methyl iodide (342 mg, 2.41 mmol) in one portion at rt under nitrogen. The mixture was stirred at 50° C. for 12 hrs. The mixture was then poured into water (10 mL). The aqueous phase was extracted with ethyl acetate (3×20 mL) the combined organic phase was washed with brine (3×20 mL), dried over anhydrous sodium sulfate, filtered and concentrated in vacuo to give the title compound. $^1$H-NMR (DMSO-d6, 400 MHz): δ=7.31 (s, 1H), 7.15 (s, 1H), 4.03 (s, 3H), 3.97 (s, 3H), 3.86 (s, 3H).

Step 5—4,5-Dichloro-6-methoxy-1-methyl-indole-2-carboxylic acid

To a solution of methyl 4,5-dichloro-6-methoxy-1-methyl-indole-2-carboxylate (200 mg, 694 umol) in a mixture solvent of tetrahydrofuran (10 mL) and water (10 mL) was added lithium hydroxide (49.8 mg, 2.08 mmol) in one portion at rt under nitrogen. The mixture was stirred at rt for 12 hrs. The mixture was concentrated in vacuo, the residue was adjusted to pH=0.3 with 3N hydrochloric acid (3 mL). The solid was filtered and concentrated in vacuum to give the title compound. $^1$H NMR (400 MHz, DMSO-d6) δ=12.90 (br. s., 1H), 7.29 (s, 1H), 7.10 (s, 1H), 4.02 (s, 3H), 3.98 (s, 3H).

4-Chloro-6-methoxy-1-methyl-indole-2-carboxylic acid (Intermediate G)

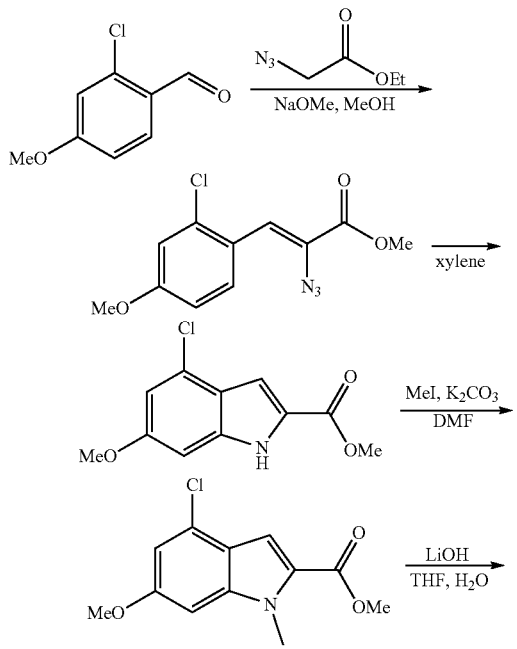

-continued

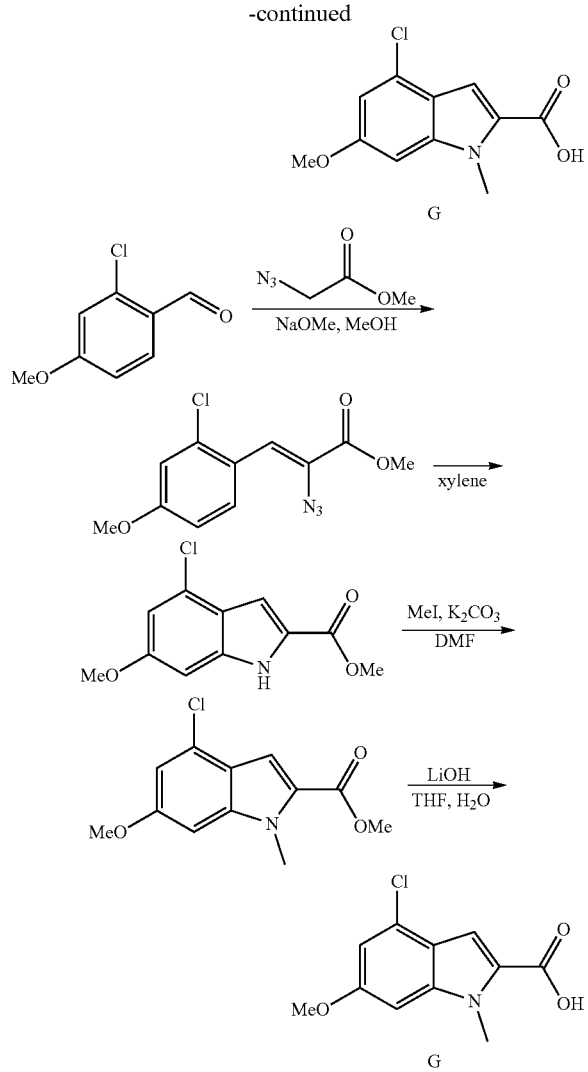

Step 1—Methyl (Z)-2-azido-3-(2-chloro-4-methoxyphenyl)prop-2-enoate

To a mixture of sodium methoxide (950 mg, 17.6 mmol) in methanol (10 mL) was added 2-chloro-4-methoxy-benzaldehyde (1.00 g, 5.86 mmol) and ethyl 2-azidoacetate (2.27 g, 17.6 mmol) in methanol (10 mL) dropwise at −40° C. under nitrogen. The mixture was stirred at −40° C. for 30 minutes, then the mixture was warmed to rt and stirred for 1.5 hours. On completion, the reaction was poured into water (50 mL) and the reaction was filtrated and the filter cake was dried in vacuo to give the title compound. $^1$H NMR (400 MHz, CDCl$_3$) δ=8.39-8.15 (m, 1H), 7.43-7.16 (m, 1H), 7.09-6.15 (m, 2H), 3.95 (s, 3H), 3.88 (s, 3H).

Step 2—Methyl 4-chloro-6-methoxy-1H-indole-2-carboxylate

Methyl (Z)-2-azido-3-(2-chloro-4-methoxy-phenyl)prop-2-enoate (440 mg, 1.64 mmol) was dissolved in xylene (10 mL) under nitrogen. The mixture was heated to 140° C. and stirred for 1 hour. On completion, the reaction was concentrated in vacuo to give the title compound (370 mg, crude) as yellow solid. $^1$H NMR (400 MHz, CDCl$_3$) δ=8.96 (s, 1H), 7.28 (s, 1H), 6.88 (s, 1H), 6.76 (s, 1H), 3.95 (s, 3H), 3.86 (s, 3H).

Step 3—Methyl 4-chloro-6-methoxy-1-methyl-indole-2-carboxylate

To a mixture of methyl 4-chloro-6-methoxy-1H-indole-2-carboxylate (250 mg, 1.04 mmol) and potassium carbonate (431 mg, 3.12 mmol) in N,N-dimethylformamide (5 mL) was added methyl iodide (738 mg, 5.20 mmol) in one portion at rt under nitrogen. The mixture was stirred at rt for 30 minutes, then the mixture was heated to 60° C. and stirred for 1.5 hours. On completion, the reaction was poured into water (15 mL) and was stirred for 10 minutes. The reaction was filtrated and the solid was dried in vacuo to give the title compound. $^1$H NMR (400 MHz, DMSO-d6) δ=7.12 (s, 1H), 7.10 (s, 1H), 6.91 (s, 1H), 3.99 (s, 3H), 3.85 (s, 3H), 3.83 (s, 3H).

Step 4—4-Chloro-6-methoxy-1-methyl-indole-2-carboxylic acid

To a mixture of methyl 4-chloro-6-methoxy-1-methyl-indole-2-carboxylate (90.0 mg, 355 umol) in tetrahydrofuran (1 mL) and water (1 mL) was added lithium hydroxide (68.0 mg, 2.84 mmol) in one portion at rt under nitrogen. The mixture was stirred at rt and stirred for 2 hours. The reaction was concentrated in vacuo. On completion, the residue was poured into water (10 mL) and acidified by 2 N hydrochloric acid (2 mL) to pH=1-2. The mixture was filtrated and the solid was dried in vacuo to give the title compound. LCMS: (ES$^+$) m/z (M+H)$^+$=240.1, tR=0.804.

4,5-Dichloro-6-hydroxy-1-methyl-indole-2-carboxylic acid (Intermediate H)

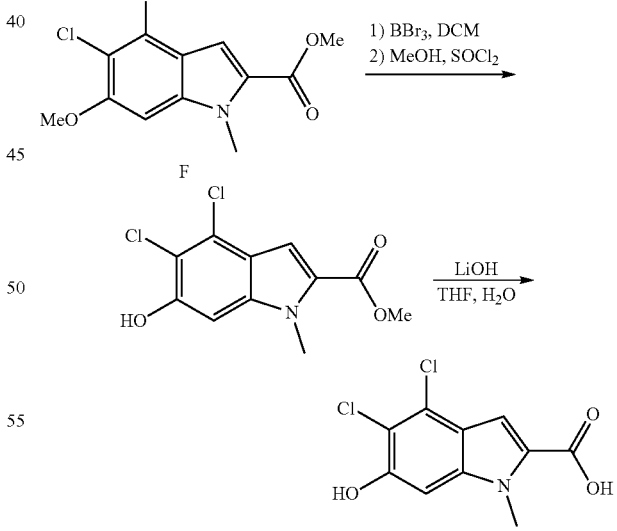

Step 1—Methyl 4,5-dichloro-6-hydroxy-1-methyl-indole-2-carboxylate

To a solution of methyl 4,5-dichloro-6-methoxy-1-methyl-indole-2-carboxylate (1.60 g, 5.55 mmol) in dichloromethane (20 mL) was added boron tribromide (2.78 g, 11.1 mmol, 1.07 mL) at 0° C., then the mixture was stirred at rt for 16 hours. On completion, the mixture was diluted with dichloromethane (20 mL), then the solution was poured into water (30 mL). The mixture was filtered and the filtrate was extracted with dichloromethane (3×30 mL). The combined organic phase was concentrated, and the residue was combined with filter cake and dried in vacuo to give a mixture of 4,5-dichloro-6-hydroxy-1-methyl-1H-indole-2-carboxylic acid and its methyl ester.

To a solution of a mixture of 4,5-dichloro-6-hydroxy-1-methyl-1H-indole-2-carboxylic acid and its methyl ester (0.44 g, 5.54 mmol) in methanol (20 mL) was added thionyl chloride (725 mg, 6.09 mmol) at rt, then the mixture was stirred at 50° C. for 16 hours. On completion, the mixture was concentrated in vacuo and the residue was triturated with methanol (10 mL); the mixture was filtered to get the filter cake and the filter cake was dried in vacuo to give the title compound. $^1$H NMR (400 MHz, DMSO-d6) δ=10.71 (br. s., 1H), 7.10 (s, 1H), 6.98 (s, 1H), 3.91 (s, 3H), 3.86 (s, 3H).

Step 2—4,5-Dichloro-6-hydroxy-1-methyl-indole-2-carboxylic acid

To a solution of methyl 4,5-dichloro-6-hydroxy-1-methyl-indole-2-carboxylate (500 mg, 1.82 mmol) in tetrahydrofuran (5 mL) and water (5 mL) was added lithium hydroxide (130 mg, 5.46 mmol). The mixture was stirred at rt for 16 hours. On completion, the mixture was diluted with water (10 mL) and extracted with ethyl acetate (2×20 mL). The aqueous phase was adjusted to pH=4-5 with hydrochloric acid (2 N) and filtered to get the filter cake. The filter cake was dried in vacuo to give the title compound. $^1$H NMR (300 MHz, DMSO-d6) δ=13.00 (br. s., 1H), 10.66 (s, 1H), 7.08 (s, 1H), 6.99 (s, 1H), 3.98 (s, 3H).

4-Chloro-6-hydroxy-1-methyl-indole-2-carboxylic acid (Intermediate I)

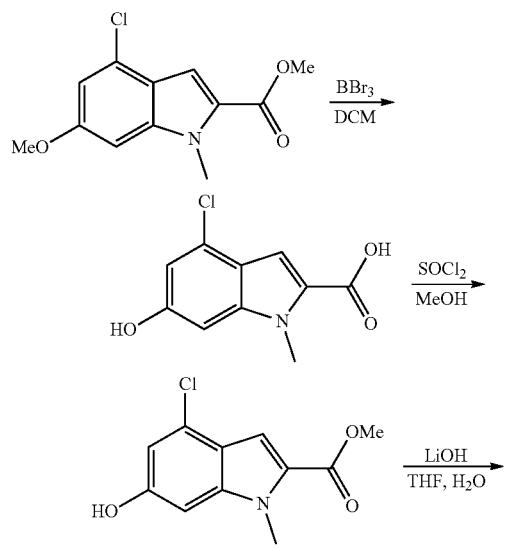

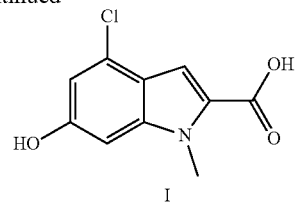

Step 1—4-Chloro-6-hydroxy-1-methyl-indole-2-carboxylic acid

To a mixture of methyl 4-chloro-6-methoxy-1-methyl-indole-2-carboxylate (400 mg, 1.58 mmol) in dichloromethane (30 mL) was added boron tribromide (3.96 g, 15.8 mmol) in one portion at 0° C. under nitrogen. The mixture was stirred at 0° C. for 30 min, then at rt for 15.5 hours. On completion, the reaction was poured into saturated aqueous sodium bicarbonate (200 mL) and acidified with concentrated hydrochloric acid until pH=1-2. The reaction was concentrated in vacuo. The mixture was filtrated and the aqueous phase was extracted with dichloromethane (3×10 mL). The organic layer was combined and concentrated in vacuo to give the title compound. $^1$H NMR (400 MHz, DMSO-d$_6$) δ=12.83 (br s, 1H), 9.99 (s, 1H), 7.05 (s, 1H), 6.80-6.75 (m, 2H), 3.90 (s, 3H).

Step 2—Methyl 4-chloro-6-methoxy-1H-indole-2-carboxylate

To a mixture of 4-chloro-6-hydroxy-1-methyl-indole-2-carboxylic acid (400 mg, 1.77 mmol) in methanol (15 mL) was added thionyl chloride (422 mg, 3.55 mmol) at rt under nitrogen. The mixture was stirred at rt for 30 min, then at 62° C. for 15.5 hrs. On completion, the reaction was concentrated in vacuo to give the title compound.

Step 3—4-Chloro-6-hydroxy-1-methyl-indole-2-carboxylic acid

To a mixture of methyl 4-chloro-6-hydroxy-1-methyl-indole-2-carboxylate (400 mg, 1.67 mmol) in tetrahydrofuran (10 mL) and water (5 mL) was added lithium hydroxide (160 mg, 6.68 mmol) in one portion at rt. The mixture was stirred at rt for 30 min, then at 50° C. for 2.5 hrs. On completion, the mixture was concentrated in vacuo to remove the organic solvent. The aqueous phase was acidified with hydrochloric acid (2 N) until pH=1-2. The solid was collected by filtration, and dried in vacuo to give the title compound. $^1$H NMR (400 MHz, DMSO-d$_6$) δ=12.86 (br s, 1H), 9.90 (s, 1H), 7.05 (s, 1H), 6.78-6.76 (m, 2H), 3.90 (s, 3H).

9-Chloro-6-methyl-3,6-dihydro-2H-[1,4]dioxino[2,3-f]indole-7-carboxylic acid (Intermediate J)

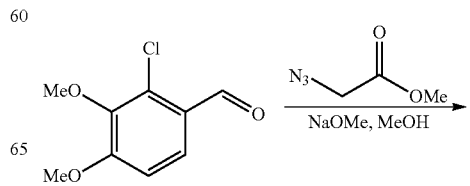

-continued

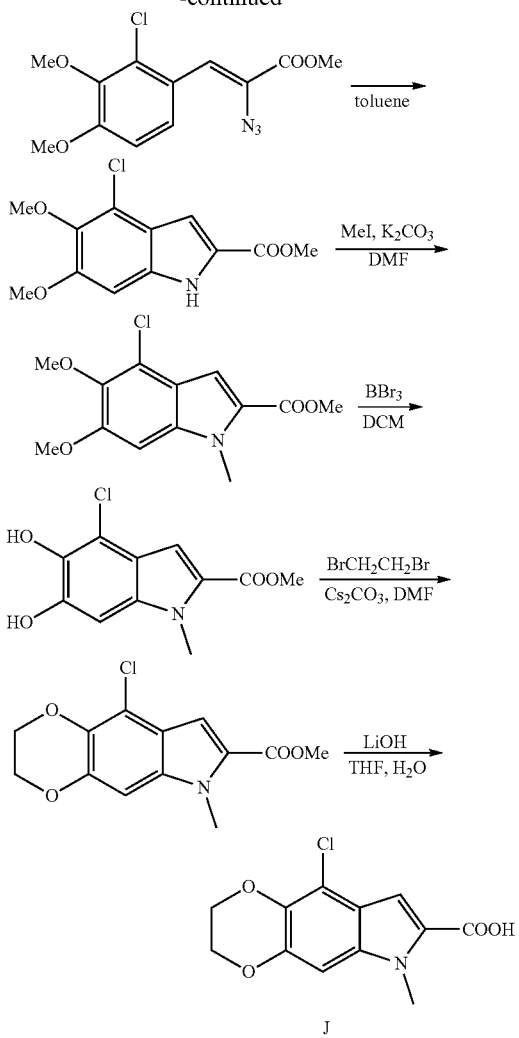

Step 1—(Z)-Methyl 2-azido-3-(2-chloro-3,4-dimethoxy-phenyl)prop-2-enoate

To a solution of sodium methoxide (6.46 g, 120 mmol) in methanol (100 mL) was added a mixture of 2-chloro-3,4-dimethoxy-benzaldehyde (8.00 g, 40.0 mmol) and methyl 2-azidoacetate (13.8 g, 120 mmol) in methanol (100 mL) at −40° C. The mixture was stirred from −40° C. to rt in 2 hours and then at rt for 3 hours. On completion, the mixture was poured into water (50 mL) where a solid formed. The solid was collected by filtration, washed with methanol (50 mL) to give the title compound. $^1$H NMR (400 MHz, DMSO-d$_6$) δ=8.02 (d, J=9.0 Hz, 1H), 7.15 (d, J=9.0 Hz, 1H), 7.13 (s, 1H), 3.89 (s, 3H), 3.88 (s, 3H), 3.76 (s, 3H).

Step 2—Methyl 4-chloro-5,6-dimethoxy-1H-indole-2-carboxylate

A solution of methyl (Z)-2-azido-3-(2-chloro-3,4-dimethoxy-phenyl)prop-2-enoate (4.00 g, 13.4 mmol) in toluene (60 mL) was stirred at 110° C. for 2 hours. On completion, the reaction mixture was concentrated. The residue was triturated with toluene (20 mL) to give the title compound. LCMS: (ES$^-$) m/z (M+H)$^+$=270.1, tR=0.782.

Step 3—Methyl 4-chloro-5,6-dimethoxy-1-methyl-indole-2-carboxylate

To the solution of methyl 4-chloro-5,6-dimethoxy-1H-indole-2-carboxylate (1.20 g, 4.45 mmol) and potassium carbonate (922 mg, 6.67 mmol) in N,N-dimethylformamide (8 mL) was added methyl iodide (1.89 g, 13.4 mmol). The reaction mixture was stirred at 60° C. for 12 hours. On completion, the mixture was poured into water (20 mL), where a solid formed. The solid was collected by filtration to give the title compound. $^1$H NMR (400 MHz, DMSO-d6) δ=7.19 (s, 1H), 7.12 (s, 1H), 4.01 (s, 3H), 3.94 (s, 3H), 3.85 (s, 3H), 3.76 (s, 3H).

Step 4—Methyl 4-chloro-5,6-dihydroxy-1-methyl-indole-2-carboxylate

To the solution of methyl 4-chloro-5,6-dimethoxy-1-methyl-indole-2-carboxylate (500 mg, 1.76 mmol) in dichloromethane (15 mL) was added tribromoborane (4.41 g, 17.6 mmol) at −78° C. The reaction mixture was stirred from −78° C. to rt in 2 hours, then at rt for 3 hours. On completion, the mixture was poured into water (20 mL) and extracted with ethyl acetate (3×50 mL). The combined organic layers were dried over anhydrous sodium sulfate and concentrated. The residue was purified by chromatography (petroleum ether:ethyl acetate=4:1) to give the title product. $^1$H NMR (400 MHz, DMSO-d6) δ=10.08 (s, 1H), 8.94 (s, 1H), 7.01 (s, 1H), 6.83 (s, 1H), 3.90 (s, 3H), 3.82 (s, 3H).

Step 5—Methyl 9-chloro-6-methyl-3,6-dihydro-2H-[1,4]dioxino[2,3-f]indole-7-carboxylate To the solution of methyl 4-chloro-5,6-dihydroxy-1-methyl-indole-2-carboxylate (380 mg, 1.49 mmol) in N,N-dimethylformamide (3 mL) was added 1,2-dibromoethane (335 mg, 1.78 mmol) and cesium carbonate (1.45 g, 4.46 mmol). The reaction mixture was stirred at 70° C. for 2 hrs. On completion, the mixture was diluted with water (20 mL) and extracted with ethyl acetate (3×10 mL). The combined organic layers were dried over anhydrous sodium sulfate and concentrated in vacuo. The residue was purified by chromatography (petroleum ether:ethyl acetate=8:1) to give the title compound. LCMS: (ES$^+$) m/z (M+H)$^+$=282.0, tR=0.898.

Step 6—9-Chloro-6-methyl-3,6-dihydro-2H-[1,4]dioxino[2,3-f]indole-7-carboxylic acid To the solution of methyl 9-chloro-6-methyl-2,3-dihydro-[1,4]dioxino[2,3-f]indole-7-carboxylate (100 mg, 355 umol) in tetrahydrofuran (10 mL) and water (3 mL) was added lithium hydroxide (17.0 mg, 710 umol). The reaction mixture was stirred at 60° C. for 4 hrs. On completion, the mixture was concentrated in vacuo to remove the organic solvent, and then acidified by hydrochloric acid (2 N). The solid was collected by filtration, washed with water (5 mL) to give the title product. $^1$H NMR (400 MHz, DMSO-d6) δ=12.92 (br. s., 1H), 7.09 (s, 1H), 7.03 (s, 1H), 4.37-4.29 (m, 4H), 3.93 (s, 3H).

Methyl 4-chloro-5-hydroxy-1-methyl-indole-2-carboxylate (Intermediate K)

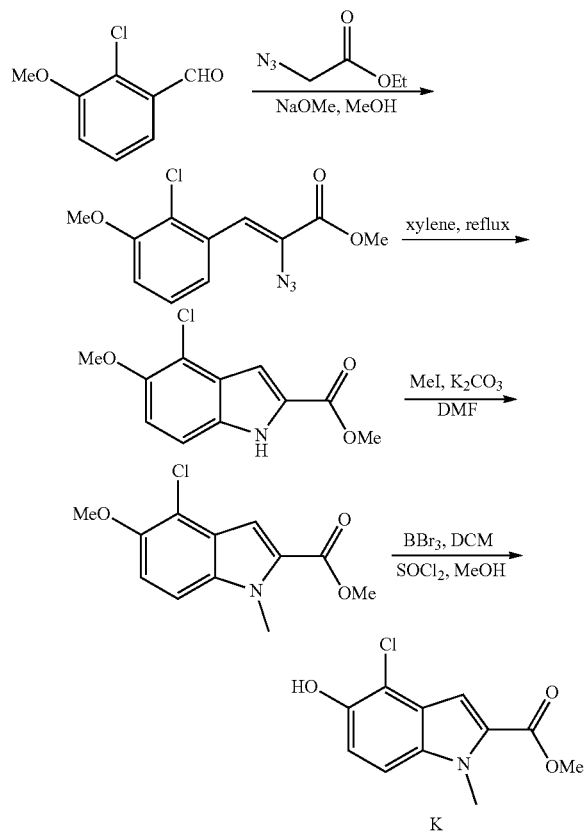

Step 1—Methyl-2-azido-3-(2-chloro-3-methoxyphenyl)prop-2-enoate

To a solution of sodium thiomethoxide (9.50 g, 175 mmol) in methanol (100 mL) was added dropwise a solution of 2-chloro-3-methoxy-benzaldehyde (10.0 g, 58.6 mmol) and ethyl 2-azidoacetate (22.7 g, 175 mmol) in methanol (100 mL) at −40° C. After the reaction mixture was stirred at −50° C. for 2 hr, it was warmed to rt during 2 hrs. The reaction mixture was then stirred at rt for 14 hrs. On completion, the mixture was poured into ice water (300 mL) and extracted with dichloromethane (2×200 mL), the combined organic layers were dried over anhydrous sodium sulfate, filtered and concentrated in vacuo to give a residue. The residue was purified with silica gel chromatography (petroleum ether:ethyl acetate=20:1) to afford the title compound. $^1$H NMR (400 MHz, CDCl3) δ=7.77 (dd, J=1.0, 8.0 Hz, 1H), 7.36 (s, 1H), 7.32-7.25 (m, 1H), 6.95 (dd, J=1.2, 8.2 Hz, 1H), 3.96 (s, 3H), 3.94 (s, 3H).

Step 2—Methyl 4-chloro-5-methoxy-1H-indole-2-carboxylate

A solution of methyl-2-azido-3-(2-chloro-3-methoxyphenyl)prop-2-enoate (10.0 g, 37.3 mmol) in xylene (150 mL) was stirred at 160° C. for 5 hrs. On completion, the mixture was concentrated in vacuo to give a residue. The residue was triturated with a mixture of petroleum ether (100 mL), dichloromethane (5 mL) and methanol (5 mL) to afford the title compound. $^1$H NMR (400 MHz, DMSO-d$_6$) δ=12.16 (br. s., 1H), 7.40 (dd, J=0.6, 9.0 Hz, 1H), 7.24 (d, J=9.0 Hz, 1H), 7.04 (s, 1H), 3.89 (s, 3H), 3.86 (s, 3H).

Step 3—Methyl 4-chloro-5-methoxy-1-methyl-indole-2-carboxylate

To a mixture of methyl 4-chloro-5-methoxy-1H-indole-2-carboxylate (7.34 g, 30.6 mmol) and potassium carbonate (16.9 g, 122 mmol) in N,N-dimethylformamide (80 mL) was added methyl iodide (21.7 g, 153 mmol), and the mixture was stirred at 60° C. for 16 hrs. On completion, the reaction mixture was filtered; the filtrate was washed with water (100 mL), extracted with ethyl acetate (2×100 mL). The combined organic layer was dried over anhydrous sodium sulfate, concentrated in vacuo to afford the title compound. $^1$H NMR (400 MHz, CDCl3) δ=7.34 (s, 1H), 7.27 (d, J=9.0 Hz, 1H), 7.14 (d, J=9.0, 1H), 4.07 (s, 3H), 3.97 (s, 3H), 3.94 (s, 3H).

Step 4—Methyl 4-chloro-5-hydroxy-1-methyl-indole-2-carboxylate

To a solution of methyl 4-chloro-5-methoxy-1-methyl-indole-2-carboxylate (3.00 g, 11.8 mmol) in dichloromethane (40 mL) was added a solution of boron tribromide (23.7 g, 94.6 mmol) in dichloromethane (40 mL) dropwise at −50° C. The mixture was stirred at −50° C. for 2 hrs and then was allowed to warmed to rt and stirred 15 hrs. On completion, methanol (15 mL) was added dropwise into the mixture at 0° C. The mixture was concentrated in vacuo, washed with water (20 mL), extracted with ethyl acetate (3×30 mL). The combined organic layer was dried over anhydrous sodium sulfate and filtered. The filtrate was concentrated in vacuo to give 3 g of mixture of methyl 4-chloro-5-hydroxy-1-methyl-indole-2-carboxylate and 4-chloro-5-hydroxy-1-methyl-indole-2-carboxylic acid as yellow solid. To this crude solid in methanol (40 mL) was added sulfur dichloride (8.20 g, 68.9 mmol) dropwise at 100° C. The resulting mixture was stirred at 100° C. for 15 hrs. On completion, the mixture was concentrated in vacuo to give a residue. The residue was triturated in petroleum ether (50 mL) to give the title compound. $^1$H NMR (400 MHz, DMSO-d$_6$) δ=9.69 (s, 1H), 7.43 (d, J=8.7 Hz, 1H), 7.11-7.05 (m, 2H), 3.99 (s, 3H), 3.86 (s, 3H).

4-Chloro-5-cyclopropyl-1-methyl-1H-indole-2-carboxylic acid (Intermediate L)

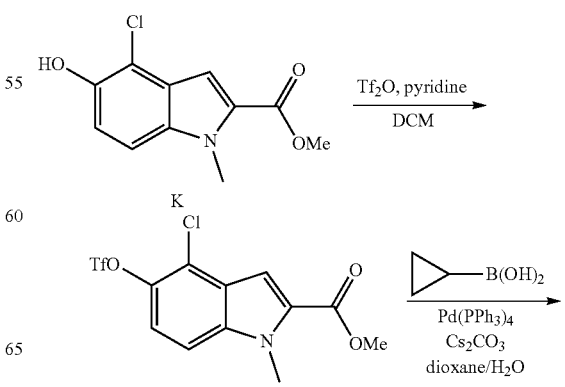

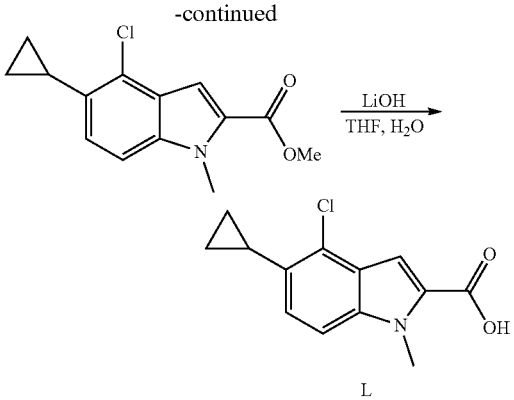

Step 1—Methyl 4-chloro-1-methyl-5-(((trifluoromethyl)sulfonyl)oxy)-1H-indole-2-carboxylate To a mixture of methyl 4-chloro-5-hydroxy-1-methyl-indole-2-carboxylate (1.00 g, 4.17 mmol) and pyridine (495 mg, 6.26 mmol) in dichloromethane (10 mL) was added trifluoromethanesulfonic anhydride (1.30 g, 4.59 mmol). The reaction mixture was stirred at rt for 12 hrs. On completion, the mixture was concentrated. The residue was purified by chromatography (petroleum ether:ethyl acetate=15/1) to give the title compound. $^1$H NMR (400 MHz, DMSO-$d_6$) δ=7.81 (d, J=9.0 Hz, 1H), 7.54 (d, J=9.0 Hz, 1H), 7.33 (s, 1H), 4.08 (s, 3H), 3.90 (s, 3H).

Step 2—Methyl 4-chloro-5-cyclopropyl-1-methyl-1H-indole-2-carboxylate

A mixture of methyl 4-chloro-1-methyl-5-(trifluoromethylsulfonyloxy)indole-2-carboxylate (500 mg, 1.35 mmol), cyclopropylboronic acid (406 mg, 4.72 mmol), Pd(PPh$_3$)$_4$ (156 mg, 135.00 umol) and cesium carbonate (880 mg, 2.70 mmol) in dioxane (15 mL) and water (3 mL) was stirred at 100° C. for 2 hrs. On completion, the mixture was concentrated. The residue was purified by chromatography (petroleum ether:ethyl acetate=60:1) to give the title compound. LCMS: (ES$^+$) m/z (M+H)$^+$=264.2, tR=1.009.

Step 3—4-Chloro-5-cyclopropyl-1-methyl-1H-indole-2-carboxylic acid

To the solution of methyl 4-chloro-5-cyclopropyl-1-methyl-indole-2-carboxylate (180 mg, 683 umol) in tetrahydrofuran (10 mL) and water (3 mL) was added lithium hydroxide (49.0 mg, 2.05 mmol). The mixture was stirred at 60° C. for 12 hrs. On completion, the mixture was concentrated to remove the organic solvent and the aqueous phase was acidified with hydrochloric acid (2 N). The solid that formed was then collected by filtration and washed with water (5 mL) to give the title compound. LCMS: (ES$^+$) m/z (M+H)$^+$=248.0, tR=0.839.

4-chloro-6-methoxy-1,5-dimethyl-indole-2-carboxylic acid (Intermediate M)

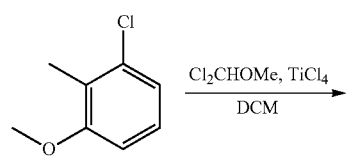

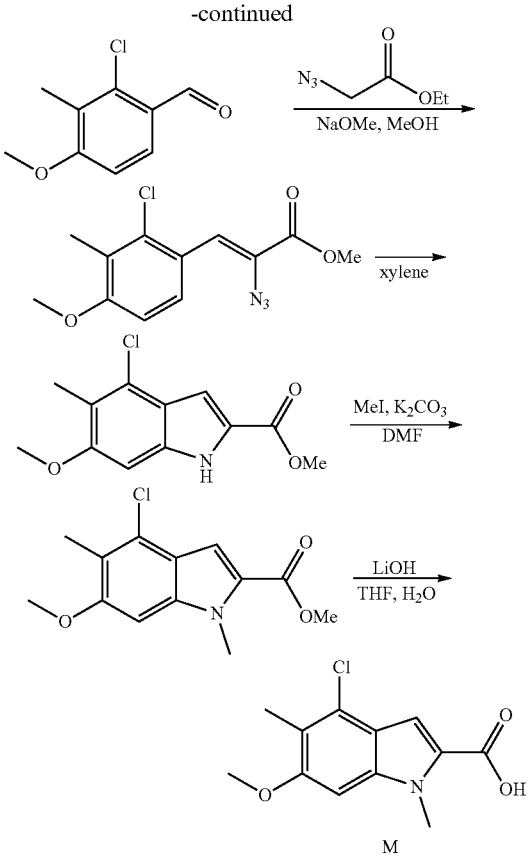

Step 1—2-Chloro-4-methoxy-3-methyl-benzaldehyde

To a solution of 1-chloro-3-methoxy-2-methyl-benzene (6.20 g, 39.6 mmol) in dichloromethane (60 mL) was added TiCl$_4$ (12.7 g, 67.3 mmol) dropwise at 0° C. under nitrogen. Then dichloro(methoxy)methane (4.55 g, 39.6 mmol) was added to the solution dropwise at 0° C. under nitrogen, and the solution was stirred at rt for 5 hrs. On completion, the reaction was poured into water (200 mL). The aqueous phase was extracted with ethyl acetate (3×300 mL). The combined organic phase was washed with brine (3×200 mL), dried over anhydrous sodium sulfate, filtered and concentrated in vacuo. The residue was purified by silica gel chromatography (petroleum ether:ethyl acetate=100:1 to 10:1) to give the title compound. $^1$H NMR (400 MHz, DMSO-d6): δ=10.24 (s, 1H), 7.78-7.76 (d, J=8.8 Hz, 1H), 7.16-6.14 (d, J=8.4 Hz, 1H), 3.91 (s, 3H), 2.25 (s, 3H).

Step 2—Methyl (Z)-2-azido-3-(2-chloro-4-methoxy-3-methyl-phenyl)prop-2-enoate

To a solution of sodium methoxide (4.39 g, 81.3 mmol) in methanol (300 mL) was added 2-chloro-4-methoxy-3-methyl-benzaldehyde (5.00 g, 27.1 mmol) in several portions at −20° C. under nitrogen. Then ethyl 2-azidoacetate (10.5 g, 81.3 mmol) was added to the solution dropwise at −20° C. under nitrogen. The mixture was stirred at rt for 12 hrs. On completion, the mixture was poured into water (500 mL) and extracted with ethyl acetate (3×500 mL). The combined organic phase was washed with saturated brine (3×500 mL), dried over anhydrous sodium methoxide, filtered and concentrated in vacuo. The residue was purified by column chromatography (petroleum ether:ethyl acetate=100:1 to 1:1) to give the title compound. LCMS: (ES$^+$) m/z (M+H)$^+$=282.02, tR=0.998.

Step 3—Methyl 4-chloro-6-methoxy-5-methyl-1H-indole-2-carboxylate

Methyl (Z)-2-azido-3-(2-chloro-4-methoxy-3-methylphenyl) prop-2-enoate (4.00 g, 14.2 mmol) was added to xylene (100 mL) in one portion at rt, then the solution was stirred at 120° C. for 12 hrs. The mixture was concentrated in vacuo. The residue was washed with (petroleum ether: ethyl acetate=10:1, 50 mL) to give the title compound. $^1$H-NMR (DMSO-d$_6$, 400 MHz): δ=12.02 (br. s., 1H), 7.01 (s, 1H), 6.86 (s, 1H), 3.86 (s, 3H), 3.85 (s, 3H), 2.26 (s, 3H).

Step 4—Methyl 4-chloro-6-methoxy-1,5-dimethyl-indole-2-carboxylate

To a solution of methyl 4-chloro-6-methoxy-5-methyl-1H-indole-2-carboxylate (3.00 g, 11.8 mmol) in N,N-dimethylformamide (10 mL) was added potassium carbonate (4.90 g, 35.5 mmol) and methyl iodide (5.04 g, 35.5 mmol) in one portion at rt under nitrogen. The mixture was stirred at 50° C. for 12 hrs. On completion, the residue was poured into water (10 mL). The aqueous phase was extracted with ethyl acetate (3×20 mL). The combined organic phase was washed with brine (3×20 mL), dried over anhydrous sodium sulfate, filtered and concentrated in vacuo to give the title compound. LCMS: (ES$^+$) m/z (M+H)$^+$=268.07, tR=0.778.

Step 5—4-chloro-6-methoxy-1,5-dimethyl-indole-2-carboxylic acid

To a solution of methyl 4-chloro-6-methoxy-1,5-dimethyl-indole-2-carboxylate (3.00 g, 11.2 mmol) in a mixture solvent of tetrahydrofuran (10 mL) and water (10 mL) was added lithium hydroxide (269 g, 11.2 mmol) in one portion at rt under nitrogen. The mixture was stirred at rt for 12 hrs. On completion, the mixture was concentrated in vacuo, and the residue was adjusted to pH=0.3 with 3N hydrochloric acid (3 mL). The solid was filtered and concentrated in vacuum to give the title compound. $^1$H NMR (400 MHz, DMSO-d6) δ=7.06 (s, 2H), 3.99 (s, 3H), 3.90 (s, 3H), 2.26 (s, 3H).

4-Chloro-5-fluoro-6-methoxy-1-methyl-1H-indole-2-carboxylic acid (Intermediate N)

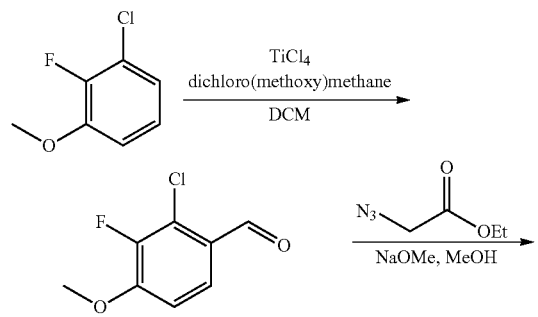

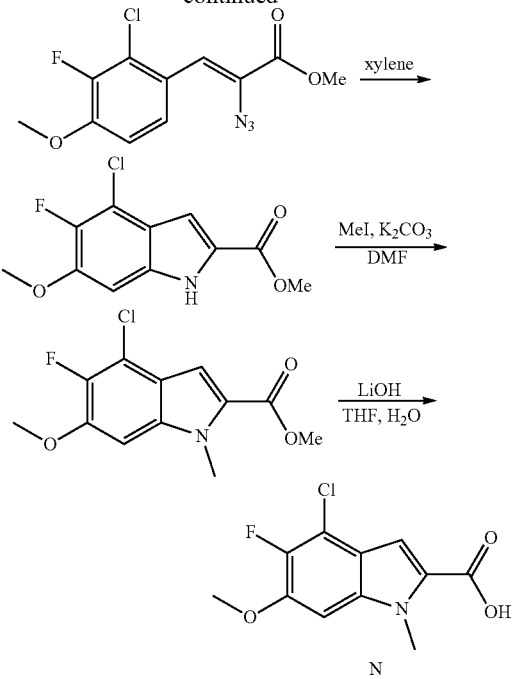

Step 1—2-Chloro-3-fluoro-4-methoxybenzaldehyde

To a mixture of 1-chloro-2-fluoro-3-methoxy-benzene (5.00 g, 31.1 mmol) in dichloromethane (40 mL) was added titanium tetrachloride (10.0 g, 52.9 mmol) dropwise at 0° C. under a nitrogen. Dichloro(methoxy)methane (3.58 g, 31.1 mmol) was then added to the solution. Then the mixture was stirred at rt for 3 hours. On completion, the residue was poured into ice-water (50 mL) and extracted with ethyl acetate (50 mL). The combined organic layer was washed with brine (50 mL), dried with anhydrous sodium sulfate, filtered and concentrated in vacuo. The residue was purified by silica gel chromatography eluted with (petroleum ether/ethyl acetate=20/1 to 3/1) to give the title compound. $^1$H NMR (400 MHz, DMSO-d$_6$) δ=10.15 (s, 1H), 7.74 (d, J=6.8 Hz, 1H), 7.37 (d, J=5.9 Hz, 1H), 3.98 (s, 3H).

Step 2—(Z)-methyl 2-azido-3-(2-chloro-3-fluoro-4-methoxyphenyl)acrylate

To a solution of sodium methoxide (1.72 g, 31.8 mmol) in methanol (25 mL) was added a solution of 2-chloro-3-fluoro-4-methoxy-benzaldehyde (2.00 g, 10.6 mmol) and ethyl azidoacetate (4.11 g, 31.8 mmol) in methanol (25 mL) at −20 OC under nitrogen. The mixture was stirred at rt for 5 hours. On completion, the mixture was poured into ice-water (50 mL) and a large amount of precipitate formed. The solution was filtered and the filter cake collected. The filter cake was then dissolved in dichloromethane and dried over anhydrous sodium sulfate, filtered and concentrated under reduced pressure to give the title compound. $^1$H NMR (400 MHz, DMSO-d$_6$) δ=8.09 (dd, J=9.0, 1.9 Hz, 1H), 7.27 (t, J=8.8 Hz, 1H), 7.05 (s, 1H), 3.93 (s, 3H), 3.88 (s, 3H).

Step 3—Methyl 4-chloro-5-fluoro-6-methoxy-1H-indole-2-carboxylate (Z)-methyl-2-azido-3-(2-chloro-3-fluoro-4-methoxy-phenyl)prop-2-enoate (1.80 g, 6.30 mmol) was added to xylene (20 mL) in one portion at rt. The solution was stirred at 180° C. for 2.5 hours. On completion, the residue was cooled where a precipitation formed. The solution was filtered to give the crude compound. The crude product was used directly in the next step without further purification.

Step 4—Methyl 4-chloro-5-fluoro-6-methoxy-1-methyl-1H-indole-2-carboxylate

To a solution of methyl 4-chloro-5-fluoro-6-methoxy-1H-indole-2-carboxylate (1.00 g, 3.88 mmol) in N,N-dimethylformamide (15 mL) was added potassium carbonate (1.61 g, 11.6 mmol) and iodomethane (1.65 g, 11.6 mmol) in one portion at rt under nitrogen, and the mixture was stirred at 50° C. for 4 hours. On completion, the residue was poured into ice-water (50 mL). The aqueous layer was extracted with ethyl acetate (50 mL) and combined organic layer was washed with brine (30 mL), dried over anhydrous sodium sulfate, filtered and concentrated in vacuo to give the title compound. $^1$H NMR (400 MHz, DMSO-$d_6$) δ=7.31 (d, J=6.8 Hz, 1H), 7.14 (s, 1H), 4.01 (s, 3H), 3.96 (s, 3H), 3.85 (s, 3H).

Step 5—4-Chloro-5-fluoro-6-methoxy-1-methyl-1H-indole-2-carboxylic acid

To a solution of methyl 4-chloro-5-fluoro-6-methoxy-1-methyl-1H-indole-2-carboxylate (1.00 g) in anhydrous tetrahydrofuran (20.00 mL) and water (20.00 mL) was added lithium hydroxide (264 mg, 11.0 mmol) in one portion at rt under nitrogen. The solution was stirred for 2 hours at rt. On completion, the mixture was concentrated in vacuo to remove the tetrahydrofuran, then the residue was adjusted to pH=2 with hydrochloric acid (3 M) and a precipitate emerged. The solid was filtered and dried in vacuo to give the title compound. $^1$H NMR (400 MHz, DMSO-$d_6$) δ=7.31 (d, J=6.6 Hz, 1H), 7.13 (s, 1H), 4.03 (s, 3H), 3.96 (s, 3H).

N-acetylsulfamoyl chloride (Intermediate O)

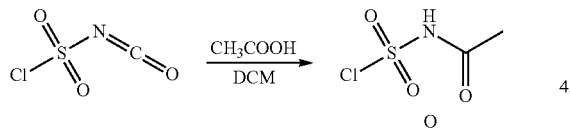

To a solution of N-(oxomethylene)sulfamoyl chloride (70.0 g, 495 mmol) in dichloromethane (50 mL) was added acetic acid (29.7 g, 495 mmol) dropwise at 0° C. The reaction was stirred at 0° C. for 3 hrs. On completion, the reaction was concentrated in vacuo, and the residue was washed with (petroleum ether:ethyl acetate=10:1, 2×500 mL) to give the title compound. $^1$H NMR (400 MHz, DMSO-$d_6$) δ=2.11 (s, 3H).

Tert-butyl chlorosulfonylcarbamate (Intermediate P)

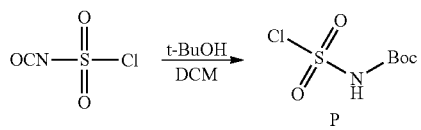

A solution of N-(oxomethylene)sulfamoyl chloride (20 g, 141 mmol) in dichloromethane (200 mL) was added dropwise into t-BuOH (13.8 g, 184 mmol) at 0° C. under a nitrogen. The reaction mixture was stirred at 0° C. for 0.5 hr. On completion, the mixture was concentrated in vacuo to give a residue (the temperature during the concentration was kept below 35° C.). The residue was triturated with a mixture solvent of petroleum ether and ethyl acetate (10:1, 50 ml) and dried over in vacuo to afford the title compound. $^1$H NMR (400 MHz, CDCl3) δ=8.62 (br. s., 1H), 1.58 (s, 9H).

Tert-butyl 4-amino-4-(3-bromophenyl) piperidine-1-carboxylate (Intermediate Q)

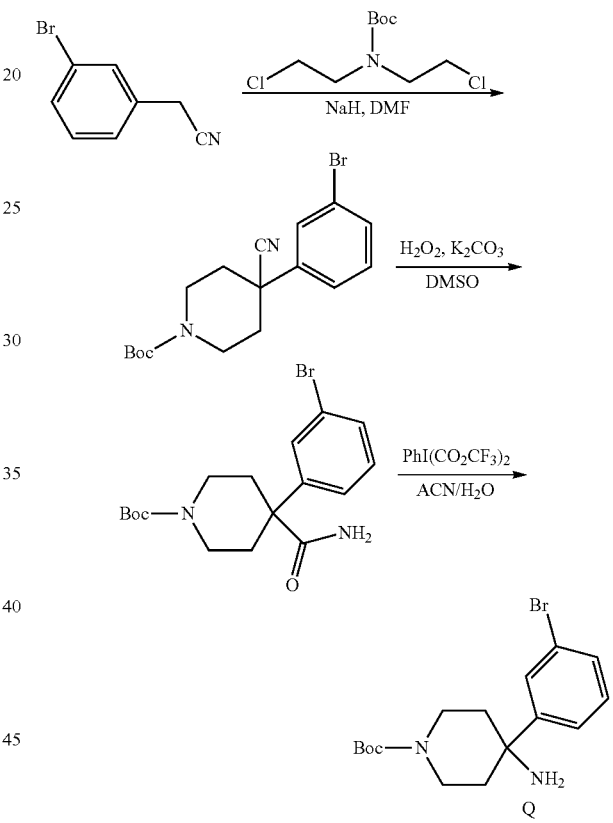

Step 1—Tert-butyl 4-(3-bromophenyl)-4-cyanopiperidine-1-carboxylate

To a solution of tert-butyl N,N-bis(2-chloroethyl)carbamate (11.6 g, 47.8 mmol, CAS #118753-70-1) and 2-(3-bromo-phenyl)acetonitrile (10.3 g, 52.5 mmol) in N,N-dimethylformamide (46 mL) was added sodium hydride (4.40 g, 110 mmol) portion-wise at 0° C. under nitrogen gas atmosphere. The reaction mixture was then warmed to 60° C. and stirred for 3 hrs. On completion, water was added to the mixture (200 mL) at rt, and the mixture was extracted with ethyl acetate (3×200 mL). The combined organic phase was washed by brine (200 mL), dried over sodium sulfate, and concentrated in vacuo to give a residue. The residue was purified by column chromatography (petroleum ether:ethyl acetate=50:1 to 10:1) to give the title compound. $^1$H NMR (400 MHz, CDCl$_3$) δ=7.62 (t, J=1.6 Hz, 1H), 7.52-7.50 (m, 1H), 7.46-7.43 (m, 1H), 7.31 (t, J=8.0 Hz, 1H), 4.32 (m, 2H), 3.21 (m, 2H), 2.11 (d, J=13.2 Hz, 2H), 1.94 (td, J=13.2, 4.4 Hz, 2H), 1.51 (s, 9H).

Step 2—Tert-butyl 4-(3-bromophenyl)-4-carbamoylpiperidine-1-carboxylate

To a mixture of tert-butyl 4-(3-bromophenyl)-4-cyano-piperidine-1-carboxylate (6.00 g, 16.4 mmol) and potassium carbonate (908 mg, 6.57 mmol) in dimethyl sulfoxide (60 mL) was added hydrogen peroxide (7.08 g, 62.4 mmol) at rt. Then, the mixture was heated to 60° C. and stirred for 3 hrs. On completion, water (100 mL) was added, during which a white solid precipitated. The mixture was filtered, and the solid was collected and dried in vacuo to give the title compound. $^1$H NMR (300 MHz, DMSO-$d_6$) δ=7.52 (s, 1H), 7.45 (d, J=7.5 Hz, 1H), 7.41-7.36 (m, 1H), 7.35-7.26 (m, 2H), 7.14 (s, 1H), 3.74 (d, J=13.2 Hz, 2H), 2.97 (br. s., 2H), 2.40 (d, J=13.2 Hz, 2H), 1.74-1.57 (m, 2H), 1.39 (s, 9H)

Step 3—Tert-butyl 4-amino-4-(3-bromophenyl)piperidine-1-carboxylate

To a solution of tert-butyl 4-(3-bromophenyl)-4-carbamoyl-piperidine-1-carboxylate (5.40 g, 14.1 mmol) in acetonitrile (27 mL) and water (27 mL) was added PhI(CF$_3$CO$_2$)$_2$ (6.66 g, 15.5 mmol) at rt. The mixture was heated to rt and stirred for 16 hrs. On completion, ethyl acetate (50 mL) was added to the mixture and the organic phase was separated. The organic phase was then washed by brine (30 mL), dried over sodium sulfate and concentrated in vacuo to give a residue which was purified by column chromatography (petroleum ether:ethyl acetate=10:1 to 1:1) to give the title compound. $^1$H NMR (400 MHz, DMSO-$d_6$) δ=7.74 (t, J=2.0 Hz, 1H), 7.51-7.48 (dd, J=7.6, 1H), 7.40 (ddd, J=7.6, 2.0, 0.8 Hz, 1H), 7.28 (t, J=8.0 Hz, 1H), 3.73 (d, J=8.8 Hz, 2H), 3.41-3.26 (m, 4H), 1.77 (td, J=13.2, 4.4 Hz, 2H), 1.52 (d, J=12.4 Hz, 2H), 1.41 (s, 9H).

Tert-butyl 4-amino-4-phenyl-piperidine-1-carboxylate (Intermediate R)

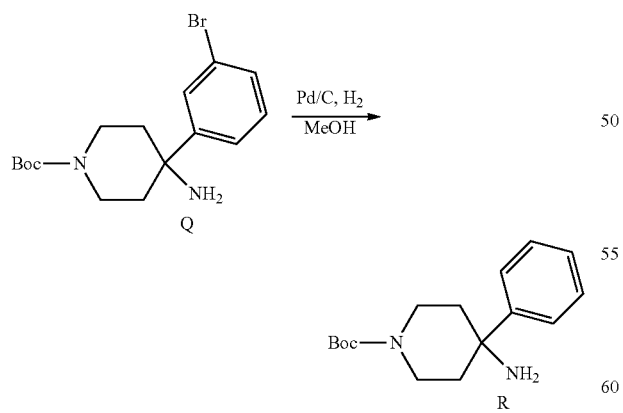

To a solution of tert-butyl 4-amino-4-(3-bromophenyl)piperidine-1-carboxylate (700 mg, 1.97 mmol) in methanol (7 mL) was added Pd—C (10%, 0.15 g) under nitrogen gas atmosphere. The suspension was degassed under vacuum and purged with hydrogen gas several times. The mixture was stirred under hydrogen gas (35 psi) at rt for 3 hrs. On completion, the mixture was filtered, and the filtrate was concentrated in vacuo to give the crude product which was used into the next step directly without further purification. $^1$H NMR (300 MHz, DMSO-$d_6$) δ=8.42 (br. s., 2H), 7.64 (d, J=7.2 Hz, 2H), 7.56-7.39 (m, 3H), 3.80-3.63 (m, 2H), 3.01 (d, J=7.3 Hz, 2H), 2.42 (d, J=14.1 Hz, 2H), 2.08-1.92 (m, 2H), 1.40 (s, 9H).

Tert-butyl 4-(3-acetamidophenyl)-4-amino piperidine-1-carboxylate (Intermediate S)

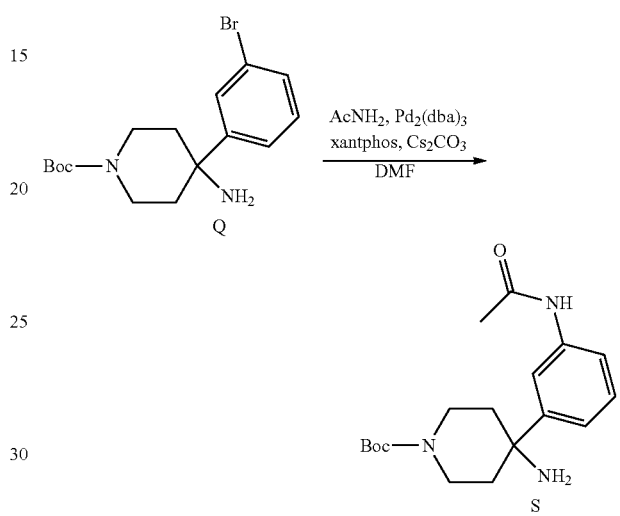

To a 100 mL three-necked round-bottomed flask charged with a mixture of tert-butyl 4-amino-4-(3-bromophenyl) piperidine-1-carboxylate (1.00 g, 2.81 mmol), acetamide (249 mg, 4.22 mmol), Pd$_2$(dba)$_3$ (257 mg, 281 umol), Xantphos (163 mg, 281 umol), and cesium carbonate (1.83 g, 5.62 mmol) was added N,N-dimethylformamide (10.0 mL) at rt. The resultant mixture was flushed with nitrogen gas three times, and heated to 100° C. and stirred for 4 hrs. On completion, the mixture was concentrated in vacuo to give a residue, to which water (20 mL) was added. The resulting mixture was extracted with dichloromethane (3×50 mL). The combined organic phase was washed by brine (50 mL), dried over sodium sulfate, and concentrated in vacuo to give a crude which was purified by column chromatography (petroleum ether:ethyl acetate=1:2 to dichloro-methane:methanol=50:1 to 20:1) to give the title compound. $^1$H NMR (300 MHz, DMSO-$d_6$) δ=9.89 (br. s, 1H), 7.63 (s, 1H), 7.52-7.48 (m, 1H), 7.26-7.20 (m, 2H) 3.68 (d, J=13.2 Hz, 2H), 3.40-3.10 (m, 4H), 2.02 (s, 3H), 1.77 (td, J=13.2, 4.2 Hz, 2H), 1.53 (d, J=17.2 Hz, 2H), 1.41 (s, 9H).

(±)-1-Benzyl-3-(3-bromophenyl)piperidin-3-amine (Intermediate T)

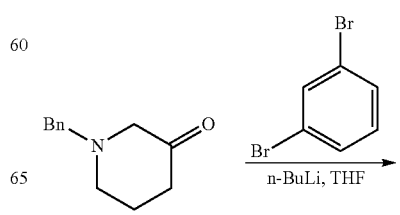

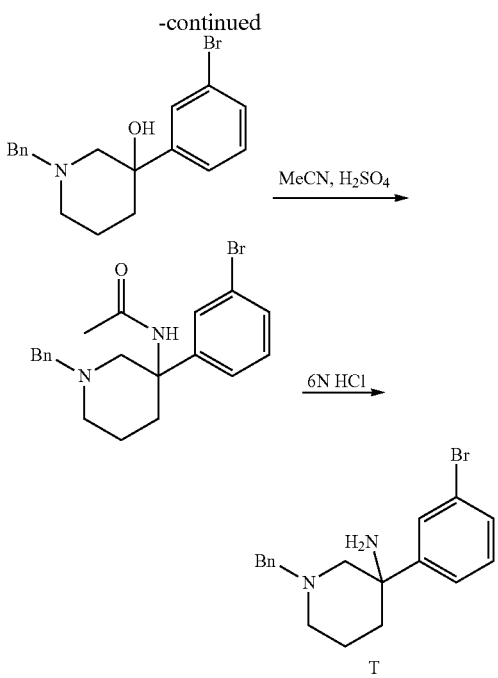

(br. s., 1H), 3.52-3.36 (m, 2H), 2.84 (d, J=11.3 Hz, 1H), 2.70-2.54 (m, 2H), 2.00-1.86 (m, 5H), 1.80-1.51 (m, 3H)

Step 3—(±)-1-Benzyl-3-(3-bromophenyl)piperidin-3-amine

A solution of (±)-N-[1-benzyl-3-(3-bromophenyl)-3-piperidyl]acetamide (4.10 g, 10.6 mmol) in hydrochloric acid (6 N, 50 mL) was stirred at 120° C. for 12 hours. On completion, the reaction mixture was quenched by addition of sodium hydroxide (1 N, 80 mL) at 0° C., then diluted with water (500 mL) and extracted with ethyl acetate (3×300 mL). The combined organic layers were washed with aqueous sodium chloride (3×50 mL), dried over sodium sulfate, filtered and concentrated in vacuo to give a residue. The residue was purified by column chromatography (petroleum ether:ethyl acetate=3:1 to dichloromethane:methanol=10:1) to give the title compound. $^1$H NMR (400 MHz, CDCl3) δ=7.76 (t, J=1.8 Hz, 1H), 7.53-7.48 (m, 1H), 7.40-7.31 (m, 5H), 7.30-7.24 (m, 1H), 7.24-7.17 (m, 1H), 3.61-3.47 (m, 2H), 2.82 (d, J=9.7 Hz, 1H), 2.62 (d, J=10.9 Hz, 1H), 2.39 (d, J=9.5 Hz, 1H), 2.12 (m, 1H), 1.95-1.75 (m, 2H), 1.69-1.59 (m, 2H).

Benzyl 3-amino-3-phenylazetidine-1-carboxylate (Intermediate U)

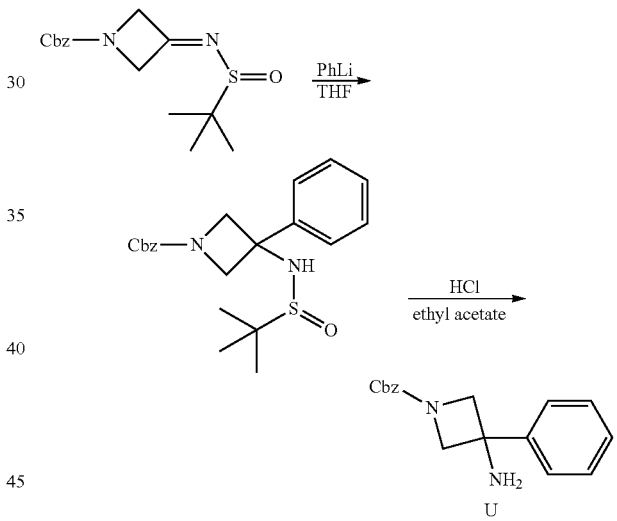

Step 1— Benzyl 3-(1,1-dimethylethylsulfinamido)-3-phenylazetidine-1-carboxylate

To the solution of benzyl 3-tert-butylsulfinyliminoazetidine-1-carboxylate (1.00 g, 3.24 mmol, MDL #: MFCD27987040) in tetrahydrofuran (10 mL) was added phenyllithium (2 M in dibutyl ether, 2.43 mL) and the mixture was stirred at 0° C. for 2 hrs. On completion, the mixture was quenched by saturated aqueous ammonium chloride solution (10 mL) and extracted with ethyl acetate (3×20 mL). The combined organic layers were dried over anhydrous sodium sulfate and concentrated to give the title compound, which was used for next step directly. LCMS: (ES$^+$) m/z (M+H)$^+$=387.1, tR=0.886.

Step 2—Benzyl 3-amino-3-phenylazetidine-1-carboxylate

A solution of benzyl 3-(tert-butylsulfinylamino)-3-phenyl-azetidine-1-carboxylate (600 mg, 1.55 mmol) in hydro- Step 1—(±)-1-Benzyl-3-(3-bromophenyl)piperidin-3-ol To a solution of 1,3-dibromobenzene (6.30 g, 26.7 mmol) in tetrahydrofuran (65 mL) was added n-BuLi (2.5 M, 10.6 mL) at −78° C. The mixture was stirred at −78° C. for 30 minutes, then 1-benzylpiperidin-3-one (5.05 g, 26.7 mmol) was added dropwise at −78° C. The mixture was stirred at 0° C. for 4 hrs. On completion, the reaction mixture was quenched by addition of aqueous ammonium chloride (100 mL) at 0° C., then diluted with water (100 mL) and extracted with ethyl acetate (3×100 mL). The combined organic layers were washed with aqueous brine (2×100 mL), dried over sodium sulfate, filtered and concentrated in vacuo to give a residue. The residue was purified by column chromatography (petroleum ether:ethyl acetate=10:1 to 1:1) to give the title compound. $^1$H NMR (400 MHz, CDCl3) δ=7.68 (t, J=1.8 Hz, 1H), 7.45-7.29 (m, 7H), 7.25-7.17 (m, 1H), 3.68-3.50 (m, 2H), 2.99-2.89 (m, 1H), 2.72 (td, J=2.0, 11.0 Hz, 1H), 2.31 (d, J=11.0 Hz, 1H), 2.14-2.05 (m, 1H), 2.04-1.90 (m, 1H), 1.85-1.64 (m, 3H).

Step 2—(±)-N-[1-benzyl-3-(3-bromophenyl)-3-piperidyl]acetamide

To a solution of (±)-1-benzyl-3-(3-bromophenyl)piperidin-3-ol (6.00 g, 17.3 mmol) in acetonitrile (45 mL) was added concentrated sulfuric acid (27.6 g, 276 mmol, 15 mL) dropwise at 0° C. The mixture was stirred at rt for 12 hours. On completion, the reaction mixture was quenched by addition of sodium hydroxide (2 N, 50 mL) at 0° C., then diluted with water (200 mL) and extracted with ethyl acetate (3×100 mL). The combined organic layers were washed with aqueous sodium chloride (2×100 mL), dried over sodium chloride, filtered and concentrated in vacuo to give a residue. The residue was purified by column chromatography (petroleum ether:ethyl acetate=5:1 to 1:1) to give the title compound. $^1$H NMR (400 MHz, CDCl3) δ=7.40 (t, J=1.8 Hz, 1H), 7.32-7.17 (m, 7H), 7.13-7.03 (m, 1H), 6.42 chloride/ethyl acetate (4 mL, 4 M) was stirred at rt for 1 hr. On completion, the mixture was concentrated to give a residue. The residue was dissolved in water (5 mL), then extracted with ethyl acetate (5 mL). The aqueous phase was separated, concentrated in vacuo to give the title compound. LCMS: (ES$^+$) m/z (M+H)$^+$=283.1, tR=0.557.

(±)-1-Benzyl-3-phenyl-pyrrolidin-3-amine (Intermediate V)

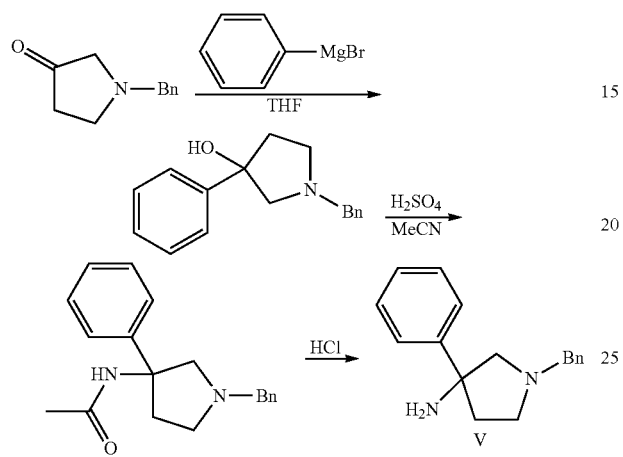

Step 1—(±)-1-Benzyl-3-phenyl-pyrrolidin-3-ol

To a solution of 1-benzylpyrrolidin-3-one (6.00 g, 34.2 mmol) in tetrahydrofuran (20 mL) was added bromo(phenyl)magnesium (3 M, 12.5 mL) dropwise at 0° C. The mixture was stirred at rt for 12 hrs. On completion, the reaction was quenched with saturated ammonium chloride (20 mL), extracted with ethyl acetate (3×50 mL), washed with brine (3×30 mL), dried over anhydrous sodium sulfate, filtered and concentrated in vacuo. The residue was purified by silica gel chromatography (petroleum ether:ethyl acetate=5:1) to give the title compound. $^1$H NMR (300 MHz, CDCl3) δ=7.46-7.38 (m, 2H), 7.32-7.22 (m, 5H), 7.21-7.12 (m, 3H), 3.67 (s, 2H), 3.15-3.01 (m, 1H), 2.91 (d, J=9.6 Hz, 1H), 2.56 (d, J=9.4 Hz, 1H), 2.47 (dt, J=6.2, 9.3 Hz, 1H), 2.36-2.23 (m, 1H), 2.20-2.07 (m, 1H).

Step 2—(±)-N-(1-benzyl-3-phenyl-pyrrolidin-3-yl) acetamide

To a solution of (±)-1-benzyl-3-phenyl-pyrrolidin-3-ol (2.00 g, 7.89 mmol) in acetonitrile (12.5 g, 304 mmol) was added sulfuric acid (9.59 g, 97.7 mmol) dropwise at 0° C., and the reaction was stirred at rt for 12 hrs. On completion the solution was poured into ice, basified with sodium hydroxide (5 N, 30 mL) and extracted with dichloromethane (3×50 mL). The combined extracts were dried over sodium sulfate, filtered and concentrated in vacuo. The residue was purified by silica gel chromatography (petroleum ether:ethyl acetate=5:1 to 1:1) to give the title compound. $^1$H NMR (400 MHz, CDCl3) δ=7.45-7.15 (m, 10H), 3.83-3.60 (m, 2H), 3.06-2.95 (m, 2H), 2.93-2.86 (m, 1H), 2.79-2.68 (m, 1H), 2.50 (dt, J=3.3, 7.0 Hz, 2H), 2.02 (s, 3H)

Step 3—(±)-1-Benzyl-3-phenyl-pyrrolidin-3-amine

A mixture of (±)-N-(1-benzyl-3-phenyl-pyrrolidin-3-yl) acetamide (2.00 g, 6.79 mmol) in hydrochloric acid (6 N, 50 mL) was stirred at 110° C. for 8 hrs. On completion the mixture was poured into ice-water (20 mL), quenched by addition of saturated sodium bicarbonate (60 mL), and extracted with ethyl acetate (3×20 mL). The combined organic phase was dried over anhydrous sodium sulfate, filtered and concentrated in vacuo. The residue was purified by chromatography on silica gel (from petroleum ether:ethyl acetate=10:1 to dichloromethane:methanol=10:1) to give the title compound. LCMS: (ES$^+$) m/z (M+H)$^+$=253.2, tR=1.312.

2-Oxo-N-pyrimidin-2-yl-oxazolidine-3-sulfonamide (Intermediate W)

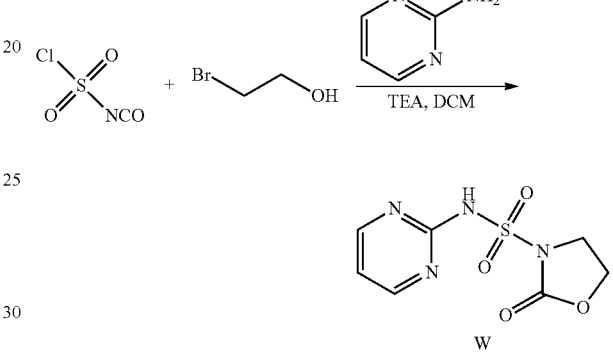

A 250 mL round-bottom flask was charged with dichloromethane (250 mL) and N-(oxomethylene) sulfamoyl chloride (14.9 g, 105 mmol). The flask was cooled in an ice bath for 20 minutes, and then 2-bromoethanol (13.1 g, 105 mmol) was added dropwise. The mixture was stirred for 2.5 hours, then a solution of pyrimidin-2-amine (10 g, 105 mmol) and triethylamine (32 g, 317 mmol) in dichloromethane (150 mL) was added dropwise via an addition funnel over 10 minutes. When the addition was complete, the cooling bath was removed, and the mixture was stirred for 2 days. On completion, to the mixture was added 2N hydrochloric acid. Then the mixture was filtered and the filter cake was washed with dichloromethane and water. The solid was dried under vacuum to give the title compound. $^1$H NMR (400 MHz, DMSO-d$_6$) δ=8.66 (d, J=5.0 Hz, 2H), 7.30-6.99 (m, 1H), 4.52-4.35 (m, 2H), 4.33-4.15 (m, 2H).

Tert-butyl 4-amino-4-(3-(ethoxycarbonyl)phenyl) piperidine-1-carboxylate (Intermediate X)

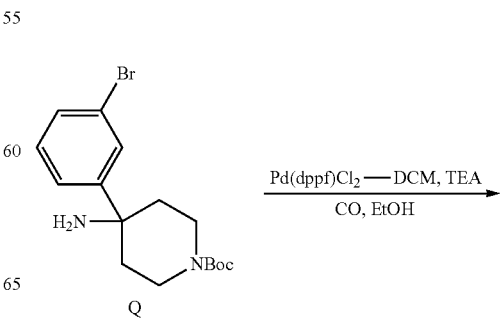

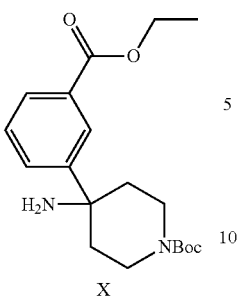

X

To a mixture of tert-butyl 4-amino-4-(3-bromophenyl)piperidine-1-carboxylate (1.80 g, 5.07 mmol) and Pd(dppf)Cl₂CH₂Cl₂ (414 mg, 507 umol) in ethanol (18.0 mL) was added triethylamine (2.57 g, 25.4 mmol) in one portion at rt under nitrogen. The mixture was flushed with carbon monoxide (50 psi) three times, then heated to 85° C. and stirred for 16 hrs. On completion, the mixture was filtered, and the filtrate was concentrated in vacuo to give a residue which was purified by column chromatography (petroleum ether:ethyl acetate=10:1 to 2:1) to give the title compound. ¹H NMR (400 MHz, DMSO-d₆) δ=8.13 (s, 1H), 7.81 (dd, J=7.6, 1.6 Hz, 2H), 7.47 (t, J=8.0 Hz, 1H), 4.33 (q, J=7.2 Hz, 2H), 3.75 (d, J=10.8 Hz, 2H), 3.19-3.28 (m, 2H), 2.00 (br. s, 2H), 1.77-1.82 (m, 2H), 1.57 (d, J=12.4 Hz, 2H), 1.42 (s, 9H), 1.33 (t, J=7.2 Hz, 3H).

Tert-butyl 4-amino-4-(4-ethoxycarbonylphenyl)piperidine-1-carboxylate (Intermediate Y)

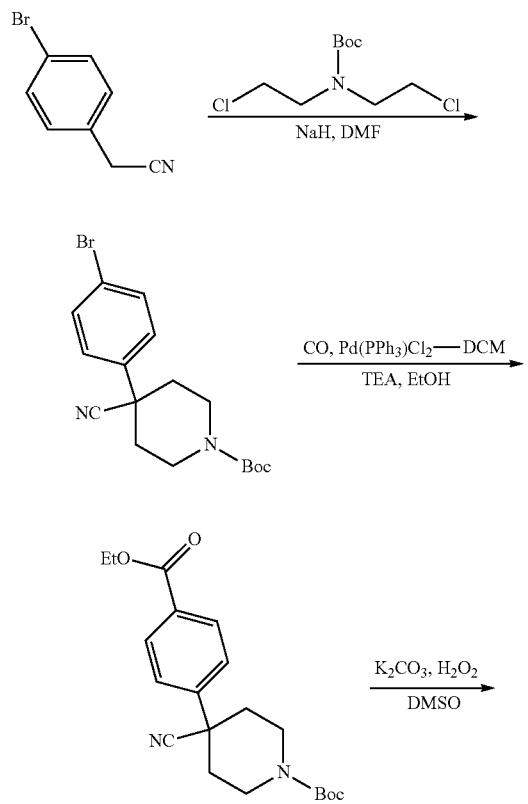

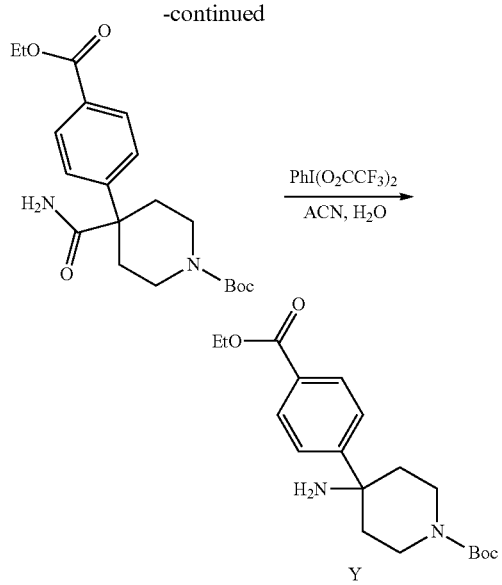

Y

Step 1—Tert-butyl 4-(4-bromophenyl)-4-cyano-piperidine-1-carboxylate

To a solution of 2-(4-bromophenyl)acetonitrile (2.67 g, 13.6 mmol) and tert-butyl N,N-bis(2-chloroethyl)carbamate (3.00 g, 12.3 mmol) in N,N-dimethylformamide (20 mL) was added sodium hydride (1.14 g, 28.5 mmol) portion-wise at 0° C. under a nitrogen atmosphere. After stirring at 0° C. for 0.5 hr, more N,N-dimethylformamide (20 mL) was added into the mixture and the mixture was heated to 60° C. and stirred for 16 hrs. On completion, the mixture was quenched with ice water (150 mL) and extracted with ethyl acetate (2×200 mL). The combined organic layer was dried over anhydrous sodium sulfate, filtered and concentrated in vacuum to give a residue. The residue was purified with silica gel chromatography (petroleum ether:ethyl acetate=20:1) to give the title compound. ¹H NMR (400 MHz, CDCl3) δ=7.47 (d, J=8.7 Hz, 2H), 7.28 (d, J=8.7 Hz, 2H), 4.41-4.00 (m, 2H), 3.25-3.05 (m, 2H), 2.00 (d, J=12.7 Hz, 2H), 1.83 (dt, J=4.3, 13.1 Hz, 2H), 1.41 (s, 9H).

Step 2—Tert-butyl 4-cyano-4-(4-ethoxycarbonylphenyl)piperidine-1-carboxylate

To a solution of tert-butyl 4-(4-bromophenyl)-4-cyano-piperidine-1-carboxylate (2.60 g, 7.12 mmol) and Pd(dppf)Cl2.CH2Cl2 (581 mg, 712 umol) in ethanol (30 mL) was added triethylamine (3.60 g, 35.6 mmol,). The mixture was bubbled with carbonic oxide at 70° C. under 50 psi then stirred at 70° C. for 16 hrs. On completion, the mixture was concentrated in vacuo to give a residue. The residue was purified with silica gel chromatography (petroleum ether:ethyl acetate=20:1) to give the title compound. ¹H NMR (400 MHz, DMSO-d₆) δ=8.02 (d, J=8.4 Hz, 2H), 7.73 (d, J=8.4 Hz, 2H), 4.33 (q, J=7.2 Hz, 2H), 4.16 (d, J=14.2 Hz, 2H), 3.10-2.90 (m, 2H), 2.18-2.11 (m, 2H), 2.04-1.90 (m, 2H), 1.43 (s, 9H), 1.33 (t, J=7.1 Hz, 3H).

Step 3— Tert-butyl 4-carbamoyl-4-(4-ethoxycarbonylphenyl)piperidine-1-carboxylate To a solution of tert-butyl 4-cyano-4-(4-ethoxycarbonylphenyl)piperidine-1-carboxylate (2.30 g, 6.42 mmol) and potassium carbonate (354 mg, 2.57 mmol) in dimethyl sulfoxide (25 mL) was added hydrogen peroxide (5.82 g, 51.3 mmol). The mixture was heated to 60° C. and stirred at 60° C. for 16 hrs. On completion, water (40 mL) was added into the mixture. After stirring at rt for 2 hrs a solid precipitate formed which was filtered. The solid was dried in vacuo to give the title compound. $^1$H NMR (400 MHz, DMSO-d6) δ=7.93 (d, J=8.4 Hz, 2H), 7.55-7.51 (d, J=8.4 Hz, 2H), 4.31 (q, J=7.2 Hz, 2H), 3.72 (d, J=13.4 Hz, 2H), 3.10-2.94 (m, 2H), 2.43 (d, J=13.4 Hz, 2H), 1.76-1.67 (m, 2H), 1.39 (s, 9H), 1.31 (t, J=7.1 Hz, 3H).

Step 4-Tert-butyl 4-amino-4-(4-ethoxycarbonylphenyl)piperidine-1-carboxylate To a mixture of tert-butyl 4-carbamoyl-4-(4-ethoxycarbonylphenyl)piperidine-1-carboxylate (1.34 g, 3.56 mmol) in acetonitrile (5 mL) and water (5 mL) was added PhI(O$_2$CCF$_3$)$_2$ (1.68 g, 3.92 mmol) in one portion and the mixture was stirred at rt for 16 hrs. On completion, the mixture was concentrated in vacuo to give a residue. The residue was extracted with ethyl acetate (3×40 mL), washed with water (30 mL) and the combined organic layer was dried over anhydrous sodium sulfate, filtered and concentrated in vacuo to give a residue. The residue was purified with silica gel chromatograph (dichloromethane:methanol=40:1) to give the title compound. $^1$H NMR (400 MHz, DMSO-d6) δ=8.48 (br. s., 2H), 8.07-8.01 (d, J=8.7 Hz, 2H), 7.79 (d, J=8.7 Hz, 2H), 4.35 (q, J=7.2 Hz, 2H), 3.77-3.62 (m, 2H), 3.05 (m, 2H), 2.44 (d, J=14.8 Hz, 2H), 2.06-1.93 (m, 2H), 1.41 (s, 9H), 1.34 (t, J=7.1 Hz, 3H).

(±)-1-Benzyl-3-(4-bromophenyl)piperidin-3-amine (Intermediate Z)

Step 1—(±)-1-Benzyl-3-(4-bromophenyl)piperidin-3-ol

To a solution of 1-bromo-4-iodo-benzene (3.30 g, 11.66 mmol) in tetrahydrofuran (50 mL) was added n-BuLi (2.5 M, 4.99 mL) dropwise. The reaction mixture was stirred at −60 OC for 1 hr. Then a solution of 1-benzylpiperidin-3-one (2.21 g, 11.66 mmol) in tetrahydrofuran (10 mL) was added to the reaction mixture at −60 OC and the mixture was warmed to rt and stirred for 15 hrs. On completion, the reaction mixture was quenched with saturated ammonium chloride solution (50 mL) at 0° C. and extracted with ethyl acetate (3×40 mL). The combined organic layers were dried over anhydrous sodium sulfate, filtrated and concentrated in vacuo to give a crude product which was purified by column chromatography (petroleum ether:ethyl acetate=7:1 to 3:1) to give the title compound. $^1$H NMR (400 MHz, CDCl3) δ=7.50-7.25 (m, 9H), 3.97 (s, 1H), 3.69-3.53 (m, 2H), 2.95 (d, J=10.42 Hz, 1H), 2.71 (d, J=11.04 Hz, 1H), 2.30 (d, J=11.04 Hz, 1H), 2.12-2.04 (m, 1H), 2.00-1.94 (m, 1H), 1.83-1.65 (m, 3H).

Step 2—(±)-N-(1-benzyl-3-(4-bromophenyl)piperidin-3-yl)acetamide

To a solution of (±)-1-benzyl-3-(4-bromophenyl)piperidin-3-ol (1.05 g, 3.03 mmol) in acetonitrile (20 mL) was added concentrated sulfuric acid (2.97 g, 30.32 mmol) at 0-rt. The reaction mixture was stirred for 48 hrs. On completion, the reaction mixture was concentrated in vacuo. The residue was diluted with ethyl acetate (50 mL) and basified with saturated sodium hydrogen carbonate solution (40 mL). Then the aqueous phase was extracted with ethyl acetate (3×20 mL). The combined organic layers were dried over anhydrous sodium sulfate, filtrated and concentrated in vacuo to give a crude product which was purified by column chromatography (petroleum ether:ethyl acetate=3:1 to 0:1) to give the title compound. $^1$H NMR (300 MHz, CDCl3) δ=7.48-7.16 (m, 9H), 6.51 (br. s., 1H), 3.64-3.43 (m, 2H), 2.93 (d, J=11.11 Hz, 1H), 2.68 (d, J=11.49 Hz, 2H), 2.11-1.95 (m, 4H), 1.88-1.61 (m, 4H).

Step 3—(±)-1-Benzyl-3-(4-bromophenyl)piperidin-3-amine

A solution of (±)-N-[1-benzyl-3-(4-bromophenyl)-3-piperidyl]acetamide (1.05 g, 2.71 mmol) in hydrochloric acid solution (9 M, 13 mL) was stirred at 120° C. for 24 hrs. On completion, the reaction mixture was quenched with sodium bicarbonate solution until pH=8-9 at 0° C., and the aqueous phase was extracted with ethyl acetate (3×20 mL). The combined organic layers were dried over anhydrous sodium sulfate, filtrated and concentrated in vacuo to give the title compound. $^1$H NMR (400 MHz, CDCl3) δ=7.38-7.13 (m, 9H), 3.45 (s, 2H), 2.73 (d, J=10.16 Hz, 1H), 2.53 (d, J=10.79 Hz, 1H), 2.27 (d, J=10.42 Hz, 1H), 2.06-1.93 (m, 1H), 1.87-1.67 (m, 5H), 1.55-1.48 (m, 1H).

Ethyl 4-(3-amino-1-benzylpiperidin-3-yl)benzoate (Intermediate AA)

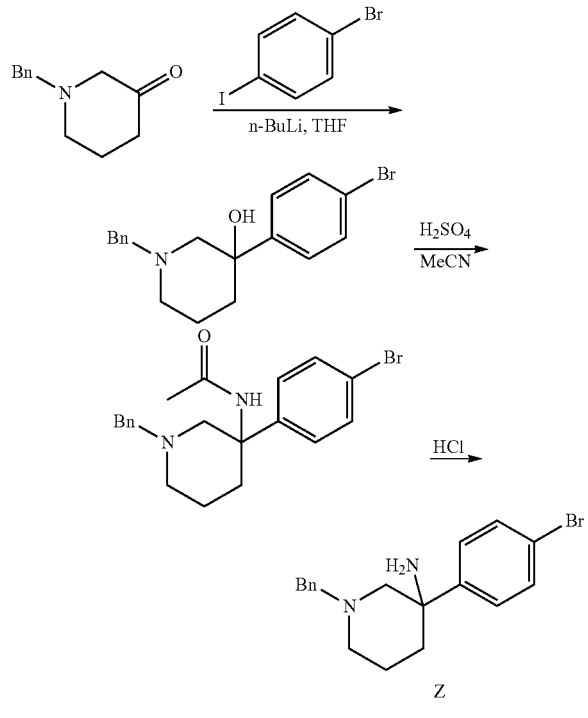

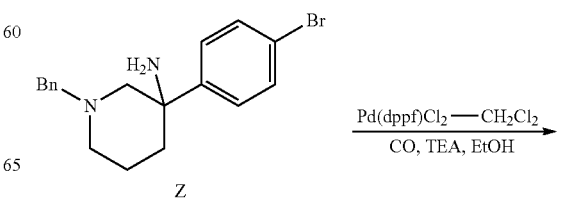

-continued

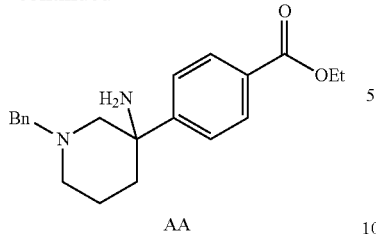

AA

To a solution of (±)-benzyl-3-(4-bromophenyl)piperidin-3-amine (650 mg, 1.88 mmol) and triethylamine (951 mg, 9.40 mmol) in ethanol (20 mL) was added Pd(dppf)Cl$_2$—CH$_2$Cl$_2$ (153 mg, 188 umol) and the reaction mixture was stirred at 80° C. for 24 hrs under carbon monoxide (50 psi). On completion, the reaction mixture was concentrated in vacuo to give a crude product which was purified by column chromatography (dichloromethane:methanol=1:0 to 30:1) to give the title compound. LCMS: (ES$^+$) m/z (M+H)$^+$=339.2.

(±)-Ethyl 3-(3-amino-1-benzyl-3-piperidyl)benzoate
(Intermediate AB)

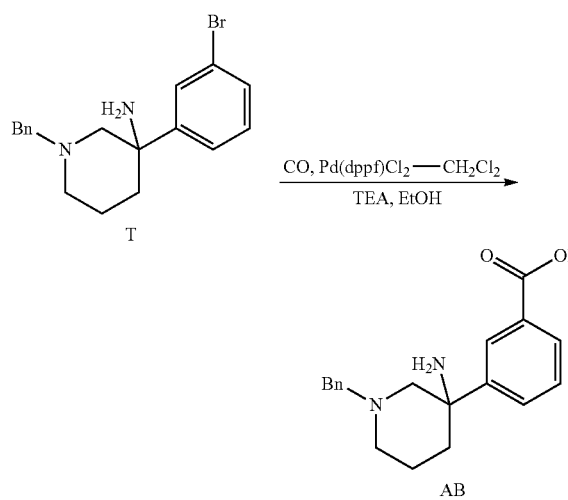

To a mixture of (±)-1-benzyl-3-(3-bromophenyl)piperidin-3-amine (500 mg, 1.45 mmol) and Pd(dppf)Cl$_2$—CH$_2$Cl$_2$ (118 mg, 144 umol) in ethyl alcohol (18 mL) was added triethylamine (732.67 mg, 7.24 mmol) in one portion at rt under nitrogen. The mixture was stirred at 85° C. under carbon monoxide (50 psi) for 12 hrs. On completion, the mixture was concentrated in vacuo and the residue was purified by chromatography on silica gel (petroleum ether:ethyl acetate=1:1 to dichloromethane:methanol=30:1) to give the title compound. LCMS: (ES$^+$) m/z (M+H)$^+$=339.2, tR=0.642.

(±)-3-(3-Bromophenyl)tetrahydrofuran-3-amine (Intermediate AC)

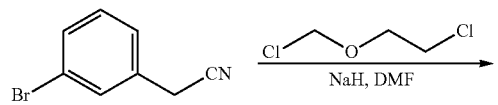

-continued

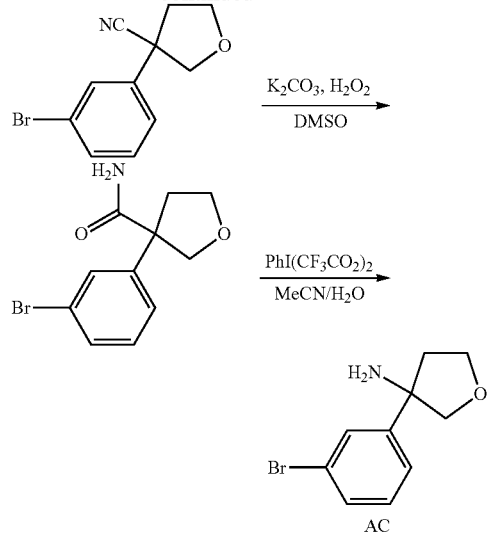

Step 1—(±)-3-(3-Bromophenyl)tetrahydrofuran-3-carbonitrile

To a solution of sodium hydride (1.84 g, 76.5 mmol) in dimethyl formamide (30 mL) was added a solution of 2-(3-bromophenyl)acetonitrile (5.00 g, 25.5 mmol) and 1-chloro-2-(chloromethoxy)ethane (3.45 g, 26.7 mmol) in dimethyl formamide (20 mL) at −20° C. under nitrogen atmosphere. The mixture was stirred at 20-25° C. for 16 hrs. On completion, the mixture was poured into water (50 mL) and extracted with ethyl acetate (2×60 mL). The combined organic phase was washed with brine (100 mL) and concentrated to give the crude product, which was purified by column chromatography (petroleum ether:ethyl acetate=50:1 to 8:1) to give the title compound. $^1$H NMR (400 MHz, CDCl3) δ=7.65 (t, J=1.8 Hz, 1H), 7.54-7.49 (m, 1H), 7.48-7.41 (m, 1H), 7.34-7.26 (m, 1H), 4.36 (d, J=9.0 Hz, 1H), 4.26-4.12 (m, 2H), 4.07 (d, J=9.0 Hz, 1H), 2.87-2.77 (m, 1H), 2.46 (td, J=8.1, 13.1 Hz, 1H)

Step 2—(±)-3-(3-Bromophenyl)tetrahydrofuran-3-carboxamide

To a solution of (±)-3-(3-bromophenyl)tetrahydrofuran-3-carbonitrile (2.00 g, 7.93 mmol) and potassium carbonate (438 mg, 3.17 mmol) in dimethyl sulfoxide (10 mL) was added hydrogen peroxide (3.43 g, 30.2 mmol, 30%) in one portion at 20° C. Then the mixture was stirred at 20-25° C. for 3 hrs. On completion, the mixture was diluted with water (20 mL) and extracted with ethyl acetate (2×20 mL). The combined organic phase washed with brine (30 mL) and concentrated to give the crude product. The crude product was recrystallized by petroleum ether:ethyl acetate=1:1 (10 mL) and filtered to give the title compound. $^1$H NMR (400 MHz, CDCl3) δ=7.48 (d, J=1.4 Hz, 1H), 7.47-7.39 (m, 1H), 7.32-7.24 (m, 2H), 5.70 (br. s., 2H), 4.44 (d, J=8.9 Hz, 1H), 4.13-3.91 (m, 3H), 2.89-2.73 (m, 1H), 2.37-2.22 (m, 1H).

Step 3—(±)-3-(3-Bromophenyl)tetrahydrofuran-3-amine

To a solution of (±)-3-(3-bromophenyl)tetrahydrofuran-3-carboxamide (1.85 g, 6.85 mmol) in acetonitrile (10 mL)

and water (10 mL) was added [phenyl-(2,2,2-trifluoroacetyl) oxy-iodanyl] 2,2,2-trifluoroacetate (3.24 g, 7.53 mmol) at 20-25° C. The mixture was stirred at 20-25° C. for 12 hrs under nitrogen atmosphere. On completion, the mixture was adjusted to pH=9-10 with ammonium hydroxide and concentrated to remove the acetonitrile. Then to the mixture was added water (10 mL) and the solution was extracted with dichloromethane (2×10 mL). The combined organic phase was concentrated to give the title compound. $^1$H NMR (400 MHz, CDCl3) δ=7.66 (t, J=1.8 Hz, 1H), 7.45-7.38 (m, 2H), 7.31-7.19 (m, 1H), 4.24-4.15 (m, 1H), 4.10 (dt, J=4.0, 8.8 Hz, 1H), 3.95-3.83 (m, 2H), 2.39 (td, J=8.8, 12.5 Hz, 1H), 2.20-2.11 (m, 1H).

(±)-3-(4-Bromophenyl)tetrahydrofuran-3-amine (Intermediate AD)

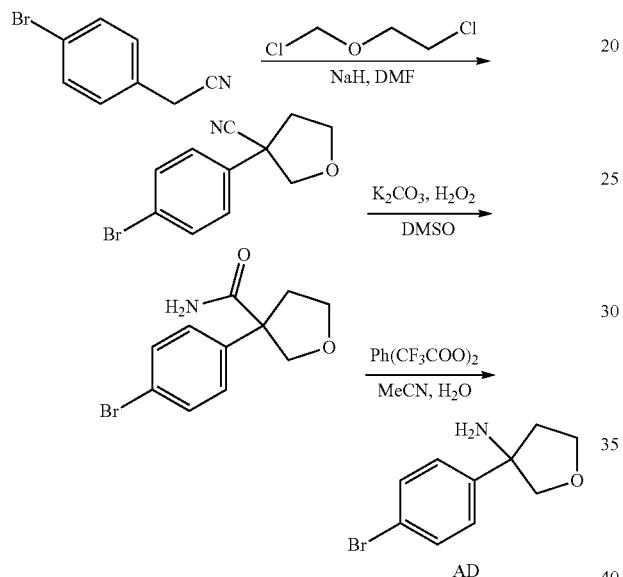

Step 1—(±)-3-(4-Bromophenyl)tetrahydrofuran-3-carbonitrile

To a solution of sodium hydride (1.06 g, 44.3 mmol) in dimethyl formamide (30 mL) was added a solution of 1-chloro-2-(chloromethoxy)ethane (2.00 g, 15.5 mmol) and 2-(4-bromophenyl)acetonitrile (2.90 g, 14.7 mmol) in dimethyl formamide (20 mL) dropwise at −20 OC, and the reaction mixture was stirred at rt for 16 hrs. On completion, the mixture was poured into water (80 mL) and extracted with ethyl acetate (3×60 mL). The combined organic phase was washed with brine (3×70 mL) and concentrated in vacuo to give a crude product which was purified by column chromatography (petroleum ether:ethyl acetate=50:1-15:1) to give the title compound. $^1$H NMR (300 MHz, CDCl3) δ=7.56 (d, J=8.7 Hz, 2H), 7.38 (d, J=8.7 Hz, 2H), 4.35 (d, J=9.0 Hz, 1H), 4.24-4.13 (m, 2H), 4.04 (d, J=9.0 Hz, 1H), 2.82 (ddd, J=5.1, 7.2, 12.8 Hz, 1H), 2.43 (td, J=8.1, 13.0 Hz, 1H).

Step 2—(±)-3-(4-Bromophenyl)tetrahydrofuran-3-carboxamide

To a solution of (±)-3-(4-bromophenyl)tetrahydrofuran-3-carbonitrile (900 mg, 3.57 mmol) and potassium carbonate (197 mg, 1.43 mmol, 0.40 eq) in dimethyl sulfoxide (10 mL) was added hydrogen peroxide (1.31 mL, 30%) dropwise at rt, and the reaction mixture was stirred at rt for 2 hrs. On completion, the reaction mixture was diluted with water (30 mL) and extracted with ethyl acetate (3×20 mL). The combined organic phase washed with brine (30 mL) and concentrated in vacuo to give a crude product. The product was recrystallized by petroleum ether:ethyl acetate=1:1 (10 mL) and filtered to give a residue and the residue was dried in vacuo to give the title compound. $^1$H NMR (300 MHz, CDCl3) δ=7.44 (d, J=8.7 Hz, 2H), 7.13 (d, J=8.5 Hz, 2H), 5.55-5.20 (m, 2H), 4.36 (d, J=8.9 Hz, 1H), 4.08-3.82 (m, 3H), 2.82-2.69 (m, 1H), 2.22 (ddd, J=6.8, 8.2, 12.5 Hz, 1H).

Step 3—(±)-3-(4-Bromophenyl)tetrahydrofuran-3-amine

To a solution of (±)-3-(4-bromophenyl)tetrahydrofuran-3-carboxamide (300 mg, 1.11 mmol) in a mixture of acetonitrile (10 mL) and water (10 mL) was added [phenyl-(2,2,2-trifluoroacetyl)oxy-iodanyl] 2,2,2-trifluoroacetate (525 mg, 1.22 mmol) at rt and the reaction mixture was stirred at rt for 12 hrs. On completion, the reaction mixture was adjusted to pH=9-10 with ammonium hydroxide and concentrated in vacuo to remove acetonitrile. Then to the mixture was added water (10 mL) and the solution was extracted with ethyl acetate (2×10 mL). The combined organic phase was concentrated to give the title compound. $^1$H NMR (300 MHz, DMSO-$d_6$) δ=7.48 (q, J=8.7 Hz, 4H), 4.06-3.97 (m, 1H), 3.90 (dt, J=4.0, 8.3 Hz, 1H), 3.74-3.66 (m, 2H), 2.17 (td, J=8.5, 12.2 Hz, 1H), 2.09-1.94 (m, 1H).

(±)-Methyl 4-(3-aminooxetan-3-yl)benzoate (Intermediate AE)

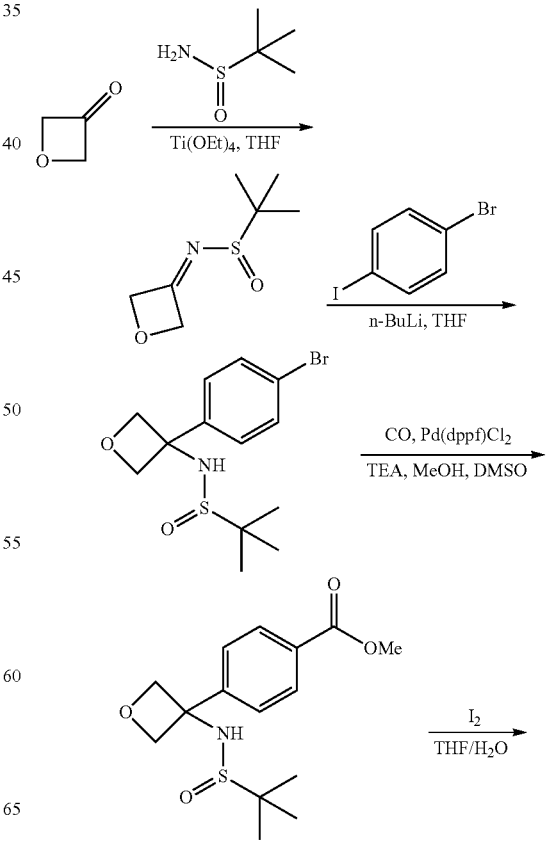

-continued

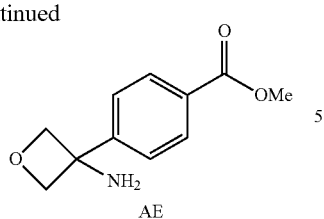

AE

Step 1—2-(±)-Methyl-N-(oxetan-3-ylidene)propane-2-sulfinamide

To a solution of oxetan-3-one (2.50 g, 34.6 mmol) and (±)-2-methylpropane-2-sulfinamide (4.20 g, 34.6 mmol) in anhydrous tetrahydrofuran (25 mL) was added tetraethoxytitanium (11.0 g, 48.5 mmol, 10 mL) dropwise at rt and the reaction mixture was stirred at 50° C. for 3 hrs. On completion, the reaction mixture was poured into 100 mL cool water and filtered. The filtrate was extracted with dichloromethane (3×100 mL). The combined organic layer was dried over anhydrous sodium sulfate, filtered and concentrated in vacuo. The resulting solid was purified by silica gel chromatography (petroleum ether:ethyl acetate=20:1) to give the title compound. $^1$H NMR (400 MHz, CDCl$_3$) δ=5.83-5.76 (m, 1H), 5.70-5.62 (m, 1H), 5.52-5.40 (m, 2H), 1.27 (s, 9H).

Step 2—(±)-N-[3-(4-bromophenyl)oxetan-3-yl]-2-methyl-propane-2-sulfinamide

To a solution of 1-bromo-4-iodo-benzene (806 mg, 2.85 mmol) in anhydrous tetrahydrofuran (20 mL) was added n-BuLi (2.5 M, 1.14 mL) dropwise at −70° C. and the reaction mixture was stirred for 10 min under nitrogen. Then a solution of (±)-2-methyl-N-(oxetan-3-ylidene) propane-2-sulfinamide (500 mg, 2.85 mmol, CAS #1158098-73-7) in anhydrous tetrahydrofuran (5 mL) was added dropwise and the reaction mixture was stirred at −70° C. for 20 min. Then the reaction mixture was stirred at rt for 30 min. On completion, the reaction mixture was poured into 100 mL cool water and the aqueous phase was extracted with dichloromethane (3×100 mL). The combined organic layer was dried over anhydrous sodium sulfate, filtrated and concentrated in vacuo. The resulting oil was purified by silica gel chromatography (petroleum ether:ethyl acetate=1:1) to give the title compound. LCMS: (ES$^+$) m/z (M+H)$^+$=334.0, tR=1.195. $^1$H NMR (400 MHz, CDCl$_3$) δ=7.48 (d, J=8.5 Hz, 2H), 7.23-7.16 (d, J=8.5 Hz, 2H), 5.09 (d, J=6.9 Hz, 1H), 5.01-4.92 (m, 2H), 4.89-4.83 (d, J=6.9 Hz, 1H), 4.02 (s, 1H), 1.14 (s, 9H).

Step 3—(±)-Methyl 4-[3-(tert-butyl sulfinylamino) oxetan-3-yl]benzoate

A solution of (±)-N-[3-(4-bromophenyl)oxetan-3-yl]-2-methyl-propane-2-sulfinamide (500 mg, 1.50 mmol), triethylamine (455 mg, 4.50 mmol, 623 uL) and Pd(dppf) Cl2.CH$_2$Cl$_2$ (244 mg, 300 umol) in a mixture of methanol (20 mL) and dimethyl sulfoxide (4 mL) was stirred at 80° C. under carbon monoxide (50 psi) for 16 hrs. On completion, the reaction mixture was concentrated in vacuo. The resulting oil was purified by silica gel chromatography (dichloromethane:methanol=50:1) to give the title compound. LCMS: (ES$^+$) m/z (M+H)$^+$=312.1, tR=1.065. $^1$H NMR (400 MHz, CDCl$_3$) δ=8.12-8.07 (m, 2H), 7.51-7.46 (m, 2H), 5.22 (d, J=7.0 Hz, 1H), 5.08-5.03 (m, 2H), 5.00-4.96 (m, 1H), 3.94 (s, 3H), 1.22 (s, 9H).

Step 4—(1)-Methyl 4-(3-aminooxetan-3-yl)benzoate

To a solution of (±)-methyl 4-[3-(tert-butylsulfinylamino) oxetan-3-yl]benzoate (290 mg, 931 umol) in a mixture of tetrahydrofuran (1 mL) and water (300 uL) was added iodine (47.2 mg, 186 umol, 37.5 uL) and the reaction mixture was stirred at 50° C. for 12 hrs. On completion, the reaction mixture was concentrated in vacuo. The resulting oil was basified with aqueous saturated sodium bicarbonate until pH=9 and the aqueous phase was extracted with dichloromethane (3×30 mL). The combined organic layer was dried over anhydrous sodium sulfate, filtrated and concentrated in vacuo to give the title compound as black brown oil. LCMS: (ES$^+$) m/z (M−NH2)$^+$=191.1, tR=0.809.

(±)-Ethyl 4-(3-aminotetrahydro-2H-pyran-3-yl) benzoate (Intermediate AF)

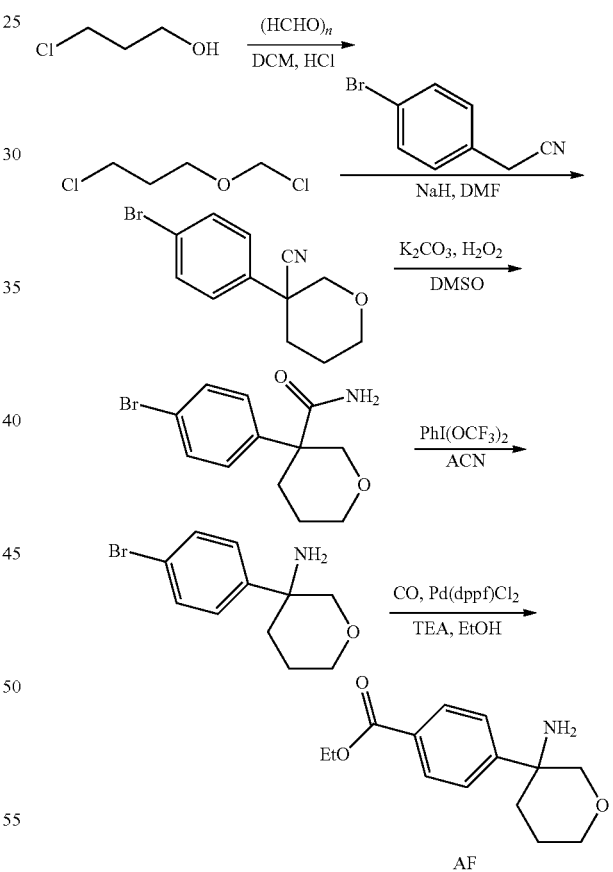

AF

Step 1—1-Chloro-3-(chloromethoxy)propane

To a solution of paraformaldehyde (6.0 g, 66.6 mmol) in dichloromethane (300 mL) was bubbled HCl (gas) at −10° C. until the solution became clear. Then, 3-chloropropan-1-ol (18.9 g, 200 mmol, 16.7 mL) was added dropwise and the reaction mixture was stirred at −10° C. for 10 mins. On completion, the reaction was poured into a suspension of anhydrous potassium carbonate (100 g) in dichloromethane (300 mL) and stirred until bubbling ceased. The reaction mixture was filtered and concentrated in vacuo to give the desired product. $^1$H NMR (400 MHz, DMSO-d6) δ=5.52 (s, 2H), 3.86 (t, J=6.0 Hz, 2H), 3.67-3.63 (m, 2H), 2.14-2.07 (m, 2H).

Step 2—(±)-3-(4-Bromophenyl)tetrahydro-2H-pyran-3-carbonitrile

To a solution of sodium hydride (3.40 g, 85.3 mmol, 60% purity) in N,N-dimethylformamide (80 mL) was added a solution of 2-(4-bromophenyl)acetonitrile (8.00 g, 40.8 mmol) and 1-chloro-3-(chloromethoxy)propane (5.60 g, 39 mmol) in N,N-dimethylformamide (50 mL) portion-wise at −40° C. under nitrogen. The reaction mixture was warmed to rt with stirring for 12 hrs. On completion, to the reaction mixture was added water (200 mL) and the solution was extracted with ethyl acetate (3×100 mL). The organic layers were washed with brine (200 mL), dried over anhydrous sodium sulfate, and concentrated in vacuo. The solid was purified by silica gel chromatography (petroleum: ethyl acetate=20:1) to give the title compound. $^1$H NMR (400 MHz, CDCl$_3$) δ=7.56 (d, J=8.4 Hz, 2H), 7.38 (d, J=8.4 Hz, 2H), 4.10 (dd, J=11.2, 2.4 Hz, 2H), 3.55 (d, J=11.4 Hz, 1H), 3.53-3.45 (m, 1H), 2.33 (dd, J=11.2, 2.0 Hz, 1H), 2.26-2.15 (m, 1H), 2.15-2.04 (m, 1H), 1.82-1.74 (m, 1H).

Step 3—(±)-3-(4-Bromophenyl)tetrahydro-2H-pyran-3-carboxamide

To a mixture of (±)-3-(4-bromophenyl)tetrahydropyran-3-carbonitrile (1.10 g, 4.20 mmol) and anhydrous potassium carbonate (235 mg, 1.70 mmol) in dimethyl sulfoxide (5 mL) was added hydrogen peroxide (1.80 g, 16.1 mmol, 1.5 mL, 30% purity) in one portion at rt. Then, the mixture was heated to 60° C. and stirred for 3 hrs. On completion, the reaction mixture was diluted with water (20 mL) where a precipitate formed. The white precipitated solid was filtered and dried in vacuo to give the title compound. $^1$H NMR (400 MHz, DMSO-d6) δ=7.59 (d, J=8.4 Hz, 2H), 7.38 (d, J=8.4 Hz, 2H), 7.23 (br. s., 1H), 7.11 (br. s., 1H), 4.28 (d, J=11.4 Hz, 1H), 3.78 (d, J=11.8 Hz, 1H), 3.74-3.66 (m, 1H), 3.54-3.47 (m, 1H), 2.50-2.41 (m, 1H), 2.03-1.90 (m, 1H), 1.70-1.59 (m, 1H), 1.51 (m, 1H)

Step 4—(±)-3-(4-Bromophenyl)tetrahydro-2H-pyran-3-amine

To a solution of (±)-3-(4-bromophenyl)tetrahydropyran-3-carboxamide (1.10 g, 4.00 mmol) in acetonitrile (10 mL) and water (10 mL) was added PhI(CF$_3$CO$_2$)$_2$ (1.90 g, 4.40 mmol) at rt. The reaction mixture was stirred at rt under nitrogen for 12 hrs. On completion, the reaction mixture was diluted with water (20 mL), extracted with ethyl acetate (3×50 mL), dried over anhydrous sodium sulfate and concentrated in vacuo to give a yellow oil. The yellow oil was purified by silica gel chromatography (dichloromethane:methanol=50:1) to give the title compound. $^1$H NMR (400 MHz, CDCl$_3$) δ=7.47 (s, 4H), 3.90 (td, J=11.2, 4.0 Hz, 1H), 3.72 (d, J=11.2 Hz, 1H), 3.59-3.50 (m, 2H), 2.12-2.06 (m, 1H), 1.92 (ddt, J=14.2, 10.2, 4.4 Hz, 1H), 1.76 (d, J=6.0 Hz, 1H), 1.61-1.52 (m, 1H).

Step 5—(1)-Ethyl 4-(3-aminotetrahydro-2H-pyran-3-yl) benzoate

To a mixture of (±)-3-(4-bromophenyl)tetrahydropyran-3-amine (200 mg, 781 umol) and triethylamine (395 mg, 3.90 mmol) in ethanol (10.0 mL) was added Pd(dppf)Cl$_2$—CH$_2$Cl$_2$ (63.8 mg, 78.1 umol) in one portion under nitrogen. The mixture was flushed with monocarboxide (50 psi) three times, then it was heated to 85° C. and stirred for 16 hrs. On completion, the reaction mixture was concentrated in vacuo to give the crude product. The crude product was purified by silica gel chromatography (dichloromethane:methanol=50:1) to give the title compound. LCMS: (ES$^+$) m/z (M−NH$_2$)$^+$ =233.2, tR=0.569.

(±)-Methyl 4-(3-aminotetrahydrofuran-3-yl)-2-bromobenzoate (Intermediate AG)

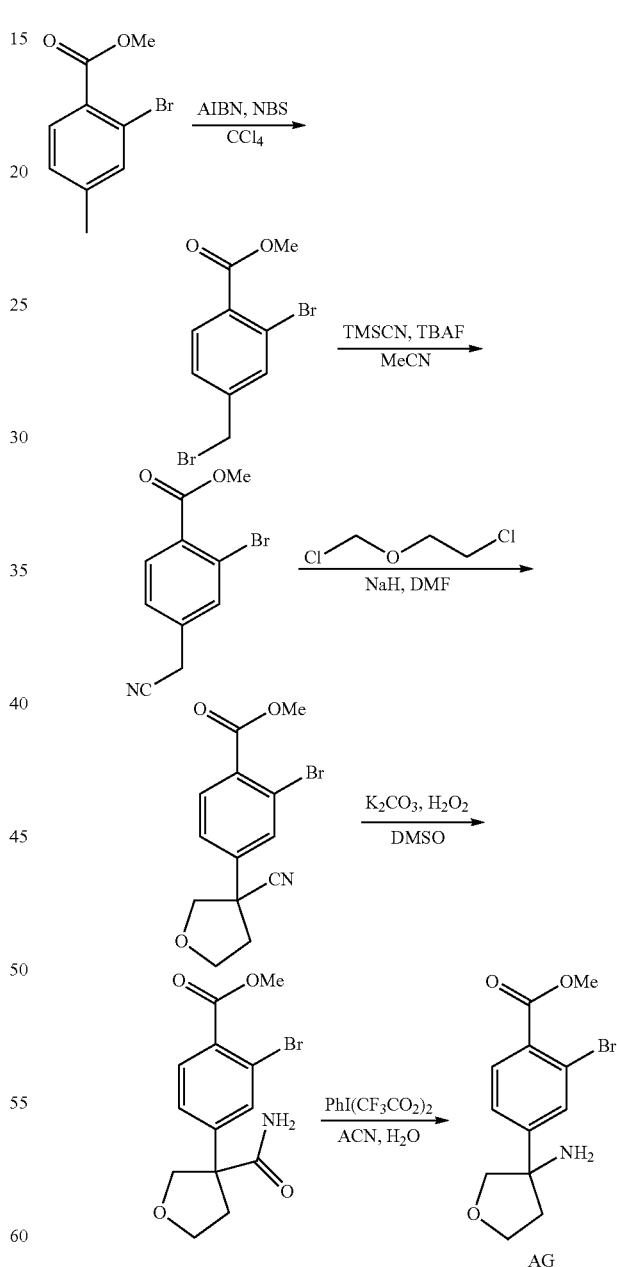

AG

Step 1—Methyl 2-bromo-4-(bromomethyl)benzoate

To a solution of methyl 2-bromo-4-methylbenzoate (50.0 g, 218 mmol) in perchloromethane (500 mL) was added 2,2'-(diazene-1,2-diyl)bis(2-methylpropanenitrile) (3.58 g, 21.8 mmol) and 1-bromopyrrolidine-2,5-dione (42.7 g, 240 mmol) in acetonitrile was stirred at 70° C. for 12 hrs. On completion, the reaction mixture was cooled to rt and filtered. The filtrate was concentrated under reduced pressure to afford the title compound which was used into the next step without further purification.

Step 2—Methyl 2-bromo-4-(cyanomethyl)benzoate

To a solution of trimethylsilanecarbonitrile (57.9 g, 584 mmol) and tetrabutylammonium fluoride (152 g, 584 mmol) in acetonitrile (900 mL) was added methyl 2-bromo-4-(bromomethyl)benzoate (60.0 g, 194 mmol). The mixture was stirred at rt for 10 min. On completion, to the reaction mixture was added water (500 mL), then the mixture was concentrated to remove most of the acetonitrile. The mixture was then extracted with ethyl acetate (500 mL). The organic layer was separated, washed with brine (100 mL), dried over anhydrous sodium sulfate, and filtered. The filtrate was concentrated under vacuum to afford the crude product, which was purified by column chromatography (petroleum ether:ethyl acetate=10:1 to 5:1) to afford the title compound. $^1$H NMR (400 MHz, CDCl3) δ=7.76 (d, J=8.0 Hz, 1H), 7.60-7.56 (m, 1H), 7.29 (td, J=0.9, 8.0 Hz, 1H), 3.87 (s, 3H), 3.71 (s, 2H).

Step 3—(±)-Methyl 2-bromo-4-(3-cyanotetrahydrofuran-3-yl)benzoate

To a solution of sodium hydride (3.46 g, 86.6 mmol) in N,N-dimethylformamide (100 mL) was added methyl 2-bromo-4-(cyanomethyl)benzoate (10.0 g, 39.3 mmol) and 1-chloro-2-(chloromethoxy)ethane (5.33 g, 41.3 mmol) at −10 OC, and then the mixture was stirred at 0° C. for 20 min. On completion, the reaction mixture was quenched by water at 0° C., and then extracted with ethyl acetate (300 mL). The combined organic layer was washed with brine, dried over anhydrous sodium sulfate, filtered and concentrated under reduced pressure to give a residue. The residue was purified by column chromatography (petroleum ether:ethyl acetate=10:1 to 5:1) to afford the title compound. $^1$H NMR (300 MHz, CDCl$_3$) δ=7.82 (d, J=8.4 Hz, 1H), 7.78 (d, J=2.0 Hz, 1H), 7.50 (dd, J=8.4, 2.0 Hz, 1H), 4.31 (d, J=9.2 Hz, 1H), 4.21-4.06 (m, 3H), 3.93 (s, 3H), 2.84-2.80 (m, 1H), 2.46-2.41 (m, 1H).

Step 4—(±)-Methyl 2-bromo-4-(3-carbamoyltetrahydrofuran-3-yl)benzoate

To a solution of (±)-methyl 2-bromo-4-(3-cyanotetrahydrofuran-3-yl)benzoate (11.0 g, 35.4 mmol) in dimethyl sulfoxide (100 mL) was added hydrogen peroxide (20.1 g, 177 mmol) and potassium carbonate (9.80 g, 70.9 mmol). The mixture was stirred at rt for 2 hrs. On completion, the reaction mixture was diluted with water (200 ml) and then extracted with ethyl acetate (500 mL). The organic layer was dried over anhydrous sodium sulfate and filtered; the filtrate was concentrated under vacuum to afford the title compound. $^1$H NMR (300 MHz, DMSO-d$_6$) δ=7.76 (d, J=8.4 Hz, 1H), 7.65 (d, J=2.0 Hz, 1H), 7.42 (dd, J=8.4, 2.0 Hz, 2H), 7.20 (s, 1H), 4.44 (d, J=8.4 Hz, 1H), 3.86 (s, 3H), 3.76-3.73 (m, 3H), 2.85-2.82 (m, 1H), 2.17-2.13 (m, 1H).

Step 5—(±)-Methyl 4-(3-aminotetrahydrofuran-3-yl)-2-bromobenzoate

To a solution of (±)-methyl 2-bromo-4-(3-carbamoyltetrahydrofuran-3-yl)benzoate (2.00 g, 6.09 mmol) in acetonitrile (5 mL) and water (1 mL) was added PhI(CF$_3$CO$_2$)$_2$ (2.62 g, 6.09 mmol). The mixture was stirred at rt for 12 hrs. On completion, the reaction mixture was concentrated under vacuum to afford a residue. The residue was diluted with water (50 mL) and extracted with ethyl acetate (50 mL). The aqueous layer was separated and adjusted with NaHCO$_3$ (sat.) to pH=10, and then extracted with ethyl acetate (500 mL). The organic layer was dried over anhydrous sodium sulfate and filtered. The filtrate was concentrated under vacuum to afford the title compound. $^1$H NMR (400 MHz, DMSO-d$_6$) δ=7.90 (d, J=1.6 Hz, 1H), 7.74 (d, J=8.4 Hz, 1H), 7.59 (dd, J=8.4, 1.6 Hz, 1H), 4.04-4.01 (m, 1H), 3.85 (s, 3H), 3.75 (d, J=8.4 Hz, 1H), 3.69 (d, J=8.4 Hz, 1H), 2.23-2.16 (m, 2H), 2.06-1.99 (m, 1H).

(±)-Methyl 4-(3-amino-1-benzyl-pyrrolidin-3-yl)benzoate (Intermediate AH)

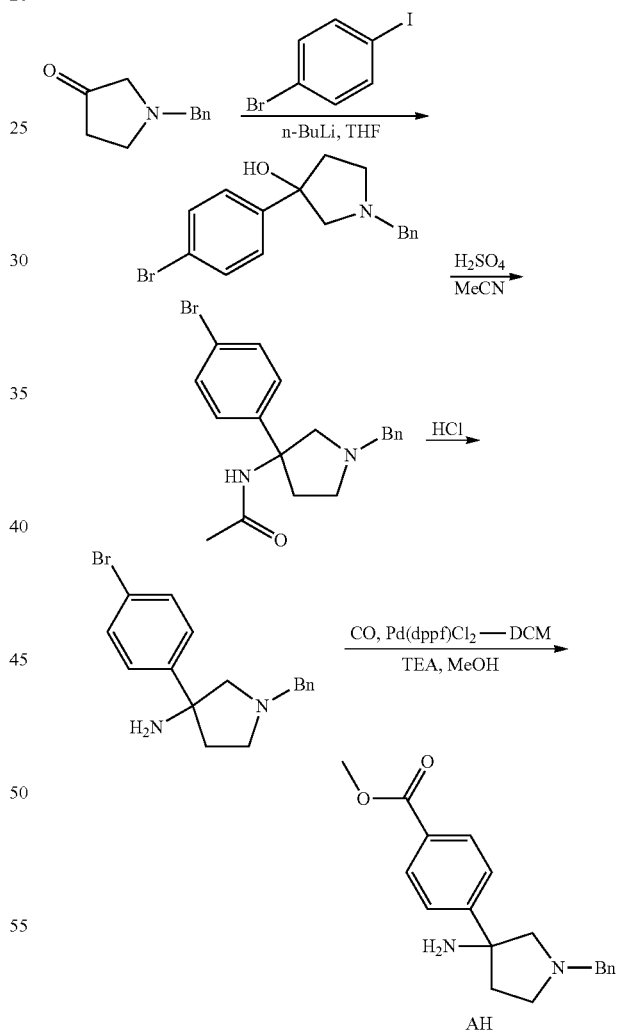

Step 1—(±)-1-Benzyl-3-(4-bromophenyl)pyrrolidin-3-ol

To a solution of 1-bromo-4-iodo-benzene (8.88 g, 31.3 mmol) in tetrahydrofuran (80 mL) was added n-BuLi (2.5 M, 12.5 mL) at −78° C., the mixture was stirred at −78° C.

for 0.5 hr. Then 1-benzylpyrrolidin-3-one (5.00 g, 4.67 mL) was added dropwise, and the mixture was stirred at −78° C. for another 0.5 hrs, and then warmed to rt with stirring for 12 hrs. On completion, the mixture was diluted with saturated ammonium chloride (20 mL) and extracted with ethyl acetate (3×60 mL). The combined organic phase was dried over anhydrous sodium sulfate, filtered and concentrated in vacuo. The residue was purified by chromatography on silica gel (petroleum ether:ethyl acetate=5:1) to give the title compound. $^1$H NMR (400 MHz, CDCl3) δ=7.41-7.35 (m, 2H), 7.32-7.28 (m, 2H), 7.27-7.22 (m, 3H), 7.21-7.15 (m, 2H), 3.65 (s, 2H), 3.06 (dt, J=5.0, 8.8 Hz, 1H), 2.98 (br. s., 1H), 2.86 (d, J=9.4 Hz, 1H), 2.51 (d, J=9.4 Hz, 1H), 2.49-2.42 (m, 1H), 2.28-2.19 (m, 1H), 2.16-2.07 (m, 1H).

Step 2—(±)-N-[1-Benzyl-3-(4-bromophenyl)pyrrolidin-3-yl]acetamide

To a solution of (±)-1-benzyl-3-(4-bromophenyl)pyrrolidin-3-ol (6.10 g, 18.36 mmol) in acetonitrile (75 mL) was added concentrated sulfuric acid (43.2 g, 440 mmol, 23.5 mL) at 0° C., and the reaction was stirred at rt for 12 hrs. On completion, sodium hydroxide (18.7 g, 469 mmol) was added to the mixture at 0° C., then water (30 mL) was added. The resulting mixture was extracted with ethyl acetate (3×50 mL), the combined organic layers were washed with brine, dried over anhydrous sodium sulfate, filtered and concentrated in vacuo. The residue was purified by chromatography on silica gel (petroleum ether:ethyl acetate=5:1 to dichloromethane:methanol=10:1) to give the title compound. $^1$H NMR (400 MHz, CDCl3) δ=7.45-7.40 (m, 2H), 7.39-7.32 (m, 4H), 7.31-7.23 (m, 3H), 6.17 (s, 1H), 3.79-3.60 (m, 2H), 3.00-2.91 (m, 2H), 2.91-2.84 (m, 1H), 2.75 (dt, J=7.2, 8.1 Hz, 1H), 2.47-2.37 (m, 2H), 2.01 (s, 3H)

Step 3—(±)-1-Benzyl-3-(4-bromophenyl)pyrrolidin-3-amine

A solution of (±)-N-[1-benzyl-3-(4-bromophenyl)pyrrolidin-3-yl]acetamide (4.00 g, 10.7 mmol) in hydrochloric acid (6 M, 30 mL) was stirred at 110° C. for 12 hrs. On completion, sodium hydroxide (34.3 g, 857 mmol) was added to the mixture at 0° C. and the mixture was filtered. The filter cake was dissolved in water (20 mL) and extracted with ethyl acetate (3×20 mL). The combined organic phase was dried over anhydrous sodium sulfate, filtered and concentrated in vacuo to give the title compound. $^1$H NMR (400 MHz, CDCl3) δ=7.40-7.35 (m, 2H), 7.33-7.22 (m, 5H), 7.22-7.13 (m, 2H), 3.75-3.61 (m, 2H), 3.03 (dt, J=6.0, 8.7 Hz, 1H), 2.81-2.74 (m, 1H), 2.73-2.65 (m, 1H), 2.63-2.50 (m, 1H), 2.24 (ddd, J=5.9, 9.3, 13.3 Hz, 1H), 1.98 (ddd, J=5.8, 7.7, 13.3 Hz, 1H).

Step 4—(±)-Methyl 4-(3-amino-1-benzyl-pyrrolidin-3-yl)benzoate

To a solution of (1)-1-benzyl-3-(4-bromophenyl)pyrrolidin-3-amine (2.50 g, 7.55 mmol) in methanol (50 mL) was added Pd(dppf)Cl$_2$—CH$_2$Cl$_2$ (616 mg, 754 umol) and triethylamine (763 mg, 7.55 mmol). The mixture was purged with carbon monoxide (50 psi) three times, then, it was heated to 85° C. and stirred for 12 hrs. On completion, the reaction was filtered and the filtrate was concentrated in vacuo. The mixture was acidified to pH=4~5 with hydrochloric acid (1 N). The solution was washed with ethyl acetate (3×10 mL). The aqueous phase was basified to pH=8~9 with sodium hydroxide, and extracted with dichloromethane (3×10 mL). The combined organic phase was dried over anhydrous sodium sulfate, filtered and concentrated in vacuo to give the title product (800 mg, 34% yield) as brown oil. LCMS: (ES$^+$) m/z (M+H)$^+$=331.2, tR=0.497.

(±)-(3-Ethoxy-2-methyl-3-oxo-propanoyl)oxypotassium (Intermediate AI)

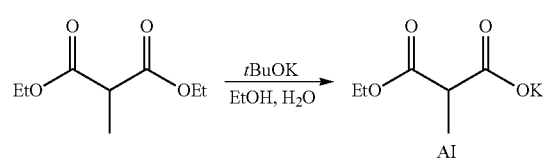

A mixture of diethyl 2-methylpropanedioate (5.00 g, 28.7 mmol) and water (517 uL, 28.7 mmol) in ethanol (30 mL) was stirred at 40° C. for 2 hours. Then a solution of potassium tert-butoxide (3.22 g, 28.7 mmol) in ethanol (30 mL) was added dropwise during 0.5 hour and the reaction mixture was stirred at 40° C. for 2.5 hours. On completion, the reaction mixture was concentrated in vacuo and methyl tert-butyl ether (50 mL) was added. The mixture was filtered and the filter cake was washed with a solution of methyl tert-butyl ether and ethanol (30 mL: 10 mL). The resulting solid was dried in vacuo at 50° C. for 3 hours to give the title compound. $^1$H NMR (400 MHz, D$_2$O) δ=4.10 (q, J=7.0 Hz, 2H), 3.28 (q, J=7.0 Hz, 1H), 1.22 (d, J=7.2 Hz, 3H), 1.17 (t, J=7.0 Hz, 3H).

(±)-Methyl 4-(3-aminotetrahydrofuran-3-yl)-3-chloro-benzoate (Intermediate

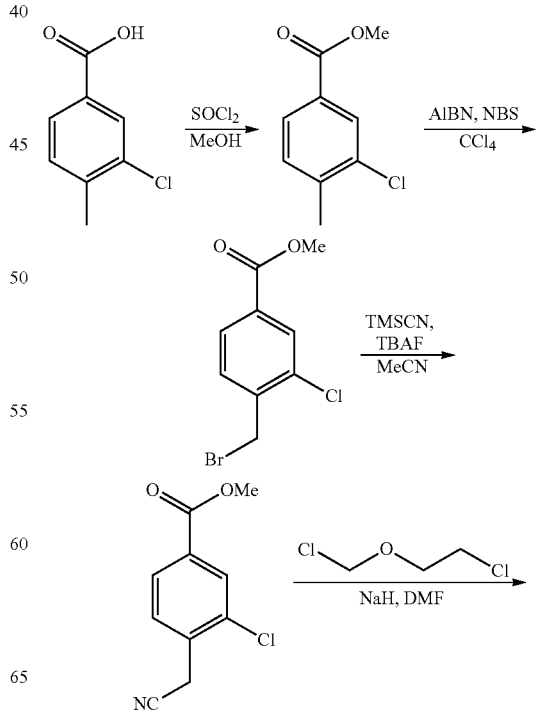

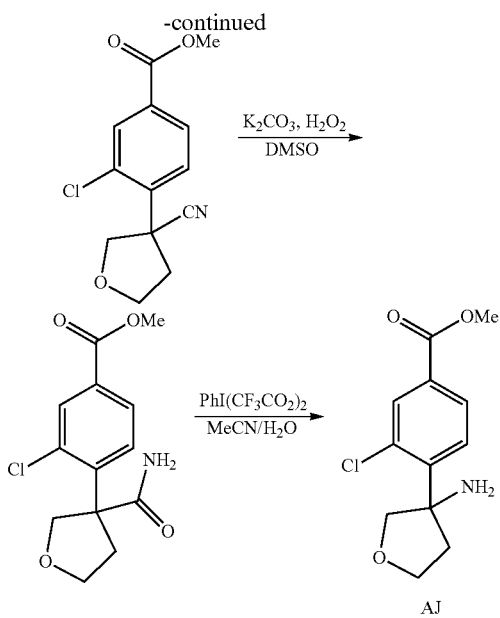

AJ

Step 1—Methyl 3-chloro-4-methyl-benzoate

To a solution of 3-chloro-4-methyl-benzoic acid (20.0 g, 117 mmol) in methanol (200 mL) was added thionyl chloride (65.6 g, 551 mmol). The mixture was heated to 100° C. and stirred at 100° C. for 16 hours. On completion, the mixture was concentrated in vacuo to give a residue. The residue was purified with silica gel chromatography (petroleum ether:ethyl acetate=80:1) to give the title compound. $^1$H NMR (400 MHz, CDCl$_3$) δ=8.01 (s, 1H), 7.83 (d, J=8.0 Hz, 1H), 7.30 (d, J=8.0 Hz, 1H), 3.91 (s, 3H), 2.43 (s, 3H).

Step 2—Methyl 4-(bromomethyl)-3-chloro-benzoate

To a solution of methyl 3-chloro-4-methyl-benzoate (22.5 g, 121 mmol) and 2,2-azobisisobutyronitrile (2.00 g, 12.2 mmol) in carbon tetrachloride (300 mL) was added 1-bromopyrrolidine-2,5-dione (23.8 g, 134 mmol) portion wise. The mixture was heated to 100° C. and stirred at 100° C. for 15 hours. On completion, the mixture was concentrated in vacuo to give a solid. The solid was washed with water (200 mL) and extracted with DCM (2×150 mL). The combined organic layer was dried over anhydrous sodium sulfate, filtered and concentrated in vacuum to give a residue. The residue was purified with silica gel chromatograph (petroleum ether:ethyl acetate=100:1) to give the title compound. $^1$H NMR (400 MHz, CDCl$_3$) δ=7.99 (d, J=1.5 Hz, 1H), 7.84 (dd, J=1.6, 8.0 Hz, 1H), 7.45 (d, J=8.0 Hz, 1H), 4.53 (s, 2H), 3.86 (s, 3H).

Step 3— 3-Chloro-4-(cyanomethyl)benzoate

To a solution of trimethylsilanecarbonitrile (8.47 g, 85.3 mmol) and tetrabutylammonium fluoride (1 M, 85.3 mL) in acetonitrile (600 mL) was added dropwise a solution of methyl 4-(bromomethyl)-3-chloro-benzoate (15.0 g, 56.9 mmol) in acetonitrile (120 mL), and the resulting mixture was stirred at rt for 10 min. On completion, water (50 mL) was added into the mixture. The mixture was concentrated in vacuo. The residue was extracted with dichloromethane (2×50 mL), the combined organic layer was dried over anhydrous sodium sulfate, filtered and concentrated in vacuum to give a residue. The residue was purified with silica gel chromatograph (petroleum ether:ethyl acetate=20:1) to give the title compound. $^1$H NMR (400 MHz, CDCl$_3$) δ=8.12 (d, J=1.8 Hz, 1H), 8.01 (dd, J=1.6, 8.0 Hz, 1H), 7.65 (d, J=8.0 Hz, 1H), 3.97 (s, 3H), 3.92 (s, 2H).

Step 4—(±)-Methyl 3-chloro-4-(3-cyanotetrahydrofuran-3-yl)benzoate

To a mixture of sodium hydride (419 mg, 10.5 mmol, 60% purity) in 10 mL N,N-dimethylformamide was added a solution of methyl 3-chloro-4-(cyanomethyl)benzoate (1.00 g, 4.77 mmol) and 1-chloro-2-(chloromethoxy)ethane (799 mg, 6.20 mmol) in 10 mL N,N-dimethylformamide dropwise at −10° C. to −5° C. Then the mixture was stirred at 0° C. for 0.5 hour. The mixture was stirred at rt for 6 hours. On completion, the reaction mixture was poured into ice-water (50 mL) and stirred for 10 minutes. The reaction mixture was extracted with ethyl acetate (3×50 mL). The organic layers were dried with anhydrous sodium sulfate, filtrated and concentrated in vacuo. The residue was purified by prep-column chromatography (petroleum ether:ethyl acetate=20:1) to give the title compound. $^1$H NMR (400 MHz, CDCl$_3$) δ=8.16 (d, J=1.5 Hz, 1H), 7.98 (dd, J=1.6, 8.2 Hz, 1H), 7.50 (d, J=8.3 Hz, 1H), 4.64 (d, J=9.0 Hz, 1H), 4.28-4.16 (m, 2H), 4.10 (dt, J=5.0, 8.4 Hz, 1H), 3.97 (s, 3H), 2.94 (ddd, J=4.9, 7.3, 12.6 Hz, 1H), 2.66 (td, J=7.8, 12.8 Hz, 1H).

Step 5—(±)-Methyl 4-(3-carbamoyltetrahydrofuran-3-yl)-3-chloro-benzoate

To a solution of (±)-methyl 3-chloro-4-(3-cyanotetrahydrofuran-3-yl)benzoate (260 mg, 978 umol) and potassium carbonate (54.1 mg, 391 umol) in dimethyl sulfoxide (6 mL) was added hydrogen peroxide (886 mg, 7.82 mmol). The mixture was stirred at rt for 3 hours. On completion, the mixture was washed with sat. sodium thiosulfate (20 mL) and extracted with ethyl acetate (3×30 mL). The organic layers were dried with anhydrous sodium sulfate, filtrated and concentrated to give the title compound. $^1$H NMR (400 MHz, CDCl$_3$) δ=8.12 (d, J=1.8 Hz, 1H), 7.99 (dd, J=1.6, 8.2 Hz, 1H), 7.58 (d, J=8.3 Hz, 1H), 5.49 (br. s., 2H), 4.52 (d, J=9.5 Hz, 1H), 4.19 (d, J=9.5 Hz, 1H), 4.11 (d, J=6.5 Hz, 1H), 4.05-3.91 (m, 4H), 3.03-2.89 (m, 1H), 2.55-2.34 (m, 1H).

Step 6—(±)-Methyl 4-(3-aminotetrahydrofuran-3-yl)-3-chloro-benzoate

To a mixture of (±)-methyl 4-(3-carbamoyltetrahydrofuran-3-yl)-3-chloro-benzoate (250 mg, 881 umol) in acetonitrile (3 mL) and water (3 mL) was added PhI(O2CCF3)2 (416 mg, 969 umol) in one portion and the mixture was stirred at rt for 16 hours. On completion, the mixture was washed with 1 N hydrochloric acid (3 mL) and extracted with ethyl acetate (2×20 mL). Then the water layer was washed with sat. sodium bicarbonate until pH=9.0. Then the mixture was extracted with dichloromethane (3×30 mL). The organic layer was dried with anhydrous sodium sulfate, filtrated and concentrated to give the title compound. $^1$H NMR (400 MHz, CDCl$_3$) δ=8.08 (d, J=1.5 Hz, 1H), 7.92 (dd, J=1.6, 8.2 Hz, 1H), 7.46 (d, J=8.3 Hz, 1H), 4.27 (d, J=9.0 Hz, 1H), 4.24-4.15 (m, 1H), 4.13-4.02 (m, 2H), 3.95 (s, 3H), 2.52 (td, J=8.8, 12.3 Hz, 1H), 2.43-2.34 (m, 1H).

(±)-Methyl 4-(3-aminotetrahydrofuran-3-yl)-3-bromo-benzoate (Intermediate

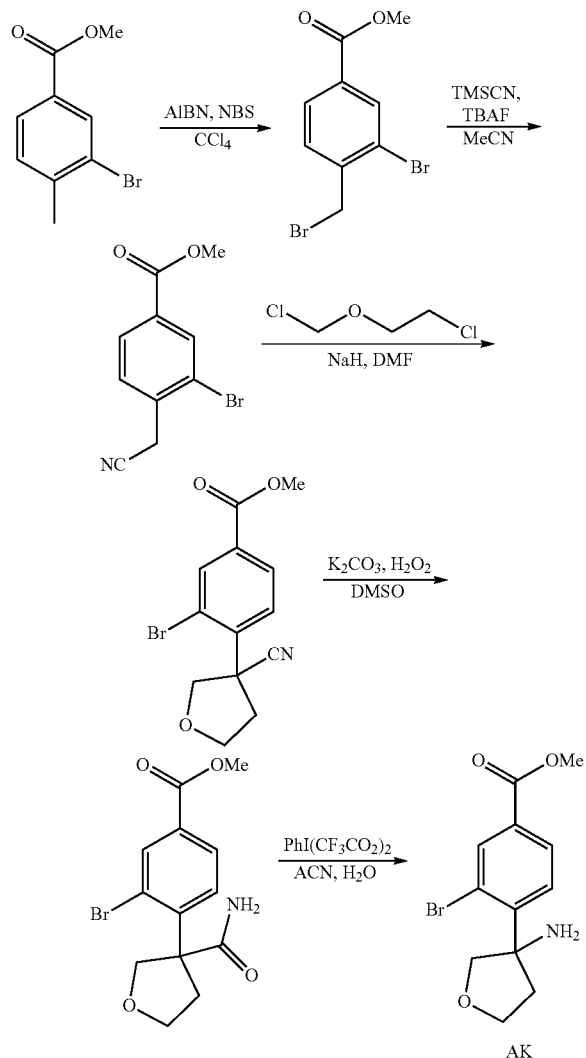

Step 1—Methyl 3-bromo-4-(bromomethyl)benzoate

To a solution of methyl 3-bromo-4-methyl-benzoate (29.0 g, 126 mmol) and 2,2-azobisisobutyronitrile (2.08 g, 12.6 mmol) in carbon tetrachloride (400 mL) was added N-bromosuccinimide (24.7 g, 139 mmol) portion-wise. The mixture was heated to 100° C. and stirred at 100° C. for 15 hrs. On completion, the mixture was concentrated in vacuo to give a solid. The solid was washed with water (200 mL) and extracted with dichloromethane (2×200 mL). The combined organic layer was dried over anhydrous sodium sulfate, filtered and concentrated under vacuum to give a residue. The residue was purified with silica gel chromatography (petroleum ether:ethyl acetate=100:1) to afford the title compound. $^1$H NMR (400 MHz, CDCl3) δ=8.27 (d, J=1.6 Hz, 1H), 7.98 (dd, J=1.7, 8.0 Hz, 1H), 7.55 (d, J=8.0 Hz, 1H), 4.63 (s, 2H), 3.95 (s, 3H).

Step 2—Methyl 3-bromo-4-(cyanomethyl)benzoate

To a solution of trimethylsilyl cyanide (13.5 g, 136 mmol, 17 mL) and tetrabutylammonium fluoride (1 M, 136 mL) in acetonitrile (600 mL) was added dropwise a solution of methyl 3-bromo-4-(bromomethyl)benzoate (28.0 g, 90.9 mmol) in acetonitrile (120 mL), and the resulting mixture was stirred at rt for 10 min. On completion, the mixture was quenched with water (50 mL) and concentrated in vacuo. The leftover solution was then extracted with dichloromethane (2×200 mL), the combined organic layer was dried over anhydrous sodium sulfate, filtered and concentrated in vacuum to give a residue. The residue was purified with silica gel chromatography (petroleum ether:ethyl acetate=20:1) to afford the title compound. $^1$H NMR (400 MHz, CDCl3) δ=8.30 (d, J=1.6 Hz, 1H), 8.05 (dd, J=1.6, 8.0 Hz, 1H), 7.66 (d, J=8.0 Hz, 1H), 3.97 (s, 3H), 3.92 (s, 2H).

Step 3—(±)-Methyl 3-bromo-4-(3-cyanotetrahydrofuran-3-yl)benzoate

To a solution of sodium hydride (346 mg, 8.66 mmol) in N,N-dimethylformamide (30 mL) was added dropwise a solution of methyl 3-bromo-4-(cyanomethyl)benzoate (1.00 g, 3.94 mmol) and 1-chloro-2-(chloromethoxy)ethane (659 mg, 5.12 mmol) in N,N-dimethylformamide (10 mL) at −5° C. The resulting mixture was stirred at 0° C. for 1 hr and then slowly warmed to rt and stirred at rt for 1 hr. On completion, the mixture was slowly poured into ice water (100 mL), washed with brine and extracted with ethyl acetate (2×150 mL). The combined organic layer was dried over anhydrous sodium sulfate, filtered and concentrated under vacuum to give a residue. The residue was purified with silica gel chromatography (petroleum ether:ethyl acetate=20:1) to afford the title compound. $^1$H NMR (400 MHz, CDCl3) δ=8.37 (d, J=1.8 Hz, 1H), 8.02 (dd, J=1.8, 8.3 Hz, 1H), 7.48 (d, J=8.3 Hz, 1H), 4.67 (d, J=9.2 Hz, 1H), 4.29 (d, J=9.2 Hz, 1H), 4.24-4.17 (m, 1H), 4.10 (dt, J=5.0, 8.4 Hz, 1H), 3.97 (s, 3H), 2.98 (ddd, J=4.9, 7.4, 12.7 Hz, 1H), 2.68 (td, J=7.7, 12.9 Hz, 1H).

Step 4—(±)-Methyl 3-bromo-4-(3-carbamoyltetrahydrofuran-3-yl)benzoate

To a solution of (±)-methyl 3-bromo-4-(3-cyanotetrahydrofuran-3-yl)benzoate (1.00 g, 3.22 mmol) and potassium carbonate (178 mg, 1.29 mmol) in dimethyl sulfoxide (10 mL) was added hydrogen peroxide (2.92 g, 25.7 mmol). The mixture was stirred at rt for 2 hrs. On completion, the mixture was quenched with sodium sulfite solution (10 mL) and was extracted with ethyl acetate (3×40 mL). The combined organic layer was then washed with water (50 mL), brine (50 mL), and was dried over anhydrous sodium sulfate, filtered and concentrated in vacuum to give the title compound. $^1$H NMR (400 MHz, CDCl3) δ=8.31 (d, J=1.8 Hz, 1H), 8.02 (dd, J=1.8, 8.2 Hz, 1H), 7.57 (d, J=8.2 Hz, 1H), 5.57-5.32 (m, 2H), 4.49 (d, J=9.3 Hz, 1H), 4.24 (d, J=9.3 Hz, 1H), 4.14-4.04 (m, 1H), 3.95 (s, 3H), 3.94-3.88 (m, 1H), 3.01-2.98 (m, 1H), 2.54-2.33 (m, 1H).

Step 5—(±)-Methyl 4-(3-aminotetrahydrofuran-3-yl)-3-bromo-benzoate

To a mixture of (±)-methyl 3-bromo-4-(3-carbamoyltetrahydrofuran-3-yl)benzoate (600 mg, 1.83 mmol) in acetonitrile (8 mL) and water (8 mL) was added PhI(O$_2$CCF$_3$)$_2$ (864 mg, 2.01 mmol) in one portion, and the mixture was stirred at rt for 16 hrs. On completion, the mixture was concentrated in vacuo. 1N HCl (8 mL) was added into the mixture, and the mixture was washed with ethyl acetate (50 mL). The aqueous layer was then basified with sodium bicarbonate to pH=9 and extracted with dichloromethane (2×50 mL). The combined organic layer was dried over anhydrous sodium sulfate, filtered and concentrated under vacuum to give the title compound. $^1$H NMR (400 MHz, CDCl3) δ=8.29 (d, J=1.8 Hz, 1H), 7.96 (dd, J=1.8, 8.2 Hz, 1H), 7.45 (d, J=8.3 Hz, 1H), 4.34 (d, J=8.8 Hz, 1H), 4.19 (dt, J=6.8, 8.5 Hz, 1H), 4.12 (d, J=8.8 Hz, 1H), 4.05 (dt, J=3.5, 8.4 Hz, 1H), 3.95 (s, 3H), 2.58-2.48 (m, 1H), 2.47-2.39 (m, 1H).

(±)-Methyl 4-(3-aminotetrahydrofuran-3-yl)-3-cyano-benzoate (Intermediate AL)

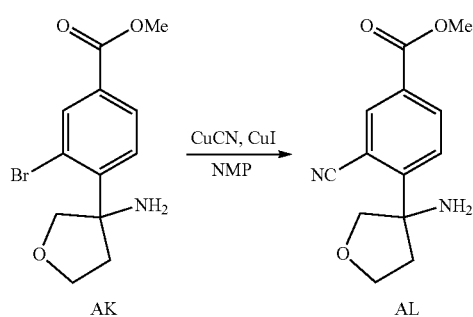

To a mixture of (±)-methyl 4-(3-aminotetrahydrofuran-3-yl)-3-bromo-benzoate (150 mg, 499 umol) and copper cyanide (89.5 mg, 999 umol) in 1-methyl-2-pyrrolidinone (4 mL) was added copper iodide (19.0 mg, 99.9 umol) under a nitrogen atmosphere. The mixture was heated to 180° C. and stirred at 180° C. for 5 hrs. On completion, the mixture was washed with water (30 mL) and extracted with dichloromethane (2×20 mL). The combined organic layer was dried over anhydrous sodium sulfate, filtered and concentrated in vacuum to give a residue. The residue was purified with silica gel chromatography (dichloromethane:methanol=10:1) to afford the title compound. LCMS: (ES$^+$) m/z (M+H)$^+$=247.2, tR=0.703.

Methyl 4-(4-aminotetrahydropyran-4-yl)benzoate (Intermediate AM)

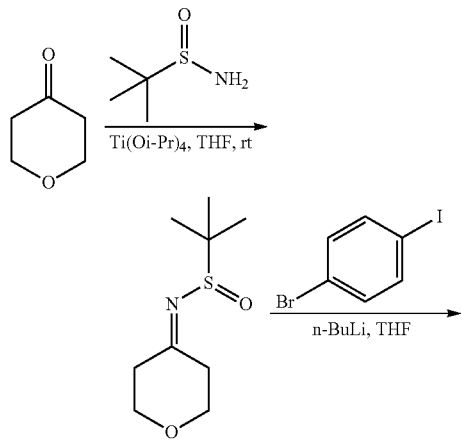

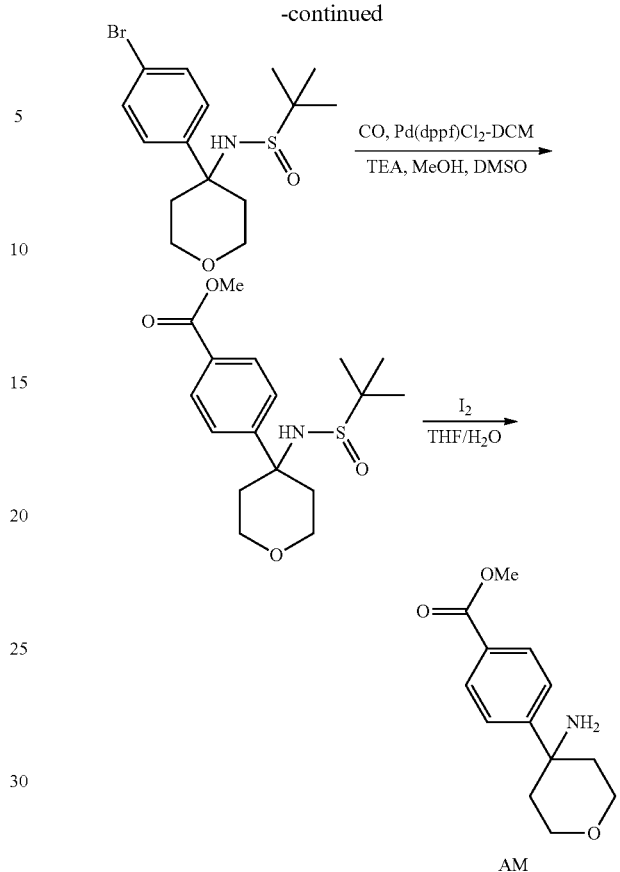

Step 1-2—(±)-Methyl-N-tetrahydropyran-4-ylidene-propane-2-sulfinamide

To a solution of tetrahydropyran-4-one (5.00 g, 49.9 mmol) and (±)-2-methylpropane-2-sulfinamide (5.39 g, 44.4 mmol) in tetrahydrofuran (80 mL) was added tetraethoxytitanium (20.0 g, 87.8 mmol) dropwise and the reaction mixture was stirred at rt for 3 hrs. On completion, the reaction mixture was poured into 500 mL cooled water and the mixture was filtrated. The filtrate was extracted with dichloromethane (3×200 mL). The combined organic layer was dried over anhydrous sodium sulfate, filtrated and concentrated in vacuo. The resulting oil was purified by silica gel chromatography (petroleum ether:ethyl acetate=1:1) to give the title compound. LCMS: (ES$^+$) m/z (M+H)$^+$=204.1, tR=0.695. $^1$H NMR (400 MHz, CDCl$_3$) δ=3.99 (t, J=6.0 Hz, 2H), 3.86 (t, J=5.8 Hz, 2H), 2.57 (t, J=5.8 Hz, 2H), 2.52 (t, J=6.2 Hz, 2H), 1.26 (s, 9H).

Step 2—(±)-N-[4-(4-bromophenyl)tetrahydropyran-4-yl]-2-methyl-propane-2-sulfinamide To a solution of 1-bromo-4-iodo-benzene (2.78 g, 9.84 mmol) in anhydrous tetrahydrofuran (100 mL) was added n-butyllithium (2.5 M, 3.94 mL) dropwise at −70 OC and the reaction mixture was stirred under nitrogen for 0.5 hr. Then a solution of (±)-2-methyl-N-tetrahydropyran-4-ylidene-propane-2-sulfinamide (2.00 g, 9.84 mmol) in anhydrous tetrahydrofuran (20.0 mL) was added dropwise and the reaction mixture was stirred at −70 OC for 0.5 hrs. Then the reaction mixture was warmed to rt during 1 hr and stirred at rt for 1 hr. On completion, the reaction mixture was poured into 300 mL cooled water. The aqueous phase was extracted with dichloromethane (3×100 mL). The combined organic layer was dried over anhydrous sodium sulfate, filtrated and concentrated in vacuo. The resulting oil was purified by silica gel chromatography (dichloromethane:methanol= 10:1) to give the title compound. $^1$H NMR (400 MHz, CDCl$_3$) δ=7.50 (d, J=8.4 Hz, 2H), 7.33 (d, J=8.4 Hz, 2H), 4.25-4.05 (m, 2H), 3.96-3.87 (m, 2H), 2.44-2.40 (m, 2H), 2.21-2.11 (m, 2H), 1.16 (s, 9H).

Step 3—(±)-Methyl 4-[4-(tert-butylsulfinylamino) tetrahydropyran-4-yl]benzoate

To a mixture of (±)-N-[4-(4-bromophenyl)tetrahydropyran-4-yl]-2-methyl-propane-2-sulfinamide (200 mg, 555 umol) and triethylamine (56.1 mg, 555 umol) in a mixture of dimethyl sulfoxide (5 mL) and methanol (20 mL) was added Pd(dppf)Cl$_2$.CH$_2$Cl$_2$ (453 mg, 555 umol) and the reaction mixture was stirred at 80° C. under carbon monoxide (50 psi) for 16 hrs. On completion, the reaction mixture was concentrated in vacuo. Then 50 mL water was added and the aqueous phase was extracted with dichloromethane (3×50 mL). The combined organic layer was dried over anhydrous sodium sulfate, filtrated and concentrated in vacuo. The resulting oil was purified by silica gel chromatography (dichloromethane:methanol=20:1) to give the title compound. LCMS: (ES$^+$) m/z (M+H)$^+$=340.2, tR=0.666.

Step 4—Methyl 4-(4-aminotetrahydropyran-4-yl)benzoate

To a solution of (±)-methyl 4-[4-(tert-butylsulfinylamino) tetrahydropyran-4-yl]benzoate (300 mg, 883 umol) in a mixture of water (3 mL) and tetrahydrofuran (10 mL) was added iodine (44.8 mg, 176 umol) and the reaction mixture was stirred at 50° C. for 5 hrs. On completion, the reaction mixture was concentrated in vacuo to remove the tetrahydrofuran. The aqueous phase was basified with aqueous saturated sodium bicarbonate until pH=9 and extracted with dichloromethane (3×20 mL). The combined organic layer was dried over anhydrous sodium sulfate, filtrated and concentrated in vacuo to give the title compound. LCMS: (ES$^+$) m/z (M−NH2)$^+$=219.1, tR=0.989.

(±)-Ethyl 4-(3-aminotetrahydrofuran-3-yl)benzoate (Intermediate AN)

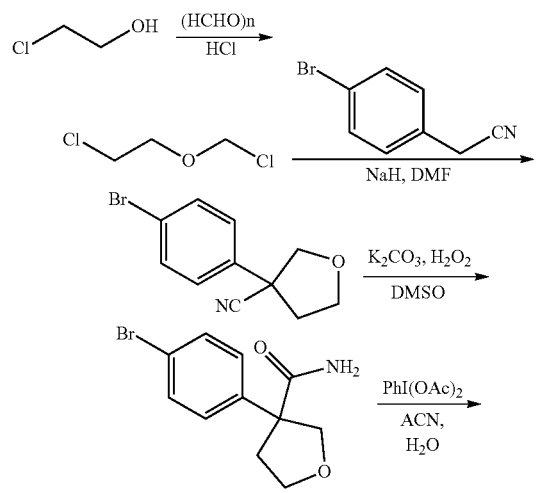

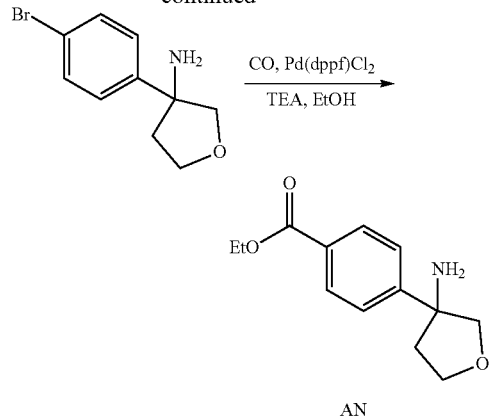

Step 1—1-Chloro-2-(chloromethoxy)ethane

To a solution of paraformaldehyde (29.5 g, 328 mmol) in dichloromethane (600 mL) was bubbled HCl (gas) at −10 OC until the solution became clear. Then, 2-chloroethanol (80.0 g, 994 mmol, 66.7 mL) was added dropwise, and the HCl gas was discontinued. The reaction mixture was stirred at −10° C. for 10 mins. On completion, the reaction was poured into a suspension of anhydrous potassium carbonate (200 g) in dichloromethane (300 mL) and stirred until bubbling ceased. The reaction mixture was filtered and concentrated in vacuo to give the title compound. $^1$H NMR (400 MHz, CDCl3) δ=5.54 (s, 2H), 3.96 (t, J=5.6 Hz, 2H), 3.70 (t, J=5.6 Hz, 2H).

Step 2-(±)-3-(4-Bromophenyl)tetrahydrofuran-3-carbonitrile

To a solution of NaH (4.69 g, 117 mmol, 60% purity) in N,N-dimethylformamide (200 mL) was added 2-(4-bromophenyl)acetonitrile (10.0 g, 51.0 mmol, CAS #16532-79-9) and 1-chloro-2-(chloromethoxy)ethane (7.90 g, 61.2 mmol) in N,N-dimethylformamide (100 mL) portion-wise at 0° C. under a nitrogen. The reaction mixture was warmed to rt with stirring for 12 hrs. On completion, to the reaction mixture was added water (200 mL) then it was extracted with ethyl acetate (3×500 mL). The organic layers were washed with brine (200 mL), dried over anhydrous sodium sulfate, and concentrated in vacuo to give a black solid. The solid was purified by silica gel chromatography (petroleum ether:ethyl acetate=50:1) to give the title compound. $^1$H NMR (400 MHz, CDCl3) δ=7.47 (d, J=8.5 Hz, 2H), 7.29 (d, J=8.8 Hz, 2H), 4.26 (d, J=9.0 Hz, 1H), 4.14-4.04 (m, 2H), 3.96 (d, J=9.0 Hz, 1H), 2.78-2.68 (m, 1H), 2.34 (td, J=8.1, 13.0 Hz, 1H).

Step 3—(±)-3-(4-Bromophenyl)tetrahydrofuran-3-carboxamide

To a mixture of (±) 3-(4-bromophenyl)tetrahydrofuran-3-carbonitrile (8.00 g, 31.7 mmol) and H$_2$O$_2$ (13.7 g, 121 mmol, 11.6 mL, 30% purity) in dimethyl sulfoxide (60 mL) was added potassium carbonate (1.75 g, 12.7 mmol) in one portion at rt. Then the mixture was heated to 60° C. (oil-bath temperature) and stirred for 3 hours. On completion, the reaction mixture was diluted with water (120 mL), filtered and dried in vacuo to give the title compound. $^1$H NMR (400

MHz, DMSO-d$_6$) δ=7.54 (d, J=8.5 Hz, 2H), 7.30 (br. s., 1H), 7.27 (d, J=8.5 Hz, 2H), 7.08 (br. s., 1H), 4.45 (d, J=8.5 Hz, 1H), 3.82-3.69 (m, 3H), 2.82 (ddd, J=5.3, 7.2, 12.4 Hz, 1H), 2.10 (td, J=8.0, 12.5 Hz, 1H).

Step 4—(±)-3-(4-Bromophenyl)tetrahydrofuran-3-amine

To a solution of (±) 3-(4-bromophenyl)tetrahydrofuran-3-carboxamide (8.33 g, 30.8 mmol) in acetonitrile (40 mL) and water (40 mL) was added PhI(OAc)$_2$ (11.92 g, 37.01 mmol) at rt. The reaction mixture was stirred at rt for 12 hrs. On completion, the reaction mixture was concentrated in vacuo. The residue was acidified with HCl (2N, 15 mL) to pH=2 and the aqueous layer was washed with ethyl acetate (100 mL). To the aqueous layer was then added saturated NaHCO$_3$ to pH=9. The aqueous layer was then extracted with ethyl acetate (3×200 mL). The combined organic layer was washed with brine (100 mL), dried over anhydrous sodium sulfate, and concentrated in vacuo to give the title compound. $^1$H NMR (400 MHz, CDCl3) δ=7.50 (d, J=8.5 Hz, 2H), 7.37 (d, J=8.5 Hz, 2H), 4.24-4.14 (m, 1H), 4.14-4.04 (m, 1H), 3.95-3.83 (m, 2H), 2.37 (td, J=8.8, 12.5 Hz, 1H), 2.14 (ddd, J=4.1, 7.5, 12.2 Hz, 1H)

Step 5—(±)-Ethyl 4-(3-aminotetrahydrofuran-3-yl)benzoate

To a mixture of (±) 3-(4-bromophenyl)tetrahydrofuran-3-amine (4.93 g, 20.4 mmol) and TEA (10.3 g, 14.0 mL) in ethanol (50 mL) was added Pd(dppf)Cl$_2$-DCM (1.66 g, 2.04 mmol) in one portion under nitrogen. The mixture was flushed with CO (50 psi) three times then heated to 85° C. and stirred for 16 hours. On completion, the reaction mixture was filtered and concentrated in vacuo to give a residue. The residue was dissolved in a mixture of dichloromethane and water (40 mL/80 mL). Then, the mixture was acidified with HCl (2 N) 60 mL to pH=2, and washed with DCM. The aqueous layer was basified with saturated NaHCO$_3$ (80 mL). Then the mixture was extracted with dichloromethane (3×50 mL), dried over anhydrous sodium sulfate and concentrated in vacuo to give the title compound. LCMS: (ES$^+$) m/z (M-NH$_2$)$^+$=219.2, tR=0.570.

(±)-Methyl 4-(3-aminotetrahydrofuran-3-yl)-3-fluorobenzoate (Intermediate AO)

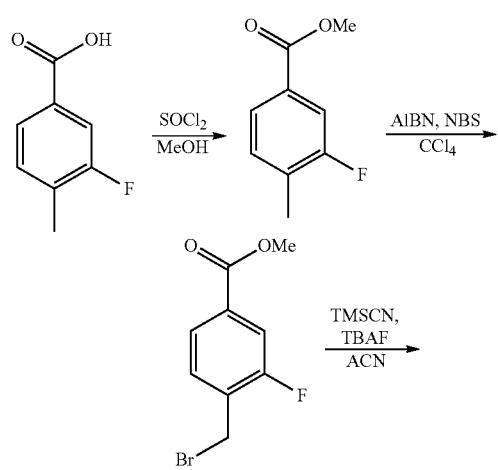

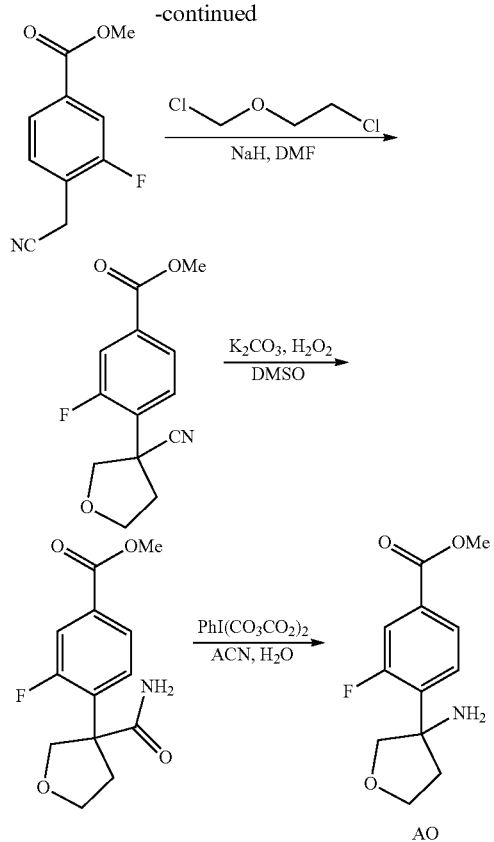

Step 1—Methyl 3-fluoro-4-methylbenzoate

A solution of 3-fluoro-4-methyl-benzoic acid (10.0 g, 64.9 mmol) in methanol (150 mL) was heated from rt to 65° C. Then thionyl chloride (12.3 g, 103 mmol, 7.50 mL) was added dropwise at 65° C., and the mixture was stirred at 65° C. for 16 hours. On completion, the mixture was concentrated, diluted with ethyl acetate (150 mL), washed with water (2×50 mL) and brine (1×50 mL), dried and concentrated to get the title compound. $^1$H NMR (400 MHz, CDCl$_3$) δ=7.64 (d, J=8.0 Hz, 1H), 7.58 (d, J=10.3 Hz, 1H), 7.22-7.12 (m, 1H), 3.83 (s, 3H), 2.25 (d, J=1.3 Hz, 3H).

Step 2—Methyl 4-(bromomethyl)-3-fluorobenzoate

To a solution of methyl 3-fluoro-4-methyl-benzoate (9.90 g, 58.9 mmol) in carbon tetrachloride (120 mL) was added 2,2-azobisisobutyronitrile (966 mg, 5.89 mmol) and n-bromosuccinimide (11.0 g, 61.8 mmol) at rt, then the mixture was heated to reflux at 78° C. for 16 hours. On completion, the solvent was removed in vacuo, and the residue was dissolved with ethyl acetate (200 mL), washed with water (2×50 mL), brine (1×50 mL), dried and concentrated to give the title compound (crude). $^1$H NMR (400 MHz, CDCl$_3$) δ=7.83 (dd, J=1.1, 7.9 Hz, 1H), 7.74 (dd, J=1.1, 9.9 Hz, 1H), 7.49 (t, J=7.7 Hz, 1H), 4.53 (s, 2H), 3.94 (s, 3H).

Step 3—Methyl 4-(cyanomethyl)-3-fluorobenzoate

To a solution of trimethylsilanecarbonitrile (400 mg, 4.04 mmol) and tetrabutylammonium fluoride (1.06 g, 4.04 mmol) in acetonitrile (20.0 mL) was added a solution of methyl 4-(bromomethyl)-3-fluoro-benzoate (500 mg, 2.02 mmol) in acetonitrile (10 mL) dropwise at 0° C. The mixture was stirred at rt for 10 minutes. On completion, water (50 mL) was added into the mixture. Then the mixture was extracted with ethyl acetate (2×50 mL), the combined organic phase was dried over with anhydrous sodium sulfate, filtered, and concentrated in vacuo to give brown oil. The oil was purified by silica gel chromatograph (petroleum ether:ethyl acetate=20:1) to give the title compound. $^1$H NMR (400 MHz, CDCl$_3$) δ=7.89 (d, J=7.8 Hz, 1H), 7.78 (d, J=10.3 Hz, 1H), 7.56 (t, J=7.7 Hz, 1H), 3.95 (s, 3H), 3.84 (s, 2H).

Step 4—(±)-Methyl 4-(3-cyanotetrahydrofuran-3-yl)-3-fluorobenzoate

A solution of sodium hydride (372 mg, 15.5 mmol) in dimethyl formamide (10 mL) was stirred at −5° C., then a solution of methyl 4-(cyanomethyl)-3-fluoro-benzoate (1.00 g, 5.18 mmol) and 1-chloro-2-(chloromethoxy)ethane (734 mg, 5.70 mmol) in dimethyl formamide (10 mL) was added dropwise at −5° C. The mixture was stirred at rt for 16 hours. On completion, the mixture was poured into water (60 mL), then the aqueous phase was extracted with ethyl acetate (3×30 mL). The combined extracts were washed with brine (30 mL), dried and concentrated. The mixture was purified by column chromatography (petroleum ether:ethyl acetate=20:1 to 5:1) to give the title compound. $^1$H NMR (400 MHz, CDCl$_3$) δ=7.88 (dd, J=1.4, 8.2 Hz, 1H), 7.84-7.77 (m, 1H), 7.59-7.51 (m, 1H), 4.52 (dd, J=2.0, 9.0 Hz, 1H), 4.28-4.19 (m, 1H), 4.13 (d, J=7.0 Hz, 2H), 3.98 (s, 3H), 2.89-2.79 (m, 1H), 2.60 (td, J=7.8, 12.9 Hz, 1H).

Step 5—(±)-Methyl 4-(3-carbamoyltetrahydrofuran-3-yl)-3-fluorobenzoate

To a suspension of (±)-methyl 4-(3-cyanotetrahydrofuran-3-yl)-3-fluoro-benzoate (610 mg, 2.45 mmol) and potassium carbonate (135 mg, 980 umol) in dimethyl sulfoxide (20 mL) was added hydrogen peroxide (30% wt, 833 mg, 7.35 mmol, 750 uL) in one portion at rt. Then the mixture was stirred at rt for 3 hours. On completion, the mixture was poured into water (60 mL), then the aqueous phase was extracted with ethyl acetate (3×30 mL). The combined organic extracts were washed with brine (30 mL), dried and concentrated to give the title compound. LCMS: (ES$^+$) m/z (M+H)$^+$=268.0, tR=0.981.

Step 6—(±)-Methyl 4-(3-aminotetrahydrofuran-3-yl)-3-fluorobenzoate

To a solution of methyl 4-(3-carbamoyltetrahydrofuran-3-yl)-3-fluoro-benzoate (390 mg, 1.46 mmol) in acetonitrile (25 mL) and water (25 mL) was added PhI(CO$_2$CF$_3$)$_2$ (787 mg, 1.83 mmol) in one portion at rt, then the mixture was stirred at rt for 16 hours. On completion, the acetonitrile was removed in vacuo, and the residue was diluted with water (60 mL) and acidified with 1N HCl, then extracted with dichloromethane (2×30 mL) and the organic phase was discarded. Then the aqueous phase was basified with 1 M sodium hydroxide to pH=7-8, and the mixture was extracted with ethyl acetate (3×30 mL). The combined extracts were washed with brine (30 mL), dried and concentrated to give the title compound. LCMS: (ES$^+$) m/z (M−NH2)$^+$=223.0, tR=1.01.

2—(Chloromethyl)-1-((2-(trimethylsilyl)ethoxy)methyl)-1H-imidazole (Intermediate AP)

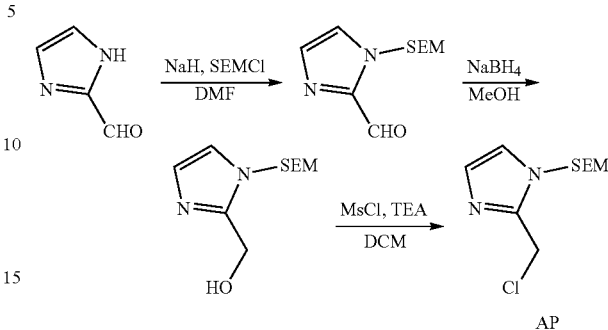

Step 1—1-((2-(Trimethylsilyl)ethoxy)methyl)-1H-imidazole-2-carbaldehyde

To a mixture of sodium hydride (500 mg, 12.5 mmol) in N,N-dimethylformamide (10 mL) was added 1H-imidazole-2-carbaldehyde (1.00 g, 10.4 mmol). The reaction mixture was stirred at rt for 1.5 hrs. Then 2-(chloromethoxy)ethyl-trimethyl-silane (2.08 g, 12.5 mmol) was added at 0° C. The reaction mixture was stirred at rt for 16 hrs. On completion, the mixture was quenched by water (50 mL) and extracted with ethyl acetate (3×100 mL). The combined organic layers were dried over sodium sulfate and concentrated in vacuo. The residue was purified by chromatography (petroleum ether:ethyl acetate=5:1) to give the title compound. $^1$H NMR (400 MHz, CDCl3) δ=9.85 (s, 1H), 7.39 (s, 1H), 7.35 (s, 1H), 5.80 (s, 2H), 3.59 (t, J=8.4 Hz, 2H), 0.92-1.00 (m, 2H), 0.003 (s, 9H).

Step 2—1-((2-(Trimethylsilyl)ethoxy)methyl)-1H-imidazole-2-carbaldehyde

To a solution of 1-(2-trimethylsilylethoxymethyl)imidazole-2-carbaldehyde (2.00 g, 8.84 mmol) in methanol (20 mL) was added sodium hydroboronate (334 mg, 8.84 mmol) in three portions at −10° C. Then the reaction mixture was stirred at rt for 1 h. On completion, the mixture was quenched with water (20 mL) and extracted with dichloromethane (3×30 mL). The combined organic layers were dried over sodium sulfate and concentrated in vacuo. The residue was purified by silica gel chromatography (petroleum ether:ethyl acetate=10:1 to 1:1) to give the title compound. $^1$H NMR (400 MHz, DMSO-d6) δ=7.26 (s, 1H), 6.86 (d, J=1.2 Hz, 1H), 5.41 (s, 2H), 5.36 (t, J=4.8 Hz, 1H), 4.54 (d, J=5.2 Hz, 2H), 3.53 (t, J=8.0 Hz, 2H), 0.86-0.90 (m, 2H), 0.00 (s, 9H).

Step 3—2—(Chloromethyl)-1-((2-(trimethylsilyl)ethoxy)methyl)-1H-imidazole

To a mixture of [1-(2-trimethylsilylethoxymethyl)imidazol-2-yl]methanol (300 mg, 1.31 mmol) and triethylamine (265 mg, 2.62 mmol) in dichloromethane (10 mL) was added methanesulfonyl chloride (130 mg, 1.13 mmol) in one portion at 0° C. under nitrogen. The mixture was stirred at 0° C. for 1 h. On completion, the mixture was quenched with saturated aqueous citric acid solution (10 mL) and water (30 mL), then extracted with dichloromethane (2×30 mL). The combined organic layers were washed with saturated aqueous sodium bicarbonate (60 mL), dried over sodium sulfate, and concentrated in vacuo to give the title compound, which was used in next step directly. ¹H NMR (400 MHz, CDCl3) δ=7.13-7.18 (m, 2H), 5.46 (s, 2H), 4.92 (s, 2H), 3.54-3.58 (m, 2H), 0.94 (t, J=8.4 Hz, 2H), 0.00 (s, 9H).

(±)-4—(Chloromethyl)-1-methyl-pyrrolidin-2-one (Intermediate AQ)

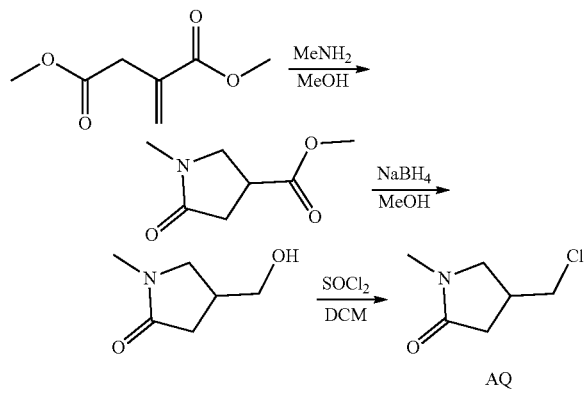

Step 1—(±)-Methyl 1-methyl-5-oxo-pyrrolidine-3-carboxylate

To a solution of dimethyl 2-methylenebutanedioate (15.0 g, 94.8 mmol) in methanol (150 mL) was added methanamine (4.42 g, 142 mmol), and the mixture was stirred at rt for 12 hrs. On completion, the reaction was concentrated in vacuo and the residue was purified by chromatography on silica gel (petroleum ether:ethyl acetate=5:1 to dichloromethane:methanol=10:1) to give the title compound. ¹H NMR (400 MHz, CDCl3) δ=3.74 (s, 3H), 3.65-3.50 (m, 2H), 3.30-3.14 (m, 1H), 2.85 (s, 3H), 2.74-2.55 (m, 2H)

Step 2—(±)-4-(Hydroxymethyl)-1-methyl-pyrrolidin-2-one

To a solution of (±)-methyl 1-methyl-5-oxo-pyrrolidine-3-carboxylate (4.00 g, 25.4 mmol) in methanol (10 mL) was added sodium borohydride (2.89 g, 76.3 mmol) at 0° C., and the mixture was stirred at rt for 3 hrs. On completion, the reaction was adjusted pH to 4-5 with concentrated hydrochloric acid and the mixture was concentrated in vacuo. The residue was diluted with solvent (50 mL, dichloromethane:methanol=10:1), filtered, and the filtrate was concentrated to give the title compound. ¹H NMR (400 MHz, CDCl3) δ=3.72-3.60 (m, 2H), 3.58-3.46 (m, 1H), 3.35-3.25 (m, 1H), 2.88 (s, 3H), 2.66-2.50 (m, 2H), 2.31 (m, 1H)

Step 3—(±)-4—(Chloromethyl)-1-methyl-pyrrolidin-2-one

To a solution of (±)-4-(hydroxymethyl)-1-methyl-pyrrolidin-2-one (1.00 g, 7.74 mmol) in dichloromethane (8 mL) was added thionyl chloride (2.30 g, 19.3 mmol), and the mixture was stirred at 60° C. for 5 hrs. On completion, the mixture was concentrated in vacuo and the residue was purified by chromatography on silica gel (petroleum ether:ethyl acetate=1:1 to dichloromethane:methanol=20:1) to give the title compound. Used crude in the next reaction.

3—(Chloromethyl)tetrahydrofuran (Intermediate AR)

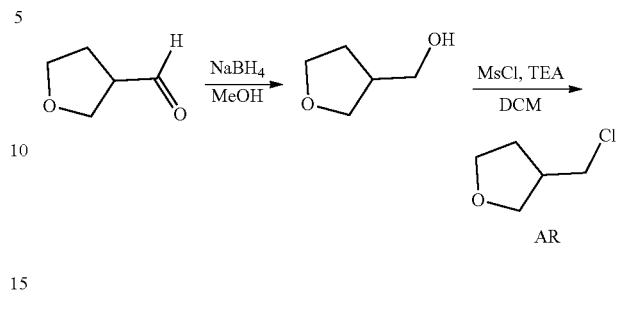

Step 1—Tetrahydrofuran-3-ylmethanol

To a solution of tetrahydrofuran-3-carbaldehyde (3.00 g, 29.9 mmol) in anhydrous methanol (30 mL) was added sodium borohydride (1.70 g, 44.9 mmol) in 3 portions. The mixture was stirred at 0° C. for 2 hrs. On completion, the reaction was quenched with ice water (5 mL) and concentrated in vacuo. The residue was triturated with a mixture of dichloromethane:methanol=10:1 (30 mL). The mixture was filtered; the filtrate was dried over anhydrous sodium sulfate, filtered and concentrated in vacuo to give the title compound. ¹H NMR (300 MHz, CDCl3) δ=3.84-3.74 (m, 2H), 3.73-3.62 (m, 1H), 3.61-3.41 (m, 3H), 3.18 (br. s., 1H), 2.51-2.33 (m, 1H), 2.03-1.89 (m, 1H), 1.57 (dt, J=7.3, 12.9 Hz, 1H).

Step 2-3—(Chloromethyl)tetrahydrofuran

To a solution of tetrahydrofuran-3-ylmethanol (150 mg, 1.47 mmol) and triethylamine (371 mg, 3.68 mmol) in anhydrous dichloromethane (10 mL) was added methanesulfonyl chloride (252 mg, 2.21 mmol) dropwise at 0° C. Then the mixture was stirred at rt for 2 hrs. On completion, the reaction mixture was filtered through a plug of Celite and the filtrate was concentrated in vacuo to give the title compound. ¹H NMR (400 MHz, CDCl3) δ=3.84-3.75 (m, 2H), 3.69 (q, J=7.8 Hz, 1H), 3.59-3.52 (m, 1H), 3.48-3.42 (m, 1H), 2.67-2.48 (m, 1H), 2.14-1.95 (m, 1H), 1.70-1.52 (m, 1H).

3—(Chloromethyl)oxetane (Intermediate AS)

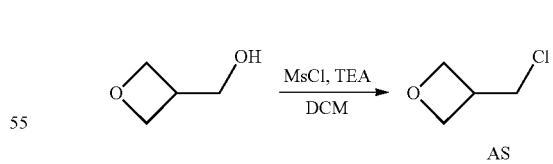

To a solution of oxetan-3-ylmethanol (500 mg, 5.68 mmol) and triethylamine (1.44 g, 14.2 mmol) in anhydrous dichloromethane (20 mL) was added methanesulfonyl chloride (975 mg, 8.52 mmol) dropwise at 0° C. Then, the mixture was stirred at rt for 2 hrs. On completion, the reaction mixture was quenched with ice water (10 mL), diluted with water (20 mL) and extracted with dichloromethane (2×20 mL). The combined organic layers were dried over anhydrous sodium sulfate, filtered, and concentrated in vacuo to give the title compound. ¹H NMR (400 MHz, CDCl3) δ=4.78-4.71 (m, 2H), 4.44-4.37 (m, 2H), 3.61 (s, 2H), 3.39-3.28 (m, 1H).

(±)-Ethyl 6-(3-aminotetrahydrofuran-3-yl)pyridine-3-carboxylate (Intermediate AT)

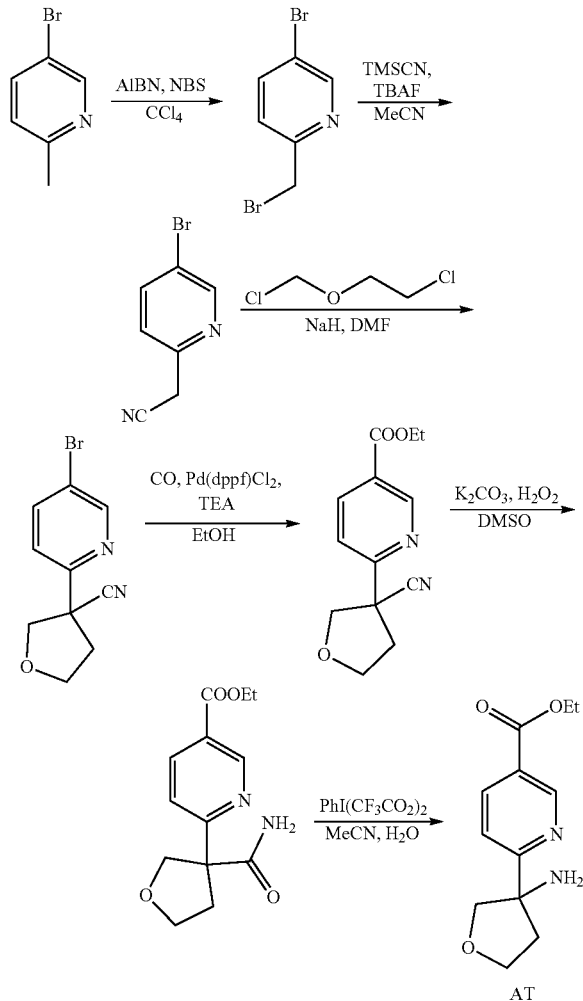

Step 1—5-bromo-2-(bromomethyl)pyridine

To a solution of 5-bromo-2-methyl-pyridine (32.0 g, 186 mmol) in carbon tetrachloride (50 mL) was added 2,2-azobisisobutyronitrile (2.44 g, 14.8 mmol) and N-bromosuccinimide (39.7 g, 223 mmol), and the mixture was stirred at 90° C. for 12 hrs under nitrogen atmosphere. On completion, the mixture was concentrated to give a residue. The residue was purified by chromatography on silica gel (petroleum ether:ethyl acetate=80:1 to 20:1) to give the title compound. ¹H NMR (400 MHz, CDCl3) δ=8.62 (d, J=2.4 Hz, 1H), 7.62 (dd, J=2.4, 8.0 Hz, 1H), 7.35 (d, J=8.0 Hz, 1H), 4.41 (s, 2H).

Step 2—2-(5-bromo-2-pyridyl)acetonitrile

To a solution of trimethylsilyl cyanide (5.34 g, 53.8 mmol) in acetonitrile (50 mL) was added tetrabutylammonium fluoride (1 M in tetrahydrofuran, 35.8 mL, 35.8 mmol), and the mixture was stirred at rt for 0.1 hr. Then 5-bromo-2-(bromomethyl)pyridine (9.00 g, 35.8 mmol) in acetonitrile (20 mL) was added and the mixture was stirred at rt for 0.2 hr. On completion, the reaction mixture was concentrated to remove the acetonitrile and then the mixture was diluted with water (30 mL) and extracted with ethyl acetate (3×80 mL). The combined organic layer was washed with brine (3×30 mL), dried over anhydrous sodium sulfate, filtered and concentrated to give a residue. The residue was purified by chromatography on silica gel (petroleum ether:ethyl acetate=50:1 to 5:1) to give the title compound. ¹H NMR (400 MHz, DMSO-d6) δ=8.71 (d, J=2.3 Hz, 1H), 8.10 (dd, J=2.3, 8.5 Hz, 1H), 7.41 (d, J=8.5 Hz, 1H), 4.22 (s, 2H).

Step 3—(±)-3-(5-bromo-2-pyridyl)tetrahydrofuran-3-carbonitrile

To a mixture of sodium hydride (1.70 g, 42.44 mmol, 60% purity) in dimethyl formamide (200 mL) was added 2-(5-bromo-2-pyridyl)acetonitrile (3.80 g, 19.2 mmol) and 1-chloro-2-(chloromethoxy)ethane (2.61 g, 20.2 mmol) in dimethyl formamide (150 mL) at −10° C. The mixture was stirred at −10° C. for 0.3 hr. On completion, the reaction mixture was quenched by addition of water (50 mL) at 0° C., and then extracted with ethyl acetate (3×200 mL). The combined organic layers were washed with brine (7×200 mL), dried over anhydrous sodium, filtered and concentrated under reduced pressure to give a residue. The residue was purified by chromatography on silica gel (petroleum ether: ethyl acetate=10:1 to 5:1) to give the title compound. ¹H NMR (400 MHz, CDCl3) δ=8.60 (d, J=1.9 Hz, 1H), 7.81 (dd, J=2.3, 8.3 Hz, 1H), 7.50 (d, J=8.4 Hz, 1H), 4.31 (d, J=8.8 Hz, 1H), 4.14-4.06 (m, 3H), 2.75-2.66 (m, 1H), 2.65-2.57 (m, 1H).

Step 4—(±)-ethyl 6-(3-cyanotetrahydrofuran-3-yl)pyridine-3-carboxylate

To a solution of (±)-3-(5-bromo-2-pyridyl)tetrahydrofuran-3-carbonitrile (2.40 g, 9.48 mmol) in ethanol (50 mL) was added Pd(dppf)Cl2.CH2Cl2 (774 mg, 948 umol) and triethylamine (2.88 g, 28.44 mmol). The mixture was purged with CO (50 psi) three times, then it was heated to 90° C. and stirred for 12 hrs under CO (50 psi). On completion, the reaction was concentrated in vacuo to give a residue. The residue was purified by chromatography on silica gel (petroleum ether:ethyl acetate=50:1 to 3:1) to give the title compound. ¹H NMR (400 MHz, CDCl3) δ=9.22 (d, J=2.1 Hz, 1H), 8.37 (dd, J=2.2, 8.2 Hz, 1H), 7.78 (d, J=8.2 Hz, 1H), 4.50-4.40 (m, 3H), 4.28-4.18 (m, 3H), 2.89-2.81 (m, 1H), 2.78-2.68 (m, 1H), 1.44 (t, J=7.1 Hz, 3H).

Step 5—(±)-ethyl 6-(3-carbamoyltetrahydrofuran-3-yl)pyridine-3-carboxylate

To a solution of (±)-ethyl 6-(3-cyanotetrahydrofuran-3-yl)pyridine-3-carboxylate (700 mg, 2.84 mmol) in dimethyl sulfoxide (6 mL) was added potassium carbonate (785 mg, 5.68 mmol) and hydrogen peroxide (3.22 g, 28.4 mmol, 30% purity), and the mixture was stirred at rt for 12 hrs. On completion, the mixture was diluted with water (10 mL) and extracted with dichloromethane (3×20 mL). The organic layer was washed with water (3×10 mL), dried over anhydrous sodium sulfate, filtered and concentrated to give the title compound. ¹H NMR (400 MHz, CDCl3) δ=9.19 (dd, J=0.8, 2.2 Hz, 1H), 8.31 (dd, J=2.3, 8.3 Hz, 1H), 7.46 (dd, J=0.8, 8.2 Hz, 1H), 6.59 (br. s., 1H), 5.45 (br. s., 1H), 4.57 (d, J=9.2 Hz, 1H), 4.44 (q, J=7.1 Hz, 2H), 4.27 (d, J=9.2 Hz, 1H), 4.13-4.05 (m, 1H), 3.97 (dt, J=5.3, 8.4 Hz, 1H), 2.95 (ddd, J=5.5, 7.6, 12.7 Hz, 1H), 2.56 (ddd, J=6.9, 8.3, 12.5 Hz, 1H), 1.43 (t, J=7.2 Hz, 3H).

Step 6—(±)-Ethyl 6-(3-aminotetrahydrofuran-3-yl)pyridine-3-carboxylate

To a solution of (±)-ethyl 6-(3-carbamoyltetrahydrofuran-3-yl)pyridine-3-carboxylate (200 mg, 756 umol) in acetonitrile (5 mL) and water (1 mL) was added [bis(trifluoroacetoxy)iodo]benzene (390 mg, 908 umol). The mixture was stirred at 30° C. for 12 hrs. On completion, the mixture was concentrated to remove acetonitrile, diluted with saturated potassium carbonate (10 mL) and extracted with dichloromethane (3×50 mL). The combined organic layer was washed with water (3×30 mL), dried over anhydrous sodium sulfate, filtered and concentrated to give the title compound. $^1$H NMR (400 MHz, CDCl3) δ=9.16 (d, J=1.5 Hz, 1H), 8.28 (d, 8.2 Hz, 1H), 7.64 (d, J=8.3 Hz, 1H), 4.45-4.39 (m, 2H), 4.21 (q, J=7.9 Hz, 1H), 4.16-4.06 (m, 3H), 2.65-2.49 (m, 2H), 1.40 (t, J=7.6 Hz, 3H).

(±)-Ethyl 5-(3-aminotetrahydrofuran-3-yl)pyridine-2-carboxylate (Intermediate AU)

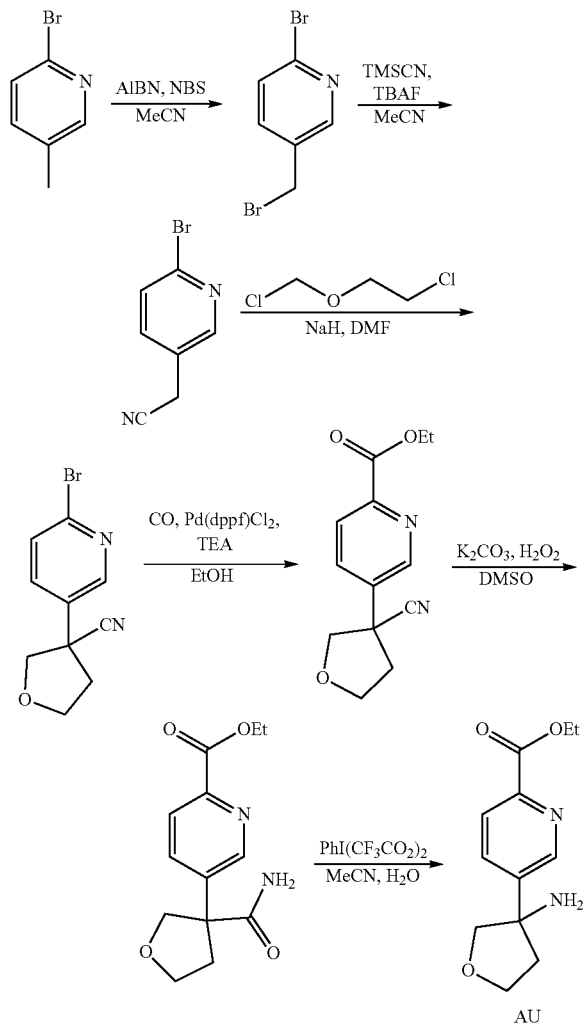

Step 1—2-bromo-5-(bromomethyl)pyridine

To a solution of 2-bromo-5-methyl-pyridine (20.0 g, 116 mmol) in acetonitrile (300 mL) was added 2,2-azobisisobutyronitrile (1.91 g, 11.63 mmol) and N-bromosuccinimide (24.8 g, 139 mmol), and the mixture was stirred at 90° C. for 12 hrs under nitrogen atmosphere. On completion, the reaction was concentrated to give a residue. The residue was purified by chromatography on silica gel (petroleum ether: ethyl acetate=10:1 to 5:1) to give the title compound. $^1$H NMR (400 MHz, CDCl3) δ=8.40 (d, J=2.4 Hz, 1H), 7.62 (dd, J=2.6, 8.2 Hz, 1H), 7.51 (d, J=8.3 Hz, 1H), 4.42 (s, 2H).

Step 2—2-(6-bromo-3-pyridyl)acetonitrile

To a solution of trimethylsilyl cyanide (2.37 g, 23.9 mmol) in acetonitrile (30 mL) was added tetrabutylammonium fluoride (1 M in tetrahydrofuran, 6.25 g, 23.9 mmol), and the mixture was stirred at rt for 0.1 hr. Then 2-bromo-5-(bromomethyl)pyridine (4.00 g, 15.9 mmol) in acetonitrile (20 mL) was added, and the mixture was stirred at rt for 0.2 hr. On completion, the reaction was concentrated to remove acetonitrile and then diluted with water (30 mL). The mixture was extracted with ethyl acetate (3×80 mL), washed with brine (3×30 mL), dried over anhydrous sodium sulfate, filtered and concentrated in vacuo to give a residue. The residue was purified by chromatography on silica gel (petroleum ether:ethyl acetate=50:1 to 5:1) to give the title compound. $^1$H NMR (400 MHz, CDCl3) δ=8.34 (d, J=1.8 Hz, 1H), 7.61-7.56 (m, 1H), 7.55-7.51 (m, 1H), 3.74 (s, 2H).

Step 3—(±)-3-(6-bromo-3-pyridyl)tetrahydrofuran-3-carbonitrile

To a mixture of sodium hydride (8.93 g, 22.3 mmol, 60% purity) in dimethyl formamide (200 mL) was added (±)-2-(6-bromo-3-pyridyl)acetonitrile (2.00 g, 10.1 mmol) and 1-chloro-2-(chloromethoxy)ethane (1.37 g, 10.6 mmol) in dimethyl formamide (50 mL) at −10 OC, and the mixture was stirred at −10° C. for 0.3 hr. On completion, the reaction mixture was quenched by addition of water (50 mL) at 0° C., and then extracted with ethyl acetate (3×200 mL). The combined organic layers were washed with brine (7×200 mL), dried over anhydrous sodium, filtered and concentrated under reduced pressure to give a residue. The residue was purified by chromatography on silica gel (petroleum ether: ethyl acetate=10:1 to 5:1) to give the title compound. $^1$H NMR (400 MHz, CDCl3) δ=8.53 (d, J=2.5 Hz, 1H), 7.67 (dd, J=2.5, 8.4 Hz, 1H), 7.54 (d, J=8.4 Hz, 1H), 4.32 (d, J=9.0 Hz, 1H), 4.24-4.13 (m, 2H), 4.07 (d, J=9.0 Hz, 1H), 2.87-2.83 (m, 1H), 2.48-2.35 (m, 1H).

Step 4—(±)-ethyl 5-(3-cyanotetrahydrofuran-3-yl)pyridine-2-carboxylate

To a solution of (±)-3-(6-bromo-3-pyridyl)tetrahydrofuran-3-carbonitrile (1.50 g, 5.93 mmol) in ethanol (50 mL) was added Pd(dppf)Cl$_2$.CH$_2$Cl$_2$ (484 mg, 593 umol) and triethylamine (1.80 g, 17.8 mmol). The mixture was purged with carbon monoxide (50 psi) three times, then it was heated to 90° C. and stirred for 12 hrs under carbon monoxide (50 psi). On completion, the reaction was concentrated to give a residue. The residue was purified by chromatography on silica gel (petroleum ether:ethyl acetate=50:1 to 2:1) to give the title compound. $^1$H NMR (400 MHz, CDCl3) δ=8.89 (d, J=2.3 Hz, 1H), 8.17 (d, J=8.3 Hz, 1H), 7.98 (dd, J=2.3, 8.3 Hz, 1H), 4.50 (q, J=7.2 Hz, 2H), 4.36 (d, J=9.3 Hz, 1H), 4.27-4.12 (m, 3H), 2.94-2.83 (m, 1H), 2.50-2.45 (m, 1H), 1.45 (t, J=7.2 Hz, 3H).

Step 5—(±)-ethyl 5-(3-carbamoyltetrahydrofuran-3-yl)pyridine-2-carboxylate

To a solution of (±)-ethyl 5-(3-cyanotetrahydrofuran-3-yl)pyridine-2-carboxylate (500 mg, 2.03 mmol) in dimethyl sulfoxide (10 mL) was added potassium carbonate (561 mg, 4.06 mmol) and hydrogen peroxide (1.15 g, 10.1 mmol, 30% in water), and the mixture was stirred at rt for 12 hrs. On completion, the mixture was diluted with water (10 mL) and extracted with dichloromethane (3×20 mL). The organic layer was washed with water (3×10 mL), dried over anhydrous sodium sulfate, filtered and concentrated to give the title compound. $^1$H NMR (400 MHz, CDCl3) δ=8.71 (s, 1H), 8.15 (d, J=8.2 Hz, 1H), 7.81 (dd, J=2.0, 8.2 Hz, 1H), 5.98-5.52 (m, 2H), 4.56-4.45 (m, 3H), 4.18-4.10 (m, 1H), 4.08-3.98 (m, 2H), 2.92 (ddd, J=5.8, 7.6, 12.9 Hz, 1H), 2.45-2.33 (m, 1H), 1.46 (t, J=7.1 Hz, 3H)

Step 6—(±)-ethyl 5-(3-aminotetrahydrofuran-3-yl)pyridine-2-carboxylate

To a solution of (±)-ethyl 5-(3-carbamoyltetrahydrofuran-3-yl)pyridine-2-carboxylate (300 mg, 1.14 mmol) in acetonitrile (5 mL) and water (1 mL) was added [bis(trifluoroacetoxy)iodo]benzene (585 mg, 1.36 mmol). The mixture was stirred at rt for 12 hrs. On completion, the mixture was concentrated to remove acetonitrile and diluted with saturated potassium carbonate water (10 mL) and extracted with dichloromethane (3×50 mL). The organic layer was washed with water (3×30 mL), dried over anhydrous sodium sulfate, filtered and concentrated to give the title compound. $^1$HNMR (400 MHz, CDCl3) δ=8.92 (s, 1H), 8.15-8.05 (m, 1H), 8.02-7.95 (m, 1H), 4.50 (q, J=7.0 Hz, 2H), 4.28-4.07 (m, 2H), 3.96-3.84 (m, 2H), 2.45-2.39 (m, 1H), 2.26-2.15 (m, 1H), 1.47 (t, J=7.1 Hz, 3H).

(±)-Ethyl 2-(4-(3-cyanotetrahydrofuran-3-yl)phenyl) acetate (Intermediate AV) & (±)-Ethyl 2-(4-(3-aminotetrahydrofuran-3-yl)phenyl)-2-methylpropanoate (Intermediate AW)

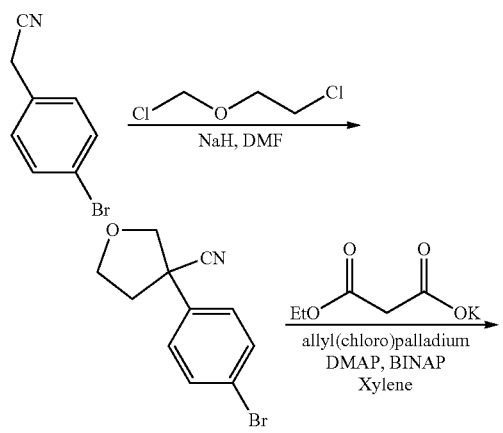

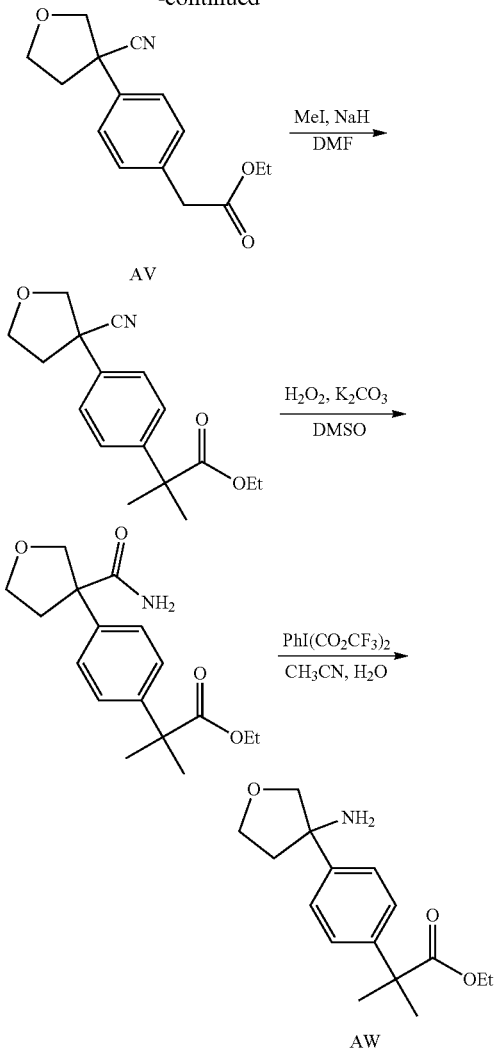

Step 1—(±)-3-(4-Bromophenyl)tetrahydrofuran-3-carbonitrile

To a solution of sodium hydride (4.69 g, 117 mmol, 60% oil dispersion) in N,N-dimethyl formamide (200 mL) was added 2-(4-bromophenyl)acetonitrile (10.0 g, 51.01 mmol) and 1-chloro-2-(chloromethoxy)ethane (7.90 g, 61.2 mmol) in N,N-dimethyl formamide (100 mL) dropwise at 0° C. under nitrogen. The reaction mixture was warmed to rt with stirring for 12 hrs. On completion, the reaction mixture was poured into water (1200 mL) and extracted with ethyl acetate (3×500 mL). The combined organic layers were washed with brine (200 mL), dried over anhydrous sodium sulfate, and concentrated in vacuo. The residue was purified by silica gel chromatography (petroleum ether:ethyl acetate=50:1 to 20:1) to give the title compound. LCMS: (ES$^+$) m/z (M+H)$^+$=252.0, tR=1.228

Step 2—(±)-Ethyl 2-(4-(3-cyanotetrahydrofuran-3-yl)phenyl)acetate

A solution of (±)-3-(4-bromophenyl)tetrahydrofuran-3-carbonitrile (1.41 g, 5.59 mmol), allyl(chloro)palladium (51.16 mg, 279.50 umol), dimethylaminopyridine (68.3 mg, 559 umol), 1,1'-al naphthalene-2,2-diphenyl phosphine (348.25 mg, 559.00 umol) in xylene (20 mL) was stirred at rt for 30 min under nitrogen. Then (3-ethoxy-3-oxo-propanoyl)oxypotassium (1.90 g, 11.18 mmol) was added in one portion and the reaction mixture was stirred at 140° C. for 16 hrs. On completion, ethyl acetate (20 mL) was added to the mixture, the solution was then washed with water (2×10 mL) and brine (10 mL). The organic layer was separated, dried and concentrated in vacuo. The residue was purified by silica gel chromatography (petroleum ether:ethyl acetate=20:1 to 10:1) to give the title compound. $^1$H NMR (400 MHz, CDCl$_3$) δ=7.37 (d, J=8.3 Hz, 2H), 7.26 (d, J=8.3 Hz, 2H), 4.29 (d, J=9.0 Hz, 1H), 4.17-4.07 (m, 4H), 3.96 (d, J=8.8 Hz, 1H), 3.55 (s, 2H), 2.71 (td, J=6.1, 12.6 Hz, 1H), 2.38 (td, J=8.1, 13.0 Hz, 1H), 1.19 (t, J=7.2 Hz, 3H).

Step 3—(±)-Ethyl 2-(4-(3-cyanotetrahydrofuran-3-yl)phenyl)-2-methylpropanoate To a solution of (±)-ethyl 2-[4-(3-cyanotetrahydrofuran-3-yl)phenyl]acetate (1.02 g, 3.93 mmol) in N,N-dimethyl formamide (10 mL) was added sodium hydride (377 mg, 15.7 mmol) in one portion at 0° C. Then iodomethane (3.35 g, 23.6 mmol) was added to the solution dropwise and the mixture was stirred at 60° C. for 4 hrs. On completion, the mixture was poured into water (50 mL) and the mixture was extracted with ethyl acetate (3×20 mL). The combined organic layers were washed with water (20 mL), brine (20 mL), dried over anhydrous sodium sulfate, and concentrated in vacuo. The residue was purified by silica gel chromatography (petroleum ether:ethyl acetate=20:1 to 10:1) to give the title compound. $^1$H NMR (300 MHz, CDCl$_3$) δ=7.43 (d, J=11.2 Hz, 2H), 7.38 (d, J=11.2 Hz, 2H), 4.36 (d, J=9.0 Hz, 1H), 4.25-4.08 (m, 4H), 4.04 (d, J=8.9 Hz, 1H), 2.86-2.71 (m, 1H), 2.46 (td, J=8.1, 13.0 Hz, 1H), 1.58 (s, 6H), 1.21 (t, J=7.2 Hz, 3H).

Step 4—(±)-Ethyl 2-(4-(3-carbamoyltetrahydrofuran-3-yl)phenyl)-2-methylpropanoate To a solution of (±)-ethyl 2-[4-(3-cyanotetrahydrofuran-3-yl)phenyl]-2-methyl-propanoate (80.0 mg, 278 umol) and potassium carbonate (19.2 mg, 139 umol) in N,N-dimethyl sulfoxide (5 mL) was added hydrogen peroxide (315 mg, 835 umol, 30% purity, 286 uL) in one portion. The mixture was stirred at rt for 3 hrs. On completion, the mixture was poured into water (30 mL). The solid was collected by filtration, and dried in vacuo to give the title compound. $^1$H NMR (300 MHz, CDCl$_3$) δ=7.29 (d, J=6 Hz, 2H), 7.21 (d, J=6.0 Hz, 2H), 5.54-5.20 (m, 2H), 4.38 (d, J=8.7 Hz, 1H), 4.17-3.94 (m, 4H), 3.93-3.81 (m, 1H), 2.82-2.68 (m, 1H), 2.26 (td, J=7.5, 12.4 Hz, 1H), 1.55 (s, 6H), 1.25 (t, J=6.8 Hz, 3H).

Step 5—(±)-Ethyl 2-(4-(3-aminotetrahydrofuran-3-yl)phenyl)-2-methylpropanoate To a solution of (±)-ethyl 2-[4-(3-carbamoyltetrahydrofuran-3-yl)phenyl]-2-methyl-propanoate (90.0 mg, 295 umol) in acetonitrile (2 mL) and water (2 mL) was added PhI(CO$_2$CF$_3$)$_2$ (149 mg, 354 umol) in one portion at rt. The reaction mixture was stirred at rt for 16 hrs. On completion, the mixture was concentrated in vacuo, and the residue was diluted with water (40 mL) and washed with dichloromethane (2×30 mL). The aqueous phase was basified with aqueous sodium hydroxide (1 N) until pH=7-8, and extracted with ethyl acetate (3×30 mL). The combined organic layers were washed with brine (30 mL), dried and concentrated in vacuo to give the title compound. LCMS: (ES$^+$) m/z (M−NH$_2$)$^+$=261.1, tR=1.228.

(±)-4,5-Dichloro-N-(3-(4-(cyanomethyl)phenyl)tetrahydrofuran-3-yl)-1-methyl-1H-indole-2-carboxamide (Intermediate AX)

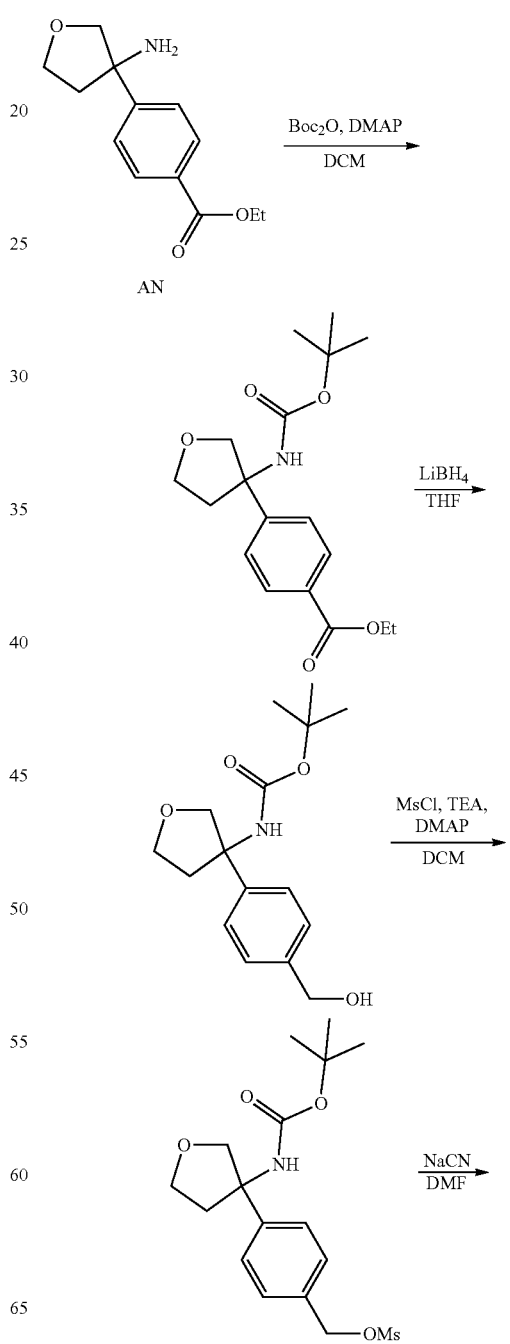

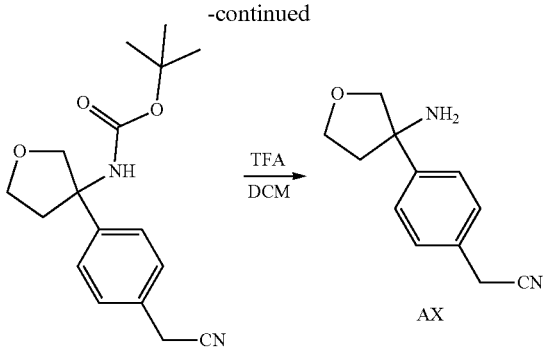

Step 1—(±)-Ethyl 4-(3-((tert-butoxycarbonyl)amino)tetrahydrofuran-3-yl)benzoate To a solution of (±)-ethyl 4-(3-aminotetrahydrofuran-3-yl)benzoate (1.00 g, 4.25 mmol) in dichloromethane (10 mL) was added di-tert-butyl dicarbonate (1.02 g, 4.68 mmol) and a catalytic amount of N,N-4-dimethylaminopyridine at rt. The reaction mixture was stirred at rt for 12 hrs. On completion, the reaction mixture was concentrated in vacuo. The residue was purified by chromatography (petroleum ether:ethyl acetate=30:1 to 10:1) to give the title compound. $^1$H NMR (400 MHz, CDCl3)=8.02 (d, J=8.5 Hz, 2H), 7.49 (d, J=8.3 Hz, 2H), 5.22 (br. s., 1H), 4.38 (q, J=7.0 Hz, 2H), 4.12-3.99 (m, 4H), 2.65-2.46 (m, 1H), 2.45-2.35 (m, 1H), 1.40 (s, 9H), 1.34-1.21 (t, J=6.8 Hz, 3H).

Step 2—(±)-Tert-butyl (3-(4-(hydroxymethyl)phenyl)tetrahydrofuran-3-yl)carbamate To a solution of (±)-ethyl 4-[3-(tert-butoxycarbonylamino)tetrahydrofuran-3-yl]benzoate (500 mg, 1.49 mmol) in anhydrous tetrahydrofuran (10 mL) was added lithium borohydride (162 mg, 7.45 mmol). The reaction mixture was stirred at rt for 12 hrs. On completion, the reaction mixture was quenched with water (10 mL) and extracted with ethyl acetate (3×50 mL). The combined organic layers were washed with brine (2×20 mL), dried over anhydrous sodium sulfate, filtered and concentrated in vacuo. The residue was purified by chromatography (petroleum ether:ethyl acetate=5:1) to give the title compound. LCMS: (ES$^+$) m/z (M−NH$_2$)$^+$=177.2, tR=0.657. $^1$H NMR (400 MHz, CDCl3) δ=7.42 (d, J=8.4 Hz, 2H), 7.34 (d, J=8.4 Hz, 2H), 5.17 (br. s., 1H), 4.69 (s, 2H), 4.11-4.01 (m, 4H), 2.60-2.45 (m, 1H), 2.44-2.37 (m, 1H), 1.38 (s, 9H).

Step 3—(±)-4-(3-((Tert-butoxycarbonyl)amino)tetrahydrofuran-3-yl)benzyl methanesulfonate To a solution of (±)-tert-butyl N-[3-[4-(hydroxymethyl)phenyl]tetrahydrofuran-3-yl]carbamate (599 mg, 2.04 mmol) in dichloromethane (20 mL) was added N,N-dimethylpyridin-4-amine (25.0 mg, 204 umol), triethylamine (413 mg, 4.08 mmol) and methanesulfonyl chloride (351 mg, 3.06 mmol) at 0° C. The reaction mixture was stirred at rt for 12 hrs. On completion, the reaction mixture was diluted with water (20 mL), the organic phase was separated, and the aqueous layer was extracted with dichloromethane (3×50 mL). The combined organic layers were washed with brine (20 mL), dried over anhydrous sodium sulfate and concentrated in vacuo to give the title compound. LCMS: (ES$^-$) m/z (M+23)$^+$=394.1, tR=0.760.

Step 5—(±)-Tert-butyl (3-(4-(cyanomethyl)phenyl)tetrahydrofuran-3-yl)carbamate To a solution of (±)-[4-[3-(tert-butoxycarbonylamino)tetrahydrofuran-3-yl]phenyl]methyl methanesulfonate (643 mg, 1.73 mmol) in N,N-dimethylformamide (6 mL) was added sodium cyanide (129 mg, 2.63 mmol) at rt. The reaction mixture was stirred at rt for 12 hrs. The resulting mixture was diluted with water (20 mL) and extracted with ethyl acetate (3×50 mL). The combined organic layer was washed with brine (2×20 mL), dried over anhydrous sodium sulfate and concentrated in vacuo. The residue was purified by chromatography (petroleum ether:ethyl acetate=5:1) to give the title compound. LCMS: (ES$^+$) m/z (M−NH$_2$)$^+$=186.2, (M+23)$^+$=325.3, tR=0.769.

Step 6—(±)-4,5-Dichloro-N-(3-(4-(cyanomethyl)phenyl)tetrahydrofuran-3-yl)-1-methyl-1H-indole-2-carboxamide To a solution of (±)-tert-butyl N-[3-[4-(cyanomethyl)phenyl]tetrahydrofuran-3-yl]carbamate (15.0 mg, 49.6 umol) in dichloromethane (2.5 mL) was added trifluoroacetic acid (500 uL, 6.75 mmol). The reaction mixture was stirred at rt for 2 hrs. On completion, the mixture was concentrated in vacuo to give the title product (320 mg, 67.4% purity, 80% yield) as yellow oil. LCMS: (ES$^+$) m/z (M−NH$_2$)$^+$=186.2, tR=0.178.

(±) Ethyl 1-[4-(3-aminotetrahydrofuran-3-yl)phenyl]cyclopropanecarboxylate (Intermediate AY)

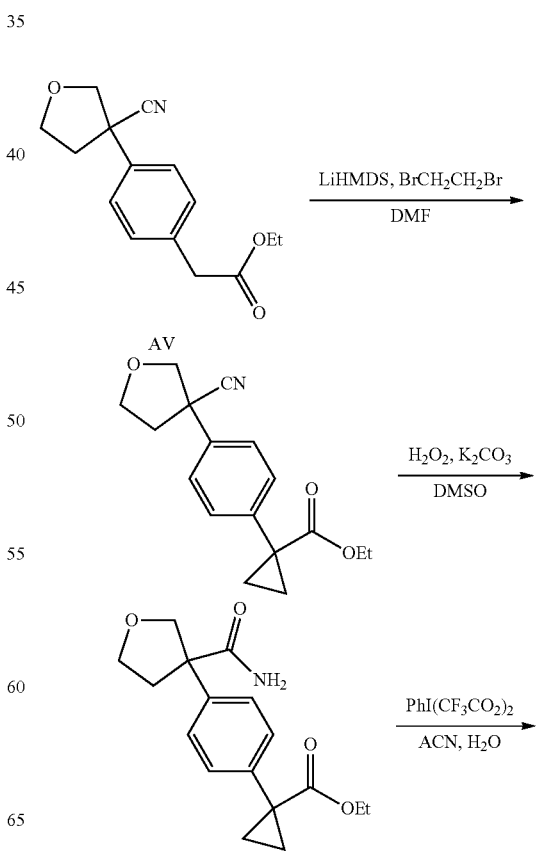

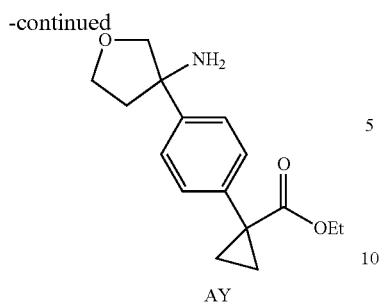

AY

Step 1—(±) Ethyl 1-[4-(3-cyanotetrahydrofuran-3-yl)phenyl]cyclopropanecarboxylate To a solution of (±) ethyl 2-[4-(3-cyanotetrahydrofuran-3-yl)phenyl]acetate (2.00 g, 7.71 mmol) in N,N-dimethylformamide (40 mL) was added LiHMDS (1 M, 30.8 mL) dropwise at rt. The mixture was stirred at the same temperature for 30 mins then 1,2-dibromoethane (2.17 g, 11.5 mmol) dissolved in N,N-dimethylformamide (10 mL) was added dropwise at rt. The mixture was stirred at rt for 2.5 hrs. On completion, the reaction mixture was poured into 30 mL of iced saturated ammonium chloride solution, and the resulting suspension was extracted with ethyl acetate (3×40 mL). The organic phase was collected, dried over anhydrous sodium sulfate, and concentrated in vacuo to get a residue. The residue was purified by column chromatography (petroleum ether:ethyl acetate=20:1 to 10:1) to give the title compound. LCMS: (ES$^+$) m/z (M+H)$^+$=286.2, tR=0.826. $^1$H NMR (400 MHz, CD$_3$Cl) δ=7.40-7.31 (m, 4H), 4.23 (d, J=9.0 Hz, 1H), 4.07-4.01 (m, 2H), 3.97 (q, J=7.2 Hz, 2H), 3.92-3.87 (m, 1H), 2.69-2.61 (m, 1H), 2.33 (td, J=8.1, 13.0 Hz, 1H), 1.51-1.46 (m, 2H), 1.07-1.01 (m, 5H).

Step 2—(±) Ethyl 1-[4-(3-carbamoyltetrahydrofuran-3-yl)phenyl]cyclopropanecarboxylate To a solution of (±) ethyl 1-[4-(3-cyanotetrahydrofuran-3-yl)phenyl]cyclopropanecarboxylate (800 mg, 2.80 mmol) in dimethyl sulfoxide (8 mL) was added potassium carbonate (193 mg, 1.40 mmol). Then, hydrogen peroxide (952 mg, 8.40 mmol, 30% wt in water, 807 uL) was added to the resulting mixture dropwise. The mixture was stirred at rt for 3 hrs. On completion, the reaction mixture was poured into 30 mL of ice water, during which a fine white solid precipitate was formed. The white solid was filtered, and the filter cake was dried in vacuo to give the title compound. $^1$H NMR (400 MHz, CD$_3$Cl) δ=7.26 (d, J=8.4 Hz, 2H), 7.17 (d, J=8.4 Hz, 2H), 5.45 (br. s., 2H), 4.37 (d, J=8.8 Hz, 1H), 4.07-3.96 (m, 4H), 3.88 (dt, J=5.5, 8.3 Hz, 1H), 2.76 (ddd, J=5.6, 7.5, 12.7 Hz, 1H), 2.30-2.21 (m, 1H), 1.56-1.50 (m, 2H), 1.13-1.08 (m, 5H).

Step 3—(±) Ethyl 1-[4-(3-aminotetrahydrofuran-3-yl)phenyl]cyclopropanecarboxylate To a solution of (±) ethyl 1-[4-(3-carbamoyltetrahydrofuran-3-yl)phenyl]cyclopropanecarboxylate (650 mg, 2.14 mmol) in acetonitrile (10 mL) and water (10 mL) was added [phenyl-(2,2,2-trifluoroacetyl)oxy-iodanyl] 2,2,2-trifluoroacetate (1.01 g, 2.35 mmol). The mixture was stirred at rt for 3 hrs. On completion, the reaction mixture was concentrated in vacuo to remove acetonitrile. The residue was diluted with 0.5 M hydrochloric acid (20 mL) and washed with ethyl acetate (2×20 mL). The combined inorganic phase layer was basified with saturated sodium bicarbonate solution until the pH=8, which was then extracted with dichloromethane (2×20 mL). The combined organic phase was dried over anhydrous sodium sulfate, filtered and concentrated in vacuo to give the title compound. LCMS: (ES$^+$) m/z (M–NH$_2$)$^+$=259.1, tR=0.554.

(±)-(2-Ethoxy-2-oxoethyl)zinc(II) bromide (Intermediate AZ)

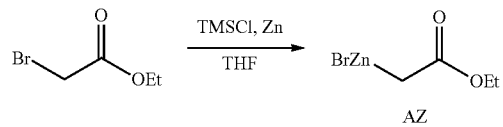

To a mixture of zinc powder (11.8 g, 180 mmol) in anhydrous tetrahydrofuran (44 mL) was added chlorotrimethylsilane (976 mg, 8.98 mmol) in one portion at rt under nitrogen. Then a solution of ethyl 2-bromoacetate (15.0 g, 89.8 mmol) in anhydrous tetrahydrofuran (110 mL) was added dropwise over 0.5 hour at 40-50° C. After the addition, the resulting mixture was stirred at 40° C. for 1 hour. The resulting solution was used in the next step directly.

Ethyl 2-(4-(3-aminooxetan-3-yl)phenyl)acetate (Intermediate BA)

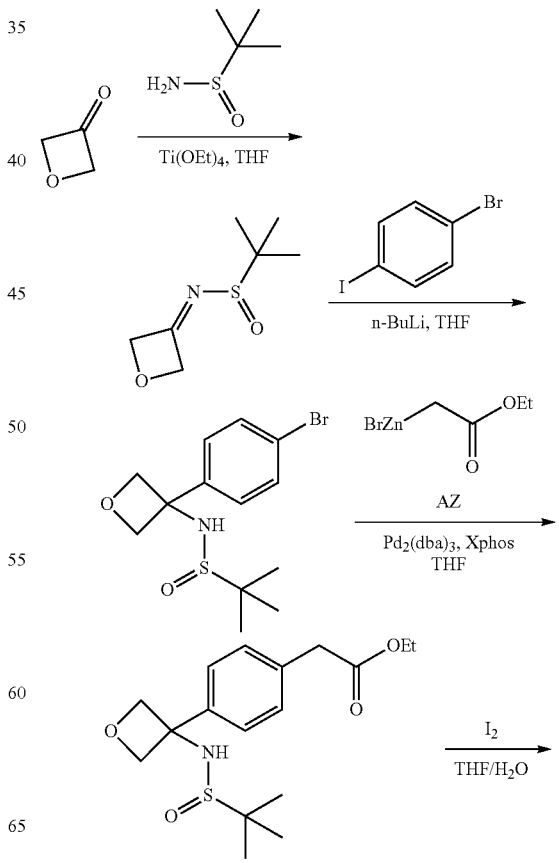

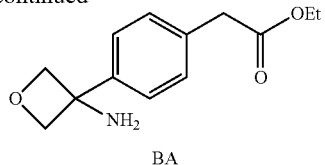

BA

Step 1—(±)-2-Methyl-N-(oxetan-3-ylidene)propane-2-sulfinamide

To a solution of oxetan-3-one (2.50 g, 34.6 mmol) and (±)-2-methylpropane-2-sulfinamide (4.20 g, 34.6 mmol) in anhydrous tetrahydrofuran (25 mL) was added tetraethoxytitanium (11.1 g, 48.5 mmol) dropwise at rt. The reaction mixture was stirred at 50° C. for 3 hours. On completion, the reaction mixture was poured into 100 mL cool water and filtered. The filtrate was extracted with dichloromethane (3×100 mL). The combined organic layer was dried over anhydrous sodium sulfate, filtrated and concentrated in vacuo. The residue was purified by silica gel chromatography (petroleum ether:ethyl acetate=20:1) to give the title compound. $^1$H NMR (400 MHz, CDCl$_3$)=5.83-5.76 (m, 1H), 5.70-5.62 (m, 1H), 5.52-5.40 (m, 2H), 1.27 (s, 9H).

Step 2—(±)-N-(3-(4-bromophenyl)oxetan-3-yl)-2-methylpropane-2-sulfinamide

To a solution of 1-bromo-4-iodo-benzene (2.52 g, 8.90 mmol) in anhydrous tetrahydrofuran (30 mL) was added n-BuLi (2.5 M, 4.45 mL) dropwise at −70° C. under nitrogen, during which the temperature was maintained below −60° C. Then the reaction mixture was stirred for 0.5 hour at −70° C. A yellow solid precipitated out during the stirring. To the reaction mixture was then added a solution of (±)-2-methyl-N-(oxetan-3-ylidene)propane-2-sulfinamide (1.30 g, 7.42 mmol) in anhydrous tetrahydrofuran (10 mL) dropwise at −70° C. The resulting mixture was warmed to rt slowly over a period of 1 hour. On completion, the reaction mixture was quenched with water (20 mL) at 0° C., then the mixture was extracted with ethyl acetate (3×30 mL). The combined organic layer was dried over anhydrous sodium sulfate and concentrated in vacuo to give the crude product. The crude product was purified by column chromatography (petroleum ether:ethyl acetate=10:1 to 1:1) to give the title compound. $^1$H NMR (400 MHz, DMSO-d6) δ=7.61 (d, J=6.4 Hz, 2H), 7.59 (d, J=6.4 Hz, 2H), 6.36 (s, 1H), 5.00 (d, J=6.3 Hz, 1H), 4.95 (d, J=4 Hz, 1H), 4.90 (d, J=4 Hz, 1H), 4.69 (d, J=6.3 Hz, 1H), 1.11 (s, 9H).

Step 3—(±)-Ethyl 2-[4-[3-(tert-butylsulfinylamino)oxetan-3-yl]phenyl]acetate To a mixture of Pd$_2$(dba)$_3$ (496 mg, 542 umol), XPhos (517 mg, 1.08 mmol) and (±)—N-[3-(4-bromophenyl)oxetan-3-yl]-2-methyl-propane-2-sulfinamide (1.80 g, 5.42 mmol) in anhydrous tetrahydrofuran (2 mL) was added a solution of bromo-(2-ethoxy-2-oxo-ethyl)zinc (0.5 M, 50 mL) in anhydrous tetrahydrofuran (50 mL) at rt under nitrogen. The reaction mixture was heated to 80° C. and stirred for 1 hour. On completion, the reaction mixture was quenched with hydrochloric acid (0.1 N, 10 mL) and diluted with water (50 mL). The mixture was extracted with ethyl acetate (3×50 mL). The combined organic layer was washed with brine (30 mL), dried over anhydrous sodium sulfate, then concentrated in vacuo to give the crude product. The crude product was purified by column chromatography (petroleum ether:ethyl acetate=10:1 to 1:1) to give the title compound. $^1$H NMR (400 MHz, DMSO-d$_6$) δ=7.44 (d, J=8.0 Hz, 2H), 7.30 (d, J=8.0 Hz, 2H), 6.29 (brs., 1H), 5.02 (d, J=6.4 Hz, 1H), 4.98 (d, J=6.8 Hz, 1H), 4.91 (d, J=6.4 Hz, 1H), 4.69 (d, J=6.4 Hz, 1H), 4.09 (q, J=7.2 Hz, 2H), 3.68 (s, 2H), 1.20 (t, J=7.2 Hz, 3H), 1.12 (s, 9H).

Step 4—Ethyl 2-(4-(3-aminooxetan-3-yl)phenyl)acetate

To a solution of (±)-ethyl 2-[4-[3-(tert-butylsulfinylamino)oxetan-3-yl]phenyl]acetate (1.00 g, 2.95 mmol) in a mixture of tetrahydrofuran (10 mL) and water (10 mL) was added iodine (74.9 mg, 295 umol) in one portion at rt under nitrogen. The resulting reaction mixture was stirred at 50° C. for 24 hours. On completion, the reaction mixture was quenched with sodium sulfite (10 mL), then extracted with DCM (3×30 mL). The combined organic layer was washed with sodium bicarbonate (100 mL), followed by brine (100 mL), dried over anhydrous sodium sulfate, and concentrated in vacuo to give the crude product. The crude product was purified by column chromatography (petroleum ether:ethyl acetate=5:1 to 1:1) to give the title compound. $^1$H NMR (300 MHz, DMSO-d$_6$) δ=7.53 (d, J=8.4 Hz, 2H), 7.27 (d, J=8.4 Hz, 2H), 4.69 (d, J=6.0 Hz, 2H), 4.64 (d, J=6.0 Hz, 2H), 4.08 (q, J=6.9 Hz, 2H), 3.65 (s, 2H), 1.19 (t, J=6.9 Hz, 3H).

Ethyl 4-(3-aminooxetan-3-yl)-3-fluoro-benzoate (Intermediate BB)

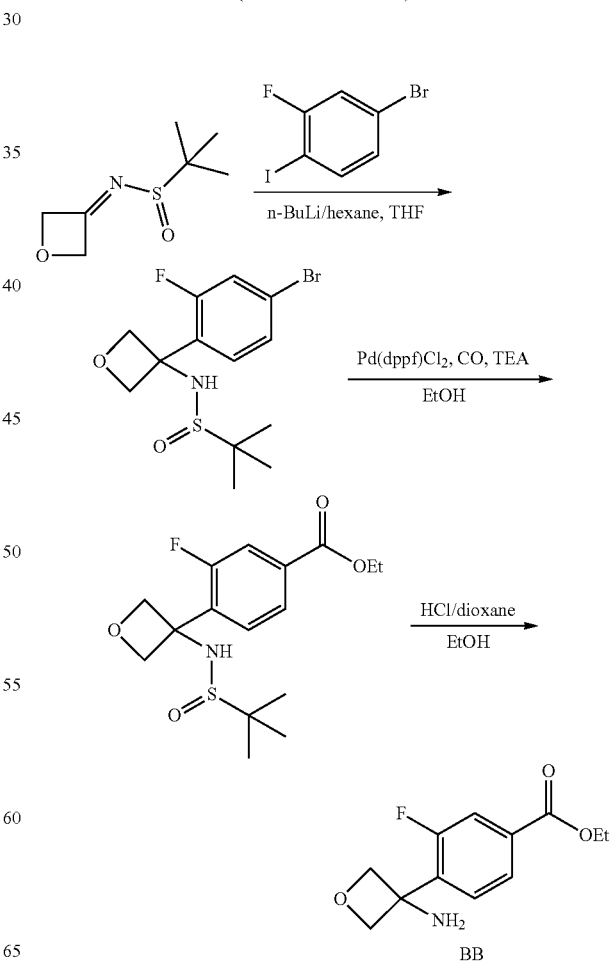

BB

Step 1—(±)-N-[3-(4-bromo-2-fluoro-phenyl)oxetan-3-yl]-2-methyl-propane-2-sulfinamide (3)

To a mixture of 4-bromo-2-fluoro-1-iodo-benzene (CAS #105931-73-5, 20.6 g, 68.5 mmol) in tetrahydrofuran (200 mL) was added a solution of n-BuLi/hexane (2.5 M, 34.24 mL) dropwise at −70 OC under nitrogen atmosphere. The resultant mixture was stirred for 30 min, then to the solution was added a solution of 2-methyl-N-(oxetan-3-ylidene)propane-2-sulfinamide (10.0 g, 57.1 mmol) in tetrahydrofuran (100 mL) dropwise. The mixture was warmed to −20 OC and stirred for 2 hrs. On completion, to the mixture was added ammonium chloride solution (50 mL, sat.), and the mixture was extracted with ethyl acetate (3×100 mL). The combined organic phase was washed with brine (300 mL), dried over sodium sulfate, and concentrated in vacuo to give a residue. The residue was purified by column chromatography (petroleum ether:ethyl acetate=10:1 to 2:1) to give the title compound. $^1$HNMR (400 M, DMSO-d$_6$) δ=7.61 (dd, J=10.4, 1.6 Hz, 1H), 7.52 (dd, J=8.4, 1.6 Hz, 1H), 7.45 (t, J=8.0 Hz, 1H), 6.47 (br, s, 1H), 5.14 (d, J=6.8 Hz, 1H), 4.99 (d, J=6.0 Hz, 1H), 4.93 (d, J=6.4 Hz, 2H), 1.11 (s, 9H).

Step 2—(±)-Ethyl 4-[3-(tert-butyl sulfinylamino)oxetan-3-yl]-3-fluoro-benzoate To a solution of (±)-N-[3-(4-bromo-2-fluoro-phenyl)oxetan-3-yl]-2-methyl-propane-2-sulfinamide (1.00 g, 1.71 mmol) in ethanol (40 mL) was added Pd(dppf)Cl$_2$ (188 mg, 256 umol) and triethylamine (866 mg, 8.57 mmol) under nitrogen. The mixture was stirred under carbon monoxide (50 psi) at 80° C. for 16 hrs. On completion, the reaction mixture was filtered and the filtrate was concentrated in vacuo to get a residue. The residue was purified by chromatography (dichloromethane:methanol=50:1 to 20:1) to give the title compound. LCMS: (ES$^+$) m/z (M+H)$^+$=344.1, tR=1.276.

Step 3—Ethyl 4-(3-aminooxetan-3-yl)-3-fluoro-benzoate

A solution of hydrogen chloride in dioxane (4 M, 502 uL) was added into a solution of the (±)-ethyl 4-[3-(tert-butylsulfinylamino)oxetan-3-yl]-3-fluoro-benzoate (460 mg, 1.34 mmol) in ethanol (1 mL) at 0° C. The mixture was stirred at 0° C. for 1 min. On completion, the reaction mixture was concentrated in vacuo. The residue was triturated with methyl tert-butyl ether (30 mL). The precipitate was filtered and dried in vacuo to give the title compound. LCMS: (ES$^+$) m/z (M−NH$_2$)$^+$=223.1, tR=0.413.

Ethyl 2-(4-(3-aminooxetan-3-yl)-3-fluorophenyl)acetate (Intermediate BC)

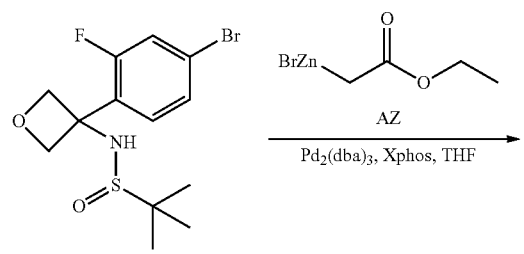

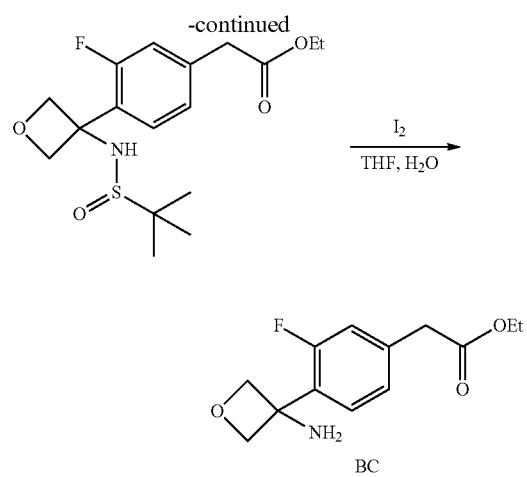

Step 1—(±)-Ethyl 2-(4-(3-(1,1-dimethylethylsulfinamido)oxetan-3-yl)-3-fluorophenyl)acetate To a mixture of Pd$_2$(dba)$_3$ (262 mg, 286 umol), XPhos (273 mg, 572 umol) and (±)-N-[3-(4-bromo-2-fluoro-phenyl)oxetan-3-yl]-2-methyl-propane-2-sulfinamide (1.00 g, 2.86 mmol, synthesized via Step 1 of Intermediate BB) in tetrahydrofuran (5 mL) was added a solution of bromo-(2-ethoxy-2-oxo-ethyl)zinc in tetrahydrofuran (0.5 M, 20 mL). The reaction mixture was stirred at 80° C. for 3 hrs. On completion, the mixture was quenched with water (50 mL). The mixture was filtered and the filtrate was extracted with ethyl acetate (3×30 mL). The combined organic layers were washed with brine (50 mL), dried over sodium sulfate, and concentrated in vacuo. The residue was purified by chromatography (petroleum ether:ethyl acetate=10:1 to 1:1) to give the title compound. $^1$H NMR (300 MHz, DMSO-d6) δ=7.37 (t, J=8.4 Hz, 1H), 7.15 (s, 1H), 7.12 (d, J=2.7 Hz, 1H), 6.37 (s, 1H), 5.12 (d, J=6.6 Hz, 1H), 4.96 (d, J=6.6 Hz, 1H), 4.88 (t, J=6.6 Hz, 2H), 4.09 (q, J=7.2 Hz, 2H), 3.72 (s, 2H), 1.17-1.21 (t, 3H), 1.04 (s, 9H).

Step 2—Ethyl 2-(4-(3-aminooxetan-3-yl)-3-fluorophenyl)acetate

To a mixture of (±)-ethyl 2-[4-[3-(tert-butylsulfinylamino)oxetan-3-yl]-3-fluoro-phenyl]acetate (560 mg, 1.57 mmol) in tetrahydrofuran (5 mL) and water (1.5 mL) was added iodine (79.7 mg, 314 umol) in one portion at rt. The mixture was stirred at 50° C. for 24 hrs. On completion, the mixture was quenched with saturated aqueous sodium sulfite (20 mL) and extracted with ethyl acetate (60 mL). The combined organic layer was washed with brine (30 mL), dried over sodium sulfate, and concentrated in vacuo. The residue was purified by chromatography (petroleum ether:ethyl acetate=10:1 to 1:1) to give the title compound. $^1$H NMR (400 MHz, DMSO-d6) δ=7.30 (t, J=8.8 Hz, 1H), 7.08-7.03 (m, 2H), 4.91 (d, J=5.2 Hz, 2H), 4.57 (d, J=6.0 Hz, 2H), 4.12 (q, J=6.8 Hz, 2H), 3.70 (s, 2H), 1.20 (t, J=7.2 Hz, 3H).

Ethyl 4-(3-aminooxetan-3-yl)-3-chlorobenzoate (Intermediate BD)

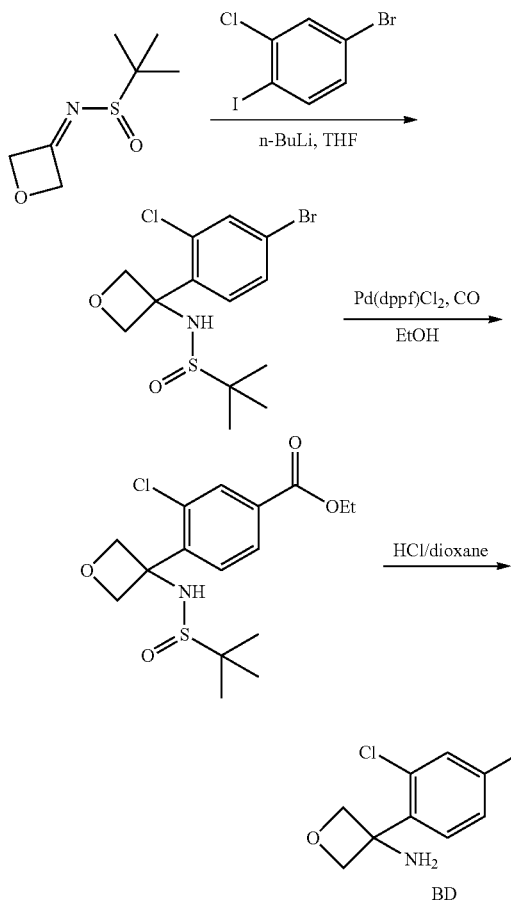

Step 1—(±)-N-(3-(4-bromo-2-chlorophenyl)oxetan-3-yl)-2-methylpropane-2-sulfinamide To a solution of 4-bromo-2-chloro-1-iodobenzene (7.77 g, 24.5 mmol) in tetrahydrofuran (60 mL) was added n-butyllithium (8.90 mL, 2.5 M) at −78° C. The mixture was stirred at −70° C. for 1 h, then (±)-2-methyl-N-(oxetan-3-ylidene)propane-2-sulfinamide (3.90 g, 22.25 mmol) in tetrahydrofuran (20 mL) was added. The reaction mixture was stirred at −78° C. for 1 h, then at rt for 4 hrs. On completion, the mixture was quenched with saturated aqueous ammonia chloride (20 mL) and extracted with ethyl acetate (3×30 mL). The combined organic layers were dried over anhydrous sodium sulfate and concentrated in vacuo. The residue was purified by chromatography (dichloromethane:methanol=50:1) to give the title compound. LCMS: (ES$^+$) m/z (M+H)$^+$=365.9, tR=0.888.

Step 2—(±)-Ethyl 3-chloro-4-(3-(1,1-dimethylethylsulfinamido)oxetan-3-yl)benzoate A mixture of (±)-N-[3-(4-bromo-2-chloro-phenyl)oxetan-3-yl]-2-methyl-propane-2-sulfinamide (500 mg, 1.36 mmol), Pd(dppf)Cl$_2$ (111 mg, 136 umol) and triethylamine (688 mg, 6.80 mmol) in ethanol (12 mL) was stirred at 80° C. under carbon monoxide (50 Psi) for 12 hrs. On completion, the mixture was concentrated. The residue was purified by chromatography (petroleum ether:ethyl acetate=1:1) to give the title compound. LCMS: (ES$^+$) m/z (M+H)$^+$=360.2, tR=0.791.

Step 3—Ethyl 4-(3-aminooxetan-3-yl)-3-chlorobenzoate

To a solution of (±)-ethyl 4-[3-(tert-butylsulfinylamino)oxetan-3-yl]-3-chloro-benzoate (340 mg, 945 umol) in ethanol (1 mL) was added hydrochloric acid/dioxane (4 M, 354 uL) at 0° C., then the mixture was stirred at 0° C. for 10 min. On completion, the reaction solvent was removed by bubbling with nitrogen. The residue was triturated with tert-butyl methyl ether (5 mL). The resulting solid was collected by filtration and washed with tert-butyl methyl ether (2 mL) to give the title compound. LCMS: (ES$^+$) m/z (M+H)$^+$=256.0, tR=0.526.

Ethyl 2-(4-(3-aminooxetan-3-yl)-3-chlorophenyl)acetate (Intermediate BE)

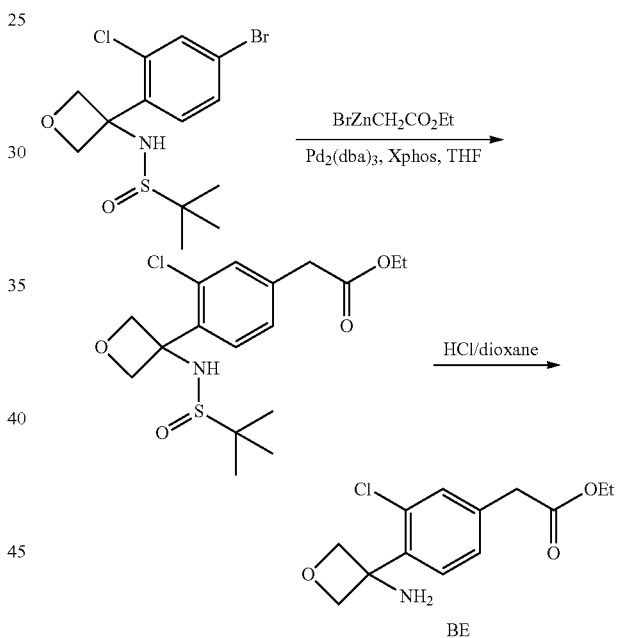

Step 1—(±)-Ethyl 2-(3-chloro-4-(3-(1,1-dimethylethylsulfinamido)oxetan-3-yl)phenyl)acetate To a mixture of (±)-N-[3-(4-bromo-2-chloro-phenyl)oxetan-3-yl]-2-methyl-propane-2-sulfinamide (700 mg, 1.91 mmol, made via Step 1 of Intermediate BD), Pd$_2$(dba)$_3$ (175 mg, 191 umol), XPhos (137 mg, 287 umol) in tetrahydrofuran (20 mL) was added bromo-(2-ethoxy-2-oxo-ethyl)zinc (0.5 M, 5 mL). The reaction mixture was stirred at 70° C. for 2 hrs. On completion, the mixture was quenched with saturated ammonium chloride (20 mL) and extracted with ethyl acetate (3×30 mL). The combined organic layers were dried over anhydrous sodium sulfate and concentrated in vacuo. The residue was purified by chromatography (dichloromethane:methanol=30:1) to give the title product. LCMS: (ES$^+$) m/z (M+H)$^+$=374.0, tR=0.751.

Step 2—Ethyl 2-(4-(3-aminooxetan-3-yl)-3-chlorophenyl)acetate

To a solution of (±)-ethyl 2-[4-[3-(tert-butylsulfinylamino)oxetan-3-yl]-3-chlorophenyl]acetate (300 mg, 802 umol) in ethanol (1 mL) was added hydrogen chloride/dioxane (4 M, 300 uL) at 0° C. The reaction mixture was stirred at 0° C. for 1 min. On completion, the mixture was concentrated in vacuo to give the title product (150 mg, 69% yield) as yellow oil. LCMS: (ES+) m/z (M+H)+=270.1, tR=0.566.

Ethyl 4-(3-aminooxetan-3-yl)-3-methylbenzoate (Intermediate BF)

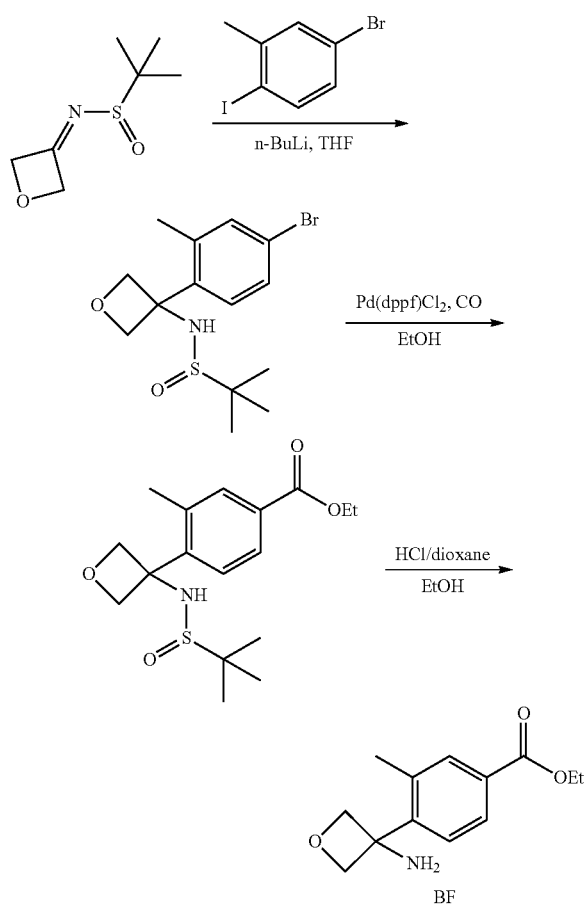

Step 1—(±)-N-(3-(4-bromo-2-methylphenyl)oxetan-3-yl)-2-methylpropane-2-sulfinamide To a solution of 4-bromo-1-iodo-2-methyl-benzene (3.73 g, 12.6 mmol) in anhydrous tetrahydrofuran (20 mL) was added n-butyllithium (2.5 M, 5.02 mL) at −70° C. for 30 min. Then, (±)-2-methyl-N-(oxetan-3-ylidene)propane-2-sulfinamide (2.00 g, 11.4 mmol) in anhydrous tetrahydrofuran (10 mL) was added at −70° C. The reaction mixture was stirred at rt for 30 min. On completion, the mixture was quenched with water (20 mL) and concentrated in vacuo to remove the organic solvent. The aqueous phase was extracted with dichloromethane (3×100 mL) and the combined organic layers were dried over anhydrous sodium sulfate and concentrated in vacuo. The residue was purified by chromatography (dichloromethane:methanol=100:1) to give the title compound. $^1$H NMR (400 MHz, CDCl3) δ=7.42-7.30 (m, 2H), 7.04 (d, J=8.0 Hz, 1H), 5.33 (d, J=7.0 Hz, 1H), 5.15 (d, J=6.8 Hz, 1H), 5.02 (d, J=6.8 Hz, 1H), 4.90 (d, J=7.0 Hz, 1H), 4.24 (s, 1H), 2.13 (s, 3H), 1.19 (s, 9H).

Step 2—(±)-Ethyl 4-(3-(1,1-dimethylethylsulfinamido)oxetan-3-yl)-3-methylbenzoate To a solution of (±)-N-[3-(4-bromo-2-methyl-phenyl)oxetan-3-yl]-2-methyl-propane-2-sulfinamide (500 mg, 1.44 mmol) and triethylamine (729 mg, 7.20 mmol) in ethanol (10 mL) was added Pd(dppf)Cl$_2$ (118 mg, 144 umol) in one portion under nitrogen. The mixture was stirred under carbon monoxide (50 psi) at 80° C. for 16 hrs. On completion, the reaction mixture was filtered and concentrated in vacuo. The residue was purified by chromatography (petroleum ether:ethyl acetate=10:1) to give the title compound. LCMS: (ES+) m/z (M+H)+=340.2, tR=0.766.

Step 3—Ethyl 4-(3-aminooxetan-3-yl)-3-methylbenzoate

To a solution of ethyl 4-[3-(tert-butylsulfinylamino)oxetan-3-yl]-3-methyl-benzoate (188 mg, 554 umol) in ethanol (2 mL) was added hydrogen chloride/dioxane (4 M, 208 uL) at 0° C. The reaction mixture was stirred at 0° C. for 1 min. On completion, the mixture was concentrated in vacuo. The residue was triturated with methyl tert-butyl ether (2 mL) and the solid was collected by filtration to give the title compound. LCMS: (ES−) m/z (M−NH$_2$)+=219.1, tR=0.512.

Ethyl 2-(4-(3-aminooxetan-3-yl)-3-methylphenyl)acetate (Intermediate BG)

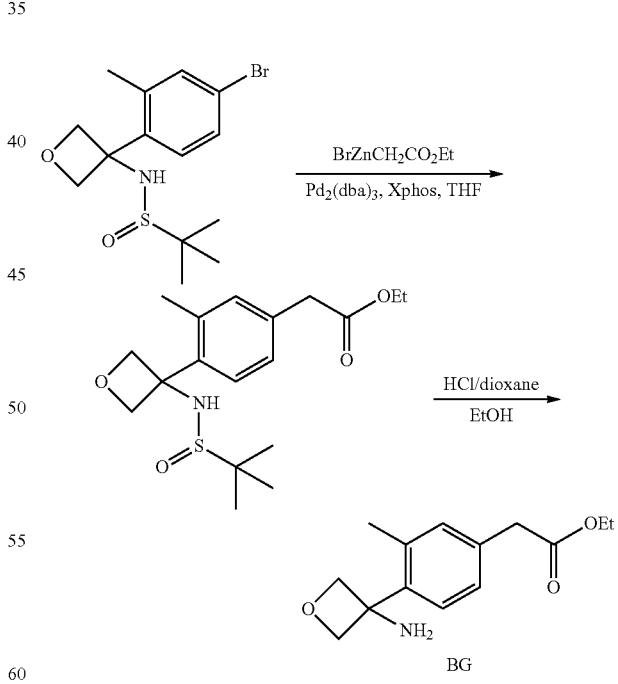

Step 1—Ethyl 2-(4-(3-(1,1-dimethylethylsulfinamido)oxetan-3-yl)-3-methylphenyl)acetate To a suspension of Pd$_2$(dba)$_3$ (146 mg, 159 umol) and Xphos (152 mg, 318 umol) in anhydrous tetrahydrofuran (5 mL) was added N-[3-(4-bromo-2-methyl-phenyl)oxetan-3-yl]-2-methyl-propane-2-sulfinamide (550 mg, 1.59 mmol, synthesized via Step 1 of Intermediate BF) under nitrogen. Then, (2-ethoxy-2-oxoethyl)zinc(II) bromide (0.5 M, 30 mL) was added dropwise to the reaction mixture at rt. The reaction mixture was stirred at 70° C. for 2.5 hrs. On completion, the reaction mixture was quenched with water (20 mL). The mixture was filtered, and the filtrate was concentrated in vacuo to remove the tetrahydrofuran. Then, the residue was extracted with ethyl acetate (3×50 mL), dried over anhydrous sodium sulfate, and concentrated in vacuo to give a residue. The residue was purified by silica gel chromatography (petroleum ether:ethyl acetate=10:1) to give the title compound. LCMS: (ES$^+$) m/z (M+1)$^+$=354.3, tR=0.757.

Step 2—Ethyl 2-(4-(3-aminooxetan-3-yl)-3-methylphenyl)acetate

To a solution of ethyl 2-[4-[3-(tert-butylsulfinylamino)oxetan-3-yl]-3-methylphenyl]acetate (120 mg, 340 umol) in ethanol (1.5 mL) was added HCl/dioxane (4 M, 127 uL) at 0° C. The reaction mixture was stirred 10 min. On completion, the reaction was concentrated in vacuo to give a residue. The residue was triturated with methyl tert-butyl ether (2 mL) and filtered to afford the title compound. LCMS: (ES$^+$) m/z (M−NH$_2$)$^+$=233.1, tR=0.512.

4-Bromo-1-iodo-2-methoxybenzene (Intermediate BH)

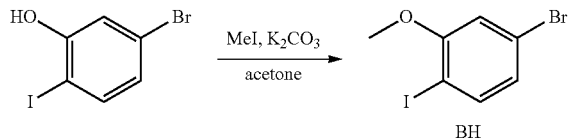

To a solution of 5-bromo-2-iodo-phenol (1.00 g, 3.35 mmol) in acetone (10.0 mL) was added iodomethane (951 mg, 6.70 mmol) and anhydrous potassium carbonate (926 mg, 6.70 mmol) at rt. The reaction mixture was stirred at rt for 12 hrs. On completion, the reaction mixture was filtered. The filtrate was concentrated in vacuo. The residue was purified by silica gel chromatography (petroleum ether) to give the title compound (1.00 g, 96% yield). $^1$H NMR (400 MHz, CDCl3) δ=7.61 (d, J=8.4 Hz, 1H), 6.95 (d, J=1.8 Hz, 1H), 6.87 (dd, J=8.4 Hz, 1.8 Hz, 1H), 3.89 (s, 3H).

Ethyl 2-(4-(3-aminooxetan-3-yl)-3-methoxyphenyl)acetate (Intermediate BI)

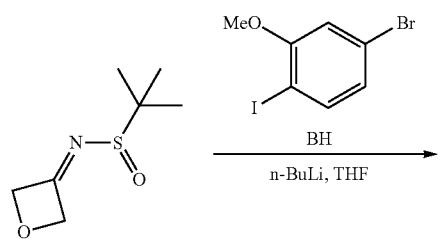

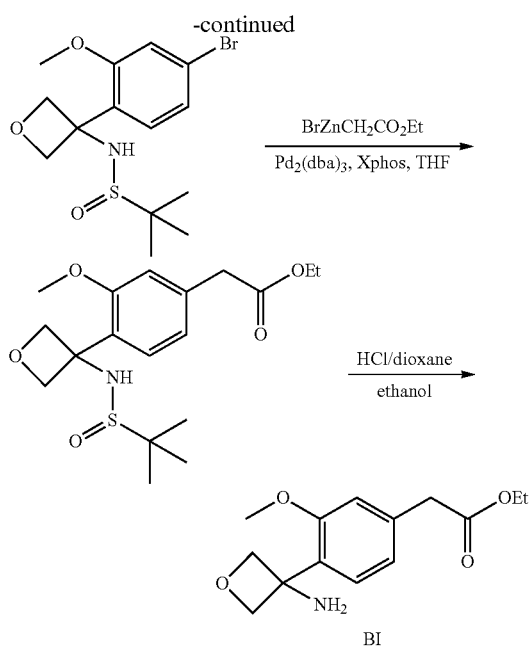

Step 1—(±)-N-(3-(4-bromo-2-methoxyphenyl)oxetan-3-yl)-2-methylpropane-2-sulfinamide To a solution of 4-bromo-1-iodo-2-methoxy-benzene (642 mg, 2.05 mmol) in anhydrous tetrahydrofuran (5 mL) was added n-BuLi (2.5 M, 820 uL) at −70° C. under a nitrogen for 30 min. Then, (±)-2-methyl-N-(oxetan-3-ylidene)propane-2-sulfinamide (360 mg, 2.05 mmol) in anhydrous tetrahydrofuran (5 mL) was added at −70° C. under a nitrogen for 30 min. The reaction mixture was stirred at 25° C. for 30 min. On completion, the reaction was quenched with saturated ammonium chloride (8 mL) and concentrated in vacuo to remove tetrahydrofuran. The residue was extracted with ethyl acetate (3×20 mL), dried over anhydrous sodium sulfate and concentrated in vacuo. The yellow oil was purified by silica gel chromatography (petroleum ether: ethyl acetate=3:1 to 1:1) to give the title compound. LCMS: (ES$^+$) m/z (M+1)$^+$=362.1, tR=0.777.

Step 2—(±)-Ethyl 2-(4-(3-(1,1-dimethylethylsulfinamido)oxetan-3-yl)-3-methoxyphenyl)acetate To a suspension of Pd$_2$(dba)$_3$ (55.6 mg, 60.7 umol) and Xphos (57.9 mg, 121 umol) in anhydrous tetrahydrofuran (3 mL) was added (±)-N-[3-(4-bromo-2-methoxy-phenyl)oxetan-3-yl]-2-methyl-propane-2-sulfinamide (220 mg, 607 umol) under nitrogen. Then, bromo-(2-ethoxy-2-oxo-ethyl)zinc (1 MIL, 607 uL, 607 umol) was added dropwise at rt for 0.5 hr. The reaction mixture was stirred at 70° C. for 2.5 hrs. On completion, the reaction mixture was diluted with water (20 mL), filtered, and the filtrate was extracted with ethyl acetate (3×50 mL). The combined organic layer was dried over anhydrous sodium sulfate and concentrated in vacuo to give the residue. The residue was purified by silica gel chromatography (petroleum ether:ethyl acetate=1:1) to give the title compound. LCMS: (ES$^+$) m/z (M+1)$^+$=370.3, tR=0.765.

Step 3—Ethyl 2-(4-(3-aminooxetan-3-yl)-3-methoxyphenyl)acetate

To a solution of (±)-ethyl 2-[4-[3-(tert-butylsulfinylamino)oxetan-3-yl]-3-methoxy-phenyl]acetate (120 mg, 325 umol) in ethanol (1 mL) was added HCl/dioxane (4 M, 122 uL) at 0° C. The reaction mixture was stirred for 0.5 hr. On completion, the reaction was concentrated in vacuo to give a residue. The residue was triturated with methyl tert-butyl ether (2 mL) and filtered to afford the title compound. LCMS: (ES⁺) m/z (M−NH$_2$)⁺=249.2, tR=0.577.

(±)-Ethyl 2-(4-(3-aminotetrahydrofuran-3-yl)-3-fluorophenyl)propanoate (Intermediate BJ) & (±)-Ethyl 2-(4-(3-aminotetrahydrofuran-3-yl)-3-fluorophenyl)-2-methylpropanoate (Intermediate BK)

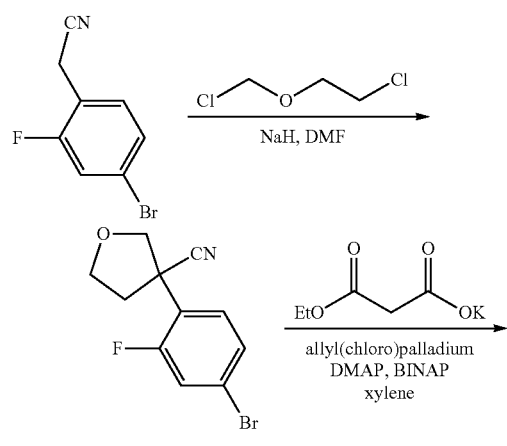

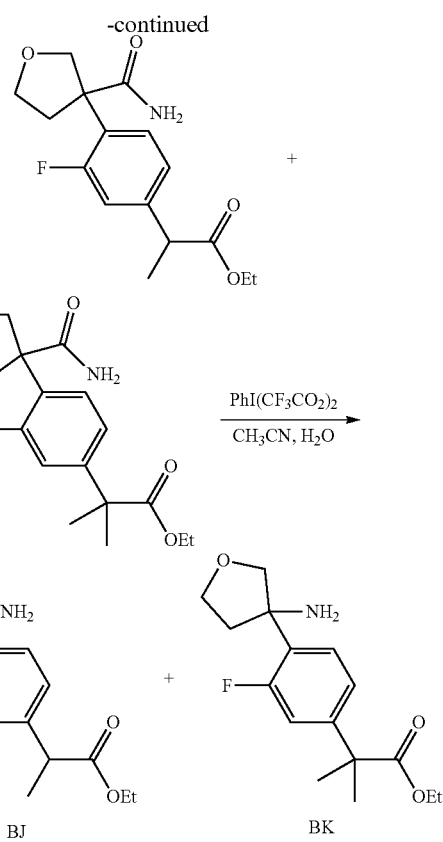

Step 1—(±)-3-(4-Bromo-2-fluorophenyl)tetrahydrofuran-3-carbonitrile

A solution of sodium hydride (1.01 g, 42.06 mmol) in dimethyl formamide (20.0 mL) was stirred at −5° C. Then a solution of 2-(4-bromo-2-fluoro-phenyl)acetonitrile (3.00 g, 14.02 mmol) and 1-chloro-2-(chloromethoxy)ethane (2.17 g, 16.82 mmol) in dimethyl formamide (10.0 mL) was added dropwise at −5° C., and the mixture was stirred at −5-10° C. for 4 hrs. On completion, the mixture was poured into water (60 mL) then the aqueous phase was extracted with ethyl acetate (3×30 mL). The combined extracts were washed with brine (30 mL), dried and concentrated to give a yellow oil. The mixture was purified by column chromatography (petroleum ether:ethyl acetate=20:1 to 10:1) to give the title compound. ¹HNMR (400 MHz, CDCl$_3$) δ=7.42-7.28 (m, 3H), 4.49 (dd, J=2.3, 9.0 Hz, 1H), 4.22 (q, J=7.6 Hz, 1H), 4.10 (dt, J=4.9, 8.5 Hz, 1H), 4.03 (d, J=9.0 Hz, 1H), 2.85-2.74 (m, 1H), 2.54 (td, J=7.8, 12.8 Hz, 1H)

Step 2—(±)-Ethyl 2-(4-(3-cyanotetrahydrofuran-3-yl)-3-fluorophenyl)acetate

A solution of (±)-3-(4-bromo-2-fluoro-phenyl)tetrahydrofuran-3-carbonitrile (3.40 g, 12.59 mmol), dimethylaminopyridine (153.79 mg, 1.26 mmol), 1,1'-al naphthalene-2,2-diphenyl phosphine (783.81 mg, 1.26 mmol), and allyl (chloro)palladium (115.15 mg, 629.50 umol) in xylene (50.0 mL) was stirred at rt for 30 min under nitrogen. Then (3-ethoxy-3-oxo-propanoyl)oxypotassium (1.04 g, 6.11 mmol) was added in one portion and the reaction mixture was stirred at 140° C. for 16 hrs. On completion, ethyl acetate (100 mL) was added to the mixture, and then the solution was washed with water (2×30 mL), brine (1×30 mL), dried and concentrated. The mixture was purified by column chromatography (petroleum ether:ethyl acetate=20:1 to 10:1) to give the title compound. ¹H NMR (400 MHz, CDCl₃) δ=7.42-7.36 (m, 1H), 7.08-7.16 (m, 2H), 4.51 (dd, J=9.0, 2.3 Hz, 1H), 4.13-4.27 (m, 4H), 4.03 (d, J=8.8 Hz, 1H), 3.63 (s, 2H), 2.75-2.85 (m, 1H), 2.57 (dt, J=12.8, 7.9 Hz, 1H), 1.28 (t, J=7.2 Hz, 3H).

Step 3—(±)-Ethyl 2-(4-(3-cyanotetrahydrofuran-3-yl)-3-fluorophenyl)propanoate & (±)-ethyl 2-(4-(3-cyanotetrahydrofuran-3-yl)-3-fluorophenyl)-2-methylpropanoate To a solution of (±)-ethyl 2-[4-(3-cyanotetrahydrofuran-3-yl)-3-fluoro-phenyl]acetate (1.49 g, 5.37 mmol,) in tetrahydrofuran (20.0 mL) was added LiHMDS (1.0 M, 8.59 mL) dropwise at −10° C. After the mixture was stirred at −10° C. for 30 min, iodomethane (762.71 mg, 5.37 mmol, 334.52 uL) was added dropwise at −10° C., then the mixture was stirred at −10-rt for 2 hrs. On completion, the mixture was poured into water (80 mL), extracted with ethyl acetate (2×30 mL), washed with brine (20 mL), dried and concentrated to give the title compounds as mixture of the mono and bis addition products.

Step 4—(±)-Ethyl 2-(4-(3-carbamoyltetrahydrofuran-3-yl)-3-fluorophenyl)propanoate & (±)-ethyl 2-(4-(3-carbamoyltetrahydrofuran-3-yl)-3-fluorophenyl)-2-methylpropanoate To a solution of (±)-ethyl 2-[4-(3-cyanotetrahydrofuran-3-yl)-3-fluorophenyl]propanoate & (±)-ethyl 2-(4-(3-cyanotetrahydrofuran-3-yl)-3-fluorophenyl)-2-methylpropanoate (a mixture) (1.40 g, 4.81 mmol) and potassium carbonate (332 mg, 2.40 mmol) in dimethyl sulfoxide (10 mL) was added hydrogen peroxide (5.45 g, 48.1 mmol) in one portion. Then the mixture was stirred at rt for 3 hours. On completion, the mixture was poured into water (60 mL), filtered, and dried in vacuo to give the title compounds (mixture). LCMS: (ES⁺) m/z (M+H)⁺=310.1; 324.1, tR=1.384.

Step 5—(±)-Ethyl 2-(4-(3-aminotetrahydrofuran-3-yl)-3-fluorophenyl)propanoate (BJ)(±)-ethyl 2-(4-(3-aminotetrahydrofuran-3-yl)-3-fluorophenyl)-2-methylpropanoate (BK)

To a solution of (±)-ethyl 2-[4-(3-carbamoyltetrahydrofuran-3-yl)-3-fluorophenyl]propanoate & (±)-ethyl 2-(4-(3-carbamoyltetrahydrofuran-3-yl)-3-fluorophenyl)-2-methylpropanoate (mixture) (1.30 g, 4.20 mmol) in acetonitrile (10 mL) and water (10 mL) was added PhI(CF₃CO₂)₂ (2.12 g, 5.04 mmol,) in one portion at rt. Then the mixture was stirred at rt for 16 hours. On completion, the acetonitrile was removed in vacuo, and the residue was diluted with water (50 mL) and acidified by hydrochloric acid (2 N) until pH=2. Then the mixture was washed with dichloromethane (2×20 mL), the aqueous phase was basified with 1M sodium hydroxide to pH=7-8, and the mixture was extracted with ethyl acetate (3×20 mL). The combined organic extracts were washed with brine (20 mL), dried and concentrated to give the title compounds (a mixture of the mono and bis addition products). LCMS: (ES⁺) m/z (M−NH₂)+=265.1; 296.1, tR=1.391.

(±)-Ethyl 2-[4-(3-aminotetrahydrofuran-3-yl)phenyl] butanoate (Intermediate BL)

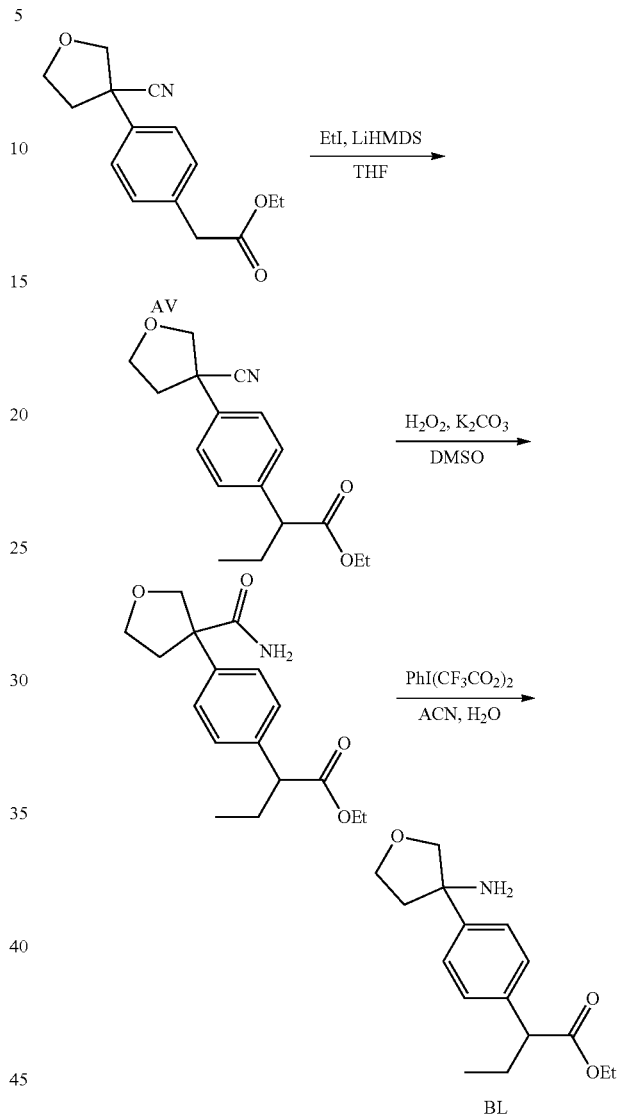

Step 1—(±)-Ethyl 2-[4-(3-cyanotetrahydrofuran-3-yl)phenyl]butanoate

To a solution of (±)-ethyl 2-[4-(3-cyanotetrahydrofuran-3-yl)phenyl]acetate (500 mg, 1.93 mmol) in tetrahydrofuran (10 mL) was added LiHMDS (1 M, 2.32 mL) dropwise at 0° C. After stirring at 0° C. for 0.5 hr, ethyl iodide (300 mg, 1.93 mmol) was added into the mixture. The resulting mixture was slowly warmed to rt and stirred at rt for 2 hrs. On completion, the mixture was quenched with ammonium chloride solution (10 mL), diluted with water (50 mL) and extracted with ethyl acetate (3×40 mL). The combined organic layer was dried over anhydrous sodium sulfate, filtered and concentrated in vacuo to give the title compound. ¹H NMR (400 MHz, CDCl₃) δ=7.38-7.32 (m, 2H), 7.28 (d, J=8.3 Hz, 2H), 4.29 (d, J=9.0 Hz, 1H), 4.16-4.07 (m, 3H), 4.07-3.99 (m, 1H), 3.96 (d, J=8.8 Hz, 1H), 3.38 (t, J=7.7 Hz, 1H), 2.80-2.63 (m, 1H), 2.38 (td, J=8.2, 12.9 Hz, 1H), 2.10-1.92 (m, 1H), 1.71 (m, 14.1 Hz, 1H), 1.15 (t, J=7.2 Hz, 3H), 0.83 (t, J=7.3 Hz, 3H).

Step 2—(±)-Ethyl 2-[4-(3-carbamoyltetrahydrofuran-3-yl)phenyl]butanoate

To a solution of (±)-ethyl 2-[4-(3-cyanotetrahydrofuran-3-yl)phenyl]butanoate (500 mg, 1.74 mmol) and potassium carbonate (96.2 mg, 696 umol) in dimethyl sulfoxide (10 mL) was added hydrogen peroxide (1.58 g, 13.9 mmol). The mixture was stirred at 50° C. for 3 hrs. On completion, the mixture was quenched with sodium sulfite solution (20 mL) and extracted with ethyl acetate (2×60 mL). The organic layer was then washed with water (50 mL), brine (50 mL), and the combined organic layer was dried over anhydrous sodium sulfate, filtered and concentrated in vacuo to give the title compound. LCMS: (ES$^+$) m/z (M+H)$^+$=306.2, tR=0.777.

Step 3—(±)-Ethyl 2-[4-(3-aminotetrahydrofuran-3-yl)phenyl]butanoate

To a mixture of (±)-ethyl 2-[4-(3-carbamoyltetrahydrofuran-3-yl)phenyl]butanoate (530 mg, 1.74 mmol) in acetonitrile (8 mL) and water (8 mL) was added PhI(O$_2$CCF$_3$)$_2$ (823 mg, 1.91 mmol) in one portion, and the mixture was stirred at rt for 16 hrs. On completion, the mixture was concentrated in vacuo. 1N HCl (8 mL) was added into the mixture and the mixture was extracted with ethyl acetate (50 mL). The aqueous layer was then basified with sodium bicarbonate to pH=9, and extracted with dichloromethane (2×60 mL). The combined organic layer was dried over anhydrous sodium sulfate, filtered and concentrated in vacuo to give the title compound. $^1$H NMR (400 MHz, CDCl$_3$) δ=7.44-7.38 (m, 2H), 7.35-7.30 (m, 2H), 4.24-4.05 (m, 4H), 3.96-3.92 (m, 1H), 3.91-3.86 (m, 1H), 3.46 (t, J=7.7 Hz, 1H), 2.40 (td, J=8.9, 12.5 Hz, 1H), 2.20-2.05 (m, 2H), 1.87-1.77 (m, 1H), 1.24 (t, J=7.2 Hz, 3H), 0.91 (t, J=7.3 Hz, 3H).

(±)-Ethyl 2-(4-(3-aminotetrahydrofuran-3-yl)phenyl)propanoate (Intermediate BM)

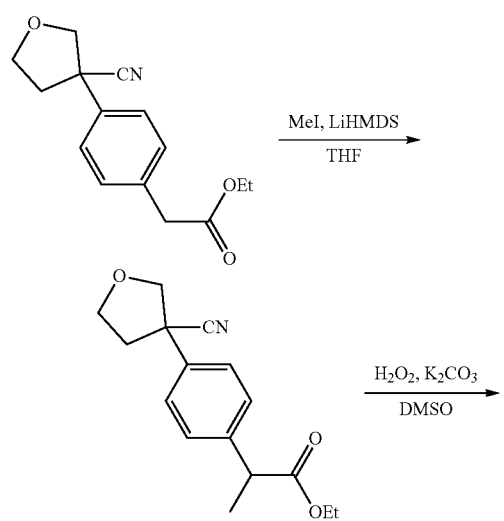

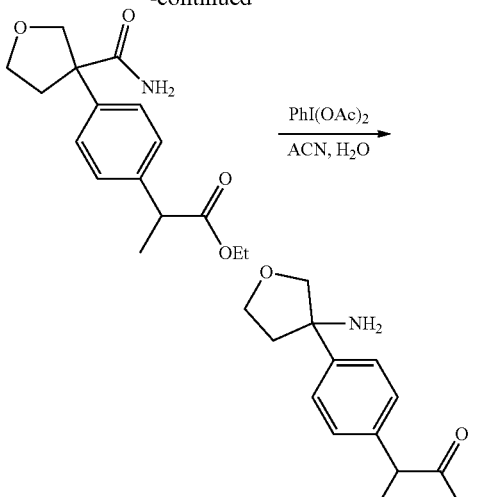

Step 1—(±)-Ethyl 2-(4-(3-cyanotetrahydrofuran-3-yl)phenyl)propanoate

To a solution of (±)-ethyl 2-[4-(3-cyanotetrahydrofuran-3-yl)phenyl]acetate (650 mg, 2.51 mmol) in tetrahydrofuran (20 mL) was added lithium bis(tert-butylsilyl)amide (1 M, 3.01 mL) at 0° C. The mixture was stirred at 0° C. for 1 hr before iodomethane (392 mg, 2.76 mmol) was added, then the mixture was stirred at rt for 1 hr. On completion, the mixture was quenched with saturated aqueous ammonium chloride (20 mL) and extracted with ethyl acetate (3×10 mL). The combined organic layers were dried over anhydrous sodium sulfate, filtered and concentrated. The residue was purified by chromatography (petroleum ether:ethyl acetate=5:1) to give the title product. $^1$H NMR (400 MHz, CDCl$_3$) δ=7.49-7.43 (m, 2H), 7.39-7.34 (m, 2H), 4.38 (d, J=9.0 Hz, 1H), 4.22-4.09 (m, 4H), 4.05 (d, J=9.0 Hz, 1H), 3.74 (q, J=7.3 Hz, 1H), 2.84-2.76 (m, 1H), 2.48 (m, 1H), 1.52 (d, J=7.0 Hz, 3H), 1.24 (t, J=7.2 Hz, 3H).

Step 2—(±)-Ethyl 2-(4-(3-carbamoyltetrahydrofuran-3-yl)phenyl)propanoate

To a mixture of (±)-ethyl 2-[4-(3-cyanotetrahydrofuran-3-yl)phenyl]propanoate (500 mg, 1.83 mmol) and potassium carbonate (101 mg, 732 umol) in dimethyl sulfoxide (2 mL) was added hydrogen peroxide (830 mg, 7.32 mmol, 30% purity). The mixture was stirred at rt for 1 hr. On completion, the reaction was quenched with water (5 mL) where a precipitate formed. The resulting solid was collected by filtration and washed with water (5 mL) to give the title compound. LCMS: (ES$^+$) m/z (M+H)$^+$=292.1, tR=0.646.

Step 3—(±)-Ethyl 2-(4-(3-aminotetrahydrofuran-3-yl)phenyl)propanoate

To a solution of (±)-ethyl 2-[4-(3-carbamoyltetrahydrofuran-3-yl)phenyl]propanoate (200 mg, 686 umol) in acetonitrile (4 mL) and water (4 mL) was added (diacetoxyiodo)benzene (243 mg, 755 umol). The mixture was stirred at rt for 1 hr. On completion, the mixture was acidified by hydrochloric acid (2 N) until pH=2, then washed with ethyl acetate (3×5 mL). The aqueous layer was separated, basified with aqueous sodium hydroxide (2 N) until pH=11, and extracted with ethyl acetate (3×5 mL). The combined organic layers were dried over anhydrous sodium sulfate and concentrated in vacuo to give the title product. LCMS: (ES+) m/z (M−NH$_2$)$^+$=247.1, tR=0.546.

(±)-Ethyl 2-[4-(3-aminooxetan-3-yl)phenyl]propanoate (Intermediate BN)

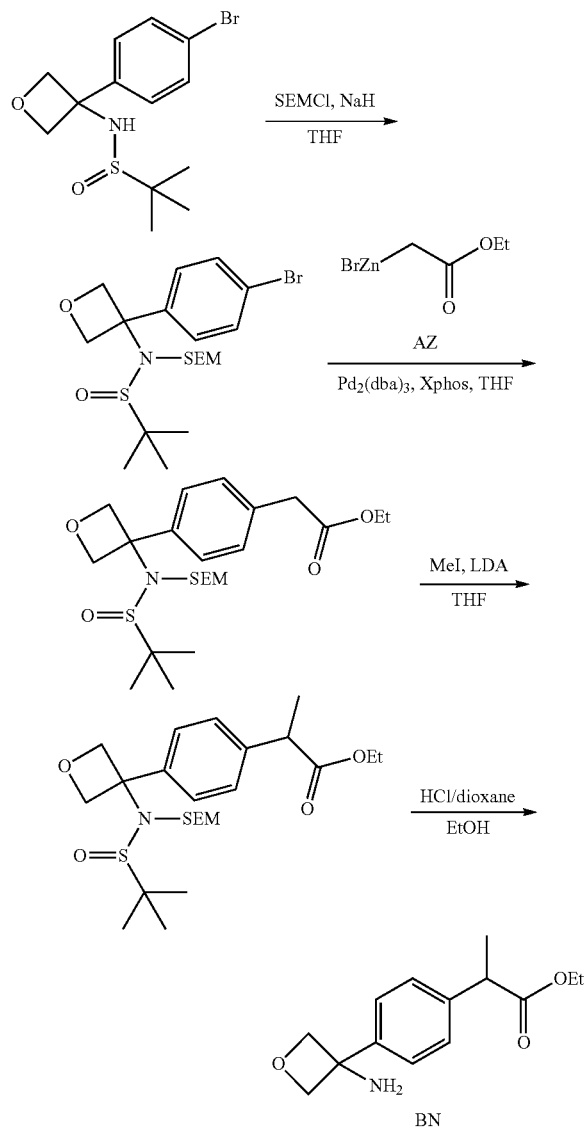

Step 1—(±)-N-[3-(4-bromophenyl)oxetan-3-yl]-2-methyl-N-(2-trimethylsilylethoxymethyl)-propane-2-sulfinamide To a solution of (±)-N-[3-(4-bromophenyl)oxetan-3-yl]-2-methyl-propane-2-sulfinamide (17.0 g, 51.1 mmol, synthesized via Steps 1-2 of Intermediate BA) in tetrahydrofuran (300 mL) was added sodium hydride (4.09 g, 102 mmol, 60%) at 0° C. and the reaction mixture was stirred for 0.5 hr. Then SEMCl (12.8 g, 76.7 mmol) was added dropwise and the reaction mixture was stirred at rt for 0.5 hr. On completion, the reaction mixture was poured into 1000 mL ice-water. The aqueous phase was then extracted with dichloromethane (3×1000 mL). The combined organic layer was dried over anhydrous sodium sulfate, filtrated and concentrated in vacuo. The solid was purified by silica gel chromatography (petroleum ether:ethyl acetate=5:1) to give title compound. $^1$H NMR (400 MHz, CDCl3) δ=7.61-7.49 (m, 4H), 5.38 (d, J=6.4 Hz, 1H), 5.26 (d, J=6.8 Hz, 1H), 4.84 (d, J=6.4 Hz, 1H), 4.72 (d, J=10.7 Hz, 1H), 4.68 (d, J=10.5 Hz, 1H), 3.82 (d, J=10.5 Hz, 1H), 3.39-3.31 (m, 2H), 1.37 (s, 9H), 0.93-0.85 (m, 2H), 0.02 (s, 9H).

Step 2—(±)-Ethyl 2-[4-[3-[tert-butylsulfinyl(2-trimethylsilylethoxymethyl)amino]oxetan-3-yl]phenyl]acetate To a solution of (±)-N-[3-(4-bromophenyl)oxetan-3-yl]-2-methyl-N-(2-trimethylsilylethoxymethyl)propane-2-sulfinamide (16.0 g, 34.5 mmol), XPhos (3.30 g, 6.92 mmol) and Pd$_2$(dba)$_3$ (3.17 g, 3.46 mmol) in tetrahydrofuran (250 mL) was added a solution of bromo-(2-ethoxy-2-oxo-ethyl)zinc (0.8 M, 64.86 mL) in tetrahydrofuran (140 mL) and the reaction mixture was stirred at 75° C. for 1 hr. On completion, the reaction mixture was quenched with 70 mL ammonium chloride saturated solution and filtered. The filtrate was extracted with ethyl acetate (3×500 mL). The combined organic layer was dried over anhydrous sodium sulfate, filtrated and concentrated in vacuo. The resulting residue was purified by silica gel chromatography (petroleum ether:ethyl acetate=5:1) to give the title compound. $^1$H NMR (400 MHz, CDCl3) δ=7.58 (d, J=8.4 Hz, 2H), 7.40 (d, J=8.4 Hz, 2H), 5.37 (d, J=6.3 Hz, 1H), 5.25 (d, J=6.7 Hz, 1H), 4.89 (d, J=6.3 Hz, 1H), 4.77 (d, J=10.5 Hz, 1H), 4.70 (s, 1H), 4.14 (q, J=7.1 Hz, 2H), 3.85 (d, J=10.5 Hz, 1H), 3.63 (s, 2H), 3.34 (t, J=8.1 Hz, 2H), 1.36 (s, 9H), 1.21 (t, J=7.2 Hz, 3H), 0.89 (dd, J=7.3, 8.9 Hz, 2H), 0.01 (s, 9H).

Step 3—(±)-Ethyl 2-[4-[3-[tert-butylsulfinyl(2-trimethylsilylethoxymethyl)amino]oxetan-3-yl]phenyl]propanoate To a solution of (±)-ethyl 2-[4-[3-[tert-butylsulfinyl(2-trimethylsilylethoxymethyl)amino]oxetan-3-yl]phenyl]acetate (800 mg, 1.70 mmol) in tetrahydrofuran (20.0 mL) was added LDA (2 M, 1.53 mL) dropwise at 0° C. and the reaction mixture was stirred for 0.5 hr. Then methyl iodide (241 mg, 1.70 mmol) in tetrahydrofuran (1 mL) was added and the reaction mixture was stirred at rt for 0.5 hr. On completion, the reaction mixture was poured into 30 mL cool water and acidified with citric acid solution until pH=6-7. The aqueous phase was extracted with dichloromethane (3×30 mL), dried over anhydrous sodium sulfate, filtrated and concentrated in vacuo. The resulting oil was purified by silica gel chromatography (petroleum ether:ethyl acetate=10:1) to give the title compound. $^1$HNMR (400 MHz, CDCl3) δ=7.58 (d, J=8.2 Hz, 2H), 7.37 (d, J=8.2 Hz, 2H), 5.38 (d, J=6.1 Hz, 1H), 5.25 (d, J=6.7 Hz, 1H), 4.89 (d, J=6.3 Hz, 1H), 4.74 (d, J=6.8 Hz, 1H), 4.72 (dd, J=1.3, 10.5 Hz, 1H), 4.20-4.08 (q, J=7.1 Hz, 2H), 3.85 (dd, J=1.3, 10.5 Hz, 1H), 3.73 (q, J=7.2 Hz, 1H), 3.35 (t, J=8.2 Hz, 2H), 1.51 (d, J=7.2 Hz, 3H), 1.37 (s, 9H), 1.23 (t, J=7.2 Hz, 3H), 0.92-0.85 (m, 2H), 0.01 (s, 9H).

Step 4—(±)-Ethyl 2-[4-(3-aminooxetan-3-yl)phenyl]propanoate

To a solution of (±)-ethyl 2-[4-[3-[tert-butylsulfinyl(2-trimethylsilylethoxymethyl)amino]oxetan-3-yl]phenyl]propanoate (700 mg, 1.45 mmol) in ethanol (8 mL) was added hydrochloric acid/dioxane (4 M, 3.62 mL) and the reaction mixture was stirred at 0° C. for 30 min. On completion, the reaction mixture was basified with saturated sodium bicarbonate solution until pH=8 and extracted with dichloromethane (3×20 mL). The combined organic layer was dried over anhydrous sodium sulfate, filtrated and concentrated in vacuo to give the title compound (400 mg, crude) as light yellow oil. LCMS: (ES$^+$) m/z (M−NH$_2$)$^+$=233.1, tR=1.024.

(±)-Ethyl 2-(4-(3-aminooxetan-3-yl)-3-fluorophenyl) propanoate (Intermediate BO) & Ethyl 2-(4-(3-aminooxetan-3-yl)-3-fluorophenyl)-2-methylpropanoate (Intermediate BP)

ethyl-silane (2.86 g, 17.1 mmol) was added dropwise. The mixture was warmed to 30° C. with stirring for 16 hrs. On completion, the reaction mixture was quenched with water (50 mL) and extracted with ethyl acetate (3×50 mL). The combined organic phase was washed by brine (100 mL), dried over sodium sulfate, and concentrated in vacuo to give the crude product. The crude product was purified by column chromatography (petroleum ether:ethyl acetate=20:1 to 10:1) to give the title compound (1.7 g, yield 37%). $^1$H NMR (300 MHz, CDCl$_3$) δ=7.33-7.18 (m, 3H), 5.22 (d, J=7.2 Hz, 1H), 5.16 (d, J=7.5 Hz, 1H), 5.04-5.08 (m, 2H), 4.53 (d, J=10.5 Hz, 1H), 4.14 (d, J=10.8 Hz, 1H), 3.44-3.28 (m, 2H), 1.24 (s, 9H), 0.86 (t, J=8.1 Hz, 2H), 0.00 (s, 9H).

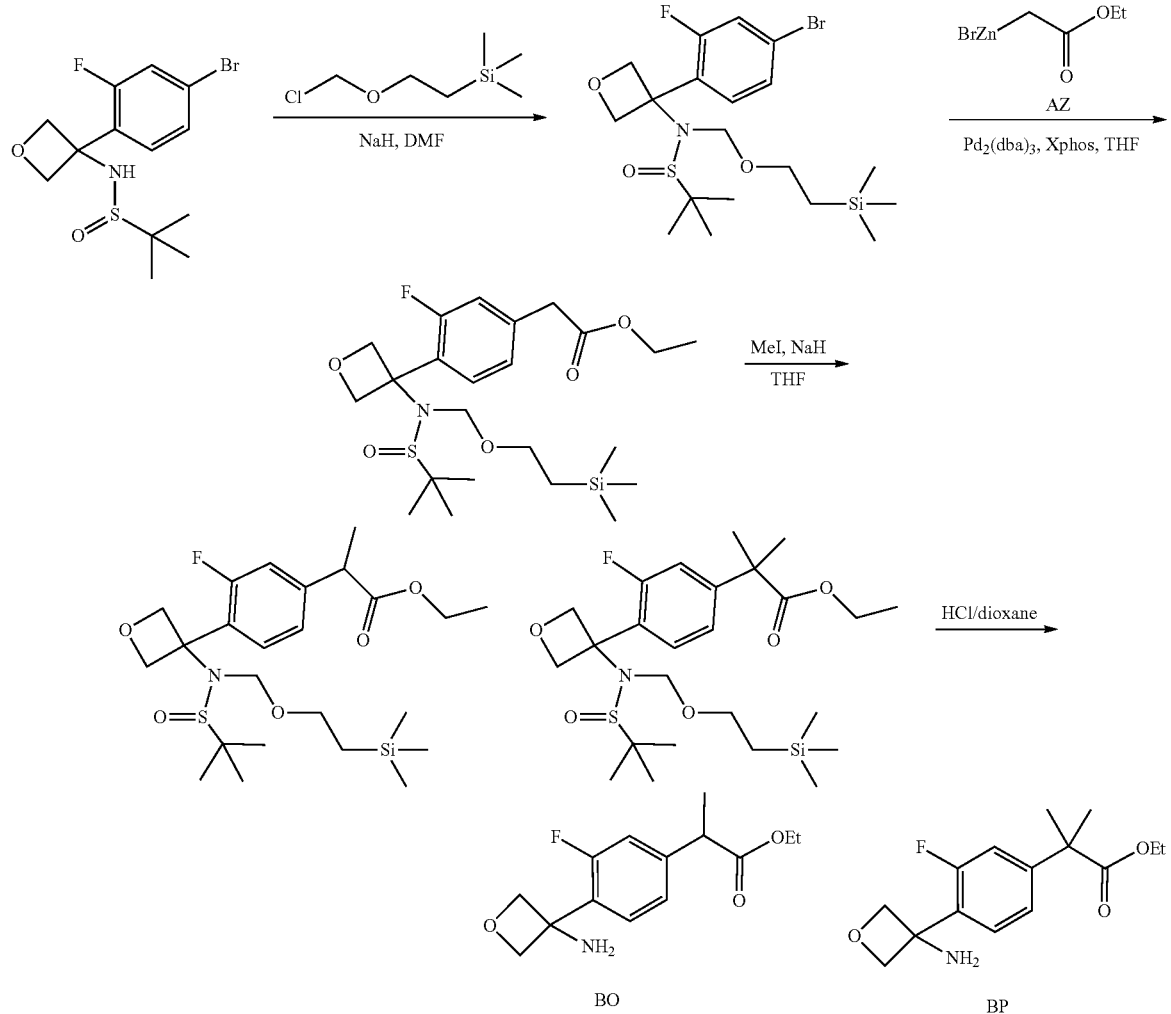

Step 1—(±)-N-(3-(4-Bromo-2-fluorophenyl)oxetan-3-yl)-2-methyl-N-((2-(trimethylsilyl)ethoxy)methyl) propane-2-sulfinamide To a solution of (±)-N-[3-(4-bromo-2-fluoro-phenyl) oxetan-3-yl]-2-methyl-propane-2-sulfinamide (3.00 g, 8.57 mmol, synthesized via Step 1 of Intermediate BB) in tetrahydrofuran (30.0 mL) was added sodium hydride (685 mg, 17.1 mmol) in portions at −10° C., and the resultant mixture was stirred for 30 min. Then, 2-(chloromethoxy)ethyl-trim- Step 2—(±)-Ethyl 2-(3-fluoro-4-(3-(2-methyl-N-((2-(trimethylsilyl)ethoxy)methyl)propan-2-ylsulfinamido) oxetan-3-yl)phenyl)acetate To a mixture of Pd$_2$(dba)$_3$ (57.2 mg, 62.4 umol) and XPhos (59.5 mg, 125 umol) was added a solution of (±)-N-[3-(4-bromo-2-fluoro-phenyl)oxetan-3-yl]-2-methyl-N-(2-trimethylsilylethoxy methyl)propane-2-sulfinamide (300 mg, 624 umol) in tetrahydrofuran (2 mL) under nitrogen. Then, a solution of bromo-(2-ethoxy-2-oxo-ethyl)zinc in tetrahydrofuran (0.5M, 5.00 mL) was added in one portion at rt. The reaction mixture was heated to 80° C. and stirred for 2 hrs. On completion, the cooled solution was quenched with water (30 mL), then filtered, and the filtrate was extracted with ethyl acetate (3×20 mL). The combined organic phase was washed with brine (50 mL), dried over sodium sulfate, and concentrated in vacuo to give a residue which was purified by column chromatography (petroleum ether:ethyl acetate=20:1 to 5:1) to give the title compound. $^1$H NMR (400 MHz, CDCl$_3$) δ=7.28 (t, J=8.0 Hz, 1H), 7.11 (d, J=7.6 Hz, 1H), 7.07 (d, J=12.0 Hz, 1H), 5.25 (d, J=7.2 Hz, 1H), 5.20 (d, J=7.2 Hz, 1H), 5.12 (d, J=7.2 Hz, 2H), 4.57 (d, J=10.8 Hz, 1H), 4.21-4.16 (m, 3H), 3.62 (s, 2H), 3.44-3.34 (m, 2H), 1.30-1.27 (m, 12H), 0.93-0.89 (m, 2H), 0.027 (s, 9H).

Step 3—(±)-Ethyl 2-(3-fluoro-4-(3-(2-methyl-N-((2-(trimethylsilyl)ethoxy)methyl) propan-2-ylsulfinamido)oxetan-3-yl)phenyl)propanoate & Ethyl 2-(4-(3-((tert-butylsulfinyl)((2-(trimethylsilyl)ethoxy)methyl)amino)oxetan-3-yl)-3-fluorophenyl)-2-methylpropanoate To a solution of (±)-ethyl 2-[4-[3-[tert-butylsulfinyl(2-trimethylsilylethoxymethyl)amino]oxetan-3-yl]-3-fluoro-phenyl]acetate (840 mg, 1.72 mmol) in tetrahydrofuran (14.0 mL) was added sodium hydride (103 mg, 2.58 mmol, 60% purity) in one portion at 0° C. The mixture was stirred at 0° C. for 30 min. Then, a solution of methyl iodide (293 mg, 2.06 mmol) in tetrahydrofuran (5.00 mL) was added dropwise at 0° C. After the addition, the resultant mixture was stirred for 3 hrs. On completion, the mixture was quenched with water (50 mL) and extracted with ethyl acetate (3×30 mL). The combined organic phase was dried over sulfate and concentrated in vacuo to give a residue which was purified by column chromatography (petroleum ether:ethyl acetate=20:1 to 5:1) to give the title compounds (as a mixture of monomethyl and gem-dimethyl) that were used directly in the next step.

Step 4—(±)-Ethyl 2-(4-(3-aminooxetan-3-yl)-3-fluorophenyl)propanoate & Ethyl 2-(4-(3-aminooxetan-3-yl)-3-fluorophenyl)-2-methylpropanoate To a mixture of (±)-ethyl 2-[4-[3-[tert-butylsulfinyl(2-trimethylsilylethoxymethyl)amino]oxetan-3-yl]-3-fluoro-phenyl]propanoate & ethyl 2-(4-(3-((tert-butylsulfinyl)((2-(trimethylsilyl)ethoxy)-methyl)amino)oxetan-3-yl)-3-fluorophenyl)-2-methylpropanoate (200 mg, 399 umol) in ethanol (1.00 mL) was added hydrochloride/dioxane (4 M, 498 uL) dropwise at 0° C. The mixture was stirred at 0° C. for 2 hrs. On completion, to the mixture was added sodium bicarbonate (sat. 5 mL) and the solution was extracted with dichloromethane (3×10 mL). The combined organic phase was washed with brine (20 mL), dried over sodium sulfate, and concentrated in vacuo to give a residue which was purified by column chromatography (petroleum ether:ethyl acetate=10:1 to 2:1) to give the title compound as a mixture of the monomethyl and gem-dimethyl. LCMS: (ES$^+$) m/z (M–NH$_2$)$^+$=251.1, tR=0.629.

(±)-Ethyl 2-[4-(3-aminooxetan-3-yl)-3-chloro-phenyl]propanoate (Intermediate BQ)

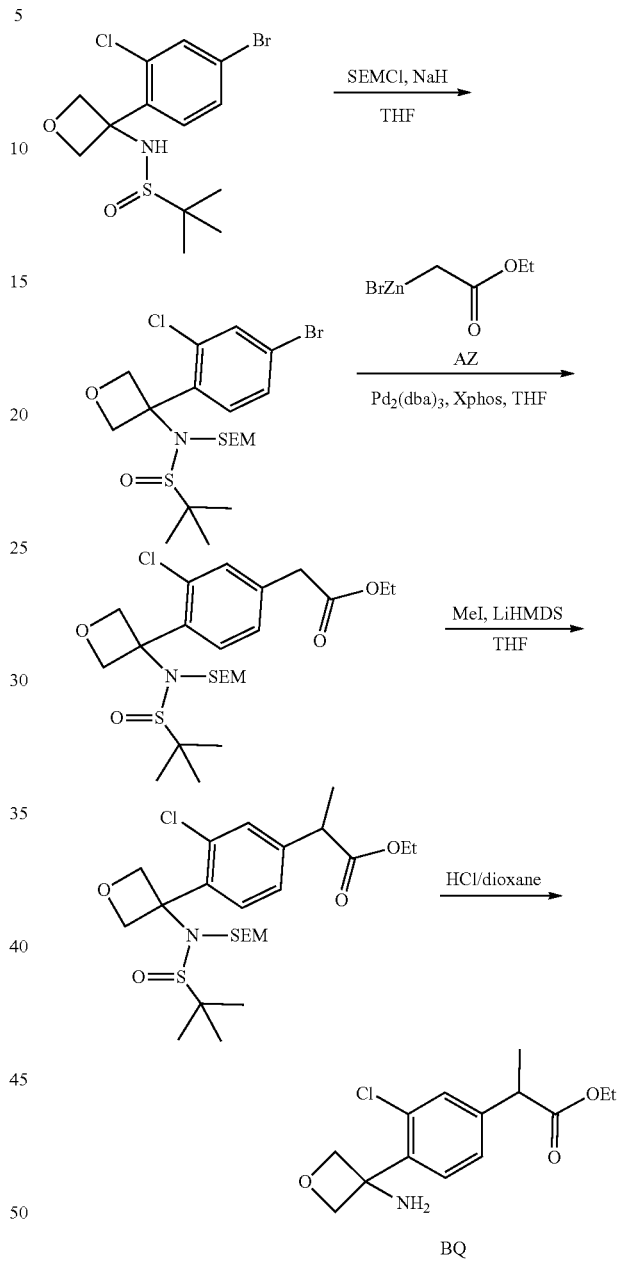

BQ

Step 1—(±)-N-[3-(4-bromo-2-chloro-phenyl)oxetan-3-yl]-2-methyl-N-(2-trimethylsilylethoxy-methyl) propane-2-sulfinamide To a solution of (±)-N-[3-(4-bromo-2-chloro-phenyl) oxetan-3-yl]-2-methyl-propane-2-sulfinamide (2.00 g, 5.45 mmol, synthesized via Step 1 of Intermediate BD) in tetrahydrofuran (30 mL) was added sodium hydride (261 mg, 10.9 mmol) at 0° C. and the reaction mixture was stirred for 0.5 hour under nitrogen. Then (2-(chloromethoxy)ethyl) trimethylsilane (1.36 g, 8.18 mmol) was added dropwise and the reaction mixture was stirred at rt for 0.5 hour. On completion, the mixture was slowly poured into ice water (100 mL), and extracted with dichloromethane (2×150 mL). The combined organic layer was dried over anhydrous sodium sulfate, filtered and concentrated in vacuo to give a residue. The residue was purified by column chromatography (petroleum ether:ethyl acetate=10:1) and concentrated in vacuo to give the title compound. $^1$H NMR (400 MHz, CDCl$_3$) δ=7.57 (d, J=2.0 Hz, 1H), 7.45 (dd, J=1.9, 8.4 Hz, 1H), 7.19 (d, J=8.3 Hz, 1H), 5.39-5.23 (m, 2H), 5.15 (dd, J=7.7, 12.4 Hz, 2H), 4.69 (d, J=10.8 Hz, 1H), 4.34 (d, J=10.5 Hz, 1H), 3.49-3.27 (m, 2H), 1.23 (s, 9H), 0.89 (t, J=8.2 Hz, 2H), 0.03 (s, 9H).

Step 2—(±)-Ethyl 2-[4-[3-[tert-butylsulfinyl(2-trimethylsilylethoxymethyl)amino]oxetan-3-yl]-3-chloro-phenyl]acetate To a solution of (±)-N-[3-(4-bromo-2-chloro-phenyl) oxetan-3-yl]-2-methyl-N-(2-trimethylsilyleth oxymethyl) propane-2-sulfinamide (1.00 g, 2.01 mmol), Pd$_2$(dba)$_3$ (184 mg, 201 umol) and XPhos (191 mg, 402 umol) in tetrahydrofuran (20 mL) was added a solution of bromo-(2-ethoxy-2-oxo-ethyl)zinc (0.6 M, 5.02 mL) in tetrahydrofuran (10 mL) and the reaction mixture was stirred at 80° C. for 1 hour under nitrogen. On completion, the mixture was quenched with 30 mL water, filtered and extracted with ethyl acetate (3×30 mL). The organic layer was dried with anhydrous sodium sulfate, filtrated and concentrated to give the residue. The crude product was purified by prep-column chromatography (petroleum ether:ethyl acetate=10:1 to 3:1) to give the title compound. $^1$H NMR (400 MHz, CDCl$_3$) δ=7.31 (s, 1H), 7.24-7.16 (m, 2H), 5.30 (dd, J=7.5, 14.6 Hz, 2H), 5.20-5.02 (m, 2H), 4.66 (d, J=10.5 Hz, 1H), 4.31 (d, J=10.8 Hz, 1H), 4.16 (q, J=7.0 Hz, 2H), 3.59 (s, 2H), 3.46-3.24 (m, 2H), 1.30-1.23 (m, 3H), 1.20 (s, 9H), 0.87 (t, J=8.2 Hz, 2H), 0.00 (s, 9H).

Step 3—(±)-2-[4-[3-[Tert-butylsulfinyl(2-trimethylsilylethoxymethyl)amino]oxetan-3-yl]-3-chlorophenyl]propanoate To a mixture of (±)-ethyl 2-[4-[3-[tert-butylsulfinyl(2-trimethylsilylethoxymethyl)amino]oxetan-3-yl]-3-chlorophenyl]acetate (400 mg, 793 umol) in tetrahydrofuran (10 mL) was added lithium diisopropylamide (2 M, 595 uL) at 0° C. Then iodomethane (112 mg, 793 umol) was added to the mixture dropwise at 0° C. The mixture was stirred at rt for 2 hours. On completion, the mixture was quenched with water (30 mL) and extracted with ethyl acetate (3×30 mL). The organic layer was dried with anhydrous sodium sulfate, filtrated and concentrated in vacuo. The residue was purified by prep-column chromatography (petroleum ether:ethyl acetate=3:1) to give the title compound. $^1$H NMR (400 MHz, CDCl$_3$) δ=7.34 (s, 1H), 7.25 (s, 2H), 5.33 (dd, J=7.7, 17.7 Hz, 2H), 5.17 (dd, J=7.5, 19.3 Hz, 2H), 4.68 (dd, J=2.9, 10.7 Hz, 1H), 4.32 (dd, J=2.3, 10.8 Hz, 1H), 4.22-4.04 (m, 2H), 3.71 (q, J=7.3 Hz, 1H), 3.49-3.27 (m, 2H), 1.51 (d, J=7.0 Hz, 3H), 1.31-1.24 (m, 3H), 1.23 (s, 9H), 0.90 (t, J=8.2 Hz, 2H), 0.03 (s, 9H).

Step 4—(±)-Ethyl 2-[4-(3-aminooxetan-3-yl)-3-chloro-phenyl]propanoate

To a mixture of (±)-ethyl 2-[4-[3-[tert-butylsulfinyl(2-trimethylsilylethoxymethyl)amino]oxetan-3-yl]-3-chloro-phenyl]propanoate (300 mg, 579 umol) in ethanol (2 mL) was added 4 N hydrochloric acid/dioxane (4 M, 145 uL). Then the mixture was stirred at 0° C. for 0.5 hour. On completion, the mixture was dried by bubbling nitrogen through the mixture. Then the residue was triturated with 20 mL methyl tert-butyl ether and filtrated to give the title compound. LCMS: (ES+) m/z (M+H)$^+$=284.1, tR=0.652.

(±) Potassium 2-cyanopropanoate (Intermediate BR)

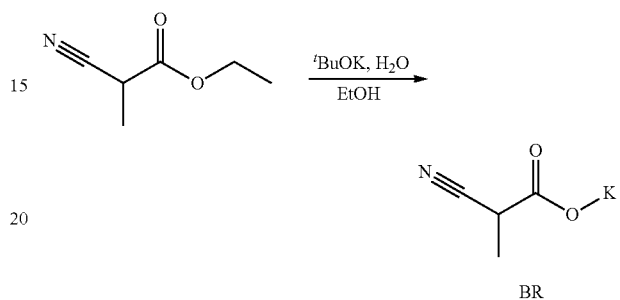

To a solution of (±) ethyl 2-cyanopropanoate (10.0 g, 78.7 mmol, CAS #1572-99-2) in ethanol (50 mL) was added water (1.42 g, 78.7 mmol). The reaction mixture was stirred at 40° C. for 2 hrs. Then a solution of tert-butoxypotassium (8.83 g, 78.7 mmol) in ethanol (50 mL) was added dropwise at 40° C. to the mixture over 0.5 hr. The reaction mixture was stirred at 40° C. for 2 hrs. On completion, the reaction mixture was concentrated in vacuo to remove ethanol. The residue was triturated with (ethanol: 2-methoxy-2-methyl-propane=1:3; 100 mL), filtered and dried to afford the title compound. $^1$H NMR (400 MHz, DMSO-d$_6$) δ=3.07 (q, J=7.2 Hz, 1H), 1.25 (d, J=7.2 Hz, 3H).

(±) 2-(4-(3-Aminotetrahydrofuran-3-yl)phenyl)propanenitrile (Intermediate BS)

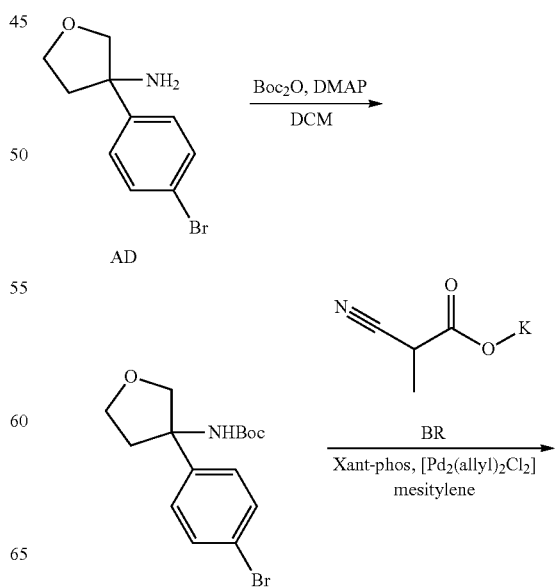

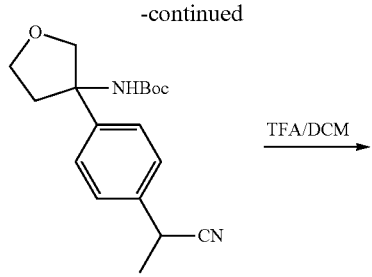

Step 1—(±) Tert-butyl (3-(4-bromophenyl)tetrahydrofuran-3-yl)carbamate

To a solution of (±) 3-(4-bromophenyl)tetrahydrofuran-3-amine (3.20 g, 13.2 mmol) in dichloromethane (30 mL) was added di-tert-butyl dicarbonate (3.17 g, 14.5 mmol, 3.34 mL) and N,N-dimethylpyridin-4-amine (162 mg, 1.32 mmol) at rt. The reaction mixture was stirred at rt for 12 hrs. On completion, the reaction mixture was concentrated in vacuo. The yellow oil was purified by silica gel chromatography (petroleum ether:ethyl acetate=30/1 to 10/1) to give the title compound. $^1$H NMR (400 MHz, DMSO-$d_6$) δ=7.68 (br. s., 1H), 7.51 (d, J=8.4 Hz, 2H), 7.29 (d, J=8.6 Hz, 2H), 4.04 (d, J=8.8 Hz, 1H), 3.97-3.90 (m, 1H), 3.88-3.82 (m, 2H), 2.51-2.49-2.37 (m, 1H), 2.10 (td, J=13.0, 8.2 Hz, 1H), 1.34 (s, 9H).

Step 2—(±) Tert-butyl (3-(4-(1-cyanoethyl)phenyl)tetrahydrofuran-3-yl)carbamate A solution of (±) tert-butyl N-[3-(4-bromophenyl)tetrahydrofuran-3-yl]carbamate (100 mg, 292 umol), Pd$_2$(allyl)$_2$Cl$_2$ (5.35 mg, 14.6 umol) and 4,5-bis(diphenylphosphino)-9,9-dimethylxanthene (25.4 mg, 43.8 umol) in mesitylene (1 mL) was stirred at rt for 0.5 hr under a nitrogen. Then, 2-cyanopropanoyloxypotassium (48.1 mg, 351 umol) was added in one portion and the reaction mixture was stirred at 140° C. for 6 hr. On completion, the reaction mixture was concentrated in vacuo, extracted with ethyl acetate (3×5 mL), filtered and concentrated in vacuo. The residue was purified by silica gel chromatography (petroleum ether:ethyl acetate=10:1) to give the title compound. $^1$H NMR (400 MHz, CDCl3) δ=7.45 (d, J=8.5 Hz, 2H), 7.38-7.33 (m, 2H), 5.19 (br. s., 1H), 4.12-4.07 (m, 2H), 4.05 (br. s., 2H), 3.91 (q, J=7.3 Hz, 1H), 2.58-2.41 (m, 1H), 2.40 (td, J=8.4, 12.8 Hz, 1H), 1.66 (d, J=7.3 Hz, 3H), 1.41 (s, 9H).

Step 3—(±) 2-(4-(3-Aminotetrahydrofuran-3-yl)phenyl)propanenitrile

To a solution of (±) tert-butyl N-[3-[4-(1-cyanoethyl)phenyl]tetrahydrofuran-3-yl]carbamate (200 mg, 632 umol) in dichloromethane (2 mL) was added trifluoroacetic acid (308 mg, 2.70 mmol). The reaction mixture was stirred at rt for 1 hrs. On completion, the reaction mixture was concentrated in vacuo to give the title compound. LCMS: (ES$^+$) m/z (M−NH$_2$)$^+$=200.2, tR=0.237.

Allyl 2-(4-(3-aminooxetan-3-yl)phenyl)-2-methylpropanoate (Intermediate BT)

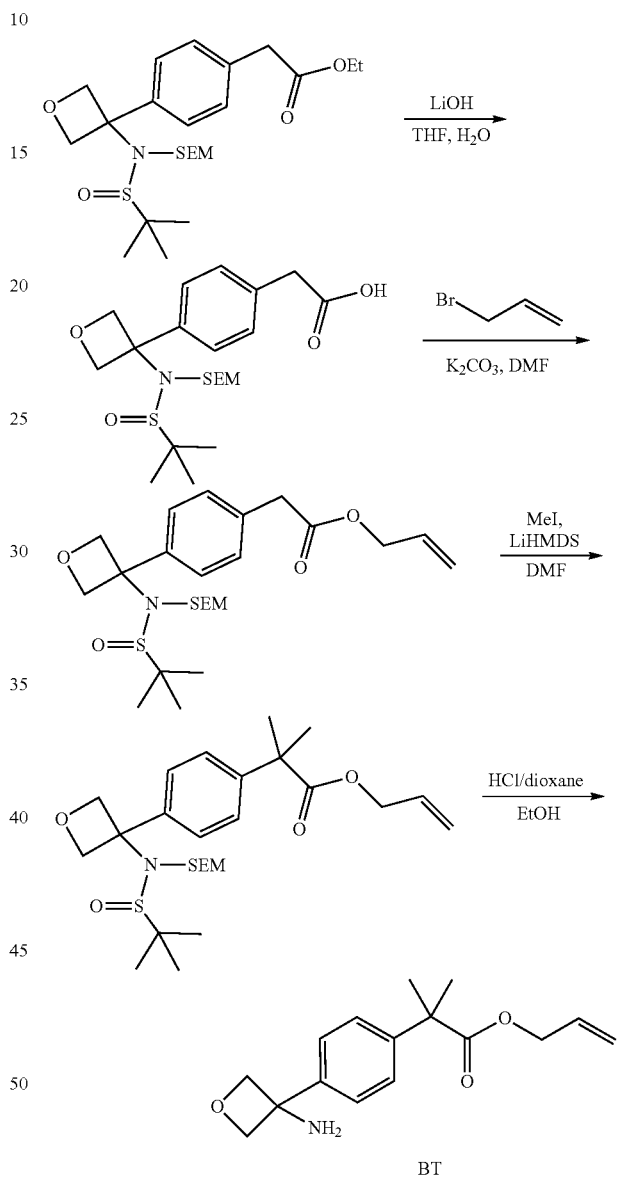

Step 1—2-[4-[3-[Tert-butylsulfinyl(2-trimethylsilylethoxymethyl)amino]oxetan-3-yl]phenyl]-acetic acid To a solution of ethyl 2-[4-[3-[tert-butylsulfinyl(2-trimethylsilylethoxymethyl)amino]oxetan-3-yl]phenyl]acetate (40.0 g, 85.1 mmol, synthesized via Steps 1-2 of Intermediate BN) in a mixture of water (150 mL) and tetrahydrofuran (300 mL) was added lithium hydroxide (6.12 g, 255 mmol) and the reaction mixture was stirred at rt for 16 hrs. On completion, the reaction mixture was poured into 3 L cool water and acidified with 1N hydrochloric acid solution until pH=4-5. The aqueous phase was extracted with ethyl acetate (3×2 L), dried over anhydrous sodium sulfate, filtrated and concentrated in vacuo to give the title compound. $^1$H NMR (400 MHz, CDCl3) δ=7.59 (d, J=8.4 Hz, 2H), 7.35 (d, J=8.3 Hz, 2H), 5.37 (d, J=6.3 Hz, 1H), 5.25 (d, J=6.8 Hz, 1H), 4.89 (d, J=6.3 Hz, 1H), 4.74 (d, J=3.4 Hz, 1H), 4.72 (d, J=7.3 Hz, 1H), 3.83 (d, J=10.5 Hz, 1H), 3.67 (s, 2H), 3.38-3.28 (m, 2H), 1.37 (s, 9H), 0.93-0.82 (m, 2H), 0.01 (s, 9H).

Step 2—Allyl 2-[4-[3-[tert-butylsulfinyl(2-trimethylsilylethoxymethyl)amino]oxetan-3-yl]phenyl]acetate To a mixture of 2-[4-[3-[tert-butylsulfinyl(2-trimethylsilylethoxymethyl)amino]oxetan-3-yl]phenyl] acetic acid (38.0 g, 86.0 mmol) and potassium carbonate (23.7 g, 172 mmol) in dimethylformamide (360 mL) was added 3-bromoprop-1-ene (20.8 g, 172 mmol) in one portion and the reaction mixture was stirred at rt for 16 hrs. On completion, the reaction mixture was poured in 3 L water and extracted with ethyl acetate (3×1 L). The combined organic layer was dried over anhydrous sodium sulfate, filtrated and concentrated in vacuo. The resulting oil was purified by silica gel chromatography (petroleum ether:ethyl acetate=10:1) to give the title compound. $^1$H NMR (400 MHz, CDCl3) δ=7.60 (d, J=8.3 Hz, 2H), 7.36 (d, J=8.2 Hz, 2H), 5.98-5.86 (m, 1H), 5.37 (d, J=6.3 Hz, 1H), 5.30 (dd, J=1.4, 17.2 Hz, 1H), 5.27-5.21 (m, 2H), 4.89 (d, J=6.3 Hz, 1H), 4.76-4.68 (m, 2H), 4.61 (d, J=5.6 Hz, 2H), 3.84 (d, J=10.5 Hz, 1H), 3.68 (s, 2H), 3.34 (t, J=8.2 Hz, 2H), 1.36 (s, 9H), 0.92-0.84 (m, 2H), 0.01 (s, 9H).

Step 3—(±)-Allyl 2-[4-[3-[tert-butylsulfinyl(2-trimethylsilylethoxymethyl)amino]oxetan-3-yl]phenyl]-2-methyl-propanoate To a solution of (±)-allyl 2-[4-[3-[tert-butylsulfinyl(2-trimethylsilylethoxymethyl)amino]oxetan-3-yl]phenyl]acetate (500 mg, 1.04 mmol) in N,N-dimethylformamide (15 mL) was added LiHMDS (1 M, 10.4 mL) dropwise at 0° C. After the reaction mixture was stirred for 0.5 hr, a solution of methyl iodide (1.48 g, 10.4 mmol) in N,N-dimethylformamide (1 mL) was added dropwise and the reaction mixture was stirred at rt for 6.5 hrs. On completion, the reaction mixture was poured into 100 mL cool water and extracted with ethyl acetate (3×50 mL). The combined layer was dried over anhydrous sodium sulfate, filtrated and concentrated in vacuo. The resulting product was purified by silica gel chromatography (petroleum ether:ethyl acetate=5:1) to give the title compound (500 mg, 50% purity, 47% yield) as colorless oil. LCMS: (ES$^+$) m/z (M+23)$^+$=532.1, tR=1.122.

Step 4—Allyl 2-(4-(3-aminooxetan-3-yl)phenyl)-2-methylpropanoate

To a solution of (±)-allyl 2-[4-[3-[tert-butylsulfinyl(2-trimethylsilylethoxymethyl)amino]oxetan-3-yl]phenyl]-2-methyl-propanoate (600 mg, 1.18 mmol) in ethanol (5 mL) was added hydrochloric acid/dioxane (4 M, 1.47 mL) and the reaction mixture was stirred at 0° C. for 30 min. On completion, the reaction mixture was basified with saturated sodium bicarbonate solution until pH=8 and extracted with dichloromethane (3×30 mL). The combined layer was dried over anhydrous sodium sulfate, filtrated and concentrated in vacuo to give the title product (451 mg, 52.5% purity, 73% yield) as a light yellow solid. LCMS: (ES$^+$) m/z (M−NH$_2$)$^+$=259.0, tR=1.209.

Allyl 1-(4-(3-aminooxetan-3-yl)phenyl)cyclopropanecarboxylate (Intermediate BU)

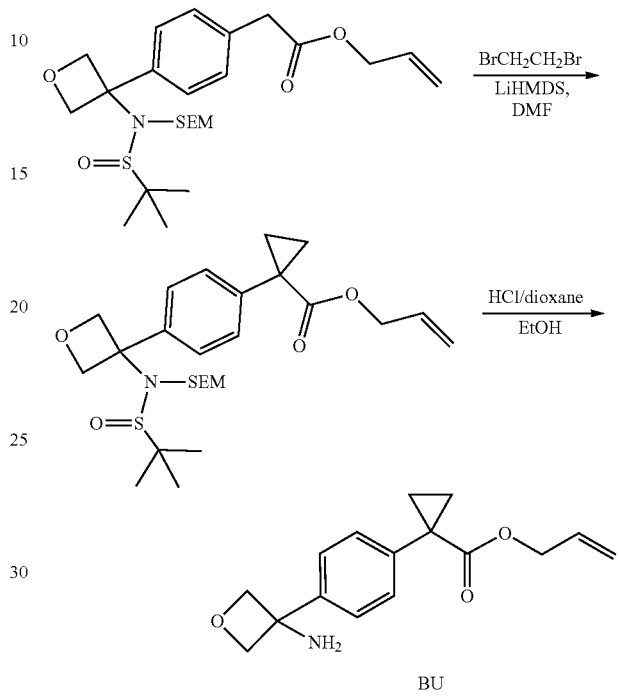

BU

Step 1—(±)-Allyl 1-(4-(3-(2-methyl-N-((2-(trimethylsilyl)ethoxy)methyl)propan-2-ylsulfinamido)oxetan-3-yl)phenyl)cyclopropanecarboxylate To a mixture of (±)-allyl 2-[4-[3-[tert-butylsulfinyl(2-trimethylsilylethoxymethyl)amino]oxetan-3-yl]phenyl]acetate (200 mg, 415 umol, synthesized via Steps 1-2 of Intermediate BT) in N,N-dimethylformamide (2.00 mL) was added the solution of LiHMDS in hexane (1.66 mL, 1.66 mmol, 1M) dropwise at rt. Then, a solution of 1,2-dibromoethane (125 mg, 664 umol) in N,N-dimethylformamide (1.00 mL) was added at rt under nitrogen atmosphere. The resultant mixture was stirred at rt for 16 hrs. On completion, to the mixture was added ammonium chloride solution (sat. 10 mL) and the mixture was extracted with ethyl acetate (3×10 mL). The combined organic phase was washed with brine (30 mL), dried over sodium sulfate, and concentrated in vacuo to give a residue which was purified by column chromatography (petroleum ether:ethyl acetate=10:1 to 5:1) to give the title compound. $^1$H NMR (400 MHz, CDCl$_3$-d) δ=7.56 (d, J=8.4 Hz, 2H), 7.40 (d, J=8.4 Hz, 2H), 5.84-5.81 (m, 1H), 5.37 (d, J=6.4 Hz, 1H), 5.24 (d, J=6.8 Hz, 1H), 5.19-5.13 (m, 2H), 4.89 (d, J=6.0 Hz, 1H), 4.74-4.69 (m, 2H), 4.55 (d, J=5.2 Hz, 2H), 3.85 (d, J=10.4 Hz, 1H), 3.34 (t, J=8.0 Hz, 2H), 1.65-1.62 (m, 2H), 1.35 (s, 9H), 1.22-1.19 (m, 2H), 0.88 (t, J=8.8 Hz, 2H), 0.00 (s, 9H).

Step 2—Allyl 1-(4-(3-aminooxetan-3-yl)phenyl)cyclopropanecarboxylate

To a solution of (±)-allyl 1-[4-[3-[tert-butylsulfinyl(2-trimethylsilylethoxymethyl)amino]oxetan-3-yl]phenyl]cyclopropanecarboxylate (100 mg, 197 umol) in ethanol (1.00 mL) was added hydrochloride/dioxane (4 M, 0.2 mL) dropwise at 0° C. The resultant mixture was stirred at 0° C. for 2 hrs. On completion, to the mixture was added sodium bicarbonate (sat. 10 mL) and the mixture was extracted with dichloromethane (3×10 mL). The combined organic phase was washed with brine (30 mL), dried over sodium sulfate, and concentrated in vacuo to give the title compound. LCMS: (ES−) m/z (M−NH$_2$)$^+$=257.2, tR=0.609.

Allyl 2-(4-(3-aminooxetan-3-yl)-3-fluorophenyl)-2-methylpropanoate (Intermediate BV)

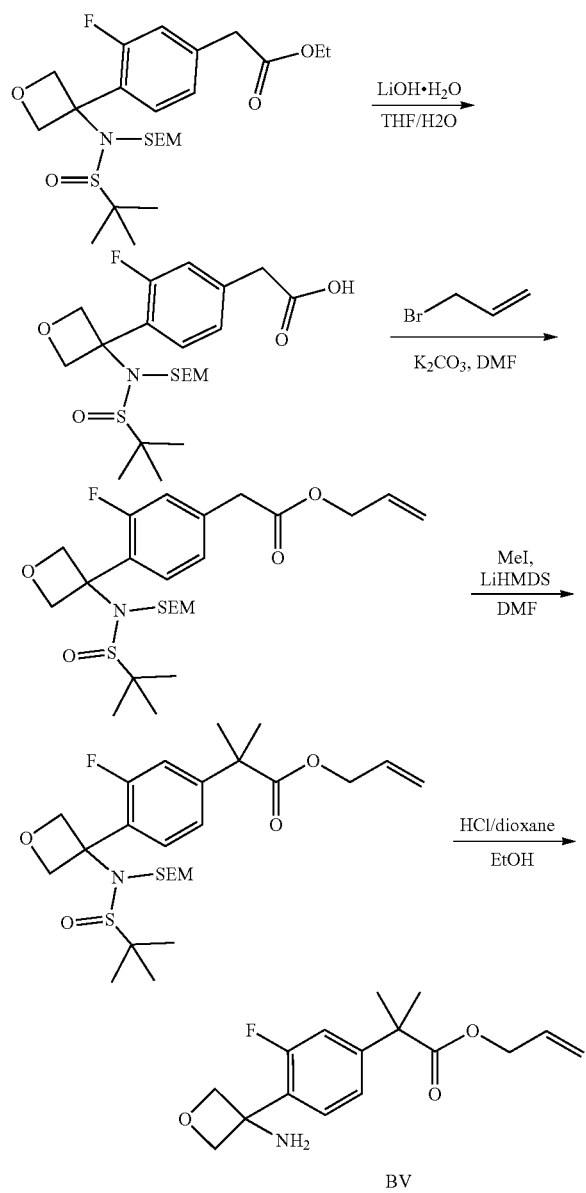

Step 1—(±)-2-(3-Fluoro-4-(3-(2-methyl-N-((2-(trimethylsilyl)ethoxy)methyl)propan-2-ylsulfinamido)oxetan-3-yl)phenyl)acetic acid To a mixture of (±)-ethyl 2-[4-[3-[tert-butylsulfinyl(2-trimethylsilylethoxymethyl)amino]oxetan-3-yl]-3-fluorophenyl]acetate (1.40 g, 2.87 mmol) in tetrahydrofuran (10.0 mL) and water (5.00 mL) was added lithium hydroxide (602 mg, 14.3 mmol) in one portion at 30° C. under nitrogen. The mixture was stirred at rt for 16 hrs. On completion, the mixture was concentrated in vacuo to remove tetrahydrofuran, and the aqueous phase was washed with ethyl acetate (10 mL) three times. To the aqueous phase was added 2 M hydrochloride acid to adjust pH=4-5. The product was extracted with dichloromethane (20 mL) three times. The combined organic phase was washed with brine (50 mL) and concentrated in vacuo to give the title compound. $^1$H NMR (400 MHz, CDCl$_3$-d) δ=7.38 (t, J=8.0 Hz, 1H), 7.17-7.13 (m, 2H), 5.10 (d, J=7.2 Hz, 1H), 5.03 (d, J=7.2 Hz, 1H), 4.98 (d, J=5.6 Hz, 2H), 4.44 (d, J=10.8 Hz, 1H), 4.01 (d, J=10.8 Hz, 1H), 3.63 (s, 2H), 3.63-3.25 (m, 2H), 1.19 (s, 9H), 0.81 (t, J=8 Hz, 2H), 0.00 (s, 9H).

Step 2—(±)-Allyl 2-(3-fluoro-4-(3-(2-methyl-N-((2-(trimethylsilyl)ethoxy)methyl)propan-2-ylsulfinamido)oxetan-3-yl)phenyl)acetate To a solution of (±)-2-[4-[3-[tert-butylsulfinyl(2-trimethylsilylethoxymethyl)amino]oxetan-3-yl]-3-fluoro-phenyl]acetic acid (1.20 g, 2.61 mmol) in N,N-dimethylformamide (10.0 mL) was added potassium carbonate (721 mg, 5.22 mmol) at rt. Then, 3-bromoprop-1-ene (632 mg, 5.22 mmol) was added dropwise under nitrogen atmosphere. The resulting mixture was stirred at rt for 16 hrs. On completion, to the mixture was added water (20 mL) and the mixture was extracted with ethyl acetate (3×20 mL). The combined organic phase was washed with brine (60 mL), dried over sodium sulfate, and concentrated in vacuo to give a residue which was purified by column chromatography (petroleum ether:ethyl acetate=15:1 to 10:1) to give the title compound. $^1$H NMR (400 MHz, CDCl$_3$-d) δ=7.26 (t, J=8.0 Hz, 1H), 7.09 (d, J=8.0 Hz, 1H), 7.05 (d, J=11.6 Hz, 1H), 5.95-5.89 (m, 1H), 5.29 (d, J=18.0 Hz, 1H), 5.24-5.21 (m, 2H), 5.18 (d, J=7.2 Hz, 1H), 5.09 (d, J=7.2 Hz, 2H), 4.60 (d, J=5.6 Hz, 2H), 4.55 (d, J=10.8 Hz, 1H), 4.15 (d, J=10.2 Hz, 1H), 3.64 (s, 2H), 3.44-3.29 (m, 2H), 1.24 (s, 9H), 0.88 (t, J=7.2 Hz, 2H), 0.00 (s, 9H).

Step 3—(±)-Allyl 2-(3-fluoro-4-(3-(2-methyl-N-((2-(trimethylsilyl)ethoxy)methyl)propan-2-ylsulfinamido)oxetan-3-yl)phenyl)-2-methylpropanoate To a solution of (±)-allyl 2-[4-[3-[tert-butylsulfinyl(2-trimethylsilylethoxymethyl)amino]oxetan-3-yl]-3-fluoro-phenyl]acetate (250 mg, 500 umol) in N,N-dimethylformamide (3.00 mL) was added the solution of LiHMDS in hexane (1 M, 5.00 mL) dropwise at 0° C. under nitrogen atmosphere. The mixture was stirred at 0° C. for 0.5 hrs, then, a solution of iodomethane (852 mg, 6.00 mmol) in N,N-dimethylformamide (0.5 mL) was added. The resultant mixture was stirred for 3 hrs at 0° C. On completion, to the mixture was added cooled ammonium chloride solution (10 mL) and the mixture was extracted with ethyl acetate (3×10 mL). The combined organic phase was washed with brine (20 mL), dried over sodium sulfate, and concentrated in vacuo to give a residue which was purified by column chromatography (petroleum ether:ethyl acetate=10:1 to 5:1) to give the title compound. $^1$H NMR (400 MHz, CDCl$_3$-d) δ=7.28 (t, J=8.0 Hz, 1H), 7.18-7.16 (m, 1H), 7.12-7.06 (m, 1H), 5.93-5.81 (m, 1H), 5.28-5.19 (m, 4H), 5.11 (d, J=7.2 Hz, 2H), 4.59-4.56 (m, 3H), 4.15 (d, J=10.4 Hz, 1H), 3.44-3.34 (m, 2H), 1.60 (s, 6H), 1.27 (s, 9H), 0.90 (t, J=6.8 Hz, 2H), 0.027 (s, 9H).

Step 4—Allyl 2-(4-(3-aminooxetan-3-yl)-3-fluorophenyl)-2-methylpropanoate

To a solution of (±)-allyl 2-[4-[3-[tert-butylsulfinyl(2-trimethylsilylethoxymethyl)amino]oxetan-3-yl]-3-fluorophenyl]-2-methyl-propanoate (100 mg, 189 umol) in ethanol (1.00 mL) was added hydrochloride/dioxane (4 M, 154 uL) dropwise at 0° C. under nitrogen atmosphere. The mixture was stirred at 0° C. for 1 hr. On completion, to the mixture was added aqueous sodium bicarbonate (5 mL, sat.) and the mixture was extracted with dichloromethane (3×5 mL). The combined organic phase was washed with brine (15 mL), dried over sodium sulfate, and concentrated in vacuo to give the title compound. LCMS: (ES$^+$) m/z (M−NH$_2$)$^+$=277.0, tR=0.586.

Ethyl 2-[4-(3-aminooxetan-3-yl)-3-chloro-phenyl]acetate (Intermediate BW)

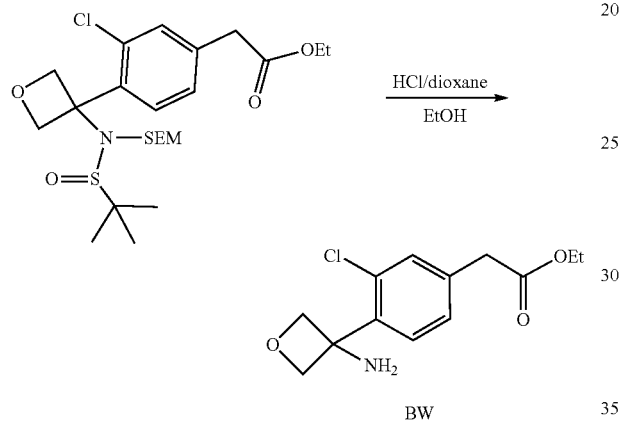

To a mixture of (±)-ethyl 2-[4-[3-[tert-butylsulfinyl(2-trimethylsilylethoxymethyl)amino]oxetan-3-yl]-3-chloro-phenyl]acetate (250 mg, 495 umol, synthesized via Steps 1-2 of BQ) in ethanol (2 mL) was added hydrochloric acid/dioxane (4 M, 124 uL) at 0° C. Then the mixture was stirred at 0° C. for 0.5 hour. On completion, the mixture was dried with bubbling nitrogen. Then the residue was triturated with 20 mL methyl tert-butyl ether and filtrated to give the title compound. LCMS: (ES+) m/z (M+H)$^+$=270.2, tR=0.609.

2-[4-(3-Aminooxetan-3-yl)-yl)phenyl]acetonitrile (Intermediate BX)

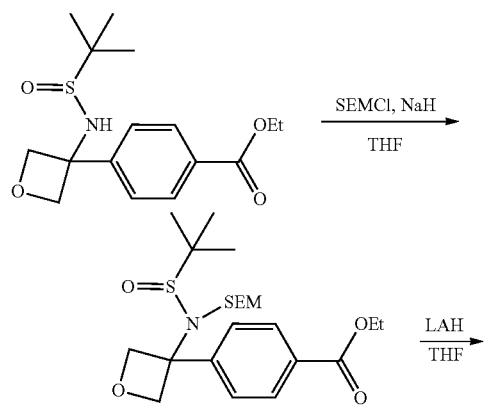

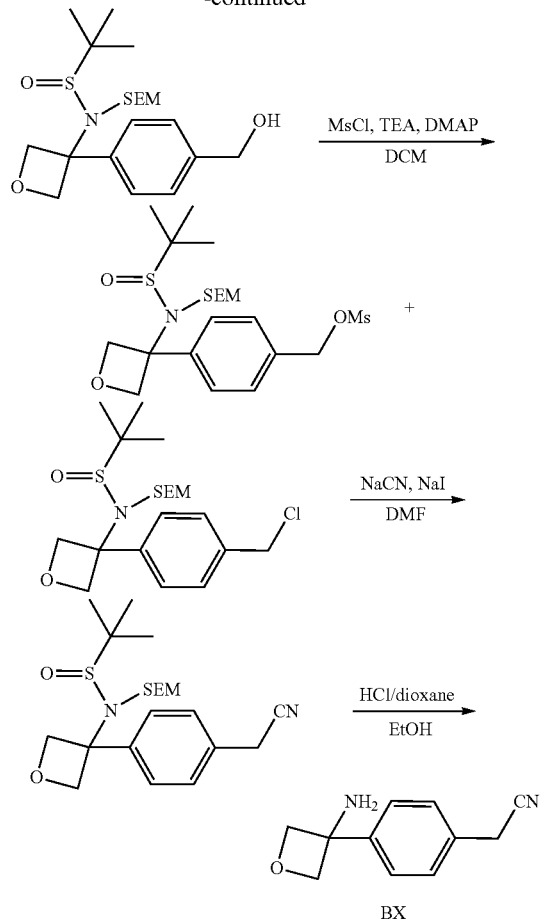

Step 1—(±)-Ethyl 4-[3-[tert-butylsulfinyl(2-trimethylsilylethoxymethyl)amino]oxetan-3-yl]benzoate To a solution of (±)-ethyl 4-[3-(tert-butylsulfinylamino)oxetan-3-yl]benzoate (4.80 g, 14.7 mmol, synthesized via Steps 1-3 of Intermediate AE) in tetrahydrofuran (100 mL) was added sodium hydride (885 mg, 22.1 mmol, 60% purity) at 0° C., and the mixture was stirred at 0° C. for 0.5 hr. SEM-Cl (3.69 g, 22.1 mmol) was added into the mixture and the resulting mixture was warmed to rt and stirred at rt for 1 hr. On completion, the mixture was poured into ice water (150 mL) and extracted with ethyl acetate (2×150 mL). The combined organic layer was dried over anhydrous sodium sulfate, filtered and concentrated in vacuo to give a residue. The residue was purified with silica gel chromatograph (petroleum ether:ethyl acetate=10:1) to afford the title compound. $^1$H NMR (400 MHz, CDCl3) δ=8.18-8.07 (m, 2H), 7.77-7.69 (m, 2H), 5.41 (d, J=6.4 Hz, 1H), 5.29 (d, J=6.8 Hz, 1H), 4.91 (d, J=6.4 Hz, 1H), 4.78-4.69 (m, 2H), 4.41 (q, J=7.1 Hz, 2H), 3.86 (d, J=10.5 Hz, 1H), 3.38-3.32 (m, 2H), 1.42 (t, J=7.2 Hz, 3H), 1.38 (s, 9H), 0.93-0.84 (m, 2H), 0.04-0.01 (s, 9H)

Step 2—(±)-N-[3-[4-(hydroxymethyl)phenyl]oxetan-3-yl]-2-methyl-N-(2-trimethylsilylethoxymethyl) propane-2-sulfinamide To a solution of (±)-ethyl 4-[3-[tert-butylsulfinyl(2-trimethylsilylethoxymethyl)amino]oxetan-3-yl]benzoate (5.10 g, 11.1 mmol) in tetrahydrofuran (100 mL) was added lithium aluminum hydride (849 mg, 22.3 mmol) at 0° C. under a nitrogen atmosphere. The mixture was stirred at 0° C. for 1 hr. On completion, water (0.5 mL) was added dropwise into the mixture followed by 15% sodium hydroxide solution (1.5 mL). After stirring for 0.5 hr, more water (1.5 mL) was added into the mixture and the resulting mixture was concentrated in vacuo to give a residue. The residue was washed with water (100 mL) and extracted with ethyl acetate (3×80 mL). The combined organic layer was dried over anhydrous sodium sulfate, filtered and concentrated in vacuo to give a residue. The residue was purified with silica gel chromatograph (petroleum ether:ethyl acetate=1:1) to afford the title compound. $^1$H NMR (400 MHz, CDCl$_3$) δ=7.65 (d, J=8.3 Hz, 2H), 7.46 (d, J=8.3 Hz, 2H), 5.39 (d, J=6.3 Hz, 1H), 5.28 (d, J=6.8 Hz, 1H), 4.93 (d, J=6.3 Hz, 1H), 4.80-4.68 (m, 4H), 3.86 (d, J=10.5 Hz, 1H), 3.36 (t, J=8.3 Hz, 2H), 1.38 (s, 9H), 0.95-0.84 (m, 2H), 0.05-0.02 (s, 9H).

Step 3—(±)-[4-[3-[Tert-butylsulfinyl(2-trimethylsilylethoxymethyl)amino]oxetan-3-yl]phenyl]methyl methanesulfonate and (±)-N-(3-(4-(chloromethyl)phenyl)oxetan-3-yl)-2-methyl-N-((2-(trimethylsilyl)ethoxy)methyl)propane-2-sulfinamide To a solution of (±)-N-[3-[4-(hydroxymethyl)phenyl]oxetan-3-yl]-2-methyl-N-(2-trimethylsilylethoxy methyl)propane-2-sulfinamide (1.00 g, 2.42 mmol), triethylamine (489 mg, 4.84 mmol) and DMAP (44.3 mg, 363 umol) in dichloromethane (30 mL) was added methanesulfonyl chloride (415 mg, 3.63 mmol,) dropwise at 0° C. The resulting mixture was allowed to warm to rt and stirred at rt for 16 hrs. On completion, water (30 mL) was added into the reaction mixture and the organic layer was separated. The organic layer was washed with brine (20 mL), dried over anhydrous sodium sulfate, filtered and concentrated in vacuo to give the title compound as a mixture of the mesylate and the chloride. LCMS: (ES$^+$) m/z (M+Na)$^+$=454.2, tR=1.065.

Step 4—(±)-N-[3-[4—(Cyanomethyl)phenyl]oxetan-3-yl]-2-methyl-N-(2-trimethylsilylethoxy-methyl)propane-2-sulfinamide To a solution of (±)-[4-[3-[tert-butylsulfinyl(2-trimethylsilylethoxymethyl)amino]oxetan-3-yl]phenyl]methylmethanesulfonate and (±)-N-(3-(4-(chloromethyl)phenyl)oxetan-3-yl)-2-methyl-N-((2-(trimethylsilyl)ethoxy)methyl)propane-2-sulfinamide (900 mg) and sodium iodide (27.4 mg, 183 umol) in N,N-dimethylformamide (20 mL) was added sodium cyanide (134 mg, 2.75 mmol), and the resulting mixture was stirred at rt for 16 hrs. On completion, the mixture was diluted with water (200 mL) and the precipitate was filtered. The filter cake was dried in vacuo to give the title compound. $^1$H NMR (400 MHz, CDCl$_3$) δ=7.69 (d, J=8.3 Hz, 2H), 7.43 (d, J=8.4 Hz, 2H), 5.40 (d, J=6.4 Hz, 1H), 5.28 (d, J=6.8 Hz, 1H), 4.88 (d, J=6.4 Hz, 1H), 4.74 (d, J=5.0 Hz, 1H), 4.72 (s, 1H), 3.83 (d, J=10.5 Hz, 1H), 3.79 (s, 2H), 3.36 (t, J=8.5 Hz, 2H), 1.39 (s, 9H), 0.93-0.87 (m, 2H), 0.05-0.02 (s, 9H).

Step 5—2-[4-(3-Aminooxetan-3-yl)phenyl]acetonitrile

To a solution of (±)-N-[3-[4-(cyanomethyl)phenyl]oxetan-3-yl]-2-methyl-N-(2-trimethylsilylethoxy methyl)propane-2-sulfinamide (250 mg, 591 umol) in ethanol (5 mL) was added hydrogen chloride/dioxane (2 mL) dropwise, and the resulting mixture was stirred at 0° C. for 0.5 hr. On completion, saturated sodium bicarbonate solution (20 mL) was added into the mixture and the mixture was extracted with ethyl acetate (2×30 mL). the combined organic layer was dried over anhydrous sodium sulfate, filtered and concentrated in vacuo to give the title compound (120 mg, 84.5% purity, 92% yield) as white solid. LCMS: (ES$^+$) m/z (M−NH$_2$)$^+$=172.0, tR=0.480.

N-((4-(3-Aminooxetan-3-yl)phenyl)sulfonyl)acetamide (Intermediate BY)

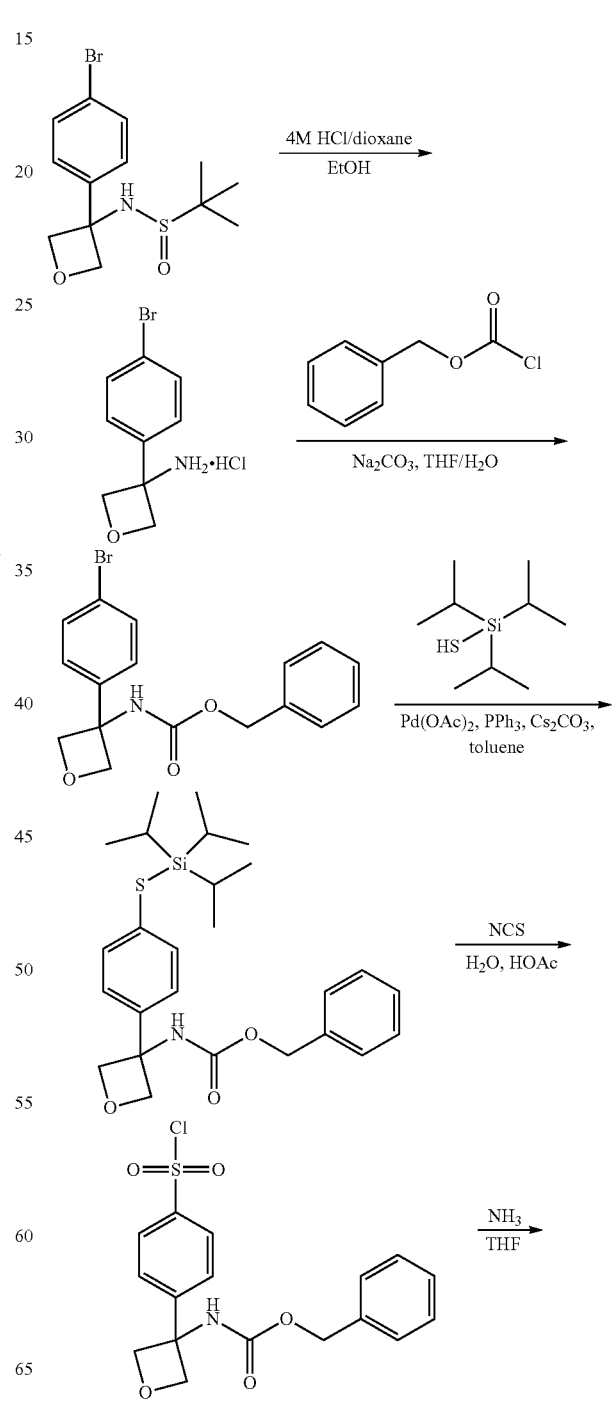

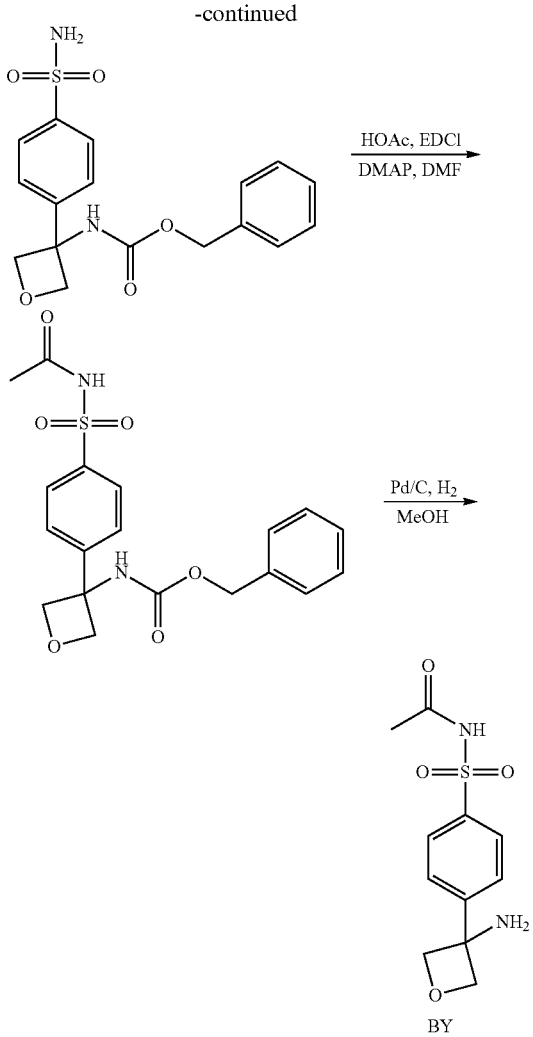

Step 1—3-(4-Bromophenyl)oxetan-3-amine hydrochloride

To a mixture of (±)-N-[3-(4-bromophenyl)oxetan-3-yl]-2-methyl-propane-2-sulfinamide (1.00 g, 3.01 mmol, synthesized via Steps 1-2 of Intermediate AE) in ethanol (10.0 mL) was added hydrochloride/dioxane (4 M, 2.00 mL) dropwise at 0° C. The mixture was stirred at 0° C. for 2 hrs. On completion, to the mixture was added 2-methoxy-2-methylpropane (30 mL) at 0° C. The mixture was filtered, and the solid was dried in vacuo to give the title compound. $^1$H NMR (400 MHz, DMSO-$d_6$) δ=9.33 (br, s, 2H), 7.71 (d, J=8.8 Hz, 2H), 7.55 (d, J=8.4 Hz, 2H), 5.00 (d, J=8.8 Hz, 2H), 4.87 (d, J=8.4 Hz, 2H).

Step 2—Benzyl (3-(4-bromophenyl)oxetan-3-yl)carbamate

To a solution of 3-(4-bromophenyl)oxetan-3-amine hydrochloride (670 mg, 2.53 mmol) in a mixture solvent of tetrahydrofuran (8.00 mL) and water (20.0 mL) was added sodium carbonate (804 mg, 7.59 mmol) in one portion at rt. Then, benzyl carbonochloridate (518 mg, 3.04 mmol) was added. The resultant mixture was stirred for 16 hrs at rt. On completion, the mixture was concentrated in vacuo to remove the tetrahydrofuran and the aqueous was extracted with ethyl acetate (3×20 mL). The combined organic phase was washed with brine (60 mL), dried over sodium sulfate, and concentrated in vacuo to give a crude product which was purified by column chromatography (petroleum ether:ethyl acetate=10:1 to 3:1) to give the title compound. $^1$H NMR (400 MHz, DMSO-$d_6$) δ=8.57 (br, s, 1H), 7.59 (d, J=8.4 Hz, 2H), 7.43 (d, J=8.4 Hz, 2H), 7.38-7.31 (m, 5H), 5.01 (s, 2H), 4.83 (d, J=6.4 Hz, 2H), 4.69 (d, J=6.4 Hz, 2H).

Step 3—Benzyl (3-(4-((triisopropylsilyl)thio)phenyl)oxetan-3-yl)carbamate

To a mixture of benzyl N-[3-(4-bromophenyl)oxetan-3-yl]carbamate (1.00 g, 2.76 mmol), palladium acetate (31.0 mg, 138 umol), triphenylphosphine (159 mg, 607 umol), and cesium carbonate (1.35 g, 4.14 mmol) in toluene (20.0 mL) was added triisopropyl(sulfanyl)silane (789 mg, 4.14 mmol) in one portion at rt under nitrogen atmosphere. The mixture was heated to 120° C. and stirred for 16 hrs. On completion, the mixture was concentrated in vacuo to remove the toluene. The residue was diluted with water (20 mL) and extracted with ethyl acetate (3×20 mL). The combined organic phase was dried over sodium sulfate and concentrated in vacuo to give a residue which was purified by column chromatography (petroleum ether:ethyl acetate=10:1 to 5:1) to give the title compound. $^1$H NMR (300 MHz, CDCl$_3$-d) δ=7.42 (d, J=8.1 Hz, 2H), 7.27-7.25 (m, 7H), 5.44 (s, 1H), 5.01 (s, 2H), 4.91 (s, 2H), 4.78 (s, 2H), 1.23-1.11 (m, 3H), 1.01 (d, J=6.9 Hz, 18H).

Step 4—Benzyl (3-(4-(chlorosulfonyl)phenyl)oxetan-3-yl)carbamate

To a mixture of benzyl N-[3-(4-triisopropylsilylsulfanylphenyl)oxetan-3-yl]carbamate (1.00 g, 2.12 mmol) in acetic acid (6.40 mL) and water (2.10 mL) was added NCS (1.16 g, 8.69 mmol) at rt and then stirred for 1 hr. On completion, to the mixture was added water (30 mL) and the mixture was extracted with ethyl acetate (3×10 mL). The combined organic phase was washed with brine (30 mL), dried over sodium sulfate, and concentrated in vacuo to give a crude product which was purified by column chromatography (petroleum ether:ethyl acetate=4:1) to give the title compound. LCMS: (ES$^-$) m/z (M+H)$^+$=382.0. tR=0.846

Step 5—Benzyl (3-(4-(chlorosulfonyl)phenyl)oxetan-3-yl)carbamate

To a solution of benzyl N-[3-(4-chlorosulfonylphenyl)oxetan-3-yl]carbamate (800 mg, 2.10 mmol) in tetrahydrofuran (5.00 mL) was added a solution of ammonia (gas) in tetrahydrofuran (4M, 10 mL) dropwise at rt. The mixture was stirred at rt for 0.5 hrs. On completion, the mixture was concentrated in vacuo to give the title compound. $^1$H NMR (300 MHz, DMSO-d6) δ=8.69 (s, 1H), 7.85 (d, J=8.1 Hz, 2H), 7.66 (d, J=8.4 Hz, 2H), 7.37-7.25 (m, 7H), 5.02 (s, 2H), 4.85 (d, J=6.6 Hz, 2H), 4.73 (d, J=6.3 Hz, 2H).

Step 6—Benzyl (3-(4-(N-acetylsulfamoyl)phenyl)oxetan-3-yl)carbamate

To a mixture of EDCI (874 mg, 4.56 mmol), N,N-dimethylpyridine (557 mg, 4.56 mmol), and acetic acid (256 mg, 4.26 mmol) in N,N-dimethylformamide (5.50 mL) was added benzyl N-[3-(4-sulfamoylphenyl)oxetan-3-yl]carbamate (550 mg, 1.52 mmol) portion-wise at rt. The mixture was stirred at rt for 2 hrs. On completion, to the mixture was added brine (15 mL) and the mixture was extracted with ethyl acetate (3×15 mL). The aqueous phase was concentrated in vacuo to give a residue which was purified by column chromatography (petroleum ether:ethyl acetate=5:1 to 1:1 to dichloromethane:methanol=10:1) to give the title compound. $^1$H NMR (400 MHz, DMSO-d6) δ=8.66 (s, 1H), 7.85 (d, J=8.4 Hz, 2H), 7.66 (d, J=8.4 Hz, 2H), 7.38 (m, 5H), 5.02 (s, 2H), 4.86-4.82 (m, 2H), 4.75-4.73 (m, 2H), 2.57 (s, 3H).

Step 7—N-((4-(3-Aminooxetan-3-yl)phenyl)sulfonyl)acetamide

To a mixture of benzyl N-[3-[4-(acetylsulfamoyl)phenyl] oxetan-3-yl]carbamate (300 mg, 742 umol) in methanol (1.00 mL) was added palladium/carbon (100 mg, 10%0 w/w) at rt under hydrogen gas (50 psi). The mixture was stirred at rt for 2 hrs. On completion, the mixture was filtered and the filtrate was concentrated in vacuo to give the title compound. LCMS: (ES$^+$) m/z (M–NH$_2$)$^+$=254.2. tR=0.208.

(±) Allyl 2-(4-(3-aminooxetan-3-yl)phenyl)butanoate (Intermediate BZ)

reaction mixture was warmed to rt and stirred for 0.5 hrs. On completion, the reaction mixture was quenched with saturated ammonium chloride (10 mL), extracted with ethyl acetate (3×50 mL), and washed with brine (20 mL). The organic layer was dried over anhydrous sodium sulfate and concentrated in vacuo to give red oil. The red oil was purified by silica gel chromatography (petroleum ether:ethyl acetate=20:1) to give the title compound. $^1$H NMR (400 MHz, CDCl3) δ=7.58 (d, J=7.4 Hz, 2H), 7.38 (d, J=8.0 Hz, 2H), 5.89 (tdd, J=16.8, 11.0, 5.6 Hz, 1H), 5.37 (d, J=6.0 Hz, 1H), 5.30-5.17 (m, 3H), 4.92-4.86 (m, 1H), 4.77-4.67 (m, 2H), 4.65-4.52 (m, 2H), 3.85 (d, J=10.6 Hz, 1H), 3.52 (t, J=7.8 Hz, 1H), 3.34 (t, J=8.2 Hz, 2H), 2.13 (td, J=14.2, 7.2 Hz, 1H), 1.82 (td, J=14.0, 7.2 Hz, 1H), 1.36 (s, 9H), 0.96-0.84 (m, 5H), −0.04 (s, 9H).

Step 2—(±) Allyl 2-(4-(3-aminooxetan-3-yl)phenyl) butanoate

To a solution of (f) allyl 2-[4-[3-[tert-butylsulfinyl(2-trimethylsilylethoxymethyl)amino]oxetan-3-yl]-phenyl]butanoate (3.20 g, 6.28 mmol) in ethanol (30 mL) was added HCl/dioxane (4 M, 3.92 mL) at 0° C. The reaction mixture was stirred at 0° C. for 2 hrs. On completion, the reaction mixture was quenched with aqueous saturated sodium bicarbonate (20 mL) and extracted with ethyl acetate (3×50 mL). The combined organic layer was washed with saturated brine (50 mL), dried over anhydrous sodium sulfate, filtered and concentrated in vacuo to give the title compound. LCMS: (ES$^+$) m/z (M–NH$_2$)$^+$=259.2, tR=0.639.

(±)-Allyl 2-[4-(3-aminooxetan-3-yl)phenyl]-2-cyclobutyl-acetate (Intermediate CA)

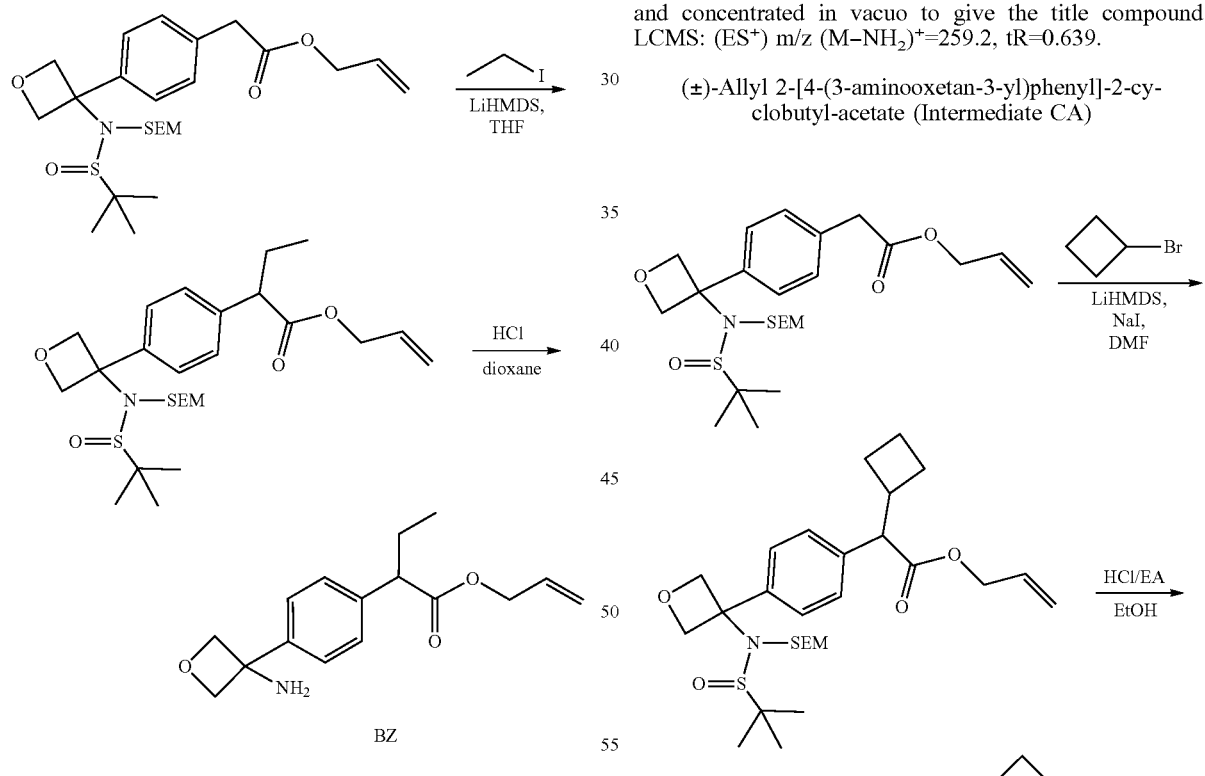

Step 1-(±) Allyl 2-(4-(3-(2-methyl-N-((2-(trimethylsilyl)ethoxy)methyl)propan-2-ylsulfinamido) oxetan-3-yl)phenyl)butanoate To a solution of allyl 2-[4-[3-[tert-butylsulfinyl(2-trimethylsilylethoxymethyl)amino]oxetan-3-yl]-phenyl]acetate (1.20 g, 2.49 mmol, synthesized via Steps 1-2 of Intermediate BT) in anhydrous tetrahydrofuran (20 mL) was added LiHMDS (1 M, 2.99 mL) at 0° C. for 0.5 hr. Then, iodoethane (388 mg, 2.49 mmol) was added at 0° C. The

Step 1—(±)-Allyl 2-[4-[3-[tert-butylsulfinyl(2-trimethylsilylethoxymethyl)amino]oxetan-3-yl]phenyl]-2-cyclobutyl-acetate To a solution of (±)-allyl 2-[4-[3-[tert-butylsulfinyl(2-trimethylsilylethoxymethyl)amino]oxetan-3-yl]phenyl]acetate (2.00 g, 4.15 mmol, synthesized via Steps 1-2 of Intermediate BT) in N,N-dimethylformamide (40 mL) was added LiHMDS (1 M, 6.23 mL) dropwise at 0° C. and the reaction mixture was stirred for 1.5 hrs. Then sodium iodide (124 mg, 830 umol) and bromocyclobutane (2.80 g, 20.7 mmol) was added in turn and the reaction mixture was stirred at rt for 1.5 hrs. On completion, the reaction mixture was poured into 100 mL cool water, acidified with citric acid solution until pH=6 and extracted with ethyl acetate (3×100 mL). The combined layer was dried over anhydrous sodium sulfate, filtrated and concentrated in vacuo. The resulting oil was purified by silica gel chromatography (petroleum ether: ethyl acetate=7:1) to give the title compound. $^1$H NMR (400 MHz, CDCl$_3$) δ=7.56 (d, J=7.9 Hz, 2H), 7.35 (d, J=8.4 Hz, 2H), 5.94-5.81 (m, 1H), 5.36 (dd, J=0.9, 6.2 Hz, 1H), 5.29-5.14 (m, 3H), 4.88 (dd, J=2.6, 6.2 Hz, 1H), 4.73 (d, J=7.0 Hz, 1H), 4.70 (dd, J=3.9, 10.7 Hz, 1H), 4.64-4.47 (m, 2H), 3.85 (dd, J=2.4, 10.5 Hz, 1H), 3.61 (d, J=10.9 Hz, 1H), 3.34 (t, J=8.2 Hz, 2H), 3.05-2.92 (m, 1H), 2.26-2.13 (m, 1H), 1.95-1.77 (m, 4H), 1.62 (br. s., 1H), 1.35 (s, 9H), 0.88 (dd, J=6.8, 9.0 Hz, 2H), 0.01 (s, 9H).

Step 2—(±)-Allyl 2-[4-(3-aminooxetan-3-yl)phenyl]-2-cyclobutyl-acetate

To a solution of (±)-allyl 2-[4-[3-[tert-butylsulfinyl(2-trimethylsilylethoxymethyl)amino]oxetan-3-yl]phenyl]-2-cyclobutyl-acetate (1.40 g, 2.61 mmol) in ethanol (10 mL) was added hydrochloric acid/ethyl acetate (4 M, 13 mL) and the reaction mixture was stirred at 0° C. for 0.5 hr. On completion, the reaction mixture was basified with saturated sodium bicarbonate (5 mL) until pH=8 and extracted with dichloromethane (3×10 mL). The combined layer was dried over anhydrous sodium sulfate, filtered and concentrated in vacuo. The resulting oil was purified by silica gel chromatography (petroleum ether:ethyl acetate=0:1) to give the title compound. LCMS: (ES$^+$) m/z (M+H)$^+$=302.0, tR=0.916.

(±)-Allyl 2-[4-(3-aminooxetan-3-yl)phenyl]-3-methyl-butanoate (Intermediate CB)

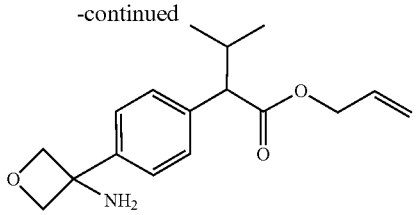

Step 1—(±)-Allyl 2-[4-[3-[tert-butylsulfinyl(2-trimethylsiylethoxymethyl)amino]oxetan-3-yl]phenyl]-3-methyl-butanoate To a solution of allyl 2-[4-[3-[tert-butylsulfinyl(2-trimethylsilylethoxymethyl)amino]oxetan-3-yl]phenyl]acetate (3.50 g, 7.27 mmol, synthesized via Steps 1-2 of Intermediate BT) in tetrahydrofuran (10 mL) was added LiHMDS (1 M, 9.45 mL) at 0° C. The reaction mixture was stirred at 0° C. for 30 min. 2-iodopropane (1.61 g, 9.45 mmol) was added to the reaction mixture and the mixture was stirred at rt for 3 hrs. On completion, the mixture was quenched with ammonium chloride solution (20 mL), extracted with ethyl acetate (2×30 mL), dried and concentrated. The residue was purified by column chromatography (petroleum ether:ethyl acetate=5:1) to give the title compound. LCMS: (ES$^+$) m/z (M+23)$^+$=546.4, tR=1.072.

Step 2—(±)-Allyl 2-[4-(3-aminooxetan-3-yl)phenyl]-3-methyl-butanoate

To a solution of (±)-allyl 2-[4-[3-[tert-butylsulfinyl(2-trimethylsilylethoxymethyl)amino]oxetan-3-yl]phenyl]-3-methyl-butanoate (2.50 g, 4.77 mmol) in ethanol (20 mL) was added hydrogen chloride/dioxane (4 M, 14 mL) at 0° C. The reaction mixture was stirred at 0° C. for 3 hrs. On completion, the reaction mixture was concentrated in vacuo to give the title compound. LCMS: (ES$^+$) m/z (M−NH$_2$)$^+$=273.3, tR=0.673.

(±)-Allyl 2-[4-(3-aminooxetan-3-yl)phenyl]-2-cyclopentyl-acetate (Intermediate CC)

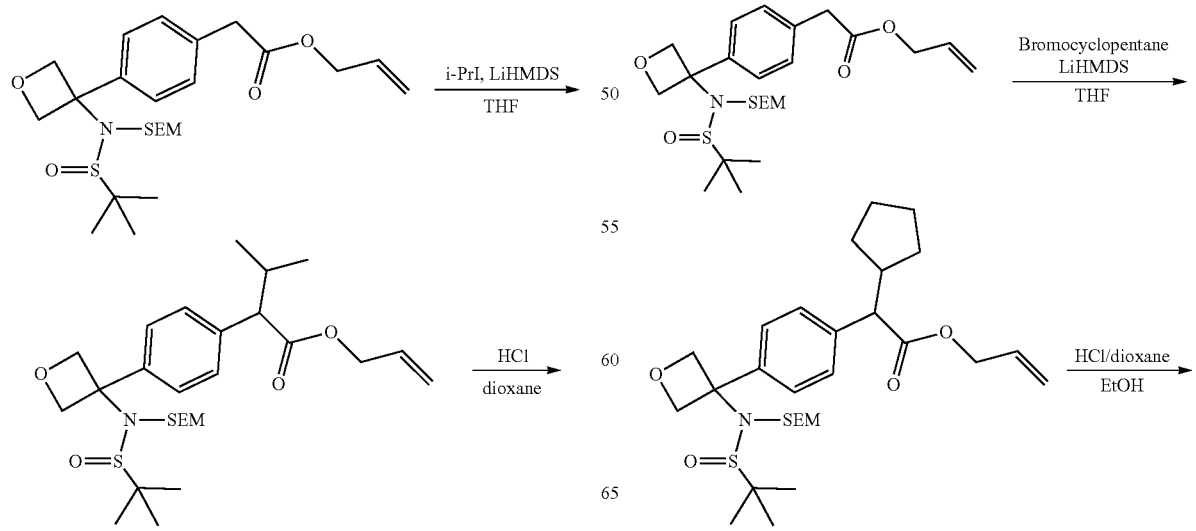

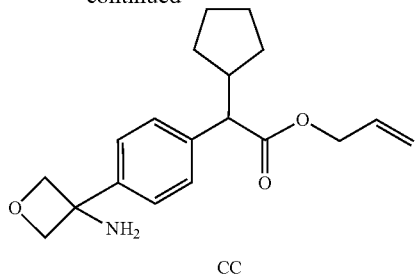

CC

Step 1—(±)-Allyl 2-[4-[3-[tert-butylsulfinyl(2-trimethylsilylethoxymethyl)amino]oxetan-3-yl]phenyl]-2-cyclopentyl-acetate To a solution of allyl 2-[4-[3-[tert-butylsulfinyl(2-trimethylsilylethoxymethyl)amino]oxetan-3-yl]phenyl]acetate (2.20 g, 4.57 mmol, synthesized via Steps 1-2 of Intermediate BT) in N,N-dimethylformamide (20 mL) was added LiHMDS (1 M, 13.7 mL) at 0° C. The reaction mixture was stirred at 0° C. for 30 min. Bromocyclopentane (2.04 g, 13.7 mmol) was added to the reaction mixture and the mixture was stirred at 50° C. for 3 hrs. On completion, the mixture was quenched with ammonium chloride solution (80 mL) and extracted with ethyl acetate (2×100 mL). The combined organic layer was washed with brine (100 mL), dried over anhydrous sodium sulfate, filtered and concentrated in vacuo to give a residue. The residue was dried in vacuo to give the title compound. $^1$H NMR (400 MHz, CDCl$_3$) δ=7.60-7.54 (m, 2H), 7.43 (d, J=8.4 Hz, 2H), 5.96-5.84 (m, 1H), 5.38 (dd, J=2.8, 6.2 Hz, 1H), 5.31-5.24 (m, 2H), 5.22 (dd, J=1.1, 10.4 Hz, 1H), 4.93-4.88 (m, 1H), 4.79-4.68 (m, 2H), 4.67-4.59 (m, 1H), 4.58-4.49 (m, 1H), 3.87 (dd, J=2.6, 10.5 Hz, 1H), 3.38 (d, J=3.5 Hz, 1H), 3.37-3.32 (m, J=6.7 Hz, 2H), 2.68-2.49 (m, 1H), 2.00-1.83 (m, 1H), 1.76-1.62 (m, 2H), 1.59-1.40 (m, 3H), 1.37 (s, 9H), 1.34-1.26 (m, 1H), 1.10-0.96 (m, 1H), 0.94-0.87 (m, 2H), 0.00 (s, 9H).

Step 2—(±)-Allyl 2-[4-(3-aminooxetan-3-yl)phenyl]-2-cyclopentyl-acetate

To a solution of (±)-allyl 2-[4-[3-[tert-butylsulfinyl(2-trimethylsilylethoxymethyl)amino]oxetan-3-yl]phenyl]-2-cyclopentyl-acetate (3.20 g, 5.85 mmol) in ethanol (20 mL) was added hydrogen chloride/dioxane (4 M, 8 mL) at 0° C. The reaction mixture was stirred at 0° C. for 2 hrs. On completion, the reaction mixture was neutralized with saturated sodium bicarbonate solution to pH=8, and extracted with dichloromethane (2×30 mL). The combined organic layer was concentrated in vacuo to give the title compound. LCMS: (ES$^+$) m/z (M–NH$_2$)$^+$=299.1, tR=0.958.

(±)-Allyl 5-acetoxy-2-[4-(3-aminooxetan-3-yl)phenyl]pentanoate (Intermediate CD)

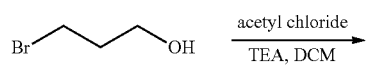

Step 1—3-bromopropyl acetate

To a solution of 3-bromopropan-1-ol (5.00 g, 35.97 mmol) in anhydrous dichloromethane 30 mL was added triethylamine (7.28 g, 71.9 mmol). Then, the mixture was cooled to 0° C. and acetyl chloride (4.24 g, 53.9 mmol) was added dropwise over 10 mins. Finally, the mixture was warmed to rt and stirred for 20 mins. On completion, the reaction mixture was quenched by addition of ice water 30 mL, and the resulting mixture was extracted with dichloromethane (2×30 mL). The combined organic layers were washed with saturated sodium bicarbonate solution 30 mL, dried over anhydrous sodium sulfate, filtered and concentrated in vacuo to give a residue. The residue was purified by distillation, collecting the fraction within 40-45° C. under reduced pressure with an oil pump to give the title compound. $^1$H NMR (400 MHz, CD$_3$Cl) δ=4.21 (t, J=6.1 Hz, 2H), 3.47 (t, J=6.6 Hz, 2H), 2.18 (quin, J=6.3 Hz, 2H), 2.06 (s, 3H).

Step 2—(±)-Allyl 5-acetoxy-2-[4-[3-[tert-butylsulfinyl(2-trimethylsilylethoxymethyl)-amino]oxetan-3-yl]phenyl]pentanoate To a solution of allyl 2-[4-[3-[tert-butylsulfinyl(2-trimethylsilylethoxymethyl)amino]oxetan-3-yl]phenyl]acetate (400 mg, 830 umol, synthesized via Steps 1-2 of Intermediate BT) in anhydrous N,N-dimethylformamide (10 mL) was added LiHMDS (1 M, 1.08 mL) dropwise at 0° C. The mixture was stirred at 0° C. for 30 min then 3-bromopropyl acetate (157 mg, 871 umol) in anhydrous N,N-dimethylformamide (5 mL) was added dropwise. Afterwards, the mix-

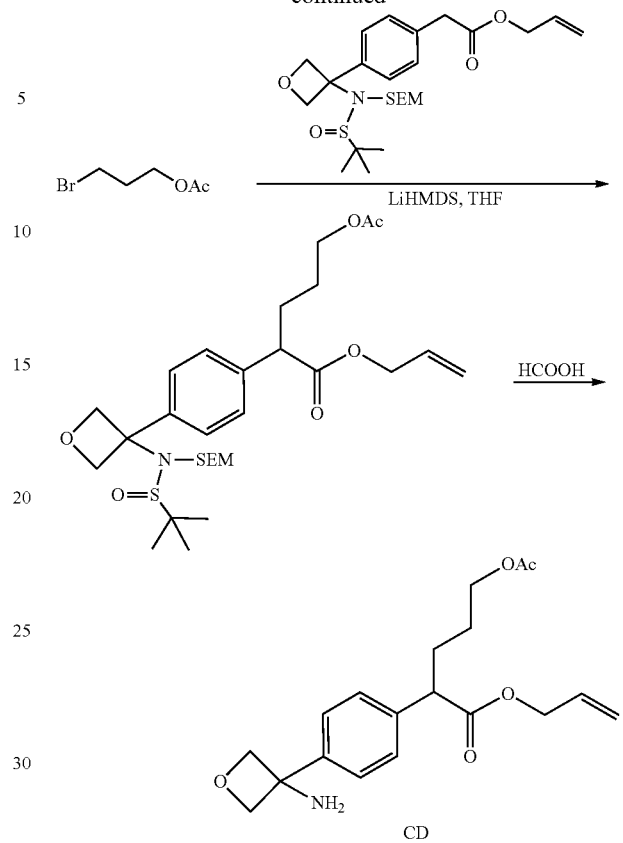

ture was warmed to rt and stirred at rt for 2.5 hrs. On completion, the reaction mixture was poured into 10 mL ice saturated ammonium chloride solution, and extracted with ethyl acetate (3×10 mL). The organic phase was collected, dried over anhydrous sodium sulfate, and concentrated in vacuo. The residue was purified by column chromatography (petroleum ether:ethyl acetate=10:1 to 5:1) to give the title compound. $^1$H NMR (400 MHz, CD$_3$Cl) δ=7.58 (d, J=8.0 Hz, 2H), 7.36 (d, J=8.4 Hz, 2H), 5.93-5.78 (m, 1H), 5.37 (d, J=6.3 Hz, 1H), 5.27-5.17 (m, 3H), 4.86 (d, J=5.4 Hz, 1H), 4.75-4.67 (m, 2H), 4.64-4.50 (m, 2H), 4.05 (t, J=6.4 Hz, 2H), 3.83 (dd, J=1.1, 10.6 Hz, 1H), 3.61 (t, J=7.7 Hz, 1H), 3.34 (t, J=8.2 Hz, 2H), 2.21-2.09 (m, 1H), 2.04 (s, 3H), 1.92-1.80 (m, 1H), 1.67-1.60 (m, 2H), 1.35 (s, 9H), 0.88 (dd, J=6.9, 8.9 Hz, 2H), 0.00 (s, 9H).

Step 3—(±)-Allyl 5-acetoxy-2-[4-(3-aminooxetan-3-yl)phenyl]pentanoate (±)-Allyl 5-acetoxy-2-[4-[3-[tert-butylsulfinyl(2-trimethylsilylethoxymethyl)amino]oxetan-3-yl]phenyl]pentanoate (260 mg, 446 umol) was dissolved in formic acid (1 mL). The mixture was stirred at rt for 2 hrs. On completion, the reaction mixture was alkalified with saturated sodium bicarbonate solution (20 mL) until the pH>7. The mixture was extracted with dichloromethane (2×15 mL), and the organic phase was collected, dried over anhydrous sodium sulfate, filtered, and concentrated in vacuo to give the title compound. LCMS: (ES$^+$) m/z (M+H)$^+$=348.3, tR=0.818.

(±)-Allyl 2-(4-(3-aminooxetan-3-yl)phenyl)pentanoate (Intermediate CE)

Step 1—(±)-Allyl 2-(4-(3-(2-methyl-N-((2-(trimethylsilyl)ethoxy)methyl)propan-2-ylsulfin-amido)oxetan-3-yl)phenyl)pentanoate To a solution of (±)-allyl 2-[4-[3-[tert-butylsulfinyl(2-trimethylsilylethoxymethyl)amino]oxetan-3-yl]phenyl]acetate (322 mg, 668 umol, synthesized via Steps 1-2 of Intermediate BT) in anhydrous tetrahydrofuran (2 mL) was added lithium diisopropylamide (2 M, 500 uL) at 0° C. for 0.5 hr. Then, 1-iodopropane (170 mg, 1.00 mmol) was added at 0° C. The reaction mixture was warmed to rt and stirred for 12 hrs. On completion, the reaction mixture was quenched with saturated ammonium chloride (1 mL), extracted with ethyl acetate (3×5 mL), and washed with brine (5 mL). The organic layer was dried over anhydrous sodium sulfate and concentrated in vacuo. The residue was purified by silica gel chromatography (petroleum ether:ethyl acetate=10:1) to give the title compound. $^1$H NMR (400 MHz, CDCl$_3$) δ=7.57 (d, J=6.8 Hz, 2H), 7.38 (d, J=8.4 Hz, 2H), 5.89 (tdd, J=16.8, 10.9, 5.6 Hz, 1H), 5.37 (dd, J=6.2, 2.0 Hz, 1H), 5.25 (dd, J=12.0, 5.4 Hz, 2H), 5.20 (d, J=10.6 Hz, 1H), 4.89 (dd, J=6.0, 3.0 Hz, 1H), 4.77-4.68 (m, 2H), 4.65-4.51 (m, 2H), 3.85 (dd, J=10.6, 1.6 Hz, 1H), 3.62 (t, J=7.8 Hz, 1H), 3.34 (t, J=8.2 Hz, 2H), 2.08 (dt, J=14.2, 8.4 Hz, 1H), 1.77 (dd, J=15.4, 6.8, Hz, 1H), 1.36 (s, 9H), 1.31-1.25 (m, 2H), 0.96-0.91 (m, 3H), 0.90-0.85 (m, J=9.0 Hz, 2H), 0.01 (s, 9H)

Step 2—(±)-Allyl 2-(4-(3-aminooxetan-3-yl)phenyl)pentanoate

To a solution of (±)-allyl2-[4-[3-[tert-butylsulfinyl(2-trimethylsilylethoxymethyl)amino]oxetan-3-yl]-phenyl]pentanoate (150 mg, 286 umol) in ethanol (2 mL) was added HCl/dioxane (4 M, 179 uL) at 0° C. The reaction mixture was stirred at 0° C. for 2 hrs. On completion, the mixture was quenched with aqueous saturated sodium bicarbonate (2 mL) and extracted with ethyl acetate (3×5 mL). The combined organic phase was washed with saturated brine (5 mL), dried over anhydrous sodium sulfate, filtered and concentrated in vacuo to give the title compound. LCMS: (ES$^+$) m/z (M−NH$_2$)$^+$=273.2, tR=0.674.

(±)-Ethyl 2-(4-(3-aminotetrahydrofuran-3-yl)phenyl)-3-methylbutanoate (Intermediate CF)

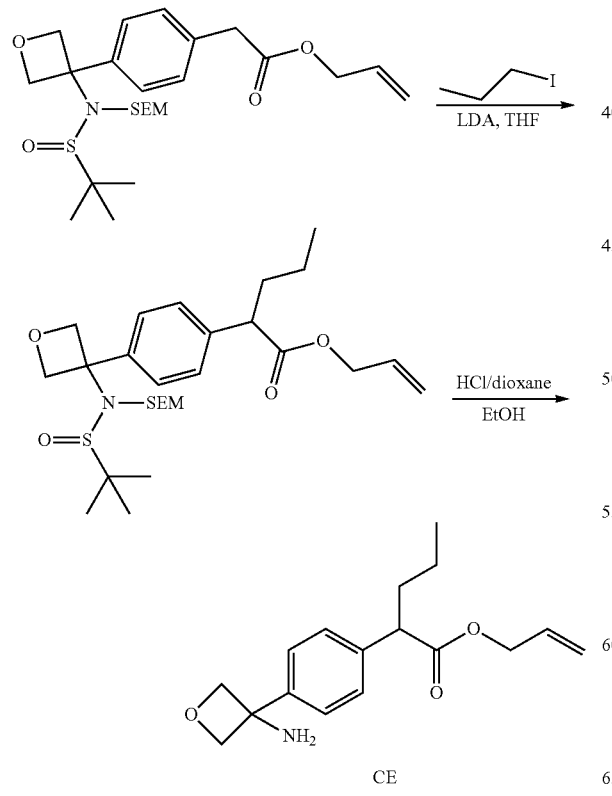

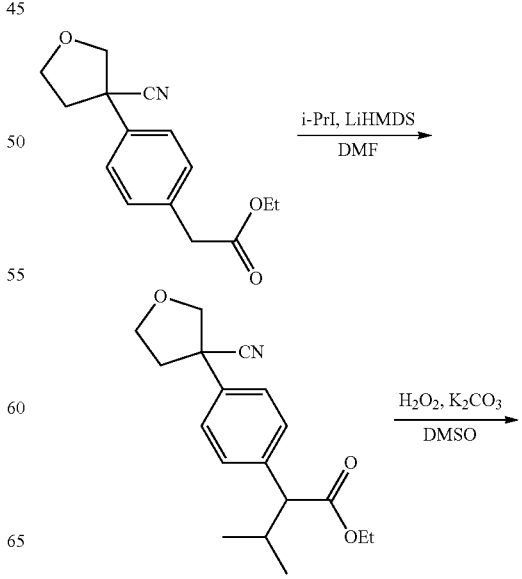

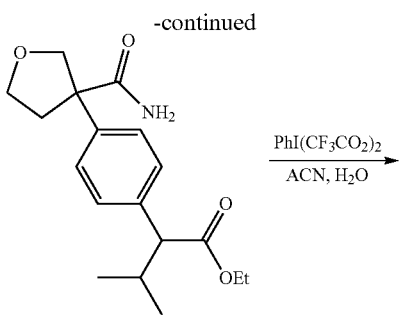

Step 1—(±)-Ethyl 2-(4-(3-cyanotetrahydrofuran-3-yl)phenyl)-3-methylbutanoate To a solution of (±)-ethyl 2-[4-(3-cyanotetrahydrofuran-3-yl)phenyl]acetate (800 mg, 3.09 mmol, synthesized via Steps 1-2 of Intermediate AW) in N,N-dimethylformamide (5 mL) was added LiHMDS (1 M, 5.56 mL) dropwise at 0° C. under nitrogen and the reaction mixture was stirred for 0.5 hr at 0° C. Then 2-iodopropane (577 mg, 3.40 mmol) was added and the reaction mixture was stirred at rt for 2.5 hr. On completion, the reaction mixture was poured into 100 mL cool water and extracted with dichloromethane (3×30 mL). The combined layer was dried over anhydrous sodium sulfate, filtrated and concentrated in vacuo. The residue was purified by silica gel chromatography (petroleum ether:ethyl acetate=20:1-5:1) to give the title compound. LCMS: (ES$^+$) m/z (M+1)$^+$=302.2, tR=0.859.

Step 2—(±)-Ethyl 2-(4-(3-carbamoyltetrahydrofuran-3-yl)phenyl)-3-methylbutanoate To a solution of (±)ethyl 2-[4-(3-cyanotetrahydrofuran-3-yl)phenyl]-3-methyl-butanoate (430 mg, 1.43 mmol) and potassium carbonate (79.0 mg, 572 umol) in dimethyl sulfoxide (10 mL) was added hydrogen peroxide (1.30 g, 11.4 mmol, 30% solution). The mixture was stirred at rt for 2 hrs. On completion, sodium sulfite solution was added to the reaction mixture and the mixture was extracted with ethyl acetate (3×20 mL). The organic layer was washed with water (20 mL) and brine (10 mL). The combined organic layer was dried over anhydrous sodium sulfate, filtered and concentrated in vacuo to give the title product. LCMS: (ES$^+$) m/z (M+H)$^+$=320.3, tR=0.799.

Step 3—(±)-Ethyl 2-(4-(3-aminotetrahydrofuran-3-yl)phenyl)-3-methylbutanoate To a mixture of ethyl (±)-2-[4-(3-carbamoyltetrahydrofuran-3-yl)phenyl]-3-methylbutanoate (420 mg, 1.31 mmol) in acetonitrile (8 mL) and water (8 mL) was added PhI(CF$_3$CO$_2$)$_2$ (619 mg, 1.44 mmol) in one portion, and the mixture was stirred at rt for 16 hrs. On completion, the mixture was concentrated in vacuo. 1N hydrochloric acid (5 mL) was added into the mixture and the mixture was washed with ethyl acetate (20 mL). The aqueous layer was then basified with sodium bicarbonate to pH=9 and extracted with dichloromethane (2×20 mL). The combined organic layer was dried over anhydrous sodium sulfate, filtered and concentrated in vacuo to give the title compound. LCMS: (ES$^+$) m/z (2M+H)$^+$=583.5, tR=0.709.

(±) Ethyl 2-(4-(3-aminotetrahydrofuran-3-yl)phenyl)pentanoate (Intermediate CG)

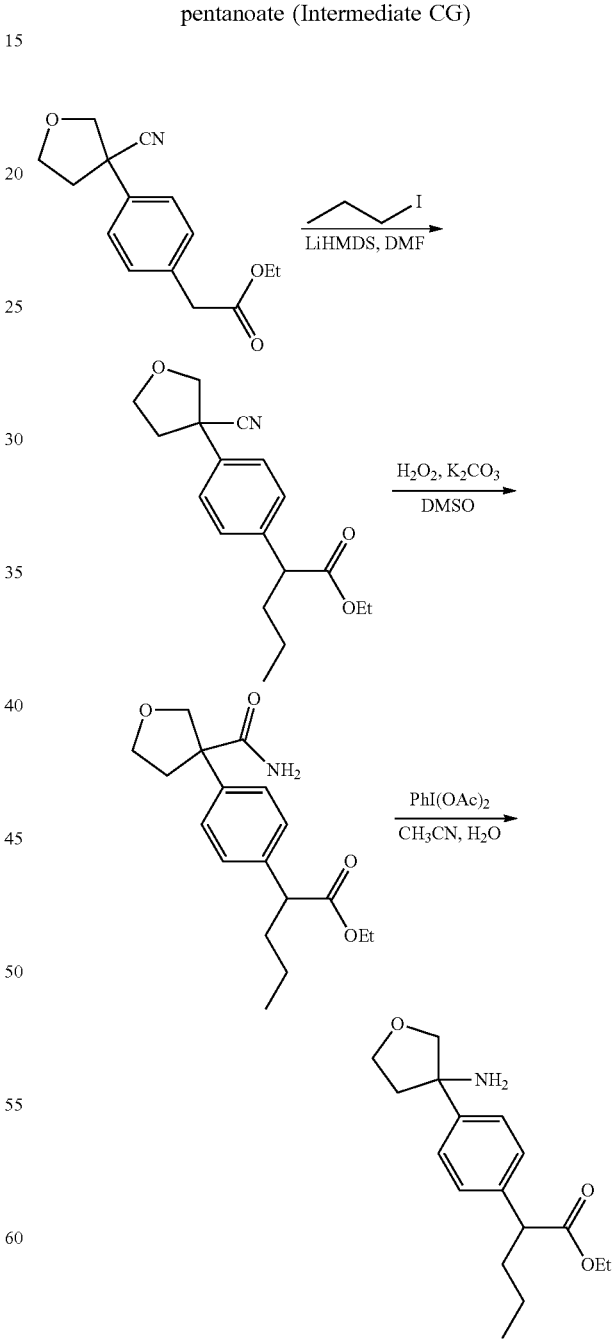

Step 1—(±) Ethyl 2-(4-(3-cyanotetrahydrofuran-3-yl)phenyl)pentanoate

To a solution of (±) ethyl 2-[4-(3-cyanotetrahydrofuran-3-yl)phenyl]acetate (100 mg, 386 umol, synthesized via Steps 1-2 of Intermediate AW) in anhydrous N,N-dimethylformamide (2 mL) was added LiHMDS (1 M, 578.47 uL) at 0° C. for 0.5 hr. Then, 1-iodopropane (72.1 mg, 424 umol) was added at 0° C. The reaction mixture was warmed to rt and stirred for 1 hr. On completion, the reaction mixture was quenched with saturated ammonium chloride (1 mL), extracted with ethyl acetate (3×5 mL), and washed with brine (5 mL). The organic layer was dried over anhydrous sodium sulfate, filtered and concentrated in vacuo to give red oil. The red oil was purified by silica gel chromatography (petroleum ether:ethyl acetate=10:1) to give the title compound. $^1$H NMR (400 MHz, CDCl3) δ=7.42 (d, J=8.4 Hz, 2H), 7.36 (d, J=8.4 Hz, 2H), 4.36 (d, J=9.0 Hz, 1H), 4.21-4.11 (m, 4H), 4.03 (d, J=9.0 Hz, 1H), 3.56 (t, J=7.8 Hz, 1H), 2.83-2.74 (m, 1H), 2.46 (td, J=13, 8.2 Hz, 1H), 2.11-1.99 (m, 1H), 1.80-1.69 (m, 1H), 1.34-1.25 (m, 2H), 1.23 (t, J=7.0 Hz, 3H), 0.92 (t, J=7.2 Hz, 3H).

Step 2—(±) ethyl 2-(4-(3-carbamoyltetrahydrofuran-3-yl)phenyl)pentanoate

To a mixture of (±) ethyl 2-[4-(3-cyanotetrahydrofuran-3-yl)phenyl]pentanoate (110 mg, 365 umol) and potassium carbonate (20.2 mg, 146 umol) in DMSO (1.50 mL) was added hydrogen peroxide (157 mg, 1.39 mmol, 133 uL, 30% solution) in one portion at rt. Then the mixture was heated to 60° C. (oil-bath temperature) and stirred for 3 hours. On completion, the reaction mixture was diluted with water (2 mL), filtered and dried in vacuo to give the title compound. The white solid was used for the next step directly without purification. LCMS: (ES$^+$) m/z (M+1)$^+$=320.1, tR=0.732.

Step 3—(±) Ethyl 2-(4-(3-aminotetrahydrofuran-3-yl)phenyl)pentanoate

To a solution of (±) ethyl 2-[4-(3-carbamoyltetrahydrofuran-3-yl)phenyl]pentanoate (110 mg, 258 umol) in acetonitrile (2 mL) and water (2 mL) was added PhI(OAc)$_2$ (100 mg, 310 umol) at rt. The reaction mixture was stirred at rt for 3 hrs. On completion, the reaction mixture was quenched with saturated sodium hypochlorite (5 mL). The reaction mixture was concentrated in vacuo. The residue was acidified with hydrochloric acid (2N, 5 mL) to pH=2 and the aqueous layer was washed with ethyl acetate (10 mL). Then to the aqueous layer was added saturated sodium bicarbonate aqueous to pH=9, and extracted with ethyl acetate (3×20 mL). The combined organic layer was washed with brine (10 mL) and dried over anhydrous sodium sulfate, filtered and concentrated in vacuo to give the title compound. LCMS: (ES$^+$) m/z (M–NH$_2$)=275.3, tR=0.718.

(±)-Ethyl 2-[4-(3-aminotetrahydrofuran-3-yl)phenyl]-2-cyclobutyl-acetate (Intermediate CH)

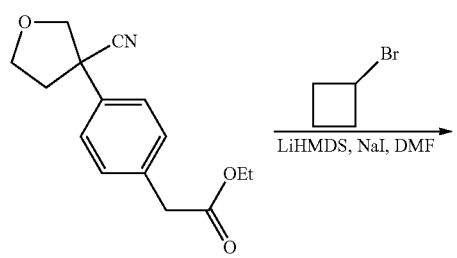

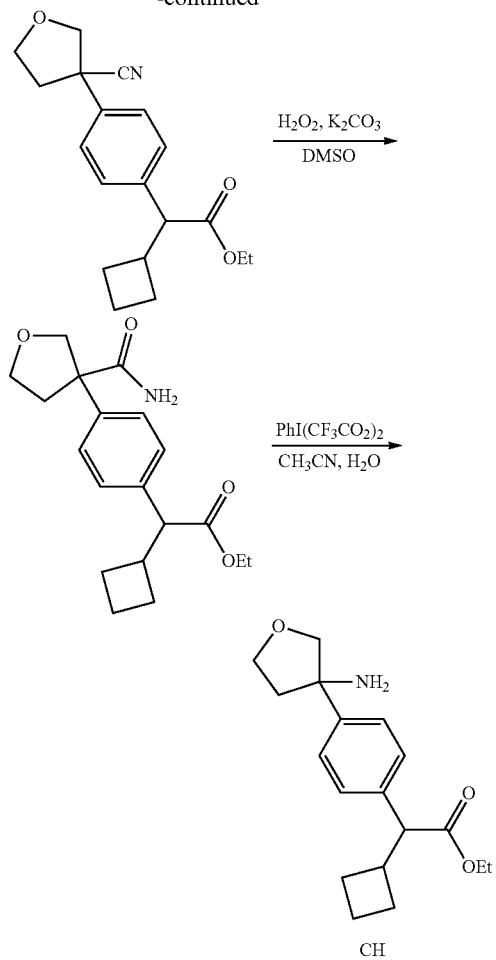

Step 1—(±)-Ethyl 2-[4-(3-cyanotetrahydrofuran-3-yl)phenyl]-2-cyclobutyl-acetate

To a solution of (±)-ethyl 2-[4-(3-cyanotetrahydrofuran-3-yl)phenyl]acetate (1.35 g, 5.21 mmol) in N,N-dimethylformamide (10 mL) was added LiHMDS (10.4 mL 10.4 mmol) dropwise at 0° C. under nitrogen, and the reaction was stirred at 0° C. for 0.5 hr. Then sodium iodide (156 mg, 1.04 mmol) and bromocyclobutane (3.52 g, 26.1 mmol) were added into the solution in one portion at 0° C., and the reaction was stirred at rt for 2 hrs. On completion, 20 mL water was added into the solution dropwise and the reaction was extracted with the EtOAc (3×50 mL), washed with water (3×50 mL), dried over anhydrous sodium sulfate, and concentrated in vacuo to give the title compound. $^1$H NMR (400 MHz, CDCl$_3$) δ=7.36-7.31 (m, 2H), 7.28-7.23 (m, 2H), 4.28 (d, J=9.0 Hz, 1H), 4.13-4.04 (m, 3H), 4.04-3.98 (m, 1H), 3.95 (dd, J=0.9, 9.0 Hz, 1H), 3.47 (d, J=10.9 Hz, 1H), 2.95-2.82 (m, 1H), 2.77-2.64 (m, 1H), 2.38 (td, J=8.2, 12.9 Hz, 1H), 2.17-2.04 (m, 1H), 1.85-1.68 (m, 4H), 1.52-1.45 (m, 1H), 1.19-1.10 (m, 3H).

Step 2—(±)-Ethyl 2-[4-(3-carbamoyltetrahydrofuran-3-yl)phenyl]-2-cyclobutyl-acetate To a solution of (±)-ethyl 2-[4-(3-cyanotetrahydrofuran-3-yl)phenyl]-2-cyclobutyl-acetate (200 mg, 638 umol) in dimethyl sulfoxide (5 mL) was added potassium carbonate (35.3 mg, 255 umol) and hydrogen peroxide (723 mg, 6.38 mmol) in one portion at rt, and the reaction was stirred at rt for 1 hr. On completion, the residue was poured into aqueous sodium sulfite (50 mL). The aqueous phase was extracted with ethyl acetate (3×20 mL). The combined organic phase was washed with brine (3×20 mL), dried over anhydrous sodium sulfate, filtered and concentrated in vacuo to give the title compound.

Step 3—(±)-Ethyl 2-[4-(3-aminotetrahydrofuran-3-yl)phenyl]-2-cyclobutyl-acetate

To a solution of (±)-ethyl 2-[4-(3-carbamoyltetrahydrofuran-3-yl)phenyl]-2-cyclobutyl-acetate (150 mg, 453 umol) in acetonitrile (5 mL) and water (5 mL) was added [phenyl-(2,2,2-trifluoroacetyl)oxy-iodanyl]2,2,2-trifluoroacetate (234 mg, 543 umol) in one portion at rt, and the reaction was stirred at rt for 12 hrs. On completion, the aqueous phase was extracted with ethyl acetate (3×20 mL). The combined organic phase was washed with brine (3×20 mL), dried over anhydrous sodium sulfate, filtered and concentrated in vacuo. The residue was purified by column chromatography (dichloromethane:methanol=100:1-10:1) to give the title compound. LCMS: (ES$^+$) m/z (M+H)$^+$=304.1, tR=0.789.

(±)-Ethyl 2-[4-(3-aminotetrahydrofuran-3-yl)phenyl]-2-cyclopentyl-acetate (Intermediate CI)

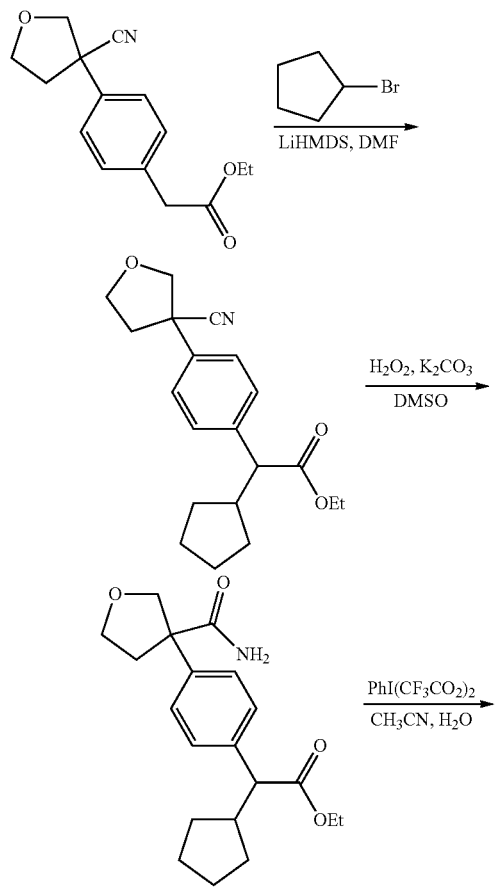

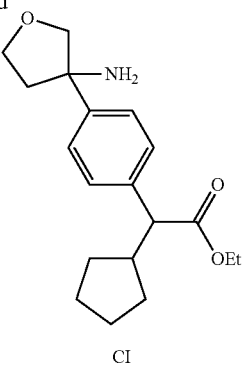

Step 1—(±)-Ethyl 2-[4-(3-cyanotetrahydrofuran-3-yl)phenyl]-2-cyclopentyl-acetate To a solution of (±)-ethyl 2-[4-(3-cyanotetrahydrofuran-3-yl)phenyl]acetate (1.00 g, 3.86 mmol) in dimethyl formamide (30 mL) was added lithium bis(trimethylsilyl)amide (1 M, 3.86 mmol) at rt. The mixture was stirred at rt for 1 hr, then bromocyclopentane (862 mg, 5.79 mmol) was added and the mixture was stirred at 50° C. for 1 hr. On completion, the mixture was diluted with saturated ammonium chloride (20 mL) and extracted with ethyl acetate (3×20 mL). The combined organic layer was dried over anhydrous sodium sulfate, filtered and concentrated. The residue was purified by chromatography on silica gel (petroleum ether:ethyl acetate=20:1 to 5:1) to give the title compound. LCMS: (ES$^+$) m:z (M+H)$^+$=328.3.

Step 2—(±)-Ethyl 2-[4-(3-carbamoyltetrahydrofuran-3-yl)phenyl]-2-cyclopentyl-acetate To a solution of ethyl (±)-2-[4-(3-cyanotetrahydrofuran-3-yl)phenyl]-2-cyclopentyl-acetate (1.00 g, 3.05 mmol) in dimethyl sulfoxide (10 mL) was added potassium carbonate (844 mg, 6.11 mmol) and hydrogen peroxide (2.59 g, 30.5 mmol, 30% solution) at rt, and the mixture was stirred at rt for 7 hrs. On completion, the mixture was diluted with water (10 mL) and extracted with dichloromethane (3×20 mL). The organic layer was washed with water (3×10 mL), dried over anhydrous sodium sulfate, filtered and concentrated to give the title compound. $^1$H NMR (400 MHz, CDCl3) δ=7.38 (d, J=8.3 Hz, 2H), 7.28 (d, J=8.3 Hz, 2H), 5.42 (br. s., 2H), 4.46 (d, J=8.8 Hz, 1H), 4.21-4.14 (m, 1H), 4.12-4.04 (m, 3H), 3.97 (q, J=7.3 Hz, 1H), 3.28 (d, J=11.0 Hz, 1H), 2.89-2.79 (m, 1H), 2.55 (m, 1H), 2.39-2.31 (m, 1H), 1.97-1.85 (m, 1H), 1.74-1.65 (m, 1H), 1.53-1.38 (m, 2H), 1.25 (t, J=7.0 Hz, 3H), 1.04-0.94 (m, 1H).

Step 3—(±)-Ethyl 2-[4-(3-aminotetrahydrofuran-3-yl)phenyl]-2-cyclopentyl-acetate To a solution of (±)-ethyl 2-[4-(3-carbamoyltetrahydrofuran-3-yl)phenyl]-2-cyclopentyl-acetate (60.0 mg, 173 umol) in acetonitrile (10 mL) and water (5 mL) was added [bis(trifluoroacetoxy)iodo]benzene (298 mg, 694 umol) and the mixture was stirred at rt for 12 hrs. On completion, the mixture adjusted to pH 7~9 with sodium bicarbonate. The mixture was then extracted with dichloromethane (2×20 mL), washed with brine (3×10 mL), and the organic layer was dried over anhydrous sodium sulfate, filtered and concentrated to give the title compound. LCMS: (ES$^+$) m:z (M−NH$_2$)$^+$=301.1.

(±)-Allyl 2-(4-(3-aminooxetan-3-yl)phenyl)-2-cyclohexylacetate (Intermediate CJ)

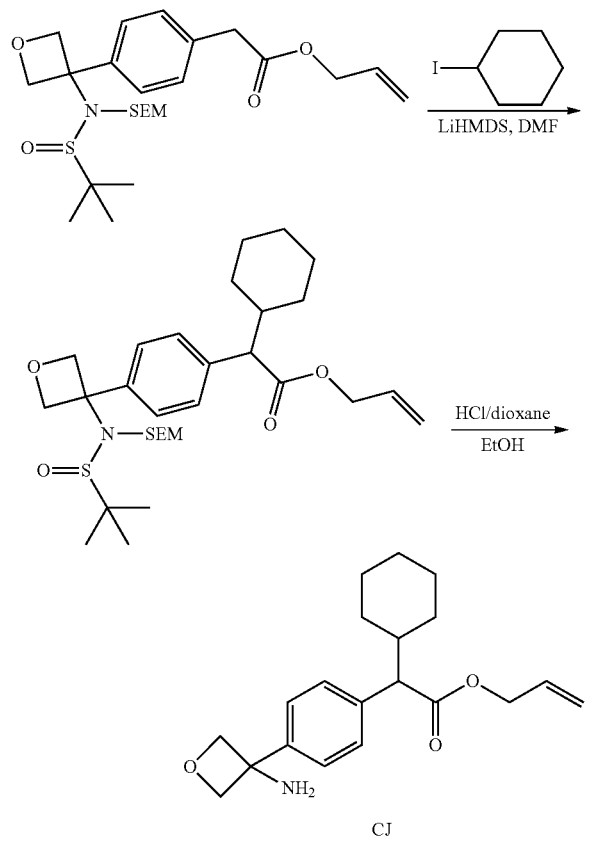

CJ

Step 1—(±)-Allyl 2-cyclohexyl-2-(4-(3-(2-methyl-N-((2-(trimethylsilyl)ethoxy)methyl)propan-2-ylsulfinamido) oxetan-3-yl)phenyl)acetate To a solution of (±)-allyl 2-[4-[3-[tert-butylsulfinyl(2-trimethylsilylethoxymethyl)amino]oxetan-3-yl]phenyl]acetate (200 mg, 415 umol, synthesized via Steps 1-2 of Intermediate BT) in N,N-dimethylformamide (5 mL) was added LiHMDS (1 M, 1.25 mL) dropwise at 0° C. After the reaction mixture was stirred for 0.5 hr, iodocyclohexane (436 mg, 2.08 mmol) was added and the reaction mixture was stirred at rt for 2 hrs. On completion, the reaction mixture was poured into 30 mL cool water and extracted with dichloromethane (3×30 mL). The combined organic layer was dried over anhydrous sodium sulfate, filtered and concentrated in vacuo. The resulting product was purified by silica gel chromatography (petroleum ether:ethyl acetate=20:1-10:1) to give the title compound. LCMS: (ES$^+$) m/z (M+23)$^+$=586.4, tR=1.229.

Step 2—(±)-Allyl 2-(4-(3-aminooxetan-3-yl)phenyl)-2-cyclohexylacetate

To a solution of (±)-allyl 2-[4-[3-[tert-butylsulfinyl(2-trimethylsilylethoxymethyl)amino]oxetan-3-yl]phenyl]-2-cyclohexyl-acetate (190 mg, 336 umol) in ethanol (10 mL) was added hydrochloric acid/dioxane (4 M, 421 uL) and the reaction mixture was stirred at 0° C. for 45 min. On completion, the reaction mixture was basified with saturated sodium bicarbonate solution until pH=8 and extracted with dichloromethane (3×20 mL). The combined organic layer was dried over anhydrous sodium sulfate, filtered and concentrated in vacuo to give the title compound. LCMS: (ES$^+$) m/z (2M+H)$^+$=659.5, (M−NH$_2$)$^+$=313.3, tR=0.789.

(±)-Allyl 2-(4-(3-aminooxetan-3-yl)phenyl)-2-(tetrahydro-2H-pyran-4-yl)acetate (Intermediate CK)

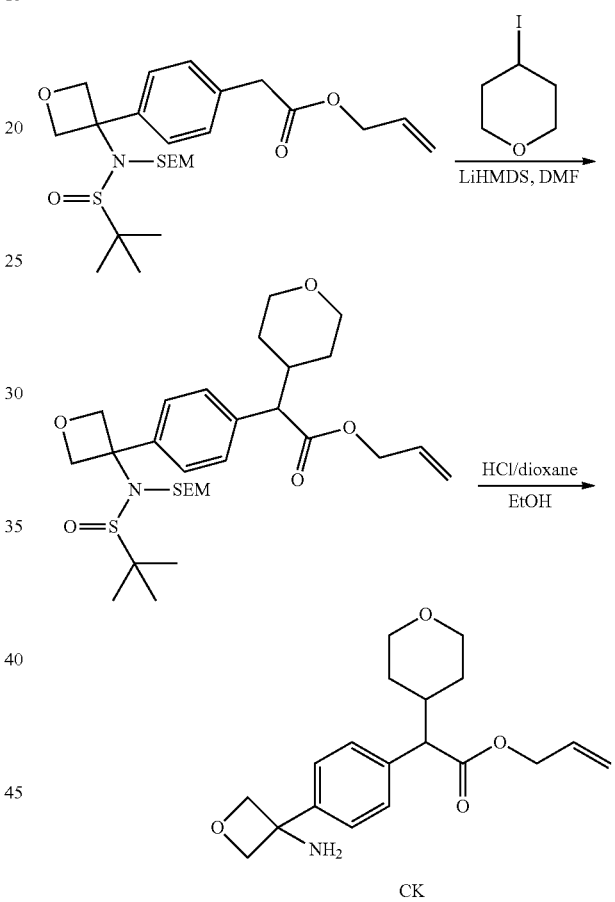

CK

Step 1—(±)-Allyl 2-(4-(3-(2-methyl-N-((2-(trimethylsilyl)ethoxy)methyl)propan-2-ylsulfinamido) oxetan-3-yl)phenyl)-2-(tetrahydro-2H-pyran-4-yl) acetate To a solution of (±)-allyl 2-[4-[3-[tert-butylsulfinyl(2-trimethylsilylethoxymethyl)amino]oxetan-3-yl]phenyl]acetate (200 mg, 415 umol, synthesized via Steps 1-2 of Intermediate BT) in N,N-dimethylformamide (5 mL) was added LiHMDS (1 M, 1.25 mL) dropwise at 0° C. After the reaction mixture was stirred for 1 hr, a solution of 4-iodotetrahydropyran (440 mg, 2.08 mmol) in N,N-dimethylformamide (1 mL) was added dropwise and the reaction mixture was stirred at rt for 6.5 hrs. On completion, the reaction mixture was poured into 100 mL cool water and extracted with ethyl acetate (3×30 mL). The combined organic layer was dried over anhydrous sodium sulfate, filtered and concentrated in vacuo. The resulting product was purified by silica gel chromatography (petroleum ether: ethyl acetate=20:1-10:1) to give the title compound. LCMS: (ES$^+$) m/z (M+23)$^+$=588.4, tR=1.071.

Step 2—(±)-Allyl 2-(4-(3-aminooxetan-3-yl)phenyl)-2-(tetrahydro-2H-pyran-4-yl)acetate To a solution of (±)-allyl 2-[4-[3-[tert-butylsulfinyl(2-trimethylsilylethoxymethyl)amino]oxetan-3-yl]phenyl]-2-tetrahydropyran-4-yl-acetate (230 mg, 406 umol) in ethanol (10 mL) was added hydrochloric acid/dioxane (4 M, 508 uL) and the reaction mixture was stirred at 0° C. for 45 min. On completion, the reaction mixture was basified with saturated sodium bicarbonate solution until pH=8 and extracted with dichloromethane (3×20 mL). The combined layer was dried over anhydrous sodium sulfate, filtrated and concentrated in vacuo to give the title compound. LCMS: (ES$^+$) m/z (2M+H)$^+$=663.4, tR=0.676.

Allyl 4-iodopiperidine-1-carboxylate (Intermediate CL)

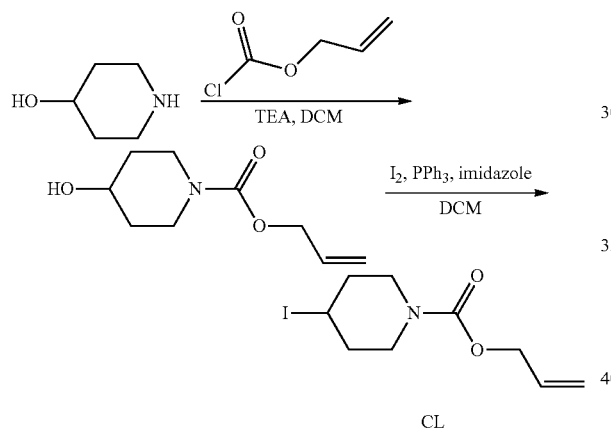

Step 1—allyl 4-hydroxypiperidine-1-carboxylate

Piperidin-4-ol (CAS #5382-16-1, 6.99 g, 69.14 mmol) was dissolved in DCM (250 mL) with stirring. TEA (10.5 g, 103.71 mmol) was added, and the solution was cooled to 0° C. Allyl carbonochloridate (CAS #2937-50-0, 10.0 g, 82.9 mmol) was added dropwise via addition funnel over 30 min. The reaction was stirred at 20° C. for 18 hr. On completion, the reaction mixture was quenched with 1N HCl and extracted with DCM. The combined organic layers were dried over Na$_2$SO$_4$, filtered, and concentrated in vacuo. The residue was purified by flash chromatography (DCM/MeOH=100/1 to 10/1) to give the title compound. $^1$H NMR (400 MHz, CDCl3) δ=5.96 (tdd, J=5.4, 10.6, 17.3 Hz, 1H), 5.36-5.28 (m, 1H), 5.23 (qd, J=1.4, 10.5 Hz, 1H), 4.61 (td, J=1.5, 5.5 Hz, 2H), 3.90 (tdd, J=4.3, 8.4, 12.6 Hz, 3H), 3.16 (ddd, J=3.0, 9.8, 13.2 Hz, 2H), 1.90 (td, J=4.0, 8.5 Hz, 2H), 1.59 (d, J=3.9 Hz, 1H), 1.57-1.38 (m, 2H)

Step 2—allyl 4-iodopiperidine-1-carboxylate

To a solution of allyl 4-hydroxypiperidine-1-carboxylate (6.00 g, 32.4 mmol) in DCM (150 mL) were added PPh$_3$ (11.05 g, 42.11 mmol) and imidazole (3.31 g, 48.59 mmol). The resulting solution was cooled to 0° C. and I$_2$ (9.87 g, 38.87 mmol) was added portion-wise. The mixture was stirred at 20° C. for 18 hr. On completion, the reaction mixture was poured into water and extracted with Et$_2$O. The combined organic phases were dried over Na$_2$SO$_4$, filtered and concentrated under reduced pressure. The residue was purified by flash chromatography on silica gel (PE/EtOAc=100:0 to 95:5 to 92:8) to give the title compound. $^1$HNMR (400 MHz, CDCl3) δ=6.03-5.88 (m, 1H), 5.36-5.18 (m, 2H), 4.61 (td, J=1.2, 5.6 Hz, 2H), 4.48 (quin, J=5.8 Hz, 1H), 3.66 (td, J=5.2, 13.6 Hz, 2H), 3.40 (td, J=5.7, 13.6 Hz, 2H), 2.06 (q, J=5.6 Hz, 4H).

(±)-Allyl 4-[2-allyloxy-1-[4-(3-aminooxetan-3-yl)phenyl]-2-oxo-ethyl]piperidine-1-carboxylate (Intermediate CM)

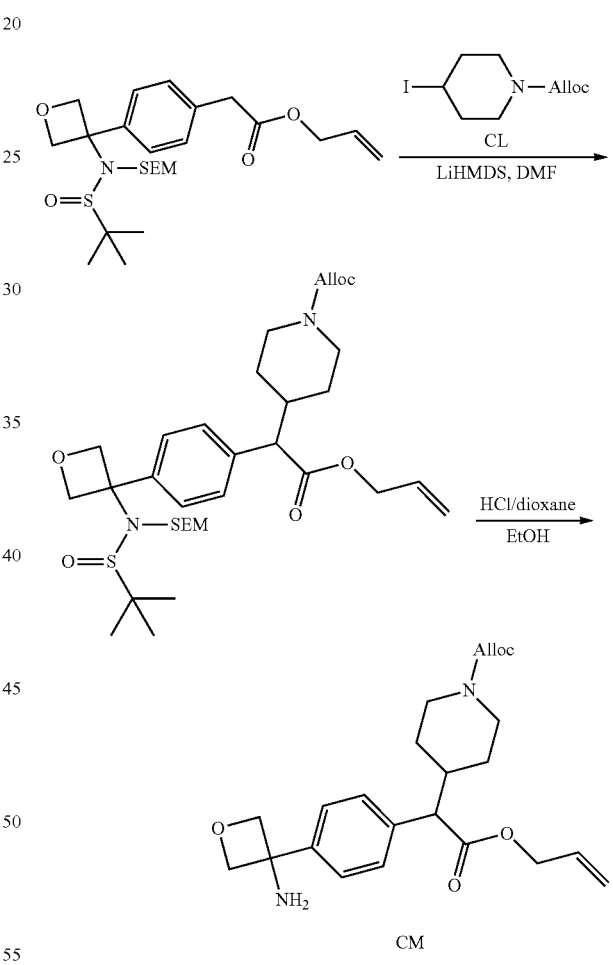

Step 1—(±)-allyl 4-[2-allyloxy-1-[4-[3-[tert-butylsulfinyl(2-trimethylsiylethoxymethyl)amino]oxetan-3-yl]phenyl]-2-oxo-ethyl]piperidine-1-carboxylate To a solution of allyl 2-[4-[3-[tert-butylsulfinyl(2-trimethylsilylethoxymethyl)amino]oxetan-3-yl]phenyl]acetate (1.50 g, 3.11 mmol, synthesized via Steps 1-2 of Intermediate BT) in THF (12 mL) was added LiHMDS (1 M, 4.67 mL) dropwise at 0° C. The mixture was stirred at 0° C. for 30 min, then allyl 4-iodopiperidine-1-carboxylate (2.75 g, 9.33 mmol) in THF (3 mL) was added dropwise. Then the mixture was warmed to rt and stirred at rt for 15.5 hrs. On completion, the reaction mixture was poured into 50 mL iced saturated ammonium chloride solution, and extracted with ethyl acetate (60 mL×3). The organic phase was collected, dried over anhydrous sodium sulfate, and concentrated in vacuo to get a residue. The residue was purified by column chromatography (SiO$_2$, Petroleum ether/Ethyl acetate=10:1 to 5:1) to give the title compound. 1H NMR (400 MHz, CDCl$_3$) δ=7.60 (dd, J=6.2, 8.1 Hz, 2H), 7.39 (d, J=8.4 Hz, 2H), 6.02-5.80 (m, 2H), 5.39 (t, J=7.0 Hz, 1H), 5.33-5.16 (m, 5H), 4.87 (dd, J=6.2, 10.1 Hz, 1H), 4.77-4.48 (m, 6H), 4.27-3.99 (m, 2H), 3.84 (dd, J=4.5, 10.5 Hz, 1H), 3.45-3.23 (m, 3H), 2.90-2.60 (m, 2H), 2.34-2.13 (m, 1H), 1.82 (d, J=12.5 Hz, 1H), 1.37 (s, 9H), 1.33-1.24 (m, 2H), 1.06-0.94 (m, 1H), 0.90 (dd, J=7.0, 9.0 Hz, 2H), 0.02 (s, 9H).

Step 2—(±)-allyl 4-[2-allyloxy-1-[4-(3-aminooxetan-3-yl)phenyl]-2-oxo-ethyl]piperidine-1-carboxylate To a solution of allyl 4-[2-allyloxy-1-[4-[3-[tert-butylsulfinyl(2-trimethylsilylethoxymethyl)amino]oxetan-3-yl]phenyl]-2-oxo-ethyl]piperidine-1-carboxylate (1.10 g, 1.70 mmol) in EtOH (10.0 mL) was added HCl/dioxane (4 M, 5.00 mL). The reaction mixture was stirred at 0° C. for 2 hr. On completion, the reaction mixture was neutralized with saturated sodium bicarbonate solution until pH=8, and extracted with dichloromethane (2×70 mL). The combined organic layer was concentrated in vacuo to give the title compound. LCMS: (ES$^+$) m/z (M+H)$^+$=415.2, tR=0.690.

(±)-Allyl 2-(4-(3-aminooxetan-3-yl)phenyl)-4-methylpentanoate (Intermediate CN)

Step 1—(±)-Allyl 4-methyl-2-(4-(3-(2-methyl-N-((2-(trimethylsilyl)ethoxy)methyl)propan-2-ylsulfinamido)oxetan-3-yl)phenyl)pentanoate To a solution of (±)-allyl 2-[4-[3-[tert-butylsulfinyl(2-trimethylsilylethoxymethyl)amino]oxetan-3-yl]phenyl]acetate (500 mg, 1.04 mmol, synthesized via Steps 1-2 of Intermediate BT) in N,N-dimethylformamide (10 mL) was added LiHMDS (1 M, 1.87 mL) dropwise at 0° C. After the reaction mixture was stirred for 0.5 hr, 1-iodo-2-methylpropane (210 mg, 1.14 mmol) was added dropwise and the reaction mixture was stirred at rt for 6.5 hrs. On completion, the reaction mixture was poured into 30 mL cool water and extracted with ethyl acetate (3×50 mL). The combined organic layer was dried over anhydrous sodium sulfate, filtrated and concentrated in vacuo. The resulting product was purified by silica gel chromatography (petroleum ether: ethyl acetate=5:1) to give the title compound. LCMS: (ES$^+$) m/z (M+23)$^+$=560.3, tR=1.103.

Step 2—(±)-Allyl 2-(4-(3-aminooxetan-3-yl)phenyl)-4-methylpentanoate

To a solution of allyl 2-[4-[3-[tert-butylsulfinyl(2-trimethylsilylethoxymethyl)amino]oxetan-3-yl]phenyl]-4-methyl-pentanoate (360 mg, 669 umol) in ethanol (10 mL) was added hydrochloric acid/dioxane (4 M, 836 uL) and the reaction mixture was stirred at 0° C. for 30 min. On completion, the reaction mixture was basified with saturated sodium bicarbonate solution until pH=8 and extracted with dichloromethane (3×30 mL). The combined organic layer was dried over anhydrous sodium sulfate, filtered and concentrated in vacuo to give the title compound. LCMS: (ES$^+$) m/z (2M+H)$^+$=607.5, tR=0.754.

(±)-Allyl 2-[4-(3-aminooxetan-3-yl)phenyl]-3-cyclopropyl-propanoate (Intermediate CO)

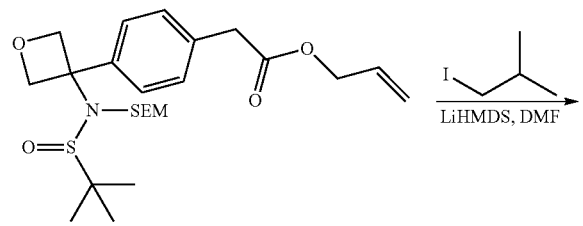

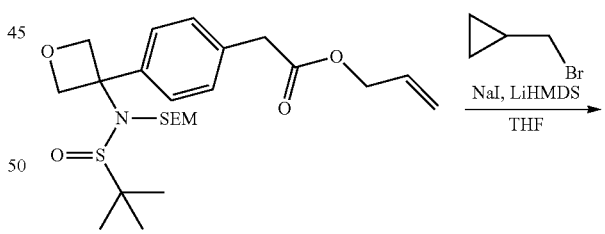

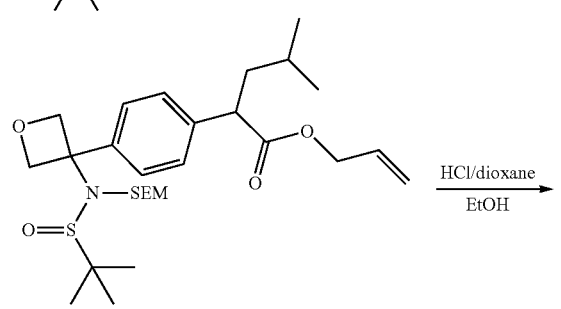

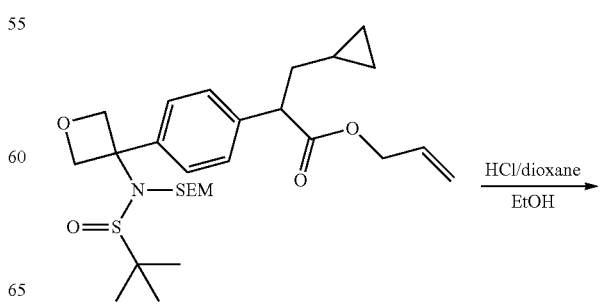

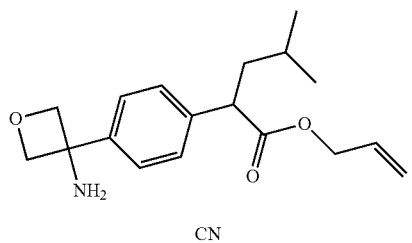

CN

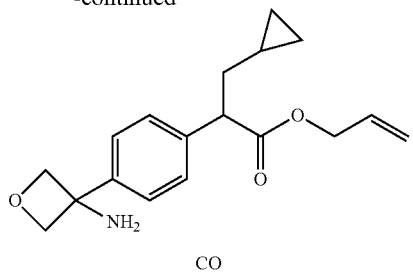

CO

Step 1—(±)-Allyl 2-[4-[3-[tert-butylsulfinyl(2-trimethylsilylethoxymethyl)amino]oxetan-3-yl]phenyl]-3-cyclopropyl-propanoate To a solution of allyl 2-[4-[3-[tert-butylsulfinyl(2-trimethylsilylethoxymethyl)amino]oxetan-3-yl]phenyl]acetate (1.00 g, 2.08 mmol, synthesized via Steps 1-2 of Intermediate BT) and sodium iodide (31.1 mg, 208 umol) in N,N-dimethylformamide (30 mL) was added LiHMDS (1 M, 3.12 mL) at 0° C. The reaction mixture was stirred at 0° C. for 30 min. Bromomethylcyclopropane (2.81 g, 20.8 mmol) was added to the reaction mixture and the mixture was stirred at rt for 16 hrs. On completion, the mixture was quenched with ammonium chloride solution (80 mL) and extracted with ethyl acetate (2×100 mL). The combined organic layer was washed with brine (100 mL), dried over anhydrous sodium sulfate, filtered and concentrated in vacuo to give a residue. The residue was purified with silica gel chromatography (petroleum ether:ethyl acetate=3:1) to give the title compound. $^1$H NMR (400 MHz, CDCl$_3$) δ=7.59 (d, J=8.4 Hz, 2H), 7.40 (d, J=8.4 Hz, 2H), 5.98-5.82 (m, 1H), 5.42-5.35 (m, 1H), 5.31-5.15 (m, 3H), 4.90 (d, J=6.1 Hz, 1H), 4.79-4.69 (m, 2H), 4.67-4.49 (m, 2H), 3.86 (d, J=11.3 Hz, 1H), 3.76 (t, J=7.7 Hz, 1H), 3.36 (t, J=8.2 Hz, 2H), 1.98-1.88 (m, 1H), 1.79 (dtd, J=4.2, 6.7, 13.8 Hz, 1H), 1.38 (s, 9H), 0.97-0.82 (m, 2H), 0.73-0.60 (m, 1H), 0.47-0.34 (m, 2H), 0.18-0.04 (m, 2H), 0.00 (s, 9H).

Step 2—(±)-Allyl 2-[4-(3-aminooxetan-3-yl)phenyl]-3-cyclopropyl-propanoate

To a solution of (±)-allyl 2-[4-[3-[tert-butylsulfinyl(2-trimethylsilylethoxymethyl)amino]oxetan-3-yl]phenyl]-3-cyclopropyl-propanoate (950 mg, 1.77 mmol) in ethanol (2 mL) was added hydrogen chloride/dioxane (4 M, 20 mL) at 0° C. The reaction mixture was stirred at 0° C. for 3 hrs. On completion, the reaction mixture was neutralized with saturated sodium bicarbonate solution to pH=8, and extracted with dichloromethane (2×70 mL). The combined organic layer was concentrated in vacuo to give the title compound. LCMS: (ES$^+$) m/z (M−NH$_2$)$^+$=285.0, tR=0.907.

(4-Iodocyclohexyl) acetate (Intermediate CP)

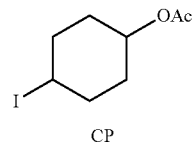

CP

Step 1—(4-Hydroxycyclohexyl) acetate

To a solution of cyclohexane-1,4-diol (20.0 g, 172 mmol) in tetrahydrofuran (20 mL) was added triethylamine (52.3 g, 516 mmol) and acetyl chloride (14.8 g, 189 mmol) dropwise, and the mixture was stirred at rt for 0.5 hr. On completion, the mixture was diluted with saturated ammonium chloride (10 mL) and extracted with ethyl acetate (3×20 mL). The combined organic layer was washed with brine (3×20 mL), dried over anhydrous sodium sulfate, filtered and concentrated. The residue was purified by chromatography on silica gel (petroleum ether:ethyl acetate=10:1 to 1:1) to give the title compound. $^1$H NMR (400 MHz, CDCl3) δ=4.88-4.65 (m, 1H), 3.85-3.61 (m, 1H), 2.08-2.00 (m, 3H), 2.00-1.95 (m, 1H), 1.91-1.81 (m, 1H), 1.77-1.49 (m, 4H), 1.50-1.38 (m, 2H).

Step 2—(4-Iodocyclohexyl) acetate

To a solution of triphenylphosphine (11.6 g, 44.5 mmol) in dichloromethane (15 mL) was added imidazole (3.03 g, 44.5 mmol) at 0° C. Iodine (11.3 g, 44.5 mmol) was added at rt and the mixture was stirred for 0.5 hr. Then (4-hydroxycyclohexyl) acetate (4.70 g, 29.7 mmol) was added to the mixture and the mixture was stirred at rt for 1 hr. On completion, the mixture was diluted with saturated ammonium chloride (20 mL) and extracted with ethyl acetate (3×30 mL). The combined organic layer was washed with brine (3×20 mL), dried over anhydrous sodium sulfate, filtered and concentrated. The residue was purified by chromatography on silica gel (petroleum ether:ethyl acetate=20:1 to 7:1) to give the title compound. $^1$H NMR (400 MHz, CDCl3) δ=4.96-4.76 (m, 1H), 4.53-4.21 (m, 1H), 2.28-2.13 (m, 2H), 2.05 (d, J=18.3 Hz, 3H), 2.01-1.81 (m, 4H), 1.77-1.66 (m, 1H), 1.58-1.47 (m, 1H).

Allyl 2-(4-acetoxycyclohexyl)-2-[4-(3-aminooxetan-3-yl)phenyl]acetate (Intermediate CQ)

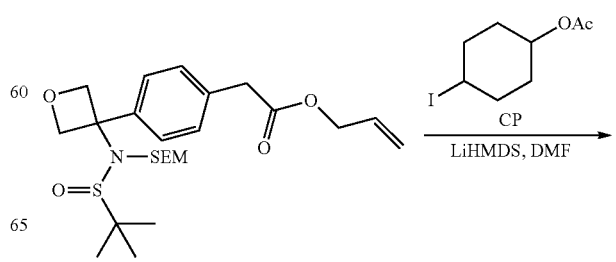

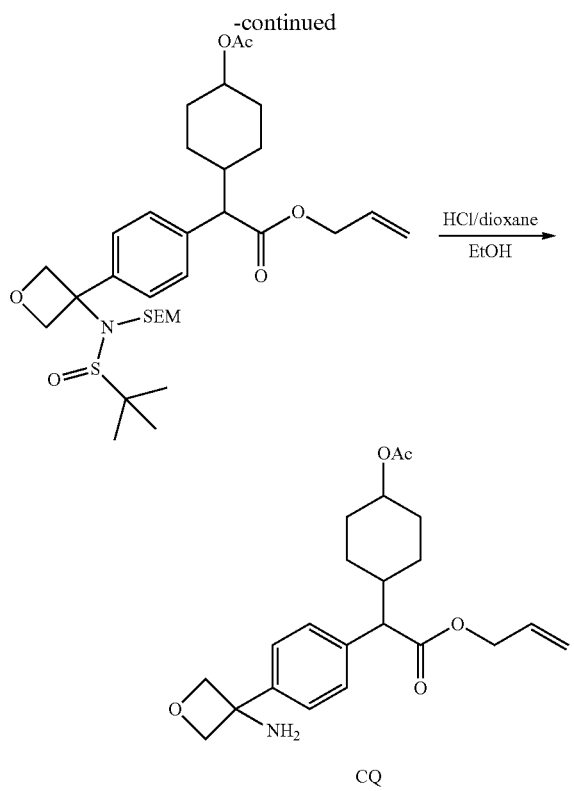

CQ

Step 1—(±)-Allyl 2-(4-acetoxycyclohexyl)-2-[4-[3-[tert-butylsulfinyl(2-trimethylsilylethoxymethyl)amino]oxetan-3-yl]phenyl]acetate To a solution of allyl 2-[4-[3-[tert-butylsulfinyl(2-trimethylsilylethoxymethyl)amino]oxetan-3-yl]phenyl]acetate (800 mg, 1.66 mmol, synthesized via Steps 1-2 of Intermediate BT) in dimethyl formamide (15 mL) was added lithium bis(trimethylsilyl)amide (1 M, 8.30 mL, 8.3 mmol) at rt. (4-Iodocyclohexyl) acetate (1.34 g, 4.98 mmol) was added dropwise, and the mixture was stirred at rt for 2 hrs under nitrogen atmosphere. On completion, the mixture was diluted with saturated ammonium chloride (30 mL) and extracted with ethyl acetate (3×30 mL). The combined organic layer was washed with brine (3×20 mL), dried over anhydrous sodium sulfate, filtered and concentrated. The residue was purified by chromatography on silica gel (petroleum ether:ethyl acetate=10:1 to 5:1) to give the title compound. $^1$H NMR (400 MHz, CDCl3) δ=7.57 (d, J=7.9 Hz, 2H), 7.39 (t, J=9.0 Hz, 2H), 5.94-5.79 (m, 1H), 5.73-5.48 (m, 1H), 5.37 (t, J=6.8 Hz, 1H), 5.28-5.20 (m, 2H), 4.98 (br. s., 1H), 4.90-4.82 (m, 1H), 4.72 (d, J=7.0 Hz, 2H), 4.65-4.58 (m, 1H), 4.54-4.46 (m, 1H), 4.12 (q, J=7.1 Hz, 1H), 3.83 (d, J=10.5 Hz, 1H), 3.34 (t, J=8.3 Hz, 2H), 2.04 (s, 3H), 1.95-1.82 (m, 2H), 1.80-1.64 (m, 2H), 1.41 (d, J=12.8 Hz, 2H), 1.35 (s, 9H), 1.22-1.11 (m, 2H), 0.95-0.81 (m, 3H), 0.00 (s, 9H).

Step 2—(±)-Allyl 2-(4-acetoxycyclohexyl)-2-[4-(3-aminooxetan-3-yl)phenyl]acetate To a solution of (±)-allyl 2-(4-acetoxycyclohexyl)-2-[4-[3-[tert-butylsulfinyl(2-trimethylsilylethoxy methyl)amino]oxetan-3-yl]phenyl]acetate (350 mg, 562 umol) in ethanol (20 mL) was added hydrochloric acid (4 M in dioxane, 1.13 mL), the mixture was stirred at 0° C. for 2 hrs. On completion, the mixture was adjusted pH to 8-9 with ammonia in water (30%) and concentrated in vacuo. The residue was purified by chromatography on silica gel (petroleum ether: ethyl acetate=1:1 to dichloromethane:methanol=30:1) to give the title compound. LCMS: (ES$^+$) m:z (M+H)$^+$=388.2, tR=0.653.

(±)-Allyl 3-[4-(3-aminooxetan-3-yl)phenyl]tetrahydrofuran-3-carboxylate (Intermediate CR)

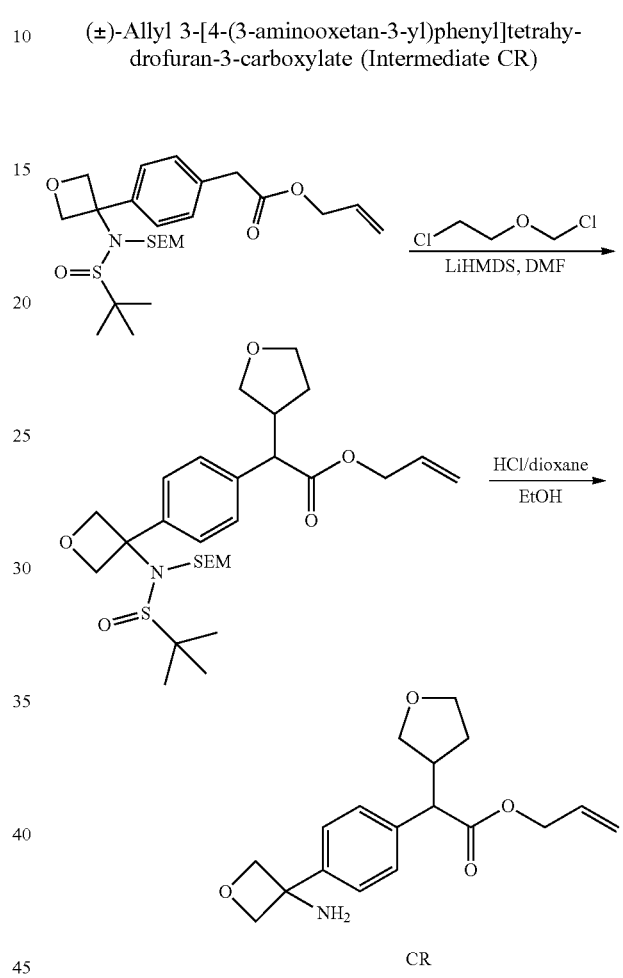

CR

Step 1—(±)-Allyl 3-[4-[3-[tert-butylsulfinyl(2-trimethylsiylethoxymethyl)amino]oxetan-3-yl]phenyl]tetrahydrofuran-3-carboxylate To a solution of (±)-allyl 2-[4-[3-[tert-butylsulfinyl(2-trimethylsilylethoxymethyl)amino]oxetan-3-yl]phenyl]acetate (200 mg, 415 umol, synthesized via Steps 1-2 of Intermediate BT) in N,N-dimethylformamide (10 mL) was added sodium hydride (41.5 mg, 1.04 mmol) and 1-chloro-2-(chloromethoxy)ethane (64.3 mg, 498 umol) in one portion at 0° C., and the reaction was stirred at 15° C. for 12 hrs. On completion, the solution was poured into water (30 mL), and extracted with ethyl acetate (3×20 mL). The combined organic phase was washed with brine (3×20 mL), dried over anhydrous sodium sulfate, filtered and concentrated in vacuo. The residue was purified by column chromatography (petroleum ether:ethyl acetate=100:1-10:1) to give the title compound. LCMS: (ES$^+$) m/z (M+23)$^+$=560.2, tR=0.984.

Step 2—(±)-Allyl 3-[4-(3-aminooxetan-3-yl)phenyl] tetrahydrofuran-3-carboxylate To a solution of (±)-allyl 3-[4-[3-[tert-butylsulfinyl(2-trimethylsilylethoxymethyl)amino]oxetan-3-yl]phenyl]tetrahydrofuran-3-carboxylate (60.0 mg, 112 umol) in ethanol (5 mL) was added hydrochloric/dioxane (4 M/L 10.0 g, 1.12 mmol) in one portion at 0° C., and the reaction was stirred at 0° C. for 1 hr. On completion, the reaction was concentrated in vacuo to give the title compound. LCMS: (ES+) m/z (M+23)+=326.1, tR=0.794.

N-((4-(3-aminooxetan-3-yl)phenyl)sulfonyl)propionamide (Intermediate CS)

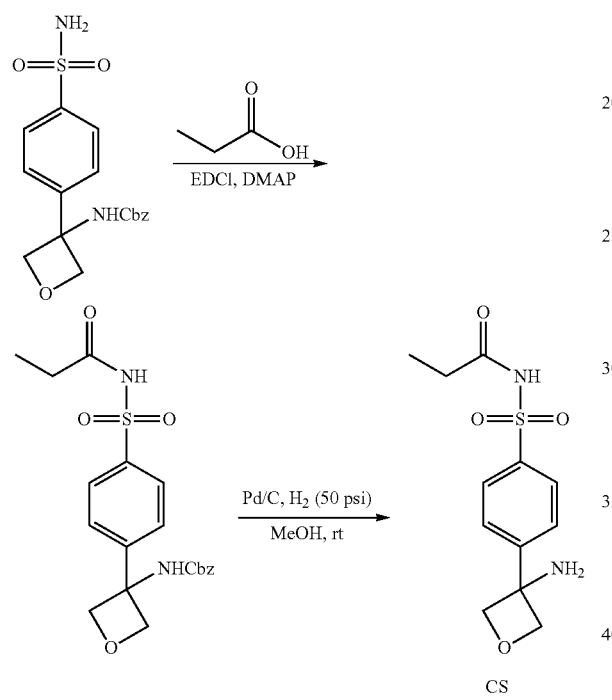

Step 1—Benzyl (3-(4-(N-propionylsulfamoyl)phenyl)oxetan-3-yl)carbamate

To a solution of propionic acid (214 mg, 2.90 mmol, 216 uL), EDCI (555 mg, 2.90 mmol) and DMAP (471 mg, 3.86 mmol) in N,N-dimethylformamide (10 mL) was added benzyl N-[3-(4-sulfamoylphenyl)oxetan-3-yl]carbamate (350 mg, 965 umol, synthesized via Steps 1-5 of Intermediate BY) at rt. The reaction mixture was stirred at rt for 24 hrs. On completion, the reaction mixture was concentrated in vacuo. To the residue was added dichloromethane (20 mL) then it was washed with citric acid (10 mL). The organic layer was washed with brine (5 mL), dried over anhydrous sodium sulfate, and concentrated in vacuo. The resulting product was purified by silica gel chromatography (dichloromethane:methanol=50:1) to give the title compound. LCMS: (ES+) m/z (M+H)+=419.2, tR=0.737.

Step 2—N-((4-(3-aminooxetan-3-yl)phenyl)sulfonyl)propionamide

To a solution of benzyl N-[3-[4-(propanoylsulfamoyl)phenyl]oxetan-3-yl]carbamate (460 mg, 1.10 mmol) in methanol (5 mL) was added Pd—C (10%, 50 mg) under nitrogen. The suspension was degassed under vacuum and purged with hydrogen several times at rt. The mixture was stirred under hydrogen (50 psi) at 50° C. for 32 hours. On completion, the mixture was extracted with dichloromethane (2×30 mL). The combined organic layer was dried over anhydrous sodium sulfate, filtered and concentrated in vacuo to give the title compound. LCMS: (ES+) m/z (2M+H)+=569.4, tR=0.271.

4-(3-Aminooxetan-3-yl)-N-(methylsulfonyl)benzamide (Intermediate CT)

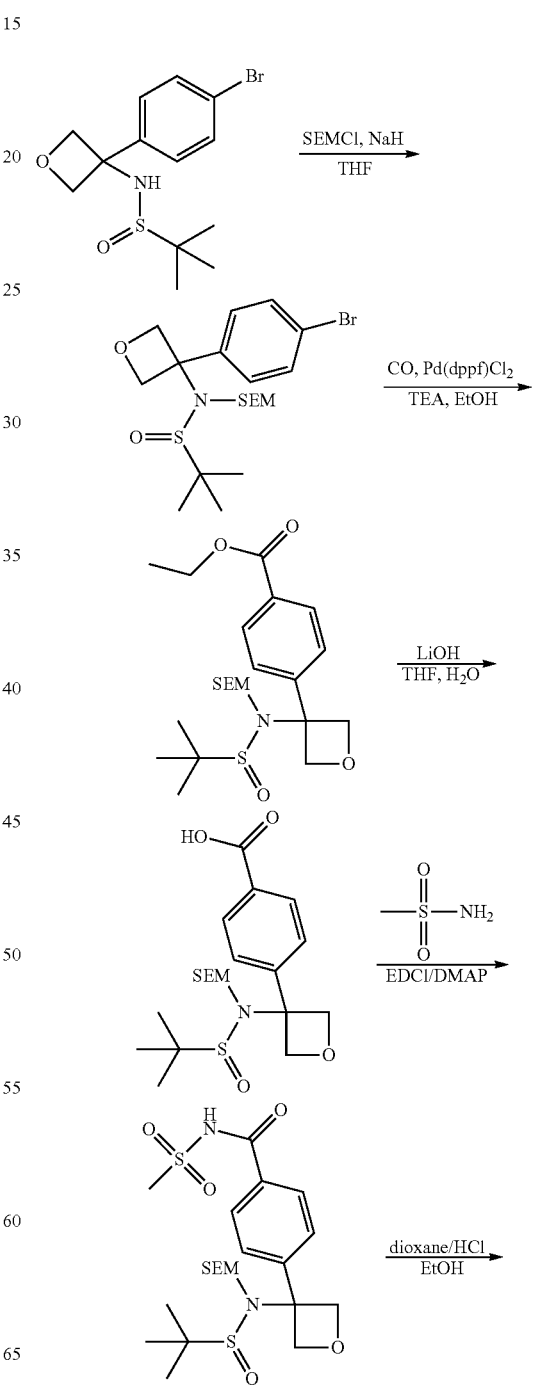

-continued

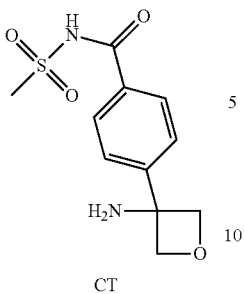

CT

Step 1—(±)-N-[3-(4-bromophenyl)oxetan-3-yl]-2-methyl-N-(2-trimethylsilylethoxymethyl)-propane-2-sulfinamide To a solution of (±)-N-[3-(4-bromophenyl)oxetan-3-yl]-2-methyl-propane-2-sulfinamide (17.0 g, 51.1 mmol, synthesized via Steps 1-2 of Intermediate AE) in tetrahydrofuran (300 mL) was added sodium hydride (4.09 g, 102 mmol, 60%) at 0° C. and the reaction mixture was stirred for 0.5 hr. Then SEMCl (12.8 g, 76.7 mmol) was added dropwise and the reaction mixture was stirred at rt for 0.5 hr. On completion, the reaction mixture was poured into 1000 mL ice-water. The aqueous phase was extracted with dichloromethane (3×1000 mL). The combined organic layer was dried over anhydrous sodium sulfate, filtrated and concentrated in vacuo. The solid was purified by silica gel chromatography (petroleum ether:ethyl acetate=5:1) to give title compound. $^1$H NMR (400 MHz, CDCl3) δ=7.61-7.49 (m, 4H), 5.38 (d, J=6.4 Hz, 1H), 5.26 (d, J=6.8 Hz, 1H), 4.84 (d, J=6.4 Hz, 1H), 4.72 (d, J=10.7 Hz, 1H), 4.68 (d, J=10.5 Hz, 1H), 3.82 (d, J=10.5 Hz, 1H), 3.39-3.31 (m, 2H), 1.37 (s, 9H), 0.93-0.85 (m, 2H), 0.02 (s, 9H).

Step 2—Ethyl 4-(3-(2-methyl-N-((2-(trimethylsilyl)ethoxy)methyl)propan-2-ylsulfinamido) oxetan-3-yl)benzoate To a mixture of N-[3-(4-bromophenyl)oxetan-3-yl]-2-methyl-N-(2-trimethylsilylethoxymethyl)propane-2-sulfinamide (9.00 g, 19.5 mmol) and triethylamine (9.85 g, 97.3 mmol) in ethanol (90 mL) was added Pd(dppf)Cl$_2$.CH$_2$Cl$_2$ (1.59 g, 1.95 mmol) in one portion under a nitrogen. The mixture was flushed with CO (50 psi) three times, then the reaction mixture was heated to 80° C. and stirred for 16 hours. On completion, the reaction mixture was filtered and concentrated in vacuo. The residue was purified by silica gel chromatography (petroleum ether:ethyl acetate=20:1) to give the title compound. LCMS: (ES$^+$) m/z (M+23)=478.3, tR=0.999.

Step 3—4-(3-(2-methyl-N-((2-(trimethylsilyl)ethoxy)methyl)propan-2-ylsulfinamido)oxetan-3-yl)benzoic acid To a solution of ethyl 4-[3-[tert-butylsulfinyl(2-trimethylsilylethoxymethyl)amino]oxetan-3-yl]benzoate (5.00 g, 11.0 mmol) in tetrahydrofuran (30 mL) and water (10 mL) was added LiOH (1.31 g, 54.9 mmol) at rt. The reaction mixture was stirred at rt for 24 hrs. On completion, the reaction mixture was concentrated in vacuo to remove the tetrahydrofuran. The residue was diluted with water (10 mL), then citric acid (1N, 20 mL) was added to pH=7 slowly. The mixture was then filtered and concentrated in vacuo to dryness to give the title compound. $^1$H NMR (400 MHz, DMSO-d$_6$) δ=13.05 (br. s., 1H), 8.00 (d, J=8.3 Hz, 2H), 7.69 (d, J=8.3 Hz, 2H), 5.21 (d, J=6.5 Hz, 1H), 5.06 (d, J=7.0 Hz, 1H), 4.86 (d, J=6.5 Hz, 1H), 4.78 (d, J=6.8 Hz, 1H), 4.51 (d, J=10.8 Hz, 1H), 3.88 (d, J=10.5 Hz, 1H), 3.32-3.24 (m, 2H), 1.27 (s, 9H), 0.82 (t, J=7.9 Hz, 2H), 0.00 (s, 9H).

Step 4—4-(3-(2-Methyl-N-((2-(trimethylsilyl)ethoxy)methyl)propan-2-ylsulfinamido)oxetan-3-yl)-N-(methylsulfonyl)benzamide To a solution of 4-[3-[tert-butylsulfinyl(2-trimethylsilylethoxymethyl)amino]oxetan-3-yl]benzoic acid (1.00 g, 2.34 mmol) in N,N-dimethylformamide (20 mL) was added EDCI (1.35 g, 7.02 mmol) at 0° C. and the mixture was stirred for 0.5 hr. Then methanesulfonamide (334 mg, 3.51 mmol) and N,N-dimethylpyridine (857 mg, 7.02 mmol) were added at 0° C. The reaction mixture was stirred at rt for 12 hrs. On completion, the reaction was concentrated in vacuo, and the residue was purified by prep-HPLC [prep-HPLC (column: Daiso 250*50 mm, 10 um; mobile phase: [water (0.225% FA)-ACN]; B %: 55ACN %-75ACN %, 28 min; 55% min)] to give the title compound. LCMS: (ES$^+$) m/z (M+23)$^+$=527.3, tR=0.888

Step 5—4-(3-Aminooxetan-3-yl)-N-(methylsulfonyl)benzamide

To a solution of 4-[3-[tert-butylsulfinyl(2-trimethylsilylethoxymethyl)amino]oxetan-3-yl]-N-methyl-sulfonyl-benzamide (250 mg, 495 umol) in ethanol (10 mL) was added HCl/dioxane (4 M, 619 uL) and the reaction mixture was stirred at 0° C. for 1 hr. The reaction mixture was basified with saturated sodium bicarbonate solution until pH=8 and extracted with dichloromethane (3×20 mL). The combined organic layer was dried over anhydrous sodium sulfate, filtered and concentrated in vacuo to give the title compound. LCMS: (ES$^+$) m/z (M+23)$^+$=293.1, tR=0.108.

General Methods:

Example 1 (Method 1)—N-(1-(N-acetylsulamoyl)-4-phenylpiperidin-4-yl)-4,5-dichloro-1-methyl-1H-indole-2-carboxamide

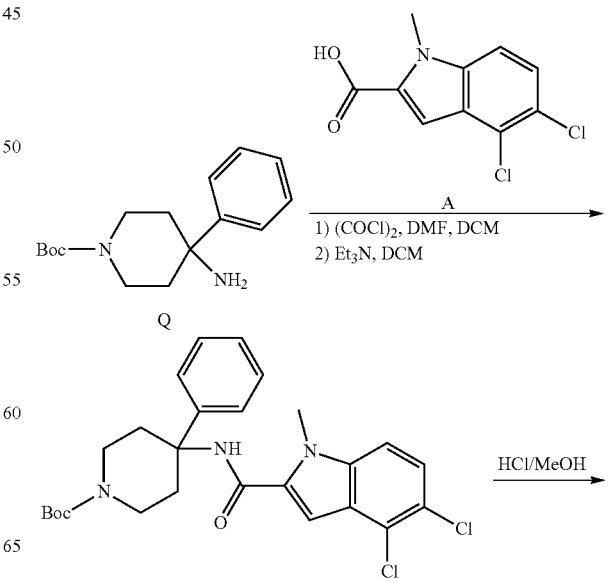

-continued

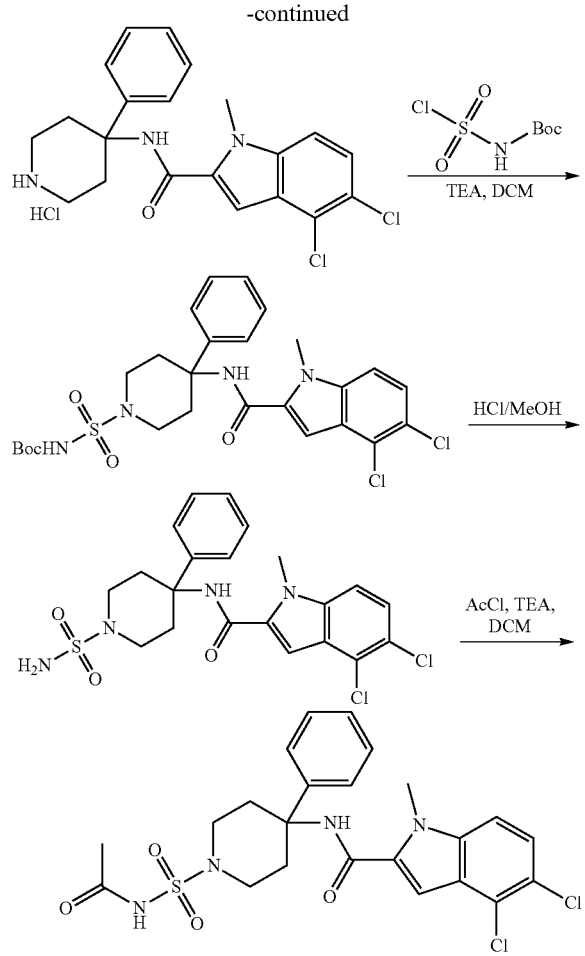

Step 1—Tert-butyl 4-(4,5-dichloro-1-methyl-1H-indole-2-carboxamido)-4-phenylpiperidine-1-carboxylate To a mixture of 4,5-dichloro-1-methyl-indole-2-carboxylic acid (1.78 g, 7.29 mmol) in dichloromethane (6.00 mL) was added N,N-dimethylformamide (53.3 mg, 729 umol), followed by oxalyl dichloride (1.85 g, 14.6 mmol) at rt. The mixture was then heated to 40° C. and stirred for 30 mins. On completion, the mixture was concentrated in vacuo to give a the title compound (1.90 g, 95% yield), which was used into the next step directly without further purification.

To a mixture of tert-butyl 4-amino-4-phenyl-piperidine-1-carboxylate (1.00 g, 3.62 mmol) and triethylamine (1.83 g, 18.1 mmol) in dichloromethane (10 mL) was added 4,5-dichloro-1-methyl-indole-2-carbonyl chloride (1.14 g, 4.34 mmol) at 0° C. The mixture was then warmed to rt and stirred for 16 hrs. On completion, the mixture was filtered, and the filtrate was concentrated in vacuo to give a residue, which was purified by column chromatography (eluent: petroleum ether:ethyl acetate=10:1 to 2:1) to give the title compound. $^1$H NMR (400 MHz, DMSO-$d_6$) δ=8.65 (br. s, 1H), 7.58 (d, J=8.8 Hz, 1H), 7.47-7.32 (m, 7H), 3.91 (d, J=12.8 Hz, 2H), 3.86 (s, 3H), 3.21-3.05 (m, 2H), 2.61 (d, J=12.8 Hz, 2H), 1.84 (t, J=12.8 Hz, 2H), 1.42 (s, 9H).

Step 2—4,5-Dichloro-1-methyl-N-(4-phenylpiperidin-4-yl)-1H-indole-2-carboxamide hydrochloride To a mixture of tert-butyl 4-[(4,5-dichloro-1-methyl-indole-2-carbonyl)amino]-4-phenyl-piperidine-1-carboxylate (800 mg, 1.59 mmol) in methanol (2 mL) was added a solution of 4 M hydrogen chloride in methanol (5 mL) at rt. The mixture was stirred at rt for 3 hrs. On completion, the mixture was concentrated in vacuo to give the title compound, which was used into the next step directly.

Step 3—Tert-butyl (4-(4,5-dichloro-1-methyl-1H-indole-2-carboxamido)-4-phenylpiperidin-1-yl)sulfonylcarbamate To a solution of 4,5-dichloro-1-methyl-N-(4-phenyl-4-piperidyl)indole-2-carboxamide-hydrochloride (700 mg, 1.60 mmol) and triethylamine (807 mg, 7.98 mmol) in dichloromethane (10 mL) was added tert-butyl N-chlorosulfonylcarbamate (344 mg, 1.60 mmol) portion-wise at 0° C. The resultant mixture was warmed to rt and stirred for 16 hrs. On completion, water (20 mL) was added to the mixture, which was then extracted with dichloromethane (3×20 mL). The combined dichloromethane phase was washed by brine (50 mL), dried over sodium sulfate, and concentrated in vacuo to give a residue, which was purified by column chromatography (petroleum:ethyl acetate=10:1 to 2:1) to give the title compound. $^1$H NMR (300 MHz, DMSO-$d_6$) δ=8.71 (br. s, 1H), 7.60 (d, J=9.0 Hz, 1H), 7.47-7.21 (m, 7H), 3.87 (s, 3H), 3.60 (d, J=12.3 Hz, 2H), 3.23 (t, J=5.7 Hz, 2H), 2.71 (d, J=12.9 Hz, 2H), 1.99 (t, J=10.2 Hz, 2H), 1.32 (s, 9H).

Step 4—4,5-Dichloro-1-methyl-N-(4-phenyl-1-sulfamoylpiperidin-4-yl)-1H-indole-2-carboxamide)

To a solution of tert-butyl N-[[4-[(4,5-dichloro-1-methyl-indole-2-carbonyl)amino]-4-phenyl-1-piperidyl]sulfonyl]carbamate (400 mg, 688 umol) in methanol (3 mL) and dichloromethane (3 mL) was added a solution of 4 M hydrogen chloride in methanol (4 mL) at rt. The mixture was stirred at rt for 2 hrs. On completion, the mixture was concentrated in vacuo to give a crude yellow solid which was purified by column chromatography (dichloromethane:methanol=100:1 to 10:1) to give the title compound. LCMS (ES+) m/z (M−H)=479, tR=1.183.

Step 5—N-(1-(N-acetylsulamoyl)-4-phenylpiperidin-4-yl)-4,5-dichloro-1-methyl-1H-indole-2-carboxamide To a solution of 4,5-dichloro-1-methyl-N-(4-phenyl-1-sulfamoyl-4-piperidyl)indole-2-carboxamide (130 mg, 270 umol) and triethylamine (54.7 mg, 540 umol) in dichloromethane (5 mL) was added acetyl chloride (31.8 mg, 405 umol) dropwise at 0° C. The resultant mixture was stirred for 16 hrs at rt. On completion, methanol (1 mL) was added to the mixture and the resulting mixture was concentrated in vacuo to give a residue. The residue was purified by prep-HPLC (Condition: water (0.05% ammonia hydroxide v/v)-ACN; Column: Phenomenex Gemini C18 250*50 10 u) to give the title compound. LCMS (ES−) m/z=521.1 (M−1), tR=1.034. $^1$HNMR (400 MHz, MeOD-$d_6$) δ=8.68 (br. s, 1H), 7.51 (dd, J=8.4, 1.2 Hz, 2H), 7.45-7.36 (m, 4H), 7.29-7.25 (m, 2H), 3.88 (s, 3H), 3.87-3.80 (m, 2H), 3.45-3.39 (m, 2H), 2.73 (d, J=12.4 Hz, 2H), 2.17 (td, J=14.0, 4.8 Hz, 2H), 2.08 (s, 3H).

Example 2—N-(4-(3-acetamidophenyl)-1-(N-acetylsulfamoyl)piperidin-4-yl)-4,5-dichloro-1-methyl-1H-indole-2-carboxamide

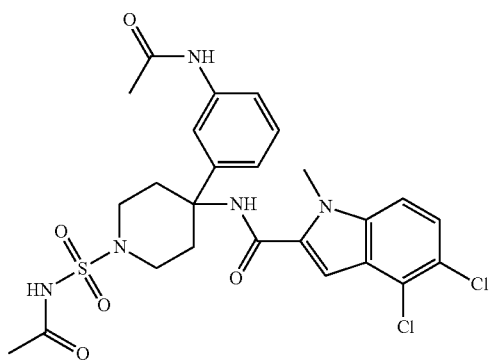 [SMILES: CC(=O)Nc1cccc(C2(NC(=O)c3cc4c(Cl)c(Cl)ccc4n3C)CCN(S(=O)(=O)NC(C)=O)CC2)c1]

N-(4-(3-acetamidophenyl)-1-(N-acetylsulfamoyl)piperidin-4-yl)-4,5-dichloro-1-methyl-1H-indole-2-carboxamide was synthesized via Method 1 with acid A and amine S. The residue from the final step was purified by prep-HPLC (Condition: water (0.05% ammonia hydroxide v/v)-ACN; Column: Phenomenex Gemini C18 250*50 10 u) to give the title compound. LCMS (ES$^+$) m/z=602 (M+23), tR=0.98. $^1$HNMR (400 MHz, MeOD-d$_6$) δ=7.82 (t, J=1.6 Hz, 1H), 7.46-7.38 (m, 3H), 7.33 (t, J=8.0 Hz, 1H), 7.26-7.23 (m, 2H), 3.90 (s, 3H), 3.79 (d, J=12.8 Hz, 2H), 3.45-3.38 (m, 2H), 2.70 (d, J=12.8 Hz, 2H), 2.21-2.13 (m, 5H), 2.09 (s, 3H).

Example 3—4,5-Dichloro-1-methyl-N-[4-phenyl-1-(pyrazin-2-ylsulfamoyl)-4-piperidyl]indole-2-carboxamide

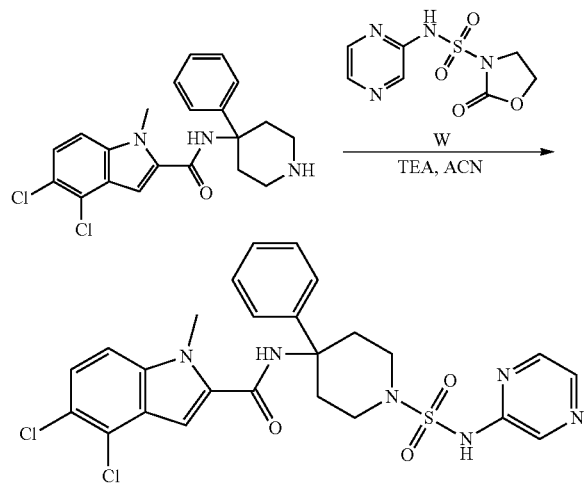

To a solution of 4,5-dichloro-1-methyl-N-(4-phenyl-4-piperidyl)indole-2-carboxamide (100 mg, 248 umol, synthesized via Method 1, Steps 1-2 as seen in Example 1) in anhydrous acetonitrile (3 mL) was added triethylamine (251 mg, 2.49 mmol). The mixture was stirred at rt for 30 mins. Then, 2-oxo-N-pyrazin-2-yl-oxazolidine-3-sulfonamide (91.0 mg, 372 umol) was added and the mixture was transferred to a microwave tube. The sealed tube was heated at 130° C. for 150 minutes under microwave. On completion, the reaction mixture was concentrated in vacuo. The residue was purified by prep-HPLC (Condition: 0.1% TFA-ACN; Column: Welch Ultimate AQ-C18 150*30 mm; Particle size: 5 um) to give the title compound. LCMS: (ES$^+$) m/z (M+H)+=559.2, tR=0.910. $^1$H NMR (400 MHz, DMSO-d$_6$) δ=11.01 (br. s., 1H), 8.66 (s, 1H), 8.43 (d, J=1.0 Hz, 1H), 8.27-8.20 (m, 2H), 7.59 (d, J=8.8 Hz, 1H), 7.46 (d, J=8.9 Hz, 1H), 7.44-7.39 (m, 2H), 7.34 (t, J=7.7 Hz, 2H), 7.27-7.21 (m, 1H), 7.14 (s, 1H), 3.83 (s, 3H), 3.67 (d, J=12.8 Hz, 2H), 3.26 (t, J=11.9 Hz, 2H), 2.72-2.61 (m, 2H), 2.01-1.87 (m, 2H).

Example 4—N-(1-(N-acetylsulfamoyl)-4-(3-cyanophenyl)piperidin-4-yl)-4,5-dichloro-1-methyl-1H-indole-2-carboxamide

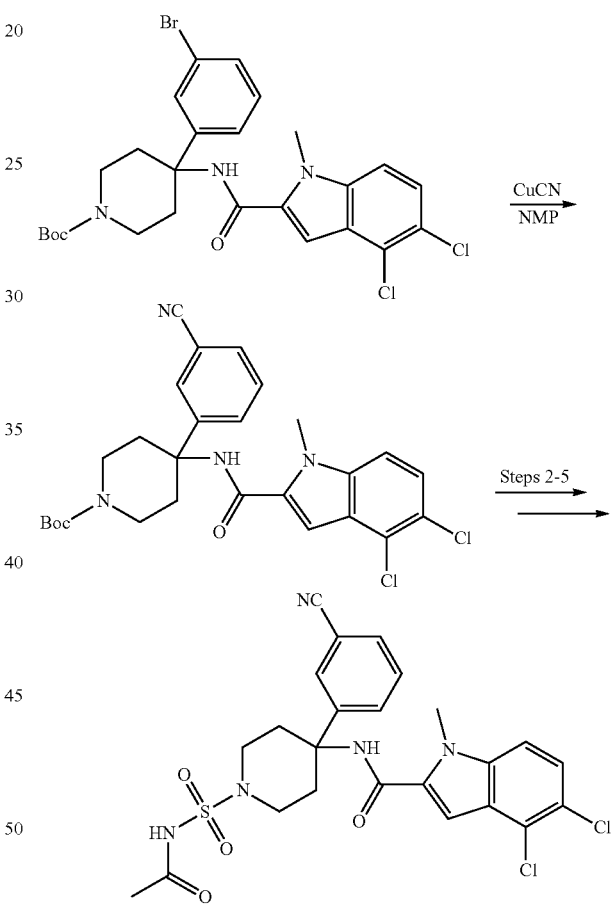

To a solution of tert-butyl 4-(3-bromophenyl)-4-[(4,5-dichloro-1-methyl-indole-2-carbonyl)amino]piperidine-1-carboxylate (950 mg, 1.63 mmol, synthesized via Method 1 with acid A and amine Q) in 1-methylpyrrolidin-2-one (15 mL) was added copper cyanide (730 mg, 8.15 mmol) at rt. The reaction mixture was stirred at 120° C. for 12 hrs. On completion, the reaction mixture was poured onto ice and extracted with ethyl acetate (3×200 mL). The organic layers were combined, washed with brine (50 mL), and concentrated in vacuo. The crude product was purified by silica gel chromatography (petroleum ether:ethyl acetate=10:1) to give tert-butyl 4-(3-cyanophenyl)-4-[(4,5-dichloro-1-methyl-indole-2-carbonyl)amino]piperidine-1-carboxylate.

LCMS: (ES⁻) m/z (M−H)⁻=525.2, tR=1.497. From tert-butyl 4-(3-cyanophenyl)-4-[(4,5-dichloro-1-methyl-indole-2-carbonyl)amino]piperidine-1-carboxylate the final product was then made via Method 1, Steps 2-5 to yield N-(1-(N-acetylsulfamoyl)-4-(3-cyanophenyl)piperidin-4-yl)-4,5-dichloro-1-methyl-1H-indole-2-carboxamide.
LCMS: (ES⁻) m/z (M−H)−=546.0, tR=1.377. ¹H NMR (400 MHz, MeOD) δ=7.90-7.83 (m, 2H), 7.68-7.62 (m, 1H), 7.61-7.55 (m, 1H), 7.48-7.34 (m, 3H), 7.32-7.27 (m, 2H), 3.89 (s, 3H), 3.76 (d, J=12.4 Hz, 2H), 3.16 (q, J=7.4 Hz, 2H), 2.69 (d, J=11.4 Hz, 2H), 2.22-2.14 (m, 2H), 2.05 (s, 3H).

Example 5—N-(4-(3-Acetamidophenyl)-1-acetylpi-peridin-4-yl)-4,5-dichloro-1-methyl-1H-indole-2-carboxamide

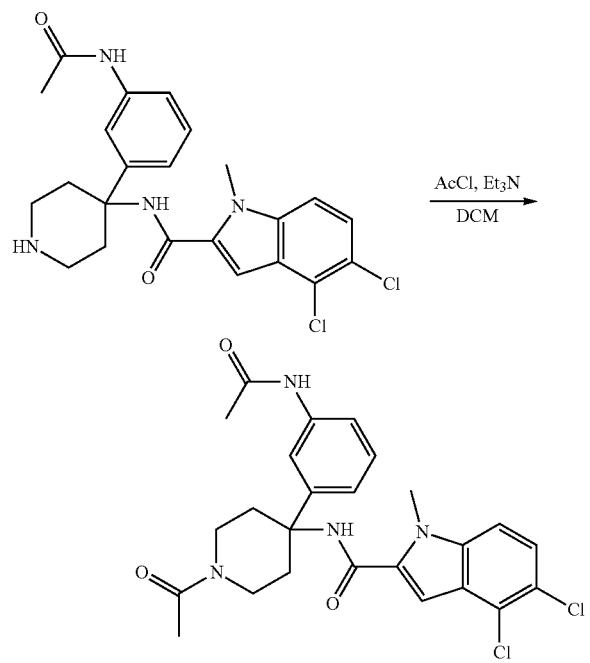 [SMILES: CC(=O)Nc1cccc(C2(NC(=O)c3cc4c(Cl)c(Cl)ccc4n3C)CCNCC2)c1 ; CC(=O)Nc1cccc(C2(NC(=O)c3cc4c(Cl)c(Cl)ccc4n3C)CCN(C(C)=O)CC2)c1]

To a solution of N-[4-(3-acetamidophenyl)-4-piperidyl]-4,5-dichloro-1-methyl-indole-2-carboxamide hydrochloride (350 mg, 706 umol, synthesized via Method 1, Steps 1-2 with acid and amine S as starting materials as seen in Example 2) and triethylamine (357 mg, 3.53 mmol) in dichloromethane (5.00 mL) was added acetyl chloride (83.1 mg, 1.06 mmol) dropwise at 0° C. The reaction mixture was warmed to rt and stirred for 0.5 hrs. On completion, water (10 mL) was added to the mixture and the organics were then extracted with dichloromethane (3×10 mL). The combined dichloromethane phase was washed with brine (30 mL) and dried over sodium sulfate. The combined dichloromethane phase was concentrated in vacuo. The residue was purified by prep-HPLC (condition: 0.1% TFA-ACN; column: Welch Ultimate AQ-C18 150*30 mm*5 um) to give the title compound. LCMS: (ES⁺) m/z (M+H)⁺=501.1, tR=0.989. ¹H NMR (400 MHz, DMSO-d6) δ=9.94 (br. s., 1H), 8.75 (s, 1H), 7.71 (s, 1H), 7.59 (d, J=8.8 Hz, 1H), 7.47-7.43 (m, 2H), 7.40 (s, 1H), 7.26 (t, J=8.0 Hz, 1H), 7.13 (d, J=7.6 Hz, 1H), 4.35 (d, J=13.2 Hz, 1H), 3.88 (s, 3H), 3.80 (d, J=13.2 Hz, 1H), 3.43 (t, J=12.4 Hz, 1H), 2.94 (t, J=12.4 Hz, 1H), 2.60 (t, J=14.8 Hz, 2H), 2.06 (s, 3H), 2.03 (s, 3H), 1.91 (td, J=13.6 Hz, 1H), 1.74 (td, J=12.8, 3.6 Hz, 1H).

Example 6 (Method 2)—(±)-4,5-dichloro-1-methyl-N-[1-(methylcarbamoylsulfamoyl)-3-phenyl-3-piperidyl]indole-2-carboxamide

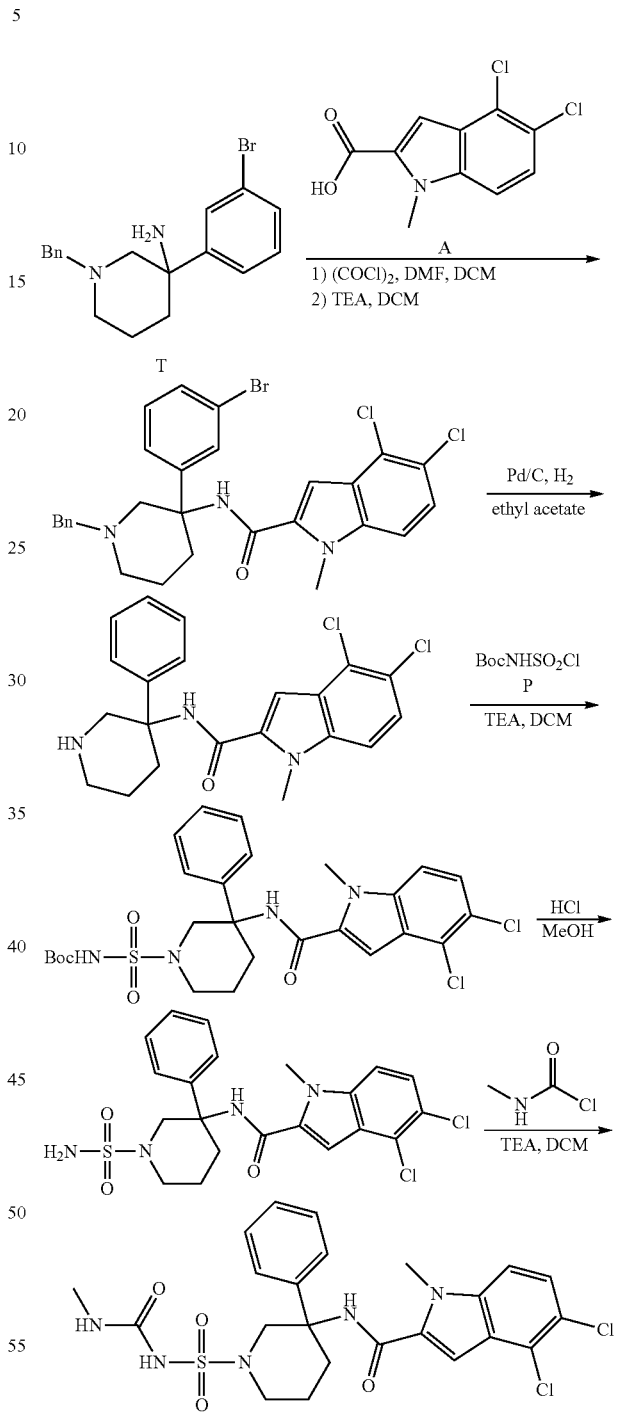

Step 1—(±)-N-[1-benzyl-3-(3-bromophenyl)-3-piperidyl]-4,5-dichloro-1-methyl-indole-2-carboxamide To a solution of 4,5-dichloro-1-methyl-indole-2-carboxylic acid (1.06 g, 4.35 mmol) in dichloromethane (10 mL) was added oxalyl chloride (1.10 g, 8.70 mmol) and dimethylformamide (21.2 mg, 290 umol). The mixture was stirred at rt for 1 hr. On completion, the solution was concentrated under reduce pressure to give a residue. The residue was dissolved in dichloromethane (10 mL) and added into a solution of (±)-1-benzyl-3-(3-bromophenyl)piperidin-3-amine (1.00 g, 2.90 mmol) and triethylamine (880 mg, 8.70 mmol), and the mixture was stirred at rt 1 hr. On completion, the reaction mixture was quenched with water (100 mL) at 0° C., and extracted with dichloromethane (3×100 mL). The combined organic layers were washed with aqueous sodium chloride (2×50 mL), dried over sodium chloride, filtered and concentrated in vacuo to give a residue. The residue was purified by column chromatography (petroleum ether:ethyl acetate=5:1 to 1:1) to give the title compound. $^1$H NMR (400 MHz, CDCl3) δ=7.55 (s, 1H), 7.43-7.40 (m, 4H), 7.37-7.32 (m, 5H), 7.23-7.19 (m, 2H), 7.06 (s, 1H), 3.97 (s, 3H), 3.64 (d, J=12.8 Hz, 1H), 3.50 (d, J=12.8 Hz, 1H), 3.01 (d, J=10.8 Hz, 1H), 2.78-2.77 (m, 2H), 2.1-1.80 (m, 5H).

Step 2—(±)-4,5-dichloro-1-methyl-N-(3-phenyl-3-piperidyl)indole-2-carboxamide

To a solution of (±)-N-[1-benzyl-3-(3-bromophenyl)-3-piperidyl]-4,5-dichloro-1-methyl-indole-2-carboxamide (450 mg, 788 umol) in ethyl acetate (5 mL) was added Pd/C (300 mg, 788 umol). The suspension was degassed under vacuum and purged with hydrogen several times. The mixture was stirred under hydrogen (15 psi) at 25° C. for 12 hours. On completion, the reaction mixture was filtered and concentrated in vacuo to give the title compound. LCMS: (ES$^+$) m/z (M+H)$^+$=402.1, tR=1.584.

Step 3—(±)-tert-butyl-N-[[3-[(4,5-dichloro-1-methyl-indole-2-carbonyl)amino]-3-phenyl-1-piperidyl]sulfonyl]carbamate To a solution of (±)-4,5-dichloro-1-methyl-N-(3-phenyl-3-piperidyl)indole-2-carboxamide (350 mg, 869 umol) in dichloromethane (2 mL) was added triethylamine (264 mg, 2.61 mmol) and tert-butyl N-chlorosulfonylcarbamate (281 mg, 1.30 mmol). The mixture was stirred at rt for 1 hour. On completion, the reaction mixture was quenched by the addition of hydrochloric acid (1 N, 10 mL) at 0° C., the solution was then diluted with dichloromethane (100 mL) separated and extracted with dichloromethane (3×50 mL). The combined organic layers were washed with aqueous sodium chloride (2×25 mL), dried over sodium sulfate, filtered and concentrated in vacuo to give the title compound. LCMS: (ES$^+$) m/z (M+23)$^+$=603.1, tR=0.897.

Step 4—(±)-4,5-dichloro-1-methyl-N-(3-phenyl-1-sulfamoyl-3-piperidyl)indole-2-carboxamide A solution of (±)-tert-butyl-N-[[3-[(4,5-dichloro-1-methyl-indole-2-carbonyl)amino]-3-phenyl-1-piperidyl]sulfonyl]carbamate (300 mg, 516 umol) in hydrogen chloride/methanol (5 mL) was stirred at rt for 1 hour. On completion, the reaction mixture was concentrated in vacuo to give the title compound. LCMS: (ES$^+$) m/z (M+H)$^+$=483.1, tR=0.800.

Step 5—(±)-4,5-dichloro-1-methyl-N-[1-(methylcarbamoylsulfamoyl)-3-phenyl-3-piperidyl]indole-2-carboxamide To a solution of (±)-4,5-dichloro-1-methyl-N-(3-phenyl-1-sulfamoyl-3-piperidyl) indole-2-carboxamide (200 mg, 386 umol) in dichloromethane (5 mL) was added triethyl-amine (117 mg, 1.16 mmol) and N-methylcarbamoyl chloride (54.2 mg, 579 umol). The mixture was stirred at rt for 1 hour. On completion, the reaction mixture was quenched by the addition of hydrochloric acid (1 N, 10 mL) at 0° C. The solution was then diluted with water (50 mL), extracted with dichloromethane (3×50 mL), and dried over anhydrous sodium sulfate. The combined organic layers were filtered and concentrated in vacuo to give a residue. The residue was purified by pre-HPLC (Phenomenex Gemini C18 250*50 10 u, water (0.05% ammonia hydroxide)-ACN) and lyophilized in vacuo to give the title compound. LCMS: (ES$^+$) m/z (M+H)$^+$=538.1, tR=0.894. $^1$H NMR (400 MHz, MeOD) δ=7.58 (d, J=7.6 Hz, 2H), 7.41-7.36 (m, 5H), 7.30-7.25 (m, 1H), 4.13-4.10 (m, 1H), 3.89 (s, 3H), 3.81-3.78 (m, 1H), 3.33-3.32 (m, 1H), 3.09-2.86 (m, 2H), 2.64 (s, 3H), 2.10-1.80 (m, 3H).

Example 7—(±)-4,5-Dichloro-N-[3-(3-cyanophenyl)-1-(methylcarbamoylsulfamoyl)-3-piperidyl]-1-methyl-indole-2-carboxamide

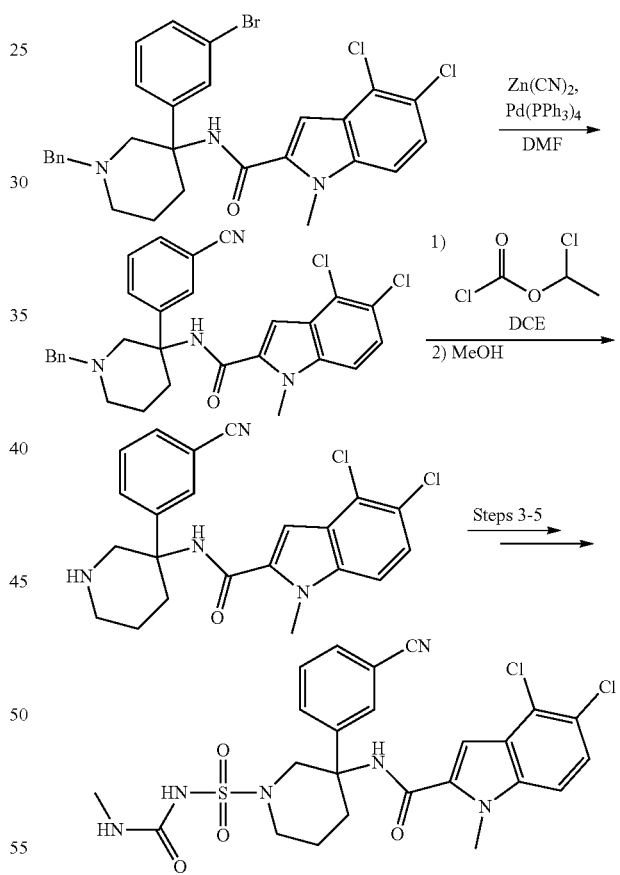

Step 1—(±)-N-[1-benzyl-3-(3-cyanophenyl)-3-piperidyl]-4,5-dichloro-1-methyl-indole-2-carboxamide To a solution of (±)-N-(1-benzyl-3-(3-bromophenyl)piperidin-3-yl)-4,5-dichloro-1-methyl-1H-indole-2-carboxamide (700 mg, 1.23 mmol, synthesized via Step 1 of Method 2 as seen above in Example 6) in dimethyl formamide (5 mL) was added zinc cyanide (433 mg, 3.69 mmol) and tetrakis (triphenylphosphine) palladium (142 mg, 123 umol). The mixture was stirred at 120° C. for 2 hours under nitrogen atmosphere. On completion, the reaction mixture was quenched by addition of water (100 mL) at 0° C., and then extracted with ethyl acetate (3×50 mL). The combined organic layers were washed with brine (2×50 mL), dried over anhydrous sodium sulfate, filtered and concentrated in vacuo to give a residue. The residue was purified by column chromatography (petroleum ether:ethyl acetate=5:1 to 1:1) to give the title compound. $^1$H NMR (400 MHz, CDCl3) δ=7.70 (s, 1H), 7.50 (d, J=8.0 Hz, 1H), 7.44 (d, J=6.8 Hz, 2H), 7.42-7.39 (m, 7H), 7.22 (d, J=8.8 Hz, 1H), 7.06 (s, 1H), 3.96 (s, 3H), 3.77 (d, J=13.2 Hz, 1H), 3.58 (d, J=13.2 Hz, 1H), 3.05 (d, J=11.2 Hz, 1H), 2.80-2.77 (m, 2H), 2.21-1.80 (m, 5H).

Step 2—(±)-4,5-Dichloro-N-[3-(3-cyanophenyl)-3-piperidyl]-1-methyl-indole-2-carboxamide To a solution of (±)-N-(1-benzyl-3-(3-cyanophenyl)piperidin-3-yl)-4,5-dichloro-1-methyl-1H-indole-2-carboxamide (500 mg, 966 umol) in 1,2-dichloroethane (2 mL) was added 1-chloroethyl carbonochloridate (2.76 g, 19.3 mmol), and the mixture was stirred at 90° C. for 12 hours. On completion, the reaction mixture was concentrated in vacuo. Then methanol (10 mL) was added to the residue and the solution was stirred at 80° C. for 1 hr. The solution was then concentrated in vacuo to remove methanol. The residue was diluted with water (30 mL) and extracted with dichloromethane (3×50 mL). The combined organic layers were washed with brine (2×50 mL), dried over anhydrous sodium sulfate, filtered and concentrated in vacuo to give the title compound, which was used into next step without further purification. LCMS: (ES$^+$) m/z (M+H)$^+$=427.1, tR=0.753.

Step 3-5—(±)-4,5-Dichloro-N-[3-(3-cyanophenyl)-1-(methylcarbamoylsulfamoyl)-3-piperidyl]-1-methyl-indole-2-carboxamide (±)-4,5-Dichloro-N-[3-(3-cyanophenyl)-3-piperidyl]-1-methyl-indole-2-carboxamide was brought on to the final product via Steps 3-5 of Method 2 to give the title compound. LCMS: (ES$^+$) m/z (M+H)$^+$=563.0, tR=0.93. $^1$H NMR (400 IMHz, DMSO-d$_6$) δ=10.27 (br. s., 1H), 8.65 (s, 1H), 8.05-7.96 (m, 1H), 7.95-7.85 (m, 1H), 7.74 (d, J=7.78 Hz, 1H), 7.64-7.52 (m, 2H), 7.45 (d, J=8.78 Hz, 1H), 7.39-7.33 (m, 1H), 6.87 (br. s., 1H), 6.31 (br. s., 1H), 3.97-3.87 (m, 2H), 3.87-3.82 (m, 3H), 3.47-3.37 (m, 1H), 3.15 (t, J=9.03 Hz, 1H), 2.56 (d, J=4.27 Hz, 3H), 2.32 (d, J=9.29 Hz, 1H), 2.06 (t, J=9.79 Hz, 1H), 1.91-1.78 (m, 1H), 1.58-1.40 (m, 1H).

Example 8 (Method 3)—(±)-N-[1-(acetylsulfamoyl)-3-phenyl-pyrrolidin-3-yl]-4,5-dichloro-1-methyl-indole-2-carboxamide

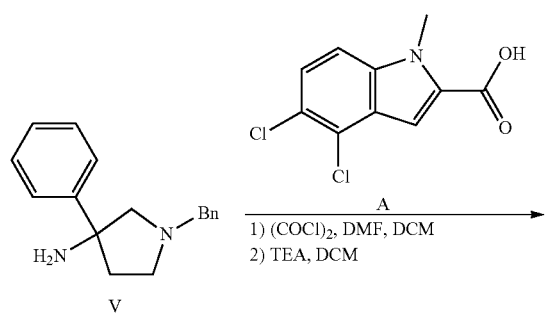

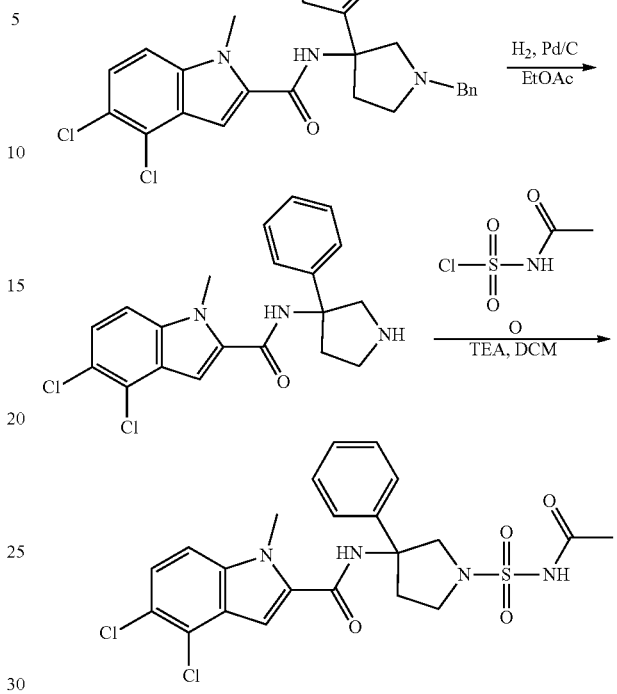

Step 1—(±)-(1-Benzyl-3-phenyl-pyrrolidin-3-yl)-4,5-dichloro-1-methyl-indole-2-carboxamide To a solution of 4,5-dichloro-1-methyl-indole-2-carboxylic acid (500 mg, 2.05 mmol) in a mixture of dichloromethane (20 mL) and N,N-dimethylformamide (157 uL) was added oxalyl chloride (1.04 g, 8.19 mmol) dropwise and the reaction mixture was stirred at rt for 1 hr. On completion, the reaction mixture was concentrated in vacuo to give 4,5-dichloro-1-methyl-indole-2-carbonyl chloride, which was used in the next step directly.

To a solution of (±)-1-benzyl-3-phenyl-pyrrolidin-3-amine (500 mg, 1.98 mmol) in dichloromethane (10 mL) was added 4,5-dichloro-1-methyl-indole-2-carbonyl chloride (500 mg, 1.98 mmol) and triethylamine (601 mg, 5.94 mmol). The reaction was stirred at rt for 12 hrs. On completion, the reaction was diluted with saturated ammonium chloride (10 mL), dried over anhydrous sodium sulfate, filtered and concentrated in vacuo. The reaction was purified by chromatography on silica gel (petroleum ether:ethyl acetate=1:1 to dichloromethane:methanol=30:1) to give the title compound. LCMS: (ES$^+$) m:z (M+H)$^-$=478.2.

Step 2—(±)-4,5-Dichloro-1-methyl-N-(3-phenylpyrrolidin-3-yl)indole-2-carboxamide To the mixture of (±)-(1-benzyl-3-phenyl-pyrrolidin-3-yl)-4,5-dichloro-1-methyl-indole-2-carboxamide (250 mg, 522 umol) in ethyl acetate (10 mL) was added Pd/C (10 mg, 10%), and the mixture was stirred at rt under hydrogen (50 psi) for 12 hrs. On completion the mixture was filtered and the filtrate was concentrated in vacuo. The residue was diluted with dichloromethane (30 mL), washed with saturated sodium bicarbonate (10 mL), dried over anhydrous sodium sulfate, filtered and concentrated. The residue was purified by chromatography on silica gel (dichloromethane:methanol=30:1) to give the title compound. LCMS: (ES+) m:z (M+H)+=388.1.

Step 3—(±)-N-[1-(acetylsulfamoyl)-3-phenyl-pyrrolidin-3-yl]-4,5-dichloro-1-methyl-indole-2-carboxamide To a solution of (±)-4,5-dichloro-1-methyl-N-(3-phenylpyrrolidin-3-yl)indole-2-carboxamide (65 mg, 167 umol) in dichloromethane (5 mL) was added N-acetylsulfamoyl chloride (52.7 mg, 334 umol) and triethylamine (67.7 mg, 669 umol), and the mixture was stirred at rt for 2 hrs. On completion, the mixture was diluted with saturated ammonium chloride (10 mL), extracted with dichloromethane (3×20 mL), dried over anhydrous sodium sulfate, filtered and concentrated in vacuo. The residue was purified by prep-HPLC (YMC-Actus ODS-AQ 150*30 5 u, water (0.1% TFA)-ACN) and lyophilized in vacuo to give the title compound. LCMS: (ES+) m:z (M+23)+=531.0, tR=0.873. 1H NMR (400 MHz, DMSO-d6) δ=11.52 (s, 1H), 9.03 (s, 1H), 7.60 (d, J=8.8 Hz, 1H), 7.46 (dd, J=8.2, 3H), 7.40 (s, 1H), 7.36 (t, J=7.7 Hz, 2H), 7.28-7.24 (m, 1H), 4.22 (d, J=10.5 Hz, 1H), 3.93 (d, J=10.5 Hz, 1H), 3.89 (s, 3H), 3.75 (d, J=7.8 Hz, 1H), 3.59-3.46 (m, 1H), 2.78-2.70 (m, 1H), 2.25 (d, J=12.8 Hz, 1H), 1.84 (s, 3H).

Example 9—N-(1-(N-acetylsulfamoyl)-3-phenylazetidin-3-yl)-4,5-dichloro-1-methyl-1H-indole-2-carboxamide

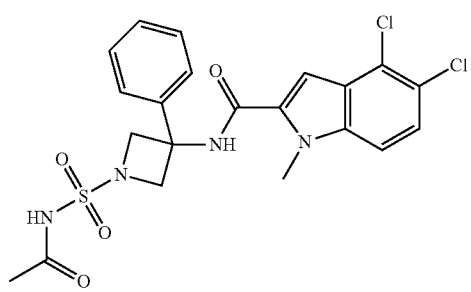 [SMILES: CC(=O)NS(=O)(=O)N1CC(NC(=O)c2cc3c(Cl)c(Cl)ccc3n2C)(c2ccccc2)C1]

N-(1-(N-acetylsulfamoyl)-3-phenylazetidin-3-yl)-4,5-dichloro-1-methyl-1H-indole-2-carboxamide was synthesized via Method 3 with acid A and amine U. In Step 2, 1 drop of HCl was added to catalyze the deprotection. The residue of the final step was purified by Prep-TLC (dichloromethane:methanol=15:1) to give the title compound. LCMS: (ES+) m/z (M+H)+=495.0, tR=0.885. 1H NMR (400 MHz, MeOD) δ=7.62 (s, 1H), 7.60 (s, 1H), 7.49-7.38 (m, 4H), 7.37-7.30 (m, 2H), 4.72 (d, J=8.8 Hz, 2H), 4.43 (d, J=8.8 Hz, 2H), 3.99 (s, 3H), 2.06 (s, 3H).

Example 10 (Method 4)—3-(1-(N-acetylsulfamoyl)-4-(4,5-dichloro-1-methyl-1H-indole-2-carboxamido)piperidin-4-yl)benzoic acid

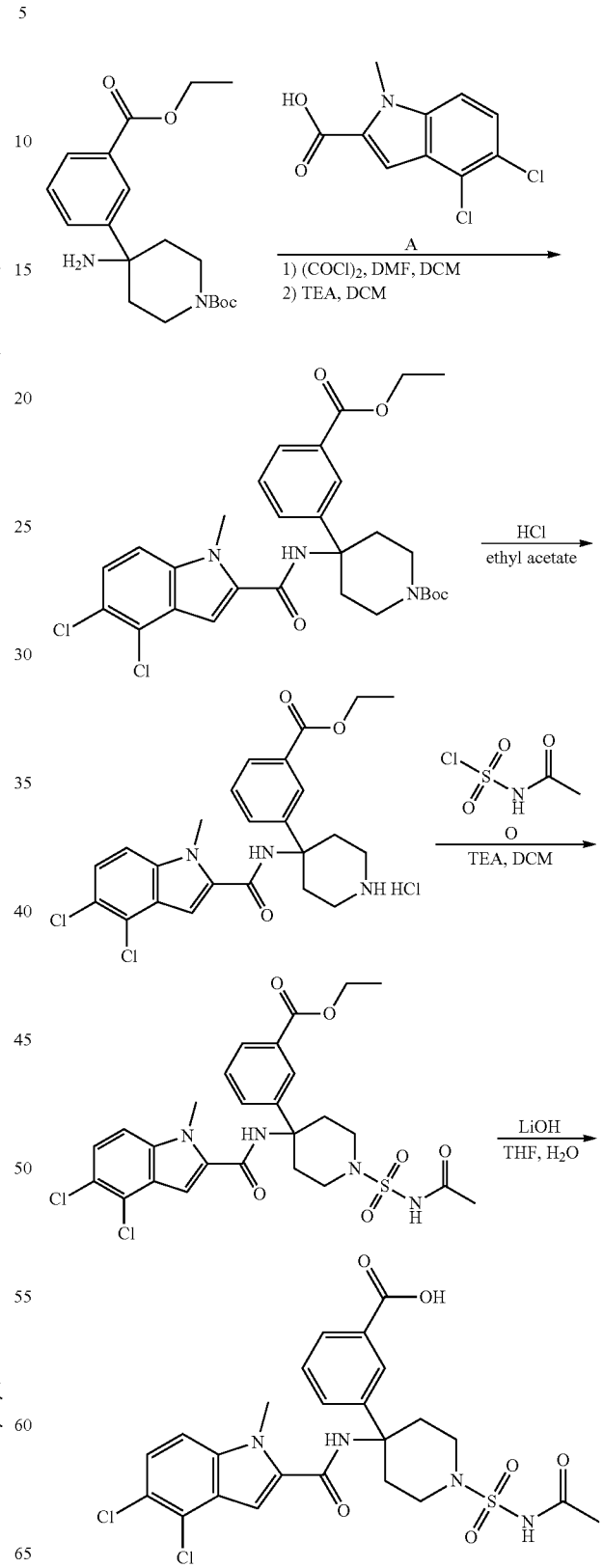

Step 1—Tert-butyl 4-(4,5-dichloro-1-methyl-1H-indole-2-carboxamido)-4-(3-(ethoxycarbonyl) piperidine-1-carboxylate To a mixture of 4,5-dichloro-1-methyl-indole-2-carboxylic acid (1.78 g, 7.29 mmol) in dichloromethane (6.00 mL) was added N,N-dimethylformamide (53.3 mg, 729 umol), followed by oxalyl dichloride (1.85 g, 14.6 mmol) in one portion at rt. The mixture was heated to 40° C. and stirred for 30 min. On completion, the mixture was concentrated in vacuo to give the title compound (crude).

To a mixture of tert-butyl 4-amino-4-(3-ethoxycarbonylphenyl)piperidine-1-carboxylate (1.40 g, 4.02 mmol) and triethylamine (1.22 g, 12.1 mmol) in dichloromethane (15.0 mL) was added 4,5-dichloro-1-methyl-indole-2-carbonyl chloride (1.27 g, 4.82 mmol) in three portions at rt. The mixture was stirred at rt for 16 hrs. On completion, the mixture was filtered, and the filtrate was concentrated in vacuo. The residue was purified by column chromatography (petroleum ether:ethyl acetate=10:1 to 5:1) to give the title compound. $^1$H NMR (400 MHz, DMSO-$d_6$) δ=8.82 (br. s, 1H), 8.07 (s, 1H), 7.84 (d, J=7.6 Hz, 1H), 7.76 (d, J=8.4 Hz, 1H), 7.60 (d, J=8.4 Hz, 1H), 7.52 (t, J=8.0 Hz, 1H), 7.46 (d, J=8.8 Hz, 1H), 7.39 (s, 1H), 4.30 (q, J=7.2 Hz, 2H), 3.94-3.85 (m, 2H) 3.85 (s, 3H), 3.16 (m, 2H), 2.61 (d, J=13.2 Hz, 2H), 1.82-1.89 (m, 2H), 1.43 (s, 9H), 1.30 (t, J=7.2 Hz, 3H).

Step 2—Ethyl 3-(4-(4,5-dichloro-1-methyl-1H-indole-2-carboxamido) piperidin-4-yl)benzoate hydrochloride To a mixture of tert-butyl 4-[(4,5-dichloro-1-methyl-indole-2-carbonyl)amino]-4-(3-ethoxycarbonylphenyl) piperidine-1-carboxylate (370 mg, 644 umol) in ethyl acetate (3.00 mL) was added hydrogen chloride/ethyl acetate (4M, 5.00 mL) in one portion at 0° C. The mixture was stirred at rt for 1 hr. On completion, the mixture was concentrated in vacuo to give the title compound which was used in the next step. LCMS: (ES$^+$) m:z (M+H)$^+$=474.1, tR=0.925.

Step 3—Ethyl 3-(1-(N-acetylsulfamoyl)-4-(4,5-dichloro-1-methyl-1H-indole-2-carboxamido) piperidin-4-yl) benzoate To a mixture of ethyl 3-[4-[(4,5-dichloro-1-methyl-indole-2-carbonyl)amino]-4-piperidyl]benzoate hydrochloride (329 mg, 644 umol) and triethylamine (326 mg, 3.22 mmol) in dichloromethane (5.00 mL) was added N-acetylsulfamoyl chloride (101 mg, 644 umol) in three portions at rt. The mixture was stirred at rt for 2 hrs. On completion, to the mixture was added water (10 mL) and then it was extracted with dichloromethane (3×10 mL). The combined organic phase was washed with brine, dried over sodium sulfate, and concentrated in vacuo to give a crude product which was purified by column chromatography (petroleum ether:ethyl acetate=7:1 to 1:1) to give the title compound. $^1$H NMR (400 MHz, DMSO-$d_6$) δ=11.53 (br. s, 1H), 8.87 (br. s, 1H), 8.06 (s, 1H), 7.86 (d, J=7.6 Hz, 1H), 7.76 (d, J=8.8 Hz, 1H), 7.62 (d, J=8.8 Hz, 1H), 7.53 (t, J=8.0 Hz, 1H), 7.47 (d, J=8.8 Hz, 1H), 7.29 (s, 1H), 4.31 (q, J=7.2 Hz, 2H), 3.86 (s, 3H), 3.63 (d, J=12.0 Hz, 2H), 3.28 (d, J=12.4 Hz, 2H), 2.67-2.70 (m, 2H), 2.01-2.06 (m, 5H), 1.31 (t, J=7.2 Hz, 3H).

Step 4—3-(1-(N-acetylsulfamoyl)-4-(4,5-dichloro-1-methyl-1H-indole-2-carboxamido) piperidin-4-yl) benzoic acid To a mixture of ethyl 3-[1-(acetylsulfamoyl)-4-[(4,5-dichloro-1-methyl-indole-2-carbonyl)amino]-4-piperidyl] benzoate (140 mg, 235 umol) in tetrahydrofuran (3.00 mL) was added the solution of lithium hydroxide (19.7 mg, 470 umol) in water (3.00 mL) dropwise at rt. The mixture was stirred at rt for 16 hrs. On completion, the mixture was concentrated in vacuo to give the aqueous phase which was cooled to 0° C., then hydrochloride solution (1N, 1 mL) was added to adjust pH to 4~5. The product was extracted with dichloromethane (3×10 mL). The combined organic phase was concentrated in vacuo to give the title product as a white solid (70 mg, 51% yield). LCMS (ESI) m/z=565 (M−H), tR=1.101. $^1$H NMR (400 MHz, DMSO-$d_6$) δ=8.85 (br. s, 1H), 8.05 (s, 1H), 7.83 (d, J=6.4 Hz, 1H), 7.73 (d, J=7.6 Hz, 1H), 7.61 (d, J=8.4 Hz, 1H), 7.46-7.52 (m, 2H), 7.28 (s, 1H), 3.85 (s, 3H), 3.63 (d, J=12.0 Hz, 2H), 3.27-3.30 (m, 2H), 2.69 (d, J=10.8 Hz, 2H), 2.00 (m, 5H).

Example 11—4-[1-(Acetylsulfamoyl)-4-[(4,5-dichloro-1-methyl-indole-2-carbonyl)amino]-4-piperidyl]benzoic acid

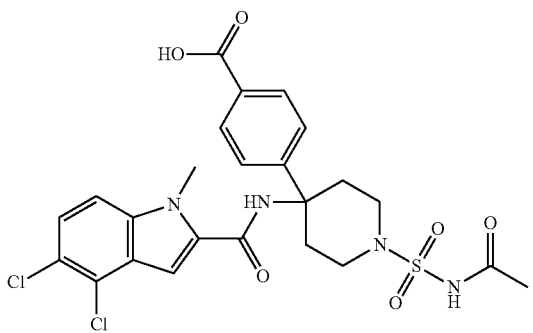 [SMILES: CC(=O)NS(=O)(=O)N1CCC(NC(=O)c2cc3c(Cl)c(Cl)ccc3n2C)(c2ccc(C(=O)O)cc2)CC1]

4-[1-(Acetylsulfamoyl)-4-[(4,5-dichloro-1-methyl-indole-2-carbonyl)amino]-4-piperidyl]benzoic acid was synthesized via Method 4 with acid A and amine Y. The residue of the final step was purified with prep-HPLC (Instrument: GX-D; Column: Boston Green ODS 150*30 5 u; Mobile phase: 0.225% formic acid-acetonitrile) to give the title compound. LCMS: (ES$^+$) m/z (M+Na)$^+$=589.0, tR=1.189. $^1$H NMR (400 MHz, DMSO-$d_6$) δ=8.81 (s, 1H), 7.92 (d, J=8.5 Hz, 2H), 7.61 (d, J=8.8 Hz, 1H), 7.57 (d, J=8.5 Hz, 2H), 7.47 (d, J=8.8 Hz, 1H), 7.31 (s, 1H), 3.85 (s, 3H), 3.59 (d, J=11.2 Hz, 2H), 3.27-3.18 (m, 2H), 2.63-2.58 (m, 2H), 2.07-1.98 (m, 2H), 1.97 (s, 3H).

Example 12—N-(1-(N-acetylsulfamoyl)-4-(3-(hydroxymethyl)phenyl)piperidin-4-yl)-4,5-dichloro-1-methyl-1H-indole-2-carboxamide

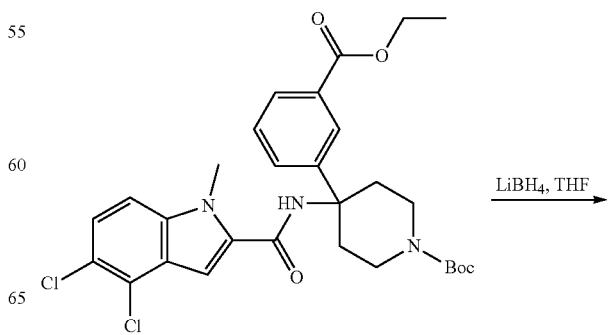

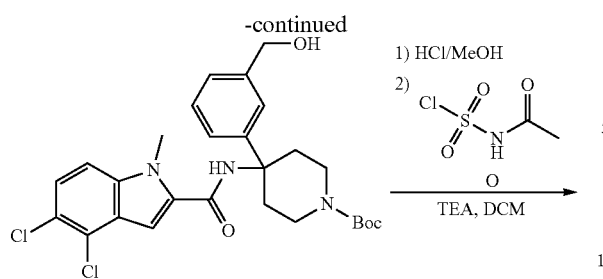

Step 1—Tert-butyl 4-(4,5-dichloro-1-methyl-1H-indole-2-carboxamido)-4-(3-(hydroxymethyl)phenyl) piperidine-1-carboxylate To a solution of tert-butyl 4-[(4,5-dichloro-1-methyl-indole-2-carbonyl)amino]-4-(3-ethoxycarbonylphenyl)piperidine-1-carboxylate (100 mg, 174 umol, synthesized via Method 1 as seen in Example 10) in tetrahydrofuran (5.00 mL) was added lithium hydroboronate (11.4 mg, 522 umol) at rt. The resultant mixture was stirred for 16 hrs. On completion, water (3 mL) was added to the mixture and then it was extracted with dichloromethane (3×5 mL). The combined dichloromethane phase was concentrated in vacuo to give a white solid. LCMS (ESI⁻) m/z (M−100)=432.1, tR=1.194.

Step 2-3—N-(1-(N-acetylsulfamoyl)-4-(3-(hydroxymethyl)phenyl)piperidin-4-yl)-4,5-dichloro-1-methyl-1H-indole-2-carboxamide Tert-butyl 4-(4,5-dichloro-1-methyl-1H-indole-2-carboxamido)-4-(3-(hydroxymethyl)phenyl) piperidine-1-carboxylate was then converted to the final product via Method 4, Steps 2-3 to yield the title compound. LCMS (ESI⁻) m/z (M−1)=551.0, tR=1.368. ¹H NMR (400 MHz, DMSO-d₆) δ=8.71 (br. s, 1H), 7.61 (d, J=8.8 Hz, 1H), 7.46 (d, J=8.8 Hz, 1H), 7.43 (s, 1H), 7.30~7.32 (m, 2H), 7.28 (s, 1H), 7.19 (d, J=6.0 Hz, 1H), 5.19 (t, J=5.2 Hz, 1H), 4.50 (d, J=4.8 Hz, 2H), 3.87 (s, 3H), 3.60 (d, J=12 Hz, 2H), 3.25 (t, J=12.4 Hz, 2H), 2.68 (d, J=12.4 Hz, 2H), 1.95~2.00 (m, 5H).

Example 13—N-(1-(N-Acetylsulfamoyl)-4-(3-aminophenyl)piperidin-4-yl)-4,5-dichloro-1-methyl-1H-indole-2-carboxamide

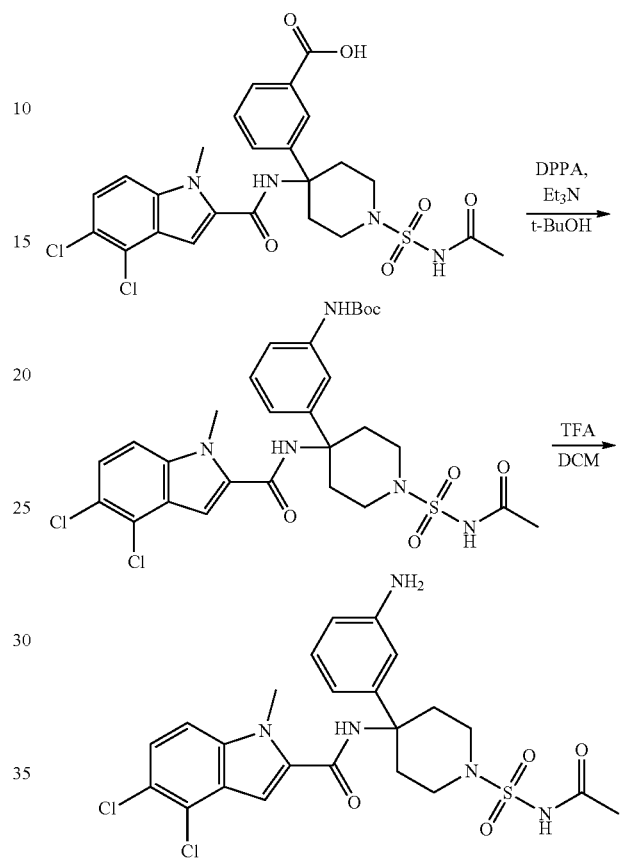

Step 1—(±)-Tert-butyl-(3-(1-(N-acetylsulfamoyl)-4-(4,5-dichloro-1-methyl-1H-indole-2-carboxamido) piperidin-4-yl)phenyl)carbamate The mixture of (±)-3-[1-(acetylsulfamoyl)-4-[(4,5-dichloro-1-methyl-indole-2-carbonyl)amino]-4-piperidyl] benzoic acid (100 mg, 176 umol, Example 10) and 3 Å MS (400 mg) was dried in vacuo to remove the water for 30 min. Then, the pre-dried solvent tert-butanol (3.00 mL) was added, followed by triethylamine (23.2 mg, 229 umol). The mixture was stirred for 30 min, and DPPA (6 drops) was added at rt. The reaction mixture was flushed with nitrogen three times and heated to 90° C. with stirring for 16 hrs. On completion, the mixture was concentrated in vacuo directly to give a residue which was purified by column chromatography (petroleum ether:ethyl acetate=10:1 to 5:1) to give the title compound as a yellow solid. ¹H NMR (400 MHz, DMSO-d₆) δ=11.50 (br. s, 1H), 9.34 (br. s, 1H), 8.74 (br. s, 1H), 7.74-7.72 (m, 1H), 7.63-7.60 (m, 1H), 7.49-7.38 (m, 2H), 7.27-7.20 (m, 2H), 7.09-7.04 (m, 1H), 3.87 (s, 3H), 3.61 (d, J=12.0 Hz, 2H), 3.30-3.24 (m, 2H), 2.64 (d, J=13.2 Hz, 2H), 2.00 (s, 3H), 1.97-1.91 (m, 2H), 1.46 (s, 9H).

Step 2-(±)-N-(1-(N-Acetylsulfamoyl)-4-(3-aminophenyl)piperidin-4-yl)-4,5-dichloro-1-methyl-1H-indole-2-carboxamide To a mixture of (±)-tert-butyl N-[3-[1-(acetylsulfamoyl)-4-[(4,5-dichloro-1-methyl-indole-2-carbonyl)amino]-4-piperidyl]phenyl]carbamate (50.0 mg, 78.3 umol) in dichloromethane (1.00 mL) was added trifluoroacetic acid (153 mg, 1.34 mmol) in one portion at rt. The mixture was stirred at rt for 16 hrs. On completion, to the mixture was added sodium bicarbonate (sat. 10 mL) to adjust the pH=8. The product was extracted with dichloromethane (3×20 mL). The combined dichloromethane phase was dried over sodium sulfate and concentrated in vacuo. The resulting residue was purified by prep-HPLC (condition: water (0.05% ammonia hydroxide v/v)-ACN; column: Phenomenex Gemini C18 250*50 10 u) to give the title compound. LCMS: (ES⁻) m/z (M−H)⁻=536.1, tR=2.201. $^1$H NMR (400 MHz, DMSO-d$_6$) δ=8.52 (br. s, 1H), 7.60 (d, J=8.8 Hz, 1H), 7.45 (d, J=8.8 Hz, 1H), 7.27 (s, 1H), 6.97 (t, J=8.0 Hz, 1H), 6.66 (s, 1H), 6.60 (d, J=7.6 Hz, 1H), 6.42 (d, J=8.0 Hz, 1H), 4.99 (br. s, 2H), 3.88 (s, 3H), 3.55-3.50 (m, 2H), 3.11 (t, J=12.0 Hz, 2H), 2.60 (d, J=13.2 Hz, 2H), 1.89-1.84 (m, 5H).

Example 14 (Method 5)—(±)-3-[3-[(4,5-Dichloro-1-methyl-indole-2-carbonyl)amino]-1-(methylcarbamoylsulfamoyl)-3-piperidyl]benzoic acid

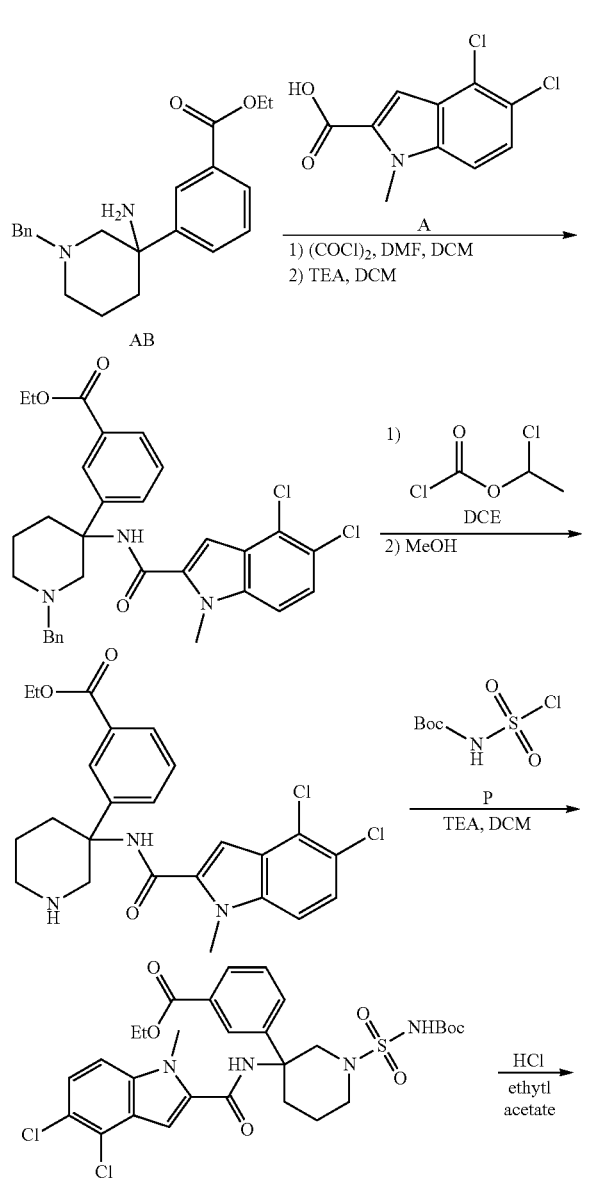

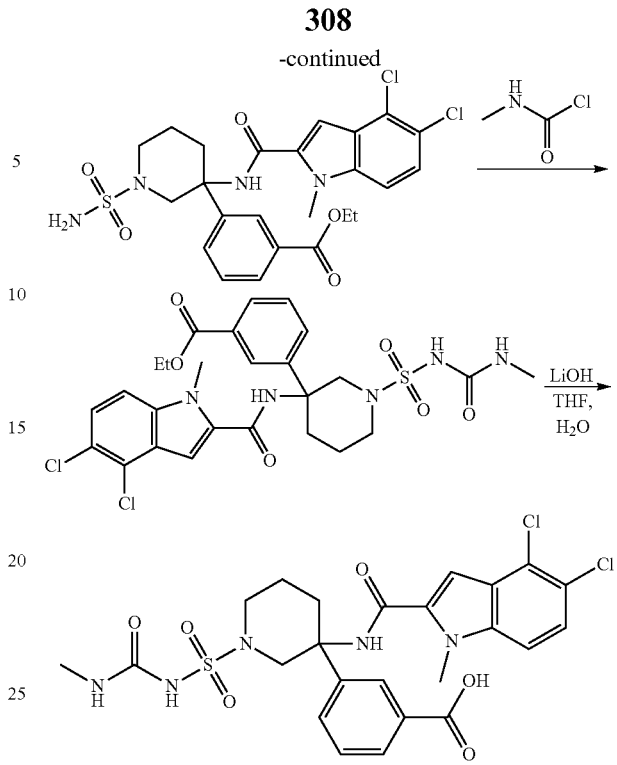

Step 1—(±)-[1-Benzyl-3-[(4,5-dichloro-1-methyl-indole-2-carbonyl)amino]-3-piperidyl]benzoate To a solution of 4,5-dichloro-1-methyl-indole-2-carboxylic acid (400 mg, 1.64 mmol) in a mixture of dichloromethane (20 mL) and N,N-dimethylformamide (150 uL) was added oxalyl chloride (1.04 g, 8.19 mmol) dropwise and the reaction mixture was stirred at rt for 1 hr. On completion, the reaction mixture was concentrated in vacuo to give 4,5-dichloro-1-methyl-indole-2-carbonyl chloride. To a solution of (±)-ethyl 3-(3-amino-1-benzyl-3-piperidyl)benzoate (309.77 mg, 1.18 mmol) and triethylamine (100 mg, 991 umol) in dichloromethane (10 mL) was added a solution of 4,5-dichloro-1-methyl-indole-2-carbonyl chloride (400 mg, 1.18 mmol) in dichloromethane (5 mL) and the mixture was stirred at rt for 12 hrs. On completion, the mixture was diluted with saturated ammonium chloride (20 mL), extracted with dichloromethane (3×20 mL) and dried over anhydrous sodium sulfate, filtrated and concentrated in vacuo. The residue was purified by silica gel chromatography (petroleum ether:ethyl acetate=1:1 to dichloromethane:methanol=10:1) to give the title compound. LCMS: (ES⁺) m:z (M+H)⁺=564.2, tR=0.760.

Step 2—(±)-Ethyl 3-[3-[(4,5-dichloro-1-methyl-indole-2-carbonyl)amino]-3-piperidyl]benzoate To a solution of (±)-[1-benzyl-3-[(4,5-dichloro-1-methyl-indole-2-carbonyl)amino]-3-piperidyl]benzoate (230 mg, 407 umol) in 1,2-dichloroethane (5 mL) was added 1-chloroethyl carbonochloridate (1.17 g, 8.15 mmol) and the reaction mixture was stirred at 100° C. for 12 hrs. On completion, the reaction mixture was concentrated in vacuo. Methanol (5 mL) was added to the residue and the mixture was stirred at 90° C. for 4 hrs. The reaction mixture was concentrated in vacuo and the residue was purified by silica gel chromatography (petroleum ether:ethyl acetate=5:1 to dichloromethane:methanol=30:1) to give the title compound. LCMS: (ES$^+$) m:z (M+H)$^+$=474.2, tR=0.775.

Step 3—(±)-Ethyl 3-[1-(tert-butoxycarbonylsulfamoyl)-3-[(4,5-dichloro-1-methyl-indole-2-carbonyl)amino]-3-piperidyl]benzoate To a solution of (±)-ethyl 3-[3-[(4,5-dichloro-1-methyl-indole-2-carbonyl)amino]-3-piperidyl]benzoate (200 mg, 421 umol) in dichloromethane (30 mL) was added triethylamine (85.3 mg, 843.2 umol) and tert-butyl N-chlorosulfonylcarbamate (118 mg, 548 umol), then the reaction mixture was stirred at rt for 0.5 hr. On completion the mixture was concentrated in vacuo to give the title compound. LCMS: (ES$^+$) m:z (M−55)$^+$=597.1, tR=0.957.

Step 4—(±)-Ethyl 3-[3-[(4,5-dichloro-1-methyl-indole-2-carbonyl)amino]-1-sulfamoyl-3-piperidyl]benzoate To a mixture of (±)-ethyl 3-[1-(tert-butoxycarbonylsulfamoyl)-3-[(4,5-dichloro-1-methyl-indole-2-carbonyl)amino]-3-piperidyl]benzoate (270 mg, 413 umol) in ethyl acetate (5 mL) was added hydrochloric acid/ethyl acetate (4 M, 6 mL) and the reaction mixture was stirred at rt for 5 hrs. On completion, the mixture was concentrated in vacuo. The residue was diluted with dichloromethane (30 mL), washed with saturated sodium bicarbonate (2×20 mL), dried over anhydrous sodium sulfate, filtered and concentrated in vacuo to give the title compound. LCMS: (ES$^+$) m:z (M+H)$^+$=553.1, tR=0.879.

Step 5—(±)-Ethyl 3-[3-[(4,5-dichloro-1-methyl-indole-2-carbonyl)amino]-1-(methylcarbamoyl-sulfamoyl)-3-piperidyl]benzoate To a solution of (±)-ethyl 3-[3-[(4,5-dichloro-1-methyl-indole-2-carbonyl)amino]-1-sulfamoyl-3-piperidyl]benzoate (170 mg, 307 umol) in dichloromethane (30 mL) was added triethylamine (310 mg, 426 uL, 3 mmol) and N-methylcarbamoyl chloride (143 mg, 1.54 mmol) and the mixture was stirred at rt for 16 hrs. On completion, the mixture was diluted with saturated ammonium chloride (20 mL), extracted with dichloromethane (3×50 mL), dried over anhydrous sodium sulfate, filtered and concentrated in vacuo. The residue was purified by prep-TLC (dichloromethane:methanol=30:1) to give the title compound. LCMS: (ES$^+$) m:z (M+H)$^+$=611.1, tR=0.913.

Step 6—(±)-3-[3-[(4,5-Dichloro-1-methyl-indole-2-carbonyl)amino]-1-(methylcarbamoyl-sulfamoyl)-3-piperidyl]benzoic acid To a solution of (±)-ethyl 3-[3-[(4,5-dichloro-1-methyl-indole-2-carbonyl)amino]-1-(methyl-carbamoylsulfamoyl)-3-piperidyl]benzoate (40.0 mg, 65.5 umol) in tetrahydrofuran (4 mL) and water (3 mL) was added lithium hydrate (6.28 mg, 262 umol) and the reaction mixture was stirred at rt for 12 hrs. On completion, the mixture was adjusted pH to 4~5 with hydrochloric acid (1 M), extracted with dichloromethane (3×20 mL), dried over anhydrous sodium sulfate, filtrated and concentrated in vacuo. The residue was purified by prep-HPLC (YMC-Actus ODS-AQ 150*30 5 u, water (0.1% TFA)-ACN) to give the title compound. LCMS: (ES$^+$) m:z (M+H)$^+$=582.1, tR=0.821. $^1$H NMR (400 MHz, DMSO-d$_6$) δ=12.98 (br. s., 1H), 10.25 (s, 1H), 8.64 (s, 1H), 8.09 (s, 1H), 7.83 (d, J=7.53 Hz, 1H), 7.78 (d, J=8.03 Hz, 1H), 7.58 (d, J=8.78 Hz, 1H), 7.49 (t, J=7.78 Hz, 1H), 7.44 (d, J=8.78 Hz, 1H), 7.32 (s, 1H), 6.30 (d, J=4.27 Hz, 1H), 4.14-4.23 (m, 1H), 3.83 (s, 3H), 3.58-3.67 (m, 1H), 3.50 (d, J=12.05 Hz, 1H), 3.00-3.10 (m, 1H), 2.54 (d, J=4.52 Hz, 3H), 2.35-2.44 (m, 1H), 1.85-2.00 (m, 2H), 1.53-1.62 (m, 1H).

Example 15—(±)-4-(3-(4,5-Dichloro-1-methyl-1H-indole-2-carboxamido)-1-(N-(methylcarbamoyl)sulfamoyl)piperidin-3-yl)benzoic acid

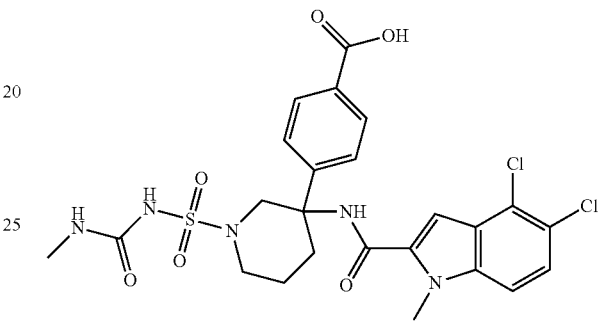

(±)-4-(3-(4,5-Dichloro-1-methyl-1H-indole-2-carboxamido)-1-(N-(methylcarbamoyl) sulfamoyl)piperidin-3-yl)benzoic acid was synthesized via Method 5 with acid A and amine AA. After Step 2, a mixture of the methyl and ethyl esters were formed. These were brought on as a mixture until the end when hydrolyzed in the final step. In Step 4, 4M HCl in MeOH was used instead of ethyl acetate as the solvent. In Step 6, MeOH used as the solvent instead of THF. The residue of the final step was purified by prep-HPLC (Welch Ultimate AQ-C18 150*30 mm*5 um, 0.1% trifluoroacetic acid-acetonitrile) to give the title compound. LCMS: (ES$^+$) m/z (M+H)$^+$=582.1, tR=0.806. $^1$H NMR (400 MHz, DMSO-d$_6$) δ=10.28 (br. s., 1H), 8.63 (s, 1H), 7.91 (d, J=8.28 Hz, 2H), 7.63 (d, J=8.41 Hz, 2H), 7.57 (d, J=8.91 Hz, 1H), 7.43 (d, J=8.78 Hz, 1H), 7.34 (s, 1H), 6.34 (d, J=4.14 Hz, 1H), 4.12 (d, J=12.17 Hz, 1H), 3.83 (s, 3H), 3.66 (d, J=12.17 Hz, 1H), 3.50 (m, 1H), 3.06 (t, J=9.60 Hz, 1H), 2.53 (d, J=4.52 Hz, 3H), 2.41-2.29 (m, 1H), 2.03-1.80 (m, 2H), 1.57 (d, J=8.66 Hz, 1H).

Example 16—(±)-4,5-Dichloro-N-[3-[3-(hydroxymethyl)phenyl]-1-(methylcarbamoyl-sulfamoyl)-3-piperidyl]-1-methyl-indole-2-carboxamide

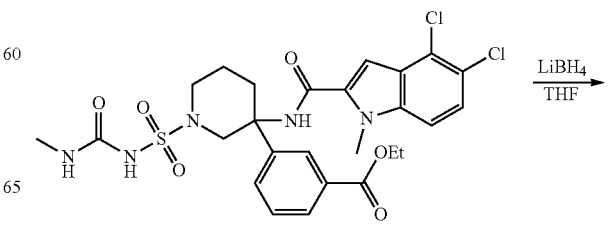

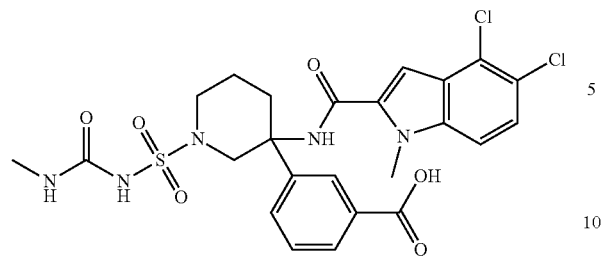

To a solution of (±)-ethyl 3-[3-[(4,5-dichloro-1-methyl-indole-2-carbonyl)amino]-1-(methylcarbamoyl sulfamoyl)-3-piperidyl]benzoate (40.0 mg, 65.52 umol, synthesized via Method 5, Steps 1-5 as seen in Example 14) in tetrahydrofuran (10 mL) was added lithium borohydride (4.28 mg, 196 umol), and the mixture was stirred at rt for 12 hrs. On completion the mixture was diluted with saturated ammonium chloride (20 mL), extracted with ethyl acetate (3×20 mL), dried over anhydrous sodium sulfate, filtrated and concentrated in vacuo. The residue was purified by prep-HPLC (YMC-Actus ODS-AQ 150*30 5 u, water (0.1% TFA)-ACN) to give the title compound. LCMS: (ES$^+$) m:z (M+H)$^+$=568.0, tR=0.813. $^1$H NMR (400 MHz, DMSO-d$_6$) δ=10.22 (br. s., 1H), 8.49 (s, 1H) 7.58 (d, J=9.0 Hz, 1H), 7.45 (d, J=3.5 Hz, 2H), 7.38 (d, J=3.6 Hz, 1H), 7.27-7.33 (m, 2H), 7.19 (d, J=7.3 Hz, 1H), 6.23-6.33 (m, 1H), 5.20 (br. s., 1H), 4.49 (d, J=4.3 Hz, 2H), 4.18 (d, J=12.6 Hz, 1H), 3.85 (s, 3H), 3.47 (d, J=12.6 Hz, 1H), 2.99 (d, J=10.5 Hz, 2H), 2.40-2.47 (m, 3H), 1.89 (d, J=10.3 Hz, 3H), 1.62 (br. s., 1H).

Example 17—(±)-4-[3-[(4,5-dichloro-1-methyl-indole-2-carbonyl)amino]-1-methyl-pyrrolidin-3-yl] benzoic acid

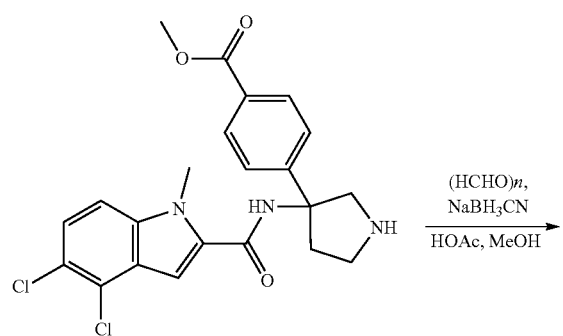

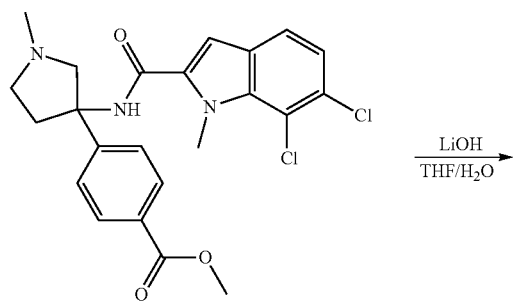

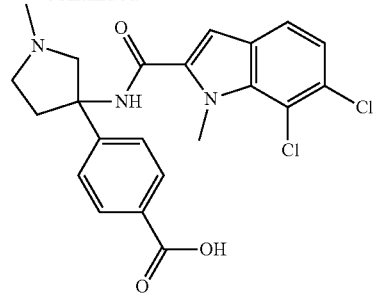

Step 1—(±)-methyl 4-[3-[(4,5-dichloro-1-methyl-indole-2-carbonyl)amino]-1-methyl-pyrrolidin-3-yl] benzoate To a solution of (±)-methyl 4-[3-[(4,5-dichloro-1-methyl-indole-2-carbonyl)amino]pyrrolidin-3-yl] benzoate (20.0 mg, 44.8 umol, synthesized via Method 5, Steps 1-2 with acid A and amine AH as starting materials) in methanol (5 mL) was added paraformaldehyde (14.3 mg, 448 umol) and acetic acid (2.69 mg, 44.8 umol), and the mixture was stirred at rt for 0.5 hr. Then sodium cyanoborohydride (28.1 mg, 448 umol) was added and the mixture was stirred at rt for 5.5 hrs. On completion, the mixture was diluted with saturated ammonium chloride (5 mL), extracted with dichloromethane (3×20 mL) and the combined organic phase was dried over anhydrous sodium sulfate, filtered and concentrated. The residue was purified by chromatography on silica gel (petroleum ether:ethyl acetate=1:1 to dichloromethane:methanol=10:1) to give the title compound. LCMS: (ES$^+$) m:z (M+H)$^+$=460.1, tR=0.737.

Step 2—(±)-4-[3-[(4,5-dichloro-1-methyl-indole-2-carbonyl)amino]-1-methyl-pyrrolidin-3-yl] benzoic acid To a solution of (±)-methyl 4-[3-[(4,5-dichloro-1-methyl-indole-2-carbonyl)amino]-1-methyl-pyrrolidin-3-yl]benzoate (60.0 mg, 130 umol) in tetrahydrofuran (5 mL) and water (5 mL) was added lithium hydroxide (3.12 mg, 389 umol), and the mixture was stirred at 50° C. for 4 hrs. On completion, the reaction was concentrated to remove the tetrahydrofuran and the aqueous phase was acidified to pH=4-5 with hydrochloric acid (1 N). The product was extracted with dichloromethane (3×5 mL), and the combined organic phase was concentrated in vacuo directly to give a residue which was purified by prep-HPLC (YMC-Actus ODS-AQ 150*30 5 u, water (0.1% TFA)-ACN) and lyophilized in vacuo to give the title compound. LCMS: (ES$^+$) m/z (M+H)$^+$=446.1, tR=0.673. $^1$H NMR (400 MHz, DMSO-d$_6$) δ=10.27 (br. s., 1H), 9.24 (br. s., 1H), 7.94 (d, J=8.0 Hz, 2H), 7.60 (d, J=7.3 Hz, 3H), 7.51-7.41 (m, 2H), 3.88 (s, 3H), 2.94 (s, 3H), 2.92-2.80 (m, 2H), 2.56-2.53 (m, 2H), 2.40-2.36 (m, 2H).

Example 18—(±)-4-[3-[(4,5-Dichloro-1-methyl-indole-2-carbonyl)amino]-1-ethyl-pyrrolidin-3-yl]benzoic acid

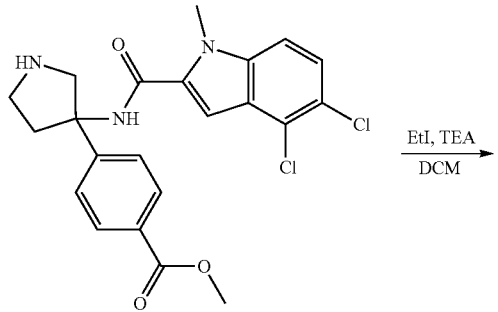

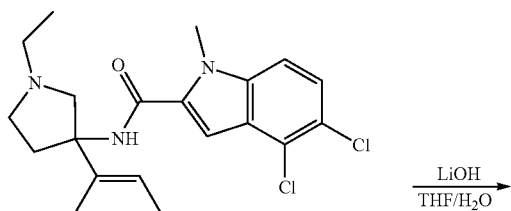

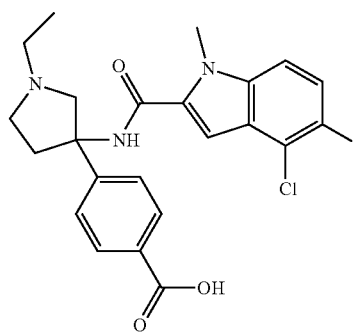

Step 1—(±)-Methyl 4-[3-[(4,5-dichloro-1-methyl-indole-2-carbonyl)amino]-1-ethyl-pyrrolidin-3-yl]benzoate To a solution of (±)-methyl 4-[3-[(4,5-dichloro-1-methyl-indole-2-carbonyl)amino]pyrrolidin-3-yl]benzoate (80.0 mg, 179 umol, synthesized via Method 5, Steps 1-2 with acid A and amine AH as starting materials) in dichloromethane (5 mL) was added triethylamine (181 mg, 1.79 mmol) and iodoethane (279 mg, 1.79 mmol) and the mixture was stirred at rt for 2 hrs. On completion, the mixture was diluted with water (5 mL), extracted with ethyl acetate (3×5 mL) and the combined organic phase was dried over anhydrous sodium sulfate, filtered and concentrated in vacuo to give a crude product. The crude was purified by chromatography on silica gel (petroleum ether:ethyl acetate=1:1 to dichloromethane:methanol=10:1) to give the title compound. LCMS: (ES$^+$) m/z (M+H)$^-$=474.1, tR=0.735.

Step 2—(±)-4-[3-[(4,5-Dichloro-1-methyl-indole-2-carbonyl)amino]-1-ethyl-pyrrolidin-3-yl]-benzoic acid To a solution of (±)-methyl 4-[3-[(4,5-dichloro-1-methyl-indole-2-carbonyl)amino]-1-ethyl-pyrrolidin-3-yl]benzoate (60.0 mg, 126 umol) in tetrahydrofuran (3 mL) and water (3 mL) was added lithium hydroxide (3.0 mg, 126 umol), and the mixture was stirred at rt for 6 hrs. On completion, the reaction was concentrated in vacuo to remove the tetrahydrofuran and the aqueous phase was acidified to pH=4~5 with hydrochloric acid (1 N). The product was extracted with dichloromethane (3×10 mL), and the combined organic phase was concentrated to give a residue which was purified byprep-HPLC (Phenomenex Gemini C18 250*50 mm*10 um, water (0.1% TFA)-ACN) to give the title compound. LCMS: (ES$^+$) m/z (M+H)$^+$=460.2, tR=0.721. $^1$H NMR (400 MHz, DMSO-d$_6$) δ=10.07 (br. s., 1H), 9.10 (s, 1H), 7.96 (d, J=8.5 Hz, 2H), 7.63 (dd, J=8.0, 4.0 Hz, 3H), 7.49-7.45 (m, 2H), 4.59 (d, J=8.0 Hz, 1H), 4.37 (d, J=6.0 Hz, 1H), 3.89 (s, 3H), 3.85-3.68 (m, 2H), 3.10-2.81 (m, 2H), 2.46-2.37 (m, 2H), 1.35-1.19 (m, 3H).

Example 19—(±)-4-[3-[(4,5-Dichloro-1-methyl-indole-2-carbonyl)amino]-1-(2,2,2-trifluoroethyl)pyrrolidin-3-yl]benzoic acid

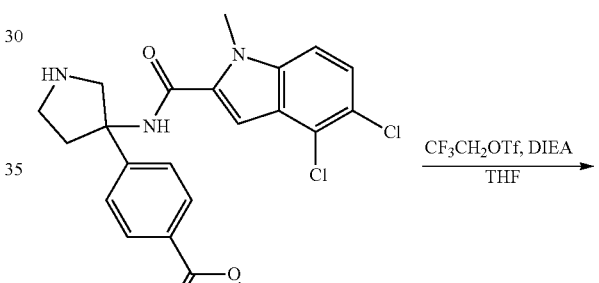

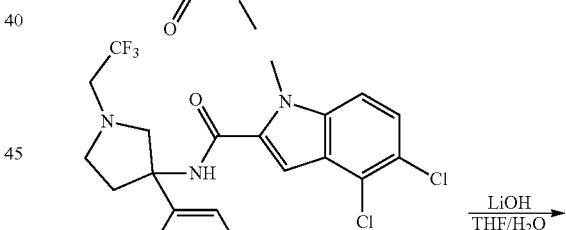

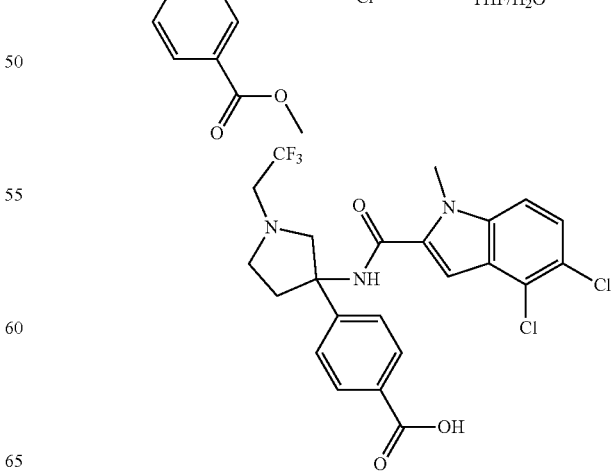

Step 1—(±)-Methyl 4-[3-[(4,5-dichloro-1-methyl-indole-2-carbonyl)amino]-1-(2,2,2-trifluoroethyl)pyrrolidin-3-yl]benzoate To a solution of (±)-methyl 4-[3-[(4,5-dichloro-1-methyl-indole-2-carbonyl)amino]pyrrolidin-3-yl]benzoate (70.0 mg, 156 umol synthesized via Method 5, Steps 1-2 with acid A and amine AH as starting materials) in tetrahydrofuran (2 mL) was added diisopropylethylamine (337 mg, 2.61 mmol) and 2,2,2-trifluoroethyl trifluoromethanesulfonate (54.6 mg, 235 umol), and the mixture was stirred at rt for 12 hrs. On completion, the mixture was diluted with water (10 mL) and extracted with dichloromethane (3×5 mL). The combined organic phase was dried over anhydrous sodium sulfate, filtered and concentrated in vacuo to give the crude product. The crude product was purified by chromatography on silica gel (petroleum ether:ethyl acetate=1:1 to dichloromethane:methanol=30:1) to give the title compound. LCMS: (ES$^+$) m/z (M+H)$^+$=528.0, tR=1.123.

Step 2 (±)-4-[3-[(4,5-Dichloro-1-methyl-indole-2-carbonyl)amino]-1-(2,2,2-trifluoroethyl)pyrrolidin-3-yl]benzoic acid To a solution of (±)-methyl 4-[3-[(4,5-dichloro-1-methyl-indole-2-carbonyl)amino]-1-(2,2,2-trifluoroethyl)pyrrolidin-3-yl]benzoate (50.0 mg, 94.6 umol) in tetrahydrofuran (3 mL) and water (3 mL) was added lithium hydroxide (2.27 mg, 94.6 umol) and the mixture was stirred at 60° C. for 3 hrs. On completion, the reaction was concentrated to remove the tetrahydrofuran and the aqueous phase was acidified to pH=4-5 with hydrochloric acid (1N). The product was extracted with dichloromethane (2×10 mL), and the combined organic phase was concentrated in vacuo to give a crude product which was purified by prep-HPLC (Phenomenex Gemini C18 250*50 mm*10 um, water (0.1% TFA)-ACN) to give the title compound. LCMS: (ES$^+$) m/z (M+H)$^+$=514.1, tR=0.912. $^1$H NMR (400 MHz, DMSO-d$_6$) δ=12.81 (br. s, 1H), 9.21 (br. s, 1H), 7.89 (d, J=8.4 Hz, 2H), 7.60 (d, J=8.8 Hz, 1H), 7.55 (d, J=8.4 Hz, 2H), 7.46-7.42 (m, 2H), 3.89 (s, 3H), 3.59-3.59 (m, 2H), 3.32-3.30 (m, 1H), 3.09-3.06 (m, 1H), 2.96-2.88 (m, 1H), 2.71-2.64 (m, 1H), 2.54-2.50 (m, 1H), 2.18-2.16 (m, 1H).

Example 20—(±)-4-[1-Acetyl-3-[(4,5-dichloro-1-methyl-indole-2-carbonyl)amino]pyrrolidin-3-yl]benzoic acid

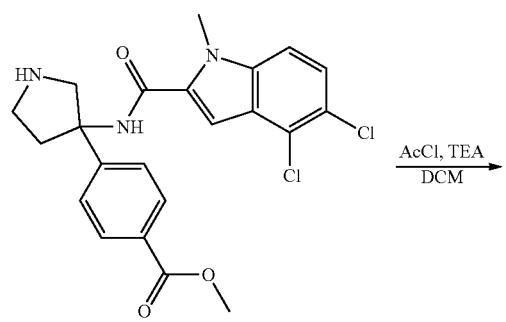

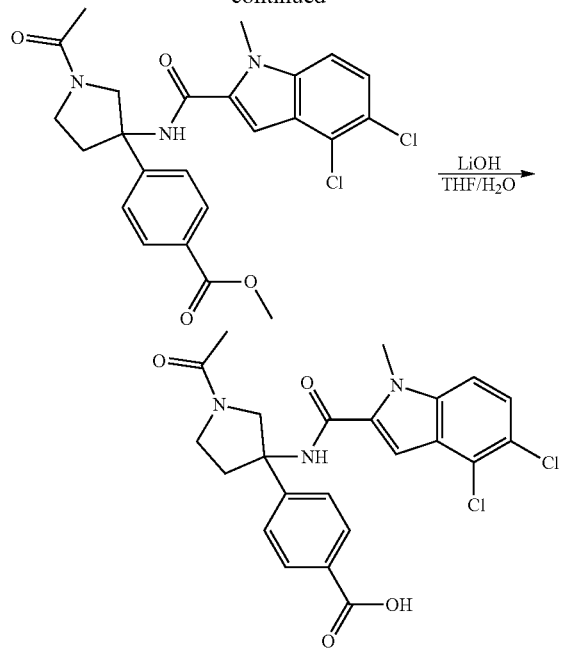

Step 1—(±)-Methyl 4-[1-acetyl-3-[(4,5-dichloro-1-methyl-indole-2-carbonyl)amino]pyrrolidin-3-yl]benzoate To a mixture of (±)-methyl-4-[3-[(4,5-dichloro-1-methyl-indole-2-carbonyl)-amino]-pyrrolidin-3-yl]-benzoate (100 mg, 224 umol, synthesized via Method 5, Steps 1-2 with acid A and amine AH as starting materials) and triethylamine (68.0 mg, 672 umol) in dichloromethane (5 mL) was added acetyl chloride (26.4 mg, 336 umol) dropwise at 0° C. under nitrogen. The mixture was stirred at rt and stirred for 0.5 hour. On completion, the reaction was concentrated in vacuo. The residue was purified by silica gel chromatography (dichloromethane:methanol=50:1) to give the title compound. $^1$H NMR (400 MHz, DMSO-d$_6$) δ=9.24 (d, J=0.28 Hz, 1H), 7.96-7.93 (m, 2H), 7.64-7.57 (m, 3H), 7.45-7.41 (m, 1H), 7.35 (s, 1H), 4.00-3.97 (m, 1H), 3.86 (d, J=0.36 Hz, 3H), 3.84 (d, J=0.16 Hz, 3H), 3.68-3.60 (m, 2H), 3.07-3.02 (m, 1H), 2.40-2.28 (m, 1H), 2.00 (d, J=8.8 Hz, 3H), 1.90 (s, 1H).

Step 2—(±)-4-[1-Acetyl-3-[(4,5-dichloro-1-methyl-indole-2-carbonyl)amino]pyrrolidin-3-yl]benzoic acid To a mixture of methyl-4-[1-acetyl-3-[(4,5-dichloro-1-methyl-indole-2-carbonyl)-amino]-pyrrolidin-3-yl]-benzoate (100 mg, 133 umol) in tetrahydrofuran (3 mL) and water (3 mL) was added lithium hydrate (47.8 mg, 2.00 mmol) in one portion at rt under nitrogen. The mixture was stirred at rt for 1 hour and then was warmed to 50° C. for 1 hour. On completion, the reaction was acidified by 2 N hydrochloric acid (1 mL) to pH=2-3 and concentrated in vacuo. The residue was purified by prep-HPLC (Condition: 0.1% TFA-ACN; Column: Phenomenex Synergi C18 100*21.2 mm*4 um) to give the title compound. LCMS: (ES$^+$) m/z (M+H)$^+$=474.2, (M+H)$^+$, tR=0.807. $^1$H NMR (400 MHz, DMSO-d$_6$) δ=12.89 (s, 1H), 9.19 (d, J=0.20 Hz, 1H), 7.94-7.91 (m, 2H), 7.64-7.57 (m, 3H), 7.54-7.40 (m, 1H), 7.33 (s, 1H), 4.24 (d, J=11.2 Hz, 1H), 4.15 (dd, J=12.0 Hz, 1H), 3.87 (d, J=0.32 Hz, 3H), 3.66-3.54 (m, 1H), 3.35-3.25 (m, 1H), 2.80-2.60 (m, 1H), 2.41-2.28 (m, 1H), 2.00 (d, J=8.4 Hz, 3H).

Example 21—(±)-4-[3-[(4,5-Dichloro-1-methyl-indole-2-carbonyl)amino]-1-phenyl-pyrrolidin-3-yl]benzoic acid

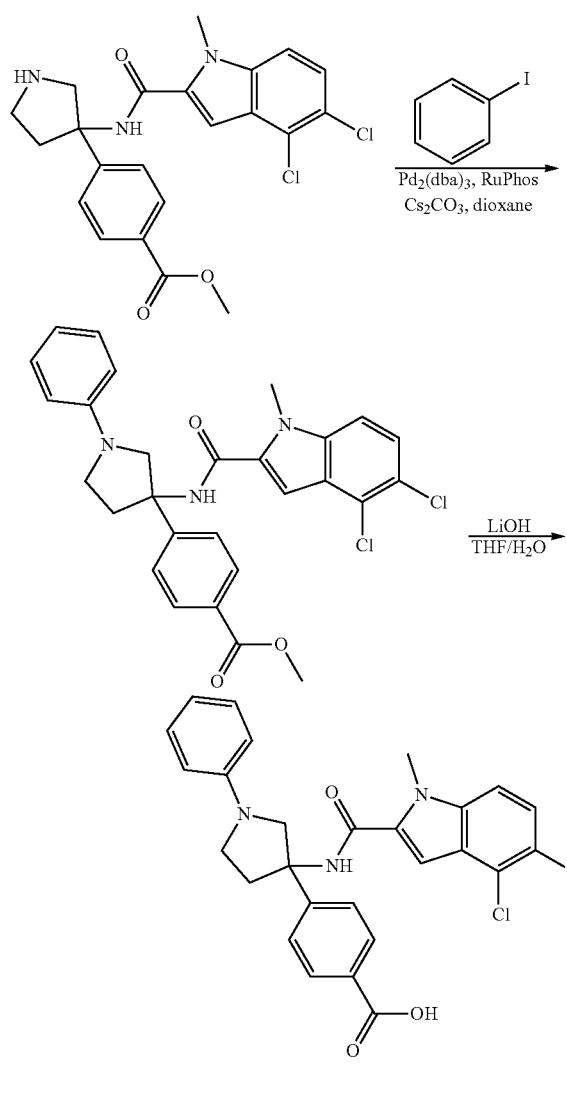

Step 1—(±)-Methyl4-[3-[(4,5-dichloro-1-methyl-indole-2-carbonyl)amino]-1-phenyl-pyrrolidin-3-yl]benzoate To a solution (±)-methyl 4-[3-[(4,5-dichloro-1-methyl-indole-2-carbonyl)amino]pyrrolidin-3-yl]benzoate (70.0 mg, 156 umol, synthesized via Method 5, Steps 1-2 with acid A and amine AH as starting materials) and iodobenzene (159 mg, 784 umol) in dioxane (5 mL) was added cesium carbonate (102 mg, 313 umol), RuPhos (36.5 mg, 78.4 umol) and Pd$_2$(dba)$_3$ (71.8 mg, 78.4 umol). The mixture was stirred at 100° C. for 16 hrs under nitrogen. To the mixture was added methanol (10 mL), then the mixture was filtered. The filtrate was concentrated to give the crude product, which was purified by prep-TLC (petroleum ether:ethyl acetate=5:1) to give the title compound. $^1$H NMR (400 MHz, CDCl$_3$) δ=2.61 (dt, J=12.6, 7.8 Hz, 1H), 2.97-2.87 (m, 1H), 3.51 (td, J=8.8, 4.0 Hz, 1H), 3.70-3.63 (m, 1H), 4.02-3.88 (m, 8H), 6.67 (d, J=8.0 Hz, 2H), 6.79 (t, J=7.2 Hz, 1H), 6.83 (s, 1H), 7.02-6.97 (m, 1H), 7.21 (d, J=8.8 Hz, 1H), 7.33-7.29 (m, 2H), 7.36 (d, J=8.8 Hz, 1H), 7.58 (d, J=8.5 Hz, 2H), 8.11-8.00 (m, 2H).

Step 2—(±)-4-[3-[(4,5-Dichloro-1-methyl-indole-2-carbonyl)amino]-1-phenyl-pyrrolidin-3-yl]benzoic acid To a solution of (±)-methyl 4-[3-[(4,5-dichloro-1-methyl-indole-2-carbonyl)amino]-1-phenyl-pyrrolidin-3-yl]benzoate (25.0 mg, 47.8 umol) in tetrahydrofuran (1 mL) and water (1 mL) was added lithium hydroxide (2.29 mg, 95.7 umol), then the mixture was stirred at rt for 48 hrs. On completion, the reaction mixture was concentrated to remove the tetrahydrofuran and the aqueous phase was acidified by HCl (2N, 0.1 mL) to pH=4-5, a white solid was precipitated out. The mixture was filtered, and the filter cake was dissolved with acetonitrile and purified by prep-HPLC (condition: water (0.225% FA)-ACN column: Boston Green ODS 150*30 5 u) and lyophilized to give the title compound. LCMS: (ES$^+$) m/z (M+H)$^+$=508.1, tR=0.946. $^1$H NMR (400 MHz, DMSO-d$_6$) δ=2.45-2.40 (m, 1H), 2.93-2.89 (m, 1H), 3.93-3.81 (m, 5H), 4.09-3.96 (m, 2H), 6.64-6.57 (m, 3H), 7.19 (t, J=7.8 Hz, 2H), 7.37 (s, 1H), 7.43 (d, J=8.8 Hz, 1H), 7.50 (d, J=8.0 Hz, 2H), 7.57 (d, J=8.8 Hz, 1H), 7.89 (d, J=8.0 Hz, 2H), 9.24 (s, 1H).

Example 22 (Method 6)—(±)-4-[3-[(4,5-Dichloro-1-methyl-indole-2-carbonyl)amino]-oxetan-3-yl]benzoic acid

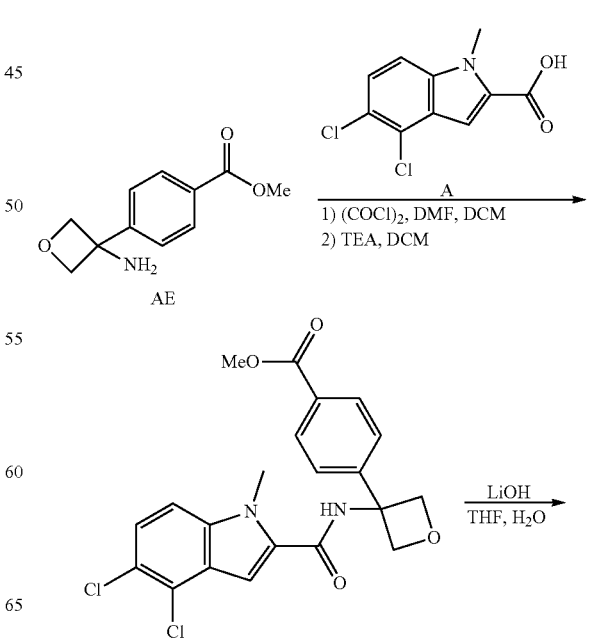

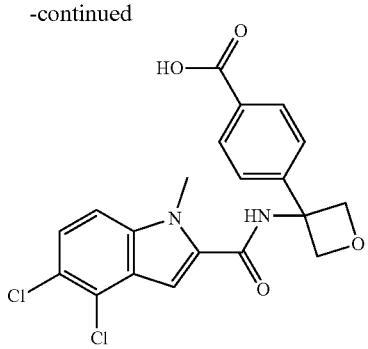

Step 1—(±)-Methyl 4-[3-[(4,5-dichloro-1-methyl-indole-2-carbonyl)amino]oxetan-3-yl]benzoate To a solution of 4,5-dichloro-1-methyl-indole-2-carboxylic acid (250 mg, 1.02 mmol) in a mixture of N,N-dimethylformamide (5 uL) and dichloromethane (30 mL) was added oxalyl chloride (195 mg, 1.54 mmol, 134 uL) dropwise and the reaction mixture was stirred at rt for 1 hr. On completion, the reaction mixture was concentrated in vacuo to give 4,5-dichloro-1-methyl-indole-2-carbonyl chloride (300 mg, crude) as white solid and for the next step directly. To a solution of (±)-methyl 4-(3-aminooxetan-3-yl)benzoate (100 mg, 482 umol) and triethylamine (195 mg, 1.93 mmol, 267 uL) in dichloromethane (20 mL) was added a solution of 4,5-dichloro-1-methyl-indole-2-carbonyl chloride (139 mg, 530 umol) in dichloromethane (10 mL) dropwise and the reaction mixture was stirred at rt for 0.5 hr. On completion, the reaction mixture was concentrated in vacuo. The resulting solid was purified by silica gel chromatography (petroleum ether:ethyl acetate=1:1) to give the title compound. LCMS: (ES$^+$) m/z (M+H)$^+$=433.0, tR=0.955. $^1$H NMR (400 MHz, CDCl$_3$) δ=8.10 (d, J=8.5 Hz, 2H), 7.70 (d, J=8.5 Hz, 2H), 7.39 (d, J=8.9 Hz, 1H), 7.27-7.23 (m, 1H), 7.13 (s, 1H), 7.08 (s, 1H), 5.16 (d, J=7.0 Hz, 2H), 5.03 (d, J=6.9 Hz, 2H), 4.01 (s, 3H), 3.93 (s, 3H).

Step 2—(±)-4-[3-[(4,5-Dichloro-1-methyl-indole-2-carbonyl)amino]oxetan-3-yl]benzoic acid To a solution of (±)-methyl 4-[3-[(4,5-dichloro-1-methyl-indole-2-carbonyl)amino]oxetan-3-yl]benzoate (100 mg, 230 umol) in a mixture of tetrahydrofuran (10 mL) and water (3 mL) was added lithium hydroxide (22.1 mg, 923 umol) and the reaction mixture was stirred at rt for 16 hrs. On completion, the reaction mixture was acidified with 1N hydrochloric acid solution until pH=6 and concentrated in vacuo to remove the tetrahydrofuran and water. The resulting solid was purified by prep-HPLC (Mobile phase: water (0.225% FA)-ACN, Column: Boston Green ODS 150*30 5 u) to give the title compound. LCMS: (ES$^+$) m/z (M+H)$^+$=419.0, tR=0.842. $^1$H NMR (400 MHz, DMSO-d$_6$) δ=9.83 (br. s, 1H), 8.00 (d, J=8.5 Hz, 2H), 7.72 (d, J=8.5 Hz, 2H), 7.63 (d, J=8.4 Hz, 1H), 7.48 (d, J=8.9 Hz, 1H), 7.44 (s, 1H), 5.07 (d, J=6.9 Hz, 2H), 4.82 (d, J=6.9 Hz, 2H), 3.96 (s, 3H).

Method 6 TABLE: Compounds Synthesized via Method 6 using the appropriate acid and amine

| Example # | Structure | Intermediate Acid | Intermediate Amine | LCMS (ES+) m/z (M + H)$^+$ | HNMR (400 MHz, DMSO-d6) δ |
|---|---|---|---|---|---|
| 23 | (±)-4-[3-(4,5-dichloro-1-methyl-1H-indole-2-amido)oxan-3-yl]benzoic acid | A | AF | 447.2 | 12.84 (br. s., 1H), 8.69 (s, 1H), 7.91 (d, J = 8.4 Hz, 2H), 7.66-7.56 (m, 3H), 7.48-7.40 (m, 2H), 4.13 (d, J = 11.4 Hz, 1H), 3.86 (s, 3H), 3.85-3.80 (m, 1H), 3.77 (d, J = 11.2 Hz, 1H), 3.56 (t, J = 9.6 Hz, 1H), 2.68 (d, J = 12.8 Hz, 1H), 2.12 (t, J = 10.2 Hz, 1H), 1.84 (d, J = 12.8 Hz, 1H), 1.50 (d, J = 13.6 Hz, 1H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 24 | (±)-3-chloro-4-[3-(4,5-dichloro-1-methyl-1H-indole-2-amido)oxolan-3-yl]benzoic acid | A | AJ | 467.0 | 9.22 (s, 1H), 7.79 (d, J = 1.3 Hz, 1H), 7.72 (dd, J = 1.5, 8.0 Hz, 1H), 7.57 (d, J = 8.8 Hz, 1H), 7.52 (d, J = 8.3 Hz, 1H), 7.43 (d, J = 9.0 Hz, 1H), 7.35 (s, 1H), 4.53 (d, J = 9.0 Hz, 1H), 4.23 (d, J = 9.3 Hz, 1H), 4.05-3.92 (m, 1H), 3.91-3.87 (m, 1H), 3.86 (s, 3H), 3.08-2.96 (m, 1H), 2.48-2.39 (m, 1H). |
| 25 | 4-[4-(4,5-dichloro-1-methyl-1H-indole-2-amido)oxan-4-yl]benzoic acid | A | AM | 446.2 | 8.80 (s, 1H), 7.93 (d, J = 8.3 Hz, 2H), 7.63-7.55 (m, 3H), 7.46 (d, J = 8.9 Hz, 1H), 7.40 (s, 1H), 3.86 (s, 3H), 3.84-3.73 (m, 4H), 2.56-2.52 (m, 2H), 2.07-1.97 (m, 2H) |
| 26 | (±)-4-[3-(4-chloro-5-methoxy-1-methyl-1H-indole-2-amido)oxolan-3-yl]benzoic acid | B | AN | 429.1 | 9.21 (s, 1H), 7.91 (d, J = 8.4 Hz, 2H), 7.54 (d, J = 8.5 Hz, 2H), 7.51 (d, J = 9.0 Hz, 1H), 7.34 (s, 1H), 7.23 d, J = 9.0 Hz, 1H), 4.22 (q, J = 9.2 Hz, 2H), 3.99-3.93 (m, 2H), 3.88 (s, 3H), 3.87 (s, 3H), 2.83-2.74 (m, 1H), 2.32 (td, J = 8.0, 13.0 Hz, 1H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 27 | (±)-6-[3-(4,5-dichloro-1-methyl-1H-indole-2-amido)oxolan-3-yl]pyridine-3-carboxylic acid | A | AT | 434.2 | 13.28 (br. s., 1H), 9.34 (s, 1H), 9.03 (d, J = 1.5 Hz, 1H), 8.23 (d, 8.4 Hz, 1H), 7.68-7.55 (m, 2H), 7.51-7.40 (m, 2H), 4.29 (d, J = 1.8 Hz, 2H), 4.00 (t, J = 6.9 Hz, 2H), 3.90 (s, 3H), 2.68-2.63 (m, 1H), 2.60-2.54 (m, 1H) |
| 28 | (±)-5-[3-(4,5-dichloro-1-methyl-1H-indole-2-amido)oxolan-3-yl]pyridine-2-carboxylic acid | A | AU | 434.2 | 12.91 (br. s., 1H), 9.38 (s, 1H), 8.77 (s, 1H), 8.09-7.96 (m, 2H), 7.60 (d, J = 9.0 Hz, 1H), 7.50-7.41 (m, 2H), 4.24 (s, 2H), 3.99 (t, J = 7.0 Hz, 2H), 3.89 (s, 3H), 2.841-2.77 (m, 1H), 2.45-2.39 (m, 1H) |
| 29 | (±)-4-[3-(4,5-dichloro-1-methyl-1H-indole-2-amido)oxolan-3-yl]-3-fluorobenzoic acid | A | AO | 451.1 | 9.25 (s, 1H), 7.80-7.71 (m, 1H), 7.69-7.52 (m, 3H), 7.43 (d, J = 8.9 Hz, 1H), 7.36 (s, 1H), 4.46 (d, J = 9.0 Hz, 1H), 4.14 (d, J = 9.2 Hz, 1H), 4.01-3.90 (m, 2H), 3.87 (s, 3H), 2.98-2.85 (m, 1H), 2.45-2.36 (m, 1H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 30 | (±)-4-[3-(4-chloro-1-methyl-1H-indole-2-amido)oxolan-3-yl]benzoic acid | C | AN | 399.2 | 9.17 (s, 1H), 7.84 (d, J = 8.1 Hz, 2H), 7.53 (d, J = 8.1 Hz, 1H), 7.44-7.36 (m, 3H), 7.32-7.24 (m, 1H), 7.23-7.14 (m, 1H), 4.25 (d, J = 9.0 Hz, 1H, 1H), 4.15 (d, J = 9.0 Hz, 1H), 4.01-3.94 (m, 2H), 3.90 (s, 3H), 2.87-2.70 (m, 1H), 2.32 (td, J = 7.8, 13.0 Hz, 1H) |
| 31 | (±)-4-[3-(4-chloro-5-fluoro-1-methyl-1H-indole-2-amido)oxolan-3-yl]benzoic acid | D | AN | 417.1 | 9.16 (s, 1H), 7.80 (d, J = 8.3 Hz, 2H), 7.59 (dd, J = 3.8, 9.0 Hz, 1H), 7.43 (s, 1H), 7.37-7.28 (m, 3H), 4.28 (d, J = 9.0 Hz, 1H), 4.10 (d, J = 9.0 Hz, 1H), 3.99-3.93 (m, 2H), 3.91 (s, 3H), 2.80 (td, J = 6.1, 12.6 Hz, 1H), 2.32 (td, J = 8.0, 12.8 Hz, 1H) |
| 32 | (±)-4-[3-(4-chloro-1,5-dimethyl-1H-indole-2-amido)oxolan-3-yl]benzoic acid | E | AN | 413.1 | 9.31-9.15 (s, 1H), 7.92 (d, J = 8.3 Hz, 2H), 7.55 (d, J = 8.3 Hz, 2H), 7.44 (d, J = 8.5 Hz, 1H), 7.39 (s, 1H), 7.29-7.19 (m, 1H), 4.29-4.16 (m, 2H), 4.02-3.93 (m, 2H), 3.88 (s, 3H), 2.80 (td, J = 6.2, 12.7 Hz, 1H), 2.43 (s, 3H), 2.36-2.28 (m, 1H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 33 | (±)-4-[3-(4,5-dichloro-6-methoxy-1-methyl-1H-indole-2-amido)oxolan-3-yl]benzoic acid | F | AN | 463.0 | 9.17 (s, 1H), 7.91 (d, J = 8.3 Hz, 2H), 7.55 (d, J = 8.3 Hz, 2H), 7.41 (s, 1H), 7.27 (s, 1H), 4.27-4.16 (m, 2H), 3.99-3.91 (m, 5H), 3.90 (s, 3H), 2.78 (td, J = 6.1, 12.6 Hz, 1H), 2.40-2.27 (m, 1H) |
| 34 | (±)-4-[3-(4-chloro-6-methoxy-1-methyl-1H-indole-2-amido)oxolan-3-yl]benzoic acid | G | AN | 429.1 | 12.83 (br s, 1H), 9.10 (s, 1H), 7.91 (d, J = 8.4 Hz, 2H), 7.55 (d, J = 8.4 Hz, 2H), 7.37 (s, 1H), 7.04 (s, 1H), 6.88 (s, 1H), 4.21 (s, 2H), 3.96-3.93 (m, 2H), 3.85 (s, 3H), 3.84 (s, 3H), 2.79-2.75 (m, 1H), 2.32-2.29 (m, 1H) |
| 35 | (±)-4-[3-{9-chloro-6-methyl-2H,3H,6H-[1,4]dioxino[2,3-f]indole-7-amido}oxolan-3-yl)benzoic acid | J | AN | 457.2 | 9.09 (s, 1H), 7.90 (d, J = 8.3 Hz, 2H), 7.53 (d, J = 8.3 Hz, 2H), 7.30 (s, 1H), 7.04 (s, 1H), 4.33 (dd, J = 4.8, 14.3 Hz, 4H), 4.25-4.17 (m, 2H), 3.99-3.92 (m, 2H), 3.79 (s, 3H), 2.78 (m, 1H), 2.33-2.26 (m, 1H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 36 | (±)-4-[3-(4-chloro-5-cyclopropyl-1-methyl-1H-indole-2-amido)oxolan-3-yl]benzoic acid | L | AN | 439.1 | 12.86 (br. s., 1H), 9.22 (s, 1H), 7.92 (d, J = 8.5 Hz, 2H), 7.56 (d, J = 8.3 Hz, 2H), 7.43 (d, J = 8.8 Hz, 1H), 7.40 (s, 1H), 6.92 (d, J = 8.5 Hz, 1H), 4.27-4.18 (m, 2H), 4.01-3.93 (m, 2H), 3.87 (s, 3H), 2.83-2.77 (m, 1H), 2.35-2.21 (m, 2H), 1.06-0.98 (m, 2H), 0.74-0.70 (m, 2H) |
| 37 | (±)-2-{4-[3-(4,5-dichloro-1-methyl-1H-indole-2-amido)oxolan-3-yl]phenyl}-2-methylpropanoic acid | A | AW | 475.1 | 9.15 (s, 1H), 7.60 (d, J = 8.8 Hz, 1H), 7.49-7.42 (m, 2H), 7.42-7.36 (m, 2H), 7.35-7.26 (m, 2H), 4.27 (d, J = 9.3 Hz, 1H), 4.11 (d, J = 9.0 Hz, 1H), 4.00-3.93 (m, 2H), 3.92 (s, 3H), 2.78 (td, J = 6.2, 12.7 Hz, 1H), 2.37-2.29 (m, 1H), 1.46 (s, 6H) |
| 38 | (±)-1-{4-[3-(4,5-dichloro-1-methyl-1H-indole-2-amido)oxolan-3-yl]phenyl}cyclopropane-1-carboxylic acid | A | AY | 473.2 | 9.14 (s, 1H), 7.60 (d, J = 8.9 Hz, 1H), 7.48-7.41 (m, 2H), 7.35 (d, J = 8 Hz, 2H), 7.25 (d, J = 8 Hz, 2H), 4.28 (d, J = 9.0 Hz, 1H), 4.11 (d, J = 9.0 Hz, 1H), 3.98-3.94 (m, 2H), 3.92 (s, 3H), 2.79 (td, J = 6.2, 12.6 Hz, 1H), 2.32 (td, J = 8.0, 12.8 Hz, 1H) 1.35 (d, J = 2.1 Hz, 2H), 0.98 (d, J = 2.0 Hz, 2H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 39 | 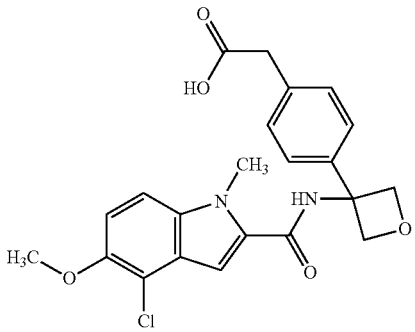 2-{4-[3-(4-chloro-5-methoxy-1-methyl-1H-indole-2-amido)oxetan-3-yl]phenyl}acetic acid | B | BA | 429.1 | 9.64 (s, 1H), 7.52 (d, J = 9.2 Hz, 1H), 7.42 (d, J = 8.4 Hz, 2H), 7.30 (s, 1H), 7.25-7.22 (m, 3H), 5.03 (d, J = 6.4 Hz, 2H), 4.77 (d, J = 6.4 Hz, 2H), 3.93 (s, 3H), 3.88 (s, 3H), 3.26 (s, 2H) |
| 40 | 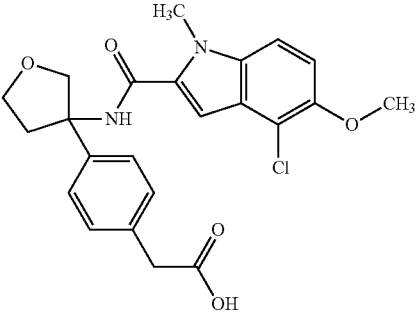 (±)-2-{4-[3-(4-chloro-5-methoxy-1-methyl-1H-indole-2-amido)oxolan-3-yl]phenyl}acetic acid | B | AV | 443.2 | 9.08 (s, 1H), 7.50 (d, J = 9.0 Hz, 1H), 7.37 (d, J = 8.3 Hz, 2H), 7.32 (s, 1H), 7.23-7.18 (m, 3H), 4.26 (d, J = 9.0 Hz, 1H), 4.12 (d, J = 9.0 Hz, 1H), 3.94 (t, J = 7.0 Hz, 2H), 3.90 (s, 3H), 3.85 (s, 3H), 3.51 (s, 2H), 2.78 (td, J = 6.1, 12.6 Hz, 1H), 2.37-2.25 (m, 1H) |
| 41 | 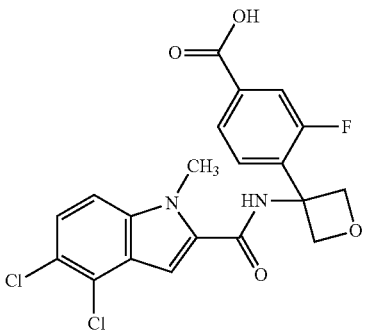 4-[3-(4,5-dichloro-1-methyl-1H-indole-2-amido)oxetan-3-yl]-3-fluorobenzoic acid | A | BB | 437.1 | 9.93 (s, 1H), 7.81-7.72 (m, 2H), 7.68 (dd, J = 1.2, 11.6 Hz, 1H), 7.59 (d, J = 8.9 Hz, 1H), 7.45 (d, J = 8.9 Hz, 1H), 7.39 (s, 1H), 5.11-5.07 (m, 2H), 5.07-5.03 (m, 2H), 3.92 (s, 3H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 42 | 4-[3-(4,5-dichloro-6-methoxy-1-methyl-1H-indole-2-amido)oxetan-3-yl]-3-fluorobenzoic acid | F | BB | 467.0 | 9.73 (s, 1H), 7.70-7.72 (d, J = 8.4 Hz, 1H), 7.58-7.61 (m, 2H), 7.33 (s, 1H), 7.25 (s, 1H), 5.01-5.07 (m, 4H), 3.94 (s, 3H), 3.91 (s, 3H) |
| 43 | 2-{4-[3-(4,5-dichloro-1-methyl-1H-indole-2-amido)oxetan-3-yl]-3-fluorophenyl}acetic acid | A | BC | 451.1 | 9.84 (s, 1H), 7.63-7.60 (m, 2H), 7.52 (t, J = 8.4 Hz, 1H), 7.45 (d, J = 8.8 Hz, 1H), 7.08~7.14 (m, 2H), 5.02~5.06 (m, 4H), 3.94 (s, 3H), 3.53 (s, 2H) |
| 44 | 2-{4-[3-(4-chloro-1,5-dimethyl-1H-indole-2-amido)oxetan-3-yl]-3-fluorophenyl}acetic acid | E | BC | 431.1 | 9.74 (s, 1H), 7.51 (t, J = 8.3 Hz, 1H), 7.43 (d, J = 8.4 Hz, 1H), 7.32 (s, 1H), 7.24 (d, J = 8.7 Hz, 1H), 7.16-7.05 (m, 2H), 5.04 (s, 4H), 3.91 (s, 3H), 3.53 (s, 2H), 2.42 (s, 3H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 45 | 2-{4-[3-(4,5-dichloro-6-methoxy-1-methyl-1H-indole-2-amido)oxetan-3-yl]-3-fluorophenyl}acetic acid | F | BC | 479.1 | 9.69 (s, 1H), 7.50 (t, J = 8.0 Hz, 1H), 7.33 (s, 1H), 7.25 (s, 1H), 7.08~7.13 (m, 2H), 5.01~5.05 (m, 4H), 3.95 (s, 3H), 3.93 (s, 3H), 3.52 (s, 2H) |
| 46 | 2-{4-[3-(4-chloro-6-methoxy-1,5-dimethyl-1H-indole-2-amido)oxetan-3-yl]-3-fluorophenyl}acetic acid | M | BC | 461.0 | 9.58 (s, 1H), 8.38 (br. s., 1H), 7.56-7.43 (m, 1H), 7.28 (s, 1H), 7.13-7.05 (m, 2H), 7.03 (s, 1H), 5.05-4.95 (m, 4H), 3.90 (s, 3H), 3.89 (s, 3H), 3.47 (s, 2H), 2.28 (s, 3H) |
| 47 | 2-{4-[3-(4-chloro-5-fluoro-6-methoxy-1-methyl-1H-indole-2-amido)oxetan-3-yl]-3-fluorophenyl}acetic acid | N | BC | 465.0 | 9.66 (s, 1H), 7.52 (t, J = 8.2 Hz, 1H), 7.35 (s, 1 H), 7.27 (d, J = 6.7 Hz, 1H), 7.13-7.08 (m, 2H), 4.98-5.08 (m, 4 H), 3.94 (s, 3H), 3.92 (s, 3H), 3.58 (s, 2H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 48 | 3-chloro-4-[3-(4,5-dichloro-1-methyl-1H-indole-2-amido)oxetan-3-yl]benzoic acid | A | BD | 453.0 | 9.96 (s, 1H), 7.93-7.82 (m, 3H), 7.59 (d, J = 8.8 Hz, 1H), 7.44 (d, J = 8.8 Hz, 1H), 7.35 (s, 1H), 5.16 (d, J = 7.3 Hz, 2H), 5.10 (d, J = 7.3 Hz, 2H), 3.90 (s, 3H) |
| 49 | 2-{3-chloro-4-[3-(4,5-dichloro-1-methyl-1H-indole-2-amido)oxetan-3-yl]phenyl}acetic acid | A | BE | 467.0 | 9.82 (s, 1H), 7.63-7.52 (m, 2H), 7.43 (d, J = 8.9 Hz, 1H), 7.34 (s, 1H), 7.26 (s, 1H), 7.14 (d, J = 7.7 Hz, 1H), 5.08 (m, 4H), 3.91 (s, 3H), 3.16 (s, 2H) |
| 50 | 4-[3-(4,5-dichloro-1-methyl-1H-indole-2-amido)oxetan-3-yl]-3-methylbenzoic acid | A | BF | 433.2 | 9.83 (s, 1H), 7.72-7.65 (m, 2H), 7.57 (d, J = 9.0 Hz, 1H), 7.48 (d, J = 7.8 Hz, 1H), 7.43 (d, J = 8.8 Hz, 1H), 7.32 (s, 1H), 5.17-5.04 (m, 4H), 3.91 (s, 3H), 2.25 (s, 3H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 51 | 2-{4-[3-(4,5-dichloro-1-methyl-1H-indole-2-amido)oxetan-3-yl]-3-methylphenyl}acetic acid | A | BG | 447.2 | 9.78 (s, 1H), 7.57 (d, J = 9.0 Hz, 1H), 7.43 (d, J = 8.8 Hz, 1H), 7.36 (d, J = 7.8 Hz, 1H), 7.31 (s, 1H), 7.01 (d, J = 8.4 Hz, 1H), 6.99 (s, 1H), 5.14-5.01 (m, 4H), 3.92 (s, 3H), 3.16 (s, 2H), 2.19 (s, 3H) |
| 52 | 2-{4-[3-(4,5-dichloro-1-methyl-1H-indole-2-amido)oxetan-3-yl]-3-methoxyphenyl}acetic acid | A | BI | 463.2 | 9.51 (s, 1H), 7.54 (d, J = 9.0 Hz, 1H), 7.43-7.35 (m, 2H), 7.32 (s, 1H), 6.90 (s, 1H), 6.81 (d, J = 7.6 Hz, 1H), 5.05-4.96 (m, 4H), 3.89 (s, 3H), 3.79 (s, 3H), 3.41 (s, 2H) |
| 53[a] | (±)-2-{4-[3-(4,5-dichloro-1-methyl-1H-indole-2-amido)oxolan-3-yl]-3-fluorophenyl}propanoic acid | A | BJ | 478.9 | 9.12 (s, 1H), 7.58 (d, J = 9.0 Hz, 1H), 7.47-7.41 (m, 2H), 7.35 (s, 1H), 7.15-7.05 (m, 2H), 4.48 (d, J = 9.0 Hz, 1H), 4.06 (d, J = 9.3 Hz, 1H), 3.99-3.92 (m, 3H), 3.90 (s, 3H), 3.65-3.55 (m, 1H), 2.96-2.87 (m, 1H), 2.44-2.32 (m, 1H), 1.34 (d, J = 7.0 Hz, 3H) |

Method 6 TABLE: Compounds Synthesized via Method 6 using the appropriate acid and amine

| Example # | Structure | Intermediate Acid | Intermediate Amine | LCMS (ES+) m/z (M + H)$^+$ | HNMR (400 MHz, DMSO-d6) δ |
|---|---|---|---|---|---|
| 54[a] | (±)-2-{4-[3-(4,5-dichloro-6-methoxy-1-methyl-1H-indole-2-amido)oxolan-3-yl]-3-fluorophenyl}propanoic acid | F | BJ | 509.0 | 8.99 (s, 1H), 7.44 (t, J = 8.2 Hz, 1H), 7.31 (s, 1H), 7.25 (s, 1H), 7.12-7.05 (m, 2H), 4.47 (d, J = 8.8 Hz, 1H), 4.06 (d, J = 9.0 Hz, 1H), 3.95 (s, 3H), 3.94-3.91 (m, 1H), 3.89 (s, 3H), 3.72-3.67 (m, 1H), 2.90 (d, J = 6.3 Hz, 1H), 2.49-2.34 (m, 2H), 1.35 (d, J = 7.0 Hz, 3H) |
| 55[a] | (±)-2-{4-[3-(4-chloro-5-methoxy-1-methyl-1H-indole-2-amido)oxolan-3-yl]-3-fluorophenyl}propanoic acid | B | BJ | 475.1 | 9.03 (s, 1H), 7.54-7.37 (m, 2H), 7.28-7.16 (m, 2H), 7.14-7.02 (m, 2H), 4.48 (d, J = 9.0 Hz, 1H), 4.07 (d, J = 9.0 Hz, 1H), 4.00-3.89 (m, 2H), 3.89 (s, 3H), 3.86 (s, 3H), 3.72-3.65 (m, 1H), 2.97-2.86 (m, 1H), 2.38 (td, J = 8.3, 13.1 Hz, 1H), 1.45-1.23 (m, 3H) |
| 56 | (±)-2-{4-[3-(4,5-dichloro-1-methyl-1H-indole-2-amido)oxolan-3-yl]phenyl}butanoic acid | A | BL | 497.2 (M + 23)$^+$ | 9.15 (s, 1H), 7.60 (d, J = 8.9 Hz, 1H), 7.46 (s, 1H), 7.43 (d, J = 5.9 Hz, 1H), 7.39 (d, J = 8.4 Hz, 2H), 7.25 (d, J = 8.4 Hz, 2H), 4.27 (d, J = 9.2 Hz, 1H), 4.11 (d, J = 9.2 Hz, 1H), 3.99-3.92 (m, 2H), 3.91 (s, 3H), 3.36 (d, J = 7.7 Hz, 1H), 2.78 (td, J = 6.2, 12.7 Hz, 1H), 2.32 (td, J = 8.0, 12.9 Hz, 1H), 2.04-1.87 (m, 1H), 1.63 (m, 13.9 Hz, 1H), 0.83 (t, J = 7.3 Hz, 3H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 57[b] | (±)-2-{4-[3-(4-choro-5-methoxy-1-methyl-1H-indole-2-amido)oxolan-3-yl]phenyl}propanoic acid | B | BM | 457.0 | 12.27 (br. s., 1H), 9.07 (s, 1H), 7.50 (d, J = 9.0 Hz, 1H), 7.39 (d, J = 8.3 Hz, 2H), 7.32 (s, 1H), 7.28-7.20 (m, 3H), 4.26 (d, J = 9.0 Hz, 1H), 4.12 (d, J = 9.3 Hz, 1H), 3.94 (t, J = 6.9 Hz, 2H), 3.89 (s, 3H), 3.88 (s, 3H), 3.64 (q, J = 7.0 Hz, 1H), 2.78 (m, 1H), 2.34-2.26 (m, 1H), 1.35 (d, J = 7.0 Hz, 3H) |
| 58 | (±)-2-{4-[3-(4,5-dichloro-1-methyl-1H-indole-2-amido)oxetan-3-yl]phenyl}propanoic acid | A | BN | 446.9 | 9.73 (s, 1H), 7.62 (d, J = 8.8 Hz, 1H), 7.53-7.45 (m, 3H), 7.42 (s, 1H), 7.31 (d, J = 8.3 Hz, 2H), 5.04 (d, J = 6.8 Hz, 2H), 4.78 (d, J = 6.7 Hz, 2H), 3.97 (s, 3H), 3.58-3.43 (m, 1H), 1.32 (d, J = 7.0 Hz, 3H) |
| 59 | (±)-2-{4-[3-(4-chloro-5-methoxy-1-methyl-1H-indole-2-amido)oxetan-3-yl]phenyl}propanoic acid | B | BN | 443.0 | 9.64 (s, 1H), 7.58-7.49 (m, 3H), 7.37-7.30 (m, 3H), 7.25 (d, J = 9.0 Hz, 1H), 5.04 (d, J = 6.7 Hz, 2H), 4.78 (d, J = 6.7 Hz, 2H), 3.94 (s, 3H), 3.89 (s, 3H), 3.63 (q, J = 6.7 Hz, 1H), 1.35 (d, J = 7.2 Hz, 3H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 60c | (±)-2-{4-[3-(4-chloro-5-methoxy-1-methyl-1H-indole-2-amido)oxetan-3-yl]-3-fluorophenyl}propanoic acid | B | BO | 461.1 | 9.75 (s, 1H), 7.53-7.49 (m, 2H), 7.28 (s, 1H), 7.23 (d, J = 9.2 Hz, 1H), 7.16-7.12 (m, 2H), 5.06-4.97 (m, 4H), 3.91 (s, 3H), 3.88 (s, 3H), 3.62-3.61 (m, 1H), 1.34 (d, J = 6.8 Hz, 3H) |
| 61c | 2-{4-[3-(4,5-dichloro-1-methyl-1H-indole-2-amido)oxetan-3-yl]-3-fluorophenyl}propanoic acid | A | BO | 465.0 | 9.83 (s, 1H), 7.59 (d, J = 8.8 Hz, 1H), 7.49 (t, J = 8.0 Hz, 1H), 7.44 (d, J = 8.8 Hz, 1H), 7.38 (s, 1H), 7.10-7.14 (m, 2H), 5.01-5.05 (m, 4H), 3.93 (s, 3H), 3.30-3.93 (m, 1H), 1.30 (d, J = 7.2 Hz, 3H) |
| 62 | 2-{3-chloro-4-[3-(4,5-dichloro-1-methyl-1H-indole-2-amido)oxetan-3-yl]phenyl}propanoic acid | A | BQ | 483.1 | 9.88 (s, 1H), 7.68 (d, J = 8.0 Hz, 1H), 7.59 (d, J = 9.0 Hz, 1H), 7.45 (d, J = 8.8 Hz, 1H), 7.35-7.30 (m, 2H), 7.29 (d, J = 8.0 Hz, 1H), 5.17-5.10 (m, 2H), 5.09-5.02 (m, 2H), 3.92 (s, 3H), 3.77-3.57 (m, 1H), 1.35 (d, J = 7.0 Hz, 3H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 63[d] | (±)-2-{4-[3-(4-chloro-5-methoxy-1-methyl-1H-indole-2-amido)oxolan-3-yl]phenyl}-2-methylpropanoic acid | B | AW | 471.2 | 9.07 (s, 1H), 7.50 (d, J = 9.0 Hz, 1H), 7.40 (d, J = 8.0 Hz, 2H), 7.35-7.29 (m, 3H), 7.23 (d, J = 9.0 Hz, 1H), 4.27 (d, J = 9.0 Hz, 1H), 4.12 (d, J = 9.3 Hz, 1H), 3.94 (t, J = 7.0 Hz, 2H), 3.89 (s, 3H), 3.88 (s, 3H), 2.79 (td, J = 6.1, 12.6 Hz, 1H), 2.31 (td, J = 7.8, 13.0 Hz, 1H), 1.46 (s, 6H) |
| 64 | 2-{3-chloro-4-[3-(4-chloro-5-methoxy-1-methyl-1H-indole-2-amido)oxetan-3-yl]phenyl}acetic acid | B | BW | 463.2 | 9.78 (s, 1H), 7.67 (d, J = 8.0 Hz, 1H), 7.49 (d, J = 9.0 Hz, 1H), 7.34 (s, 1H), 7.29-7.16 (m, 3H), 5.28-4.77 (m, 4H), 3.89 (s, 3H), 3.88 (s, 3H), 3.58 (s, 2H) |
| 65 | 4-[3-(4-chloro-5-methoxy-1-methyl-1H-indole-2-amido)oxetan-3-yl]-3-methylbenzoic acid | B | BF | 429.1 | 9.67 (s, 1H), 7.69-7.62 (m, 2H), 7.50-7.46 (m, 2H), 7.21-7.17 (m, 2H), 5.11-5.03 (m, 4H), 3.88 (s, 3H), 3.86 (s, 3H), 2.23 (s, 3H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 66 | 4-[3-(4-chloro-5-methoxy-1-methyl-1H-indole-2-amido)oxetan-3-yl]-3-fluorobenzoic acid | B | BB | 433.3 | 9.76 (s, 1H), 7.67-7.69 (d, J = 8 Hz, 1H), 7.54-7.58 (m, 2H), 7.78-7.51 (d, J = 12 Hz, 1H), 7.28 (s, 1H), 7.21-7.23 (d, J = 8 Hz, 1H), 5.02-5.07 (m, 4H), 3.89 (s, 3H), 3.87 (s, 3H) |
| 67 | 3-chloro-4-[3-(4,5-dichloro-6-methoxy-1-methyl-1H-indole-2-amido)oxetan-3-yl]benzoic acid | F | BD | 485.0 | 9.79 (s, 1H), 7.92-7.84 (m, 2H), 7.82-7.74 (m, 1H), 7.30 (s, 1H), 7.24 (s, 1H), 5.20-5.11 (d, J = 7.0 Hz,, 2H), 5.08 (d, J = 7.0 Hz, 2H), 3.95 (s, 3H), 3.90 (s, 3H) |
| 68 | 4-[3-(4,5-dichloro-6-methoxy-1-methyl-1H-indole-2-amido)oxetan-3-yl]-3-methylbenozic acid | F | BF | 462.9 | 9.57 (s, 1H), 7.71-7.63 (m, 2H), 7.49 (d, J = 7.6 Hz, 1H), 7.27-7.19 (m, 2H), 5.12 (d, J = 6.8 Hz, 2H), 5.06 (d, J = 6.4 Hz, 2H), 3.93 (s, 3H), 3.89 (s, 3H), 2.24 (s, 3H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 69 | 3-chloro-4-[3-(4-chloro-5-methoxy-1-methyl-1H-indole-2-amido)oxetan-3-yl]benzoic acid | B | BD | 449.1 | 9.88 (s, 1H), 7.95-7.83 (m, 3H), 7.49 (d, J = 9.0 Hz, 1H), 7.29-7.18 (m, 2H), 5.18-5.13 (d, J = 8.0 Hz, 2H), 5.12-5.07 (d, J = 7.6 Hz, 2H), 3.87 (s, 3H), 3.87 (s, 3H) |
| 70[e] | (±)-1-{4-[3-(4-chloro-5-methoxy-1-methyl-1H-indole-2-amido)oxolan-3-yl]phenyl}cyclopropane-1-carboxylic acid | B | AY | 469.3 | 9.04 (s, 1H), 7.50 (d, J = 9.0 Hz, 1H), 7.32 (s, 1H), 7.30-7.26 (m, 2H), 7.25-7.20 (m, 3H), 4.28 (d, J = 9.2 Hz, 1H), 4.10 (d, J = 9.0 Hz, 1H), 3.97-3.91 (m, 2H), 3.89 (s, 3H), 3.88 (s, 3H), 2.79 (td, J = 6.2, 12.6 Hz, 1H), 2.30 (td, J = 8.0, 12.9 Hz, 1H), 1.26 (d, J = 2.4 Hz, 2H), 0.82 (d, J = 2.0 Hz, 2H) |
| 71 | 2-{4-[3-(4,5-dichloro-6-methoxy-1-methyl-1H-indole-2-amido)oxetan-3-yl]phenyl}propanoic acid | F | BN | 477.1 | 9.61 (s, 1H), 7.54 (d, J = 8.3 Hz, 2H), 7.39-7.26 (m, 4H), 5.04 (d, J = 6.8 Hz, 2H), 4.78 (d, J = 6.5 Hz, 2H), 3.96 (s, 3H), 3.95 (s, 3H), 3.67 (q, J = 7.0 Hz, 1H), 1.36 (d, J = 7.3 Hz, 3H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 72 | 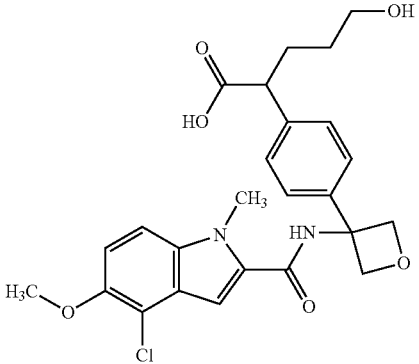<br>2-{4-[3-(4-chloro-5-methoxy-1-methyl-1H-indole-2-amido)oxetan-3-yl]phenyl}-5-hydroxypentanoic acid | B | CD | 487.2 | 9.65 (s, 1H), 7.53 (d, J = 9.0 Hz, 1H), 7.45 (d, J = 8.2 Hz, 2H), 7.33-7.27 (m, 3H), 7.24 (d, J = 9.2 Hz, 1H), 5.03 (d, J = 6.7 Hz, 2H), 4.77 (d, J = 6.5 Hz, 2H), 3.93 (s, 3H), 3.89 (s, 3H), 3.36 (t, J = 6.4 Hz, 2H), 3.26 (t, J = 6.3 Hz, 1H), 2.00-1.87 (m, 1H), 1.62-1.50 (m, 1H), 1.47-1.24 (m, 2H) |
| 73 | 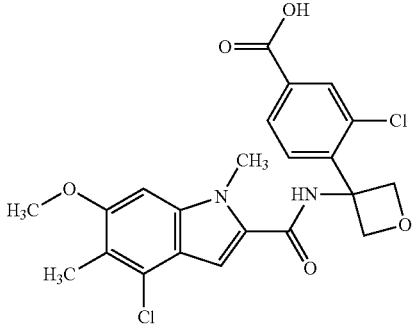<br>3-chloro-4-[3-(4-chloro-6-methoxy-1,5-dimethyl-1H-indole-2-amido)oxetan-3-yl]benzoic acid | M | BD | 463.2 | 9.69 (s, 1H), 7.92-7.84 (m, 2H), 7.77 (d, J = 12 Hz, 1H), 7.25 (s, 1H), 7.02 (s, 1H), 5.15 (d, J = 7.2 Hz, 2H), 5.08 (d, J = 7.2 Hz, 2H), 3.88 (s, 3H), 3.87 (s, 3H), 2.27 (s, 3H) |
| 74 | 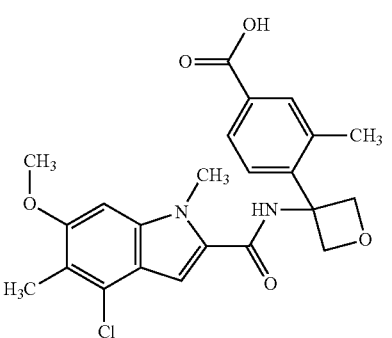<br>4-[3-(4-chloro-6-methoxy-1,5-dimethyl-1H-indole-2-amido)oxetan-3-yl]-3-methylbenzoic acid | M | BF | 443.1 | 9.57 (s, 1H), 7.69-7.66 (m, 2H), 7.52 (d, J = 8.0 Hz, 1H), 7.21 (s, 1H), 7.01 (s, 1H), 5.11 (d, J = 7.2 Hz, 2H), 5.06 (d, J = 6.8 Hz, 2H), 3.87 (s, 3H), 3.86 (s, 3H), 2.26 (s, 3H), 2.24 (s, 3H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 75 | 4-[3-(4-chloro-6-methoxy-1,5-dimethyl-1H-indole-2-amido)oxetan-3-yl]-3-fluorobenzoic acid | M | BB | 447.1 | 9.66 (s, 1H), 7.73 (d, J = 8.0 Hz, 1H), 7.65-7.60 (m, 2H), 7.30 (s, 1H), 7.03 (s, 1H), 5.08-5.02 (m, 4H), 3.90 (s, 3H), 3.89 (s, 3H), 2.27 (s, 3H) |
| 76 | 3-chloro-4-[3-(4-chloro-5-fluoro-6-methoxy-1-methyl-1H-indole-2-amido)oxetan-3-yl]benzoic acid | N | BD | 467.1 | 9.75 (s, 1H), 7.89-7.80 (m, 2H), 7.72 (d, J = 8.3 Hz, 1H), 7.32 (s, 1H), 7.27 (d, J = 6.5 Hz, 1H), 5.15 (d, J = 7.2 Hz, 2H), 5.08 (d, J = 7.2 Hz, 2H), 3.94 (s, 3H), 3.90 (s, 3H) |
| 77 | 4-[3-(4-chloro-5-fluoro-6-methoxy-1-methyl-1H-indole-2-amido)oxetan-3-yl]-3-methylbenzoic acid | N | BF | 447.1 | 9.63 (s, 1H), 7.68 (m, 2H), 7.50 (d, J = 8.0 Hz, 1H), 7.28 (s, 1H), 7.26 (d, J = 6.8 Hz, 1H), 5.12 (d, J = 7.2 Hz, 2H), 5.06 (d, J = 7.2 Hz, 2H), 3.92 (s, 3H), 3.89 (s, 3H), 2.23 (s, 3H) |

Method 6 TABLE: Compounds Synthesized via Method 6 using the appropriate acid and amine

| Example # | Structure | Intermediate Acid | Intermediate Amine | LCMS (ES+) m/z (M + H)⁺ | HNMR (400 MHz, DMSO-d6) δ |
|---|---|---|---|---|---|
| 78 | 4-[3-(4-chloro-5-fluoro-6-methoxy-1-methyl-1H-indole-2-amido)oxetan-3-yl]-3-fluorobenzoic acid | N | BB | 449.0 | 9.75 (s, 1H), 7.78-7.67 (m, 3H), 7.36 (s, 1H), 7.27 (d, J = 6.8 Hz, 1H), 5.09 (d, J = 7.0 Hz, 2H), 5.04 (d, J = 7.0 Hz, 2H), 3.94 (s, 3H), 3.91 (s, 3H) |
| 79ᶠ | (±)-2-{4-[3-(4,5-dichloro-1-methyl-1H-indole-2-amido)oxolan-3-yl]-3-fluorophenyl}-2-methylpropanoic acid | A | BK | 495.2 | 9.13 (s, 1H), 7.57 (d, J = 8.8 Hz, 1H), 7.49-7.40 (m, 2H), 7.34 (s, 1H), 7.17-7.08 (m, 2H), 4.47 (d, J = 9.0 Hz, 1H), 4.07 (d, J = 9.0 Hz, 1H), 4.00-3.91 (m, 2H), 3.89 (s, 3H), 2.95-2.87 (m, 1H), 2.43-2.34 (m, 1H), 1.46 (s, 6H) |
| 80ᶠ | (±)-2-{4-[3-(4,5-dichloro-6-methoxy-1-methyl-1H-indole-2-amido)oxolan-3-yl]-3-fluorophenyl}-2-methylpropanoic acid | F | BK | 522.9 | 8.98 (s, 1H), 7.44 (t, J = 8.7 Hz, 1H), 7.30 (s, 1H), 7.24 (s, 1H), 7.16-7.07 (m, 2H), 4.47 (d, J = 9.0 Hz, 1H), 4.06 (d, J = 9.0 Hz, 1H), 3.94 (s, 3H), 3.93-3.90 (m, 2H), 3.89 (s, 3H), 2.94-2.87 (m, 1H), 2.42-2.35 (m, 1H), 1.45 (s, 6H) |

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 81[f] | (±)-2-{4-[3-(4-chloro-5-methoxy-1-methyl-1H-indole-2-amido)oxolan-3-yl]-3-fluorophenyl}-2-methylpropanoic acid | B | BK | 489.2 | 9.04 (s, 1H), 7.54-7.39 (m, 2H), 7.29-7.18 (m, 2H), 7.17-7.05 (m, 2H), 4.47 (d, J = 8.8 Hz, 1H), 4.07 (d, J = 9.3 Hz, 1H), 4.00-3.90 (m, 2H), 3.87 (s, 3H), 3.86 (s, 3H), 2.97-2.86 (m, 1H), 2.42-2.32 (m, 1H), 1.46 (s, 6H) |
| 82 | (±)-2-{4-[3-(4,5-dichloro-6-methoxy-1-methyl-1H-indole-2-amido)oxolan-3-yl]phenyl}butanoic acid | F | BL | 505.0 | 12.3 (bs, 1H), 9.03 (s, 1H), 7.42-7.34 (m, 3H), 7.27-7.17 (m, 3H), 4.26 (d, J = 9.2 Hz, 1H), 4.12 (d, J = 9.2 Hz, 1H), 3.96 (s, 3H), 3.95-3.92 (m, 2H), 3.91 (s, 3H), 3.43-3.40 (m, 1H), 2.78 (td, J = 6.1, 12.6 Hz, 1H), 2.31 (td, J = 7.7, 13.0 Hz, 1H), 1.96 (quind, J = 7.2, 14.2 Hz, 1H), 1.64 (quind, J = 7.0, 13.9 Hz, 1H), 0.84 (t, J = 7.3 Hz, 3H) |
| 83[g] | (±)-2-{4-[3-(4,5-dichloro-6-methoxy-1-methyl-1H-indole-2-amido)oxolan-3-yl]phenyl}-3-methylbutanoic acid | F | CF | 519.3 | 9.01 (s, 1H), 7.41-7.32 (m, 3H), 7.29-7.24 (m, 3H), 4.26 (d, J = 8.5 Hz, 1H), 4.11 (d, J = 9.3 Hz, 1H), 3.96 (s, 3H), 3.95-3.92 (m, 1H), 3.91 (s, 3H), 3.03 (d, J = 10.3 Hz, 1H), 2.78 (td, J = 6.2, 12.5 Hz, 1H), 2.57-2.53 (m, 1H), 2.38-2.25 (m, 1H), 2.24-2.05 (m, 1H), 0.99 (d, J = 6.3 Hz, 3H), 0.62 (d, J = 6.5 Hz, 3H) |

-continued

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 84 | (±)-2-{4-[3-(4,5-dichloro-1-methyl-1H-indole-2-amido)oxolan-3-yl]phenyl}pentanoic acid | A | CG | 489.2 | 9.10 (s, 1H), 7.58 (d, J = 8.8 Hz, 1H), 7.43 (d, J = 8.8 Hz, 1H), 7.39 (s, 1H), 7.30 (d, J = 8.4 Hz, 2H), 7.20 (d, J = 8.4 Hz, 2H), 4.26 (d, J = 9.0 Hz, 1H), 4.07 (d, J = 9.0 Hz, 1H), 4.00-3.91 (m, 2H), 3.90 (s, 3H), 3.23-3.19 (m, 1H), 2.77 (td, J = 12.6, 6.1 Hz, 1H), 2.31-2.24 (m, 1H), 1.92-1.83 (m, 1H), 1.46 (qd, J = 15.8, 6.4 Hz, 1H), 1.28-1.19 (m, 1H), 1.19-1.11 (m, 1H), 0.82 (t, J = 7.4 Hz, 3H) |
| 85[h] | (±)-2-{4-[3-(4,5-dichloro-6-methoxy-1-methyl-1H-indole-2-amido)oxolan-3-yl]phenyl}pentanoic acid | F | CG | 519.2 | 8.98 (s, 1H), 7.36 (s, 1H), 7.30 (d, J = 8.0 Hz, 2H), 7.28-7.18 (m, 3H), 4.26 (d, J = 9.0 Hz, 1H), 4.09 (d, J = 9.0 Hz, 1H), 3.95 (s, 3H), 3.94-3.91 (m, 2H), 3.90 (s, 3H), 3.30-3.25 (m, 1H), 2.76 (td, J = 12.4, 6.2 Hz, 1H), 2.32-2.23 (m, 1H), 1.95-1.83 (m, 1H), 1.55-1.44 (m, 1H), 1.28-1.20 (m, 1H), 1.20-1.13 (m, 1H), 0.84 (t, J = 7.4 Hz, 3H) |
| 86 | (±)-2-cyclobutyl-2-{4-[3-(4,5-dichloro-1-methyl-1H-indole-2-amido)oxolan-3-yl]phenyl}acetic acid | A | CH | 501.1 | 9.14 (s, 1H), 7.60 (d, J = 8.9 Hz, 1H), 7.45 (d, J = 8.2 Hz, 2H), 7.39 (s, 1H) 7.34 (d, J = 8.2 Hz, 2H), 7.24 (d, J = 8.3 Hz, 2H), 4.26 (d, J = 9.2 Hz, 1H), 4.08 (d, J = 9.3 Hz, 1H), 3.98-3.92 (m, 2H), 3.91 (s, 3H), 2.92-2.81 (m, 1H), 2.81-2.73 (m, 1H), 2.54-2.52 (m, 1H), 2.36-2.30 (m, 1H), 2.08 (d, J = 5.0 Hz, 1H), 1.77-7.65 (m, 4H), 1.58-1.43 (m, 1H) |

-continued

Method 6 TABLE: Compounds Synthesized via Method 6 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 87[i] | 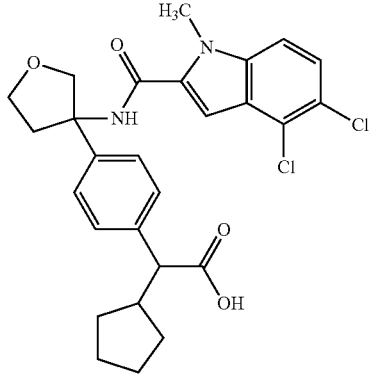<br>(±)-2-cyclopentyl-2-{4-[3-(4,5-dichloro-1-methyl-1H-indole-2-amido)oxolan-3-yl]phenyl}acetic acid | A | CI | 537.1 (M + Na)+ | 12.21 (br. s., 1H), 9.13 (s, 1H), 7.59 (d, J = 8.8 Hz, 1H), 7.45 (d, J = 8.8 Hz, 1H), 7.42 (s, 1H), 7.38 (d, J = 8.3 Hz, 2H), 7.28 (d, J = 8.3 Hz, 2H), 4.26 (d, J = 9.0 Hz, 1H), 4.10 (d, J = 9.0 Hz, 1H), 3.98-3.92 (m, 2H), 3.91 (s, 3H), 3.20 (d, J = 11.0 Hz, 1H), 2.78 (td, J = 6.1, 12.6 Hz, 1H), 2.45-2.39 (m, 1H), 2.33-2.27 (m, 1H), 1.89-1.77 (m, 1H), 1.65-1.47 (m, 3H), 1.46-1.38 (m, 1H), 1.31-1.18 (m, 2H), 1.00-0.88 (m, 1H) |
| 88[j] | 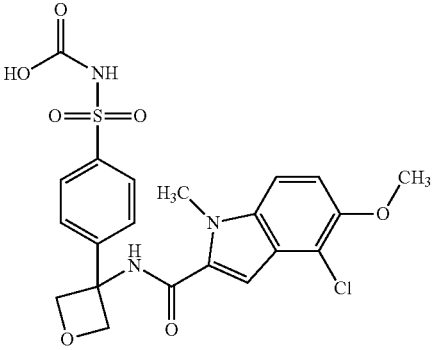<br>4-chloro-N-{3-[4-(acetamidosulfonyl)phenyl]oxetan-3-yl}-5-methoxy-1-methyl-1H-indole-2-carboxamide | B | BY | 490.0 (M − 1)+ | 9.74 (br, s, 1H), 7.87 (d, J = 8.0 Hz, 2H), 7.73 (d, J = 8.0 Hz, 2H), 7.54 (d, J = 8.8 Hz, 1H), 7.34 (s, 1H), 7.25 (d, J = 8.8 Hz, 1H), 5.06 (d, J = 7.2 Hz, 1H), 4.80 (d, J = 6.8 Hz, 2H), 3.93 (s, 3H), 3.89 (s, 3H), 1.81 (s, 3H) |

[a]Since Intermediate BJ was isolated as a mixture with Intermediate BK, the reaction formed a mixture of isomers which was separated after Step 2. In Step 2, the gem di-methyl compound was not hydrolyzed and was removed during the aqueous work-up.

[b]Step 2 run at 60° C. for 5 hrs.

[c]Since Intermediate BO was a mixture with Intermediate BP, the mixture of products was purified after the first step.

[d]Step 2 run at 50-60° C. for 6 hrs.

[e]Step 2 was heated at 60° C. for 2 hrs.

[f]Since Intermediate BK was isolated as a mixture with Intermediate BJ, the reaction formed a mixture of isomers which was separated after Step 2. This gem-dimethyl product did not react at rt, and thus was heated further to 60° C. for 6 hr to complete the hydrolysis and form the final product.

[g]Step 2 was heated at 80° C. for 32 hrs.

[h]Step 2 was heated to 60° C. for 48 hrs.

[i]Step 2 was run at 90° C. for 9 hrs.

[j]Only Step 1 was performed. No hydrolysis with LiOH.

Example 89—(±)-4-[3-[(4,5-dichloro-1-methyl-indole-2-carbonyl)amino]tetrahydro-furan-3-yl]-3-methyl-benzoic acid

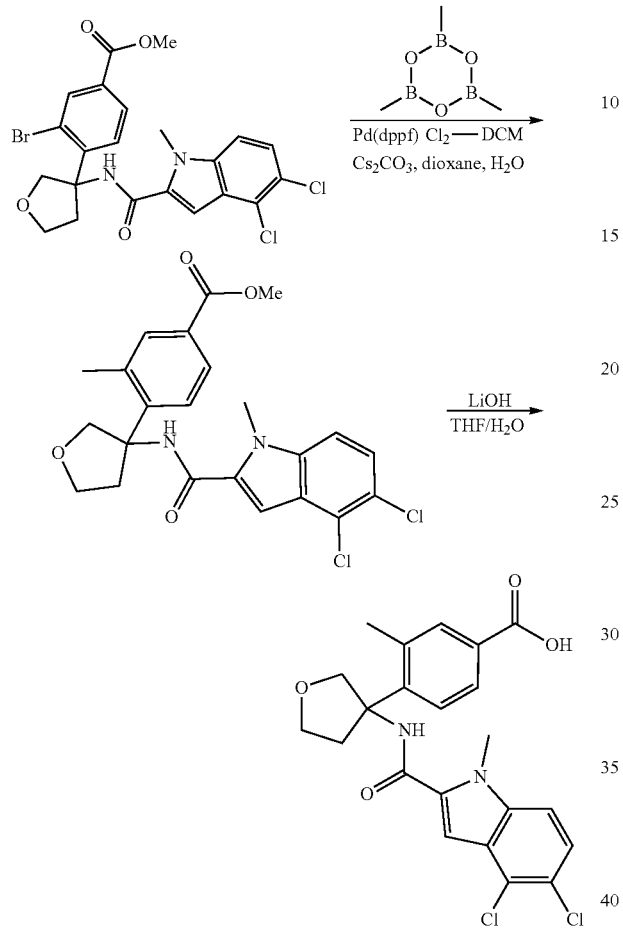

Step 1—(±)-Methyl 4-[3-[(4,5-dichloro-1-methyl-indole-2-carbonyl)amino]tetrahydrofuran-3-yl]-3-methyl-benzoate A mixture of methyl 3-bromo-4-[3-[(4,5-dichloro-1-methyl-indole-2-carbonyl)amino]tetrahydrofuran-3-yl]benzoate (150 mg, 285 umol, synthesized via Method 6, Step 1 with acid A and amine AK as starting materials), 2,4,6-trimethyl-1,3,5,2,4,6-trioxatriborinane (35.7 mg, 285 umol), cesium carbonate (185 mg, 570 umol) and Pd(dppf) Cl$_2$·CH$_2$Cl$_2$ (46.5 mg, 57.0 umol) in water (1 mL) and dioxane (5 mL) was degassed and purged with nitrogen gas for 3 times. Then the mixture was stirred at 100° C. for 16 hours under nitrogen gas atmosphere. On completion, the reaction mixture was concentrated in vacuo to give a residue. The residue was purified by column chromatography (SiO$_2$, dichloromethane:ethyl acetate=10:0 to 10:1) to give the title compound. LCMS: (ES$^+$) m/z (M+H)$^+$=461.2, tR=0.950.

Step 2—(±)-4-[3-[(4,5-dichloro-1-methyl-indole-2-carbonyl)amino]tetrahydrofuran-3-yl]-3-methyl-benzoic acid To a solution of methyl 4-[3-[(4,5-dichloro-1-methyl-indole-2-carbonyl)amino]tetrahydrofuran-3-yl]-3-methyl-benzoate (60 mg, 130 umol) in water (1 mL) and tetrahydrofuran (3 mL) was added lithium hydroxide (12.4 mg, 520 umol). The mixture was stirred at 60° C. for 16 hours. On completion, the reaction mixture was concentrated in vacuo. The residue was acidified with 1 M hydrochloric acid to pH=3. Then the mixture was concentrated in vacuo to get the crude product. The crude product was purified by prep-HPLC (Condition: water (0.1% TFA)-ACN; Column: Venusil XBP C18 150*25 mm; Particle size: 10 um) to give the title compound. LCMS: (ES$^+$) m/z (M+H)$^+$=447.2, tR=0.916. $^1$H NMR (400 MHz, DMSO-d$_6$) δ=12.80 (br. s., 1H), 9.19 (s, 1H), 7.77-7.68 (m, 2H), 7.61-7.52 (m, 2H), 7.44 (d, J=8.8 Hz, 1H), 7.37 (s, 1H), 4.44 (d, J=9.0 Hz, 1H), 4.23 (d, J=8.9 Hz, 1H), 3.97 (q, J=7.8 Hz, 2H), 3.86 (s, 3H), 3.01-2.92 (m, 1H), 2.39 (s, 3H), 2.35-2.29 (m, 1H).

Example 90—(±)-4,5-Dichloro-N-(3-(4-(cyanomethyl)phenyl)tetrahydrofuran-3-yl)-1-methyl-1H-indole-2-carboxamide

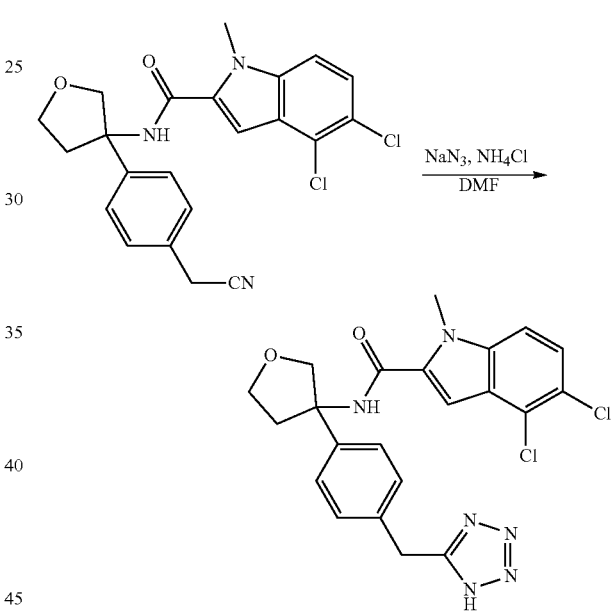

To a solution of (±)-4,5-dichloro-N-[3-[4-(cyanomethyl)phenyl]tetrahydrofuran-3-yl]-1-methyl-indole-2-carboxamide (84.0 mg, 196 umol, synthesized via Step 1 of Method 6 with acid A and amine AX) in N,N-dimethylformamide (5 mL) was added sodium azide (63.7 mg, 980 umol) and ammonium chloride (31.5 mg, 588 umol). The reaction mixture was stirred at 120° C. for 12 hrs. On completion, the mixture was diluted with water (20 mL) and extracted with ethyl acetate (3×30 mL). The combined organic layers were washed with brine (20 mL), dried over anhydrous sodium sulfate and concentrated in vacuo. The residue was purified by Prep-HPLC [Instrument: GX-A; Column: Phenomenex Gemini 150*25 mm*10 um; Condition: water (0.05% ammonia hydroxide v/v)-ACN] to give the title compound. LCMS: (ES$^+$) m/z (M+H)$^+$=471.1, tR=0.831. $^1$H NMR (400 MHz, DMSO-d$_6$) δ=9.17 (s, 1H), 7.60 (d, J=9.0 Hz, 1H), 7.45 (d, J=8.8 Hz, 1H), 7.43-7.36 (m, 3H), 7.22 (d, J=8.0 Hz, 2H), 4.24 (d, J=9.0 Hz, 1H), 4.21 (s, 2H), 4.10 (d, J=9.3 Hz, 1H), 3.96-3.92 (m, 2H), 3.90 (s, 3H), 2.77 (td, J=6.1, 12.8 Hz, 1H), 2.32-2.23 (m, 1H).

Example 91—(±)-N-(3-(4-(1-(1H-tetrazol-5-yl)ethyl)phenyl)tetrahydrofuran-3-yl)-4,5-dichloro-1-methyl-1H-indole-2-carboxamide

Example 92—4,5-Dichloro-1-methyl-N-[3-[4-(1H-tetrazol-5-ylmethyl)phenyl]oxetan-3-yl]indole-2-carboxamide

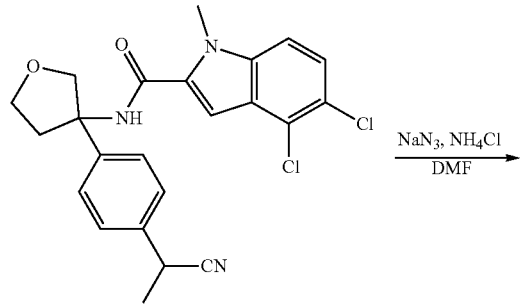

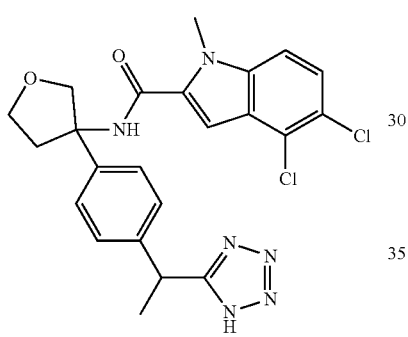

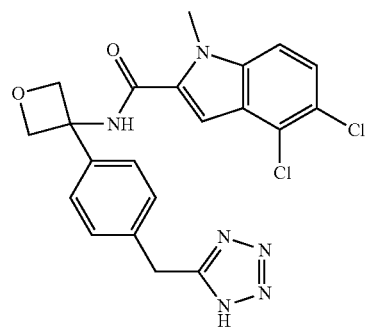

To a solution of (±)-4,5-dichloro-N-[3-[4-(1-cyanoethyl)phenyl]tetrahydrofuran-3-yl]-1-methyl-indole-2-carboxamide (90.0 mg, 203 umol, synthesized via Method 6, Step 1 with acid A and amine BS) in N,N-dimethylformamide (5 mL) was added sodium azide (66.1 mg, 1.02 mmol) and ammonium chloride (32.7 mg, 610 umol) under nitrogen. The reaction mixture was stirred at 120° C. for 12 hrs. The reaction mixture was diluted with water (20 mL) and extracted with ethyl acetate (3×30 mL). The combined organic layer was washed with saturated brine (20 mL), dried over anhydrous sodium sulfate and concentrated in vacuo. The residue was purified by prep-HPLC [Instrument: GX-h; Column: Boston pH-lex 150*25 10 um; Condition: water (0.05% ammonia hydroxide v/v)-ACN] to give the title compound. LCMS: (ES$^+$) m/z (M+H)$^+$=485.2, tR=0.861. $^1$H NMR (400 MHz, DMSO-d$_6$) δ=9.13 (s, 1H), 7.59 (d, J=9.0 Hz, 1H), 7.44 (d, J=8.8 Hz, 1H), 7.40 (s, 1H), 7.32 (d, J=8.0 Hz, 2H), 7.22 (d, J=8.2 Hz, 2H), 4.31 (q, J=7.2 Hz, 1H), 4.25 (d, J=9.0 Hz, 1H), 4.08 (dd, J=9.0, 3.6 Hz, 1H), 3.96-3.91 (m, 2H), 3.90 (s, 3H), 2.76 (td, J=12.6, 6.2 Hz, 1H), 2.32-2.24 (m, 1H), 1.56 (d, J=7.0 Hz, 3H).

To a solution of 4,5-dichloro-N-[3-[4-(cyanomethyl)phenyl]oxetan-3-yl]-1-methyl-indole-2-carboxamide (100 mg, 241 umol, synthesized via Method 6 with acid A and amine BX) in N,N-dimethylformamide (5 mL) was added NaN$_3$ (125 mg, 1.93 mmol,) and ammonium chloride (38.7 mg, 724 umol) under a nitrogen atmosphere. The reaction mixture was stirred at 120° C. for 20 hrs. On completion, water (20 mL) was added into the reaction mixture, and the mixture was carefully acidified to pH=6 with 0.5 N hydrochloric acid. The mixture was extracted with ethyl acetate (2×30 mL) and the aqueous layer was quenched with sodium hypochlorite solution and basified to pH=12 and discarded. The combined organic layer was dried over anhydrous sodium sulfate, filtered and concentrated in vacuo to give a residue. The residue was purified with prep-HPLC (Instrument: GX-D; Column: Boston Green ODS 150*30 5 u; Mobile phase: 0.225% formic acid-acetonitrile) to give the title compound. LCMS: (ES$^+$) m/z (M+H)$^+$=457.1, tR=0.830. $^1$H NMR (400 MHz, DMSO-d$_6$) δ=9.73 (s, 1H), 7.63 (d, J=8.8 Hz, 1H), 7.53 (d, J=8.2 Hz, 2H), 7.47 (d, J=8.8 Hz, 1H), 7.41 (s, 1H), 7.30 (d, J=8.0 Hz, 2H), 5.04 (d, J=6.7 Hz, 2H), 4.78 (d, J=6.7 Hz, 2H), 4.22 (s, 2H), 3.96 (s, 3H).

Example 93—N-(3-(4-(N-Acetylsulfamoyl)phenyl) oxetan-3-yl)-4,5-dichloro-1-methyl-1H-indole-2-carboxamide

Example 94—(±)-2-(4-(3-(4,5-Dichloro-1-methyl-1H-indole-2-carboxamido)tetrahydro-furan-3-yl) phenyl)-3-methylbutanoic acid

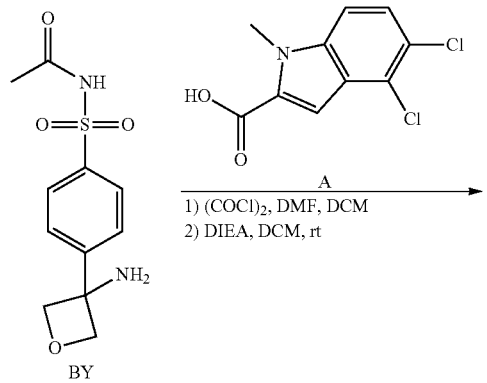

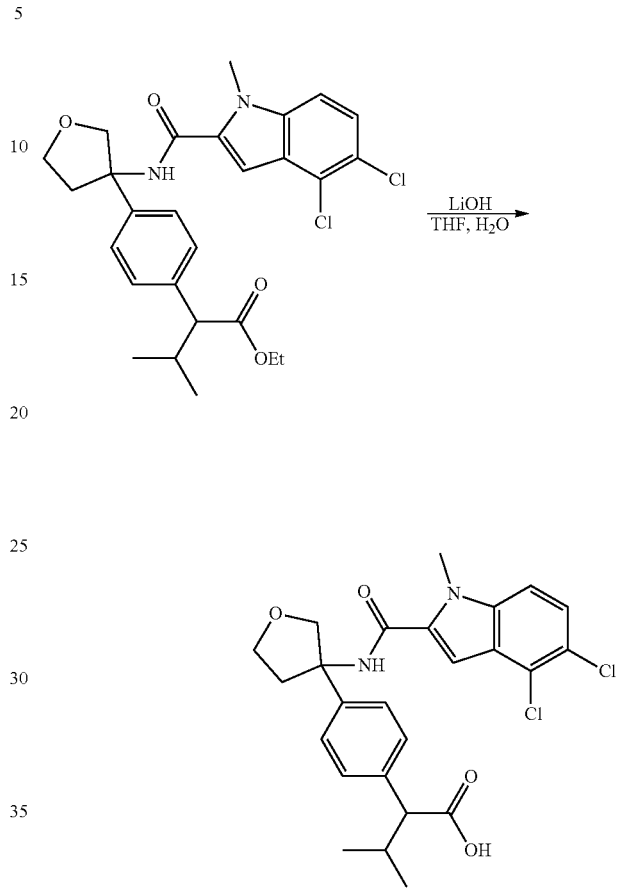

To a mixture of 4,5-dichloro-1-methyl-indole-2-carboxylic acid (140 mg, 574 umol) in dichloromethane (5.00 mL) was added N,N-dimethylformamide (4.19 mg, 57.4 umol) and oxalyl dichloride (364 mg, 2.87 mmol) at rt. The mixture was stirred at rt for 2 hrs. On completion, the mixture was concentrated in vacuo to give a crude yellow solid (152 mg) which was used in next step without any purification.

To a solution of N-[4-(3-aminooxetan-3-yl)phenyl]sulfonylacetamide (90.0 mg, 333 umol) and diisopropyethylamine (129 mg, 999 umol) in dichloromethane (5.00 mL) was added the solution of 4,5-dichloro-1-methyl-indole-2-carbonyl chloride (105 mg, 400 umol) in dichloromethane (5.00 mL) dropwise at rt. The mixture was stirred at rt for 16 hrs. On completion, the solution was quenched with citric acid solution (1M, 5 mL) and extracted with dichloromethane (10 mL). The organic phase was dried over sodium sulfate and concentrated in vacuo to give a residue which was purified by prep-HPLC (Condition: water (0.05% ammonia hydroxide v/v)-ACN; Column: Agela DuraShell 150 mm_25 mm_5 um) to give the title compound. LCMS: (ES$^+$) m/z (M−H)$^+$=494.0, tR=1.312. $^1$H NMR (400 MHz, DMSO-d6) δ=9.81 (br, s, 1H), 7.81 (d, J=8.4 Hz, 2H), 7.67-7.63 (m, 3H), 7.48 (d, J=8.8 Hz, 1H), 7.44 (s, 1H), 5.06 (d, J=6.8 Hz, 2H), 4.81 (d, J=6.8 Hz, 2H), 3.97 (s, 3H), 1.72 (s, 3H).

To a mixture of (±)-2-[4-[3-[(4,5-dichloro-1-methyl-indole-2-carbonyl)amino]tetrahydrofuran-3-yl]phenyl]-3-methyl-butanoate (156 mg, 301 umol, synthesized via Method 6, Step 1 with acid A and amine CF) in anhydrous tetrahydrofuran (6 mL) and water (3 mL) was added lithium hydroxide (36.1 mg, 1.51 mmol). Then the mixture was stirred at 80° C. for 32 hours. On completion, the mixture was adjusted to pH=4-5 with 1N hydrochloric acid, and the reaction mixture was concentrated in vacuo to give a residue. The residue was purified by pre-HPLC (Instrument: GX-F; Condition: water (0.225% FA)-ACN; Column: Phenomenex Synergi C18 150*25*10 um) to give the title compound. LCMS: (ES$^+$) m/z (M+H)$^+$=489.3, tR=0.969. $^1$H NMR (400 MHz, DMSO-d$_6$) δ=9.15 (s, 1H), 7.60 (d, J=8.8 Hz, 1H), 7.46 (d, J=8.8 Hz, 1H), 7.43 (s, 1H), 7.38 (d, J=8.0 Hz, 2H), 7.27 (d, J=8.3 Hz, 2H), 4.27 (d, J=9.3 Hz, 1H), 4.10 (d, J=9.3 Hz, 1H), 3.95 (t, J=7.4 Hz, 2H), 3.91 (s, 3H), 3.03 (d, J=10.3 Hz, 1H), 2.78 (td, J=6.1, 12.6 Hz, 1H), 2.53-2.53 (m, 1H), 2.33-2.28 (m, 1H), 0.99 (d, J=6.3 Hz, 3H), 0.62 (d, J=6.5 Hz, 3H).

Example 95 (Method 7)—(±)-4-[3-[[4,5-Dichloro-1-methyl-6-[(2-oxooxazolidin-5-yl)methoxy]indole-2-carbonyl]amino]tetrahydrofuran-3-yl]benzoic acid

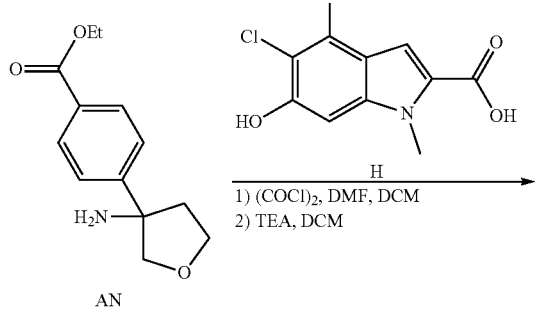

AN

Step 1—(±)-Ethyl 4-[3-[(4,5-dichloro-6-hydroxy-1-methyl-indole-2-carbonyl)amino]tetrahydro-furan-3-yl]-benzoate To a solution of 4,5-dichloro-6-hydroxy-1-methyl-indole-2-carboxylic acid (100 mg, 384 umol), HATU (160 mg, 423 umol) and triethylamine (117 mg, 1.15 mmol) in N,N-dimethylformamide (5 mL) was added (±)-ethyl 4-(3-aminotetrahydrofuran-3-yl)benzoate (90.4 mg, 388 umol) at 0° C. under nitrogen. The mixture was stirred at rt for 16 hours. On completion, to the mixture was added water (20 mL), then the mixture was adjusted to pH=4-5 with hydrochloric acid (2 N), and filtered to get the filter cake. The filter cake was dried in vacuo to obtain the title compound. LCMS: (ES$^+$) m/z (M+H)$^+$=477.0, tR=0.878. $^1$H NMR (300 MHz, DMSO-d6) δ=9.14 (s, 1H), 7.62-7.50 (m, 4H), 7.35 (s, 1H), 6.95 (s, 1H), 4.30 (q, J=7.03 Hz, 4H), 4.07-3.98 (m, 2H), 3.77 (s, 3H), 2.77 (d, J=7.16 Hz, 1H), 2.28 (br. s., 1H), 1.26-1.08 (m, 3H).

Step 2—(±)-Ethyl 4-[3-[[4,5-dichloro-1-methyl-6-[(2-oxooxazolidin-5-yl)methoxy]indole-2-carbonyl]amino]tetrahydrofuran-3-yl]benzoate To a solution of (±)-ethyl 4-[3-[(4,5-dichloro-6-hydroxy-1-methyl-indole-2-carbonyl)amino]tetrahydrofuran-3-yl]benzoate (140 mg, 293 umol) in N,N-dimethylformamide (5 mL) was added potassium carbonate (81.0 mg, 586 umol) and 5-(chloromethyl)oxazolidin-2-one (59.6 mg, 439 umol, CAS #22625-57-6). Then the mixture was stirred at 100-110° C. for 16 hours. On completion, the mixture was cooled to room temperature and water (20 mL) was added. Then the mixture was extracted with ethyl acetate (3×20 mL) and the combined phase was concentrated to obtain the crude product. The residue was purified by prep-TLC (petroleum ether:ethyl acetate=5:1 to 0:1) to obtain the title compound. $^1$H NMR (400 MHz, DMSO-d6) δ=9.20 (s, 1H), 7.96 (s, 2H), 7.65 (s, 1H), 7.58 (d, J=8.53 Hz, 2H), 7.38 (d, J=15.81 Hz, 2H), 5.03-4.96 (m, 1H), 4.38-4.27 (m, 4H), 4.21 (s, 2H), 3.99-3.93 (m, 2H), 3.88 (s, 3H), 3.68-3.63 (m, 1H), 3.44 (br. s., 1H), 2.83-2.76 (m, 1H), 2.36-2.29 (m, 1H), 1.31 (t, J=7.09 Hz, 3H).

Step 3—(±)-4-[3-[[4,5-Dichloro-1-methyl-6-[(2-oxooxazolidin-5-yl)methoxy]indole-2-carbonyl]amino]tetrahydrofuran-3-yl]benzoic acid To a solution of (±)-ethyl 4-[3-[[4,5-dichloro-1-methyl-6-[(2-oxooxazolidin-5-yl)methoxy]indole-2-carbonyl]amino]tetrahydrofuran-3-yl] benzoate (80.0 mg, 138 umol) in tetrahydrofuran (2 mL) and water (2 mL) was added lithium hydroxide (6.65 mg, 277 umol) at rt, then the mixture was stirred at rt for 16 hours. On completion, the mixture was adjusted to pH=4-5 with hydrochloric acid (2 N) and concentrated. The residue was purified by prep-HPLC (condition: water (0.225% FA)-ACN; column: Boston Green ODS 150*30 5 u) to give the title compound. $^1$H NMR (400 MHz, DMSO-d6) δ=9.16 (s, 1H), 7.89 (d, J=8.41 Hz, 2H), 7.64 (s, 1H), 7.51 (d, J=8.41 Hz, 2H), 7.37 (d, J=16.56 Hz, 2H), 5.02-4.94 (m, 1H), 4.38-4.32 (m, 1H), 4.32-4.25 (m, 1H), 4.24-4.14 (m, 2H), 3.99-3.91 (m, 2H), 3.87 (s, 3H), 3.65 (t, J=9.03 Hz, 1H), 3.43-3.40 (m, 1H), 2.81-2.72 (m, 1H), 2.32-2.26 (m, 1H).

Method 7 Table: Compounds Synthesized via Method 7 using the appropriate amine

| Example # | Structure | Intermediate Amine | LCMS (ES+) m/z (M + H)+ | HNMR (400 MHz, DMSO-d6) δ |
|---|---|---|---|---|
| 96 | 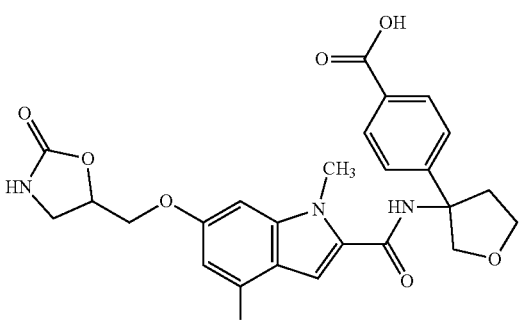<br>(±)-4-(3-{4-chloro-1-methyl-6-[(2-oxo-1,3-oxazolidin-5-yl)methoxy]-1H-indole-2-amido}oxolan-3-yl)benzoic acid | 5-(chloromethyl)oxazolidin-2-one | 514.2 | 12.82 (br s, 1H), 9.12 (s, 1H), 7.91 (d, J = 8.8 Hz, 2H), 7.61 (s, 1H), 7.55 (d, J = 8.8 Hz, 2H), 7.37(s, 1H), 7.12(s, 1H), 6.92 (s, 1H), 4.94 (t, J = 0.28 Hz, 1H), 4.27-4.24 (m, 1H), 4.21 (s, 3H), 3.96 (d, J = 4.0 Hz, 2H), 3.85 (s, 3H), 3.63 (t, J = 0.28 Hz, 1H), 3.36-3.32 (m, 1H), 2.78-2.75 (m, 1H), 2.49-2.29 (m, 1H) |
| 97 | 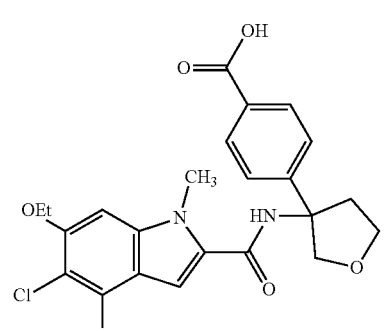<br>(±)-4-[3-(4,5-dichloro-6-ethoxy-1-methyl-1H-indole-2-amido)oxolan-3-yl]benzoic acid | EtI | 477.0 | 9.15 (s, 1H), 7.91 (d, J = 8.5 Hz, 2H), 7.53 (d, J = 8.4 Hz, 2H), 7.39 (s, 1H), 7.26 (s, 1H), 4.27-4.16 (m, 4H), 4.02-3.92 (m, 2H), 3.88 (s, 3H), 2.83-2.74 (m, 1H), 2.33-2.27 (m, 1H), 1.42 (t, J = 6.8 Hz, 3H) |
| 98 | 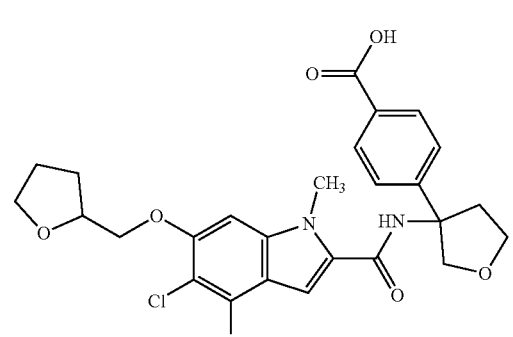<br>(±)-4-{3-[4,5-dichloro-1-methyl-6-(oxolan-2-ylmethoxy)-1H-indole-2-amido]oxolan-3-yl}benzoic acid | 2-(bromomethyl)-tetrahydrofuran | 533.1 | 9.12 (s, 1H), 8.34 (s, 1H), 7.88 (d, J = 8.4 Hz, 2H), 7.48 (d, J = 8.4 Hz, 2H), 7.38 (s, 1H), 7.29 (s, 1H), 4.22-4.24 (m, 2H), 4.16-4.18 (m, 1H), 4.13-4.14(m, 1H), 3.95-3.97 (m, 2H), 3.87 (s, 3H), 3.70-3.72 (m, 2H), 2.74-2.81 (m, 2H), 1.95-2.05 (m, 2H), 1.74-1.87 (m, 2H) |

-continued

Method 7 Table: Compounds Synthesized via Method 7 using the appropriate amine

| Example # | Structure | Intermediate Amine | LCMS (ES+) m/z (M + H)+ | HNMR (400 MHz, DMSO-d6) δ |
|---|---|---|---|---|
| 99 | 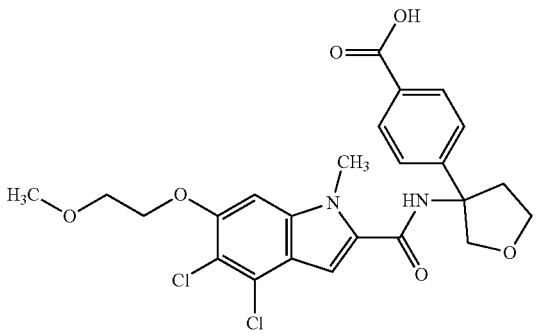 [SMILES: COCCOc1cc2c(cc(C(=O)NC3(c4ccc(C(=O)O)cc4)CCOC3)n2C)c(Cl)c1Cl]<br>(±)-4-{3-[4,5-dichloro-6-(2-methoxyethoxy)-1-methyl-1H-indole-2-amido]oxolan-3-yl}benzoic acid | 1-chloro-2-methoxy-ethane | 507.1 | 12.84 (br. s., 1H), 9.16 (s, 1H), 7.91 (d, J = 8.3 Hz, 2H), 7.54 (d, J = 8.3 Hz, 2H), 7.39 (s, 1H), 7.29 (s, 1H), 4.32-4.26 (m, 2H), 4.24-4.16 (m, 2H), 3.99-3.92 (m, 2H), 3.87 (s, 3H), 3.77-3.71 (m, 2H), 3.36 (s, 3H), 2.77 (t, J = 12.6, 1H), 2.34-2.25 (m, 1H) |
| 100 | 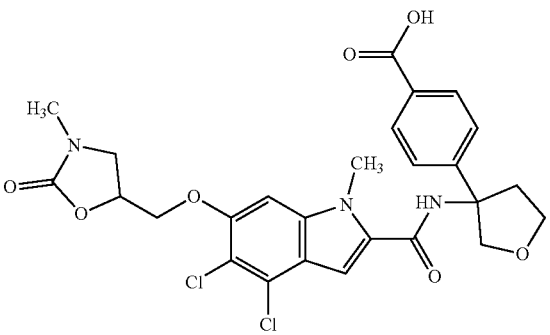 [SMILES: CN1CC(COc2cc3c(cc(C(=O)NC4(c5ccc(C(=O)O)cc5)CCOC4)n3C)c(Cl)c2Cl)OC1=O]<br>(±)-4-(3-{4,5-dichloro-1-methyl-6-[(1-methyl-5-oxopyrrolidin-3-yl)methoxy]-1H-indole-2-amido}oxolan-3-yl)benzoic acid | AQ | 560.0 | 12.96-12.73 (br. s., 1H), 9.18 (s, 1H), 7.92 (d, J = 8.3 Hz, 2H), 7.55 (d, J = 8.3 Hz, 2H), 7.40 (s, 1H), 7.33 (s, 1H), 4.21 (d, J = 3.5 Hz, 2H), 4.15-4.13 (m, 2H), 3.98-3.96 (m, 2H), 3.88 (s, 3H), 3.57 (s, 2H), 3.29-3.26 (m, 1H), 2.91-2.83 (m, 1H), 2.82-2.76 (m, 1H), 2.74 (s, 3H), 2.30-2.13 (m, 2H) |
| 101 | 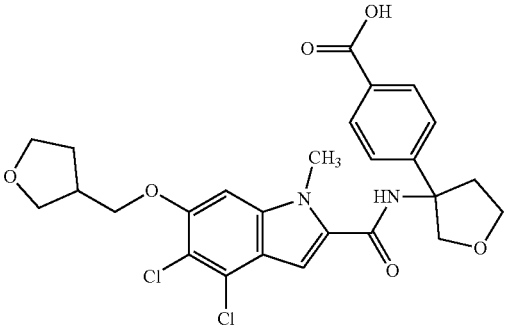 [SMILES: Cn1c(C(=O)NC2(c3ccc(C(=O)O)cc3)CCOC2)cc2c(Cl)c(Cl)c(OCC3CCOC3)cc21]<br>(±)-4-{3-[4,5-dichloro-1-methyl-6-(oxolan-3-ylmethoxy)-1H-indole-2-amido]oxolan-3-yl}benzoic acid | AR | 533.3 | 12.86 (br. s., 1H), 9.17 (s, 1H), 7.92 (d, J = 8.4 Hz, 2H), 7.55 (d, J = 8.4 Hz, 2H), 7.40 (s, 1H), 7.31 (s, 1H), 4.25-4.17 (m, 2H), 4.16-4.10 (m, 1H), 4.09-4.03 (m, 1H), 3.99-3.93 (m, 2H), 3.88 (s, 3H), 3.84-3.77 (m, 2H), 3.73-3.66 (m, 1H), 3.61 (dd, J = 5.5, 8.6 Hz, 1H), 2.81-2.70 (m, 2H), 2.32 (td, J = 7.9, 12.9 Hz, 1H), 2.11-2.01 (m, 1H), 1.73 (qd, J = 6.4, 13.1 Hz, 1H) |

Method 7 Table: Compounds Synthesized via Method 7 using the appropriate amine

| Example # | Structure | Intermediate Amine | LCMS (ES+) m/z (M + H)+ | HNMR (400 MHz, DMSO-d6) δ |
|---|---|---|---|---|
| 102 | (±)-4-(3-{4,5-dichloro-6-[2-(dimethylamino)ethoxy]-1-methyl-1H-indole-2-amido}oxolan-3-yl)benzoic acid | 2-chloro-N,N-dimethylethanamine | 520.1 | 12.91 (br s, 1H), 9.88 (br s, 1H), 9.19 (s, 1H), 7.91 (d, J = 8.4 Hz, 2H), 7.55 (d, J = 8.4 Hz, 2H), 7.43 (s, 1H), 7.38 (s, 1H), 4.52 (t, J = 4.4 Hz, 2H), 4.21 (d, J = 5.2 Hz, 2H), 3.97 (t, J = 4.4 Hz, 2H), 3.89 (s, 3H), 3.63 (d, J = 4.4 Hz, 2H), 2.94 (s, 6H), 2.75-2.70 (m, 1H), 2.33-2.30 (m, 1H) |
| 103 | (±)-4-{3-[4,5-dichloro-1-methyl-6-(oxetan-3-ylmethoxy)-1H-indole-2-amido]oxolan-3-yl}benzoic acid | AS | 519.2 | 9.18 (s, 1H), 7.92 (d, J = 8.2 Hz, 2H), 7.55 (d, J = 8.2 Hz, 2H), 7.40 (s, 1H), 7.35 (d, J = 2.3 Hz, 1H), 4.75 (dd, J = 6.0, 7.9 Hz, 2H), 4.49 (t, J = 6.4 Hz, 2H), 4.39 (d, J = 6.4 Hz, 2H), 4.25-4.18 (m, 2H), 4.00-3.93 (m, 2H), 3.89 (s, 3H), 3.51-3.43 (m, 1H), 2.78 (td, J = 6.2, 12.7 Hz, 1H), 2.32 (td, J = 8.0, 13.0 Hz, 1H) |

Example 104—(±)-4-(3-(6-(3-Amino-2-hydroxypropoxy)-4,5-dichloro-1-methyl-1H-indole-2-carboxamido)tetrahydrofuran-3-yl)benzoic acid

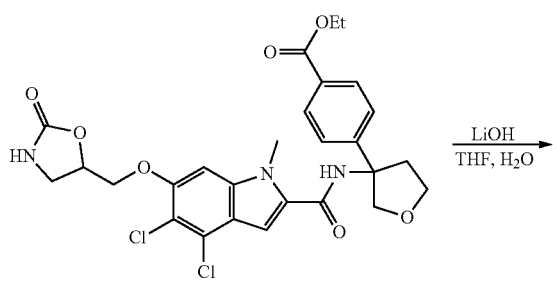

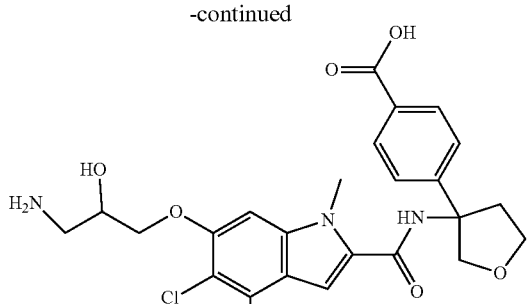

To a solution of (±)-ethyl 4-[3-[[4,5-dichloro-1-methyl-6-[(2-oxooxazolidin-5-yl)methoxy]indole-2-carbonyl]amino]tetrahydrofuran-3-yl]benzoate (80.0 mg, 138 umol, synthesized via Method 7 Steps 1-2 as seen above in Example 95) in tetrahydrofuran (2 mL) and water (2 mL)

was added lithium hydroxide (6.65 mg, 277 umol). The mixture was stirred at 30° C. for 16 hrs. On completion, the mixture was acidified by hydrochloric acid (2 N) until pH=4-5 then concentrated in vacuo. The residue was purified by Prep-HPLC (condition: water (0.225% FA)-ACN; column: Phenomenex Synergi C18 150*25*10 um) to give the title compound. LCMS: (ES⁺) m/z (M+H)⁺=522.1, tR=0.630. ¹H NMR (400 MHz, DMSO-d6) δ=9.12 (s, 1H), 8.34 (br. s., 1H), 7.87 (d, J=8.03 Hz, 2H), 7.46 (d, J=7.91 Hz, 2H), 7.38 (s, 1H), 7.30 (s, 1H), 4.21-4.25 (m, 1H), 4.14-4.19 (m, 2H), 4.12 (d, J=6.90 Hz, 2H), 3.91-3.99 (m, 3H), 3.87 (s, 3H), 3.04-3.07 (m, 1H), 2.88 (br. s., 1H), 2.75-2.79 (m, 1H), 2.27-2.32 (m, 1H).

Example 105—(±)-4-(3-(6-((1H-imidazol-2-yl)methoxy)-4,5-dichloro-1-methyl-1H-indole-2-carboxamido)tetrahydrofuran-3-yl)benzoic acid

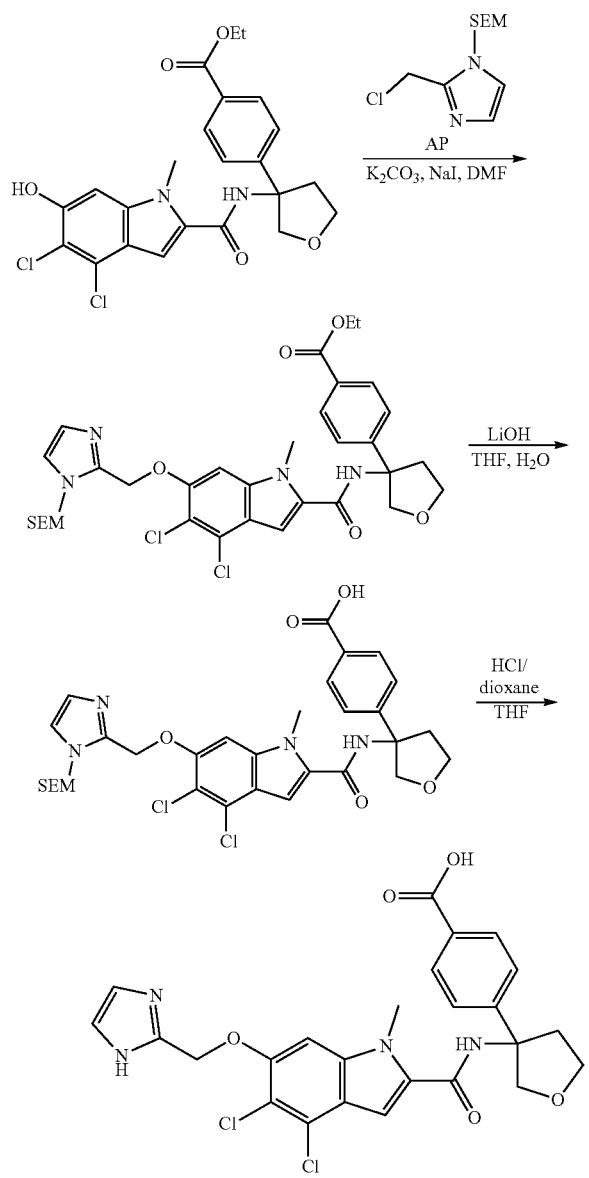

Step 1—(±)-Ethyl 4-(3-(4,5-dichloro-1-methyl-6-((1-((2-(trimethylsilyl)ethoxy)methyl)-1H-imidazol-2-yl)methoxy)-1H-indole-2-carboxamido)tetrahydrofuran-3-yl)benzoate To a mixture of (±)-ethyl 4-[3-[(4,5-dichloro-6-hydroxy-1-methyl-indole-2-carbonyl)amino]tetrahydrofuran-3-yl]benzoate (300 mg, 628 umol, synthesized via Step 1 of Method 7) and 2-[[2-(chloromethyl)imidazol-1-yl]methoxy]ethyl-trimethyl-silane (233 mg, 943 umol) in N,N-dimethylformamide (5 mL) was added potassium carbonate (174 mg, 1.26 mmol) and sodium iodide (9.42 mg, 62.9 umol) in one portion at rt under nitrogen. The mixture was stirred at 80° C. for 16 hrs. On completion, the mixture was cooled to rt, then mixture was diluted with brine (10 mL) and extracted with ethyl acetate (3×20 mL). The combined organic layers were washed with brine (50 mL), dried over sodium sulfate, and concentrated in vacuo. The residue was purified by chromatography (petroleum ether:ethyl acetate=10:1 to 0:1) to give the title compound. ¹H NMR (300 MHz, CDCl₃) δ=8.09 (d, J=8.4 Hz, 2H), 7.60 (d, J=8.4 Hz, 2H), 7.18 (s, 1H), 7.18 (s, 1H), 7.11 (d, J=1.8 Hz, 2H), 7.02 (s, 1H), 6.92 (s, 1H), 5.53 (s, 2H), 5.44 (s, 2H), 4.42 (q, J=7.2 Hz, 2H), 4.19-4.30 (m, 4H), 3.96 (s, 3H), 3.56 (t, J=8.1 Hz, 2H), 2.81-2.89 (m, 1H), 2.59-2.69 (m, 1H), 1.43 (t, J=6.9 Hz, 3H), 0.94 (t, J=8.4 Hz, 2H), 0.00 (s, 9H).

Step 2—(±)-4-(3-(4,5-Dichloro-1-methyl-6-((1-((2-(trimethylsilyl)ethoxy)methyl)-1H-imidazol-2-yl)methoxy)-1H-indole-2-carboxamido)tetrahydrofuran-3-yl)benzoic acid To a mixture of (±)-ethyl 4-[3-[[4,5-dichloro-1-methyl-6-[[1-(2-trimethylsilylethoxymethyl) imidazol-2-yl]methoxy]indole-2-carbonyl]amino]tetrahydrofuran-3-yl]benzoate (75.0 mg, 109 umol) in tetrahydrofuran (2 mL) and water (2 mL) was added lithium hydroxide (18.3 mg, 436 umol) in one portion at rt. The mixture was stirred at 80° C. for 4 hrs. On completion, the mixture was concentrated in vacuo to give the title compound. LCMS: (ES⁺) m/z (M+H)⁺=659.0, tR=0.817.

Step 3—(±)-4-(3-(6-((1H-imidazol-2-yl)methoxy)-4,5-dichloro-1-methyl-1H-indole-2-carboxamido)tetrahydrofuran-3-yl)benzoic acid To a mixture of (±)-4-[3-[[4,5-dichloro-1-methyl-6-[[1-(2-trimethylsilylethoxymethyl) imidazol-2-yl]methoxy]indole-2-carbonyl]amino]tetrahydrofuran-3-yl]benzoic acid (45.0 mg, 68.2 umol) in tetrahydrofuran (2 mL) was added hydrogen chloride/dioxane (4 M, 5 mL) in one portion at rt. The mixture was stirred at 60° C. for 4 hrs. On completion, the mixture was concentrated in vacuo. The residue was purified by Prep-HPLC (condition: water (0.05% HCl)-ACN; column: Phenomenex Synergi C18 150*30 mm*4 um) to give the title compound. LCMS: (ES⁺) m/z (M+H)⁺=529.1, tR=0.799. ¹H NMR (400 MHz, DMSO-d6) δ=9.22 (br. s, 1H), 7.92 (d, J=8.4 Hz, 2H), 7.67 (s, 2H), 7.55-7.57 (m, 3H), 7.44 (s, 1H), 5.51 (s, 2H), 4.21-4.23 (m, 2H), 3.95-3.99 (m, 2H), 3.92 (s, 3H), 2.75-2.82 (m, 2H).

Example 106—(±)-4-[3-[[4,5-Dichloro-1-methyl-6-[(3-methyl-2-oxooxazolidin-5-yl) methoxy]indole-2-carbonyl]amino]tetrahydrofuran-3-yl]benzoic acid
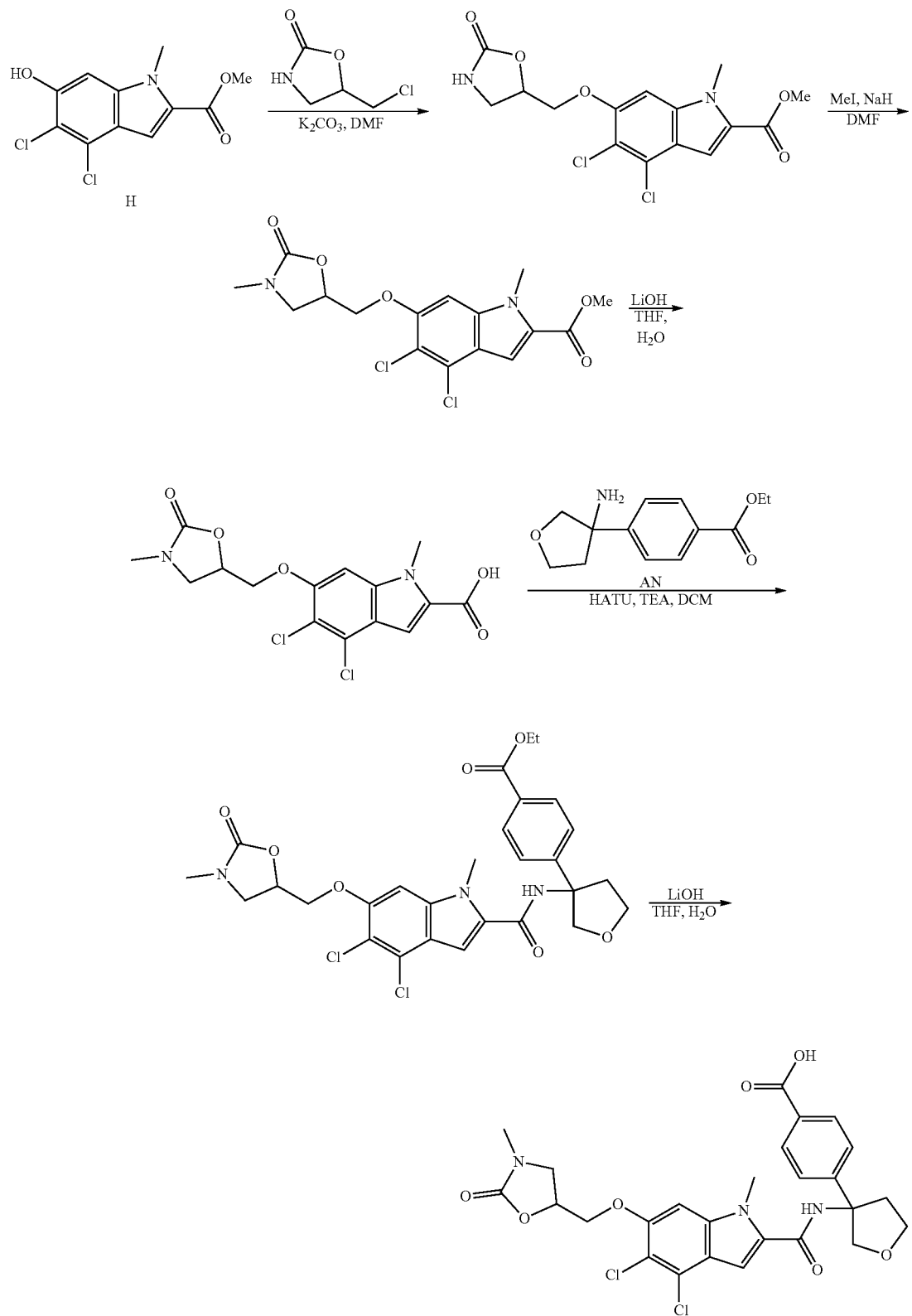

Step 1—(±)-Methyl 4,5-dichloro-1-methyl-6-[(2-oxooxazolidin-5-yl)methoxy]indole-2-carboxylate To a solution of methyl 4,5-dichloro-6-hydroxy-1-methyl-1H-indole-2-carboxylate (1.00 g, 3.65 mmol) in N,N-dimethylformamide (15 mL) was added potassium carbonate (1.01 g, 7.30 mmol) and (±)-5-(chloromethyl)oxazolidin-2-one (593.71 mg, 4.38 mmol, CAS #22625-57-6). The mixture was stirred at 100° C. for 12 hrs. On completion, the reaction mixture was quenched with water (50 mL) and extracted with ethyl acetate (3×50 mL). The combined organic layers were washed with brine (2×25 mL), dried over sodium sulfate, filtered and concentrated in vacuo. The residue was purified by silica gel chromatography (petroleum ether:ethyl acetate=5:1 to 0:1) to give the title compound. $^1$H NMR (400 MHz, DMSO-$d_6$) δ=7.67 (s, 1H), 7.41 (s, 1H), 7.16 (s, 1H), 5.06-4.97 (m, 1H), 4.43-4.28 (m, 2H), 4.03 (s, 3H), 3.86 (s, 3H), 3.68 (t, J=9.03 Hz, 1H), 3.42 (dd, J=8.53, 6.78 Hz, 1H).

Step 2—(±)-Methyl 4,5-dichloro-1-methyl-6-[(3-methyl-2-oxo-oxazolidin-5-yl)methoxy]indole-2-carboxylate To a solution of (±)-methyl 4,5-dichloro-1-methyl-6-((2-oxooxazolidin-5-yl)methoxy)-1H-indole-2-carboxylate (700 mg, 1.88 mmol) in N,N-dimethylformamide (24 mL) was added sodium hydride (113 mg, 2.81 mmol, 60% purity) at 0° C. The mixture was stirred at 0° C. for 30 min, then iodomethane (532 mg, 3.75 mmol) was added. The mixture was stirred at rt for 2 hrs. On completion, the mixture was quenched with water (200 mL) and extracted with ethyl acetate (3×50 mL). The combined organic layers were washed with brine (2×50 mL), dried over sodium sulfate, filtered and concentrated in vacuo. The residue was triturated with petroleum ether:ethyl acetate=1:1 and the solid was collected by filtration to give the title compound. $^1$H NMR (400 MHz, DMSO-$d_6$) δ=7.40 (s, 1H), 7.17 (s, 1H), 4.98-4.91 (m, 1H), 4.33-4.48 (m, 1H), 4.34-4.28 (m, 1H), 4.03 (s, 3H), 3.86 (s, 3H), 3.76 (t, J=9.03 Hz, 1H), 3.47 (dd, J=8.78, 6.02 Hz, 1H), 2.81 (s, 3H).

Step 3—(±)-4,5-Dichloro-1-methyl-6-[(3-methyl-2-oxo-oxazolidin-5-yl)methoxy]indole-2-carboxylic acid To a solution of (±)-methyl 4,5-dichloro-1-methyl-6-((3-methyl-2-oxooxazolidin-5-yl)methoxy)-1H-indole-2-carboxylate (90.0 mg, 232.4 umol) in tetrahydrofuran (5 mL) and water (2 mL) was added lithium hydroxide (19.5 mg, 464.9 umol). The mixture was stirred at rt for 2 hrs. On completion, the reaction mixture was concentrated to remove the organic solvent. The aqueous phase was acidified with hydrochloric acid (1 N) until pH=2, and extracted with ethyl acetate (3×10 mL). The combined organic layers were washed with brine (2×5 mL), dried over sodium sulfate, filtered and concentrated in vacuo to give the title compound. $^1$H NMR (400 MHz, DMSO-$d_6$) δ=7.40 (s, 1H), 7.13 (s, 1H), 4.94 (td, J=8.72, 5.65 Hz, 1H), 4.43-4.27 (m, 2H), 4.05-4.01 (m, 3H), 3.76 (t, J=9.03 Hz, 1H), 3.47 (dd, J=8.78, 6.27 Hz, 1H), 2.81 (s, 3H).

Step 4—(±)-Ethyl 4-[3-[[4,5-dichloro-1-methyl-6-[(3-methyl-2-oxo-oxazolidin-5-yl) methoxy]indole-2-carbonyl]amino]tetrahydrofuran-3-yl]benzoate To a solution of (±)-4,5-dichloro-1-methyl-6-((3-methyl-2-oxooxazolidin-5-yl) methoxy)-1H-indole-2-carboxylic acid (75.0 mg, 201 umol) in dichloromethane (5 mL) was added triethylamine (40.7 mg, 402 umol), ethyl 4-(3-aminotetrahydrofuran-3-yl)benzoate (52.0 mg, 221 umol) and HATU (76.41 mg, 200.97 umol). The mixture was stirred at rt for 2 hr. On completion, the reaction mixture was quenched with water (20 mL) and extracted with ethyl acetate (3×30 mL). The combined organic layers were washed with brine (2×15 mL), dried over sodium sulfate, and concentrated in vacuo. The residue was purified by chromatography (petroleum ether:ethyl acetate=5:1 to 0:1) to give the title compound. $^1$H NMR (400 MHz, DMSO-$d_6$) δ=9.21 (s, 1H), 7.94 (d, J=8.53 Hz, 2H), 7.58 (d, J=8.53 Hz, 2H), 7.43-7.33 (m, 2H), 4.97-4.89 (m, 1H), 4.42-4.36 (m, 1H), 4.34-4.27 (m, 3H), 4.25-4.18 (m, 2H), 4.01-3.93 (m, 2H), 3.88 (s, 3H), 3.76 (t, J=8.91 Hz, 1H), 3.47-3.43 (m, 1H), 2.81 (s, 3H), 2.72-2.69 (m, 1H), 2.36-2.28 (m, 1H), 1.31 (t, J=7.03 Hz, 3H).

Step 5—(±)-4-[3-[[4,5-Dichloro-1-methyl-6-[(3-methyl-2-oxo-oxazolidin-5-yl) methoxy]indole-2-carbonyl]amino]tetrahydrofuran-3-yl]benzoic acid To a solution of (±)-ethyl 4-(3-(4,5-dichloro-1-methyl-6-((3-methyl-2-oxooxazolidin-5-yl)methoxy)-1H-indole-2-carboxamido)tetrahydrofuran-3-yl)benzoate (40.0 mg, 67.7 umol) in tetrahydrofuran (1 mL) and water (500 uL) was added lithium hydroxide (5.42 mg, 135 umol). The mixture was stirred at rt for 12 hrs. On completion, the reaction was concentrated in vacuo to remove the organic solvent. The aqueous phase was acidified with hydrochloric acid (1 N) until pH=2, and concentrated in vacuo. The residue was purified by Prep-HPLC (Phenomenex Synergi C18 150*30 mm*4 um, water (0.225% FA)-ACN) to give the title compound. $^1$H NMR (400 MHz, DMSO-$d_6$) δ=9.14 (s, 1H), 8.39 (s, 1H), 7.90 (d, J=8.03 Hz, 2H), 7.48 (d, J=8.28 Hz, 2H), 7.40 (s, 1H), 7.35 (s, 1H), 4.93 (d, J=5.02 Hz, 1H), 4.35-4.42 (m, 1H), 4.29 (dd, J=11.04, 5.02 Hz, 1H), 4.22-4.27 (m, 1H), 4.15-4.20 (m, 1H), 3.93-3.99 (m, 2H), 3.89 (s, 3H), 3.76 (t, J=8.91 Hz, 1H), 3.47 (d, J=2.51 Hz, 1H), 2.81 (s, 3H), 2.74-2.79 (m, 1H), 2.26-2.33 (m, 1H).

Example 107 (Method 8)—2-(4-(3-(4,5-Dichloro-1-methyl-1H-indole-2-carboxamido)oxetan-3-yl)Phenyl)-2-methylpropanoic acid

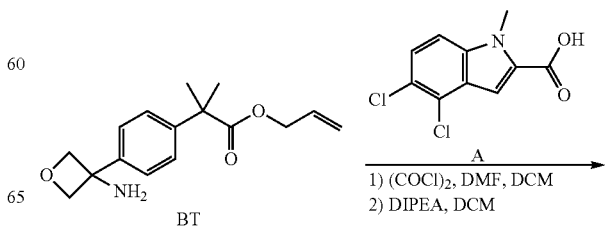

-continued

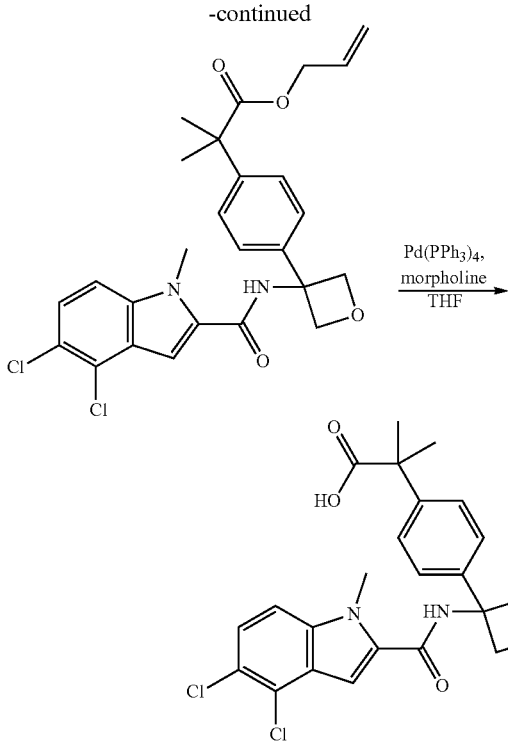

Step 1—Allyl 2-(4-(3-(4,5-dichloro-1-methyl-1H-indole-2-carboxamido)oxetan-3-yl)phenyl)-2-methylpropanoate To a mixture of 4,5-dichloro-1-methyl-indole-2-carboxylic acid (150 mg, 614 umol) and DMF (4.49 mg, 61.4 umol) in dichloromethane (10 mL) was added oxalyl chloride (390 mg, 3.07 mmol) in one portion at rt under nitrogen. The mixture was stirred at rt for 1 hr. On completion, the mixture was concentrated in vacuo. To a mixture of allyl 2-[4-(3-aminooxetan-3-yl)phenyl]-2-methyl-propanoate (150 mg, 544 umol) and diisopropylethylamine (211 mg, 1.63 mmol) in dichloromethane (10 mL) was added 4,5-dichloro-1-methyl-indole-2-carbonyl chloride (171 mg, 653 umol) in dichloromethane (10 mL) in one portion at rt under nitrogen. The mixture was stirred at rt for 16 hours. On completion, the reaction was quenched with 1 mL of ethanol. Then the mixture was diluted with water (10 mL) and extracted with dichloromethane (3×30 mL). The organic layer was dried over anhydrous sodium sulfate, filtered and concentrated in vacuo. The residue was purified by column chromatography (petroleum ether:ethyl acetate=20:1 to 8:1) to afford the title compound. LCMS: (ES$^+$) m/z (M+H)$^+$=501.2, tR=1.038.

Step 2—2-(4-(3-(4,5-Dichloro-1-methyl-1H-indole-2-carboxamido)oxetan-3-yl)Phenyl)-2-methylpropanoic acid To a mixture of allyl 2-[4-[3-[(4,5-dichloro-1-methyl-indole-2-carbonyl)amino]oxetan-3-yl]phenyl]-2-methyl-propanoate (80.0 mg, 159 umol) and Pd(PPh$_3$)$_4$ (36.8 mg, 31.9 umol) in anhydrous tetrahydrofuran (5 mL) was added morpholine (139 mg, 1.60 mmol, 140 uL) in one portion at rt under nitrogen. The mixture was stirred at 50° C. for 16 hours. On completion, the reaction mixture was concentrated in vacuo, the residue was dissolved in dichloromethane (10 mL) and washed with 1N citric acid (5 mL) until pH=3-4. The organic layer was dried over anhydrous sodium sulfate, filtrated and concentrated in vacuo. The crude product was dissolved in anhydrous tetrahydrofuran (10 mL) and thiourea (resin) (1.00 g, 13.1 mmol) was added. The mixture was stirred at rt for 16 hours. The reaction mixture was filtered and the filtrate was concentrated in vacuo to give a residue. The residue was purified by pre-HPLC (Instrument: GX-D; Condition: water (0.225% FA)-ACN; Column: Boston Green ODS 150*30 5 u) to afford the title compound. LCMS: (ES$^+$) m/z (M+H)$^+$=461.2, tR=0.930. $^1$H NMR (400 MHz, DMSO-d$_6$) δ=9.74 (s, 1H), 7.63 (d, J=9.0 Hz, 1H), 7.54 (d, J=8.3 Hz, 2H), 7.48 (d, J=8.8 Hz, 1H), 7.44-7.35 (m, 3H), 5.05 (d, J=6.8 Hz, 2H), 4.79 (d, J=6.8 Hz, 2H), 3.97 (s, 3H), 1.47 (s, 6H).

Method 8 Table: Compounds Synthesized via Method 8 using the appropriate acid and amine

| Example # | Structure | Intermediate Acid | Intermediate Amine | LCMS (ES+) m/z (M + H)$^+$ | HNMR (400 MHz, DMSO-d6) δ |
|---|---|---|---|---|---|
| 108 | 1-{4-[3-(4,5-dichloro-1-methyl-1H-indole-2-amido)oxetan-3-yl]phenyl}cyclopropane-1-carboxylic acid | A | BU | 459.2 | 9.73 (s, 1H), 7.63 (d, J = 8.8 Hz, 1H), 7.52-7.45 (m, 3H), 7.42 (s, 1H), 7.35 (d, J = 8.0 Hz, 2H), 5.06 (d, J = 7.2 Hz, 2H), 4.79 (d, J = 6.4 Hz, 2H), 3.98 (s, 3H), 1.40 (d, J = 2.4 Hz, 2H), 1.07 (d, J = 2.4 Hz, 2H) |

Method 8 Table: Compounds Synthesized via Method 8 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 109 | 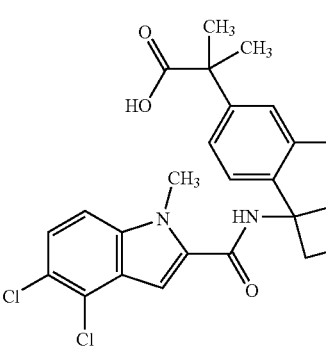<br>2-{4-[3-(4,5-dichloro-1-methyl-1H-indole-2-amido)oxetan-3-yl]-3-fluorophenyl}-2-methylpropanoic acid | A | BV | 479.2 | 9.85 (s, 1H), 7.60 (d, J = 8.8 Hz, 1H), 7.49-7.44 (m, 2H), 7.39 (s, 1H), 7.21-7.18 (m, 2H), 5.05-495 (m, 4H), 3.94 (s, 3H), 1.42 (s, 6H) |
| 110 | 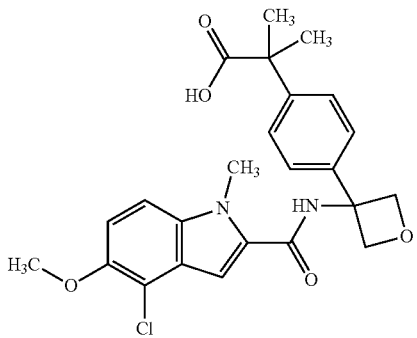 [SMILES: COc1ccc2c(cc(C(=O)NC3(c4ccc(C(C)(C)C(=O)O)cc4)COC3)n2C)c1Cl]<br>2-{4-[3-(4-chloro-5-methoxy-1-methyl-1H-indole-2-amido)oxetan-3-yl]phenyl}-2-methylpropanoic acid | B | BT | 457.3 | 9.64 (s, 1H), 7.58-7.49 (m, 3H), 7.39 (d, J = 8.3 Hz, 2H), 7.31 (s, 1H), 7.25 (d, J = 9.0 Hz, 1H), 5.05 (d, J = 6.5 Hz, 2H), 4.78 (d, J = 6.5 Hz, 2H), 3.94 (s, 3H), 3.89 (s, 3H), 1.47 (s, 6H) |
| 111 | 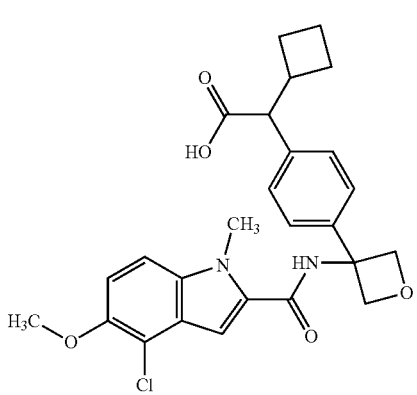 [SMILES: COc1ccc2c(cc(C(=O)NC3(c4ccc(C(C(=O)O)C5CCC5)cc4)COC3)n2C)c1Cl]<br>(±)-2-{4-[3-(4-chloro-5-methoxy-1-methyl-1H-indole-2-amido)oxetan-3-yl]phenyl}-2-cyclobutylacetic acid | B | CA | 483.3 | 9.63 (s, 1H), 7.57-7.48 (m, 3H), 7.36-7.28 (m, 3H), 7.25 (d, J = 8.9 Hz, 1H), 5.04 (d, J = 6.8 Hz, 2H), 4.77 (d, J = 6.8 Hz, 2H), 3.94 (s, 3H), 3.89 (s, 3H), 3.49 (d, J = 10.8 Hz, 1H), 2.88 (m, 1H), 2.11 (m, 1H), 1.76 (m, 4H), 1.55 (m, 1H) |

Method 8 Table: Compounds Synthesized via Method 8 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 112 | (±)-2-{4-[3-(4-chloro-5-methoxy-1-methyl-1H-indole-2-amido)oxetan-3-yl]phenyl}pentanoic acid | B | CE | 471.3 | 9.62 (s, 1H), 7.57-7.46 (m, 3H), 7.37-7.28 (m, 3H), 7.24 (d, J = 9.0 Hz, 1H), 5.03 (d, J = 6.5 Hz, 2H), 4.77 (d, J = 6.5 Hz, 2H), 3.93 (s, 3H), 3.88 (s, 3H), 3.44 (t, J = 7.8 Hz, 1H), 1.97-1.86 (m, 1H), 1.61-1.51 (m, 1H), 1.29-1.13 (m, 2H), 0.85 (t, J = 7.2 Hz, 3H) |
| 113 | (±)-2-{4-[3-(4,5-dichloro-6-methoxy-1-methyl-1H-indole-2-amido)oxetan-3-yl]phenyl}butanoic acid | F | BZ | 491.2 | 9.60 (s, 1H), 7.52 (d, J = 8.0 Hz, 2H), 7.39-7.31 (m, 3H), 7.28 (s, 1H), 5.04 (d, J = 6.8 Hz, 2H), 4.78 (d, J = 6.8 Hz, 2H), 3.97 (s, 3H), 3.96 (s, 3H), 3.39-3.39 (m, 1H), 2.05-1.90 (m, 1H), 1.66-1.63 (m, 1H), 0.84 (t, J = 7.3 Hz, 3H) |
| 114 | (±)-2-{4-[3-(4,5-dichloro-1-methyl-1H-indole-2-amido)oxetan-3-yl]phenyl}pentanoic acid | A | CE | 475.2 | 9.74 (s, 1H), 7.62 (d, J = 8.9 Hz, 1H), 7.53 (d, J = 8.3 Hz, 2H), 7.47 (d, J = 8.9 Hz, 1H), 7.42 (s, 1H), 7.33 (d, J = 8.3 Hz, 2H), 5.05 (d, J = 6.8 Hz, 2H), 4.79 (d, J = 6.7 Hz, 2H), 3.97 (s, 3H), 3.51-3.45 (t, J = 7.3 Hz, 1H), 1.99-1.87 (m, 1H), 1.67-1.55 (m, 1H), 1.33-1.13 (m, 2H), 0.86 (t, J = 7.3 Hz, 3H) |

-continued

Method 8 Table: Compounds Synthesized via Method 8 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 115 | (±)-2-{4-[3-(4,5-dichloro-6-methoxy-1-methyl-1H-indole-2-amido)oxetan-3-yl]phenyl}pentanoic acid | F | CE | 505.0 | 9.59 (s, 1H), 7.51 (d, J = 8.3 Hz, 2H), 7.37-7.31 (m, 3H), 7.29 (s, 1H), 5.03 (d, J = 6.8 Hz, 2H), 4.78 (d, J = 6.8 Hz, 2H), 3.97 (s, 3H), 3.96 (s, 3H), 2.68 (s, 1H), 1.93 (d, J = 9.2 Hz, 1H), 1.60 (d, J = 8.7 Hz, 1H), 1.28-1.15 (m, 2H), 0.87 (t, J = 7.3 Hz, 3H) |
| 116 | (±)-2-cyclobutyl-2-{4-[3-(4,5-dichloro-1-methyl-1H-indole-2-amido)oxetan-3-yl]phenyl}acetic acid | A | CA | 487.3 | 9.72 (s, 1H), 7.63 (d, J = 8.9 Hz, 1H), 7.53 (d, J = 8.3 Hz, 2H), 7.48 (d, J = 8.8 Hz, 1H), 7.42 (s, 1H), 7.32 (d, J = 8.3 Hz, 2H), 5.05 (d, J = 6.8 Hz, 2H), 4.78 (d, J = 6.8 Hz, 2H), 3.97 (s, 3H), 3.53 (d, J = 11.0 Hz, 1H), 2.87 (td, J = 7.5, 10.8 Hz, 1H), 2.16-2.04 (m, 1H), 1.85-1.67 (m, 4H), 1.62-1.49 (m, 1H) |
| 117 | (±)-2-cyclobutyl-2-{4-[3-(4,5-dichloro-6-methoxy-1-methyl-1H-indole-2-amido)oxetan-3-yl]phenyl}acetic acid | F | CA | 517.2 | 9.58 (s, 1H), 7.51 (d, J = 8.3 Hz, 2H), 7.36 (s, 1H), 7.31 (d, J = 8.3 Hz, 2H), 7.29 (s, 1H), 5.03 (d, J = 6.8 Hz, 2H), 4.77 (d, J = 6.8 Hz, 2H), 3.97 (s, 3H), 3.96 (s, 3H), 3.50 (d, J = 10.9 Hz, 1H), 2.92-2.82 (m, 1H), 2.13-2.07 (m, 1H), 1.84-1.68 (m, 4H), 1.59-1.49 (m, 1H) |

-continued

Method 8 Table: Compounds Synthesized via Method 8 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 118 | (±)-2-cyclopentyl-2-{4-[3-(4,5-dichloro-6-methoxy-1-methyl-1H-indole-2-amido)oxetan-3-yl]phenyl}acetic acid | F | CC | 531.3 | 9.59 (s, 1H), 7.52 (d, J = 8.2 Hz, 2H), 7.37 (m, 3H), 7.29 (s, 1H), 5.04 (d, J = 6.8 Hz, 2H), 4.78 (d, J = 6.8 Hz, 2H), 3.97 (s, 3H), 3.96 (s, 3H), 3.22 (d, J = 10.8 Hz, 1H), 2.43 (m., 1H), 1.93-1.79 (m, 1H), 1.67-1.50 (m, 3H), 1.43 (m, 1H), 1.35-1.22 (m, 2H), 0.97-0.93 (m, 1H) |
| 119 | (±)-ethoxy-1-methyl-1H-indole-2-amido)oxetan-3-yl]phenyl}-2-cyclohexylacetic acid | B | CJ | 511.3 | 9.63 (s, 1H), 7.55-7.46 (m, 3H), 7.37-7.30 (m, 3H), 7.25 (d, J = 9.3 Hz, 1H), 5.04 (d, J = 6.8 Hz, 2H), 4.77 (d, J = 6.8 Hz, 2H), 3.93 (s, 3H), 3.89 (s, 3H), 3.12 (d, J = 10.3 Hz, 1H), 1.93-1.80 (m, 2H), 1.69 (d, J = 10.8 Hz, 1H), 1.59-1.50 (m, 2H), 1.21 (d, J = 10.3 Hz, 2H), 1.17-0.94 (m, 3H), 0.72 (d, J = 11.0 Hz, 1H) |
| 120 | (±)-2-{4-[3-(4-chloro-5-methoxy-1-methyl-1H-indole-2-amido)oxetan-3- | B | CK | 513.3 | 9.63 (s, 1H), 7.56-7.49 (m, 3H), 7.36 (d, J = 8.0 Hz, 2H), 7.31 (s, 1H), 7.25 (d, J = 9.0 Hz, 1H), 5.04 (d, J = 6.8 Hz, 2H), 4.77 (d, J = 6.8 Hz, 2H), 3.91 (d, J = 17.8 Hz, 6H), 3.86 (d, J = 14.3 Hz, 1H), 3.73 (d, J = 11.0 Hz, 1H), 3.29 (t, J = 11.3 Hz, 1H), 3.19 (d, J = 10.0 Hz, 2H), 2.10 (d, J = 16.8 Hz, 1H), 1.72 (d, J = 12.3 Hz, 1H), 1.37-1.19 (m, 1H), 1.09-0.98 (m, 2H) |

-continued

Method 8 Table: Compounds Synthesized via Method 8 using the appropriate acid and amine

| Example # | Structure | Intermediate Acid | Intermediate Amine | LCMS (ES+) m/z (M + H)+ | HNMR (400 MHz, DMSO-d6) δ |
|---|---|---|---|---|---|
| 121 | (±)-2-{4-[3-(4-chloro-5-methoxy-1-methyl-1H-indole-2-amido)oxetan-3-yl]phenyl}-2-(piperidin-4-yl)acetic acid | B | CM | 512.2 | 9.63 (s, 1H), 7.53 (d, J = 9.2 Hz, 1H), 7.49 (d, J = 8.2 Hz, 2H), 7.34 (d, J = 8.3 Hz, 2H), 7.31 (s, 1H), 7.25 (d, J = 9.2 Hz, 1H), 5.04 (d, J = 6.8 Hz, 2H), 4.77 (d, J = 6.8 Hz, 2H), 3.94 (s, 3H), 3.89 (s, 3H), 3.15-3.06 (m, 1H), 2.94 (d, J = 11.3 Hz, 1H), 2.27-2.21 (m, 3H), 2.08-1.78 (m, 2H), 1.27-1.14 (m, 2H), 0.97 (d, J = 9.9 Hz, 1H) |
| 122 | (±)-2-{4-[3-(4,5-dichloro-6-methoxy-1-methyl-1H-indole-2-amido)oxetan-3-yl]phenyl}-4-methylpentanoic acid | F | CN | 519.2 | 9.60 (s, 1H), 7.52 (d, J = 8.3 Hz, 2H), 7.39-7.31 (m, 3H), 7.28 (s, 1H), 5.04 (d, J = 6.5 Hz, 2H), 4.78 (d, J = 6.5 Hz, 2H), 3.96 (s, 3H), 3.96 (s, 3H), 3.58-3.49 (m, 1H), 1.92-1.77 (m, 1H), 1.54 (td, J = 6.9, 13.5 Hz, 1H), 1.40 (td, J = 6.6, 13.2 Hz, 1H), 0.86 (d, J = 6.3 Hz, 6H) |
| 123 | (±)-3-cyclopropyl-2-{4-[3-(4,5-dichloro-6-methoxy-1-methyl-1H-indole-2- | F | CO | 517.2 | 9.53 (s, 1H), 7.44 (d, J = 8.2 Hz, 2H), 7.30-7.23 (m, 3H), 7.20 (s, 1H), 4.96 (d, J = 6.8 Hz, 2H), 4.70 (d, J = 6.8 Hz, 2H), 3.88 (s, 3H), 3.87 (s, 3H), 3.47 (t, J = 7.4 Hz, 1H), 1.83-1.73 (m, 1H), 1.45 (m, 1H), 0.60-0.46 (m, 1H), 0.33-0.19 (m, 2H), 0.08--0.10 (m, 2H) |

Method 8 Table: Compounds Synthesized via Method 8 using the appropriate acid and amine

| Example # | Structure | Intermediate Acid | Intermediate Amine | LCMS (ES+) m/z (M + H)⁺ | HNMR (400 MHz, DMSO-d6) δ |
|---|---|---|---|---|---|
| | amido)oxetan-3-yl]phenyl}propanoic acid | | | | |
| 124 | (±)-3-cyclopropyl-2-{4-[3-(4,5-dichloro-1-methyl-1H-indole-2-amido)oxetan-3-yl]phenyl}propanoic acid | A | CO | 487.2 | 9.74 (s, 1H), 7.63 (d, J = 8.8 Hz, 1H), 7.53 (d, J = 8.0 Hz, 2H), 7.47 (d, J = 8.8 Hz, 1H), 7.42 (s, 1H), 7.34 (d, J = 8.0 Hz, 2H), 5.05 (d, J = 6.8 Hz, 2H), 4.78 (d, J = 6.8 Hz, 2H), 3.97 (s, 3H), 3.58 (t, J = 7.4 Hz, 1H), 1.94-1.77 (m, 1H), 1.55 (td, J = 6.6, 13.6 Hz, 1H), 0.73-0.51 (m, 1H), 0.35 (d, J = 7.8 Hz, 2H), 0.16-0.06 (m, 2H) |
| 125[a] | (±)-3-{4-[3-(4,5-dichloro-1-methyl-1H-indole-2-amido)oxetan-3-yl]phenyl}oxolane-3-carboxylic acid | A | CR | 489.1 | 9.75 (s, 1H), 7.63 (d, J = 9.0 Hz, 1H), 7.47 (d, J = 8.8 Hz, 3H), 7.41 (s, 1H), 7.33 (d, J = 7.9 Hz, 2H), 5.03 (d, J = 6.8 Hz, 2H), 4.76 (d, J = 6.8 Hz, 2H), 4.59 (d, J = 6.1 Hz, 1H), 3.95 (s, 3H), 3.81-3.72 (m, 1H), 3.63 (d, J = 8.5 Hz, 1H), 2.99-2.90 (m, 1H), 2.53-2.53 (m, 1H) |

[a]Step 1 was run at 0° C. for 1 hr. Step 2 was run at rt for 12 hrs.

Example 126—(±)-2-(4-(3-(4-chloro-5-methoxy-1-methyl-1H-indole-2-carboxamido)oxetan-3-yl)phenyl)butanoic acid

Example 127—(±)-2-[4-[3-[(4-Chloro-5-methoxy-1-methyl-indole-2-carbonyl)amino]-oxetan-3-yl]phenyl]-3-methyl-butanoic acid

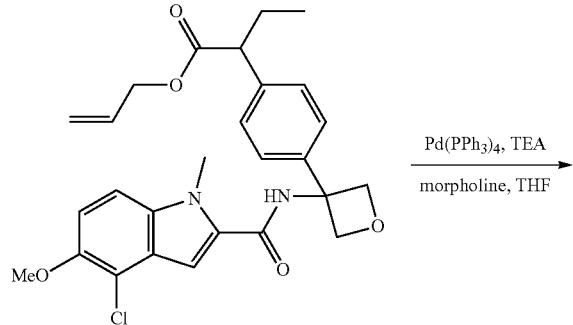

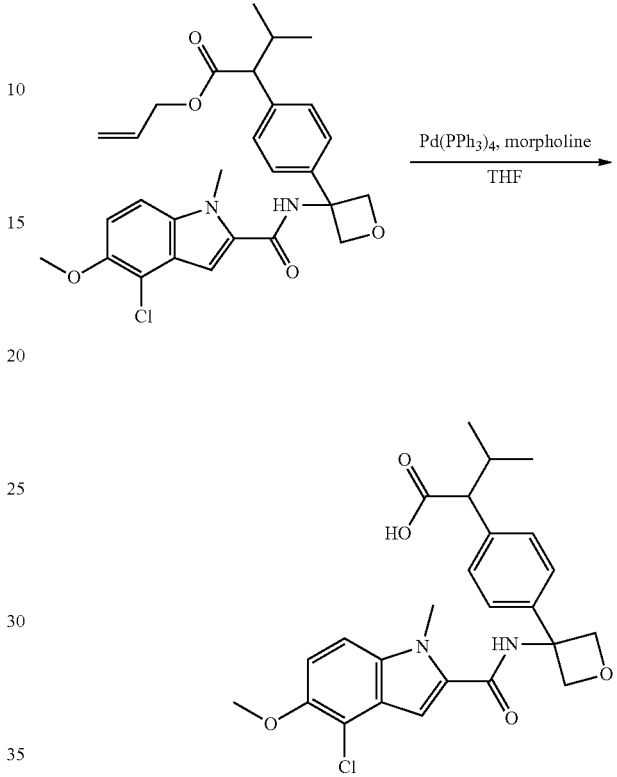

To a solution of (±)-allyl 2-[4-[3-[(4-chloro-5-methoxy-1-methyl-indole-2-carbonyl)amino]oxetan-3-yl]phenyl]butanoate (724 mg, 945 umol, synthesized via Method 8, Step 1 with acid B and amine BZ) and morpholine (823 mg, 9.45 mmol) in tetrahydrofuran (10 mL) was added Pd(PPh$_3$)$_4$ (218 mg, 189 umol) under a nitrogen. The reaction mixture was stirred at 40° C. for 12 hrs. On completion, the reaction mixture was concentrated in vacuo, the residue was dissolved in dichloromethane (50 mL) and washed with 1N citric acid (5 mL) until pH=3-4. The organic layer was dried over anhydrous sodium sulfate, filtrated and concentrated in vacuo. The crude product was dissolved in anhydrous tetrahydrofuran (30 mL) and thiourea (resin) (1.00 g, 13.1 mmol) was added. The mixture was stirred at rt for 16 hours. Then the reaction mixture was filtered and the filtrate was concentrated in vacuo to give a residue. The residue was purified by prep-HPLC [Instrument: GX-A; Column: Phenomenex Gemini 150*25 mm*10 um; Condition: water (0.05% ammonia hydroxide v/v)-ACN] to give the title compound. LCMS: (ES$^+$) m/z (M+1)$^+$=457.2, tR=0.823. $^1$H NMR (400 MHz, DMSO-d$_6$) δ=9.63 (s, 1H), 7.57-7.48 (m, 3H), 7.36-7.29 (m, 3H), 7.25 (d, J=9.0 Hz, 1H), 5.04 (d, J=6.8 Hz, 2H), 4.78 (d, J=6.6 Hz, 2H), 3.94 (s, 3H), 3.89 (s, 3H), 3.44 (t, J=7.8 Hz, 1H), 2.00-1.92 (m, 1H), 1.62 (td, J=7.1, 13.7 Hz, 1H), 0.83 (t, J=7.4 Hz, 3H).

To a solution of (±)-allyl 2-[4-[3-[(4-chloro-5-methoxy-1-methyl-indole-2-carbonyl)amino]oxetan-3-yl]phenyl]-3-methyl-butanoate (300 mg, 587 umol, synthesized via Step 1 of Method 8 with acid B and amine CB) and morpholine (51 mg, 587 umol) in tetrahydrofuran (10 mL) was added Pd(PPh$_3$)$_4$ (67.8 mg, 58.7 umol) under a nitrogen atmosphere, and the mixture was stirred at 50° C. for 12 hrs. On completion, the mixture was concentrated in vacuo to give a residue. The residue was washed with 1N HCl (3 mL), diluted with water (20 mL) and extracted with ethyl acetate (2×30 mL). The combined organic layer was dried over anhydrous sodium sulfate, filtered and concentrated in vacuo to give a residue. The residue was dissolved in tetrahydrofuran (20 mL) and thiourea (resin) (44.7 mg, 587.07 umol,) was added. The mixture was stirred at rt for 2 hours. Then the reaction mixture was filtered and the filtrate was concentrated in vacuo to give a residue. The residue was purified with prep-HPLC (Instrument: GX-D; Column: Phenomenex Synergi C18 150*25*10 um; Mobile phase: 0.225% formic acid-acetonitrile) to give the title compound. LCMS: (ES$^+$) m/z (M+H)$^+$=471.3, tR=0.891. $^1$H NMR (400 MHz, DMSO-d$_6$) δ=9.63 (s, 1H), 7.57-7.48 (m, 3H), 7.39-7.32 (m, 2H), 7.31 (s, 1H), 7.25 (d, J=9.0 Hz, 1H), 5.05 (d, J=6.8 Hz, 2H), 4.78 (d, J=6.8 Hz, 2H), 3.94 (s, 3H), 3.89 (s, 3H), 3.06 (d, J=10.4 Hz, 1H), 2.28-2.12 (m, 1H), 1.00 (d, J=6.4 Hz, 3H), 0.64 (d, J=6.7 Hz, 3H).

Example 128 & 129—(2R)-2-[4-[3-[(4-chloro-5-methoxy-1-methyl-indole-2-carbonyl)amino]oxetan-3-yl]phenyl]-3-methyl-butanoic acid & (2S)-2-[4-[3-[(4-chloro-5-methoxy-1-methyl-indole-2-carbonyl)amino]oxetan-3-yl]phenyl]-3-methyl-butanoic acid

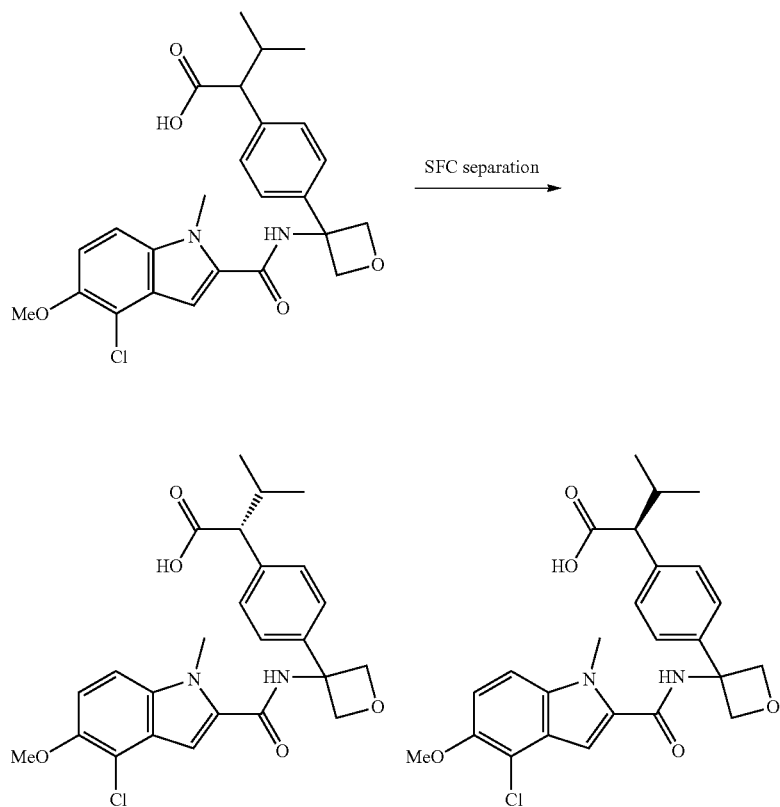 [SMILES: COc1ccc2c(cc(C(=O)NC3(c4ccc(C(C(=O)O)C(C)C)cc4)COC3)n2C)c1Cl ; COc1ccc2c(cc(C(=O)NC3(c4ccc([C@H](C(=O)O)C(C)C)cc4)COC3)n2C)c1Cl ; COc1ccc2c(cc(C(=O)NC3(c4ccc([C@@H](C(=O)O)C(C)C)cc4)COC3)n2C)c1Cl]

(±)-2-[4-[3-[(4-Chloro-5-methoxy-1-methyl-indole-2-carbonyl)amino]oxetan-3-yl]phenyl]-3-methyl-butanoic acid (300 mg, 637 umol, Example 127) was purified by chiral SFC (Instrument: SFC-1; Column: OD (250 mm*30 mm, 10 um); Condition: Base-methanol,) to give Example 128 (2R)-2-[4-[3-[(4-chloro-5-methoxy-1-methyl-indole-2-carbonyl)amino]oxetan-3-yl]phenyl]-3-methyl-butanoic acid or (2S)-2-[4-[3-[(4-chloro-5-methoxy-1-methyl-indole-2-carbonyl)amino]oxetan-3-yl]phenyl]-3-methyl-butanoic acid (77.0 mg, ee: 100%, cSFC, tR=0.993.) and impure Example 129 (2S)-2-[4-[3-[(4-chloro-5-methoxy-1-methyl-indole-2-carbonyl)amino]oxetan-3-yl]phenyl]-3-methyl-butanoic acid or (2R)-2-[4-[3-[(4-chloro-5-methoxy-1-methyl-indole-2-carbonyl)amino]oxetan-3-yl]phenyl]-3-methyl-butanoic acid (120 mg, ee: 93%, cSFC, tR=1.147.). Then impure Example 128 was further purified by chiral SFC (Instrument: SFC-1; Column: AD (250 mm*30 mm, 10 um); Condition: Base-methanol,) to give Example 128 (2S)-2-[4-[3-[(4-chloro-5-methoxy-1-methyl-indole-2-carbonyl)amino]oxetan-3-yl]phenyl]-3-methyl-butanoic acid or (2R)-2-[4-[3-[(4-chloro-5-methoxy-1-methyl-indole-2-carbonyl)amino]oxetan-3-yl]phenyl]-3-methyl-butanoic acid (95.5 mg, ee: 100%).

Example 128 (2R)-2-[4-[3-[(4-chloro-5-methoxy-1-methyl-indole-2-carbonyl)amino]oxetan-3-yl]phenyl]-3-methyl-butanoic acid or (2S)-2-[4-[3-[(4-chloro-5-methoxy-1-methyl-indole-2-carbonyl)amino]oxetan-3-yl]phenyl]-3-methyl-butanoic acid (77.0 mg, ee: 100%) was obtained as a yellow solid. LCMS: (ES⁻) m/z (M–H)⁻=471.2, tR=0.871. cSFC, tR=0.993. $^1$H NMR (400 MHz, DMSO-$d_6$) δ=9.63 (s, 1H), 7.53 (dd, J=2.6, 8.7 Hz, 3H), 7.35 (d, J=8.3 Hz, 2H), 7.31 (s, 1H), 7.25 (d, J=9.0 Hz, 1H), 5.04 (d, J=6.8 Hz, 2H), 4.78 (d, J=7.3 Hz, 2H), 3.94 (s, 3H), 3.89 (s, 3H), 3.08 (d, J=10.3 Hz, 1H), 2.21 (td, J=6.5, 10.4 Hz, 1H), 1.00 (d, J=6.4 Hz, 3H), 0.64 (d, J=6.7 Hz, 3H).

Example 129 (2S)-2-[4-[3-[(4-chloro-5-methoxy-1-methyl-indole-2-carbonyl)amino]oxetan-3-yl]phenyl]-3-methyl-butanoic acid or (2R)-2-[4-[3-[(4-chloro-5-methoxy-1-methyl-indole-2-carbonyl)amino]oxetan-3-yl]phenyl]-3-methyl-butanoic acid (95.5 mg, ee: 100%) was obtained as a yellow solid. LCMS: (ES⁻) m/z (M–H)⁻=471.2, tR=0.871. cSFC, tR=1.147. $^1$H NMR (400 MHz, DMSO-$d_6$) δ=9.62 (s, 1H), 7.49-7.55 (m, 3H), 7.34 (d, J=8.3 Hz, 2H), 7.30 (s, 1H), 7.25 (d, J=9.2 Hz, 1H), 5.04 (d, J=6.8 Hz, 2H), 4.78 (d, J=6.4 Hz, 2H), 3.94 (s, 3H), 3.89 (s, 3H), 3.07 (d, J=10.7 Hz, 1H), 2.21 (dd, J=17.1, 6.6 Hz, 1H), 1.00 (d, J=6.4 Hz, 3H).

Example 130—(±)-2-[4-[3-[(4-chloro-5-methoxy-1-methyl-indole-2-carbonyl)amino]-oxetan-3-yl]phenyl]-2-cyclopentyl-acetic acid

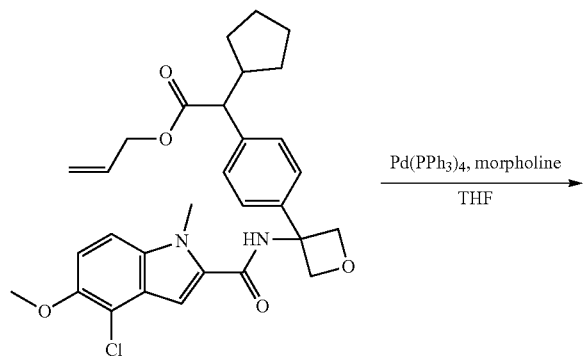

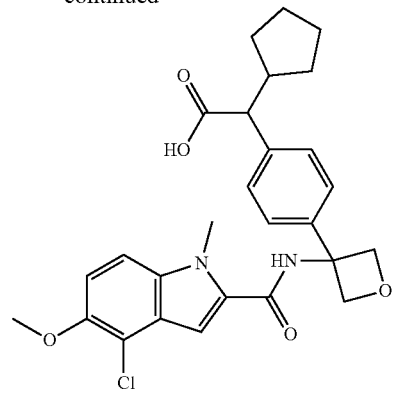

To a solution of (±)-allyl 2-[4-[3-[(4-chloro-5-methoxy-1-methyl-indole-2-carbonyl)amino]oxetan-3-yl]phenyl]-2-cyclopentyl-acetate (1.70 g, 3.17 mmol, synthesized via Step 1 of Method 8 with acid B and amine CC) and morpholine (1.66 g, 19.0 mmol) in tetrahydrofuran (30 mL) was added Pd(PPh$_3$)$_4$ (366 mg, 317 umol) under a nitrogen atmosphere, and the mixture was stirred at 50° C. for 24 hrs. On completion, the mixture was concentrated in vacuo to give a residue. The residue was washed with citric acid (50 mL), and extracted with ethyl acetate (2×60 mL). The combined organic layer was dried over anhydrous sodium sulfate, filtered and concentrated in vacuum to give a residue. The residue was dissolved in tetrahydrofuran (50 mL) and thiourea (resin) (5 g) was added. The mixture was stirred at 25° C. for 3 hours. Then the reaction mixture was filtrated and the filtrate was concentrated in vacuo to give a residue. The residue was purified with prep-HPLC (Instrument: HPLC-A; Column: Phenomenex Gemini C18 250*50 mm*10 um; Mobile phase: 0.225% formic acid-acetonitrile) to give the title compound. LCMS: (ES⁺) m/z (M+H)⁺=497.3, tR=0.925. $^1$H NMR (400 MHz, DMSO-$d_6$) δ=12.28 (br. s., 1H), 9.63 (s, 1H), 7.54 (d, J=8.4 Hz, 3H), 7.37 (d, J=8.4 Hz, 2H), 7.31 (s, 1H), 7.25 (d, J=9.0 Hz, 1H), 5.05 (d, J=6.7 Hz, 2H), 4.78 (d, J=6.8 Hz, 2H), 3.94 (s, 3H), 3.89 (s, 3H), 3.25 (d, J=11.0 Hz, 1H), 2.48-2.40 (m, 1H), 1.92-1.77 (m, 1H), 1.70-1.49 (m, 3H), 1.49-1.37 (m, 1H), 1.36-1.16 (m, 2H), 0.97 (qd, J=8.2, 12.4 Hz, 1H).

Example 131 & 132—(2S)-2-[4-[3-[(4-chloro-5-methoxy-1-methyl-indole-2-carbonyl)amino]oxetan-3-yl]phenyl]-2-cyclopentyl-acetic acid & (2R)-2-[4-[3-[(4-chloro-5-methoxy-1-methyl-indole-2-carbonyl)amino]oxetan-3-yl]phenyl]-2-cyclopentyl-acetic acid

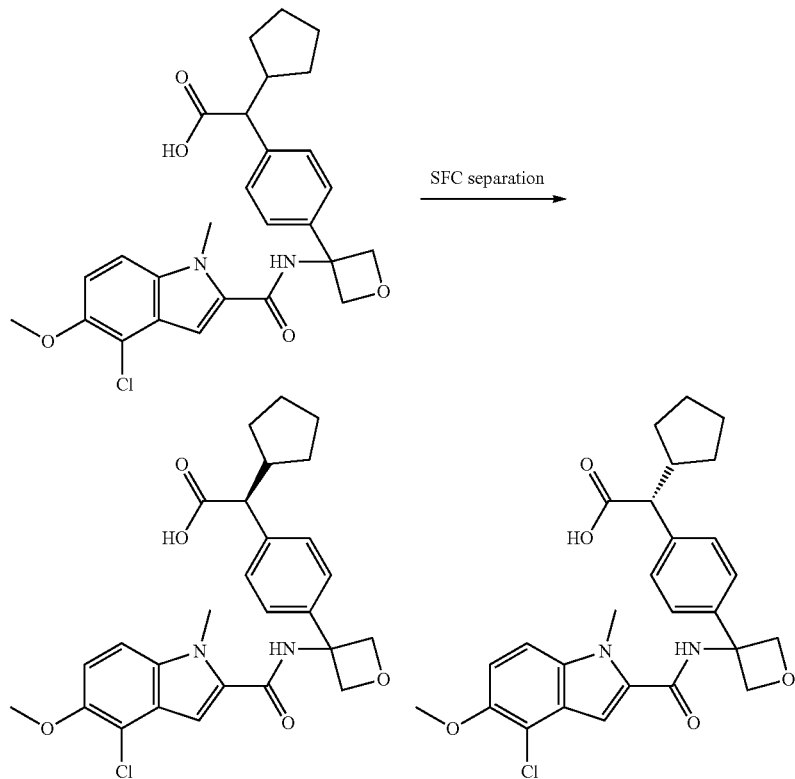

(±)-2-[4-[3-[(4-chloro-5-methoxy-1-methyl-indole-2-carbonyl)amino]oxetan-3-yl]phenyl]-2-cyclopentyl-acetic acid (570 mg, 1.15 mmol, Example 130) was purified with SFC ("AS-3S_5_5_40_3ML Column: Chiralpak AS-3 150×4.6 mm I.D., 3 um Mobile phase: ethanol (0.05% DEA) in $CO_2$ from 5% to 40% Flow rate: 3 mL/min Wavelength: 220 nm") to give (2S)-2-[4-[3-[(4-chloro-5-methoxy-1-methyl-indole-2-carbonyl)amino]oxetan-3-yl]phenyl]-2-cyclopentyl-acetic acid or (2R)-2-[4-[3-[(4-chloro-5-methoxy-1-methyl-indole-2-carbonyl)amino]oxetan-3-yl]phenyl]-2-cyclopentyl-acetic acid (254 mg, 44% yield) (peak 1: cSFC=3.201) and (2R)-2-[4-[3-[(4-chloro-5-methoxy-1-methyl-indole-2-carbonyl)amino]oxetan-3-yl]phenyl]-2-cyclopentyl-acetic acid or (2S)-2-[4-[3-[(4-chloro-5-methoxy-1-methyl-indole-2-carbonyl)amino]oxetan-3-yl]phenyl]-2-cyclopentyl-acetic acid (276 mg, 48% yield) (peak 2: cSFC=3.570).
(2S)-2-[4-[3-[(4-chloro-5-methoxy-1-methyl-indole-2-carbonyl)amino]oxetan-3-yl]phenyl]-2-cyclopentyl-acetic acid or (2R)-2-[4-[3-[(4-chloro-5-methoxy-1-methyl-indole-2-carbonyl)amino]oxetan-3-yl]phenyl]-2-cyclopentyl-acetic acid (Example 131) (peak 1: cSFC=3.201): LCMS: $(ES^+)$ m/z $(M+H)^+$=497.3, tR=0.934. $^1$H NMR (400 MHz, DMSO-$d_6$) δ=9.64 (s, 1H), 7.56-7.51 (m, 3H), 7.37 (d, J=8.0 Hz, 2H), 7.31 (s, 1H), 7.26 (d, J=9.3 Hz, 1H), 5.04 (d, J=6.9 Hz, 2H), 4.78 (d, J=6.4 Hz, 2H), 3.94 (s, 3H), 3.89 (s, 3H), 3.23 (d, J=10.8 Hz, 1H), 2.44-2.41 (m, 1H), 1.87-1.80 (m, 1H), 1.63-1.50 (m, 3H), 1.45-1.40 (m, 1H), 1.32-1.22 (m, 2H), 1.00-0.92 (m, 1H).

(2R)-2-[4-[3-[(4-chloro-5-methoxy-1-methyl-indole-2-carbonyl)amino]oxetan-3-yl]phenyl]-2-cyclopentyl-acetic acid or (2S)-2-[4-[3-[(4-chloro-5-methoxy-1-methyl-indole-2-carbonyl)amino]oxetan-3-yl]phenyl]-2-cyclopentyl-acetic acid (Example 132) (peak 2: cSFC=3.570): LCMS: (ES+) m/z (M+H)+=497.3, tR=0.930. $^1$H NMR (400 MHz, DMSO-$d_6$) δ=12.55-11.72 (m, 1H), 9.63 (s, 1H), 7.56-7.51 (m, 3H), 7.37 (d, J=8.3 Hz, 2H), 7.31 (s, 1H), 7.25 (d, J=9.2 Hz, 1H), 5.05 (d, J=6.8 Hz, 2H), 4.78 (d, J=7.5 Hz, 2H), 3.94 (s, 3H), 3.89 (s, 3H), 3.24 (d, J=11.0 Hz, 1H), 2.48-2.41 (m, 1H), 1.89-1.78 (m, 1H), 1.66-1.49 (m, 3H), 1.47-1.37 (m, 1H), 1.37-1.11 (m, 3H), 0.97 (m, 1H).

Example 133—(±)-2-(4-(3-(4,5-dichloro-1-methyl-1H-indole-2-carboxamido)oxetan-3-yl)phenyl)butanoic acid

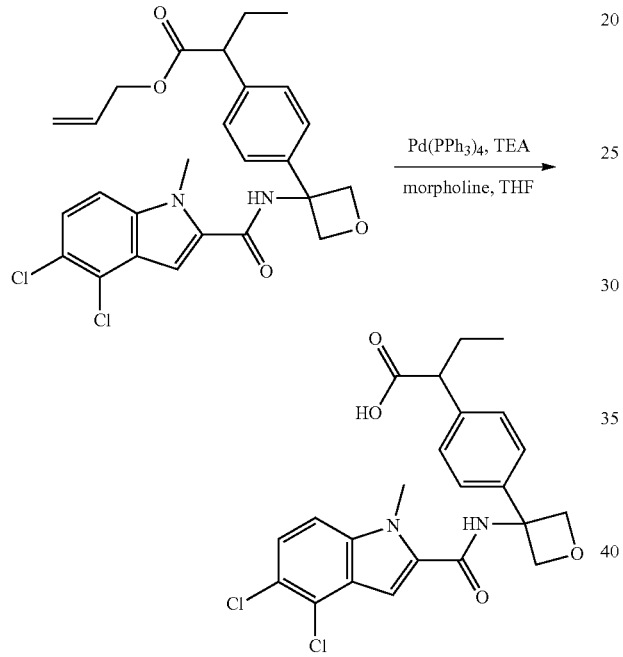

To a solution of (±)-allyl2-[4-[3-[(4,5-dichloro-1-methyl-indole-2-carbonyl)amino]oxetan-3-yl]phenyl]butanoate (746 mg, 1.07 mmol, synthesized via Step 1 of Method 8 with acid A and amine BZ) and morpholine (931 mg, 10.7 mmol) in tetrahydrofuran (10 mL) was added Pd(PPh$_3$)$_4$ (247 mg, 214 umol) under a nitrogen. The reaction mixture was stirred at 40° C. for 12 hrs. On completion, the reaction mixture was concentrated in vacuo, and the residue was dissolved in dichloromethane (50 mL) and washed with 1N citric acid (5 mL) until pH=3-4. The organic layer was dried over anhydrous sodium sulfate, filtrated and concentrated in vacuo. The crude product was dissolved in anhydrous tetrahydrofuran (30 mL) and thiourea (resin) (1.00 g, 13.1 mmol) was added. The mixture was stirred at rt for 16 hours. Then the reaction mixture was filtered and the filtrate was concentrated in vacuo to give a residue. The residue was purified by prep-HPLC [Instrument: GX-F; Column: Boston Green ODS 150*30 5 u; Condition: water (0.225% FA)-ACN] to give the title compound. LCMS: (ES+) m/z (M+1)+=461.3, tR=0.883. $^1$H NMR (400 MHz, DMSO-$d_6$) δ=9.73 (s, 1H), 7.63 (d, J=8.8 Hz, 1H), 7.54 (d, J=8.3 Hz, 2H), 7.48 (d, J=9.0 Hz, 1H), 7.42 (s, 1H), 7.33 (d, J=8.3 Hz, 2H), 5.05 (d, J=6.8 Hz, 2H), 4.79 (d, J=6.8 Hz, 2H), 3.97 (s, 3H), 3.44 (t, J=7.8 Hz, 1H)), 2.02-1.93 (m, 1H), 1.65 (td, J=7.1, 13.7 Hz, 1H), 0.84 (t, J=7.3 Hz, 3H).

Example 134—(±)-2-[4-[3-[(4,5-Dichloro-1-methyl-indole-2-carbonyl)amino]oxetan-3-yl]phenyl]-3-methyl-butanoic acid

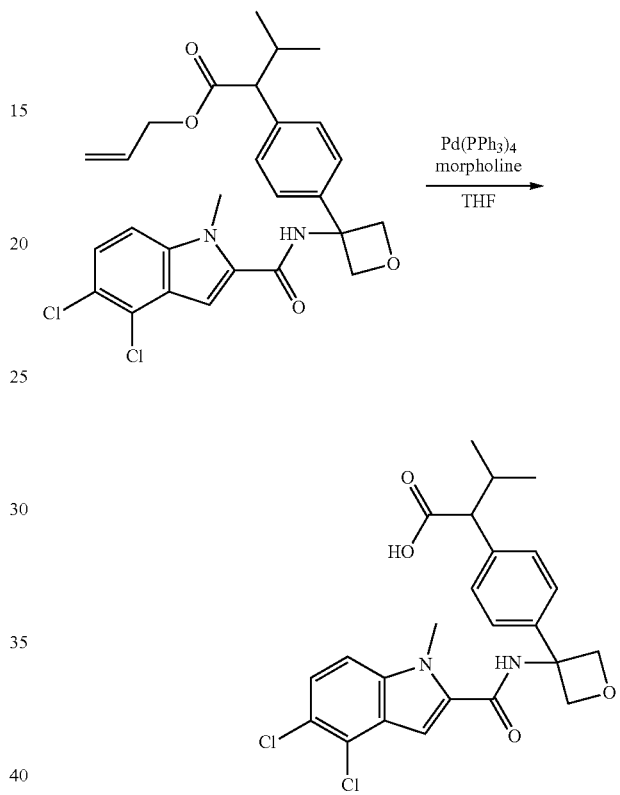

To a solution of (±)-allyl 2-[4-[3-[(4,5-dichloro-1-methyl-indole-2-carbonyl)amino]oxetan-3-yl]phenyl]-3-methyl-butanoate (500 mg, 970 umol, synthesized via Step 1 of Method 8 with acid A and amine CB) and morpholine (507 mg, 5.82 mmol) in tetrahydrofuran (20 mL) was added Pd(PPh$_3$)$_4$ (112 mg, 97.0 umol) under nitrogen, and the mixture was stirred at 40° C. for 16 hours. On completion, the mixture was concentrated, washed with 100 mL water, and extracted with ethyl acetate (3×50 mL). The organic layer was dried with anhydrous sodium sulfate, filtrated and concentrated. The residue was dissolved in 20 mL of tetrahydrofuran and thiourea (resin) (1.00 g, 13.1 mmol) was added. The mixture was stirred at rt for 2 hours. Then the reaction mixture was filtered and the filtrate was concentrated in vacuo to give a residue. The residue was purified by prep-HPLC (condition: water (0.225% FA)-ACN; column: Boston Green ODS 150*30 5 u) to give the title compound. LCMS: (ES+) m/z (M+H)+=475.1, tR=0.890. $^1$H NMR (400 MHz, DMSO-d6) δ=9.72 (s, 1H), 7.63 (d, J=8.8 Hz, 1H), 7.54 (d, J=8.0 Hz, 2H), 7.48 (d, J=8.8 Hz, 1H), 7.42 (s, 1H), 7.35 (d, J=8.0 Hz, 2H), 5.05 (d, J=6.5 Hz, 2H), 4.79 (d, J=6.5 Hz, 2H), 3.97 (s, 3H), 3.11 (d, J=10.3 Hz, 1H), 2.22 (td, J=6.6, 10.5 Hz, 1H), 1.01 (d, J=6.3 Hz, 3H), 0.65 (d, J=6.8 Hz, 3H).

Example 135—(±)-2-[4-[3-[(4,5-Dichloro-6-methoxy-1-methyl-indole-2-carbonyl)amino]oxetan-3-yl]phenyl]-3-methyl-butanoic acid

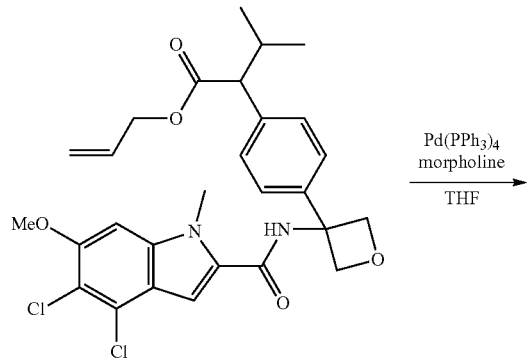

Example 136—(±)-2-Cyclopentyl-2-[4-[3-[(4,5-dichloro-1-methyl-indole-2-carbonyl)amino]oxetan-3-yl]phenyl]acetic acid

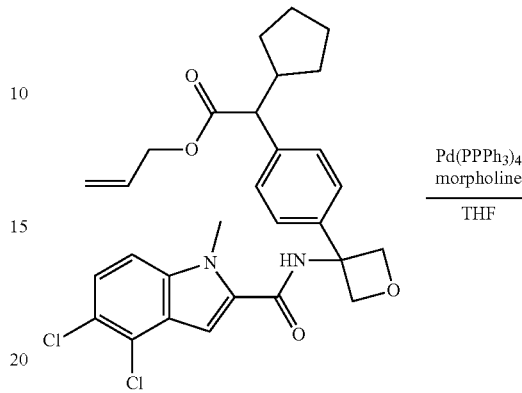

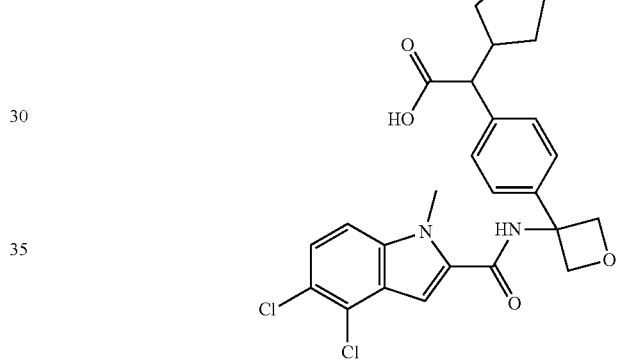

To a solution of (±)-allyl 2-[4-[3-[(4,5-dichloro-6-methoxy-1-methyl-indole-2-carbonyl)amino]oxetan-3-yl]phenyl]-3-methyl-butanoate (500 mg, 917 umol, synthesized via Step 1 of Method 8 with acid F and amine CB) and morpholine (479 mg, 5.50 mmol) in tetrahydrofuran (10 mL) was added Pd(PPh$_3$)$_4$ (106 mg, 91.7 umol) under nitrogen, and the mixture was stirred at 40° C. for 16 hours. On completion, the mixture was concentrated and washed with 100 mL water and extracted with ethyl acetate (3×50 mL). The organic layer was dried with anhydrous sodium sulfate, filtrated and concentrated. The residue was dissolved in 20 mL tetrahydrofuran and thiourea (resin) (1.00 g, 13.1 mmol) was added. The mixture was stirred at rt for 2 hours. Then the reaction mixture was filtered and the filtrate was concentrated in vacuo to give a residue. The residue was purified by prep-HPLC (condition: water (0.225% FA)-ACN; column: Boston Green ODS 150*30 5 u) to give the title compound. LCMS: (ES+) m/z (M+H)$^+$=505.2, tR=0.938. $^1$HNMR (400 MHz, DMSO-d6) δ=9.58 (s, 1H), 7.53 (d, J=8.3 Hz, 2H), 7.40-7.32 (m, 3H), 7.29 (s, 1H), 5.04 (d, J=6.5 Hz, 2H), 4.78 (d, J=6.5 Hz, 2H), 3.97 (d, J=2.3 Hz, 6H), 3.10 (d, J=10.5 Hz, 1H), 2.29-2.16 (m, 1H), 1.01 (d, J=6.5 Hz, 3H), 0.65 (d, J=6.8 Hz, 3H).

To a mixture of (±)-allyl 2-cyclopentyl-2-[4-[3-[(4,5-dichloro-1-methyl-indole-2-carbonyl)amino]oxetan-3-yl]phenyl]acetate (100 mg, 185 umol, synthesized via Step 1 of Method 8 with acid A and amine CC) in tetrahydrofuran (5.00 mL) was added Pd(PPh$_3$)$_4$ (21.3 mg, 18.5 umol) and morpholine (96.5 mg, 1.11 mmol) in one portion at rt under N$_2$. The mixture was stirred at rt for 16 hrs. On completion, the reaction was concentrated in vacuo, the residue was dissolved in dichloromethane (10 mL) and washed with citric acid. Then the organic layer was separated and concentrated in vacuo. The residue was dissolved in tetrahydrofuran (10 mL) and thiourea (resin) (1.00 g, 13.1 mmol) was added and the mixture was stirred at 25° C. for 16 hours. The mixture was filtered and the filtrate was concentrated in vacuo. The residue was purified by Prep-HPLC (condition: water (0.225% FA)-ACN; Phenomenex Synergi C18 150*25*10 um) to give the title compound. LCMS (ES+): m/z (M+H)$^+$=501.2, tR=0.947 min. $^1$H NMR (400 MHz, DMSO-d$_6$) δ=9.70 (s, 1H), 7.63 (d, J=8.8 Hz, 1H), 7.52 (d, J=8.4 Hz, 2H), 7.48 (d, J=8.8 Hz, 1H), 7.40 (s, 1H), 7.37 (d, J=8.4 Hz, 2H), 5.05 (d, J=6.8 Hz, 2H), 4.78 (d, J=6.4 Hz, 2H), 3.96 (s, 3H), 3.34-3.19 (m, 1H), 2.50-2.44 (m, 1H), 1.84-1.82 (m, 1H), 1.59-1.53 (m, 3H), 1.51-1.50 (m, 1H), 1.29-1.23 (m, 2H), 0.95-0.90 (m, 1H).

Example 137—(±)-2-(4-(3-(4,5-Dichloro-1-methyl-1H-indole-2-carboxamido)oxetan-3-yl)phenyl)-4-methylpentanoic acid

Example 138—(±)-2-[4-[3-[(4-Chloro-5-methoxy-1-methyl-indole-2-carbonyl)amino]oxetan-3-yl]phenyl]-2-(4-hydroxycyclohexyl)acetic acid

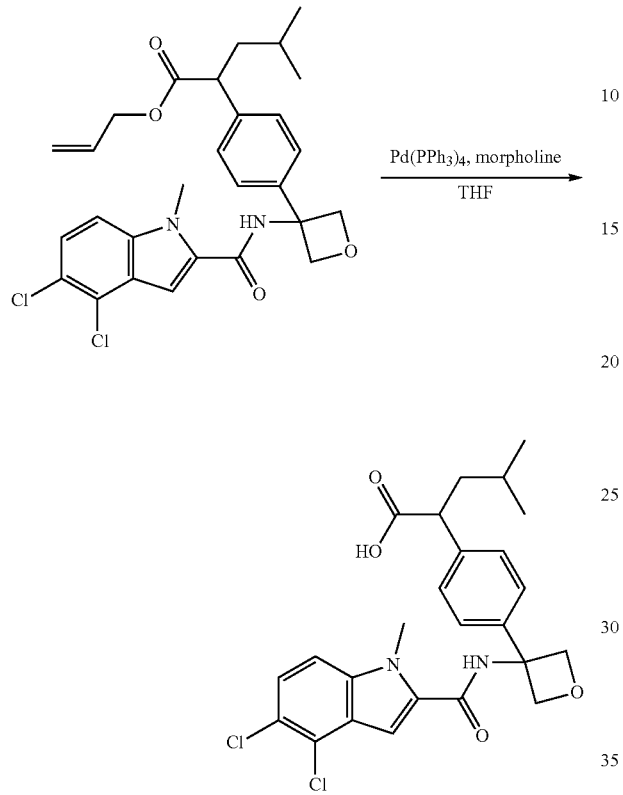

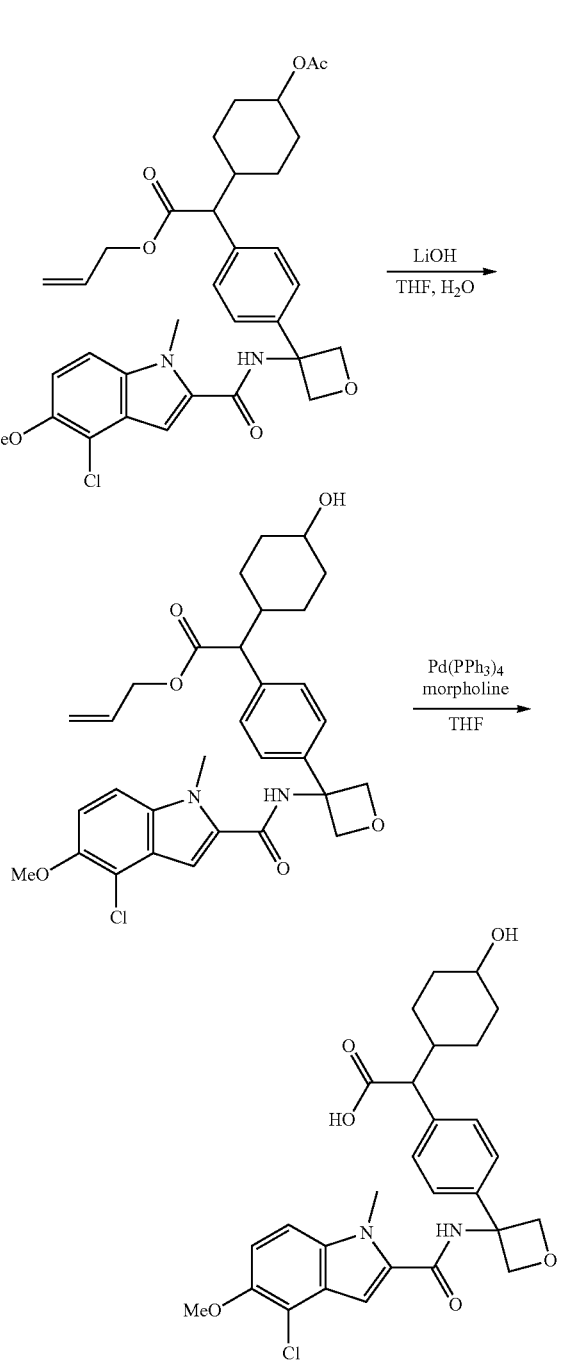

To a mixture of (±)-allyl 2-[4-[3-[(4,5-dichloro-1-methyl-indole-2-carbonyl)amino]oxetan-3-yl]phenyl]-4-methyl-pentanoate (75.0 mg, 141 umol, synthesized via Step 1 of Method 8 with acid A and amine CN) and Pd(PPh$_3$)$_4$ (32.7 mg, 28.3 umol) in anhydrous tetrahydrofuran (5 mL) was added morpholine (123 mg, 1.42 mmol, 124 uL) in one portion at rt under nitrogen. The mixture was stirred at 50° C. for 16 hours. On completion, the reaction mixture was concentrated in vacuo, the residue was dissolved in dichloromethane (10 mL) and washed with 1N citric acid (5 mL) until pH=3-4. The organic layer was dried over anhydrous sodium sulfate, filtered and concentrated in vacuo. The crude product was dissolved in anhydrous tetrahydrofuran (10 mL) and thiourea (resin) (1.00 g, 13.1 mmol) was added. The mixture was stirred at rt for 16 hours. The reaction mixture was filtered and the filtrate was concentrated in vacuo to give a residue. The residue was purified by pre-HPLC (Instrument: GX-D; Condition: water (0.225% FA)-ACN; Column: Boston Green ODS150*30 5 u) to give the title compound. LCMS: (ES$^+$) m/z (M+H)$^+$=511.2, tR=0.986. $^1$H NMR (400 MHz, DMSO-d$_6$) δ=9.74 (s, 1H), 7.63 (d, J=8.8 Hz, 1H), 7.52 (d, J=8.0 Hz, 2H), 7.48 (d, J=8.8 Hz, 1H), 7.42 (s, 1H), 7.35 (d, J=8.0 Hz, 2H), 5.05 (d, J=6.5 Hz, 2H), 4.78 (d, J=6.8 Hz, 2H), 3.97 (s, 3H), 3.54 (br. s., 1H), 1.91-1.75 (m, 1H), 1.54 (td, J=6.9, 13.5 Hz, 1H), 1.47-1.30 (m, 1H), 0.86 (d, J=6.5 Hz, 6H).

Step 1—(±)-Allyl 2-[4-[3-[(4-chloro-5-methoxy-1-methyl-indole-2-carbonyl)amino]oxetan-3-yl]phenyl]-2-(4-hydroxycyclohexyl)acetate To a solution of (±)-allyl 2-(4-acetoxycyclohexyl)-2-[4-[3-[(4-chloro-5-methoxy-1-methyl-indole-2-carbonyl)amino]oxetan-3-yl]phenyl]acetate (130 mg, 213 umol, synthesized via Method 8 Step 1 with acid B and amine CQ) in tetrahydrofuran (10 mL) and water (2 mL) was added lithium hydroxide (35.7 mg, 1.49 mmol) and methanol (5 mL), and the mixture was stirred at rt for 12 hrs. On completion, the mixture was diluted with saturated ammonium chloride (10 mL) and extracted with ethyl acetate (3×15 mL). The combined organic layer was washed with brine (3×20 mL), dried over anhydrous sodium sulfate, filtered and concentrated. The residue was purified by Prep-TLC (petroleum ether:ethyl acetate=2:3) to give the title compound. LCMS: (ES$^+$) m:z (M+H)$^+$=567.2, tR=0.890.

Step 2—(±)-2-[4-[3-[(4-Chloro-5-methoxy-1-methyl-indole-2-carbonyl)amino]oxetan-3-yl]phenyl]-2-(4-hydroxycyclohexyl)acetic acid To a solution of (±)-allyl 2-[4-[3-[(4-chloro-5-methoxy-1-methyl-indole-2-carbonyl)amino]oxetan-3-yl]phenyl]-2-(4-hydroxycyclohexyl)acetate (80.0 mg, 141 umol) and morpholine (73.7 mg, 846 umol) in tetrahydrofuran (20 mL) was added Pd(PPh$_3$)$_4$ (16.3 mg, 14.1 umol) under a nitrogen atmosphere, and the mixture was stirred at 40° C. for 16 hrs. On completion, the mixture was concentrated, washed with water (15 mL) and extracted with ethyl acetate (3×20 mL). The organic layer was dried with anhydrous sodium sulfate, filtrated and concentrated. The residue was dissolved in tetrahydrofuran (20 mL) and thiourea (resin) (100 mg, 1.31 mmol) was added. The mixture was stirred at rt for 12 hrs. Then the reaction mixture was filtered and the filtrate was concentrated in vacuo to give a residue. The residue was purified by prep-HPLC (condition: water (0.05% ammonia hydroxide v/v)-ACN; column: Phenomenex Gemini 150*25 mm*10 um) to give the title compound. LCMS: (ES$^+$) m:z (M+H)$^+$=527.0, (M+39)$^+$=564.9, tR=0.708. $^1$H NMR (400 MHz, DMSO-d$_6$) δ=9.61 (s, 1H), 7.52 (d, J=9.0 Hz, 2H), 7.47 (d, J=7.8 Hz, 2H), 7.32-7.29 (m, 3H), 7.24 (d, J=9.0 Hz, 1H), 5.03 (d, J=6.8 Hz, 2H), 4.76 (d, J=6.5 Hz, 2H), 4.44 (br. s., 1H), 3.93 (s, 3H), 3.88 (s, 3H), 2.99-2.93 (m, 1H), 2.42 (m, 1H), 1.82-1.79 (m 4H), 1.66-1.63 (m, 1H), 1.49-1.40 (m, 1H), 1.14-1.10 (m, 2H), 1.00-0.95 (m, 1H).

Other Methods

Example 139, 140, & 141—(±)-Dichloro-N-[3-(3-cyanophenyl)tetrahydrofuran-3-yl]-1-methyl-indole-2-carboxamide, (±)-N-[3-(3-Carbamoylphenyl)tetrahydrofuran-3-yl]-4,5-dichloro-1-methyl-indole-2-carboxamide, & (±)-4-[3-[(4,5-Dichloro-1-methyl-indole-2-carbonyl)amino]tetrahydrofuran-3-yl] benzoic acid

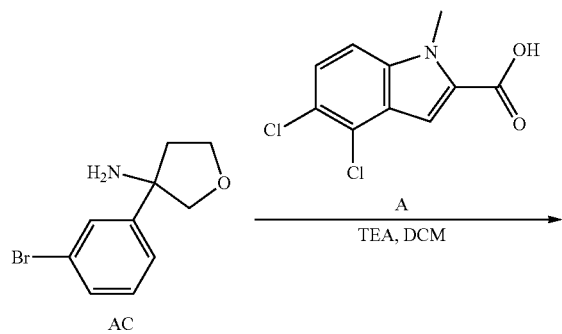

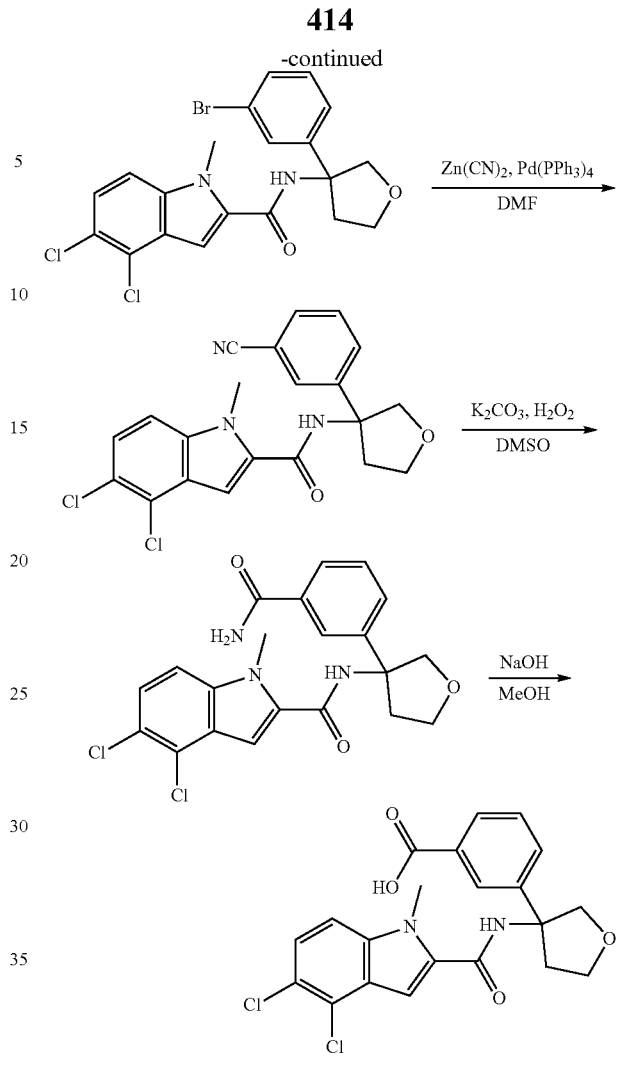

Step 1—(±)-N-[3-(3-Bromophenyl)tetrahydrofuran-3-yl]-4,5-dichloro-1-methyl-indole-2-carboxamide To a solution of 4,5-dichloro-1-methyl-indole-2-carboxylic acid (580 mg, 2.38 mmol) in a mixture of dichloromethane (20 mL) and N,N-dimethylformamide (157 uL) was added oxalyl chloride (904 mg, 7.13 mmol) dropwise and the reaction mixture was stirred at rt for 1 hr. On completion, the reaction mixture was concentrated in vacuo to give 4,5-dichloro-1-methyl-indole-2-carbonyl chloride (597 mg, crude) as a white solid, which was used in the next step directly.

A solution of (±)-3-(3-bromophenyl)tetrahydrofuran-3-amine (500 mg, 2.07 mmol) and triethylamine (628 mg, 6.21 mmol) in dichloromethane (8 mL), was added a solution of 4,5-dichloro-1-methyl-indole-2-carbonyl chloride (597 mg, 2.28 mmol) in dichloromethane (2 mL) under nitrogen atmosphere. Then the reaction was stirred at rt for 1.5 hrs. On completion, the mixture was adjusted to pH=5-6 with hydrochloric acid (1N). Then to the mixture was added water (20 mL) and the solution was extracted with dichloromethane (2×15 mL). The combined organic phase was washed with brine and concentrated to give the title compound. LCMS: (ES$^+$) m/z (M+H)$^+$=469.0, tR=1.024, Step 2 (Example 139)—(±)-Dichloro-N-[3-(3-cya-nophenyl)tetrahydrofuran-3-yl]-1-methyl-indole-2-carboxamide To a solution of (±)-N-[3-(3-bromophenyl)tetrahydrofuran-3-yl]-4,5-dichloro-1-methyl-indole-2-carboxamide (700 mg, 1.50 mmol) in dimethyl formamide (10 mL) was added zinc cyanide (528 mg, 4.50 mmol) and tetrakis(triphenylphosphine) palladium (173 mg, 150 umol), and the mixture was stirred at 120° C. for 2 hrs. On completion, to the mixture was added ethyl acetate (30 mL), then the mixture was filtered, and the filtrate was washed with water (2×30 mL). The organic phase was washed with brine and filtered again and the filtrate was concentrated to give a residue. The residue was dissolve with petroleum ether:ethyl acetate=1:1 (10 mL) and filtered to get the filter cake. The filter cake was dried in vacuo to give the title compound. LCMS: (ES⁺) m/z (M+H)⁺=414.0, tR=0.916. ¹H NMR (400 MHz, CDCl₃) δ=7.78 (d, J=1.4 Hz, 1H), 7.74 (dt, J=7.91, 1H), 7.56-7.62 (m, 1H), 7.53-7.46 (m, 1H), 7.37 (d, J=8.8 Hz, 1H), 7.23 (d, J=8.8 Hz, 1H), 7.05 (s, 1H), 6.84 (s, 1H), 4.28-4.20 (m, 1H), 4.20-4.14 (m, 3H), 4.01-3.91 (m, 3H), 2.84-2.74 (m, 1H), 2.57 (dt, J=13.2, 1H).

Step 3 (Example 140)—(±)-N-[3-(3-Carbamoylphenyl)tetrahydrofuran-3-yl]-4,5-dichloro-1-methyl-indole-2-carboxamide To a solution of (±)-4,5-dichloro-N-[3-(3-cyanophenyl)tetrahydrofuran-3-yl]-1-methyl-indole-2-carboxamide (120 mg, 289 umol) and potassium carbonate (16 mg, 115 umol) in dimethyl sulfoxide (5 mL) was added hydrogen peroxide (105 uL, 30%) in one portion at rt, and the mixture was stirred at 20-25° C. for 2 hrs. On completion, the mixture was diluted with water (20 mL) and filtered. The filter cake was washed with petroleum ether (2 mL), then the filter cake was dried in vacuo to give the title compound. LCMS: (ES⁺) m/z (M+H)⁺=432.0, tR=0.868. ¹H NMR (300 MHz, dimethylsulfoxide-d6) δ=9.23 (s, 1H), 8.06-7.92 (m, 2H), 7.74 (d, J=7.9 Hz, 1H), 7.64-7.54 (m, 2H), 7.48-7.39 (m, 3H), 7.35 (br. s., 1H), 4.31-4.24 (m, 1H), 4.20-4.14 (m, 1H), 3.96 (t, J=6.9 Hz, 2H), 3.89 (s, 3H), 2.86-2.71 (m, 1H), 2.39-2.25 (m, 1H).

Step 4 (Example 141)—(±)-4-[3-[(4,5-Dichloro-1-methyl-indole-2-carbonyl)amino]tetrahydrofuran-3-yl]benzoic acid To a solution of (±)-N-[3-(3-carbamoylphenyl)tetrahydrofuran-3-yl]-4,5-dichloro-1-methyl-indole-2-carboxamide (100 mg, 231 umol) in methanol (10 mL) was added sodium hydroxide (10 mL, 30% wt in water). Then the mixture was stirred at 90° C. for 16 hrs. On completion, the mixture was cooled to 20-25° C., then the pH was adjusted to 1-2 with aq. hydrochloric acid (2 N), concentrated to removed methanol, and the mixture was filtered to give the filter cake. The filter cake was purification by prep-HPLC (Phenomenex Gemini C18 250×50 mm×10 um, 0.1% TFA-ACN) to give the title compound. LCMS: (ES⁺) m/z (M+H)⁺=433.0, tR=0.981, ¹H NMR (400 MHz, dimethylsulfoxide-d6) δ=9.26 (s, 1H), 8.01 (s, 1H), 7.78 (d, J=7.6 Hz, 1H), 7.55-7.62 (m, 2H), 7.47-7.34 (m, 3H), 4.27 (d, J=9.2 Hz, 1H), 4.16 (d, J=9.2 Hz, 1H), 3.95 (t, J=7.0 Hz, 2H), 3.89 (s, 3H), 2.80 (dt, J=12.5, 1H), 2.26-2.33 (m, 1H).

Example 142, 143, 144, & 145—(±)-N-[3-(4-Bromophenyl)tetrahydrofuran-3-yl]-4,5-dichloro-1-methyl-indole-2-carboxamide, (±)-N-(3-(((Tert-butyldiphenylsilyl)oxy)methyl)-piperidin-3-yl)-4,5-dichloro-1-methyl-1H-indole-2-carboxamide, (±)-N-[3-(4-Carbamoyl-phenyl)tetrahydrofuran-3-yl]-4,5-dichloro-1-methyl-indole-2-carboxamide, & (±)-4-[3-[(4,5-Dichloro-1-methyl-indole-2-carbonyl)amino]tetrahydrofuran-3-yl]benzoic acid

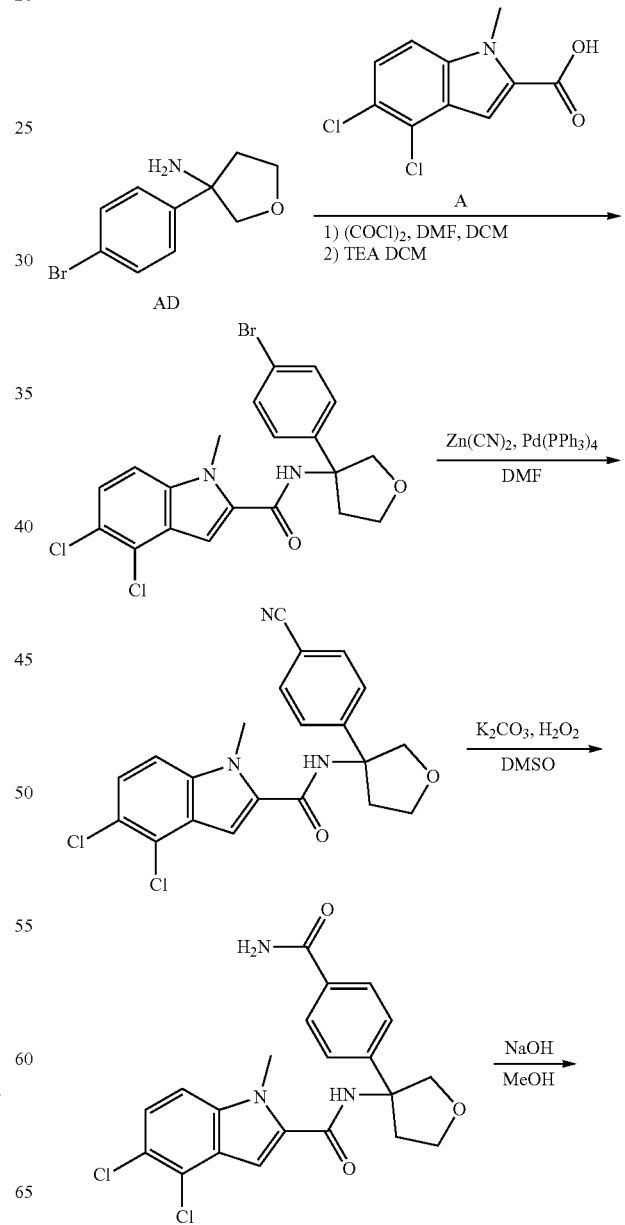

-continued

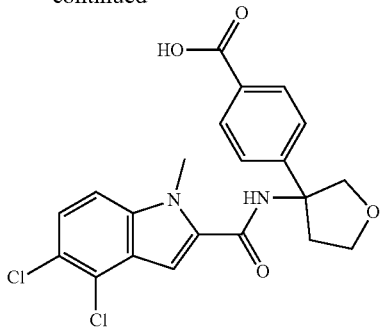

Step 1 (Example 142)—(±)-N-[3-(4-Bromophenyl)tetrahydrofuran-3-yl]-4,5-dichloro-1-methyl-indole-2-carboxamide To a solution of 4,5-dichloro-1-methyl-indole-2-carboxylic acid (230 mg, 942 umol) and N,N-dimethylformamide (4.13 mg, 56.5 umol) in dichloromethane (10 mL) was added oxalyl chloride (358 mg, 2.83 mmol) dropwise at 0° C. and the reaction mixture was stirred at 25° C. for 1 hr. On completion, the mixture was concentrated in vacuo to remove the solvent to give 4,5-dichloro-1-methyl-indole-2-carbonyl chloride (250 mg, crude) which was used to the next step directly.

To a solution of (±)-3-(4-bromophenyl)tetrahydrofuran-3-amine (200 mg, 826 umol) and triethylamine (208 mg, 2.07 mmol) in dichloromethane (5 mL) was added a solution of 4,5-dichloro-1-methyl-indole-2-carbonyl chloride (238 mg, 908 umol) in dichloromethane (5 mL) dropwise at 0° C. and the reaction was stirred at rt for 16 hrs. On completion, the mixture was adjusted to pH=5-6 with hydrochloric acid solution (1N), then the mixture was added water (30 mL) and extracted with ethyl acetate (2×20 mL). The combined organic phase was washed with brine and concentrated in vacuo to give the title compound. LCMS: (ES$^+$) m/z (M+H)$^+$=469.0, tR=1.048, $^1$H NMR (400 MHz, CDCl3) δ=7.53-7.50 (m, 2H), 7.40-7.36 (m, 3H), 7.23 (d, J=8.9 Hz, 1H), 7.03 (s, 1H), 6.84 (s, 1H), 4.25 (d, J=9.7 Hz, 1H), 4.16 (dd, J=5.7, 8.6 Hz, 2H), 4.11 (d, J=9.7 Hz, 1H), 3.97 (s, 3H), 2.86-2.77 (m, 1H), 2.62-2.52 (m, 1H).

Step 2 (Example 143)—(±)-N-(3-(((Tert-butyldiphenylsilyl)oxy)methyl)piperidin-3-yl)-4,5-dichloro-1-methyl-1H-indole-2-carboxamide To a solution of (±)-N-[3-(4-bromophenyl)tetrahydrofuran-3-yl]-4,5-dichloro-1-methyl-indole-2-carboxamide (370 mg, 790 umol) in dimethyl formamide (5 mL) was added zinc cyanide (278 mg, 2.37 mmol) and Pd(PPh$_3$)$_4$ (91.3 mg, 79.0 umol) and the reaction mixture was stirred at 120° C. for 2 hrs. On completion, water (10 mL) was added to the reaction mixture and it was extracted with ethyl acetate (2×15 mL). The combined organic phase was washed with brine and filtered, and the filtrate was concentrated in vacuo to give a crude product. The crude product was purified by column chromatography (petroleum ether:ethyl acetate=10:1-3:1) to give the title compound. LCMS: (ES$^+$) m/z (M+H)$^+$=414.0, tR=0.986, $^1$H NMR (400 MHz, CDCl3) δ=7.72-7.66 (m, 2H), 7.64-7.59 (m, 2H), 7.39 (d, J=8.8 Hz, 1H), 7.24 (d, J=9.0 Hz, 1H), 7.08 (s, 1H), 6.94 (s, 1H), 4.24-4.14 (m, 4H), 3.97 (s, 3H), 2.79 (td, J=6.1, 12.7 Hz, 1H), 2.59 (td, J=8.3, 13.2 Hz, 1H).

Step 3 (Example 144)—(±)-N-[3-(4-Carbamoylphenyl)tetrahydrofuran-3-yl]-4,5-dichloro-1-methyl-indole-2-carboxamide To a solution of (±)-4,5-dichloro-N-[3-(4-cyanophenyl)tetrahydrofuran-3-yl]-1-methyl-indole-2-carboxamide (240 mg, 579 umol) and potassium carbonate (32.0 mg, 231 umol) in dimethyl sulfoxide (5 mL) was added hydrogen peroxide (249 mg, 2.20 mmol) in one portion at rt, then the reaction mixture was stirred at rt for 2.5 hrs. On completion, the mixture was diluted with water (40 mL) and filtered, and the filter cake was diluted with ethyl acetate (20 mL) and washed with water (2×20 mL). Then the organic phase was concentrated in vacuo to give the title compound. LCMS: (ES$^+$) m/z (M+H)$^+$=432.1, tR=0.796. $^1$H NMR (400 MHz, DMSO-d$_6$) δ=9.26 (s, 1H), 7.93 (br. s., 1H), 7.83 (d, J=8.2 Hz, 2H), 7.61 (d, J=8.8 Hz, 1H), 7.50 (d, J=8.3 Hz, 2H), 7.48-7.43 (m, 2H), 7.32 (br. s., 1H), 4.29-4.22 (m, 1H), 4.20-4.13 (m, 1H), 3.96 (t, J=6.8 Hz, 2H), 3.90 (s, 3H), 2.83-2.74 (m, 1H), 2.35-2.29 (m, 1H)

Step 4 (Example 145)—(±)-4-[3-[(4,5-Dichloro-1-methyl-indole-2-carbonyl)amino]tetrahydrofuran-3-yl]benzoic acid To a solution of (±)-N-[3-(4-carbamoylphenyl)tetrahydrofuran-3-yl]-4,5-dichloro-1-methyl-indole-2-carboxamide (230 mg, 532 umol) in methanol (20 mL) was added sodium hydroxide (4.00 g in 25 mL water). Then the mixture was stirred at 90° C. for 16 hrs. On completion, the mixture was cooled to rt and concentrated in vacuo to remove the methanol. Then water (20 mL) was added to the mixture and was washed with ethyl acetate (40 mL). The aqueous phase was adjusted to pH=3-4 with concentrated hydrochloric acid and filtered. The filter cake was dissolved in methanol (10 mL) and water (20 mL) was added. Then the reaction mixture was lyophilized to give the title compound. LCMS: (ES$^+$) m/z (M+H)$^+$=433.0, tR=0.973 $^1$H NMR (400 MHz, DMSO-d$_6$) δ=9.28 (s, 1H), 7.89 (d, J=8.2 Hz, 2H), 7.61 (d, J=8.9 Hz, 1H), 7.51 (d, J=8.3 Hz, 2H), 7.48-7.44 (m, 2H), 4.28-4.23 (m, 1H), 4.21-4.16 (m, 1H), 4.00-3.93 (m, 2H), 3.91 (s, 3H), 2.79 (td, J=6.2, 12.7 Hz, 1H), 2.38-2.29 (m, 1H).

Example 146 & 147—(S)—4-[(3)-3-[(4,5-Dichloro-1-methyl-indole-2-carbonyl)amino]-tetrahydrofuran-3-yl]benzoic acid & (R)-4-[(3)-3-[(4,5-dichloro-1-methyl-indole-2-carbonyl)-amino]-tetrahydrofuran-3-yl]benzoic acid

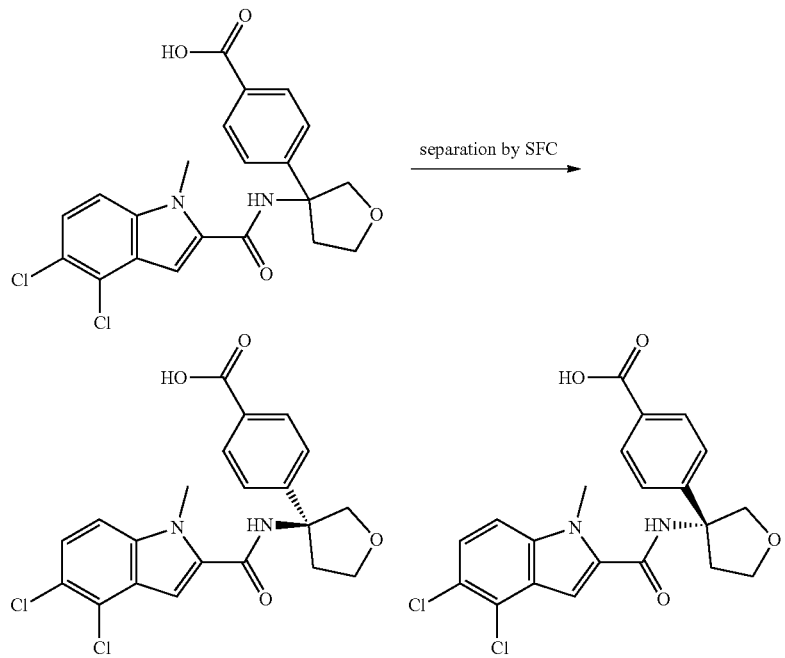

Compound of Example 145 was separated by SFC to give (S)—4-[(3)-3-[(4,5-Dichloro-1-methyl-indole-2-carbonyl)amino]-tetrahydrofuran-3-yl]benzoic acid and (R)-4-[(3)-3-[(4,5-Dichloro-1-methyl-indole-2-carbonyl)amino]-tetrahydrofuran-3-yl]benzoic acid. SFC (Condition: Base-MeOH, Column: OD (250 mm*30 mm, 10 um), Instrument: SFC-A).

Example 146 (peak 1): (S)—4-[(3)-3-[(4,5-Dichloro-1-methyl-indole-2-carbonyl)amino]-tetrahydrofuran-3-yl]benzoic acid or (R)-4-[(3)-3-[(4,5-Dichloro-1-methyl-indole-2-carbonyl)amino]-tetrahydrofuran-3-yl]benzoic acid: cSFC analytical tR: 3.708 min., ee: 98.3%; LCMS: (ES$^+$) m/z (M+H)$^+$=433.0, tR=0.967. $^1$H NMR (400 MHz, DMSO-d$_6$) δ=9.28 (s, 1H), 7.89 (d, J=8.0 Hz, 2H), 7.60 (d, J=8.8 Hz, 1H), 7.52 (d, J=8.3 Hz, 2H), 7.48-7.42 (m, 2H), 4.27 (d, J=8.8 Hz, 1H), 4.20 (d, J=8.8 Hz, 1H), 3.99-3.93 (m, 2H), 3.90 (s, 3H), 2.79 (td, J=6.2, 12.7 Hz, 1H), 2.35-2.30 (m, 1H).

Example 147 (peak 2): (R)-4-[(3)-3-[(4,5-Dichloro-1-methyl-indole-2-carbonyl)amino]-tetrahydrofuran-3-yl]benzoic acid or (S)—4-[(3)-3-[(4,5-Dichloro-1-methyl-indole-2-carbonyl)amino]-tetrahydrofuran-3-yl]benzoic acid: cSFC analytical tR: 4.591 min., ee: 97.7%; LCMS: (ES$^+$) m/z (M+H)$^+$=433.0, tR=0.964. $^1$H NMR (400 MHz, DMSO-d$_6$) δ=9.18 (s, 1H), 7.80 (d, J=7.8 Hz, 2H), 7.60 (d, J=8.8 Hz, 1H), 7.49-7.40 (m, 2H), 7.34 (d, J=8.0 Hz, 2H), 4.29 (d, J=9.0 Hz, 1H), 4.13 (d, J=9.0 Hz, 1H), 3.95 (t, J=7.0 Hz, 2H), 3.91 (s, 3H), 2.80 (td, J=6.0, 12.5 Hz, 1H), 2.37-2.29 (m, 1H).

Example 148 (±)-4,5-Dichloro-1-methyl-N-[3-[4-(1H-tetrazol-5-yl)phenyl]tetrahydro-furan-3-yl]indole-2-carboxamide

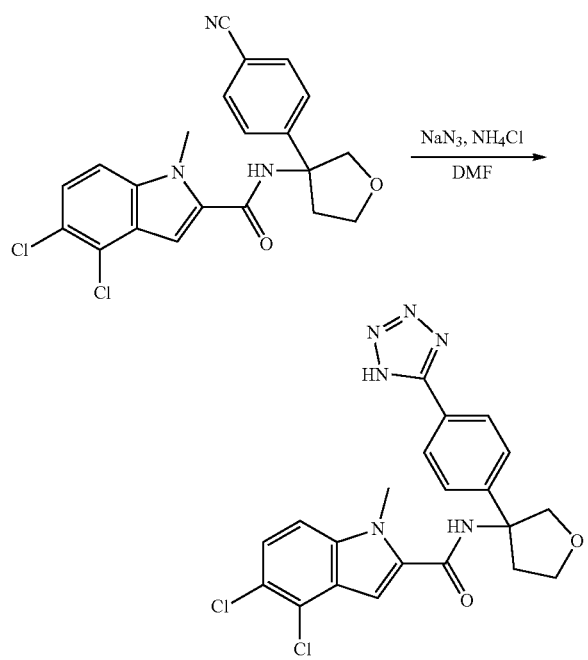

4,5-dichloro-N-[3-(4-cyanophenyl)tetrahydrofuran-3-yl]-1-methyl-indole-2-carboxamide (95.0 mg, 229 umol, Example 143), sodium azide (17.8 mg, 275 umol) and ammonium chloride (14.7 mg, 275 umol) were placed into a three neck flask under nitrogen. Then dimethyl formamide (2 mL) was added and the solution was heated at 120° C. for 5 day under nitrogen. On completion, the reaction mixture was cooled to room temperature and poured into water, and adjusted to pH=3-4 with hydrochloric acid solution (2N). Then the mixture was filtered. The filter cake was purified by prep-HPLC (condition: water (0.05% ammonia hydroxide v/v)-ACN; column: Phenomenex Gemini C18 250*50 10 u) to give the title compound. LCMS: (ES+) m/z (M+1)$^+$=457.1, tR=1.367. $^1$H NMR (400 MHz, DMSO-d$_6$) δ=9.31 (s, 1H), 8.01 (d, J=8.5 Hz, 2H), 7.67 (d, J=8.5 Hz, 2H), 7.60 (d, J=9.0 Hz, 1H), 7.49-7.41 (m, 2H), 4.24 (q, J=9.1 Hz, 2H), 4.02-3.95 (m, 2H), 3.90 (s, 3H), 2.81 (td, J=6.3, 12.7 Hz, 1H), 2.37 (td, J=7.9, 13.1 Hz, 1H).

Example 149—(±)-2-[4-[3-[(4,5-Dichloro-1-methyl-indole-2-carbonyl)amino]tetrahydrofuran-3-yl]phenyl]acetic acid

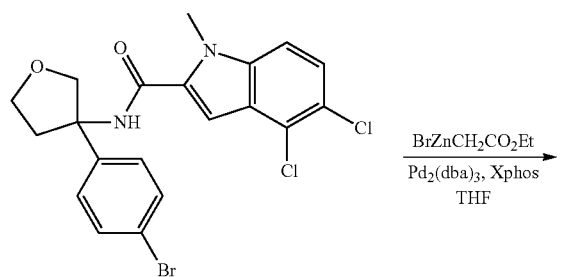

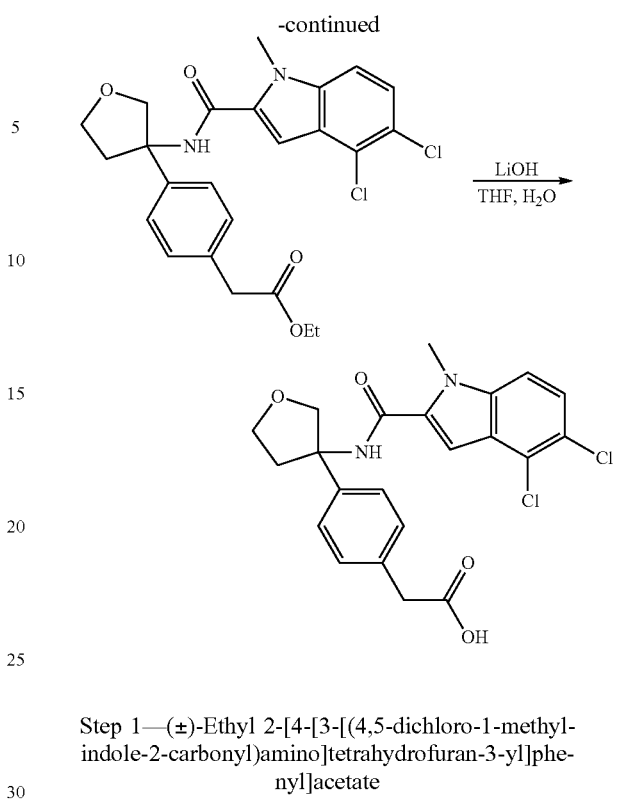

Step 1—(±)-Ethyl 2-[4-[3-[(4,5-dichloro-1-methyl-indole-2-carbonyl)amino]tetrahydrofuran-3-yl]phenyl]acetate To a mixture of Xphos (61.1 mg, 128 umol), Pd$_2$(dba)$_3$ (58.6 mg, 64.0 umol) and (±)-N-[3-(4-bromophenyl)tetrahydrofuran-3-yl]-4,5-dichloro-1-methyl-indole-2-carboxamide (300 mg, 640 umol, Example 142) in anhydrous tetrahydrofuran (4 mL) was added a solution of bromo-(2-ethoxy-2-oxo-ethyl)zinc (0.5M) in anhydrous tetrahydrofuran (10 mL) at rt and the reaction mixture was stirred at 80° C. for 1 hr under nitrogen. On completion, the reaction mixture was concentrated in vacuo to give the crude product, which was purified by silica gel chromatography (petroleum ether:ethyl acetate=5:1) to give the title compound. LCMS: (ES$^+$) m/z (M+H)$^+$=475.1, tR=1.598. $^1$H NMR (400 MHz, CDCl$_3$) δ=7.49-7.42 (m, 2H), 7.40-7.38 (m, 1H), 7.36 (d, J=2.6 Hz, 2H), 7.25-7.21 (m, 1H), 7.02 (s, 1H), 4.74 (d, J=10.0 Hz, 1H), 4.61-4.53 (m, 1H), 4.22-4.18 (m, 2H), 4.14 (q, J=7.1 Hz, 2H), 3.99 (s, 3H), 3.66 (s, 2H), 2.96-2.85 (m, 1H), 2.84-2.73 (m, 1H), 1.27 (t, J=7.2 Hz, 3H).

Step 2—(±)-2-[4-[3-[(4,5-Dichloro-1-methyl-indole-2-carbonyl)amino]tetrahydrofuran-3-yl]phenyl] acetic acid To a solution of (±)-ethyl 2-[4-[3-[(4,5-dichloro-1-methyl-indole-2-carbonyl)amino]tetrahydrofuran-3-yl]phenyl]acetate (800 mg, 673 umol) in a mixture of tetrahydrofuran (10 mL) and water (10 mL) was added lithium hydroxide (48.3 mg, 2.02 mmol) and the reaction mixture was stirred at rt for 16 hrs. On completion, the reaction mixture was concentrated in vacuo to remove tetrahydrofuran and the aqueous phase was acidified with 1N hydrochloric acid (5 mL) until pH=3-4. The resulting mixture was filtrated and the filter cake was washed with water (3×10 mL). The solid was dried in vacuo to give the title compound. LCMS: (ES$^+$) m/z (M+H)$^+$=448.8, tR=0.935. $^1$H NMR (400 MHz, DMSO-d$_6$) δ=9.11 (br. s., 1H), 7.55 (d, J=8.8 Hz, 1H), 7.42 (d, J=8.8 Hz, 1H), 7.39 (s, 1H), 7.31 (d, J=7.4 Hz, 2H), 7.18 (d, J=7.8 Hz, 2H), 4.25 (d, J=9.0 Hz, 1H), 4.08 (d, J=8.8 Hz, 1H), 3.91 (d, J=7.0 Hz, 2H), 3.88 (s, 3H), 3.30-3.23 (m, 2H), 2.81-2.69 (m, 1H), 2.36-2.26 (m, 1H).

Example 150 & 151 (S)—2-(4-(3-(4,5-dichloro-1-methyl-1H-indole-2-carboxamido)-tetrahydrofuran-3-yl)phenyl)acetic acid and (R)-2-(4-(3-(4,5-dichloro-1-methyl-1H-indole-2-carboxamido)tetrahydrofuran-3-yl)phenyl)acetic acid

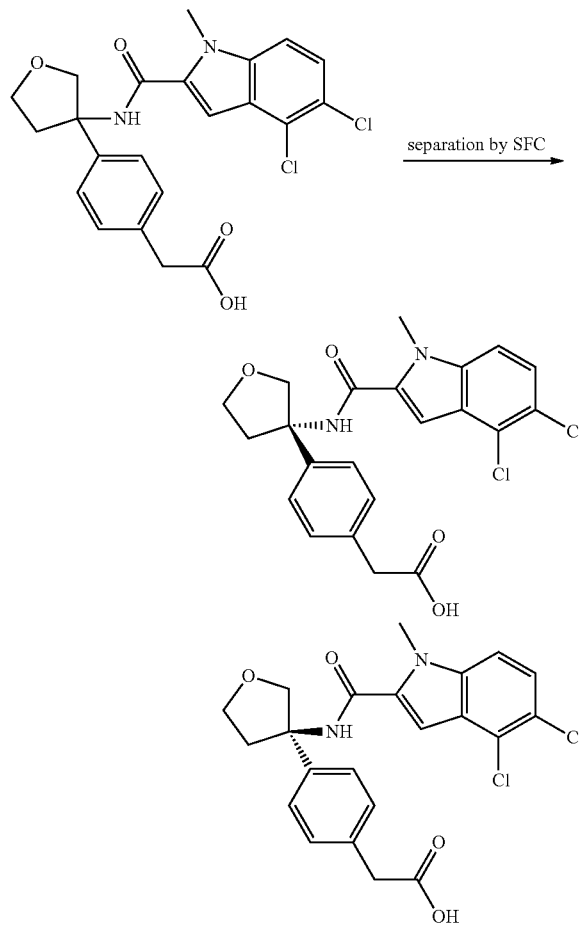

200 mg of (±)-2-[4-[3-[(4,5-Dichloro-1-methyl-indole-2-carbonyl)amino]tetrahydrofuran-3-yl]phenyl] acetic acid (Example 149) was separated by SFC (OD-3S_3_5_40_3ML Column: Chiralcel OD-3 100×4.6 mm I.D., 3 um. Mobile phase: methanol (0.05% DEA) in $CO_2$ from 5% to 40% Flow rate: 3 mL/min Wavelength: 220 nm) to give the two enantiomers. (S)—2-(4-(3-(4,5-dichloro-1-methyl-1H-indole-2-carboxamido)tetrahydrofuran-3-yl)phenyl)acetic acid or (R)-2-(4-(3-(4,5-dichloro-1-methyl-1H-indole-2-carboxamido)tetrahydrofuran-3-yl)phenyl)acetic acid (Example 150, peak 1). cSFC analytical tR: 3.763 min., ee: 100%; LCMS: (ES$^+$) m/z (M+H)$^+$=447.1, tR=0.846. $^1$H NMR (400 MHz, DMSO-d$_6$) δ=9.14 (s, 1H), 7.57 (d, J=8.9 Hz, 1H), 7.44 (d, J=8.8 Hz, 1H), 7.41 (s, 1H), 7.31 (d, J=8.2 Hz, 2H), 7.19 (d, J=8.3 Hz, 2H), 4.26 (d, J=9.2 Hz, 1H), 4.09 (d, J=9.0 Hz, 1H), 3.97-3.91 (m, 2H), 3.89 (s, 3H), 3.32 (br. s., 2H), 2.82-2.73 (m, 1H), 2.34-2.24 (m, 1H). (R)-2-(4-(3-(4,5-dichloro-1-methyl-1H-indole-2-carboxamido)tetrahydrofuran-3-yl)phenyl)-acetic acid or (S)—2-(4-(3-(4,5-dichloro-1-methyl-1H-indole-2-carboxamido)tetrahydrofuran-3-yl)phenyl)acetic acid (Example 151, peak 2). cSFC analytical tR: 4.376 min., ee: 97.2%; LCMS: (ES$^+$) m/z (M+H)$^+$=447.1, tR=0.869. $^1$H NMR (400 MHz, DMSO-d$_6$) δ=9.15 (s, 1H), 7.57 (d, J=8.8 Hz, 1H), 7.44 (d, J=8.8 Hz, 1H), 7.41 (s, 1H), 7.31 (d, J=8.2 Hz, 2H), 7.19 (d, J=8.2 Hz, 2H), 4.26 (d, J=9.0 Hz, 1H), 4.09 (d, J=9.2 Hz, 1H), 3.97-3.91 (m, 2H), 3.89 (s, 3H), 3.34 (br. s., 2H), 2.77 (td, J=6.1, 12.6 Hz, 1H), 2.35-2.23 (m, 1H).

Example 152—(±)-2-[4-[3-[(4,5-dichloro-1-methyl-indole-2-carbonyl)amino]tetrahydrofuran-3-yl]phenyl]propanoic acid

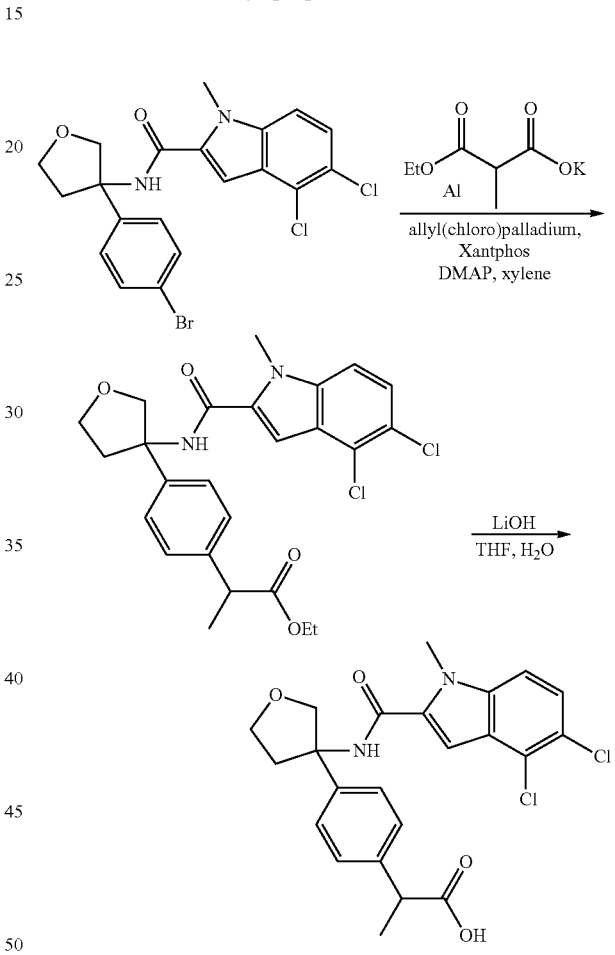

Step 1—(±)-Ethyl-2-[4-[3-[(4,5-dichloro-1-methyl-indole-2-carbonyl)amino]tetrahydrofuran-3-yl]phenyl] propanoate A mixture of (±)-N-[3-(4-bromophenyl)tetrahydrofuran-3-yl]-4,5-dichloro-1-methyl-indole-2-carboxamide (700 mg, 1.50 mmol Example 142), (5-diphenylphosphanyl-9,9-dimethyl-xanthen-4-yl)-diphenyl-phosphane (43.4 mg, 75.0 umol), N,N-dimethylpyridin-4-amine (183 mg, 1.50 mmol) and allyl(chloro) palladium (13.7 mg, 75.0 umol) in xylene (20 mL) was stirred at rt for 10 minutes under nitrogen. Then (3-ethoxy-2-methyl-3-oxo-propanoyl)oxypotassium (1.11 g, 6.00 mmol) was added in one portion and the reaction mixture was stirred at 130° C. for 30 minutes. On completion, the reaction mixture was concentrated in vacuo. The resulting solid was purified by silica gel chromatography (petroleum ether:ethyl acetate=3:1) to give the title compound. LCMS: (ES+) m/z (M+H)+=489.0, tR=1.695.

Step 2—(±)-2-[4-[3-[(4,5-dichloro-1-methyl-indole-2-carbonyl)amino]tetrahydrofuran-3-yl]phenyl] propanoic acid To a solution of (±)-ethyl 2-[4-[3-[(4,5-dichloro-1-methyl-indole-2-carbonyl)amino]tetrahydrofuran-3-yl]phenyl]propanoate (30.0 mg, 61.3 umol) in a mixture of tetrahydrofuran (4 mL) and water (4 mL) was added lithium hydroxide (7.34 mg, 306 umol) and the reaction mixture was stirred at rt for 16 hours. On completion, the reaction mixture was concentrated in vacuo to removal tetrahydrofuran and the aqueous phase was acidified with 1 N hydrochloric acid (1 mL) until pH=6. The solution was concentrated in vacuo. The resulting residue was purified by prep-HPLC [water (10 mM NH$_4$HCO$_3$)-ACN, Phenomenex Gemini C18 250*50 10 u] to give the title compound. LCMS: (ES+) m/z (M+H)+=461.0, tR=0.897. $^1$H NMR (400 MHz, DMSO-d$_6$) δ=9.11 (s, 1H), 7.59 (d, J=8.9 Hz, 1H), 7.44 (d, J=8.8 Hz, 1H), 7.41 (s, 1H), 7.28 (d, J=8.4 Hz, 2H), 7.22 (d, J=8.4 Hz, 2H), 4.26 (d, J=9.0 Hz, 1H), 4.08 (dd, J=3.3, 9.0 Hz, 1H), 3.96-3.89 (m, 5H), 3.25 (d, J=6.8 Hz, 1H), 2.77 (td, J=6.3, 12.5 Hz, 1H), 2.34-2.26 (m, 1H), 1.22 (d, J=7.0 Hz, 3H).

Example 153—(±)-2-[3-[3-[(4,5-Dichloro-1-methyl-indole-2-carbonyl)amino]tetrahydrofuran-3-yl]phenyl]acetic acid

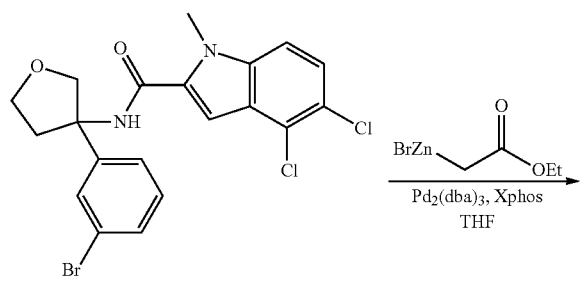

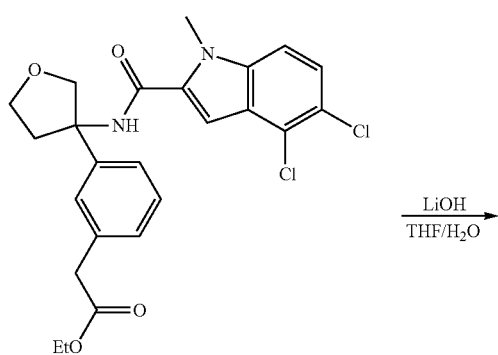

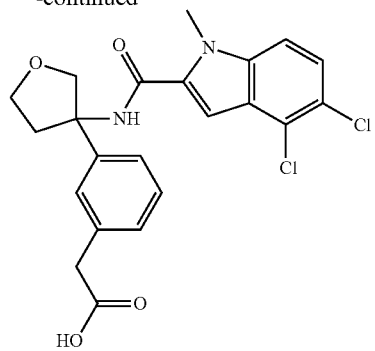

Step 1—(±)-Ethyl 2-[3-[3-[(4,5-dichloro-1-methyl-indole-2-carbonyl)amino]tetrahydrofuran-3-yl]phenyl]acetate To a solution of (±)-N-[3-(3-bromophenyl)tetrahydrofuran-3-yl]-4,5-dichloro-1-methyl-indole-2-carboxamide (300 mg, 640 umol, synthesized via Method 6, Step 1 with acid A and amine AC) in THF (2 mL) was added Pd$_2$(dba)$_3$ (58.6 mg, 64.0 umol) and XPhos (61.1 mg, 128 umol) at rt under nitrogen. Then a solution of bromo-(2-ethoxy-2-oxo-ethyl) zinc (1.04 g, 4.49 mmol) in anhydrous tetrahydrofuran (10 mL) was added, and the reaction mixture was stirred at 80° C. for 5 hours under nitrogen. The mixture was cooled to room temperature and water (50 mL) was added. Then the mixture was filtered. The filter cake was washed with dichloromethane (3×30 mL). The combined organic washings were concentrated to get the crude product. The crude was purified by column chromatography (SiO$_2$, petroleum ether:ethyl acetate=10:1 to 5:1) to get the title compound. $^1$H NMR (300 MHz, CDCl$_3$) δ=7.37-7.28 (m, 3H), 7.22-7.09 (m, 3H), 6.99-6.91 (m, 1H), 6.76 (s, 1H), 4.17-3.97 (m, 6H), 3.89 (s, 3H), 3.56 (s, 2H), 2.84-2.68 (m, 1H), 2.53 (dt, J=12.90, 8.34 Hz, 1H), 1.13-1.19 (m, 3H).

Step 2—(±)-2-[3-[3-[(4,5-Dichloro-1-methyl-indole-2-carbonyl)amino]tetrahydrofuran-3-yl]phenyl] acetic acid To a solution of (±)-ethyl 2-[3-[3-[(4,5-dichloro-1-methyl-indole-2-carbonyl)amino]tetrahydrofuran-3-yl]phenyl]acetate (200 mg, 420 umol) in tetrahydrofuran (5 mL) and water (2 mL) was added lithium hydroxide (30.2 mg, 1.26 mmol) and the mixture was stirred at rt for 16 hours. To the mixture was added water (20 mL), then it was washed with ethyl acetate (2×20 mL). Then the aqueous phase was adjusted to pH=4-5 with aq. hydrochloric acid (2 N) and filtered. The filter cake was triturated with dichloromethane to give the title compound. LCMS: (ES−) m/z (M+H)+=447.1, tR=0.854. $^1$H NMR (400 MHz, DMSO-d$_6$) δ=9.18 (s, 1H), 7.60 (d, J=8.91 Hz, 1H), 7.45 (d, J=8.91 Hz, 1H), 7.39 (s, 1H), 7.36-7.23 (m, 3H), 7.13 (d, J=7.15 Hz, 1H), 4.25 (d, J=9.16 Hz, 1H), 4.12 (d, J=9.16 Hz, 1H), 3.98-3.92 (m, 2H), 3.90 (s, 3H), 3.54 (s, 2H), 2.82-2.74 (m, 1H), 2.32-2.25 (m, 1H).

Example 154—(±)-2-Cyano-4-(3-(4,5-dichloro-1-methyl-1H-indole-2-carboxamido)tetrahydrofuran-3-yl)benzoic acid

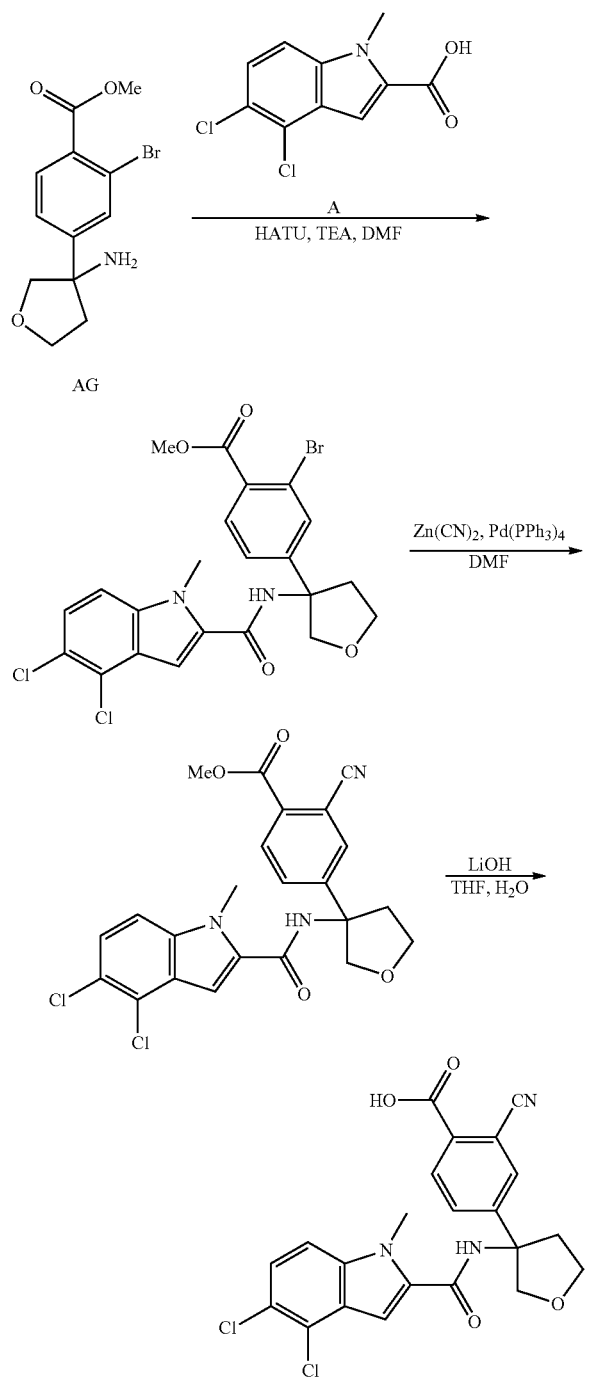

AG

Step 1—(±)-Methyl 2-bromo-4-(3-(4,5-dichloro-1-methyl-1H-indole-2-carboxamido)tetrahydrofuran-3-yl)benzoate To a solution of (±)-methyl 4-(3-aminotetrahydrofuran-3-yl)-2-bromobenzoate (800 mg, 2.67 mmol) and 4,5-dichloro-1-methyl-1H-indole-2-carboxylic acid (651 mg, 2.67 mmol) in dichloromethane (15 mL) was added triethylamine (540 mg, 5.34 mmol) and HATU (1.12 g, 2.94 mmol). The mixture was stirred at rt for 12 hrs. On completion, the reaction mixture was concentrated under vacuum to afford the crude product which was purified by column chromatography (petroleum ether:ethyl acetate=3:1) to afford the title compound. $^1$H NMR (400 MHz, DMSO-d$_6$) δ=9.33 (s, 1H), 7.78-7.74 (m, 2H), 7.62-7.59 (m, 2H), 7.48-7.44 (m, 2H), 4.24-4.19 (m, 2H), 3.98-3.94 (m, 2H), 3.91 (s, 3H), 3.85 (s, 3H), 2.76-2.74 (m, 1H), 2.36-2.34 (m, 1H).

Step 2—(±)-Methyl 2-cyano-4-(3-(4,5-dichloro-1-methyl-1H-indole-2-carboxamido)tetrahydrofuran-3-yl)benzoate To a solution of (±)-methyl 2-bromo-4-(3-(4,5-dichloro-1-methyl-1H-indole-2-carboxamido)tetrahydrofuran-3-yl)benzoate (300 mg, 570 umol) in N,N-formamide (5 mL) was added Pd(PPh$_3$)$_4$ (65.8 mg, 57.0 umol) and dicyanozinc (200 mg, 1.71 mmol). The mixture was flushed with nitrogen, stirred at 120° C. for 12 hrs. On completion, the reaction mixture was concentrated under vacuum to afford the crude product, which was purified by prep-TLC (petroleum ether:ethyl acetate=3:1) to afford the title compound.

Step 3—(±)-2-Cyano-4-(3-(4,5-dichloro-1-methyl-1H-indole-2-carboxamido)tetrahydrofuran-3-yl)benzoic acid To a solution of (±)-methyl 2-cyano-4-(3-(4,5-dichloro-1-methyl-1H-indole-2-carboxamido)tetrahydrofuran-3-yl)benzoate (94.2 mg, 0.2 mmol) in tetrahydrofuran (1.00 mL) and water (1.00 mL) was added lithium hydroxide (21 mg, 0.5 mmol) at rt, and the resultant mixture was stirred for 16 hrs. On completion, the mixture was concentrated in vacuo to remove the tetrahydrofuran. The aqueous phase was acidified with hydrochloride solution (0.1 mL, 2N) to pH=5 at 0° C. A white solid precipitated; the solid was filtered, and dried in vacuo to give the title compound. LCMS: (ES$^+$) m/z (M+H)$^+$=458.1, tR=0.692 $^1$H NMR (400 MHz, DMSO-d$_6$) δ=9.29 (br. s, 1H), 7.93 (d, J=6.0 Hz, 1H), 7.71 (s, 1H), 7.67 (d, J=8.4 Hz, 1H), 7.61 (d, J=9.2 Hz, 1H), 7.46 (d, J=8.8 Hz, 1H), 7.44 (s, 1H), 4.24-4.18 (m, 2H), 3.98-3.95 (m, 2H), 3.90 (s, 3H), 2.81-2.68 (m, 1H), 2.40-2.34 (m, 1H).

Example 155—(±)-4-[3-[(4,5-Dichloro-1-methyl-indole-2-carbonyl)amino]tetrahydro-furan-3-yl]-2-methyl-benzoic acid

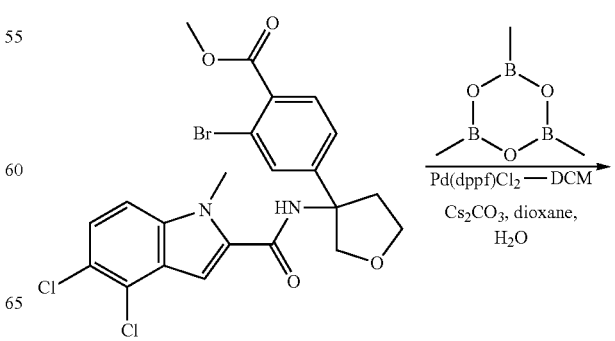

4.19-4.11 (m, 1H), 3.98-3.92 (m, 2H), 3.91 (s, 3H), 2.81-2.72 (m, 1H), 2.56-2.51 (m, 3H), 2.33-2.28 (m, 1H).

Example 156—(±)-4-[3-[(4,5-Dichloro-1-methyl-indole-2-carbonyl)amino]tetrahydro-furan-3-yl]-2-ethyl-benzoic acid

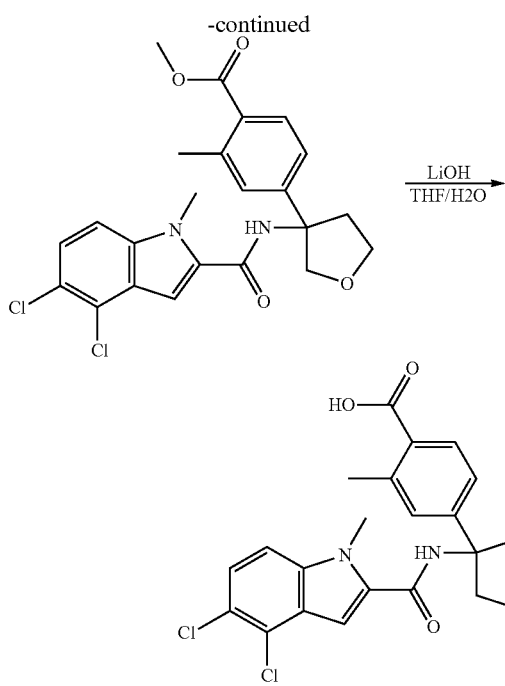
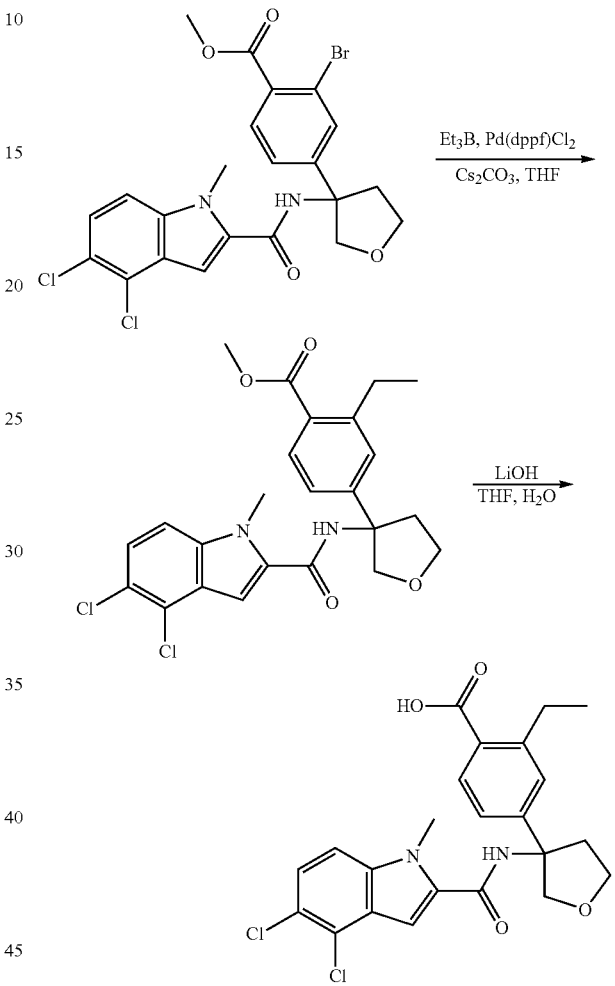

Step 1—(±)-methyl-4-[3-[(4,5-dichloro-1-methyl-indole-2-carbonyl)amino]tetrahydrofuran-3-yl]-2-methyl-benzoate A mixture of (±)-methyl 2-bromo-4-[3-[(4,5-dichloro-1-methyl-indole-2-carbonyl)amino]tetrahydrofuran-3-yl]benzoate (200 mg, 380 umol, synthesized from Step 1 as seen above in Example 154), 2,4,6-trimethyl-1,3,5,2,4,6-trioxatriborinane (47.7 mg, 380 umol), cesium carbonate (247 mg, 760 umol) and Pd(dppf)Cl$_2$—CH$_2$Cl$_2$ (62.0 mg, 76.0 umol) in water (1 mL) and dioxane (5 mL) was degassed and purged with nitrogen gas 3 times, and then the mixture was stirred at 100° C. for 4 hours under nitrogen gas atmosphere. On completion, the reaction mixture was concentrated in vacuo to get a residue. The residue was purified by column chromatography (dichloromethane:ethyl acetate=10:0 to 10:1) to give the title compound. LCMS: (ES$^+$) m/z (M+H)$^+$=461.1, tR=0.941.

Step 2—(±)-4-[3-[(4,5-Dichloro-1-methyl-indole-2-carbonyl)amino]tetrahydrofuran-3-yl]-2-methyl-benzoic acid To a solution of (±)-methyl 4-[3-[(4,5-dichloro-1-methyl-indole-2-carbonyl)amino]tetrahydrofuran-3-yl]-2-methyl-benzoate (120 mg, 260 umol) in water (2 mL) and tetrahydrofuran (8 mL) was added lithium hydroxide (37.3 mg, 1.56 mmol). The mixture was stirred at 60° C. for 16 hours. On completion, the reaction mixture was concentrated in vacuo to give a residue. The residue was acidified with 1 M hydrochloric acid to pH=3. Then the mixture was concentrated in vacuo to get the crude product. The crude product was purified by prep-HPLC (Condition: water (0.1% TFA)-CAN; Column: Venusil XBP C18 150×25 mm×10 um) to give the title compound. LCMS: (ES$^+$) m/z (M+H)$^+$=447.1, tR=0.865. $^1$H NMR (400 MHz, DMSO-d$_6$) δ=9.22 (s, 1H), 7.71 (d, J=8.3 Hz, 1H), 7.61 (d, J=8.9 Hz, 1H), 7.46 (d, J=8.8 Hz, 1H), 7.43 (s, 1H), 7.28 (br. s., 2H), 4.25-4.20 (m, 1H), Step 1—(±)-Methyl 4-[3-[(4,5-dichloro-1-methyl-indole-2-carbonyl)amino]tetrahydrofuran-3-yl]-2-ethyl-benzoate To a solution of methyl (±)-2-bromo-4-[3-[(4,5-dichloro-1-methyl-indole-2-carbonyl)amino]tetrahydrofuran-3-yl]benzoate (100 mg, 190 umol, synthesized from Step 1 as seen above in Example 154) and cesium carbonate (123 mg, 380 umol) in tetrahydrofuran (2 mL) was added Pd(dppf)Cl$_2$ (13.9 mg, 19.0 umol) and triethylborane (37.2 mg, 380 umol). The mixture was stirred at 60° C. for 16 hrs. On completion, the mixture was quenched with water (20 mL) and extracted with ethyl acetate (2×15 mL). The combined organic layers were washed with brine and concentrated in vacuo. The residue was purified by chromatography (petroleum ether:ethyl acetate=10:1 to 4:1) to give the title compound. $^1$H NMR (400 MHz, DMSO-d6) δ=9.26 (s, 1H), 7.75 (d, J=8.2 Hz, 1H), 7.61 (d, J=8.8 Hz, 1H), 7.46 (d, J=8.8 Hz, 1H), 7.42 (s, 1H), 7.39 (d, J=1.51 Hz, 1H), 7.3-7.32 (m, 1H), 4.26-4.15 (m, 2H), 4.01-3.93 (m, 2H), 3.90 (s, 3H), 3.81 (s, 3H), 2.89 (q, J=7.5 Hz, 2H), 2.81-2.73 (m, 1H), 2.33 (dd, J=7.5, 5.4 Hz, 1H), 1.14 (t, J=7.4 Hz, 3H).

Step 2—(±)-4-[3-[(4,5-Dichloro-1-methyl-indole-2-carbonyl)amino]tetrahydrofuran-3-yl]-2-ethyl-benzoic acid To a solution of (±)-methyl 4-[3-[(4,5-dichloro-1-methyl-indole-2-carbonyl)amino]tetrahydrofuran-3-yl]-2-ethyl-benzoate (40.0 mg, 84.1 umol) in tetrahydrofuran (4 mL) and water (2 mL) was added lithium hydroxide (16.1 mg, 673 umol). The mixture was stirred at rt for 32 hrs. On completion, the mixture was concentrated to remove the organic solvent, the residue was diluted with water (20 mL), and extracted with dichloromethane (3×20 mL). The aqueous phase was acidified by hydrochloric acid (2 N) until pH=3-4. The aqueous phase was then extracted with ethyl acetate (2×20 mL), dried and concentrated in vacuo. The residue was purified by Prep-HPLC (condition: water (0.225% FA)-ACN column: Phenomenex Synergi C18 150*25*10 um) to give the title compound. LCMS: (ES+) m/z (M+H)+=461.0, tR=0.840. 1H NMR (300 MHz, DMSO-d6) δ=9.24 (s, 1H), 7.72 (d, J=7.9 Hz, 1H), 7.60 (d, J=8.8 Hz, 1H), 7.45 (d, J=8.8 Hz, 1H), 7.41 (s, 1H), 7.37-7.25 (m, 2H), 4.20 (q, J=9.2 Hz, 2H), 3.99-3.93 (m, 2H), 3.90 (s, 3H), 2.91 (q, J=7.5 Hz, 2H), 2.81-2.74 (m, 1H), 2.37-2.30 (m, 1H), 1.13 (t, J=7.3 Hz, 3H).

Example 157—(±)-2-cyclopropyl-4-[3-[(4,5-dichloro-1-methyl-indole-2-carbonyl)amino]-tetrahydrofuran-3-yl]benzoic acid

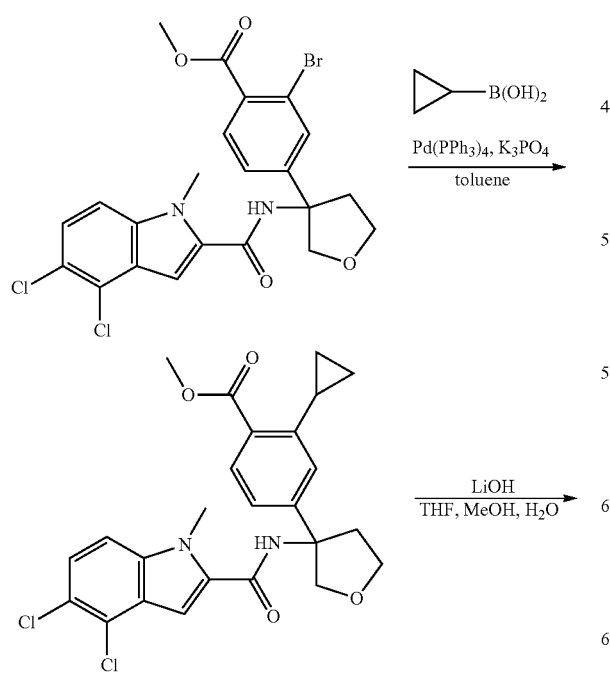

Step 1—(±)-methyl 2-cyclopropyl-4-[3-[(4,5-dichloro-1-methyl-indole-2-carbonyl)amino]-tetrahydrofuran-3-yl]benzoate To a solution of (±)-methyl 2-bromo-4-[3-[(4,5-dichloro-1-methyl-indole-2-carbonyl)amino]tetrahydrofuran-3-yl]benzoate (120 mg, 228 umol, synthesized from Step 1 as seen above in Example 154) in toluene (5 mL) and water (1 mL) was added cyclopropylboronic acid (29.3 mg, 342 umol) and potassium phosphate (145 mg, 684 umol). To the mixture was added tetrakis(triphenylphosphine) palladium (0) (52.7 mg, 45.6 umol) under nitrogen atmosphere. The reaction was stirred at 100° C. for 24 hrs under nitrogen. On completion, the mixture was concentrated in vacuo. The residue was purified by chromatography on silica gel (petroleum ether:ethyl acetate=1:1 to dichloromethane:methanol=10:1) to give the title compound. LCMS: (ES+) m/z (M+H)+=487.1, tR=0.843.

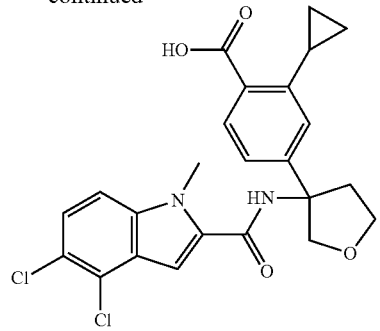

Step 2—(±)-2-cyclopropyl-4-[3-[(4,5-dichloro-1-methyl-indole-2-carbonyl)amino]-tetrahydrofuran-3-yl]benzoic acid To a solution of (±)-methyl 2-cyclopropyl-4-[3-[(4,5-dichloro-1-methyl-indole-2-carbonyl)amino]tetrahydrofuran-3-yl]benzoate (40.0 mg, 82.0 umol) in tetrahydrofuran (5 mL) was added lithium hydroxide (15.7 mg, 656 umol) in water (500 uL) and methanol (1 mL), and the mixture was stirred at 60° C. for 3 hours. On completion, the mixture was adjusted to pH=4-5 with HCl (4 M in dioxane). The residue was purified by prep-HPLC (YMC-Actus ODS-AQ 150*30 5 u, water (0.1% TFA)-ACN) to give the title compound. LCMS: (ES+) m/z (M+H)+=473.1, tR=0.844. 1H NMR (400 MHz, DMSO-d6) δ=12.79 (br. s., 1H), 9.21 (s, 1H), 7.68 (d, J=8.3 Hz, 1H), 7.60 (d, J=9.0 Hz, 1H), 7.46 (d, J=8.8 Hz, 1H), 7.40 (s, 1H), 7.28 (d, J=8.0 Hz, 1H), 7.02 (s, 1H), 4.17 (d, J=6.8 Hz, 2H), 3.94 (d, J=7.3 Hz, 2H), 3.90 (s, 3H), 2.68-2.77 (m, 2H), 2.30 (t, J=6.6 Hz, 1H), 0.95 (d, J=8.5 Hz, 2H), 0.61 (t, J=7.4 Hz, 2H).

Example 158—(±)-2-[3-Cyano-4-[3-[(4,5-dichloro-1-methyl-indole-2-carbonyl)amino]tetrahydro-furan-3-yl]phenyl]acetic acid

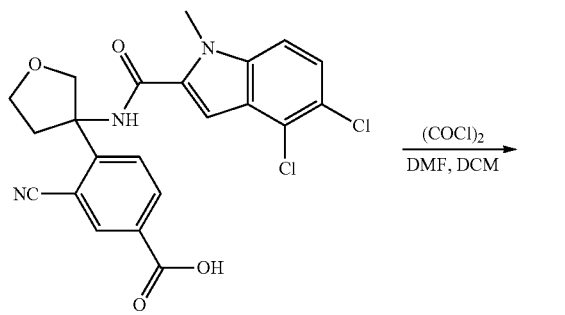

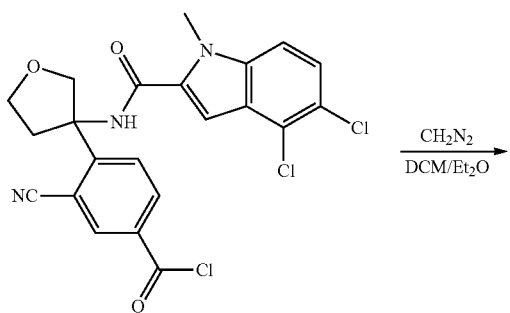

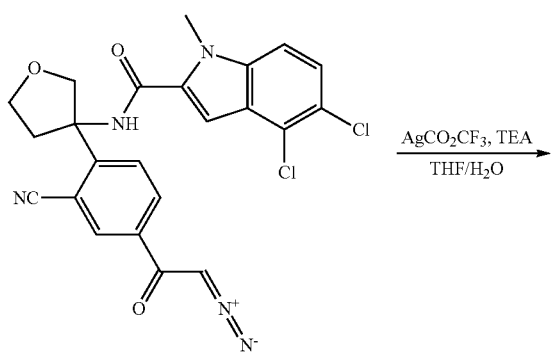

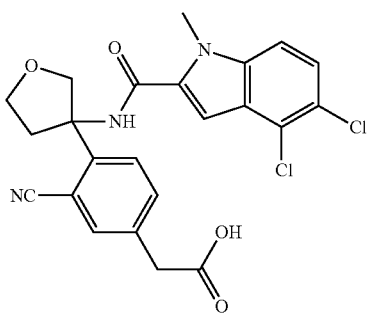

Step 1—(±)-3-Cyano-4-[3-[(4,5-dichloro-1-methyl-indole-2-carbonyl)amino]tetrahydrofuran-3-yl]benzoylchloride To a mixture of (±)-3-cyano-4-[3-[(4,5-dichloro-1-methyl-indole-2-carbonyl)amino]tetrahydrofuran-3-yl]benzoic acid (120 mg, 261 umol, synthesized via Method 6, Step 1 with acid A and amine AL) and a catalytic amount of N,N-dimethylformamide in dichloromethane (10 mL) was added oxalyl chloride (66.4 mg, 523 umol) dropwise. The mixture was stirred at rt for 2 hrs. On completion, the mixture was concentrated in vacuo to afford the title compound which was used for next step directly.

Step 2—(±)-4,5-Dichloro-N-[3-[2-cyano-4-(2-diazoethyl)phenyl]tetrahydrofuran-3-yl]-1-methyl-indole-2-carboxamide A solution containing potassium hydroxide (1.12 g, 19.9 mmol) in water (3 mL) and 2-(2-ethoxyethoxy)ethanol (6.54 g, 48.7 mmol) were placed in the distillation flask. A solution containing N-4-dimethyl-N-nitroso-benzenesulfonamide (4.00 g, 18.7 mmol) in ether (30 mL) was placed in the addition funnel, meanwhile the receiving flask was cooled to 0° C. After heating the distillation flask to 70° C., N-4-dimethyl-N-nitroso-benzenesulfonamide (4.00 g, 18.7 mmol) in ether (30 mL) was added dropwise over 0.5 hour. diazomethane (433 mg, 10.3 mmol) in ether (30 mL) was collected as the distillate.

To a solution of (±)-3-cyano-4-[3-[(4,5-dichloro-1-methyl-indole-2-carbonyl)-amino]tetrahydrofuran-3-yl] benzoyl chloride (120 mg, 251 umol) in dichloromethane (10 mL) was added dropwise a solution of diazomethane (190 mg, 4.53 mmol) in ether (5 mL), and the mixture was stirred at rt for 16 hrs. On completion, diluted acetic acid (5 mL) was added into the mixture, the mixture was basified with sodium bicarbonate solution to pH=9, and extracted with ethyl acetate (2×50 mL). The combined organic layer was dried over anhydrous sodium sulfate, filtered and concentrated in vacuum to give a residue. The residue was purified by silica gel chromatography (petroleum ether:ethyl acetate=3:1) to afford the title compound. LCMS: (ES$^+$) m/z (M+H)$^+$=482.2, tR=0.879.

Step 3—(±)-2-[3-Cyano-4-[3-[(4,5-dichloro-1-methyl-indole-2-carbonyl)amino]tetrahydrofuran-3-yl]phenyl]acetic acid To a mixture of (±)-4,5-dichloro-N-[3-[2-cyano-4-(2-diazoacetyl)phenyl]tetrahydrofuran-3-yl]-1-methyl-indole-2-carboxamide (45.0 mg, 93.3 umol) in tetrahydrofuran (4 mL) and water (0.4 mL) was added triethylamine (28.3 mg, 279 umol) and (2,2,2-trifluoroacetyl)oxysilver (20.6 mg, 93.3 umol). The mixture was stirred at rt for 16 hrs. On completion, the mixture was filtered and the filtrate was concentrated in vacuo to give a residue. The residue was purified with prep-HPLC (Instrument: GX-D; Column: Boston Green ODS 150*30 5 u; Mobile phase: 0.225% formic acid-acetonitrile) to afford the title compound. LCMS: (ES+) m/z (M+H)$^+$=472.1, tR=0.786. $^1$H NMR (400 MHz, DMSO-d$_6$) δ=10.89 (br. s., 1H), 8.37 (s, 1H), 7.93 (s, 1H), 7.65 (d, J=8.9 Hz, 1H), 7.61 (s, 2H), 7.52-7.45 (m, 2H), 4.21-4.17 (m, 5H), 4.01 (d, J=8.7 Hz, 1H), 3.84 (d, J=8.7 Hz, 1H), 3.69 (s, 2H), 2.59-2.55 (m, 1H), 2.37 (t, J=7.6 Hz, 1H).

Example 159—2-(4-(3-(4,5-Dichloro-1-methyl-1H-indole-2-carboxamido)oxetan-3-yl)-phenyl)acetic acid

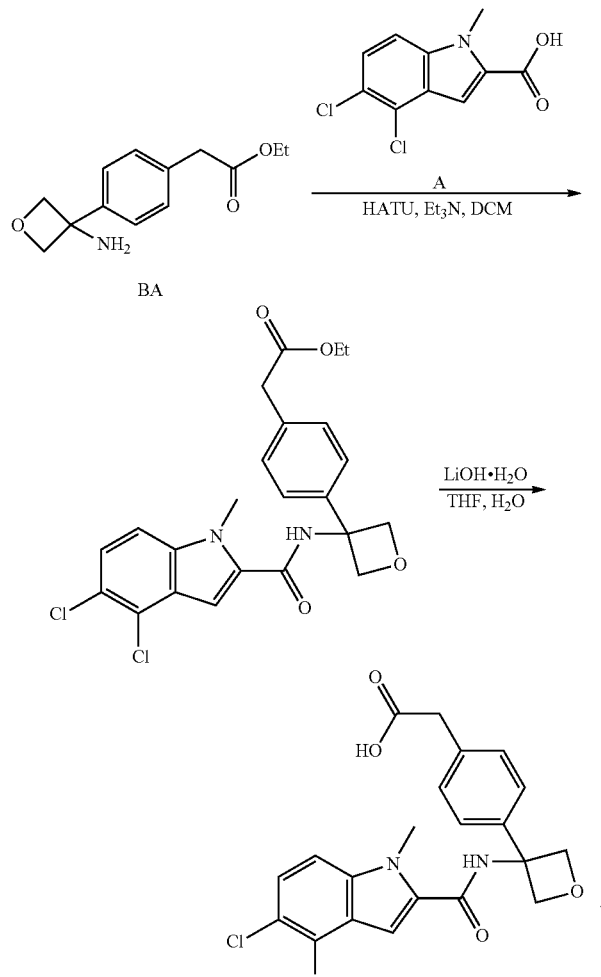

Step 1—Ethyl 2-(4-(3-(4,5-dichloro-1-methyl-1H-indole-2-carboxamido) oxetan-3-yl)phenyl) acetate To a solution of 4,5-dichloro-1-methyl-indole-2-carboxylic acid (156 mg, 638 umol), HATU (259 mg, 680 umol), and triethylamine (129 mg, 1.28 mmol) in methylene dichloride (10 mL) was added ethyl 2-[4-(3-aminooxetan-3-yl)phenyl]acetate (100 mg, 425 umol) at rt. Then the reaction mixture was stirred at rt for 16 hours under nitrogen. On completion, the reaction mixture was concentrated in vacuo. The residue was diluted with ethyl acetate (30 mL), washed with aqueous hydrochloric acid (0.1N, 20 mL), followed by sat. sodium bicarbonate (20 mL), and brine (30 mL). The organic layer was dried over anhydrous sodium sulfate and concentrated in vacuo to give a crude product that was used as in next step. LCMS: (ES$^+$) m/z (M+H)$^+$=461.1, tR=0.925.

Step 2—2-(4-(3-(4,5-Dichloro-1-methyl-1H-indole-2-carboxamido)oxetan-3-yl)phenyl)acetic acid To a solution of ethyl 2-[4-[3-[(4,5-dichloro-1-methyl-indole-2-carbonyl)amino]oxetan-3-yl]phenyl]acetate (150 mg, 325 umol) in a mixture solvent of tetrahydrofuran (8 mL) and water (2 mL) was added lithium hydroxide (54.6 mg, 1.30 mmol) in one portion at rt. The reaction mixture was stirred for 3 hours. On completion, the mixture was concentrated in vacuo to give the crude product. The crude product was purified by prep-HPLC (condition: water (0.05/0 ammonia hydroxide v/v-ACN; column: Phenomenex Gemini 150*25 mm*10 um) to give the title compound. LCMS: (ES$^+$) m/z (M+H)$^+$=431.0, tR=1.349. $^1$H NMR (400 MHz, DMSO-d$_6$) δ=9.75 (brs., 1H), 7.62 (d, J=8.8 Hz, 1H), 7.46 (d, J=8.8 Hz, 1H), 7.43-7.41 (m, 3H), 7.23 (d, J=8.0 Hz, 1H), 5.04 (d, J=6.8 Hz, 2H), 4.77 (d, J=6.4 Hz, 2H), 3.98 (s, 3H), 3.24 (s, 2H).

Example 160 & 161 (S)—2-[4-[3-[(4,5-dichloro-1-methyl-indole-2-carbonyl)amino]oxetan-3-yl]phenyl]propanoic acid & (R)-2-[4-[3-[(4,5-dichloro-1-methyl-indole-2-carbonyl)amino]oxetan-3-yl]phenyl]propanoic acid

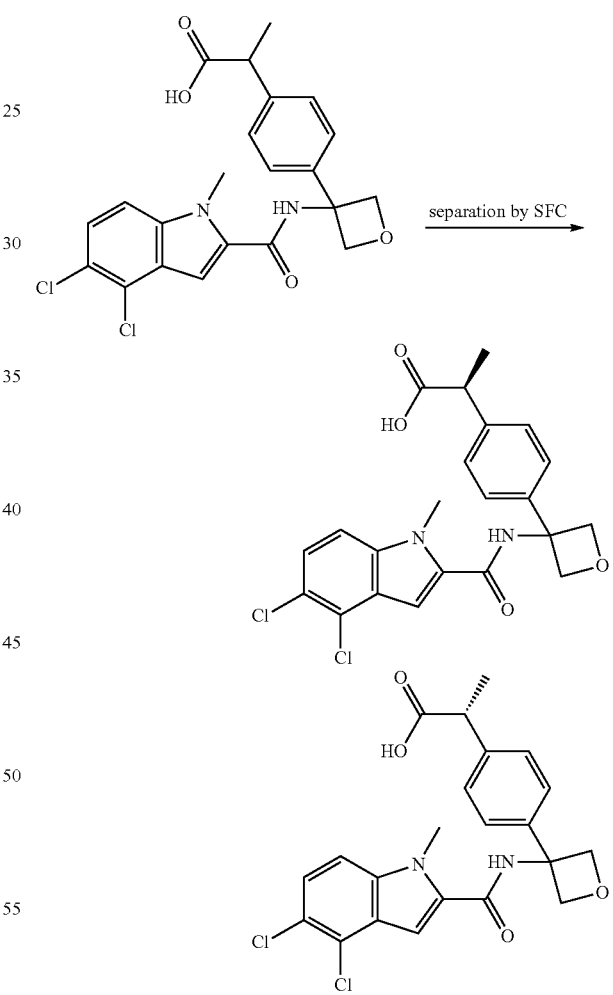

(±)-2-[4-[3-[(4,5-dichloro-1-methyl-indole-2-carbonyl)amino]oxetan-3-yl]phenyl]propanoic acid (230 mg, Example 58) was purified by SFC (Condition: Base-IPA, Column: AS (250 mm*30 mm, 10 um) Instrument: SFC-A) to give two enantiomers. Then the two enantiomers were purified by prep-HPLC (condition: water (0.05% ammonia hydroxide v/v)-ACN; Column: Phenomenex Gemini 150*25 mm*10 um):

(S)—2-[4-[3-[(4,5-dichloro-1-methyl-indole-2-carbonyl) amino]oxetan-3-yl]phenyl]propanoic acid or (R)-2-[4-[3-[(4,5-dichloro-1-methyl-indole-2-carbonyl)amino]oxetan-3-yl]phenyl]propanoic acid (Example 160) peak 1. cSFC analytical tR: 3.383 min., ee: 96%; LCMS: (ES$^+$) m/z (M+H)$^+$=447.0, tR=0.746. $^1$HNMR (400 MHz, DMSO-d$_6$) δ=9.74 (s, 1H), 7.62 (d, J=8.9 Hz, 1H), 7.50 (d, J=8.3 Hz, 2H), 7.47 (d, J=8.9 Hz, 1H), 7.42 (s, 1H), 7.31 (d, J=8.3 Hz, 2H), 5.04 (d, J=6.8 Hz, 2H), 4.79 (d, J=6.8 Hz, 2H), 3.97 (s, 3H), 3.60-3.58 (m, 1H), 1.33 (d, J=7.2 Hz, 3H).

(R)-2-[4-[3-[(4,5-dichloro-1-methyl-indole-2-carbonyl) amino]oxetan-3-yl]phenyl]propanoic acid or (S)—2-[4-[3-[(4,5-dichloro-1-methyl-indole-2-carbonyl)amino]oxetan-3-yl]phenyl]propanoic acid (Example 161) peak 2. cSFC analytical tR: 3.571 min., ee: 92%; LCMS: (ES$^+$) m/z (M+H)$^+$=446.9, tR=0.743. $^1$H NMR (400 MHz, DMSO-d$_6$) δ=9.73 (s, 1H), 7.62 (d, J=8.9 Hz, 1H), 7.52-7.45 (m, 3H), 7.41 (s, 1H), 7.32 (d, J=8.3 Hz, 2H), 5.04 (d, J=6.7 Hz, 2H), 4.78 (d, J=6.5 Hz, 2H), 3.96 (s, 3H), 3.51 (d, J=7.4 Hz, 1H), 1.32 (d, J=7.2 Hz, 3H).

Example 162—(±)-2-Cyclopropyl-2-(4-(3-(4,5-dichloro-1-methyl-1H-indole-2-carbox-amido)tetrahydro furan-3-yl)phenyl)acetic acid

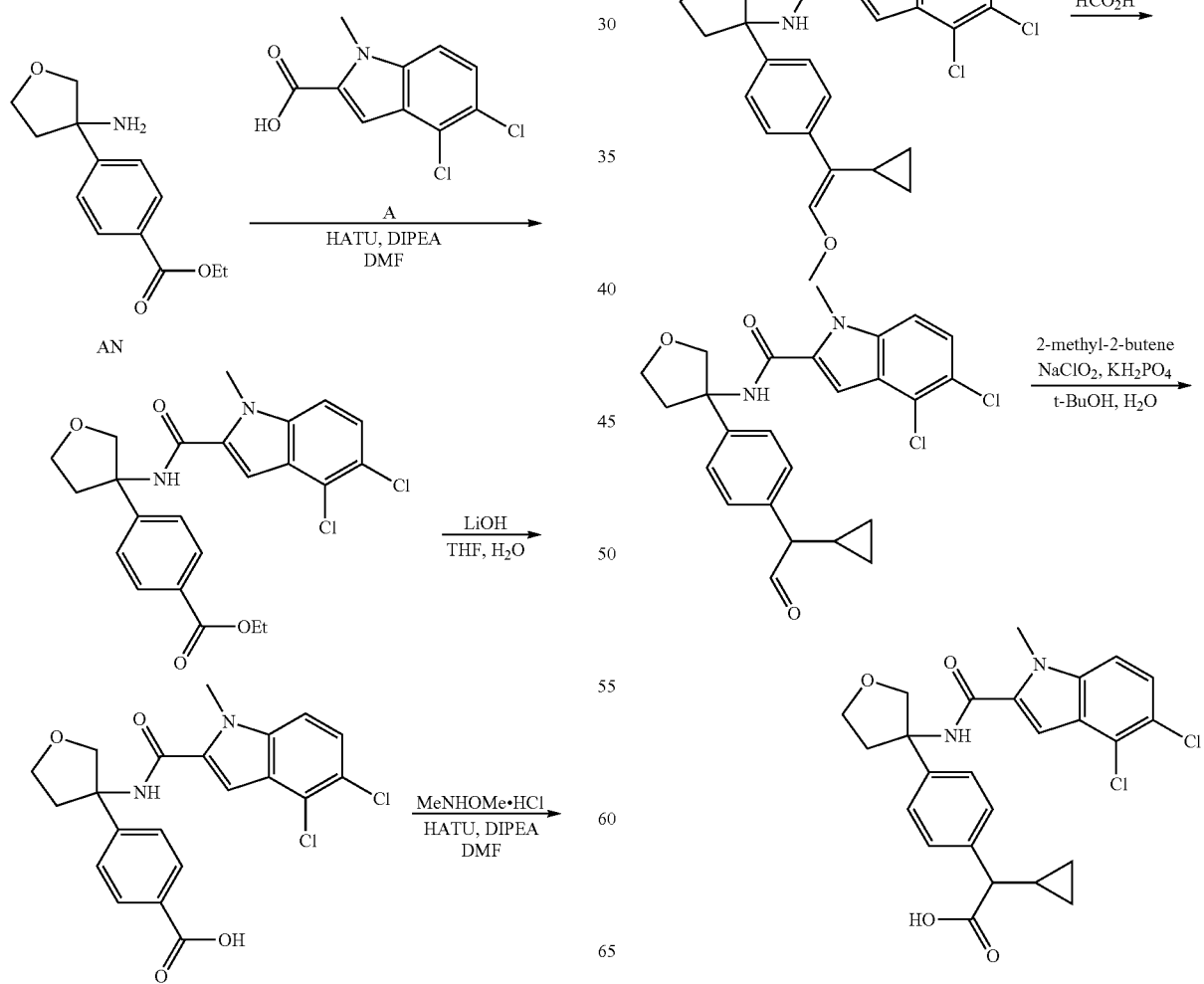

Step 1—(±)-Ethyl 4-(3-(4,5-dichloro-1-methyl-1H-indole-2-carboxamido)tetrahydrofuran-3-yl) benzoate A solution of 4,5-dichloro-1-methyl-indole-2-carboxylic acid (415 mg, 1.70 mmol), diisopropylethylamine (659 mg, 5.10 mmol) and HATU (711 mg, 1.87 mmol) in N,N-dimethylacetamide (4 mL) was stirred at rt for 1 hr. Then (±)-ethyl 4-(3-aminotetrahydrofuran-3-yl)benzoate (400 mg, 1.70 mmol) was added. The mixture was stirred at rt for 12 hrs. On completion, the mixture was quenched with water (10 mL). The solid was collected by filtration and washed with water (6 mL) to give the title compound. LCMS: (ES+) m/z (M+H)$^+$=461.0, tR=1.078.

Step 2—(±)-4-(3-(4,5-Dichloro-1-methyl-1H-indole-2-carboxamido)tetrahydrofuran-3-yl)benzoic acid To a solution of (±)-ethyl 4-[3-[(4,5-dichloro-1-methyl-indole-2-carbonyl)amino]tetrahydrofuran-3-yl] benzoate (640 mg, 1.39 mmol) in tetrahydrofuran (12 mL) and water (4 mL) was added lithium hydroxide (100 mg, 4.17 mmol). The mixture was stirred at 60° C. for 12 hrs. On completion, the mixture was concentrated to remove the organic solvent, then acidified with hydrochloric acid (2 N) until pH=2. The solid was collected by filtration and washed with water (5 mL) to give the title compound. LCMS: (ES$^+$) m/z (M+H)$^+$=433.0, tR=0.888.

Step 3—(±)-Methyl 4-(1-(hydroxyimino)ethyl)cyclohexanecarboxylate

To a solution of (±)-4-[3-[(4,5-dichloro-1-methyl-indole-2-carbonyl)amino]tetrahydrofuran-3-yl]benzoic acid (580 mg, 1.34 mmol) and diisopropylethylamine (519 mg, 4.02 mmol) in N,N-dimethylacetamide (4 mL) was added HATU (600 mg, 1.47 mmol). The mixture was stirred at rt for 1 hr, then N-methoxymethanamine (144 mg, 1.47 mmol) was added. The mixture was stirred at rt for 2 hrs. On completion, the mixture was quenched with water (10 mL). The solid was collected by filtration and washed with water (10 mL) to give the title compound. LCMS: (ES$^-$) m/z (M+H)$^+$=476.0, tR=0.903.

Step 4—(±)-4,5-Dichloro-N-(3-(4-(cyclopropanecarbonyl)phenyl)tetrahydrofuran-3-yl)-1-methyl-1H-indole-2-carboxamide To a solution of (±)-4,5-dichloro-N-[3-[4-[methoxy(methyl)carbamoyl]phenyl]tetrahydrofuran-3-yl]-1-methyl-indole-2-carboxamide (500 mg, 1.05 mmol) in tetrahydrofuran (10 mL) was added bromo(cyclopropyl)magnesium (1.2 M, 1.75 mL). The mixture was stirred at rt for 1 hr. On completion, the mixture was quenched with water (10 mL) and extracted with ethyl acetate (3×10 mL). The combined organic layers were dried over anhydrous sodium sulfate and concentrated in vacuo. The residue was purified by chromatography (dichloromethane:ethyl acetate=15:1) to give the title compound. LCMS: (ES$^+$) m/z (M+H)$^+$=457.0, tR=1.056. $^1$H NMR (400 MHz, DMSO-d$_6$) δ=9.32 (s, 1H), 8.03 (d, J=8.3 Hz, 2H), 7.61 (d, J=8.0 Hz, 3H), 7.49-7.44 (m, 2H), 4.29-4.18 (m, 2H), 4.02-3.95 (m, 2H), 3.91 (s, 3H), 2.36-2.29 (m, 1H), 1.06-0.98 (m, 4H).

Step 5—(±)-4,5-Dichloro-N-(3-(4-(1-cyclopropyl-2-methoxyvinyl)phenyl)tetrahydrofuran-3-yl)-1-methyl-1H-indole-2-carboxamide To the suspension of methoxymethyl(triphenyl)phosphonium chloride (225 mg, 656 umol) in tetrahydrofuran (2 mL) was added n-butyllithium (2.5 M, 276 uL) at 0° C. The mixture was stirred at 0° C. for 0.5 hr, then (±)-4,5-dichloro-N-[3-[4-(cyclopropanecarbonyl)phenyl]tetrahydrofuran-3-yl]-1-methyl-indole-2-carboxamide (150 mg, 328 umol) was added. The mixture was stirred at rt for 12 hrs. On completion, the mixture was quenched with water (5 mL) and extracted with ethyl acetate (3×10 mL). The combined organic layers were dried over anhydrous sodium sulfate and concentrated in vacuo. The residue was purified by chromatography (petroleum ether:ethyl acetate=4:1) to give the title compound. LCMS: (ES$^+$) m/z (M+H)$^+$=485.1, tR=1.208.

Step 6—(±)-4,5-Dichloro-N-(3-(4-(1-cyclopropyl-2-oxoethyl)phenyl)tetrahydrofuran-3-yl)-1-methyl-1H-indole-2-carboxamide A mixture of (±)-4,5-dichloro-N-[3-[4-[(E)-1-cyclopropyl-2-methoxyvinyl]phenyl]tetrahydrofuran-3-yl]-1-methyl-indole-2-carboxamide (80.0 mg, 165 umol) in formic acid (79.2 mg, 1.65 mmol) was stirred at rt for 8 hrs. On completion, the mixture was quenched with water (5 mL). The solid was collected by filtration and washed with water (5 mL) to give the title compound. LCMS: (ES$^+$) m/z (M+H)$^+$=471.1, tR=1.042.

Step 7—(±)-2-Cyclopropyl-2-(4-(3-(4,5-dichloro-1-methyl-1H-indole-2-carboxamido)tetrahydro furan-3-yl)phenyl)acetic acid To a solution of (±)-4,5-dichloro-N-[3-[4-(1-cyclopropyl-2-oxo-ethyl)phenyl]tetrahydrofuran-3-yl]-1-methyl-indole-2-carboxamide (40.0 mg, 84.9 umol) in tert-butanol (2 mL) was added 2-methylbut-2-ene (59.5 mg, 849 umol), aqueous sodium dihydrogen phosphate (0.85 M, 499 uL) and aqueous sodium chlorite (0.51 M, 499 uL). The mixture was stirred at rt for 1 hr. On completion, the mixture was diluted with water (5 mL) and extracted with ethyl acetate (3×10 mL). The combined organic layers were dried over anhydrous sodium sulfate and concentrated in vacuo. The residue was purified by prep-HPLC (column: YMC-Actus ODS-AQ 150*30 5 u; mobile phase: [water (0.1% TFA)-ACN]; ACN %: 45%-75%, 11 min) to give the title compound. LCMS: (ES$^+$) m/z (M+H)$^+$=487.1, tR=0.904. $^1$H NMR (400 MHz, DMSO-d$_6$) δ=12.34 (br. s., 1H), 9.18 (s, 1H), 7.61 (d, J=8.8 Hz, 1H), 7.49-7.43 (m, 2H), 7.42-7.37 (m, 2H), 7.34-7.29 (m, 2H), 4.27 (d, J=9.3 Hz, 1H), 4.12 (d, J=9.0 Hz, 1H), 3.99-3.93 (m, 2H), 3.92 (s, 3H), 2.85-2.71 (m, 2H), 2.35-2.29 (m, 1H), 1.33 (br. s., 1H), 0.63-0.54 (m, 1H), 0.48-0.39 (m, 1H), 0.35-0.26 (m, 1H), 0.14 (m, 1H).

Example 163—(±)-2-Cyclopropyl-2-(4-(3-(4,5-dichloro-6-methoxy-1-methyl-1H-indole-2-carboxamido)tetrahydrofuran-3-yl)phenyl)acetic acid

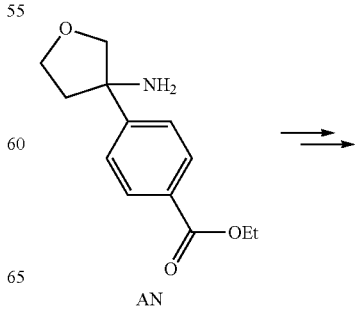

AN

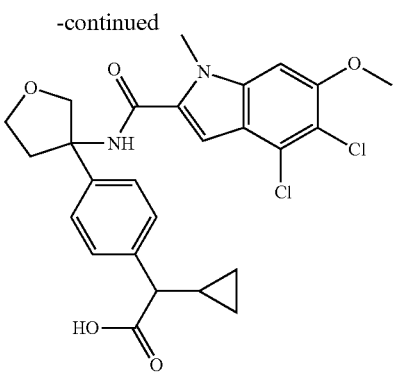

(±)-2-Cyclopropyl-2-(4-(3-(4,5-dichloro-6-methoxy-1-methyl-1H-indole-2-carboxamido)tetrahydrofuran-3-yl)phenyl)acetic acid was made in the same method as Example 162, starting with acid F and amine AN in the first step. In the final step, the residue was purified by prep-HPLC (column: Waters Xbridge 150*25 5 u; mobile phase: [water (0.05% ammonia hydroxide v/v)-ACN]; ACN %: 15%-45%, 10 min) to give the title compound. LCMS (ES⁺): 517.0 m/z (M+H)⁺, tR=0.767 min. ¹H NMR (400 MHz, DMSO-d₆) δ=9.0.2 (s, 1H), 7.38 (d, J=7.6 Hz, 3H), 7.34-7.28 (m, 2H), 7.25 (s, 1H), 4.26 (d, J=9.2 Hz, 1H), 4.11 (d, J=8.8 Hz, 1H), 3.94 (s, 3H), 3.92 (br s, 2H), 3.90 (s, 3H), 2.80-2.75 (m, 1H), 2.66 (d, J=10.4 Hz, 1H), 2.31-2.28 (m, 1H), 1.35-1.30 (m, 1H), 0.54-0.52 (m, 1H), 0.39-0.38 (m, 1H), 0.28-0.27 (m, 1H), 0.09-0.06 (m, 1H).

Example 164—4-Chloro-5-methoxy-1-methyl-N-(3-(4-(N-propionylsulfamoyl)phenyl)-oxetan-3-yl)-1H-indole-2-carboxamide

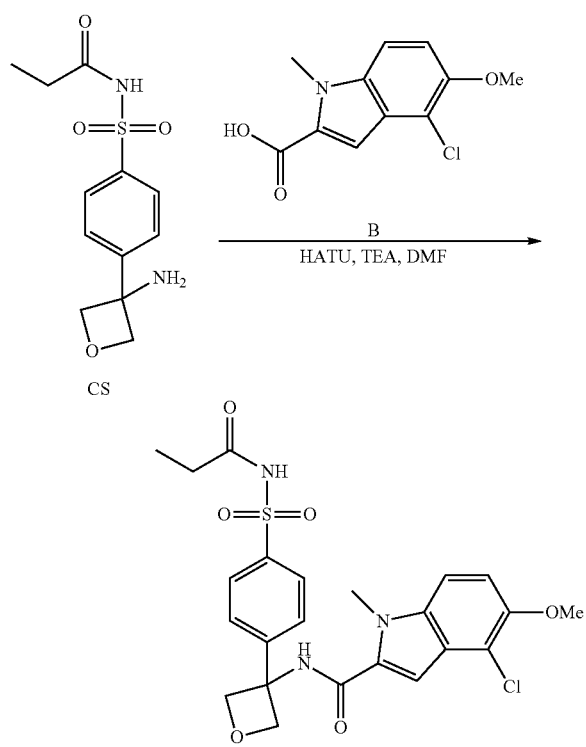

To a solution of N-[4-(3-aminooxetan-3-yl)phenyl]sulfonylpropanamide (140 mg, 492 umol) and 4-chloro-5-methoxy-1-methyl-indole-2-carboxylic acid (118 mg, 492 umol) in N,N-dimethylformamide (15 mL) was added HATU (374 mg, 984 umol) and triethylamine (149 mg, 1.48 mmol, 204 uL). On completion, the reaction mixture was concentrated in vacuo. The residue was dissolved in dichloromethane (10 mL) and washed with 1N citric acid (5 mL) until pH=3-4. The organic layer was dried over anhydrous sodium sulfate, filtrated and concentrated in vacuo. The residue was purified by prep-HPLC (Instrument: LC-L; Condition: water (0.225% FA)-ACN; Column: Phenomenex Synergi C18 150*30 mm*4 um) to afford to afford the title product (63.1 mg, 25% yield) as white solid. LCMS: (ES⁺) m/z (M+H)⁺=506.1, tR=0.804. ¹H NMR (400 MHz, DMSO-d₆) δ=9.76 (s, 1H), 7.95 (d, J=8.3 Hz, 2H), 7.81 (d, J=8.3 Hz, 2H), 7.59-7.49 (d, J=9.0 Hz, 1H), 7.35 (s, 1H), 7.26 (d, J=9.0 Hz, 1H), 5.07 (d, J=6.8 Hz, 2H), 4.81 (d, J=6.8 Hz, 2H), 3.94 (s, 3H), 3.90 (s, 3H), 2.20 (q, J=7.5 Hz, 2H), 0.89 (t, J=7.5 Hz, 3H).

Example 165—4-Chloro-5-methoxy-1-methyl-N-(3-(4-((methylsulfonyl)carbamoyl)-phenyl)oxetan-3-yl)-1H-indole-2-carboxamide

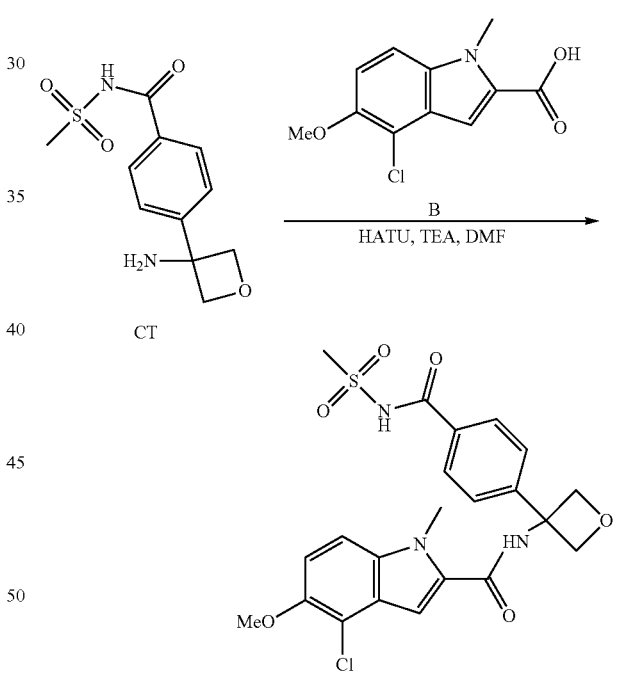

To a solution of 4-(3-aminooxetan-3-yl)-N-methylsulfonyl-benzamide (133 mg, 492 umol) and 4-chloro-5-methoxy-1-methyl-indole-2-carboxylic acid (118 mg, 492 umol) in N,N-dimethylformamide (8 mL) was added HATU (374 mg, 984 umol) and triethylamine (149 mg, 1.48 mmol). The reaction mixture was stirred at rt for 16 hrs under nitrogen. The reaction mixture was concentrated in vacuo. The residue was dissolved in dichloromethane (10 mL) and washed with 1N citric acid (5 mL) until pH=3-4. The organic layer was dried over anhydrous sodium sulfate, filtrated and concentrated in vacuo. The residue was purified by pre-HPLC (Instrument: GX-C; Condition: water (0.225% FA)-ACN; Column: Boston Green ODS 150*30 5 u) to give the title compound. LCMS: (ES+) m/z (M+H)+=492.2, tR=0.804. $^1$H NMR (400 MHz, DMSO-d$_6$) δ=12.18 (br. s., 1H), 9.75 (s, 1H), 7.99 (d, J=8.5 Hz, 2H), 7.72 (d, J=8.3 Hz, 2H), 7.54 (d, J=9.0 Hz, 1H), 7.33 (s, 1H), 7.26 (d, J=9.3 Hz, 1H), 5.07 (d, J=6.8 Hz, 2H), 4.81 (d, J=6.8 Hz, 2H), 3.93 (s, 3H), 3.89 (s, 3H), 3.34 (s, 3H).

Example 166: 3-Phosphoglycerate Dehydrogenase (PHGDH) Diaphorase Coupled Assay

Full length (FL) 3-Phosphoglycerate Dehydrogenase (PHGDH) Diaphorase coupled assay (500 uM NAD)

PHGDH activity was determined by detecting the NADH produced during the reaction. Diaphorase was used to catalyze the oxidation of NADH with the concomitant reduction of resazurin to the fluorescent product resorufin. Resorufin fluorescence quantitatively reflected the production of NADH by the PHGDH reaction. To drive the forward reaction, two enzymes in the serine synthesis pathway subsequent to PHGDH, Phosphoserine aminotransferase (PSAT1) and phosphoserine phosphatase (PSPH) were also added to the reaction.

Briefly, serial dilution of compounds were incubated in a volume of 20 μL in 384 well plates with the assay mixture containing 5 nM PHGDH, 500 nM PSAT1, 500 nM PSPH, 500 μM NAD+, 80 uM 3-phosphoglycerate, 1 mM glutamate, 57 uM Resazurin and 0.2 mg/ml Diaphorase in assay buffer containing 50 mM Trisethanoloamine (TEA) pH8.0, 10 mM MgCl$_2$, 0.01% Tween-20 and 0.05% Bovine Serum Albumin (BSA). The plate was then incubated at 30° C. for 60 minutes and resorufin fluorescence was measured at emission wavelength 598 nm following excitation at 525 nm. The positive control consisted of the complete reaction mixture with 4% DMSO and was set to 0% inhibition. The negative control consisted of the reaction mix lacking PHGDH with 4% DMSO and was set to 100% inhibition. Percent inhibition with the compounds was then calculated by normalizing the fluorescence observed at a given compound concentration to the positive and negative controls. IC$_{50}$ was calculated by plotting the % inhibition versus concentration and using hyperbolic fit to determine compound concentration corresponding to 50% inhibition.

Full length (FL) 3-Phosphoglycerate Dehydrogenase (PHGDH) Diaphorase coupled assay (20 uM NAD)

Serial dilution of compounds were incubated in a volume of 20 μL in 384 well plates with the assay mixture containing 10 nM PHGDH, 500 nM PSAT1, 500 nM PSPH, 20 μM NAD+, 80 uM 3-phosphoglycerate, 1 mM glutamate, 57 uM Resazurin and 0.2 mg/ml Diaphorase in assay buffer containing 50 mM Trisethanoloamine (TEA) pH8.0, 10 mM MgCl$_2$, 0.01% Tween-20 and 0.05% Bovine Serum Albumin (BSA). The plate was then incubated at 30° C. for 60 minutes and resorufin fluorescence was measured at emission wavelength 598 nm following excitation at 525 nm. The positive control consisted of the complete reaction mixture with 4% DMSO and was set to 0% inhibition. The negative control consisted of the reaction mix lacking PHGDH with 4% DMSO and was set to 100% inhibition. Percent inhibition with the compounds was then calculated by normalizing the fluorescence observed at a given compound concentration to the positive and negative controls. IC$_{50}$ was calculated by plotting the % inhibition versus concentration and using hyperbolic fit to determine compound concentration corresponding to 50% inhibition.

Assay Results

Table 2 shows the activity of selected compounds of this invention in the full-length PHGDH activity inhibition assay. The compound numbers correspond to the compound numbers in Table 1 and Experimental numbers ("e" numbers), above. Compounds having an activity designated as "A" provided an IC$_{50}$ of 0.001-1 μM; compounds having an activity designated as "B" provided an IC$_{50}$ of 1-5 μM; compounds having an activity designated as "C" provided an IC$_{50}$ of 5-10 μM and compounds having an activity designated as "D" provided an IC$_{50}$>10 μM. "NA" stands for "not assayed."

TABLE 2

PHGDH Activity Inhibition Data

| Compound/Experimental # | FL Diaphorase 500 μM NAD | FL Diaphorase 20 μM NAD |
|---|---|---|
| I-1 e3 | A | NA |
| I-2 e125 | A | NA |
| I-3 e124 | A | NA |
| I-4 e123 | A | NA |
| I-5 or I-6 e132 peak 2 | A | NA |
| I-6 or I-5 e131 peak 1 | A | NA |
| I-7 e117 | A | NA |
| I-8 e116 | A | NA |
| I-9 e137 | A | NA |
| I-10 e120 | A | NA |
| I-11 e72 | A | NA |
| I-12 e86 | A | NA |
| I-13 e111 | A | NA |
| I-14 e113 | A | NA |
| I-15 e162 | A | NA |
| I-16 e87 | A | NA |
| I-17 e85 | A | NA |
| I-18 e84 | A | NA |
| I-19 e94 | A | NA |
| I-20 e83 | A | NA |
| I-21 e127 | A | NA |
| I-22 e118 | A | NA |
| I-23 e82 | A | NA |
| I-24 e114 | A | NA |
| I-25 e136 | A | NA |
| I-26 e130 | A | NA |
| I-27 e110 | A | NA |
| I-28 e108 | A | NA |
| I-29 e135 | A | NA |
| I-30 e134 | A | NA |
| I-31 e112 | A | NA |
| I-32 e64 | A | NA |
| I-33 e62 | A | NA |
| I-34 or I-35 e161 peak 2 | A | NA |
| I-35 or I-34 e160 peak 1 | A | NA |
| I-36 e107 | A | NA |
| I-37 e109 | A | NA |
| I-38 e115 | A | NA |
| I-39 e81 | A | NA |
| I-40 e55 | A | NA |
| I-41 e92 | A | NA |
| I-42 e133 | A | NA |
| I-43 e126 | A | NA |
| I-44 e76 | A | NA |
| I-45 e74 | A | NA |
| I-46 e73 | A | NA |
| I-47 e77 | A | NA |
| I-48 e71 | A | NA |
| I-49 e60 | A | NA |
| I-50 e75 | A | NA |
| I-51 e68 | A | NA |
| I-52 e91 | A | NA |
| I-53 e80 | A | NA |
| I-54 e79 | A | NA |

TABLE 2-continued

PHGDH Activity Inhibition Data

| Compound #(I-X) | FL Diaphorase 500 μM NAD | FL Diaphorase 20 μM NAD |
| --- | --- | --- |
| I-55 e54 | A | NA |
| I-56 e78 | A | NA |
| I-57 e53 | A | NA |
| I-58 e70 | A | NA |
| I-59 e38 | A | NA |
| I-60 e65 | A | NA |
| I-61 e47 | A | NA |
| I-62 e46 | A | NA |
| I-63 e44 | A | NA |
| I-64 e57 | A | NA |
| I-65 e69 | A | NA |
| I-66 e67 | A | NA |
| I-67 e59 | A | NA |
| I-68 e58 | A | NA |
| I-69 e52 | C | NA |
| I-70 e61 | A | NA |
| I-71 e158 | B | NA |
| I-72 e56 | A | NA |
| I-73 e28 | B | NA |
| I-74 e27 | A | NA |
| I-75 e66 | A | NA |
| I-76 e42 | A | NA |
| I-77 e63 | A | NA |
| I-78 e40 | A | NA |
| I-79 e41 | A | NA |
| I-80 e103 | A | NA |
| I-81 e105 | A | NA |
| I-82 e51 | A | NA |
| I-83 e50 | A | NA |
| I-84 e49 | A | NA |
| I-85 e48 | A | NA |
| I-86 e45 | A | NA |
| I-87 e37 | A | NA |
| I-88 e156 | B | NA |
| I-89 e104 | B | NA |
| I-90 e43 | A | NA |
| I-91 e90 | A | NA |
| I-92 e101 | A | NA |
| I-93 e106 | A | NA |
| I-94 e98 | A | NA |
| I-95 e96 | B | NA |
| I-96 e36 | A | NA |
| I-97 e102 | A | NA |
| I-98 e155 | A | NA |
| I-99 e89 | A | NA |
| I-100 e99 | A | NA |
| I-101 e157 | B | NA |
| I-102 e100 | A | NA |
| I-103 e39 | A | NA |
| I-104 e97 | A | NA |
| I-105 e152 | A | NA |
| I-106 e31 | B | NA |
| I-107 e24 | A | NA |
| I-108 or I-109 e151 peak 2 | A | NA |
| I-109 or I-108 e150 peak1 | A | NA |
| I-110 e20 | A | NA |
| I-111 e95 | A | NA |
| I-112 e159 | A | NA |
| I-113 e35 | A | NA |
| I-114 e34 | B | NA |
| I-115 e33 | A | NA |
| I-116 e32 | A | NA |
| I-117 e30 | B | NA |
| I-118 e29 | A | NA |
| I-119 e153 | A | NA |
| I-120 e154 | A | NA |
| I-121 e21 | B | NA |
| I-122 e26 | A | NA |
| I-123 e23 | A | NA |
| I-124 e25 | B | NA |
| I-125 e19 | B | NA |
| I-126 e18 | C | NA |
| I-127 e22 | — | A |
| I-128 e148 | — | A |
| I-129 e149 | — | A |
| I-130 e17 | — | A |
| I-131 e144 | — | B |
| I-132 or I-133 e147 peak 2 | NA | A |
| I-133 or I-132 e146 peak 1 | — | A |
| I-134 e143 | NA | B |
| I-135 e142 | NA | B |
| I-136 e145 | — | A |
| I-137 e141 | NA | A |
| I-138 e16 | NA | C |
| I-139 e14 | — | B |
| I-140 e15 | NA | A |
| I-141 e140 | NA | B |
| I-142 e7 | NA | C |
| I-143 e139 | NA | B |
| I-144 e11 | NA | A |
| I-145 e13 | NA | C |
| I-146 e6 | NA | C |
| I-147 e8 | NA | B |
| I-148 e9 | NA | C |
| I-149 e12 | NA | C |
| I-150 e5 | NA | C |
| I-151 e10 | NA | B |
| I-152 e3 | NA | B |
| I-153 e2 | NA | C |
| I-154 e4 | NA | C |
| I-155 e1 | NA | C |
| I-156 e119 | A | NA |
| I-157 or I-158 e128 peak 1 | A | NA |
| I-158 or I-157 e129 peak 2 | A | NA |
| I-159 e121 | A | NA |
| I-160 e138 | A | NA |
| I-161 e164 | A | NA |
| I-162 e165 | A | NA |
| I-163 e163 | A | NA |
| I-164 e88 | A | NA |
| I-165 e120 | A | NA |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

I claim:
1. A compound of formula I:

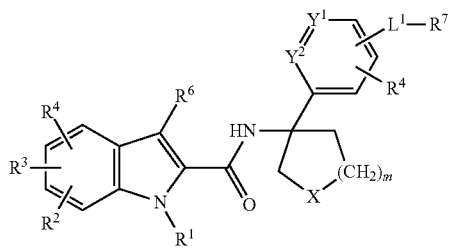

or a pharmaceutically acceptable salt thereof, wherein:
$R^1$ is methyl;
each of $R^2$ and $R^3$ is independently halogen, —OR, —CN, $C_{1-6}$ aliphatic optionally substituted with 1, 2, or 3 halogens, or -L-R'; or $R^2$ and $R^3$ are optionally taken together with the carbon atoms to which they are attached and any intervening atoms to form a 5-8 membered partially unsaturated ring having 0-2 heteroatoms independently selected from nitrogen, oxygen, or sulfur;
$R^4$ is hydrogen, halogen, —$OR^5$, —CN, $C_{1-6}$ aliphatic optionally substituted with 1, 2, or 3 halogens, or -L-R';
each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
$R^5$ is hydrogen, —$(CH_2)_n$-phenyl, —$(CH_2)_n$-Cy', or $C_{1-6}$ alkyl optionally substituted with 1, 2, or 3 halogens;
each L is independently a $C_{1-6}$ bivalent straight or branched hydrocarbon chain wherein 1-4 methylene units of the chain are independently and optionally replaced with —O—, —C(O)—, —C(O)O—, —OC(O)—, —OC(O)N(R)—, —(R)NC(O)O—, —C(O)N(R)—, —(R)NC(O)—, —N(R)—, —N(R)C(O)N(R)—, —S—, —SO—, or —$SO_2$—;
each R' is independently hydrogen, $C_{1-6}$ aliphatic, or an optionally substituted 4-8 membered saturated or partially unsaturated monocyclic heterocyclic ring having 1-3 heteroatoms independently selected from nitrogen, oxygen, or sulfur;
$R^6$ is hydrogen or $C_{1-4}$ alkyl;
$R^7$ is hydrogen, —$CO_2R$, optionally substituted $C_{1-6}$ aliphatic, -Cy-, or a bivalent 3-7 membered ring;
$L^1$ is —$SO_2NH$—,

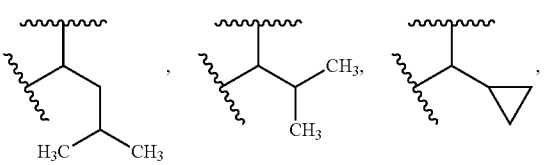

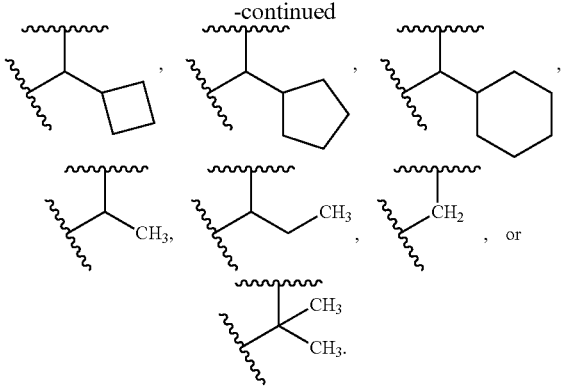

-Cy- is a bivalent 6-membered arylene ring containing 0-2 nitrogen atoms, or a bivalent 5-membered heteroarylene ring with 1-4 heteroatoms independently selected from nitrogen, oxygen, or sulfur, or a bivalent partially unsaturated 8-10 membered bicyclic heterocyclene ring with 1-4 heteroatoms independently selected from nitrogen, oxygen, or sulfur, wherein -Cy- is optionally substituted with 1 or 2 substituents independently selected from $C_{1-4}$ alkyl or —OR;
-Cy' is a 4-8 membered saturated or partially unsaturated monocyclic heterocyclic ring having 1-2 heteroatoms independently selected from nitrogen, oxygen, or sulfur;
$R^{10}$ is $C_{1-6}$ aliphatic optionally substituted with 1, 2, or 3 halogens, —$C(O)CH_3$, or —$SO_2$—$N(R^1)(R^{11})$;
$R^{11}$ is —$C(O)CH_3$, —$C(O)NHR^1$, or pyrazinyl;
n is independently 0, 1, 2, 3, 4, or 5;
m is independently 0, 1, or 2;
X is O, S, or —$N(R^{10})$—; and
each of $Y^1$ and $Y^2$ is independently =N— or =$C(R^4)$—.
2. The compound according to claim 1, wherein $R^2$ is halogen, —OR, —CN, or -L-R'.
3. The compound according to claim 1, wherein $R^2$ is F, Cl, —$CF_3$, —$OCF_3$, —$OCHF_2$, —$OCH_2Ph$, —$OCH_3$, —CN, —$CH_3$,

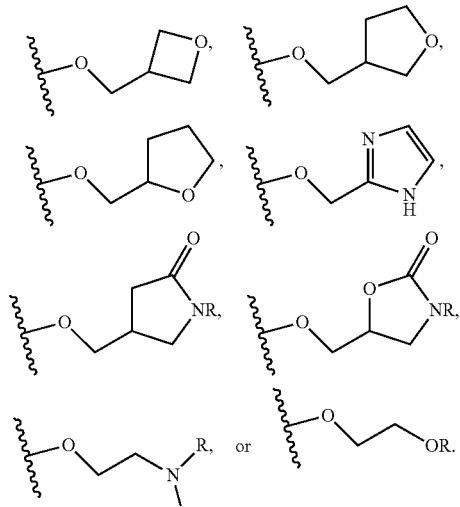

4. The compound according to claim 1, wherein $R^3$ is halogen or —OR.

5. The compound according to claim 1, wherein both of $R^2$ and $R^3$ are halogen.

6. The compound according to claim 1, wherein $R^4$ is hydrogen.

7. The compound according to claim 1, wherein $L^1$ is

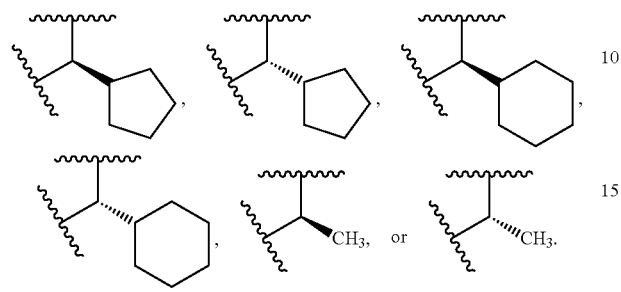

8. The compound according to claim 1, wherein $R^7$ is hydrogen, methyl, ethyl, cyclopropyl, cyclobutyl, tetrazolyl, or —CO$_2$H.

9. The compound according to claim 1, wherein X is O.

10. The compound according to claim 1, wherein X is —N(R$^{10}$)—.

11. The compound according to claim 1, wherein said compound is selected from Formulae II-a, II-b, II-c, II-d, II-e, III-a, III-b, III-c, III-d, III-e, III-f, III-g, III-h, or III-i:

II-a

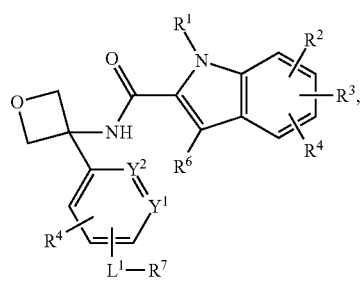

II-b

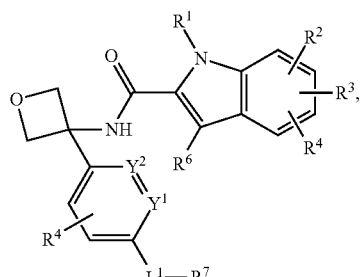

II-c

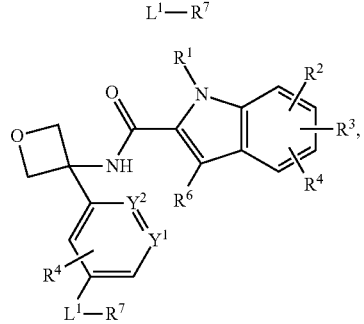

-continued

II-d

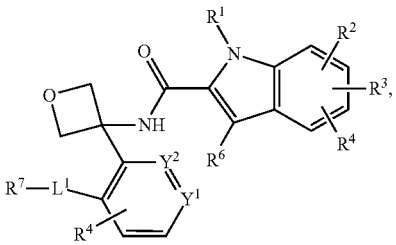

II-e

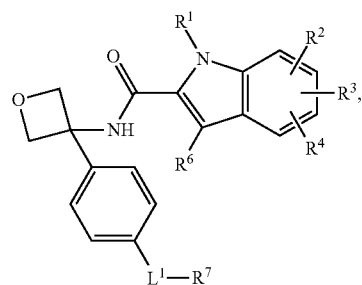

III-a

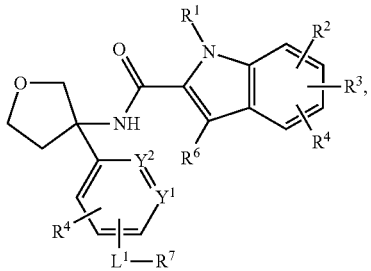

III-b

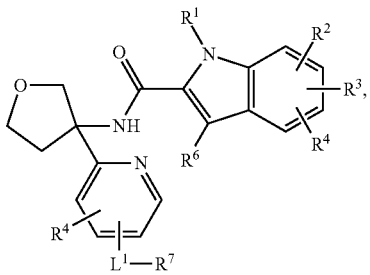

III-c

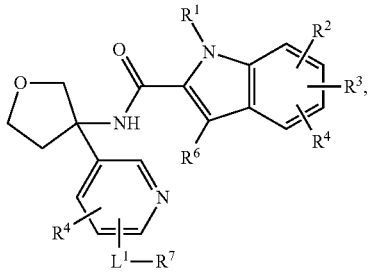

-continued

III-d

III-e

III-f

III-g

III-h

-continued

III-i or a pharmaceutically acceptable salt thereof.

12. The compound according to claim 1, wherein the compound is selected from one of the following:

I-1

I-5

I-6

I-7
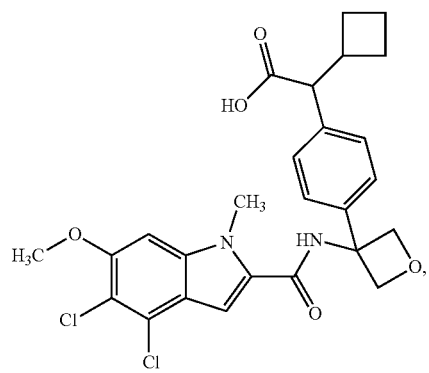
I-8
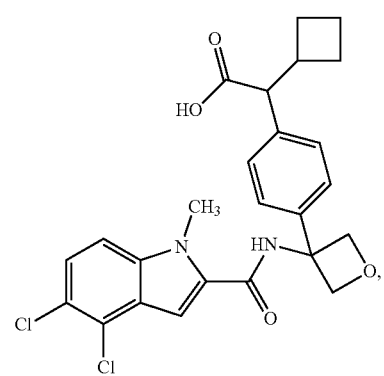
I-9
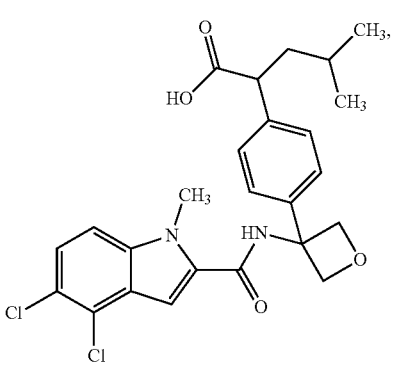
I-10
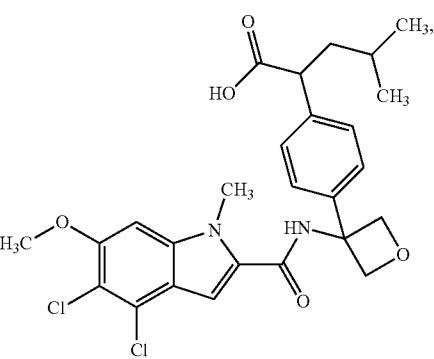
I-12
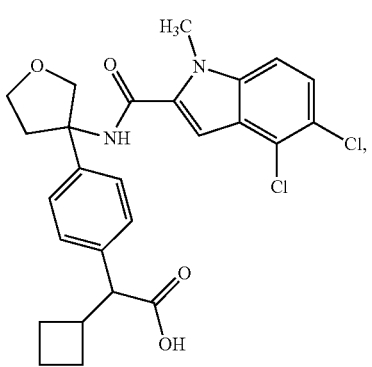
I-13
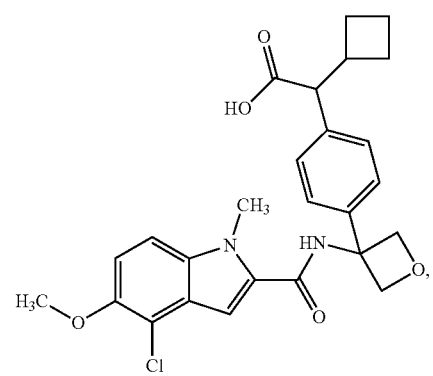
I-14
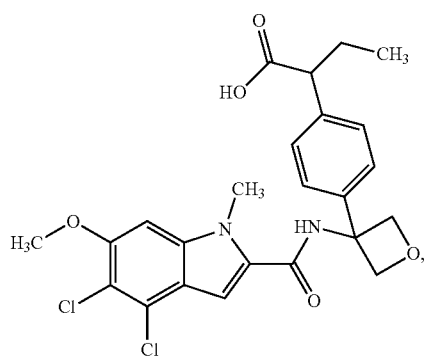
I-15
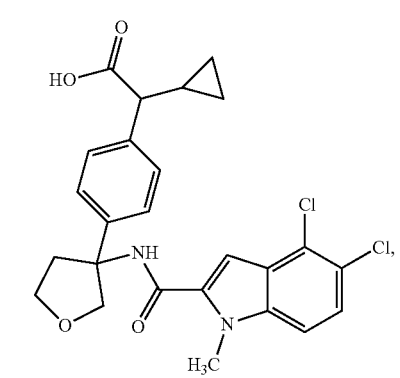

I-16
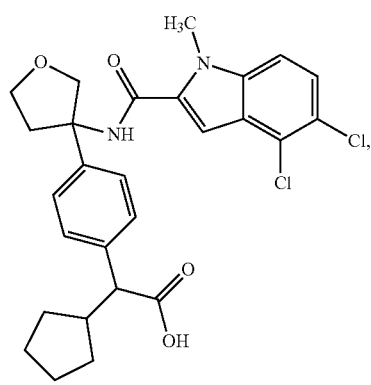
I-19
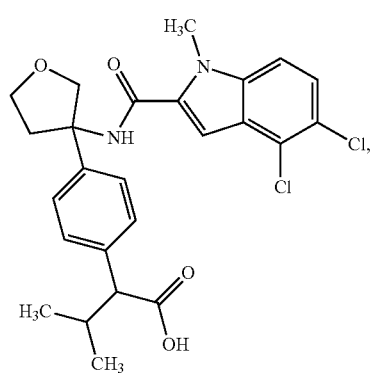
I-20
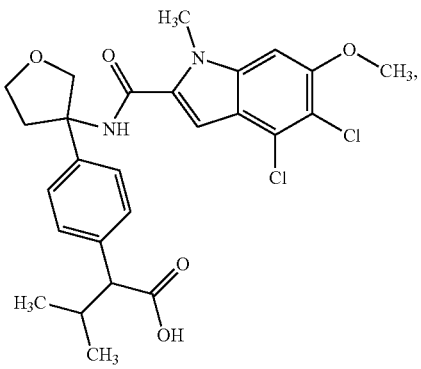
I-21
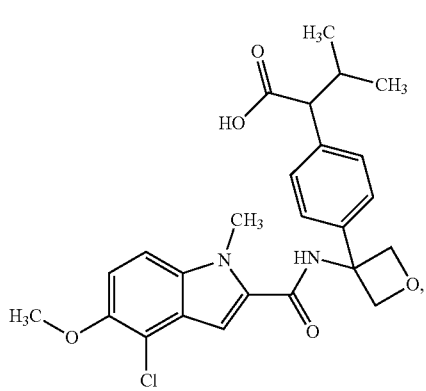
I-22
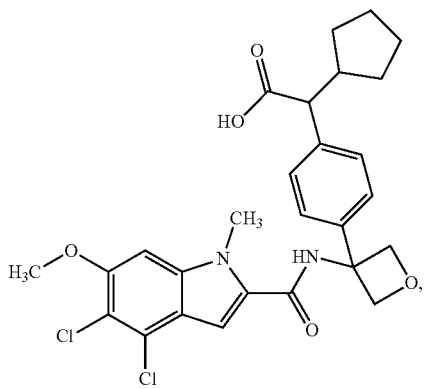
I-23
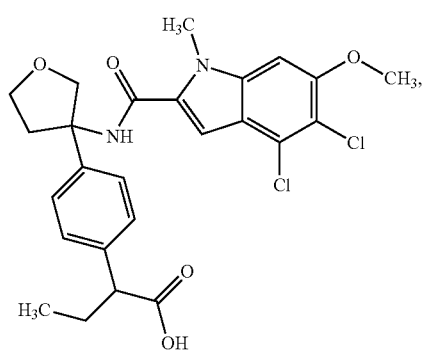
I-25
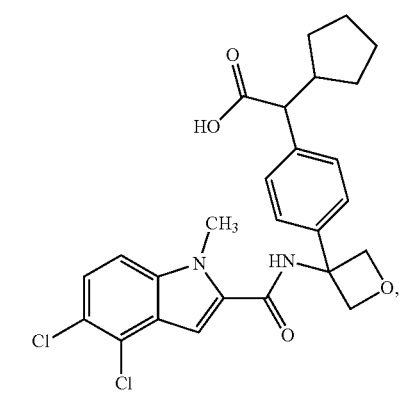
I-26
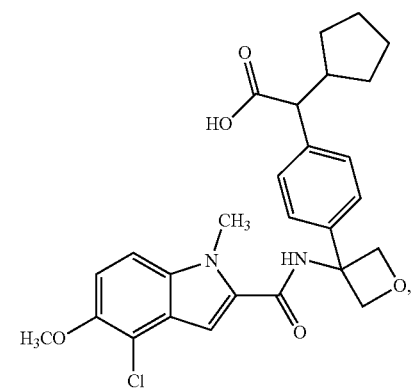

I-27
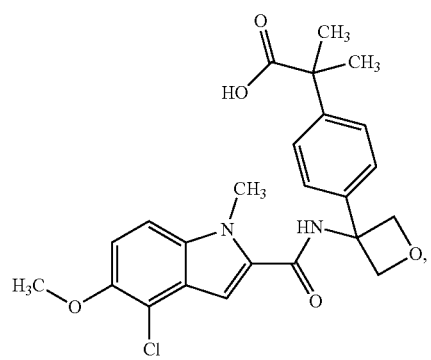
I-29
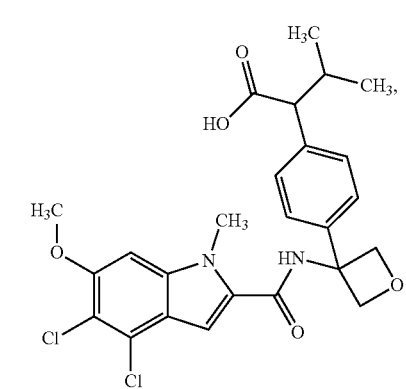
I-30
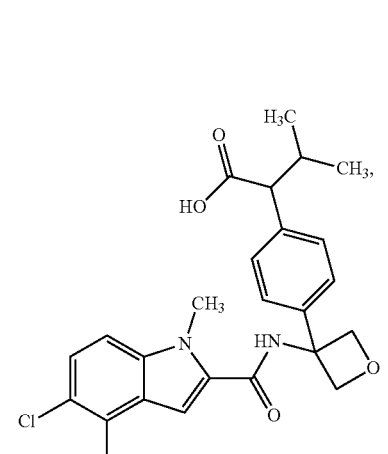
I-32
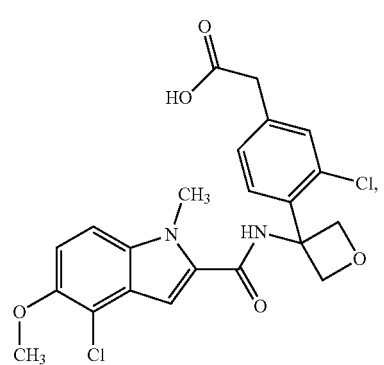
I-33
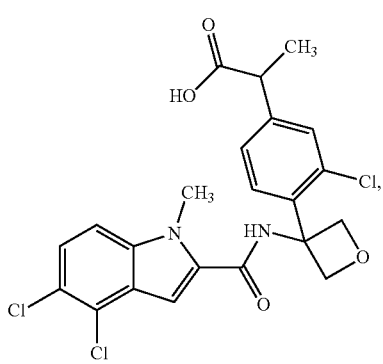
I-34
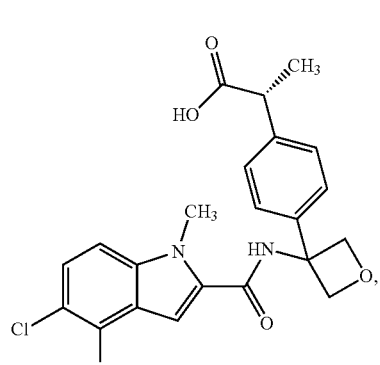
I-35
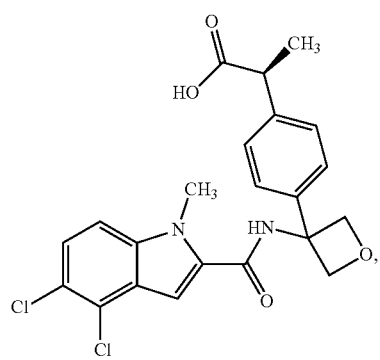
I-36
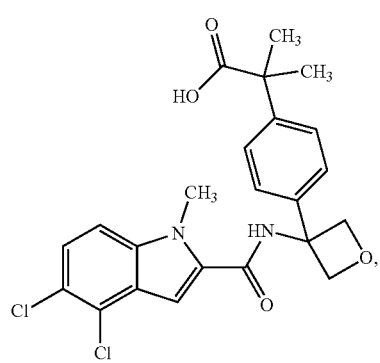

I-37
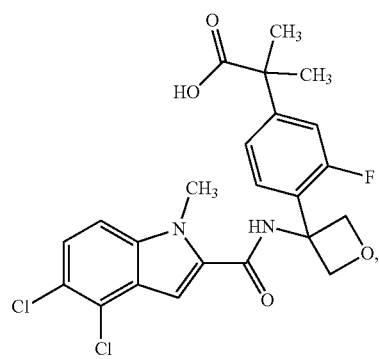
I-39
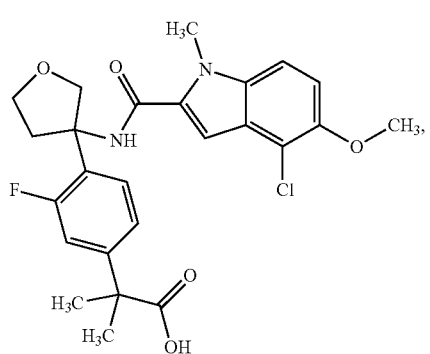
I-40
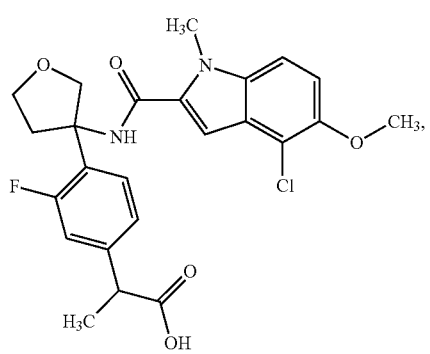
I-41
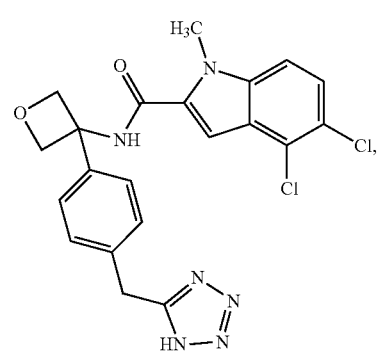
I-42
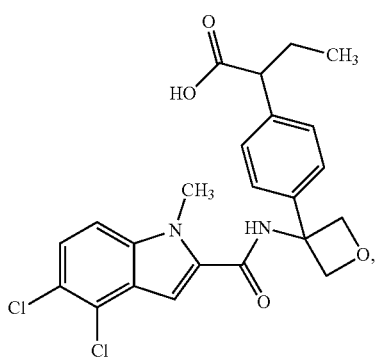
I-43
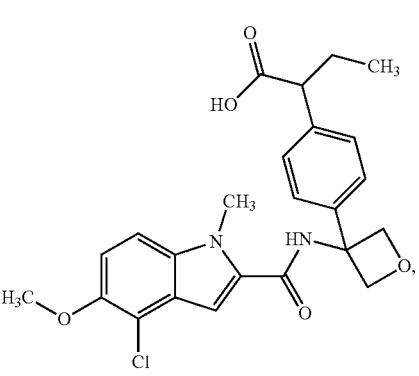
I-45
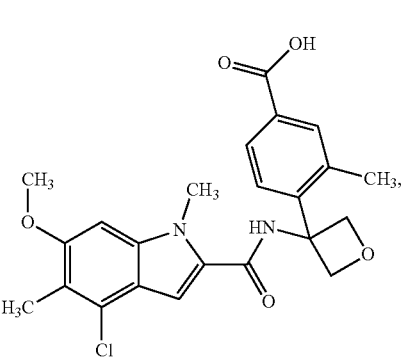
I-47
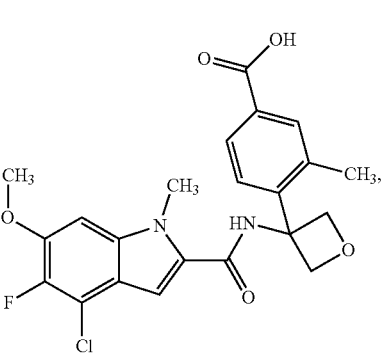

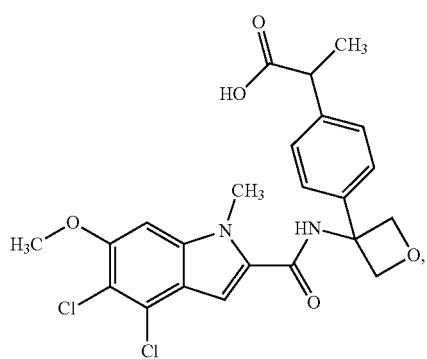 I-48
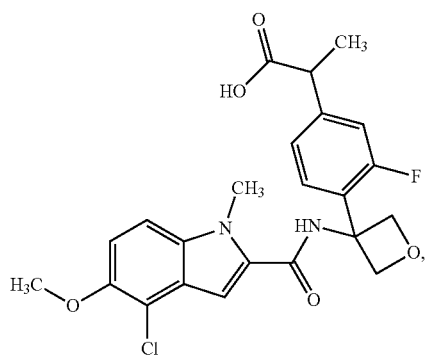 I-49
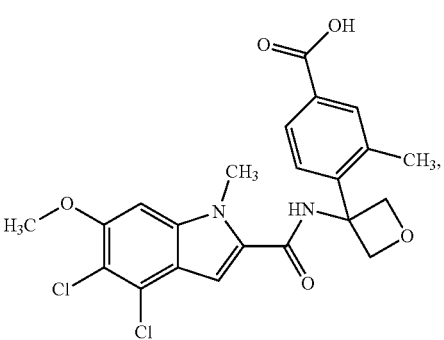 I-51
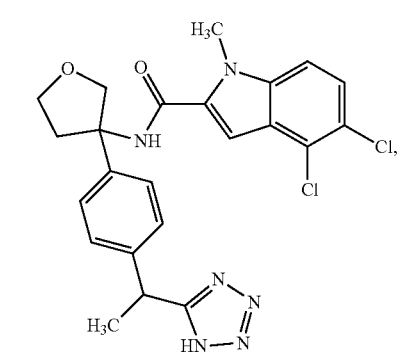 I-52
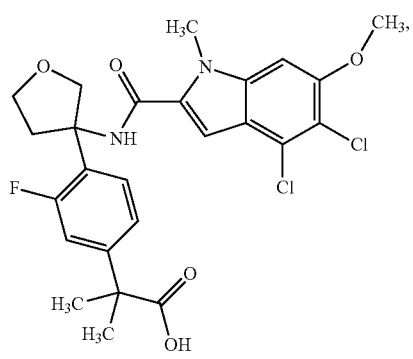 I-53
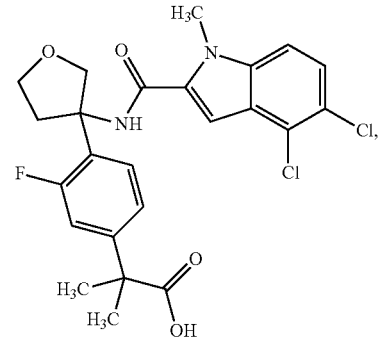 I-54
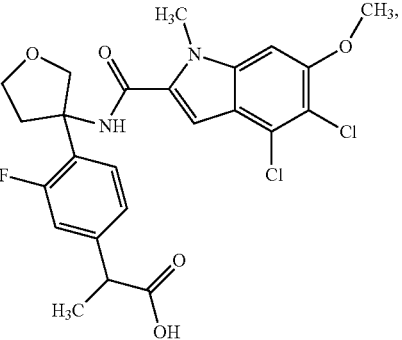 I-55
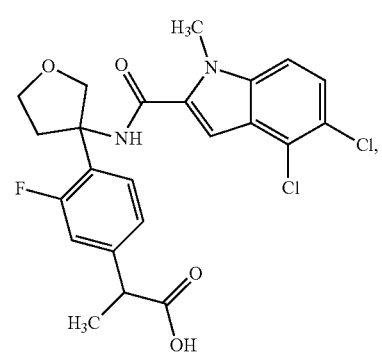 I-57

I-60 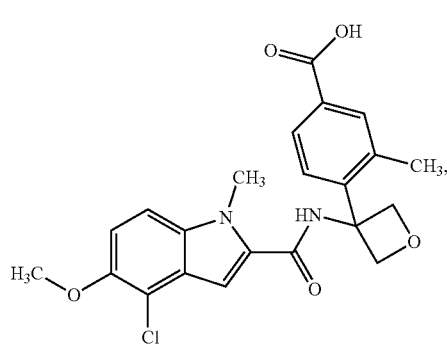
I-61 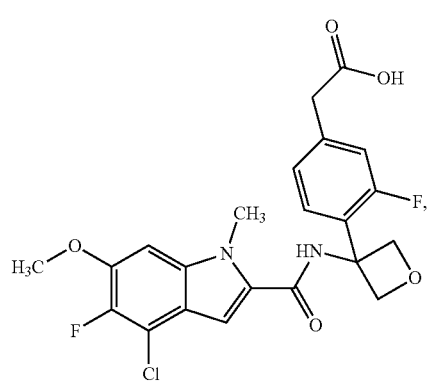
I-62 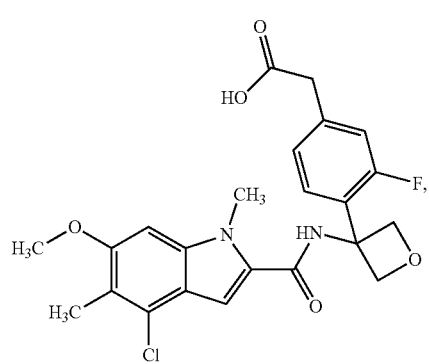
I-63 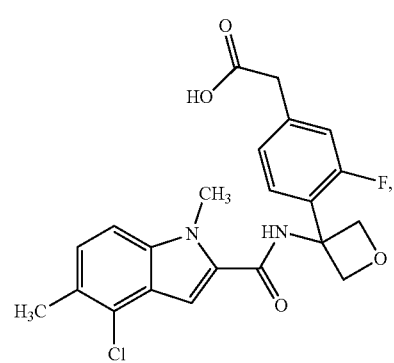
I-64 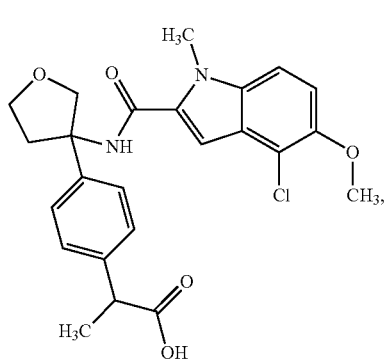
I-67 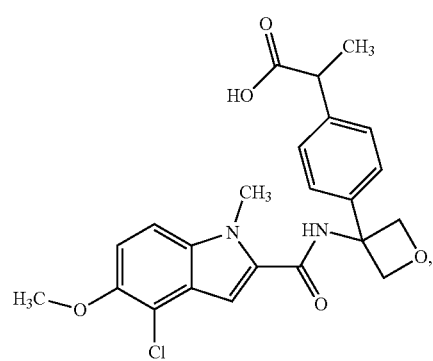
I-68 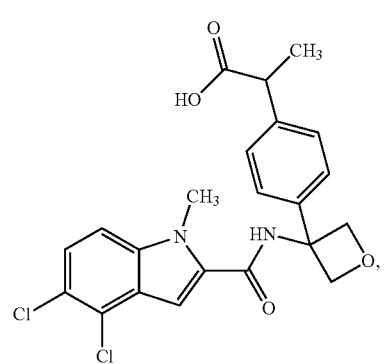
I-69 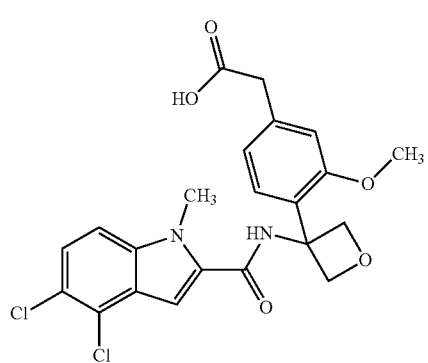

I-70
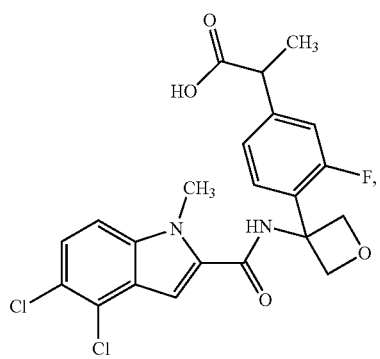
I-71
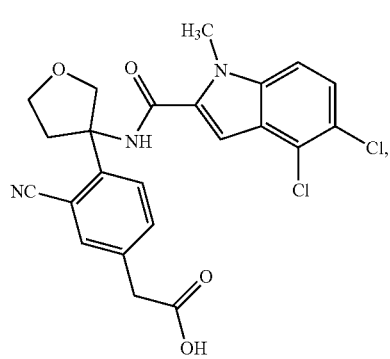
I-72
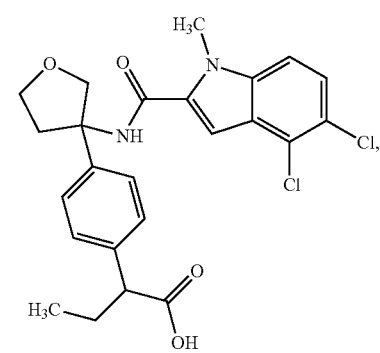
I-77
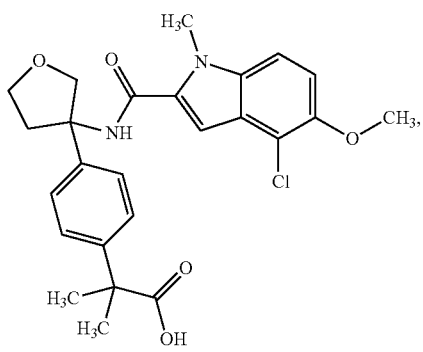
I-78
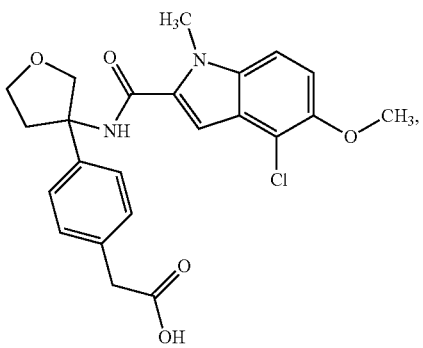
I-82
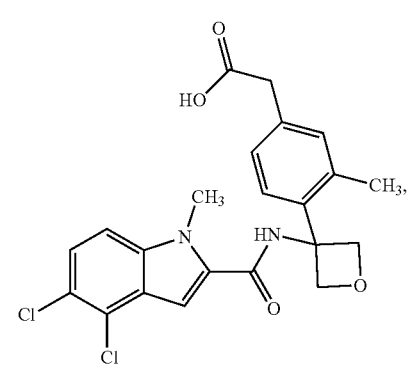
I-83
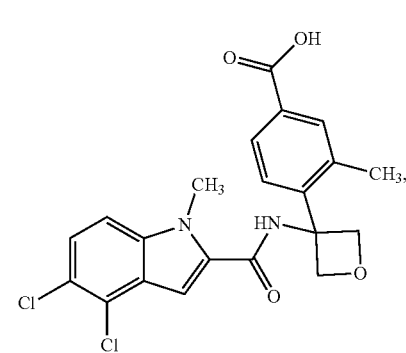
I-84
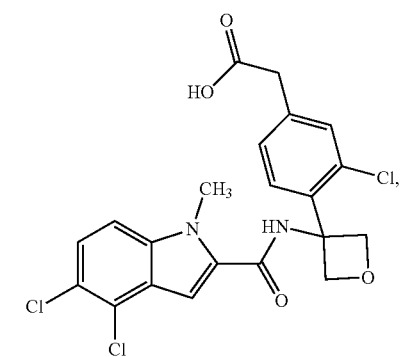

I-86
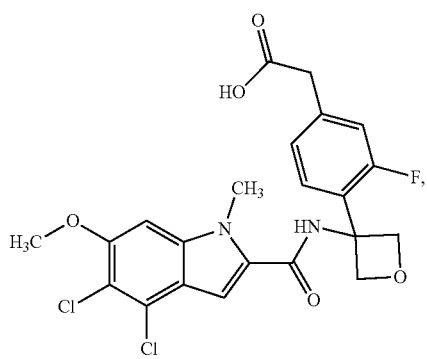
I-87
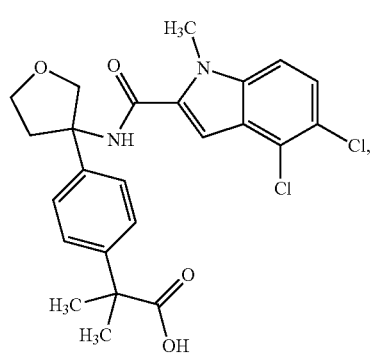
I-88
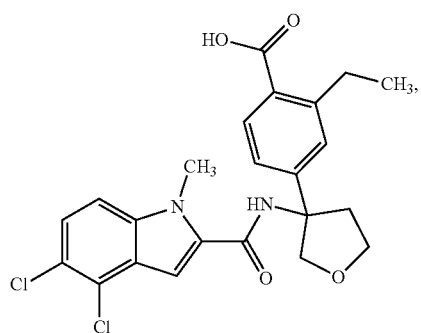
I-90
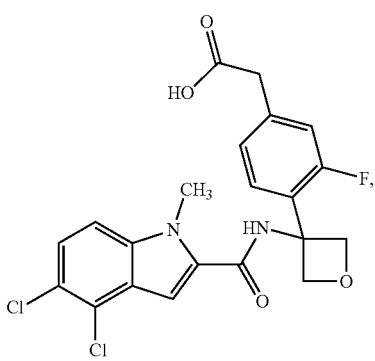
I-91
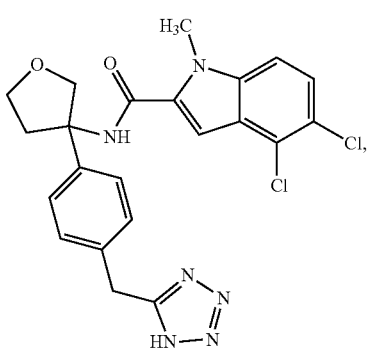
I-98
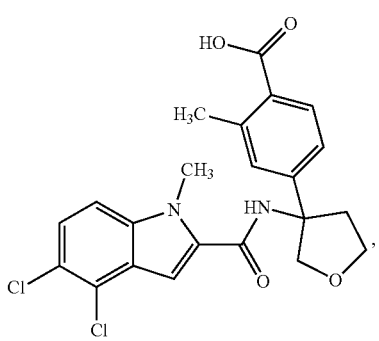
I-99
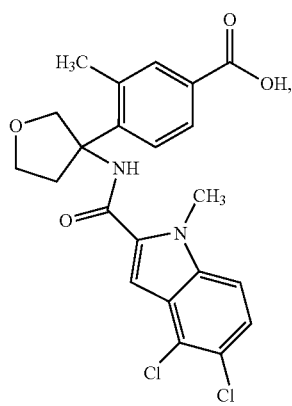
I-103
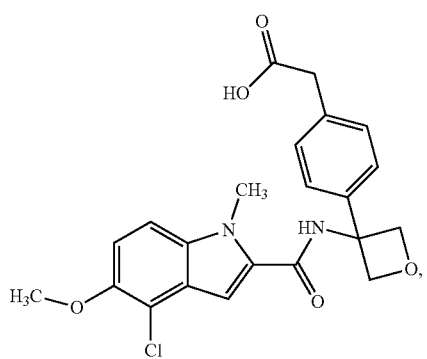

I-105
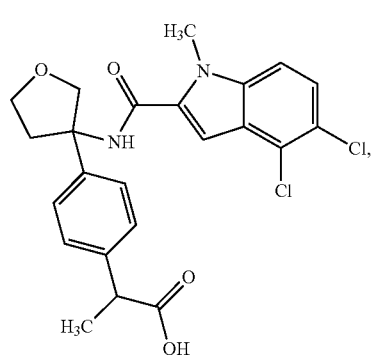
I-108
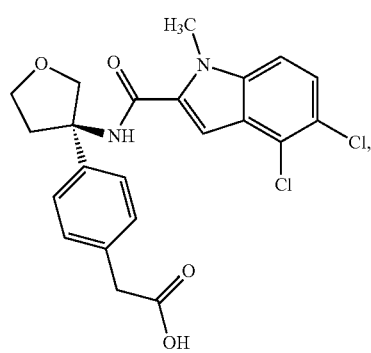
I-109
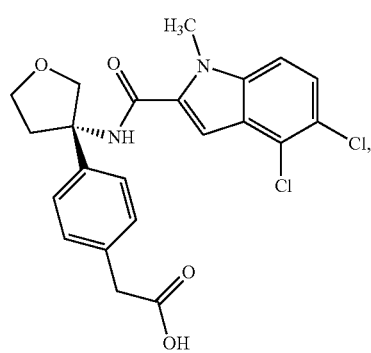
I-112
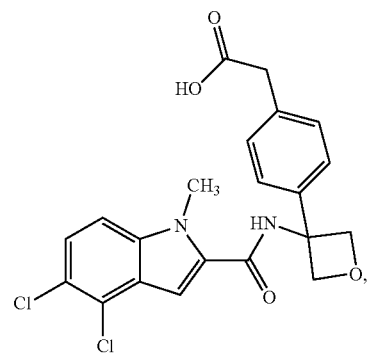
I-119
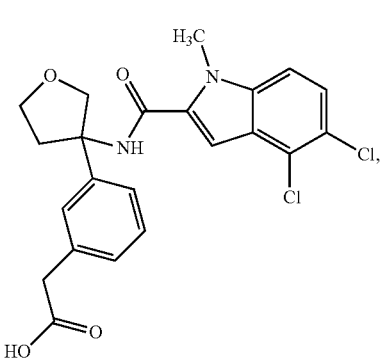
I-129
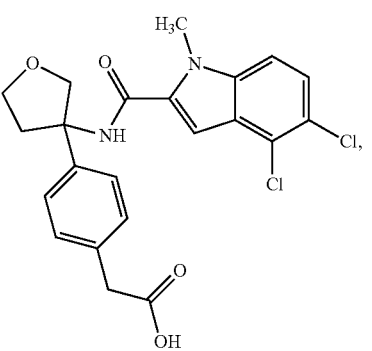
I-138
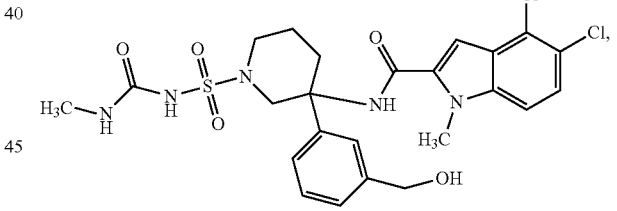
I-149
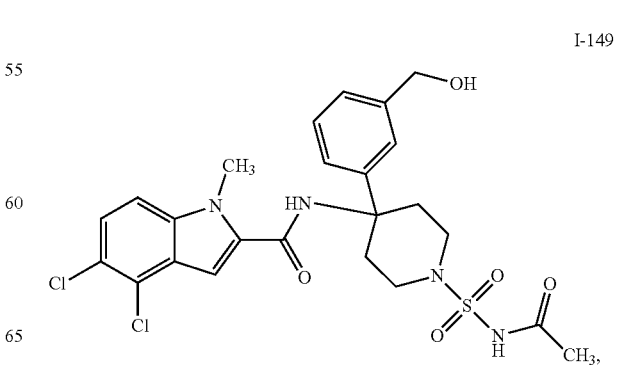

-continued

I-156

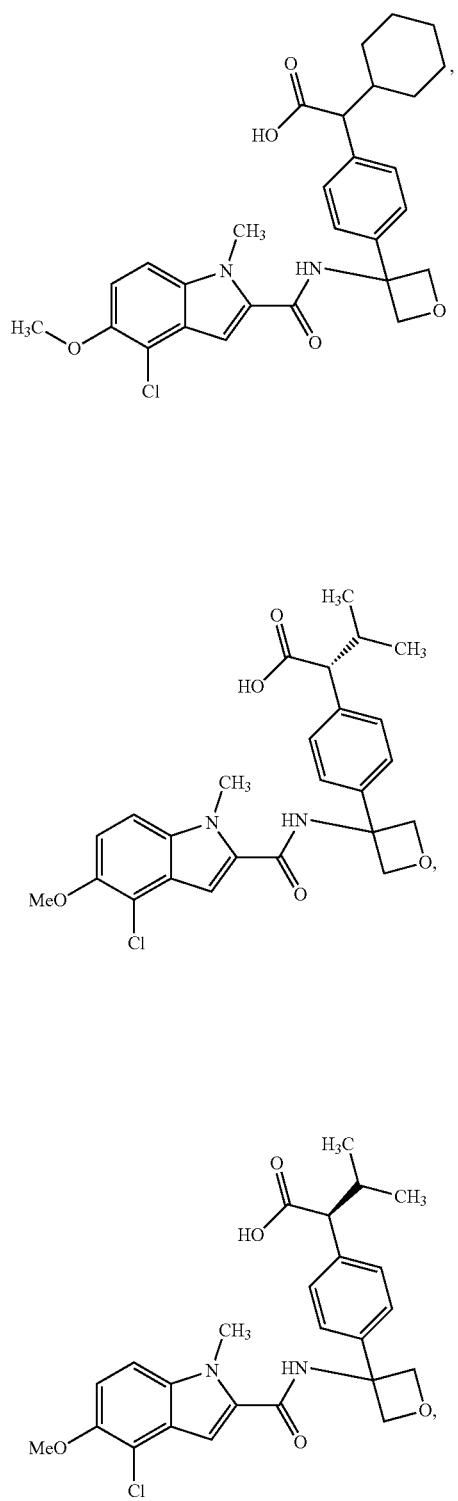

I-157

I-158

-continued

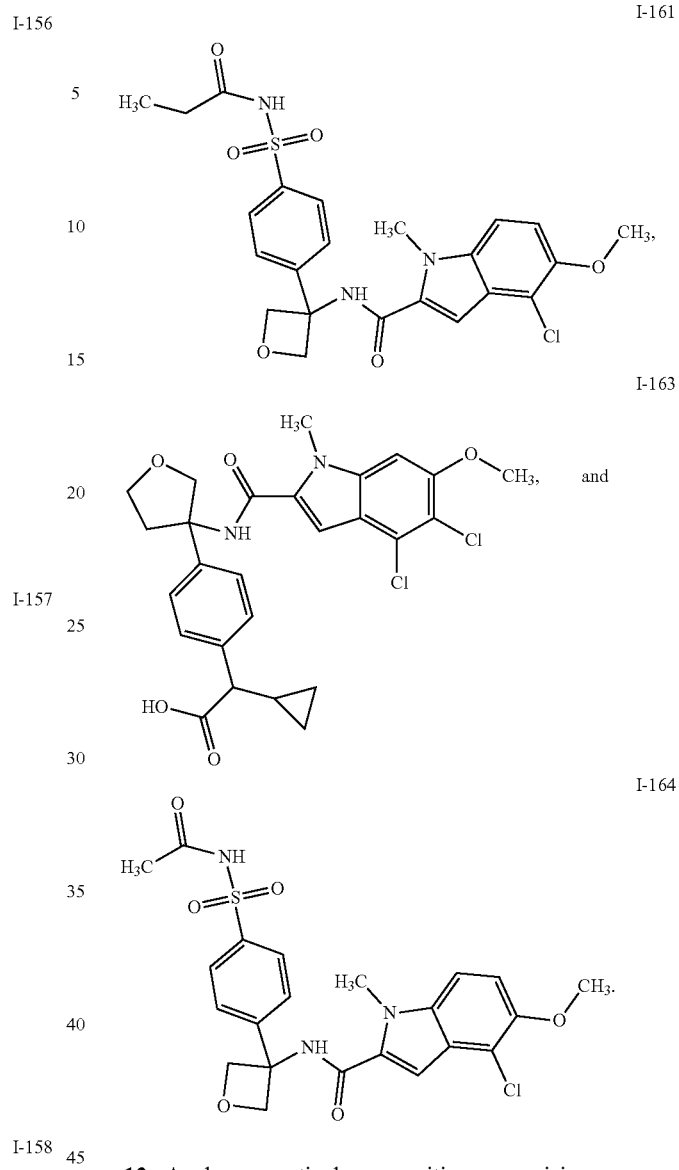

I-161

I-163 and

I-164

13. A pharmaceutical composition comprising a compound according to claim 1, or a pharmaceutically acceptable salt thereof, and a pharmaceutically acceptable adjuvant, carrier, or vehicle.

14. A method for treating cancer in a patient in need thereof, comprising administering to said patient the compound of claim 1, wherein the cancer is melanoma or breast cancer.

15. A method for treating a tumor in a patient in need thereof, comprising administering to said patient the compound of claim 1, wherein the tumor comprises lung cancer.

16. The method of claim 15, wherein the tumor comprises a small cell lung cancer (SCLC) or a non-small cell lung cancer (NSCLC).

* * * * *